US012753411B2

(12) United States Patent
Gannon et al.

(10) Patent No.: US 12,753,411 B2
(45) Date of Patent: Oct. 6, 2026

(54) GENE THERAPY FOR NEURODEGENERATIVE DISORDERS USING POLYNUCLEOTIDE SILENCING AND REPLACEMENT

(71) Applicant: The Brigham and Women's Hospital, Inc., Boston, MA (US)

(72) Inventors: Kimberley S. Gannon, Boston, MA (US); Neil R. Hackett, Boston, MA (US); Martin Goulet, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 720 days.

(21) Appl. No.: 17/794,225

(22) PCT Filed: Jan. 29, 2021

(86) PCT No.: PCT/US2021/015911

§ 371 (c)(1),
(2) Date: Jul. 20, 2022

(87) PCT Pub. No.: WO2021/155296

PCT Pub. Date: Aug. 5, 2021

(65) Prior Publication Data

US 2023/0136245 A1 May 4, 2023

Related U.S. Application Data

(60) Provisional application No. 62/968,707, filed on Jan. 31, 2020.

(51) Int. Cl.

| | |
|---|---|
| ***C12N 15/113*** | (2010.01) |
| ***A61K 48/00*** | (2006.01) |
| ***C12N 9/64*** | (2006.01) |
| ***C12N 15/86*** | (2006.01) |

(52) U.S. Cl.

CPC ........ *C12N 15/1138* (2013.01); *C12N 9/6478* (2013.01); *C12N 15/86* (2013.01); *C12Y 304/23046* (2013.01); *A61K 48/00* (2013.01); *C12N 2310/11* (2013.01); *C12N 2310/141* (2013.01); *C12N 2310/531* (2013.01); *C12N 2750/14143* (2013.01)

(58) Field of Classification Search

CPC .. C12N 15/1138; C12N 9/6478; C12N 15/86; C12Y 304/23046

See application file for complete search history.

(56) References Cited

U.S. PATENT DOCUMENTS

| | | | | |
|---|---|---|---|---|
| 5,328,470 | A | 7/1994 | Nabel et al. | |
| 5,658,776 | A | 8/1997 | Flotte et al. | |
| 6,020,143 | A | 2/2000 | George-Hyslop | |
| 6,180,613 | B1 | 1/2001 | Kaplitt et al. | |
| 6,395,960 | B1 | 5/2002 | George-Hyslop | |
| 6,503,888 | B1 | 1/2003 | Kaplitt et al. | |
| 6,686,449 | B2 | 2/2004 | Carter et al. | |
| 6,783,955 | B2 | 8/2004 | Arvizu et al. | |
| 6,979,537 | B2 | 12/2005 | McCarthy et al. | |
| 7,271,313 | B2 | 9/2007 | Shen | |
| 7,498,316 | B2 * | 3/2009 | Xu | C12Y 115/01001 436/6 |
| 7,709,616 | B2 * | 5/2010 | Bentwich | C12Q 1/6876 435/375 |
| 8,129,334 | B2 | 3/2012 | Dewji et al. | |
| 9,512,191 | B2 | 12/2016 | Dewji et al. | |
| 9,956,271 | B2 | 5/2018 | Guild et al. | |
| 10,221,223 | B2 * | 3/2019 | Dewji | C07K 14/4711 |
| 2002/0015939 | A1 | 2/2002 | McCarthy et al. | |
| 2002/0082211 | A1 | 6/2002 | Arvizu et al. | |
| 2003/0065141 | A1 | 4/2003 | Carter et al. | |
| 2005/0288243 | A1 * | 12/2005 | Xu | C12N 9/0089 435/6.16 |
| 2007/0134761 | A1 | 6/2007 | Charellard | |
| 2009/0305946 | A1 | 12/2009 | Dewji et al. | |
| 2011/0201052 | A1 | 8/2011 | Raitano et al. | |
| 2017/0073384 | A1 | 3/2017 | Dewji et al. | |
| 2018/0094280 | A1 | 4/2018 | Kutner et al. | |
| 2018/0169148 | A1 | 6/2018 | Adair et al. | |
| 2019/0134155 | A1 | 5/2019 | Kaetzel et al. | |
| 2021/0108186 | A1 | 4/2021 | Shen et al. | |
| 2022/0235374 | A1 | 7/2022 | Shen et al. | |
| 2023/0068087 | A1 | 3/2023 | Gannon et al. | |

FOREIGN PATENT DOCUMENTS

| | | | |
|---|---|---|---|
| CN | 103282374 | A | 9/2013 |
| CN | 103816540 | A | 5/2014 |
| CN | 106604988 | A | 4/2017 |
| CN | 107614008 | A | 1/2018 |
| EP | 0826042 | B1 | 8/2008 |
| EP | 2010663 | | 1/2009 |
| JP | H11504214 | A | 4/1999 |
| JP | 2013509890 | | 3/2013 |
| JP | 2013107890 | | 6/2013 |
| JP | 2016523835 | | 8/2016 |
| JP | 2018510615 | A | 4/2018 |

(Continued)

OTHER PUBLICATIONS

Seok et al. (Mol Cells. May 31, 2016;39(5):375-81. doi: 10.14348/molcells.2016.0013. Epub Apr. 27, 2016.) (Year: 2016).*

Riolo et al. (Methods Protoc. Dec. 24, 2020;4(1):1. doi: 10.3390/mps4010001.) (Year: 2020).*

Kilikevicius et al (Nucleic Acids Res. Jan. 25, 2022;50(2):617-634. doi: 10.1093/nar/gkab1256.) (Year: 2022).*

Borel et al. (Mol Ther. Apr. 2014;22(4):692-701. doi: 10.1038/mt.2013.285. Epub Dec. 19, 2013.) (Year: 2014).*

(Continued)

*Primary Examiner* — Fereydoun G Sajjadi
*Assistant Examiner* — Joel D Levin
(74) *Attorney, Agent, or Firm* — Fish & Richardson P.C.

(57) ABSTRACT

The disclosure relates to nucleic acid expression cassettes and vectors for the treatment of neurodegenerative disorders. Methods of treating neurodegenerative disorders such as Alzheimer's disease, frontotemporal dementia, frontotemporal lobar degeneration, Pick's disease, Lewy body dementia, memory loss, cognitive impairment, and mild cognitive impairment are also provided.

20 Claims, 16 Drawing Sheets

Figure 1:
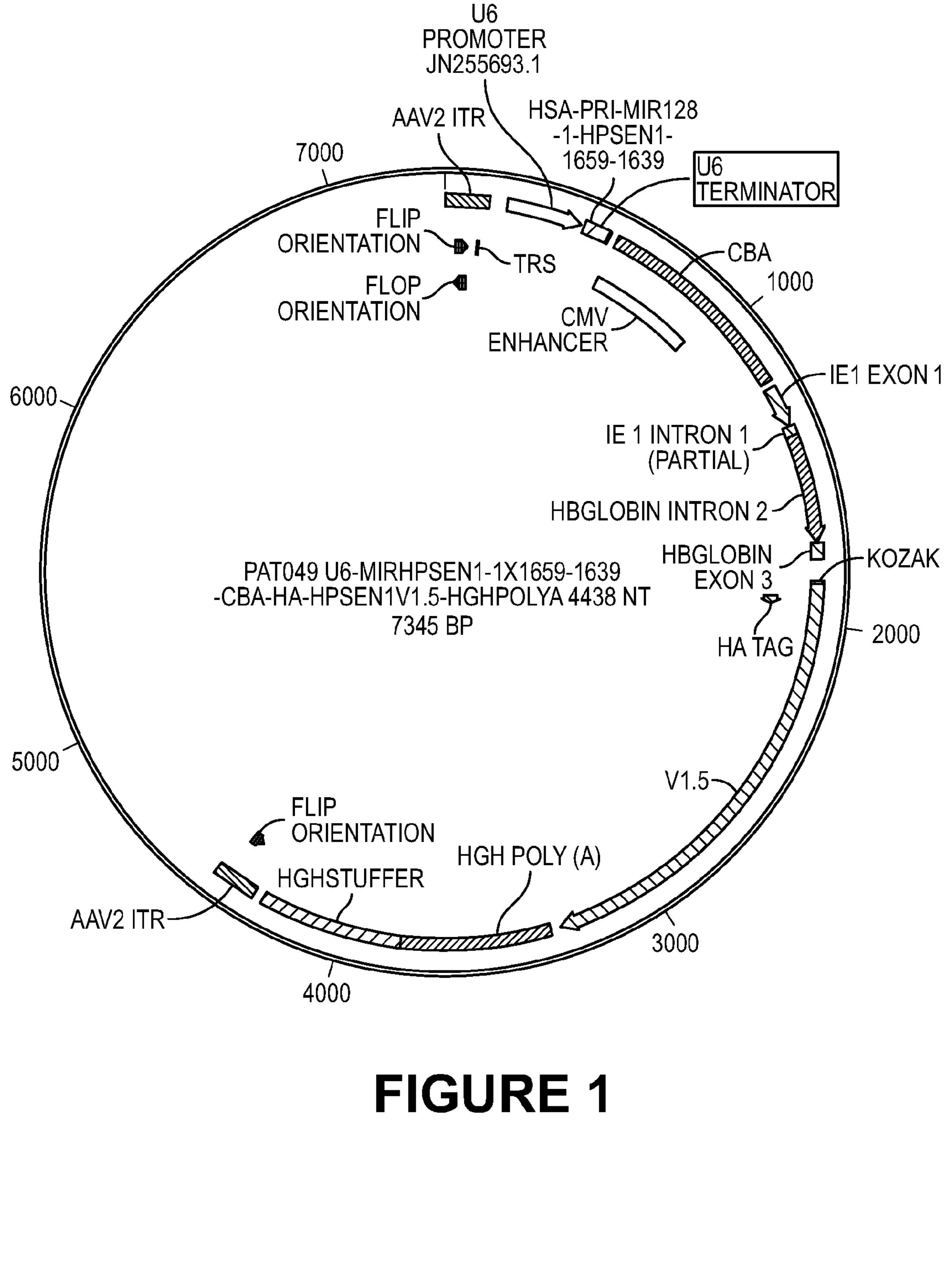

Specification includes a Sequence Listing.

(56) References Cited

FOREIGN PATENT DOCUMENTS

| | | | | |
|---|---|---|---|---|
| JP | 2021525245 A | 9/2021 | | |
| WO | WO 1995/00655 | 1/1995 | | |
| WO | WO 1995/11984 | 5/1995 | | |
| WO | WO 1995/27071 | 10/1995 | | |
| WO | WO 2000/003248 A1 | 1/2000 | | |
| WO | WO 2001/051671 A2 | 7/2001 | | |
| WO | WO-2005003350 A2 * | 1/2005 | ............. | A61K 45/06 |
| WO | WO 2005/037226 A2 | 4/2005 | | |
| WO | WO-2005116250 A2 * | 12/2005 | ........... | C12N 15/111 |
| WO | WO 2009/042727 | 4/2009 | | |
| WO | WO 2015/006743 A1 | 1/2015 | | |
| WO | WO 2016/209654 A1 | 12/2016 | | |
| WO | WO 2017/191274 | 11/2017 | | |
| WO | WO 2017/205767 A1 | 11/2017 | | |
| WO | WO 2018/045022 A1 | 3/2018 | | |
| WO | WO 2018/140532 | 8/2018 | | |
| WO | WO 2018/175443 A1 | 9/2018 | | |
| WO | WO 2018/222890 | 12/2018 | | |
| WO | WO 2019/028306 | 2/2019 | | |
| WO | WO 2019/226832 | 11/2019 | | |
| WO | WO 2021/155296 | 8/2021 | | |

OTHER PUBLICATIONS

O'Reilly et al. (Am J Hum Genet. Jul. 2007;81(1):127-35. doi: 10.1086/519025. Epub May 23, 2007.) (Year: 2007).*

Mauro et al. (Trends Mol Med. Nov. 2014;20(11):604-13. doi: 10.1016/j.molmed.2014.09.003. Epub Sep. 25, 2014.) (Year: 2014) ( Year: 2014).*

CN Office Action in Chinese Appln. No. 201980049127.3, mailed on Oct. 30, 2023, 26 pages (with English translation).

EP Partial European Search Report in European Appln. No. 20893982.7, mailed on Nov. 15, 2023, 14 pages.

NCBI sequence NM_000021.3, "Homo sapiens presenilin 1 (PSEN1), transcript variant 1, mRNA," dated Dec. 18, 2017, 7 pages.

NCBI reference sequence : NM_007318.2, "*Homo sapiens* presenilin 1 (PSEN1), transcript variant 2, mRNA," dated Jun. 18, 2017, 7 pages.

Wang et al., "Visualization of Alzheimer's disease related α-/β-/γ-secretase ternary complex by bimolecular fluorescence complementation based fluorescence resonance energy transfer," Frontiers in Molecular Neuroscience, Nov. 2018, 11:431, 9 pages.

CN Office Action in Chinese Appln. No. 202080052274.9, mailed on Mar. 12, 2024, 9 pages (with English translation).

EP Extended European Search Report in European Appln. No. 21747911.2, mailed on Mar. 14, 2024, 11 pages.

GenBank Accession No. NM_000021.4, "*Homo sapiens* presenilin 1 (PSEN1), transcript variant 1, mRNA," Nov. 20, 2018, 7 pages.

JP Office Action in Japanese Appln. No. 2020-565341, mailed on Jan. 9, 2024, 14 pages (with English translation).

Millington-Ward et al., "Suppression and replacement gene therapy for autosomal dominant disease in a murine model of dominant retinitis pigmentosa," Molecular Therapy, Apr. 2011, 19(4):642-9.

Montenegro et al., "Human Presenilin-1 delivered by AAV9 rescues impaired γ-secretase activity, memory deficits, and neurodegeneration in Psen mutant mice," Proceedings of the National Academy of Sciences, Oct. 2023, 120(42):e2306714120, 8 pages.

Pelletier et al., "RNA based gene therapy for dominantly inherited diseases," Current Gene Therapy, Feb. 2006, 6(1):131-46.

Pimenova et al., "Novel presenilin 1 and 2 double knock-out cell line for in vitro validation of PSEN1 and PSEN2 mutations," Neurobiology of Disease, Feb. 2020, 138, 24 pages.

Sierant et al., "Specific silencing of L392V PSEN1 mutant allele by RNA interference," International Journal of Alzheimer's Disease, Jan. 2011, vol. 2011, 14 pages.

Trochet et al., "Therapy for dominant inherited diseases by allele-specific RNA interference: successes and pitfalls," Current Gene Therapy, Oct. 2015, 15(5):503, 27 pages.

Uniprot Accession No. P49768.1, "Presenilin-1," Oct. 1, 1996, 55 pages.

Uniprot Accession No. P49810.1, "Presenilin-2," Oct. 1, 1996, 14 pages.

JP Office Action in Japanese Appln. No. 2021-569550, mailed on May 28, 2024, 8 pages (with English translation).

Bryan et al., "Implications of protein fold switching," Current Opinion in Structural Biology, 2013, 2(23):314-6.

Bulcha et al., "Viral vector platforms within the gene therapy landscape," Signal Transduction and Targeted Therapy, Feb. 2021, 6(1):53, 24 pages.

Chávez-Gutiérrez et al., "Mechanisms of neurodegeneration-Insights from familial Alzheimer's disease," Seminars in Cell & Developmental Biology, Sep. 2020, (105):75-85.

Cruz et al., "Protein function prediction," Functional Genomics: Methods and Protocols, 3rd edition, Aug. 2018, 55, 22 pages.

Hur, "γ-Secretase in Alzheimer's disease, " Experimental & Molecular Medicine, Apr. 2022, 54(4):433, 14 pages.

Ingusci et al., "Gene therapy tools for brain diseases," Frontiers in Pharmacology, Jul. 2019, 10:724, 19 pages.

Kabir et al, "Exploring the role of PSEN mutations in the pathogenesis of Alzheimer's disease, " Neurotoxicity Research, Dec. 2020, 38:833-49.

Kotterman et al., "Engineering adeno-associated viruses for clinical gene therapy," Nature Reviews Genetics, Jul. 2014, 15(7):445, 18 pages.

Lenzi et al., Gene Transfer Research: The Evolution of Clinical Science, NCBI Bookshelf, A Service of the National Library of Medicine, National Institute of Health, Oversight and Review of Clinical Gene Transfer Protocols: Assessing the Role of the Recombinant DNA Advisory Committee, National Academies Press, Mar. 2014, 16 pages.

Maqbool et al., "The substrate-binding protein in bacterial ABC transporters: dissecting roles in the evolution of substrate specificity," Biochemical Society Transactions, Oct. 2015, 43(5):1011-7.

Shim et al., "Nonviral delivery systems for cancer gene therapy: strategies and challenges," Current Gene Therapy, Feb. 2018, 18(1):3-20.

Stepanichev, "Gene editing and Alzheimer's disease: is there light at the end of the tunnel?," Frontiers in Genome Editing, Jun. 2020, 2:4, 10 pages.

Sudhakar et al., Gene therapy for neurodegenerative diseases, Neurotherapeutics, Jan. 2019, 16(1):166-75.

Acosta-Baena et al., "Pre-dementia clinical stages in presenilin 1 E280A familial early-onset Alzheimer's disease: a retrospective cohort study," The Lancet Neurology, Mar. 1, 2011, 10(3):213-20.

Amtul et al., "A presenilin 1 mutation associated with familial frontotemporal dementia inhibits γ-secretase cleavage of APP and notch," Neurobiology of Disease, Mar. 1, 2002, 9(2):269-73.

Asokan et al., "The AAV vector toolkit: poised at the clinical crossroads," Molecular Therapy, Apr. 1, 2012, 20(4):699-708.

Ausubel et al., "Current Protocols in Molecular Biology, Sections 9.10-9.14," Greene Publishing Associates, 1989, 51 pages.

Beglopoulos et al., "Reduced β-amyloid production and increased inflammatory responses in presenilin conditional knock-out mice," Journal of Biological Chemistry, Nov. 5, 2004, 279(45):46907-14.

Bentahir et al., "Presenilin clinical mutations can affect γ-secretase activity by different mechanisms," Journal of Neurochemistry, Feb. 2006, 96(3):732-42.

Bessis et al., "Immune responses to gene therapy vectors: influence on vector function and effector mechanisms," Gene Therapy, Oct. 2004, 11(1):S10-7.

Bird et al., "Wide range in age of onset for chromosome 1-related familial Alzheimer's disease," Annals of Neurology, Dec. 1996, 40(6):932-936.

Bose et al., "Role of nucleolin in human parainfluenza virus type 3 infection of human lung epithelial cells," Journal of Virology, Aug. 1, 2004, 78(15):8146-58.

Brouwers et al., "Molecular genetics of Alzheimer's disease: an update," Annals of Medicine, Jan. 1, 2008, 40(8):562-83.

(56) References Cited

OTHER PUBLICATIONS

Brunkan et al., "Two domains within the first putative transmembrane domain of presenilin 1 differentially influence presenilinase and γ-secretase activity," Journal of Neurochemistry, Sep. 2005, 94(5):1315-28.
Cai et al., "Mutations in presenilin 2 and its implications in Alzheimer's disease and other dementia-associated disorders," Clinical Interventions in Aging, Jul. 2015, 10:1163-1172.
Chen et al., "Enhancing the Utility of Adeno-Associated Virus Gene Transfer through Inducible Tissue-Specific Expression," Human Gene Therapy Methods, Aug. 2013, 24(4):270-278.
Chen et al., "Gene therapy for brain tumors: regression of experimental gliomas by adenovirus-mediated gene transfer in vivo," Proceedings of the National Academy of Sciences, Apr. 12, 1994, 91(8):3054-7.
Chen et al., "Presenilin 1 mutations activate γ42-secretase but reciprocally inhibit e- secretase cleavage of amyloid precursor protein (APP) and S3-cleavage of notch," Journal of Biological Chemistry, Sep. 27, 2002, 277(39):36521-6.
Colin et al., "Engineered lentiviral vector targeting astrocytes in vivo," Glia, Apr. 2009, 57(6):667-79.
Cressant et al., "Improved behavior and neuropathology in the mouse model of Sanfilippo type IIIB disease after adeno-associated virus-mediated gene transfer in the striatum," Journal of Neuroscience, Nov. 10, 2004, 24(45):10229-39.
Crook et al., "A variant of Alzheimer's disease with spastic paraparesis and unusual plaques due to deletion of exon 9 of presenilin 1," Nature Medicine, Apr. 1998, 4(4):452-5.
Dana et al., "Molecular mechanisms and biological functions of siRNA," International Journal of Biomedical Science, Jun. 2017, 13(2):48-57.
De Jonghe et al., "Aberrant splicing in the presenilin-1 intron 4 mutation causes presenile Alzheimer's disease by increased Aβ42 secretion," Human Molecular Genetics, Aug. 1, 1999, 8(8):1529-40.
De Strooper, "Loss-of-function presenilin mutations in Alzheimer disease: Talking Point on the role of presenilin mutations in Alzheimer disease," EMBO Reports, Feb. 2007, 8(2):141-6.
Deyle et al., "Adeno-associated virus vector integration," Current Opinion in Molecular Therapeutics, Aug. 2009, 11(4):442, 11 pages.
Dittgen et al., "Lentivirus-based genetic manipulations of cortical neurons and their optical and electrophysiological monitoring in vivo," Proceedings of the National Academy of Sciences, Dec. 28, 2004, 101(52):18206-11.
Doll et al., "Comparison of promoter strengths on gene delivery into mammalian brain cells using AAV vectors," Gene Therapy, May 1, 1996, 3(5):437-47.
Dong et al., "Poly (d, 1-lactide-co-glycolide)/montmorillonite nanoparticles for oral delivery of anticancer drugs," Biomaterials, Oct. 1, 2005, 26(30):6068-76.
Duff et al., "Increased amyloid-β42 (43) in brains of mice expressing mutant presenilin 1," Nature, Oct. 1996, 383(6602):710-3.
Elbashir et al., "Duplexes of 21±nucleotide RNAs mediate RNA interference in cultured mammalian cells," Nature, May 2001, 411:494-498.
EP Extended Search Report in European Appln. No. 19808081.4, dated Feb. 21, 2022, 7 pages.
EP Extended Search Report in European Appln. No. 20813435.3. dated Jun. 12, 2023, 6 pages.
EP Supplementary European Search Report in European Appln. No. 19808081.4, dated Mar. 11, 2022, 8 pages.
Felsenstein et al., "O1-11-03: Endogenous cholesterol metabolites as potential Alzheimer's therapeutics," Alzheimer's & Dementia, Jul. 2012, 8(4S Part 3):P104-5.
Feng et al., "Forebrain degeneration and ventricle enlargement caused by double knockout of Alzheimer's presenilin-1 and presenilin-2," Proceedings of the National Academy of Sciences, May 25, 2004, 101(21):8162-7.
Flotte et al., "Gene expression from adeno-associated virus vectors in airway epithelial cells," Am J Respir Cell Mol Biol, Sep. 1, 1992, 7(3):349-56.
Foley et al., "Intra-arterial delivery of AAV vectors to the mouse brain after mannitol mediated blood brain barrier disruption," Journal of Controlled Release, Dec. 28, 2014, 196:71-8.
GenBank Accession No. AAW01891, "Sequence 12 from patent U.S. Pat. No. 6,783,955," dated Dec. 14, 2004, 1 page.
GenBank Accession No. AFD46703, "Sequence 2 from patent U.S. Pat. No. 8,129,334," Mar. 14, 2012, 1 page.
GenBank Accession No. NM_000021.3, "Homo sapiens presenilin 1 (PSEN1), transcript variant 1, mRNA," dated Aug. 7, 2008, 5 pages.
GenBank Accession No. NM_000447.2, "Homo sapiens presenilin 2 (Alzheimer disease 4) (PSEN2), transcript variant 1, mRNA," dated Aug. 17, 2007, 4 pages.
GenBank Accession No. NM 007318.2, "*Homo sapiens* presenilin 1 (PSEN1), transcript variant 2, mRNA," dated Aug. 7, 2008, 5 pages.
GenBank Accession No. NM 012486.2, "*Homo sapiens* presenilin 2 (PSEN2), transcript variant 2, mRNA," dated Aug. 17, 2007, 6 pages.
GenBank Accession No. NP 000438.2, "presenilin-2 isoform 1 [*Homo sapiens*]," May 14, 2018, 4 pages.
Gholizadeh et al., "Reduced phenotypic severity following adeno-associated virus-mediated Fmr1 gene delivery in fragile X mice," Neuropsychopharmacology, Dec. 2014, 39(13):3100-11.
Gonçalves et al., "Adeno-associated virus: from defective virus to effective vector," Virology Journal, Dec. 2005, 2(1):1-7.
Gray et al., "Optimizing promoters for recombinant adeno-associated virus-mediated gene expression in the peripheral and central nervous system using self-complementary vectors," Human Gene Therapy, Sep. 2011, 22:1143-1153.
Haberman et al., "Inducible long-term gene expression in brain with adeno-associated virus gene transfer," Gene Therapy, Dec. 1998, 5(12):1604-11.
Handler et al., "Presenilin-1 regulates neuronal differentiation during neurogenesis," Development, Jun. 15, 2000, 127(12):2593-606.
Heilig et al., "A presenilin-1 mutation identified in familial Alzheimer disease with cotton wool plaques causes a nearly complete loss of γ-secretase activity," Journal of Biological Chemistry, Jul. 16, 2010, 285(29):22350-9.
Heilig et al., "Trans-dominant negative effects of pathogenic PSEN1 mutations on γ-secretase activity and Aβ production," Journal of Neuroscience, Jul. 10, 2013, 33(28):11606-17.
Henikoff et al., "Amino acid substitution matrices from protein blocks," Proceedings of the National Academy of Sciences, Nov. 15, 1992, 89(22):10915-9.
Hermonat et al., "Use of adeno-associated virus as a mammalian DNA cloning vector: transduction of neomycin resistance into mammalian tissue culture cells," Proceedings of the National Academy of Sciences, Oct. 1, 1984, 81(20):6466-70.
Herreman et al., "β-Secretase activity requires the presenilin-dependent trafficking of nicastrin through the Golgi apparatus but not its complex glycosylation," Journal of Cell Science, Mar. 15, 2003, 116(6):1127-36.
Herskowitz, "Functional inactivation of genes by dominant negative mutations," Nature, Sep. 1987, 329(6136):219-22.
Hester et al., "AAV as a gene transfer vector for the treatment of neurological disorders: novel treatment thoughts for ALS," Current Gene Therapy, Oct. 1, 2009, 9(5):428-33.
Hiltunen et al., "Identification of a novel 4.6-kb genomic deletion in presenilin-1 gene which results in exclusion of exon 9 in a Finnish early onset Alzheimer's disease family: an Alu core sequence-stimulated recombination?," European Journal of Human Genetics, Apr. 2000, 8(4):259-66.
Hitoshi Niwa et al., "Efficient selection for high-expression transfectants with a novel eukaryotic vector," Gene, Dec. 15, 1991, 108(2):193-9.
Hsu et al., "Discovery and validation of autosomal dominant Alzheimer's disease mutations," Alzheimer's Research & Therapy, Dec. 2018, 10(1):1-8.
Iwata et al., "Global brain delivery of neprilysin gene by intravascular administration of AAV vector in mice," Scientific Reports, Mar. 18, 2013, 3(1):1-8.

(56) References Cited

OTHER PUBLICATIONS

Jackson et al., "AAV9 supports wide-scale transduction of the CNS and TDP-43 disease modeling in adult rats," Molecular Therapy-Methods & Clinical Development, Jan. 1, 2015, 2:15036, 8 pages.
JP Japanese Office Action in Japanese Appln. No. 2020-565341, Apr. 4, 2023, 11 pages (with English translation).
Kang et al., "An evolutionarily conserved role of presenilin in neuronal protection in the aging *Drosophila* brain," Genetics, Jul. 1, 2017, 206(3):1479-93.
Karabinos et al., "Essential roles for four cytoplasmic intermediate filament proteins in Caenorhabditis elegans development," Proceedings of the National Academy of Sciences of the United States of America, Jul. 2001, 98(14):7863-7868.
Kelleher et al., "Presenilin-1 mutations and Alzheimer's disease," Proceedings of the National Academy of Sciences, Jan. 24, 2017, 114(4):629-31.
Kim et al., "Presenilins are required for maintenance of neural stem cells in the developing brain," Molecular Neurodegeneration, Dec. 2008, 3(1):1-3.
Kim et al., "Viral transduction of the neonatal brain delivers controllable genetic mosaicism for visualising and manipulating neuronal circuits in vivo," European Journal of Neuroscience, Apr. 2013, 37(8):1203-20.
Klein et al., "Dose and promoter effects of adeno-associated viral vector for green fluorescent protein expression in the rat brain," Experimental Neurology, Jul. 1, 2002, 176(1):66-74.
Kosik et al., "Homozygosity of the autosomal dominant Alzheimer disease presenilin 1 E280A mutation," Neurology, Jan. 13, 2015, 84(2):206-8.
Kumar-Singh et al., "Mean age-of-onset of familial alzheimer disease caused by presenilin mutations correlates with both increased Aβ42 and decreased Aβ40," Human Mutation, Jul. 2006, 27(7):686-95.
Lalli et al., "Origin of the PSEN1 E280A mutation causing early-onset Alzheimer's disease," Alzheimer's & Dementia, Oct. 2014, 10:S277-83.
Langer et al., "New methods of drug delivery," Science, Sep. 28, 1990, 249(4976):1527-33.
Lanoiselée et al., "APP, PSEN1, and PSEN2 mutations in early onset Alzheimer disease: A genetic screening study of familial and sporadic cases," PLOS Medicine, Mar. 2017, 14(3):e102270, 16 pages.
Lebkowski et al., "Adeno-associated virus: a vector system for efficient introduction and integration of DNA into a variety of mammalian cell types,". Molecular and Cellular Biology, Oct. 1, 1988, 8(10):3988-96.
Lee et al., "Presenilins regulate synaptic plasticity and mitochondrial calcium homeostasis in the hippocampal mossy fiber pathway," Molecular Neurodegeneration, Dec. 2017, 12(1):1-5.
Lee et al., "Synaptic function of nicastrin in hippocampal neurons," Proceedings of the National Academy of Sciences, Jun. 17, 2014, 111(24):8973-8.
Lei et al., "Structure-function analysis of human glucose-6-phosphatase, the enzyme deficient in glycogen storage disease type 1a," Journal of Biological Chemistry, May 19, 1995, 270(20):11882-6.
Lemere et al., "The E280A presenilin 1 Alzheimer mutation produces increased A⊕42 deposition and severe cerebellar pathology," Nature Medicine, Oct. 1996, 2(10):1146-50.
Levitan et al., "Assessment of normal and mutant human presenilin function in Caenorhabditis elegans," Proceedings of the National Academy of Sciences, Dec. 10, 1996, 93(25):14940-4.
Levy-Lahad et al., "Candidate gene for the chromosome 1 familial Alzheimer's disease locus," Science, Aug. 18, 1995, 269(5226):973-7.
Ling et al., "Enhanced transgene expression from recombinant single-stranded D-sequence-substituted adeno-associated virus vectors in human cell lines in vitro and in murine hepatocytes in vivo," Journal of Virology, Jan. 2015, 89(2):952-61.
Liu et al., "Systematic comparison of 2A peptides for cloning multi-genes in a polycistronic vector," Scientific Reports, May 19, 2017, 7(1):1-9.
Löbenberg et al., "Improved body distribution of 14C-labelled AZT bound to nanoparticles in rats determined by radioluminography," Journal of Drug Targeting, Jan. 1, 1998, 5(3):171-9.
Lopera et al., "Clinical features of early-onset Alzheimer disease in a large kindred with an E280A presenilin-1 mutation," Jama, Mar. 12, 1997, 277(10):793-9.
Marambaud et al., "A presenilin-1/γ-secretase cleavage releases the E-cadherin intracellular domain and regulates disassembly of adherens junctions," The EMBO Journal, Apr. 15, 2002, 21(8):1948-56.
Matsushita et al., "Adeno-associated virus vectors can be efficiently produced without helper virus," Gene Therapy, Jul. 1998, 5:938-945.
Mauro et al., "A critical analysis of codon optimization in human therapeutics," Trends in Molecular Medicine, Nov. 1, 2014, 20(11):604-13.
Mayford et al., "Control of memory formation through regulated expression of a CaMKII transgene," Science, Dec. 6, 1996, 274(5293):1678-83.
McLaughlin et al., "Adeno-associated virus general transduction vectors: analysis of proviral structures," Journal of Virology, Jun. 1, 1988, 62(6):1963-73.
McLean et al., "Widespread neuron-specific transgene expression in brain and spinal cord following synapsin promoter-driven AAV9 neonatal intracerebroventricular injection," Neuroscience Letters, Jul. 25, 2014, 576:73-8.
Mingozzi et al., "Therapeutic in vivo gene transfer for genetic disease using AAV: progress and challenges," Nature Reviews Genetics, May 2011, 12(5):341-55.
Moehlmann et al., "Presenilin-1 mutations of leucine 166 equally affect the generation of the Notch and APP intracellular domains independent of their effect on AB42 production," Proceedings of the National Academy of Sciences, Jun. 11, 2002, 99(12):8025-30.
Mucke et al., "High-level neuronal expression of Aβ1-42 in wild-type human amyloid protein precursor transgenic mice: synaptotoxicity without plaque formation," Journal of Neuroscience, Jun. 1, 2000, 20(11):4050-8.
Muzyczka, "Use of adeno-associated virus as a general transduction vector for mammalian cells," Viral Expression Vectors, 1992, vol. 1992:97-129.
Palmisano et al., "Characterization of membrane-shed microvesicles from cytokine-stimulated β-cells using proteomics strategies," Molecular & Cellular Proteomics, Aug. 1, 2012, 11(8):230-43.
Parra et al., "Memory binding and white matter integrity in familial Alzheimer's disease," Brain, May 1, 2015, 138(5):1355-69.
PCT International Preliminary Report on Patentability in International Appln. No. PCT/US2019/033616, dated Nov. 24, 2020, 12 pages.
PCT International Preliminary Report on Patentability in International Appln. No. PCT/US2020/034040, dated Nov. 16, 2021, 7 pages.
PCT International Preliminary Report on Patentability in International Appln. No. PCT/US2020/062394, mailed on May 17, 2022, 7 pages.
PCT International Preliminary Report on Patentability in International Appln. No. PCT/US2021/015911, mailed on Jul. 28, 2022, 9 pages.
PCT International Search Report and Written Opinion in International Appln. No. PCT/US2019/033616, dated Oct. 28, 2019, 18 pages.
PCT International Search Report and Written Opinion in International Appln. No. PCT/US2020/034040, dated Sep. 17, 2020, 10 pages.
PCT International Search Report and Written Opinion in International Appln. No. PCT/US2020/062394, mailed on Apr. 28, 2021, 15 pages.
PCT International Search Report and Written Opinion in International Appln. No. PCT/US2021/015911, mailed on Jun. 30, 2021, 17 pages.

(56) References Cited

OTHER PUBLICATIONS

Perez-Pinera et al., "RNA-guided gene activation by CRISPR-Cas9-based transcription factors," Oct. 2013, Nature Methods, 2013, 10(10):973-976. doi: 10.1038/nmeth.2600.
Podlisny et al., "Presenilin proteins undergo heterogeneous endoproteolysis between Thr291and Ala299and occur as stable N-and C-terminal fragments in normal and Alzheimer brain tissue," Neurobiology of Disease, Jan. 1, 1997, 3(4):325-37.
Qi et al., "Distinct mechanisms by mutant presenilin 1 and 2 leading to increased intracellular levels of amyloid β-protein 42 in Chinese hamster ovary cells," Biochemistry, Feb. 4, 2003, 42(4):1042-52.
Qian et al., "Mutant human presenilin 1 protects presenilin 1 null mouse against embryonic lethality and elevates Aβ1-42/43 expression," Neuron, Mar. 1, 1998, 20(3):611-7.
Reiman et al., "Brain imaging and fluid biomarker analysis in young adults at genetic risk for autosomal dominant Alzheimer's disease in the presenilin 1 E280A kindred: a case-control study," The Lancet Neurology, Dec. 1, 2012, 11(12):1048-56.
Rios-Romenets et al., "The value of pre-screening in the Alzheimer's Prevention Initiative (API) Autosomal Dominant Alzheimer's Disease trial," The Journal of Prevention of Alzheimer's Disease, Jan. 2018, 5(1):49-54.
Robinson et al., "Lipid nanoparticle-delivered chemically modified mRNA restores chloride secretion in cystic fibrosis," Molecular Therapy, Aug. 1, 2018, 26(8):2034-46.
Rogaev et al., "Familial Alzheimer's disease in kindreds with missense mutations in a gene on chromosome 1 related to the Alzheimer's disease type 3 gene," Nature, Aug. 1995, 376(6543):775-8.
Ryan et al., "Correlating familial Alzheimer's disease gene mutations with clinical phenotype," Biomarkers in Medicine, Feb. 2010, 4(1):99-112.
Ryman et al., "Symptom onset in autosomal dominant Alzheimer disease: a systematic review and meta-analysis," Neurology, Jul. 15, 2014, 83(3):253-60.
Saito et al., "Potent amyloidogenicity and pathogenicity of Aβ43," Nature Neuroscience, Aug. 2011, 14(8):1023-32.
Sakuma et al., "Mucoadhesion of polystyrene nanoparticles having surface hydrophilic polymeric chains in the gastrointestinal tract," International Journal of Pharmaceutics, Jan. 25, 1999, 177(2):161-72.
Samulski et al., "Helper-free stocks of recombinant adeno-associated viruses: normal integration does not require viral gene expression," Journal of Virology, Sep. 1, 1989, 63(9):3822-8.
Saura et al., "Conditional inactivation of presenilin 1 prevents amyloid accumulation and temporarily rescues contextual and spatial working memory impairments in amyloid precursor protein transgenic mice," Journal of Neuroscience, Jul. 20, 2005, 25(29):6755-64.
Saura et al., "Loss of presenilin function causes impairments of memory and synaptic plasticity followed by age-dependent neurodegeneration," Neuron, Apr. 8, 2004, 42(1):23-36.
Schroeter et al., "A presenilin dimer at the core of the γ-secretase enzyme: insights from parallel analysis of Notch 1 and APP proteolysis," Proceedings of the National Academy of Sciences, Oct. 28, 2003, 100(22):13075-80.
Sen et al., "Improved adeno-associated virus (AAV) serotype 1 and 5 vectors for gene therapy," Scientific Reports, May 2013, 3:1832, DOI: 10.1038/srep01832, 1-6.
Sepulveda-Falla et al., "Deposition of hyperphosphorylated tau in cerebellum of PS1 E280A Alzheimer's disease," Brain Pathology, Jul. 2011, 21(4):452-63.
Sepulveda-Falla et al., "Familial Alzheimer's disease-associated presenilin-1 alters cerebellar activity and calcium homeostasis," The Journal of Clinical Investigation, Apr. 1, 2014, 124(4):1552-67.
Shen et al., "Skeletal and CNS defects in Presenilin-1-deficient mice," Cell, May 16, 1997, 89(4):629-39.
Shen et al., "The presenilin hypothesis of Alzheimer's disease: evidence for a loss-of-function pathogenic mechanism," Proceedings of the National Academy of Sciences, Jan. 9, 2007, 104(2):403-9.
Sherrington et al., "Alzheimer's disease associated with mutations in presenilin 2 is rare and variably penetrant," Jul. 1996, 5(7):985-988.
Sherrington et al., "Cloning of a gene bearing missense mutations in early-onset familial Alzheimer's disease, " Nature, Jun. 1995, 375(6534):754-60.
Siman et al., "Presenilin-1 P264L knock-in mutation: differential effects on Aβ production, amyloid deposition, and neuronal vulnerability," Journal of Neuroscience, Dec. 1, 2000, 20(23):8717-26.
Song et al., "Proteolytic release and nuclear translocation of Notch-1 are induced by presenilin-1 and impaired by pathogenic presenilin-1 mutations," Proceedings of the National Academy of Sciences, Jun. 8, 1999, 96(12):6959-63.
Steiner et al., "A pathogenic presenilin-1 deletion causes abberrant Aβ42 production in the absence of congophilic amyloid plaques," Journal of Biological Chemistry, Mar. 9, 2001, 276(10):7233-9.
Sun et al., "Analysis of 138 pathogenic mutations in presenilin-1 on the in vitro production of Aβ42 and Aβ40 peptides by γ-secretase," Proceedings of the National Academy of Sciences, Jan. 24, 2017, 114(4):E476-85.
Sun et al., "Hippocampal spatial memory impairments caused by the familial Alzheimer's disease-linked presenilin 1 M146V mutation," Neurodegenerative Diseases, Aug. 2005, 2(1):6-15.
Szymczak et al., "Correction of multi-gene deficiency in vivo using a single'self-cleaving'2A 1peptide-based retroviral vector," Nature Biotechnology, May 2004, 22(5):589-94.
Tabuchi et al., "Conditional forebrain inactivation of nicastrin causes progressive memory impairment and age-related neurodegeneration," Journal of Neuroscience, Jun. 3, 2009, 29(22):7290-301.
Théry et al., "Isolation and characterization of exosomes from cell culture supernatants and biological fluids," Current Protocols in Cell Biology, Mar. 2006, 30(1):3-22.
Trichas et al., "Use of the viral 2A peptide for bicistronic expression in transgenic mice," BMC Biology, Dec. 2008, 6(1):1-3.
Tysoe et al., "A presenilin-1 truncating mutation is present in two cases with autopsy-confirmed early-onset Alzheimer disease," The American Journal of Human Genetics, Jan. 1, 1998, 62(1):70-6.
Virovic et al., "Novel delivery methods for treatment of viral hepatitis: an update," Expert Opinion on Drug Delivery, Jul. 1, 2005, 2(4):707-17.
Waldenström et al., "Cardiomyocyte microvesicles contain DNA/RNA and convey biological messages to target cells," PloS one, Apr. 10, 2012, 7(4):e34653, 7 pages.
Walker et al., "Presenilin 2 familial Alzheimer's disease mutations result in partial loss of function and dramatic changes in Aβ 42/40 ratios," Journal of Neurochemistry, Jan. 2005, 92(2):294-301.
Wang et al., "Rescue and replication of adeno-associated virus type 2 as well as vector DNA sequences from recombinant plasmids containing deletions in the viral inverted terminal repeats: Selective encapsidation of viral genomes in progeny virions," Journal of Virology, Mar. 1996, 70(3):1668-1677.
Wang et al., "Rescue and replication signals of the adeno-associated virus 2 genome," Journal of Molecular Biology, Jul. 1995, 250(5):573-580.
Wang et al., "Wild-type presenilin 1 protects against Alzheimer disease mutation-induced amyloid pathology," Journal of Biological Chemistry, Jun. 2006, 281(22):15330-6.
Watanabe et al., "Dominant negative mechanism of Presenilin-1 mutations in FAD." Proceedings of the National Academy of Sciences, Nov. 28, 2017, 114(48):12635-7.
Watanabe et al., "Familial frontotemporal dementia-associated presenilin-1 c. 548G> T mutation causes decreased mRNA expression and reduced presenilin function in knock-in mice," Journal of Neuroscience, Apr. 11, 2012, 32(15):5085-96.
Watanabe et al., "Indirect regulation of presenilins in CREB-mediated transcription," Journal of Biological Chemistry, May 15, 2009, 284(20):13705-13.

(56) References Cited

OTHER PUBLICATIONS

Watanabe et al., "Partial loss of presenilin impairs age-dependent neuronal survival in the cerebral cortex," Journal of Neuroscience, Nov. 26, 2014, 34(48):15912-22.
Wiley et al., "Familial Alzheimer's disease mutations inhibit γ-secretase-mediated liberation of β-amyloid precursor protein carboxy-terminal fragment," Journal of Neurochemistry, Sep. 2005, 94(5):1189-201.
Wines-Samuelson et al., "Characterization of age-dependent and progressive cortical neuronal degeneration in presenilin conditional mutant mice," PLoS One, Apr. 15, 2010, 5(4):e10195.
Wines-Samuelson et al., "Presenilins in the developing, adult, and aging cerebral cortex," The Neuroscientist, Oct. 2005, 11(5):441-51.
Wines-Samuelson et al., "Role of presenilin-1 in cortical lamination and survival of Cajal-Retzius neurons," Developmental Biology, Jan. 15, 2005, 277(2):332-46.
Wu et al., "Presenilins regulate calcium homeostasis and presynaptic function via ryanodine receptors in hippocampal neurons," Proceedings of the National Academy of Sciences, Sep. 10, 2013, 110(37):15091-6.
Xia et al., "Loss of Aβ43 production caused by presenilin-1 mutations in the knockin mouse brain," Neuron, Apr. 20, 2016, 90(2):417-22.
Xia et al., "Presenilin-1 knockin mice reveal loss-of-function mechanism for familial Alzheimer's disease, " Neuron, Mar. 4, 2015, 85(5):967-81.
Xia et al., "Presenilin-1 knockin mice reveal loss-of-function mechanism for familial Alzheimer's disease," Neuron, Mar. 2015, 85(5):967-981.
Xia, "Relationship between presenilinase and gamma-secretase," Drug News & Perspectives, Mar. 1, 2003, 16(2):69-74.
Xiao et al., "Production of high-titer recombinant adeno-associated virus vectors in the absence of helper adenovirus," Journal of Virology, Mar. 1998, 72(3):2224-2232.
Yu et al., "APP processing and synaptic plasticity in presenilin-1 conditional knockout mice," Neuron, Sep. 13, 2001, 31(5):713-26.
Zhang et al., "Inactivation of presenilins causes pre-synaptic impairment prior to post-synaptic dysfunction," Journal of Neurochemistry, Dec. 2010, 115(5):1215-21.
Zhang et al., "Mutation of the conserved N-terminal cysteine (Cys92) of human presenilin 1 causes increased Aβ42 secretion in mammalian cells but impaired Notch/lin-I2 signalling in C. elegans," Neuroreport, Sep. 28, 2000, 11(14):3227-30.
Zhang et al., "Presenilins are essential for regulating neurotransmitter release," Nature, Jul. 2009, 460(7255):632-6.
Zhao et al., "Mechanisms of recognition of amyloid-β (Aβ) monomer, oligomer, and fibril by homologous antibodies," Journal of Biological Chemistry, Nov. 3, 2017, 292(44):18325-43.
Zhou et al., "Dominant negative effect of the loss-of-function γ-secretase mutants on the wild-type enzyme through heterooligomerization," Proceedings of the National Academy of Sciences, Nov. 28, 2017, 114(48):12731-6.
Zimmermann et al., "Electrolyte-and pH-stabilities of aqueous solid lipid nanoparticle (SLN™) dispersions in artificial gastrointestinal media," European Journal of Pharmaceutics and Biopharmaceutics, Sep. 1, 2001, 52(2):203-10.
CN Office Action in Chinese Appln. No. 201980049127.3, mailed on Apr. 25, 2024, 9 pages (with English translation).
D'Argenio et al., "New insights into the molecular bases of familial Alzheimer's disease," Journal of Personalized Medicine, Apr. 2020, 10(2):26, 14 pages.
Deaton et al., "Presenilin 1 regulates membrane homeostatic pathways that are dysregulated in Alzheimer's disease," Journal of Alzheimer's Disease, Jan. 2020, 77(3):961, 25 pages.
EP Extended European Search Report in European Appln. No. 20893982.7, mailed on May 2, 2024, 14 pages.
Götz et al., "Rodent models for Alzheimer disease," Nature Reviews Neuroscience, Oct. 2018, 19(10):583-98.
Hudry et al., "Therapeutic AAV gene transfer to the nervous system: a clinical reality," Neuron, Mar. 2019, 101(5):839, 26 pages.
John et al., "Synaptic basis of Alzheimer's disease: Focus on synaptic amyloid beta, P-tau and mitochondria," Ageing Research Reviews, Jan. 2021, 65:101208, 35 pages.
Yang et al., "Presenilin-1 (PSEN1) mutations: clinical phenotypes beyond Alzheimer's disease," International Journal of Molecular Sciences, May 2023, 24(9):8417, 21 pages.
AU Office Action in Australian Appln. No. 2020285638, mailed on May 1, 2025, 4 pages.
Diss et al., "The genetic landscape of a physical interaction," Elife, Apr. 2018, 7:e32472, 31 pages.
Dryja et al., "Mutations within the rhodopsin gene in patients with autosomal dominant retinitis pigmentosa," New England Journal of Medicine, Nov. 1990, 323(19):1302-7.
EP Office Action in European Appln. No. 19808081.4, mailed on Apr. 23, 2025, 6 pages.
Kou et al., "Catalytic immunoglobulin gene delivery in a mouse model of Alzheimer's disease: prophylactic and therapeutic applications," Molecular Neurobiology, Feb. 2015, 51:43, 29 pages.
Castle et al., "Controlling AAV tropism in the nervous system with natural and engineered capsids," Gene Therapy for Neurological Disorders: Methods and Protocols, Jan. 2016, 133-49.
CN Office Action in Chinese Appln. No. 201980049127.3, mailed on Jul. 16, 2024, 14 pages (with English translation).
Haery et al., Adeno-associated virus technologies and methods for targeted neuronal manipulation. Frontiers in Neuroanatomy, Nov. 2019, 13:493120, 16 pages.
IL Office Action in Israeli Appln. No. 278813, mailed on Jul. 21, 2024, 4 pages (English translation).
AU Office Action in Australian Appln. No. 2019272848, mailed on Oct. 29, 2024, 5 pages.
CN Office Action in Chinese Appln. No. 201980049127.3, mailed on Dec. 18, 2024, 16 pages (with English translation).
CN Office Action in Chinese Appln. No. 202080052274.9, mailed on Sep. 26, 2024, 7 pages (with English translation).
Wang et al., "An mRNA stability complex functions with poly (A)-binding protein to stabilize mRNA in vitro," Molecular and Cellular Biology, Jul. 1999, 19(7):4552-60.
Bäck et al., "Neuronal activation stimulates cytomegalovirus promoter-driven transgene expression," Molecular Therapy Methods & Clinical Development, Sep. 2019, 14:180, 13 pages.
CA Office Action in Canadian Appln. No. 3,100,946, mailed on Feb. 5, 2025, 5 pages.
Emery, "The use of chromatin insulators to improve the expression and safety of integrating gene transfer vectors," Human Gene Therapy, Jun. 2011, 22(6):761-74.
Honda et al., "The modeling of Alzheimer's disease by the overexpression of mutant Presenilin 1 in human embryonic stem cells," Biochemical and Biophysical Research Communications, Jan. 2016, 469(3):587-92.
JP Office Action in Japanese Appln. No. 2021-569550, mailed on Jan. 14, 2025, 3 pages (with English translation).
Kim et al., "Human P-Globin Second Intron Highly Enhances Expression of Foreign Genes from Murine Cytomegalovirus Immediate-Early Promoter," Journal of Microbiology and Biotechnology, Jan. 2005, 15(3):544-50.
Leppek et al., "Functional 5' UTR mRNA structures in eukaryotic translation regulation and how to find them," Nature Reviews Molecular Cell Biology, Mar. 2018, 19(3):158, 36 pages.
Naso et al., "Adeno-associated virus (AAV) as a vector for gene therapy," BioDrugs, Aug. 2017, 31(4):317-34.
Ólafsdóttir et al., "In vitro analysis of expression vectors for DNA vaccination of horses: the effect of a Kozak sequence," Acta Veterinaria Scandinavica, Dec. 2008, 50:1-7.
Pesole et al., "UTRdb and UTRsite: specialized databases of sequences and functional elements of 5' and 3' untranslated regions of eukaryotic mRNAs, Update 2002," Nucleic Acids Research, Jan. 2002, 30(1):335-40.
Sun et al., "Analysis of 138 pathogenic mutations in presenilin-1 on the in vitro production of Aβ42 and Aβ40 peptides by γ-secretase," Proceedings of the National Academy of Sciences, Jan. 2017, 114(4):E476-85.

(56) References Cited

OTHER PUBLICATIONS

Tenchov et al., "Lipid nanoparticles—from liposomes to mRNA vaccine delivery, a landscape of research diversity and advancement," ACS Nano, Jun. 2021, 15(11):16982-7015.
Yang et al., "Influence of solubilization and AD-mutations on stability and structure of human presenilins," Scientific Reports, Dec. 2017, 7(1):17970, 12 pages.
SG Office Action in Singaporean Appln. No. 11202205560S, mailed on Jun. 5, 2025, 12 pages.

* cited by examiner

GENE THERAPY FOR NEURODEGENERATIVE DISORDERS USING POLYNUCLEOTIDE SILENCING AND REPLACEMENT

CROSS-REFERENCE TO RELATED APPLICATIONS

This application is a 35 USC § 371 National Stage application of International Application No. PCT/US2021/015911 filed Jan. 29, 2021; which claims the benefit under 35 USC § 119 (e) to U.S. application Ser. No. 62/968,707 filed Jan. 31, 2020. The disclosure of each of the prior applications is considered part of and is incorporated by reference in the disclosure of this application.

INCORPORATION BY REFERENCE OF SEQUENCE LISTING

The material in the accompanying sequence listing is hereby incorporated by reference into this application. The accompanying sequence listing text file, named PAROS1120-1 ST25.txt, was created on Jul. 20, 2022 and is 191 kB in size. The file can be accessed using Microsoft Word on a computer that uses Windows OS.

TECHNICAL FIELD

The present disclosure relates generally to gene therapy for neurodegenerative disorders, and more specifically to expression cassettes and polynucleotides for delivery of therapeutic agents.

BACKGROUND

Alzheimer's disease (AD), also referred to as Alzheimer's, is a chronic neurodegenerative disease that is the cause of a majority of neurodegenerative dementia. Symptoms include difficulty with memory, problems with language, disorientation, mood swings, loss of motivation, and other behavioral problems such as withdrawal from family and society. Bodily functions are gradually lost, ultimately leading to death. Although the disease can last for more than ten years, the average life expectancy is three to nine years following diagnosis. Familial AD (FAD) characterizes families that have more than one member with AD and usually implies multiple affected persons in more than one generation. Early-onset FAD (EOFAD) refers to families in which onset is consistently before age 60 to 65 years and often before age 55 years.

AD appears pathologically as extracellular amyloid plaques and intracellular neurofibrillary tangles in the brain. Although the cause for most cases of AD is not known, genetic factors contribute to development of disease. Early onset familial AD is characterized by autosomal dominant inheritance and by disease onset before age 65.

There is a need for compositions and methods for the treatment of neurodegenerative diseases such as AD, including effective gene and combination therapies.

SUMMARY

The present disclosure relates to polynucleotides, expression cassettes and vectors comprising such polynucleotides and/or expression cassettes for the treatment of neurodegenerative disorders. More specifically, the polynucleotides, expression cassettes and vectors utilized in the present disclosure comprise a) a first polynucleotide sequence that encodes one or more short hairpin RNAs (shRNAs) or micro interfering RNAs (miRNAs) having sufficient sequence complementarity with mRNA expressed from an endogenous presenilin 1 (PSEN1) or presenilin 2 (PSEN2) gene, to hybridize to that mRNA and inhibit expression of the encoded presenilin 1 (PSEN1) or presenilin 2 (PSEN2) protein, or the combination thereof, and b) a second polynucleotide sequence encoding a wild-type PSEN1 or PSEN2 protein, or a combination thereof. The wild-type PSEN1 or PSEN2 encoded by the second polynucleotide is expressed utilizing control sequences that are present in the expression cassette and/or vector harboring them, as opposed to endogenous control sequences. The mRNA expressed from the second polynucleotide sequence must be resistant to suppression by the short hairpin RNAs (shRNAs) or micro interfering RNAs (miRNAs) encoded by the first polynucleotide sequence. Therefore, the simultaneous expression of the wild-type PSEN1 or PSEN2 protein results in the replacement of the endogenously expressed PSEN1 or PSEN2 protein.

Presenilins can harbor mutations which cause autosomal-dominant gain of toxic function. Such mutations are distributed throughout the coding sequence for both PSEN1 and its homolog PSEN2. The ability to simultaneously suppress autosomal-dominant mutated presenilins and express the wild-type gene eliminates the need to specifically target the mutant allele. Therefore, the polynucleotides, expression cassettes, and vectors of the disclosure, and the compositions and methods of the disclosure employing them are useful for halting and/or ameliorating damage associated with mutant PSEN1 or PSEN2 or the combination thereof.

The ability of the replacement wild-type PSEN1 or PSEN2 to avoid being targeted and suppressed by the one or more shRNAs or miRNAs will depend on which locations PSEN1 or PSEN2 mRNA sequences are targeted by the shRNAs or miRNAs and what codons are used in the replacement wild-type PSEN1 or PSEN2 coding sequence. If all of the designed shRNAs or miRNAs target non-coding regions of endogenous PSEN1 or PSEN2 mRNA, then the replacement PSEN1 or PSEN2 polynucleotide sequence can be any sequence that encodes wild-type PSEN1 or PSEN2 including, but not limited to, the endogenous human PSEN1 or PSEN2 coding sequence, or a sequence wherein some or all of the codons are altered based on the redundancy of the genetic code in order to increase expression, e.g., a fully or partially codon-optimized, wild-type PSEN1 or PSEN2 polynucleotide sequence. If some or all of the shRNAs or miRNAs target coding regions of endogenous PSEN1 or PSEN2 mRNA, then the corresponding coding regions in the replacement PSEN1 or PSEN2 polynucleotide sequence must be modified so the mRNA expressed is not targeted by any of the shRNAs or miRNAs. This is achieved by modifying endogenous codons using the redundancy of the genetic code to reduce homology/complementarity of the mRNA expressed with the shRNA or miRNA sequences.

In some embodiments, the polynucleotides, expression cassettes, vectors, compositions and methods disclosed herein are useful for suppressing an endogenous PSEN1 protein while at the same time increasing levels of a wild-type PSEN1 protein. Suppression of endogenous PSEN1 protein typically is achieved through the use of one or more antisense oligonucleotides that binds to a mRNA expressed from the endogenous PSEN1 gene thereby decreasing the level of such mRNA and/or inhibiting its translation into protein. In some aspects of these embodiments, the antisense oligonucleotide is an antisense RNA encoded by a DNA sequence that is administered to a subject as part of an expression cassette or vector. Such antisense RNA include shRNAs, miRNAs, or single-stranded antisense RNAs. In alternate aspects of these embodiments, the antisense oligonucleotide is delivered directly to the subject. Such antisense oligonucleotides include siRNAs, antisense DNA oligonucleotides, external guide sequence oligonucleotides and alternate splicer oligonucleotides. In some aspects of these embodiments, a non-toxic dual function vector is provided that is capable of expressing both an antisense RNA and a wild-type PSEN1 whose expression is not suppressed that antisense RNA. In some embodiments, the antisense oligonucleotide is administered concurrently with a vector encoding wild-type PSEN1, the expression of which is not suppressed by the antisense oligonucleotide provided. In still other aspects of these embodiments, a first vector comprising a DNA sequence encoding an antisense RNA is administered concurrently with a second vector comprising a DNA sequence encoding wild-type PSEN1, the expression of which is not suppressed by the antisense RNA.

In some embodiments, the polynucleotides, expression cassettes, vectors, compositions and methods disclosed herein are useful for suppressing an endogenous PSEN2 protein while at the same time increasing levels of a wild-type PSEN2. Suppression of endogenous PSEN2 protein typically is achieved through the use of one or more antisense oligonucleotides that binds to a mRNA expressed from the endogenous PSEN2 gene thereby decreasing the level of such mRNA and/or inhibiting its translation into protein. In some aspects of these embodiments, the antisense oligonucleotide is an antisense RNA encoded by a DNA sequence that is administered to a subject as part of an expression cassette or vector. Such antisense RNA include shRNAs, miRNAs, or single-stranded antisense RNAs. In alternate aspects of these embodiments, the antisense oligonucleotide is delivered directly to the subject. Such antisense oligonucleotides include siRNAs, antisense DNA oligonucleotides, external guide sequence oligonucleotides and alternate splicer oligonucleotides. In some aspects of these embodiments, a non-toxic dual function vector is provided that is capable of expressing both an antisense RNA and a wild-type PSEN2 whose expression is not suppressed that antisense RNA. In some embodiments, the antisense oligonucleotide is administered concurrently with a vector encoding wild-type PSEN2, the expression of which is not suppressed by the antisense oligonucleotide provided. In still other aspects of these embodiments, a first vector comprising a DNA sequence encoding an antisense RNA is administered concurrently with a second vector comprising a DNA sequence encoding wild-type PSEN2, the expression of which is not suppressed by the antisense RNA.

In some embodiments, an expression cassette comprises: (I) a first polynucleotide encoding one or more shRNAs or miRNAs, each of which independently targets a coding region or a non-coding region of an endogenous mRNA expressed from each of a human wild-type and a mutant presenilin 1 (PSEN1) or each of a human wild-type and a mutant presenilin 2 (PSEN2), wherein each of the polynucleotide sequences encoding the one or more shRNA or miRNA is operably linked to one or more first promoters; and (II) a second polynucleotide encoding a wild-type PSEN1 or PSEN2 amino acid sequence, wherein the mRNA expressed from the second polynucleotide is not targeted by any of the shRNAs or miRNAs encoded by the first polynucleotide; and wherein the second polynucleotide is operably linked to a second promoter. The first polynucleotide may be positioned anywhere in the expression cassette relative to the PSEN1 or PSEN2 coding sequence, as long as its location does not prevent expression of the PSEN1 or PSEN2 coding sequence (i.e., 5' to the coding sequence, 3' to the coding sequence, or within an intron that could exist in the second promoter.

In some embodiments, an expression cassette comprises: (I) a first polynucleotide encoding one or more shRNAs or miRNAs, each of which independently targets a coding region or a non-coding region of an endogenous mRNA derived from each of a human wild-type and a mutant presenilin 1 (PSEN1), wherein each of the polynucleotide sequences encoding the one or more shRNAs or miRNAs is operably linked to one or more first promoters; and (II) a second polynucleotide encoding a wild-type PSEN1 amino acid sequence, wherein the mRNA expressed from the second polynucleotide is not targeted by any of the shRNAs encoded by the first polynucleotide; and wherein the second polynucleotide is operably linked to a second promoter.

In some embodiments, an expression cassette comprises: (I) a first polynucleotide encoding one or more shRNAs or miRNAs, each of which independently targets a coding region or a non-coding region of an endogenous mRNA derived from each of a human wild-type and a mutant presenilin 2 (PSEN2), wherein each of the polynucleotide sequences encoding the one or more shRNAs or miRNAs is operably linked to one or more first promoters; and (II) a second polynucleotide encoding a wild-type PSEN2 amino acid sequence, wherein the mRNA expressed from the second polynucleotide is not targeted by any of the shRNAs encoded by the first polynucleotide; and wherein the second polynucleotide is operably linked to a second promoter.

In certain embodiments, an expression cassette comprises: (I) a first polynucleotide encoding one or more shRNAs or miRNAs, each of which independently comprises one of: a) SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:33, SEQ ID NO: 35, SEQ ID NO:42, SEQ ID NO:43, SEQ ID NO:44, SEQ ID NO:45, SEQ ID NO: 46, SEQ ID NO:47, 448-529 of SEQ ID NO:68, nucleotides 448-529 of SEQ ID NO:69, nucleotides 448-529 of SEQ ID NO:70, or nucleotides 448-529 of SEQ ID NO:71; b) a modified version of any of the foregoing SEQ ID NOs, wherein the modification is 1, 2, 3, or 4 nucleotide changes; or c) a 19-21 base nucleotide sequence comprising 7 or more consecutive bases taken from the 5' or 3' end of any of the foregoing SEQ ID NOs or the modified version thereof, wherein the 19-21 base nucleotide sequence comprises no more than 4 mismatches with a corresponding portion of an endogenous PSEN1 mRNA, wherein each of the one or more shRNAs or miRNAs is operably linked to one or more first promoters; and (II) a second polynucleotide encoding a wild-type presenilin 1 (PSEN1) protein, wherein the second polynucleotide is not targeted by any of the shRNAs or miRNAs encoded by the first polynucleotide, and wherein the second polynucleotide is operably linked to a second promoter.

SEQ ID NO:1, SEQ ID NO:2, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:33, SEQ ID NO:35, nucleotides 448-529 of SEQ ID NO:68, nucleotides 448-529 of SEQ ID NO:69, nucleotides 448-529 of SEQ ID NO:70, and nucleotides 448-529 of SEQ ID NO:71, each encode RNA that target sequences in the non-coding portion of PSEN1 mRNA. SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO: 42, SEQ ID NO:43, SEQ ID NO:44, SEQ ID NO:45, SEQ ID NO: 46, and SEQ ID NO:47 each encode RNA that target sequences in the coding portion of PSEN1 mRNA. SEQ ID NO:33, SEQ ID NO:35, nucleotides 448-529 of SEQ ID NO:68, nucleotides 448-529 of SEQ ID NO:69, nucleotides 448-529 of SEQ ID NO:70, and nucleotides 448-529 of SEQ ID NO:71 each encode a miRNA. SEQ ID NO:44, SEQ ID NO:45, SEQ ID NO: 46, and SEQ ID NO:47 each encode a shRNA.

Each of the 1, 2, 3, or 4 nucleotide changes in the modified version of any of the above SEQ ID NOs is independently a nucleotide substitution, deletion, or addition and results in a mismatch with endogenous wild-type PSEN1 mRNA. The additional nucleotides required for a 19-21 base nucleotide sequence comprising 7 or more consecutive bases taken from the 5' or 3' end of any of the foregoing SEQ ID NOs or the modified version thereof are those that are capable of hybridizing to the region of PSEN1 mRNA immediately 5' or 3', respectively, to the regions of PSEN1 mRNA to which the 7 or more consecutive bases bind, while still allowing for up to 4 mismatches in the entire 19-21 base nucleotide sequence. For example, SEQ ID NO:1 hybridizes to nucleotides 94-115 of PSEN1 mRNA (using numbering in NM_000021.4) (See Table 2, herein). Thus, an example of a 19-21 base nucleotide sequence taken from the 5' end of SEQ ID NO:1 would contain nucleotides 2-8 with a perfect complementarity to PSEN1 mRNA and other bases would contain 1, 2, 3, or 4 nucleotide changes.

In some embodiments, and expression cassette comprises: (I) a first polynucleotide encoding one or more shRNAs or miRNAs, each of which independently comprises one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:33, SEQ ID NO: 35, SEQ ID NO:42, SEQ ID NO:43, SEQ ID NO:44, SEQ ID NO:45, SEQ ID NO: 46, SEQ ID NO:47, nucleotides 448-529 of SEQ ID NO:68, nucleotides 448-529 of SEQ ID NO:69, nucleotides 448-529 of SEQ ID NO:70, or nucleotides 448-529 of SEQ ID NO:71, wherein each of the one or more shRNAs or miRNAs is operably linked to one or more first promoters; and (II) a second polynucleotide encoding a wild-type presenilin 1 (PSEN1) protein, wherein the second polynucleotide is not targeted by any of the shRNAs or miRNAs encoded by the first polynucleotide, and wherein the second polynucleotide is operably linked to a second promoter.

In some embodiments, an expression cassette comprises: (I) a first polynucleotide encoding one or more shRNAs or miRNAs, each of which independently comprises one of SEQ ID NO:1, SEQ ID NO:2, SEQ ID NO:12, SEQ ID NO:13, SEQ ID NO:14, SEQ ID NO:15, SEQ ID NO:16, SEQ ID NO:17, SEQ ID NO:18, or SEQ ID NO:19, SEQ ID NO:33, SEQ ID NO: 35, nucleotides 448-529 of SEQ ID NO:68, nucleotides 448-529 of SEQ ID NO:69, nucleotides 448-529 of SEQ ID NO:70, or nucleotides 448-529 of SEQ ID NO:71, wherein each of the one or more shRNAs or miRNAs is operably linked to one or more first promoters; and (ii) a second polynucleotide encoding a wild-type presenilin 1 (PSEN1) protein, wherein the second polynucleotide expresses any mRNA that encodes a human, wild-type PSEN1, and wherein the second polynucleotide is operably linked to a second promoter. In some aspects of these embodiments, the second polynucleotide expresses a mRNA, wherein the coding portion of the mRNA has the same polynucleotide sequence as endogenous, human, wild-type PSEN1 mRNA. In other aspects of these embodiments, the second polynucleotide expresses a mRNA encoding wild-type PSEN1, wherein the coding portion of the mRNA has a polynucleotide sequence wherein one or more codons have been modified or optimized as compared to the coding portion of the endogenous, human, wild-type PSEN1 mRNA. In more specific aspects of these embodiments, the second polynucleotide sequence is SEQ ID NO:39, SEQ ID NO:48, or nucleotides 1906-3303 of SEQ ID NO:68.

In some embodiments, an expression cassette comprises: (I) a first polynucleotide encoding one or more shRNAs or miRNAs, each of which independently comprises one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:33, SEQ ID NO: 35, SEQ ID NO:42, SEQ ID NO:43 SEQ ID NO:44, SEQ ID NO:45, SEQ ID NO: 46, SEQ ID NO:47, nucleotides 448-529 of SEQ ID NO:68, nucleotides 448-529 of SEQ ID NO:69, nucleotides 448-529 of SEQ ID NO:70, or nucleotides 448-529 of SEQ ID NO:71, and wherein at least one shRNA or miRNAs comprises one of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO: 42, or SEQ ID NO:43, SEQ ID NO:44, SEQ ID NO:45, SEQ ID NO: 46, SEQ ID NO:47, nucleotides 497-517 of SEQ ID NO:68, nucleotides 497-517 of SEQ ID NO:69, nucleotides 497-517 of SEQ ID NO:70, nucleotides 497-517 of SEQ ID NO:71, wherein each of the one or more shRNAs or miRNAs is operably linked to one or more first promoters; and (ii) a second polynucleotide encoding a wild-type presenilin 1 (PSEN1) protein, wherein the second polynucleotide expresses a mRNA that encodes a human, wild-type PSEN1 and is not targeted by any of the shRNAs or miRNAs, and wherein the second polynucleotide is operably linked to a second promoter. In some aspects of these embodiments, the second polynucleotide expresses a mRNA encoding wild-type PSEN1 that is codon modified as compared to the coding portion of the endogenous, human, wild-type PSEN1 mRNA. In more specific aspects of these embodiments, the second polynucleotide expresses a mRNA that comprises a sufficient number of modified codons in those coding regions that are targeted by the shRNAs or miRNAs to prevent such shRNAs or miRNAs from targeting the mRNA expressed from the second polynucleotide. Typically, modifying more than 4 nucleotides in the mRNA coding sequence of the second polynucleotide to reduce homology/complementarity with the shRNA or miRNAs will prevent targeting. In even more specific aspects of these embodiments, the second polynucleotide sequence is SEQ ID NO:41.

In certain embodiments, an expression cassette comprises: (I) a first polynucleotide encoding one or more shRNAs or miRNAs, each of which independently comprises one of: a) SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:34, SEQ ID NO: 36, nucleotides 448-529 of SEQ ID NO:76, nucleotides 448-529 of SEQ ID NO:77, and nucleotides 448-529 of SEQ ID NO:78; b) a modified version of any of the foregoing SEQ ID NOs, wherein the modification is 1, 2, 3, or 4 nucleotide changes; or c) a 19-21 base nucleotide sequence comprising 7 or more consecutive bases taken from the 5' or 3' end of any of the foregoing SEQ ID NOs or the modified version thereof, wherein the 19-21 base nucleotide sequence comprises no more than 4 mismatches with a corresponding portion of an endogenous PSEN1 mRNA, wherein each of the one or more shRNAs or miRNAs is operably linked to one or more first promoters; and (II) a second polynucleotide encoding a wild-type presenilin 2 (PSEN2) protein, wherein the second polynucleotide is not targeted by any of the shRNAs or miRNAs encoded by the first polynucleotide, and wherein the second polynucleotide is operably linked to a second promoter.

SEQ ID NO:20, SEQ ID NO:21, SEQ ID NO:28, SEQ ID NO:29, SEQ ID NO:30, SEQ ID NO:31, SEQ ID NO:32, SEQ ID NO: 34, SEQ ID NO:36, nucleotides 448-529 of SEQ ID NO:76, nucleotides 448-529 of SEQ ID NO:77, and nucleotides 448-529 of SEQ ID NO:78 each encode RNA that target sequences in the non-coding portion of PSEN2 mRNA. SEQ ID NO:22, SEQ ID NO:23, SEQ ID NO:24, SEQ ID NO:25, SEQ ID NO:26, and SEQ ID NO:27 each encode RNA that target sequences in the coding portion of PSEN2 mRNA. SEQ ID NO:34, SEQ ID NO:36, nucleotides 448-529 of SEQ ID NO:76, nucleotides 448-529 of SEQ ID NO:77, and nucleotides 448-529 of SEQ ID NO:78 represent miRNA coding sequences. Each of the 1, 2, 3, or 4 nucleotide changes in the modified version of any of the above SEQ ID NOs is independently a nucleotide substitution, deletion, or addition and results in a mismatch with endogenous wild-type PSEN2 mRNA. The additional nucleotides required for a 19-21 base nucleotide sequence comprising 7 or more consecutive bases taken from the 5' or 3' end of any of the foregoing SEQ ID NOs or the modified version thereof are those that are capable of hybridizing to the region of PSEN2 mRNA immediately 5' or 3', respectively, to the regions of PSEN2 mRNA to which the 7 or more consecutive bases bind, while still allowing for up to 4 mismatches in the entire 19-21 base nucleotide sequence. For example, SEQ ID NO:20 hybridizes to nucleotides 110-135 of PSEN2 mRNA (using numbering in NM 000447.3) (See Table 3, herein). Thus, an example of a 19-21 base nucleotide sequence taken from the 5' end of SEQ ID NO:20 would contain nucleotides 2-8 with a perfect complementarity to PSEN2 mRNA and other bases would contain 1, 2, 3 or 4 nucleotide changes. Similarly, an example of a 19-21 base nucleotide sequence taken from the 3' end of SEQ ID NO:21 would contain nucleotides 2-8 with a perfect complementarity to PSEN2 mRNA and other bases would contain 1, 2, 3, or 4 nucleotide changes.

In certain embodiments, an expression cassette comprises: (I) a first polynucleotide encoding one or more shRNAs or miRNAs, each of which independently comprises one of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:34, SEQ ID NO: 36, nucleotides 448-529 of SEQ ID NO:76, nucleotides 448-529 of SEQ ID NO:77, and nucleotides 448-529 of SEQ ID NO:78, wherein each of the one or more shRNAs or miRNAs is operably linked to one or more first promoters; and (II) a second polynucleotide encoding a wild-type presenilin 2 (PSEN2) protein, wherein the second polynucleotide is not targeted by any of the shRNAs or miRNAs encoded by the first polynucleotide, and wherein the second polynucleotide is operably linked to a second promoter. SEQ ID NO:20, SEQ ID NO:21, SEQ ID NO:28, SEQ ID NO:29, SEQ ID NO:30, SEQ ID NO:31, SEQ ID NO:32, SEQ ID NO: 34, SEQ ID NO:36, nucleotides 448-529 of SEQ ID NO:76, nucleotides 448-529 of SEQ ID NO:77, and nucleotides 448-529 of SEQ ID NO:78 each encode RNA that target sequences in the non-coding portion of PSEN2 mRNA. SEQ ID NO:22, SEQ ID NO:23, SEQ ID NO:24, SEQ ID NO:25, SEQ ID NO:26, and SEQ ID NO:27 each encode RNA that target sequences in the coding portion of PSEN2 mRNA. SEQ ID NO:34, SEQ ID NO:36, nucleotides 448-529 of SEQ ID NO:76, nucleotides 448-529 of SEQ ID NO:77, and nucleotides 448-529 of SEQ ID NO:78 represent miRNA coding sequences.

In some embodiments, an expression cassette comprises: (I) a first polynucleotide encoding one or more shRNAs or miRNAs, each of which independently comprises one of SEQ ID NO:20, SEQ ID NO:21, SEQ ID NO:28, SEQ ID NO:29, SEQ ID NO:30, SEQ ID NO:31, SEQ ID NO:32, SEQ ID NO:34, SEQ ID NO:36, nucleotides 448-529 of SEQ ID NO:76, nucleotides 448-529 of SEQ ID NO:77, and nucleotides 448-529 of SEQ ID NO:78, wherein each of the one or more shRNAs or miRNAs is operably linked to one or more first promoters; and (ii) a second polynucleotide encoding a wild-type presenilin 2 (PSEN2) protein, wherein the second polynucleotide expresses any mRNA that encodes a human, wild-type PSEN2, and wherein the second polynucleotide is operably linked to a second promoter. In some aspects of these embodiments, the second polynucleotide expresses a mRNA, wherein the coding portion of the mRNA has the same polynucleotide sequence as endogenous, human, wild-type PSEN2 mRNA. In other aspects of these embodiments, the second polynucleotide expresses a mRNA encoding wild-type PSEN2, wherein the coding portion of the mRNA has a polynucleotide sequence wherein one or more codons have been modified or optimized as compared to the coding portion of the endogenous, human, wild-type PSEN2 mRNA. In more specific aspects of these embodiments, the second polynucleotide sequence is SEQ ID NO:40.

In some embodiments, an expression cassette comprises: (I) a first polynucleotide encoding one or more shRNAs or miRNAs, each of which independently comprises one of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, or SEQ ID NO:32, SEQ ID NO:34, SEQ ID NO: 36, nucleotides 448-529 of SEQ ID NO:76, nucleotides 448-529 of SEQ ID NO:77, and nucleotides 448-529 of SEQ ID NO:78; and wherein at least one shRNA or miRNAs comprises one of SEQ ID NO:22, SEQ ID NO:23, SEQ ID NO:24, SEQ ID NO:25, SEQ ID NO:26, SEQ ID NO:27, nucleotides 497-517 of SEQ ID NO:76, nucleotides 497-517 of SEQ ID NO:77, or nucleotides 497-517 of SEQ ID NO:78, wherein each of the one or more shRNAs or miRNAs is operably linked to one or more first promoters; and (ii) a second polynucleotide encoding a wild-type presenilin 2 (PSEN2) protein, wherein the second polynucleotide expresses a mRNA that encodes a human, wild-type PSEN2 and is not targeted by any of the shRNAs or miRNAs, and wherein the second polynucleotide is operably linked to a second promoter. In some aspects of these embodiments, the second polynucleotide expresses a mRNA encoding wild-type PSEN2 that is codon modified as compared to the coding portion of the endogenous, human, wild-type PSEN2 mRNA. In more specific aspects of these embodiments, the second polynucleotide expresses a mRNA that comprises a sufficient number of modified codons in those coding regions that are targeted by the shRNAs or miRNAs to prevent such shRNAs or miRNAs from targeting the mRNA expressed from the second polynucleotide.

The one or more first promoters drive expression of each shRNA or miRNA encoding sequence. Each shRNA or miRNA encoding sequence may be driven by the same or a different first promoter. When driven by the same first promoter, expression of two or more shRNA or miRNA encoding sequences may be driven by separate copies of the same first promoter or by a single copy of that first promoter. When driven by a single copy of a first promoter, two or more shRNA or miRNA encoding sequences will be located in tandem to one another in the expression cassette such that a single first promoter can drive expression of each one of those shRNA or miRNA encoding sequences. Similarly, the second promoter, which drives expression of the replacement, wild-type PSEN1 or PSEN2, may also drives expression of the shRNA or miRNA encoding sequences (i.e., the first promoter and the second promoter are the same). When driven by a single promoter, the shRNA or miRNA encoding sequences will be located in tandem with the PSEN1 or PSEN2 coding sequence in the expression cassette such that such single first promoter can drive expression of both the shRNA or miRNA encoding sequence and the PSEN1 or PSEN2 coding sequence. In certain aspects, a single promoter can drive expression of two or more shRNA or miRNA and PSEN1 or PSEN2. In some embodiments, at least one of the one or more first promoters or second promoters is a RNA polymerase III promoter or a RNA polymerase II promoter. In some more specific aspects of these embodiments, the RNA polymerase III promoter is selected from U6 promoter, a U61 promoter, a U69 promoter, a H1 promoter, or any combination thereof. In some aspects of these embodiments, at least one of the one or more first promoters or second promoter is a RNA polymerase II promoter that is a neuron-specific promoter. In some more specific aspects of these embodiments, the second promoter is a RNA polymerase II promoter that is a neuron-specific promoter. In other more specific aspects of these embodiments, the second promoter is a RNA polymerase II promoter that is a ubiquitous promoter.

In some embodiments, the disclosure provides a vector comprising any of the expression cassettes disclosed herein.

In some embodiments, the disclosure provides a set of vectors, comprising (a) a first vector comprising an expression cassette comprising a first polynucleotide encoding one or more shRNAs or miRNAs targeting either a coding region or a non-coding region of a mRNA translated from each of a human wild-type and a mutant presenilin 1 (PSEN1), or from each of a human wild-type and a mutant presenilin 2 (PSEN2), wherein each of the one or more shRNAs or miRNAs is operably linked to one or more first promoters; and (b) a second vector comprising a second polynucleotide encoding a wild-type presenilin 1 (PSEN1) amino acid sequence or a wild-type presenilin 2 (PSEN2) amino acid sequence, wherein the second polynucleotide is not targeted by any of the shRNAs or miRNAs encoded by the first vector; and wherein the second polynucleotide is operably linked to a second promoter.

In some embodiments, the disclosure provides a set of vectors, comprising (a) a first vector comprising an expression cassette comprising (a) a first polynucleotide encoding one or more shRNAs or miRNAs targeting either a coding region or a non-coding region of a mRNA translated from each of a human wild-type and a mutant presenilin 1 (PSEN1), wherein each of the one or more shRNAs or miRNAs is operably linked to one or more first promoters; and (b) a second polynucleotide encoding a wild-type presenilin 1 (PSEN1) amino acid sequence, wherein the second polynucleotide is not targeted by any of the shRNAs or miRNAs encoded by the first polynucleotide; and wherein the second polynucleotide is operably linked to a second promoter.

In some embodiments, the disclosure provides a set of vectors, comprising (a) a first vector comprising an expression cassette comprising (a) a first polynucleotide encoding one or more shRNAs or miRNAs targeting either a coding region or a non-coding region of a mRNA translated from each of a human wild-type and a mutant presenilin 2 (PSEN2), wherein each of the one or more shRNAs or miRNAs is operably linked to one or more first promoters; and (b) a second polynucleotide encoding a wild-type presenilin 2 (PSEN2) amino acid sequence, wherein the second polynucleotide is not targeted by any of the shRNAs or miRNAs encoded by the first polynucleotide; and wherein the second polynucleotide is operably linked to a second promoter.

In some embodiments of a set of vectors, each the encoded shRNAs or miRNAs in the first vector independently comprises one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:33, SEQ ID NO: 35, SEQ ID NO:42, SEQ ID NO:43, SEQ ID NO:44, SEQ ID NO:45, SEQ ID NO: 46, SEQ ID NO:47, nucleotides 448-529 of SEQ ID NO:68, nucleotides 448-529 of SEQ ID NO:69, nucleotides 448-529 of SEQ ID NO:70, or nucleotides 448-529 of SEQ ID NO:71; b) a modified version of any of the foregoing SEQ ID NOs, wherein the modification is 1, 2, 3, or 4 nucleotide changes; or c) a 19-21 base nucleotide sequence comprising 7 or more consecutive bases taken from the 5' or 3' end of any of the foregoing SEQ ID NOs or the modified version thereof, wherein the 19-21 base nucleotide sequence comprises no more than 4 mismatches with a corresponding portion of an endogenous PSEN1 mRNA.

In some embodiments of a set of vectors, each the encoded shRNAs or miRNAs in the first vector independently comprises one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:33, SEQ ID NO: 35, SEQ ID NO:42, SEQ ID NO:43, SEQ ID NO:44, SEQ ID NO:45, SEQ ID NO: 46, SEQ ID NO:47, nucleotides 448-529 of SEQ ID NO:68, nucleotides 448-529 of SEQ ID NO:69, nucleotides 448-529 of SEQ ID NO:70, or nucleotides 448-529 of SEQ ID NO:71. In some aspects of these embodiments, each of the encoded shRNAs or miRNAs each of which independently comprises one of SEQ ID NO:1, SEQ ID NO:2, SEQ ID NO:12, SEQ ID NO:13, SEQ ID NO:14, SEQ ID NO:15, SEQ ID NO:16, SEQ ID NO:17, SEQ ID NO:18, or SEQ ID NO:19, SEQ ID NO:33, SEQ ID NO: 35, nucleotides 448-529 of SEQ ID NO:68, nucleotides 448-529 of SEQ ID NO:69, nucleotides 448-529 of SEQ ID NO:70, or nucleotides 448-529 of SEQ ID NO:71. In other aspects of these embodiments, each of the encoded shRNAs or miRNAs each of which independently comprises one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:33, SEQ ID NO: 35, SEQ ID NO:42, SEQ ID NO:43 SEQ ID NO:44, SEQ ID NO:45, SEQ ID NO: 46, SEQ ID NO:47, nucleotides 448-529 of SEQ ID NO:68, nucleotides 448-529 of SEQ ID NO:69, nucleotides 448-529 of SEQ ID NO:70, or nucleotides 448-529 of SEQ ID NO:71; and wherein at least one shRNA or miRNAs comprises one of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO: 42, or SEQ ID NO:43, SEQ ID NO:44, SEQ ID NO:45, SEQ ID NO: 46, SEQ ID NO:47, nucleotides 497-517 of SEQ ID NO:68, nucleotides 497-517 of SEQ ID NO:69, nucleotides 497-517 of SEQ ID NO:70, or nucleotides 497-517 of SEQ ID NO:71.

In some embodiments of a set of vectors, when each of the shRNAs or miRNAs in the first vector targets a non-coding region present in an endogenous PSEN1 mRNA, the second polynucleotide in the second vector expresses a mRNA, wherein the coding portion of the mRNA has the same polynucleotide sequence as endogenous, human, wild-type PSEN1 mRNA. In other aspects of these embodiments, the second polynucleotide expresses a mRNA, wherein the coding portion of the mRNA has a polynucleotide sequence wherein one or more codons have been modified or optimized as compared to the coding portion of the endogenous, human, wild-type PSEN1 mRNA. In more specific aspects of these embodiments, the second polynucleotide sequence is SEQ ID NO:39. In other more specific aspects of these embodiments, the second polynucleotide sequence is SEQ ID NO:48.

In some embodiments of a set of vectors, when at least one of the shRNAs or miRNAs in the first vector targets a coding region present in an endogenous PSEN1 mRNA, the second polynucleotide in the second vector expresses a mRNA that is codon modified as compared to the coding portion of the endogenous, human, wild-type PSEN1 mRNA. In more specific aspects of these embodiments, the second polynucleotide expresses a mRNA that comprises a sufficient number of modified codons in those coding regions that are targeted by the shRNAs or miRNAs to prevent such shRNAs or miRNAs from targeting the mRNA expressed from the second polynucleotide. Typically, modifying a sufficient number of codons to create more than 4 mismatched nucleotides with the shRNA or miRNA will prevent targeting. In even more specific aspects of these embodiments, the second polynucleotide sequence is SEQ ID NO:41.

In some embodiments of a set of vectors, each the encoded shRNAs or miRNAs in the first vector independently comprises one of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:34 SEQ ID NO: 36, nucleotides 448-529 of SEQ ID NO:76, nucleotides 448-529 of SEQ ID NO:77, or nucleotides 448-529 of SEQ ID NO:78; b) a modified version of any of the foregoing SEQ ID NOs, wherein the modification is 1, 2, 3, or 4 nucleotide changes; or c) a 19-21 base nucleotide sequence comprising 7 or more consecutive bases taken from the 5' or 3' end of any of the foregoing SEQ ID NOs or the modified version thereof, wherein the 19-21 base nucleotide sequence comprises no more than 4 mismatches with a corresponding portion of an endogenous PSEN2 mRNA.

In some embodiments of a set of vectors, each the encoded shRNAs or miRNAs in the first vector independently comprises one of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:34, SEQ ID NO: 36, nucleotides 448-529 of SEQ ID NO:76, nucleotides 448-529 of SEQ ID NO:77, or nucleotides 448-529 of SEQ ID NO:78. In some aspects of these embodiments, each the encoded shRNAs or miRNAs each of which independently comprises one of SEQ ID NO:20, SEQ ID NO:21, SEQ ID NO:28, SEQ ID NO:29, SEQ ID NO:30, SEQ ID NO:31, SEQ ID NO:32, SEQ ID NO:34, SEQ ID NO:36, nucleotides 448-529 of SEQ ID NO:76, nucleotides 448-529 of SEQ ID NO:77, or nucleotides 448-529 of SEQ ID NO:78. In other aspects of these embodiments, each the encoded shRNAs or miRNAs each of which independently comprises one of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, or SEQ ID NO:32, SEQ ID NO:34, SEQ ID NO: 36, nucleotides 448-529 of SEQ ID NO:76, nucleotides 448-529 of SEQ ID NO:77, or nucleotides 448-529 of SEQ ID NO:78; and wherein at least one shRNA or miRNAs comprises one of SEQ ID NO:22, SEQ ID NO:23, SEQ ID NO:24, SEQ ID NO:25, SEQ ID NO:26, SEQ ID NO:27, nucleotides 497-517 of SEQ ID NO:76, nucleotides 497-517 of SEQ ID NO:77, or nucleotides 497-517 of SEQ ID NO:78.

In some embodiments of a set of vectors, when each of the shRNAs or miRNAs in the first vector targets a non-coding region present in an endogenous PSEN2 mRNA, the second polynucleotide in the second vector expresses a mRNA, wherein the coding portion of the mRNA has the same polynucleotide sequence as endogenous, human, wild-type PSEN2 mRNA. In other aspects of these embodiments, the second polynucleotide expresses a mRNA, wherein the coding portion of the mRNA has a polynucleotide sequence wherein one or more codons have been modified or optimized as compared to the coding portion of the endogenous, human, wild-type PSEN2 mRNA. In more specific aspects of these embodiments, the second polynucleotide sequence is SEQ ID NO:40.

In some embodiments of a set of vectors, when at least one of the shRNAs or miRNAs in the first vector targets a coding region present in an endogenous PSEN2 mRNA, the second polynucleotide in the second vector expresses a mRNA that is codon modified as compared to the coding portion of the endogenous, human, wild-type PSEN2 mRNA. In more specific aspects of these embodiments, the second polynucleotide expresses a mRNA that comprises a sufficient number of modified codons in those coding regions that are targeted by the shRNAs or miRNAs to prevent such shRNAs or miRNAs from targeting the mRNA expressed from the second polynucleotide. Typically, modifying a sufficient number of codons to create more than 4 mismatched nucleotides with the shRNA or miRNA will prevent targeting.

Each vectors in any of the foregoing embodiments can be a viral vector, such as an adeno-associated virus (AAV) vector, a retroviral vector, a lentiviral vector, or an adenoviral vector. An AAV vector can be AAV1, AAV2, AAV3, AAV4, AAV5, AAV6, AAV7, AAV8, AAV9, AAVDJ, AAVrh10, AAV11, AAV12, AAV2/1, AAV2/5, AAV2/6, AAV2/7, AAV2/8, AAV2/9, AAV2/rh10, AAV2/11, or AAV2/12, and capsid engineered adeno-associated viruses with hybrid capsids merging portions of two or more natural AAVs and/or point mutations of natural AAVs to modify tropism or evade immune detection such as PHP.B, and PHP.B derivatives [PHP.eR, PHP.S], AAV8[K137R], AAV- TT, rAAV-retro, AAV9. HR, AAV1 CAM mutants, AAV9 [586-590] swap mutants. Vectors or sets of vectors can be plasmid vectors with or without carrier such as polyamine.

In other embodiments, provided herein are kits comprising a vector or sets of vectors provided herein.

In other embodiments, an isolated polynucleotide of SEQ ID NO:41 is provided.

In still other embodiments is provided a kit comprising: (a) one or more antisense oligonucleotides, wherein each antisense oligonucleotide independently targets either a coding region or a non-coding region of an mRNA translated from each of a human wild-type and mutant presenilin 1 (PSEN1), each of a human wild-type or mutant presenilin 2 (PSEN2); and (b) a vector comprising a polynucleotide encoding a wild-type presenilin 1 (PSEN1) amino acid sequence or a wild-type presenilin 2 (PSEN2) amino acid sequence, wherein the second polynucleotide is not targeted by any of the one or more antisense oligonucleotides; and wherein the polynucleotide is operably linked to a promoter in the vector. In some aspects of these embodiments, each of the one or more antisense oligonucleotides targets either a coding region or a non-coding region of an mRNA translated from each of a human wild-type and mutant presenilin 1 (PSEN1); and the vector comprises a polynucleotide encoding a wild-type presenilin 1 (PSEN1) amino acid sequence.

In some embodiments of the kit described in the previous paragraph, each of the one or more antisense oligonucleotides is independently selected from a short hairpin RNA (shRNA), a short interfering RNA (siRNA), a micro interfering RNA (miRNA), a small temporal RNA (stRNA) or an endoribonuclease-prepared siRNA (esiRNA). In some aspects of these embodiments, at least one of the one or more antisense oligonucleotides comprises one or more modified nucleobases. In some more specific aspects of these embodiments, each of the one or more modified nucleobases is independently selected from a non-naturally occurring nucleobase, a locked nucleic acids (LNA), or a peptide nucleic acids (PNA).

Yet another embodiment provides methods of treating a neurodegenerative disease, disorder, or condition, wherein the method comprises the step of administering to a subject in need thereof:

(a) either:

(i) one or more antisense oligonucleotides, wherein each antisense oligonucleotide independently targets either a coding region or a non-coding region of an mRNA translated from each of a human wild-type and mutant presenilin 1 (PSEN1), each of a human wild-type or mutant presenilin 2 (PSEN2), or (ii) a vector comprising a first polynucleotide encoding one or more shRNAs or miRNAs targeting either a coding region or a non-coding region of a mRNA translated from each of a human wild-type and a mutant presenilin 1 (PSEN1), or from each of a human wild-type and a mutant presenilin 2 (PSEN2), wherein each of the one or more shRNAs or miRNAs is operably linked to one or more first promoters; and (b) a vector comprising a second polynucleotide encoding a wild-type presenilin 1 (PSEN1) amino acid sequence or a wild-type presenilin 2 (PSEN2) amino acid sequence, wherein the second polynucleotide is not targeted by any of the shRNAs or miRNAs encoded by the first vector; and wherein the second polynucleotide is operably linked to a second promoter.

In some aspects of these embodiments, the first polynucleotide encoding one or more shRNAs or miRNAs and the second polynucleotide encoding a wild-type presenilin 1 (PSEN1) amino acid sequence or a wild-type presenilin 2 (PSEN2) amino acid sequence are present in the same vector. Such vectors are described above as containing any of the expression vectors disclosed herein. In alternate aspects of these embodiments, the first polynucleotide encoding one or more shRNAs or miRNAs and the second polynucleotide encoding a wild-type presenilin 1 (PSEN1) amino acid sequence or a wild-type presenilin 2 (PSEN2) amino acid sequence are present in different vectors (i.e., a set of vectors). Such sets of vectors are also disclosed herein. In still other alternate aspects of these embodiments, the targeting an mRNA translated from each of a human wild-type and mutant presenilin 1 (PSEN1), each of a human wild-type or mutant presenilin 2 (PSEN2) is achieved by administering an antisense RNA molecule. Such antisense RNA molecules are also disclosed herein. In certain aspects of these embodiments, the neurodegenerative disease, disorder, or condition is Alzheimer's disease, sporadic Alzheimer's disease, familial Alzheimer's disease, frontotemporal dementia, frontotemporal lobar degeneration, Pick's disease, Lewy body dementia, memory loss, cognitive impairment, or mild cognitive impairment.

BRIEF DESCRIPTIONS OF THE DRAWINGS

Figure 2:
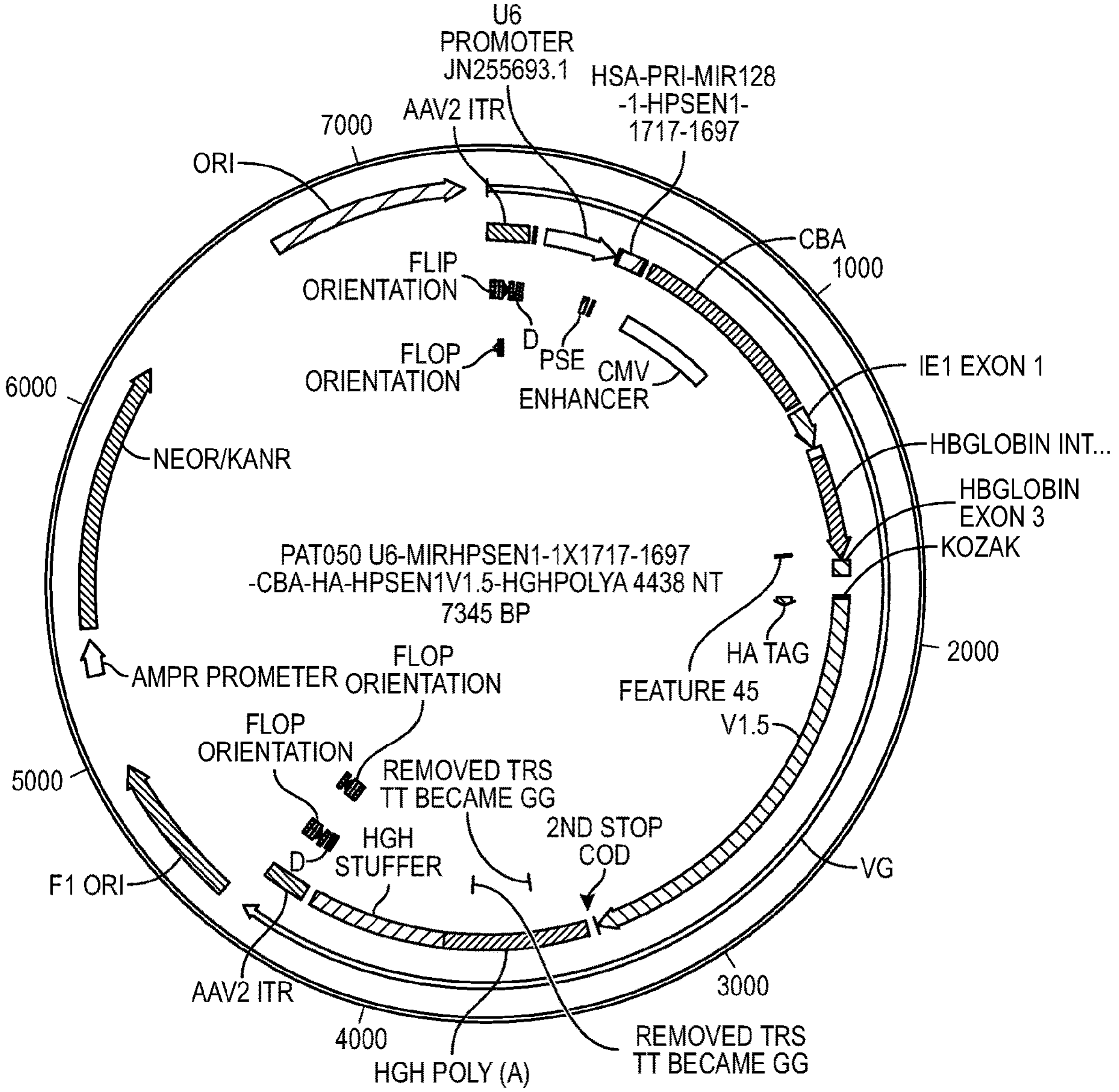
Figure 3:
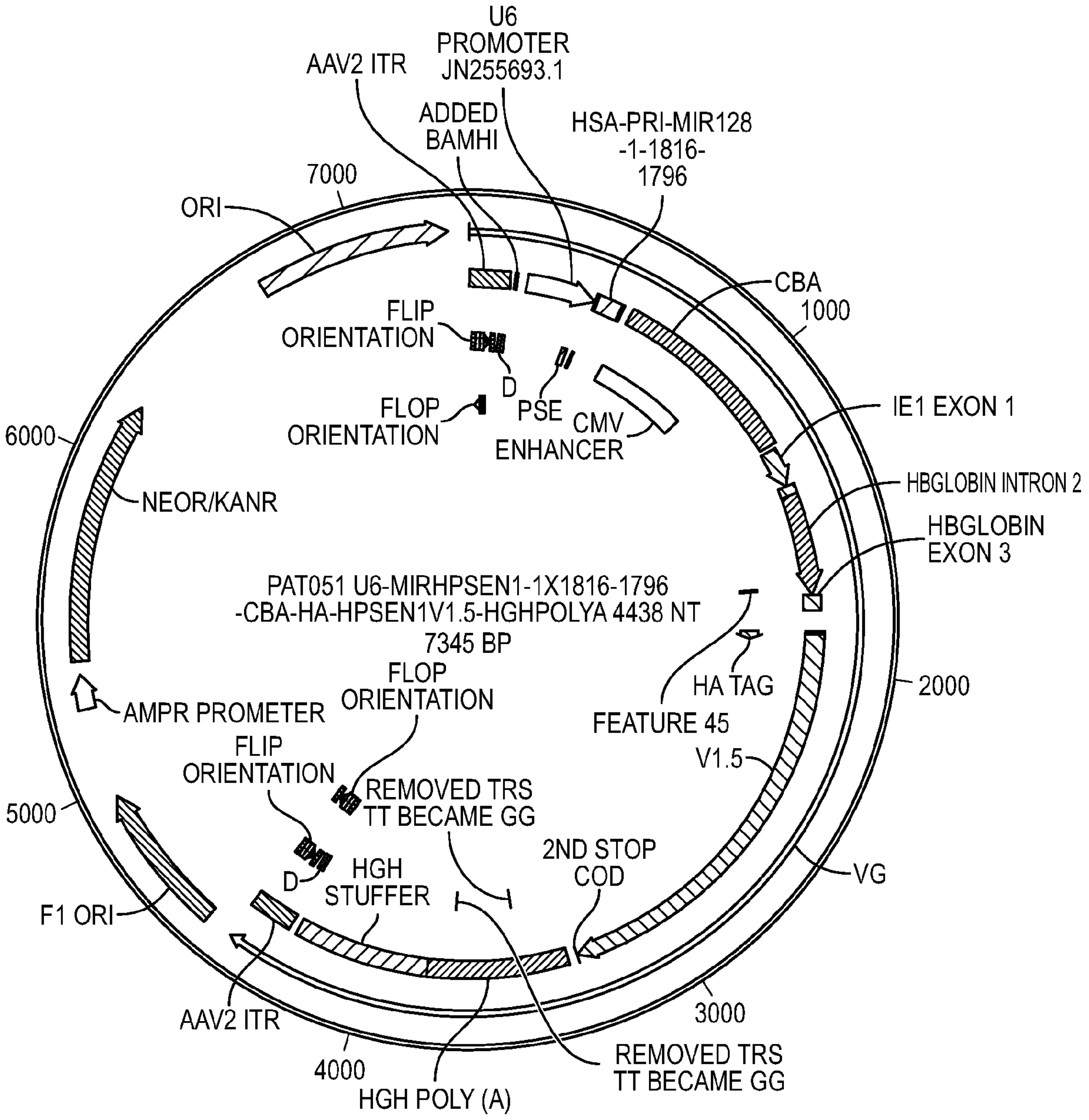
Figure 4:
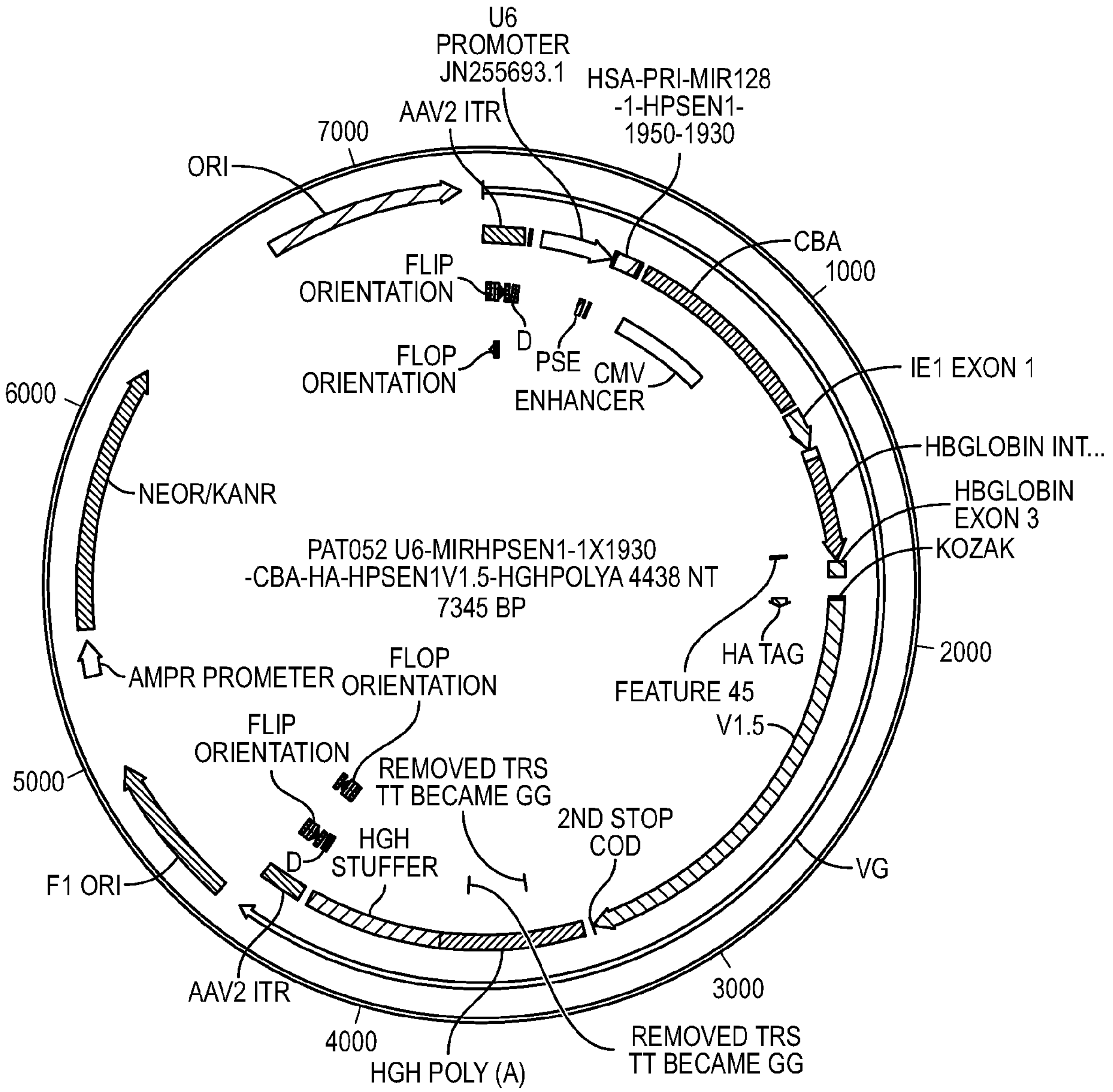
Figure 5:
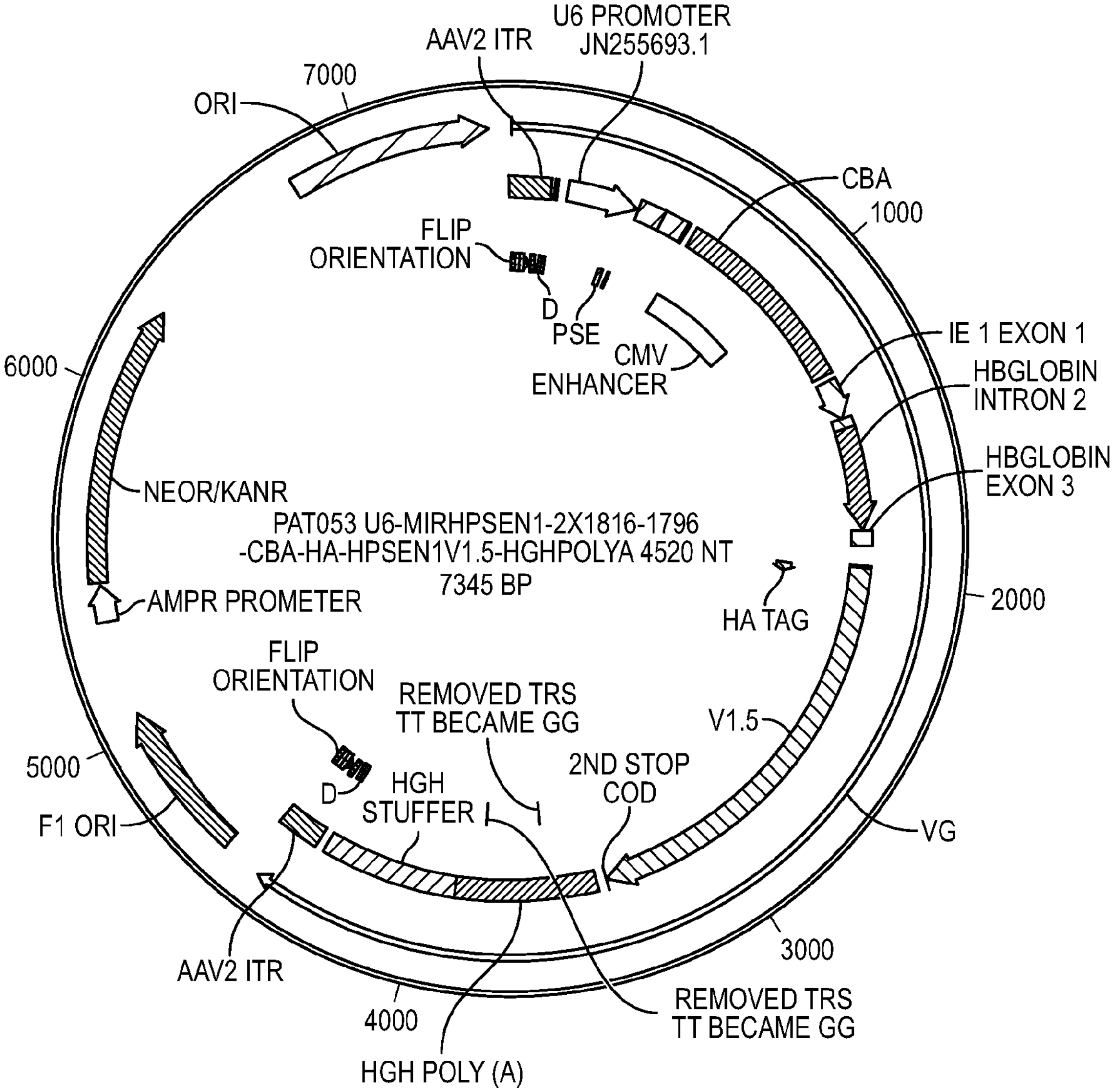
Figure 6:
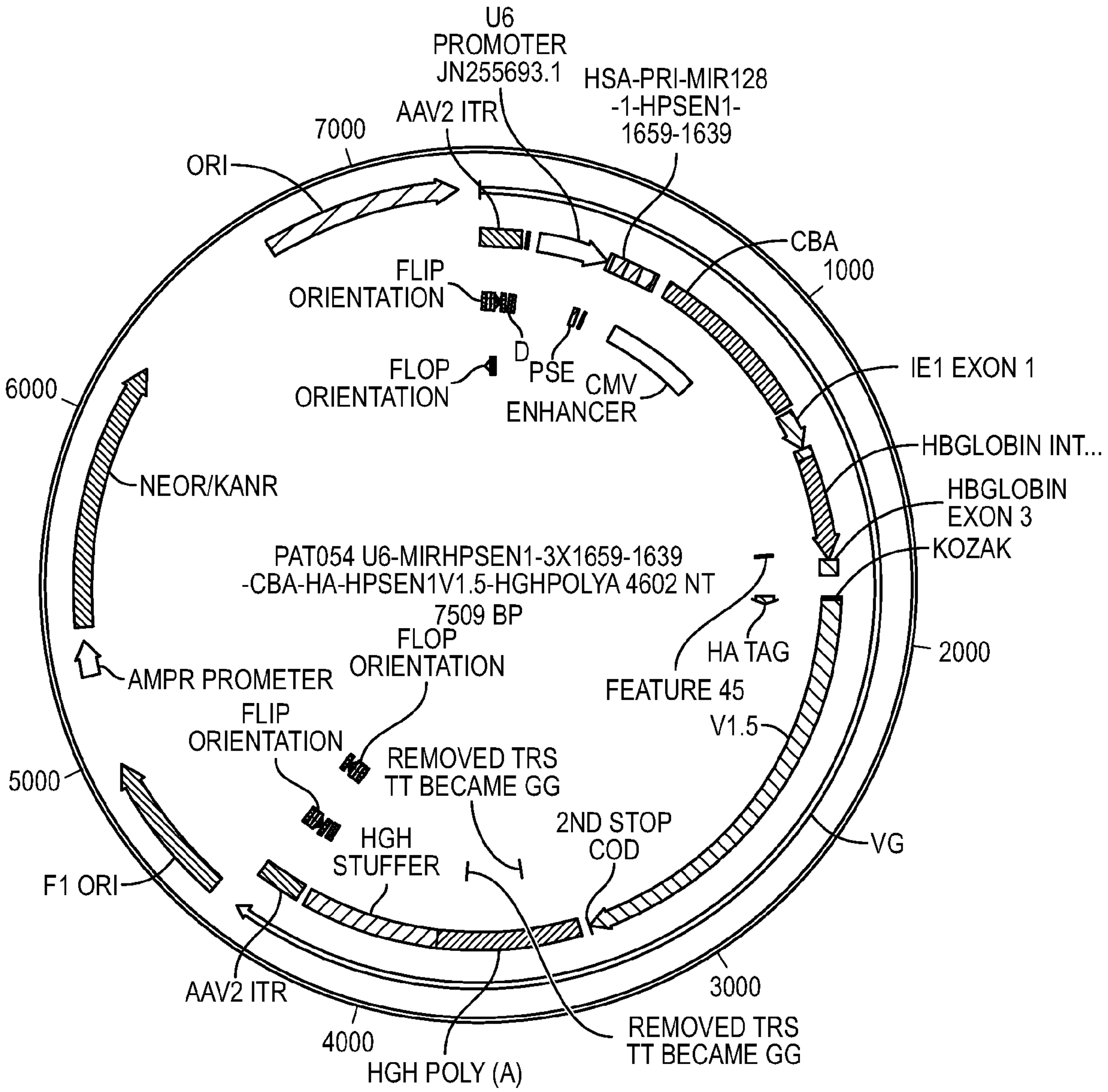
Figure 7:
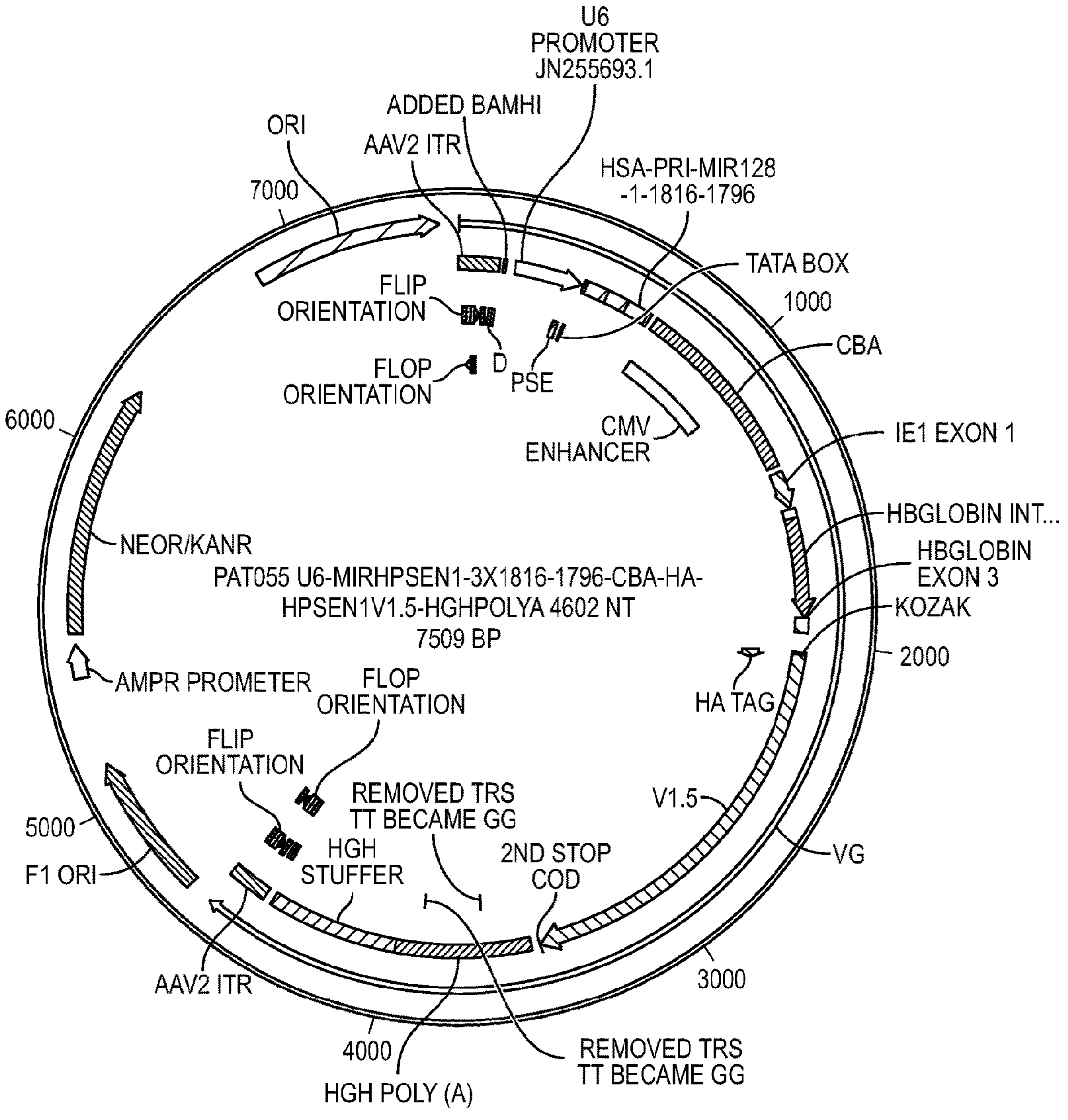
Figure 8:
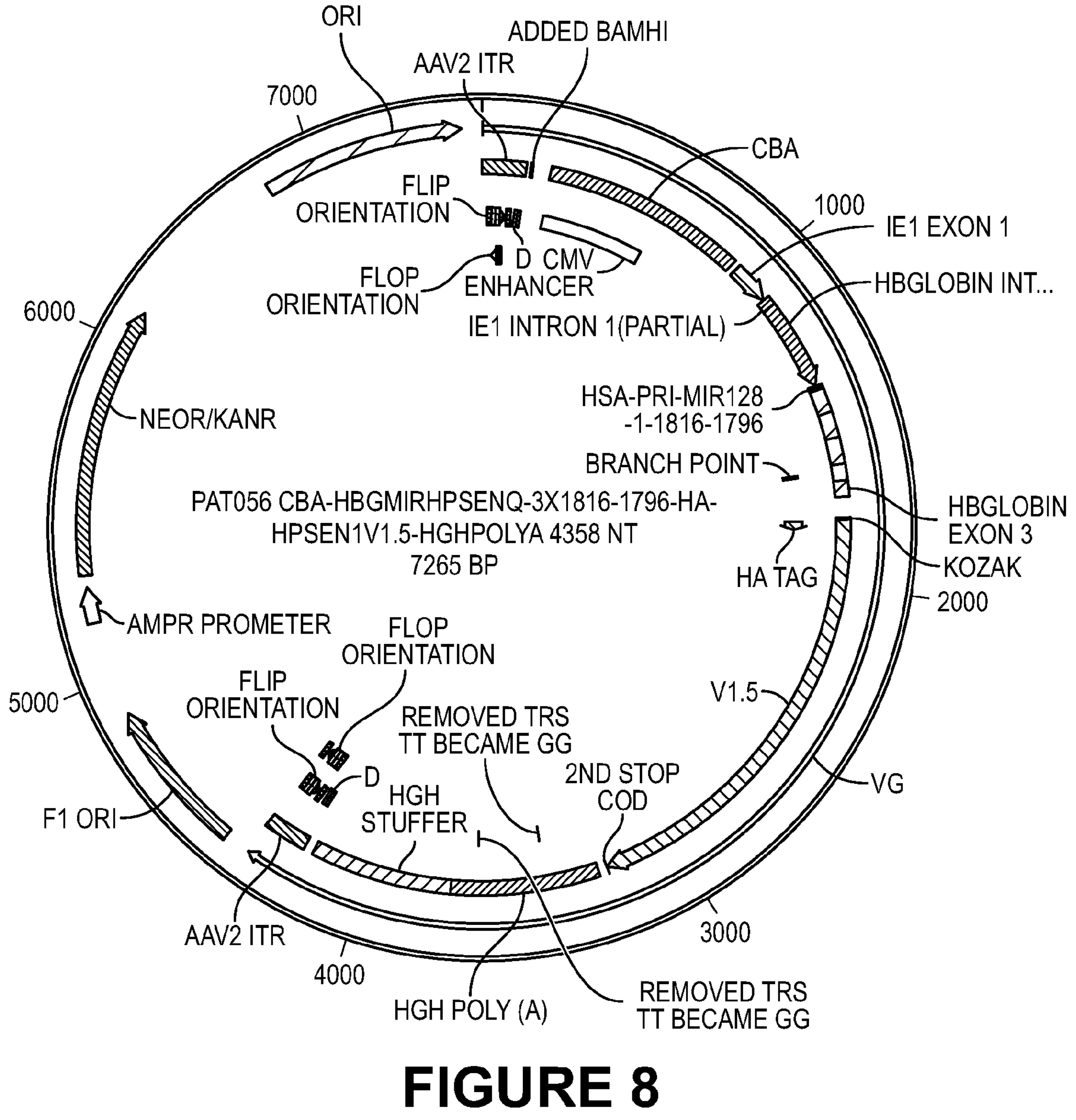
Figure 9:
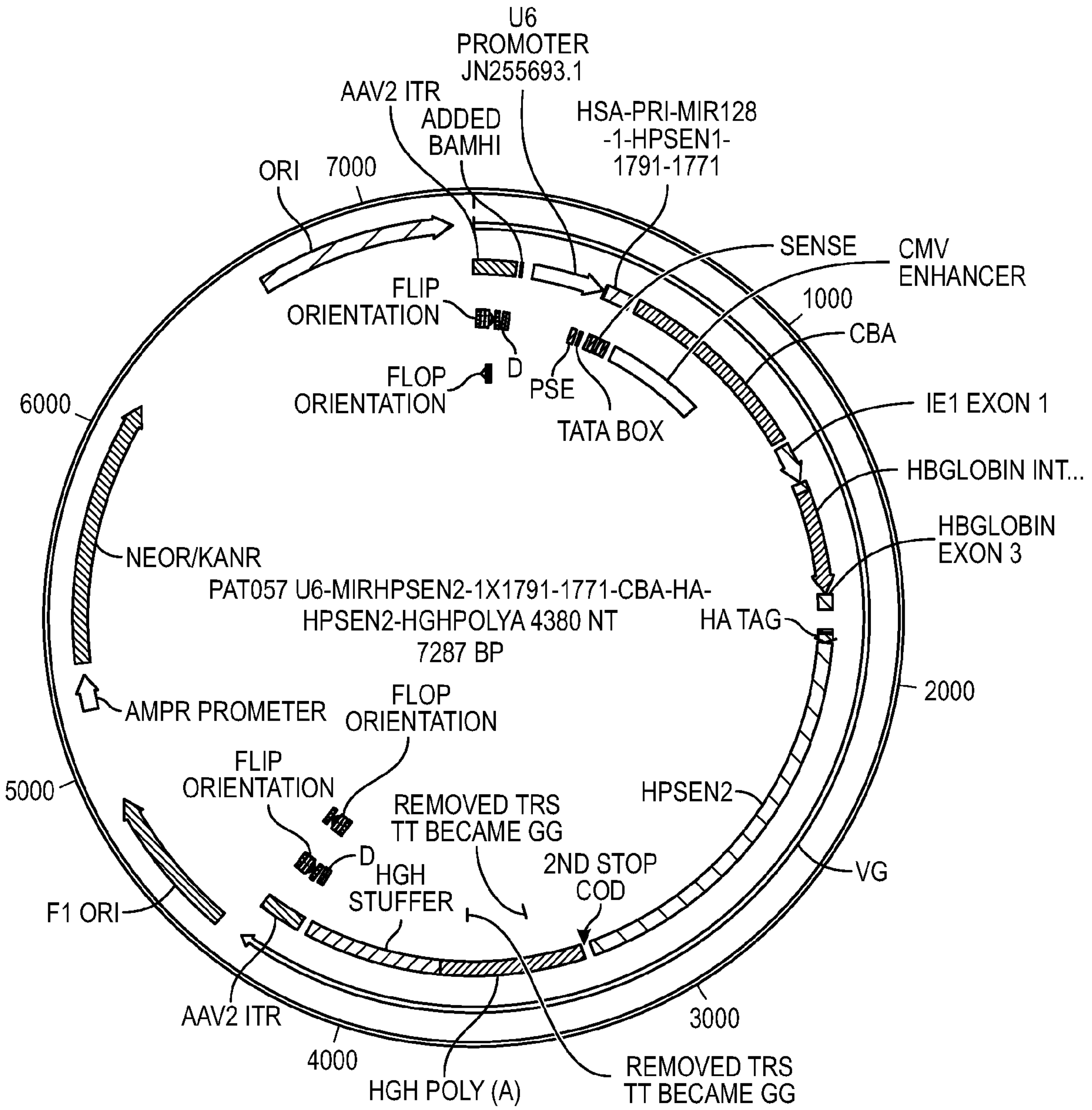
Figure 10:
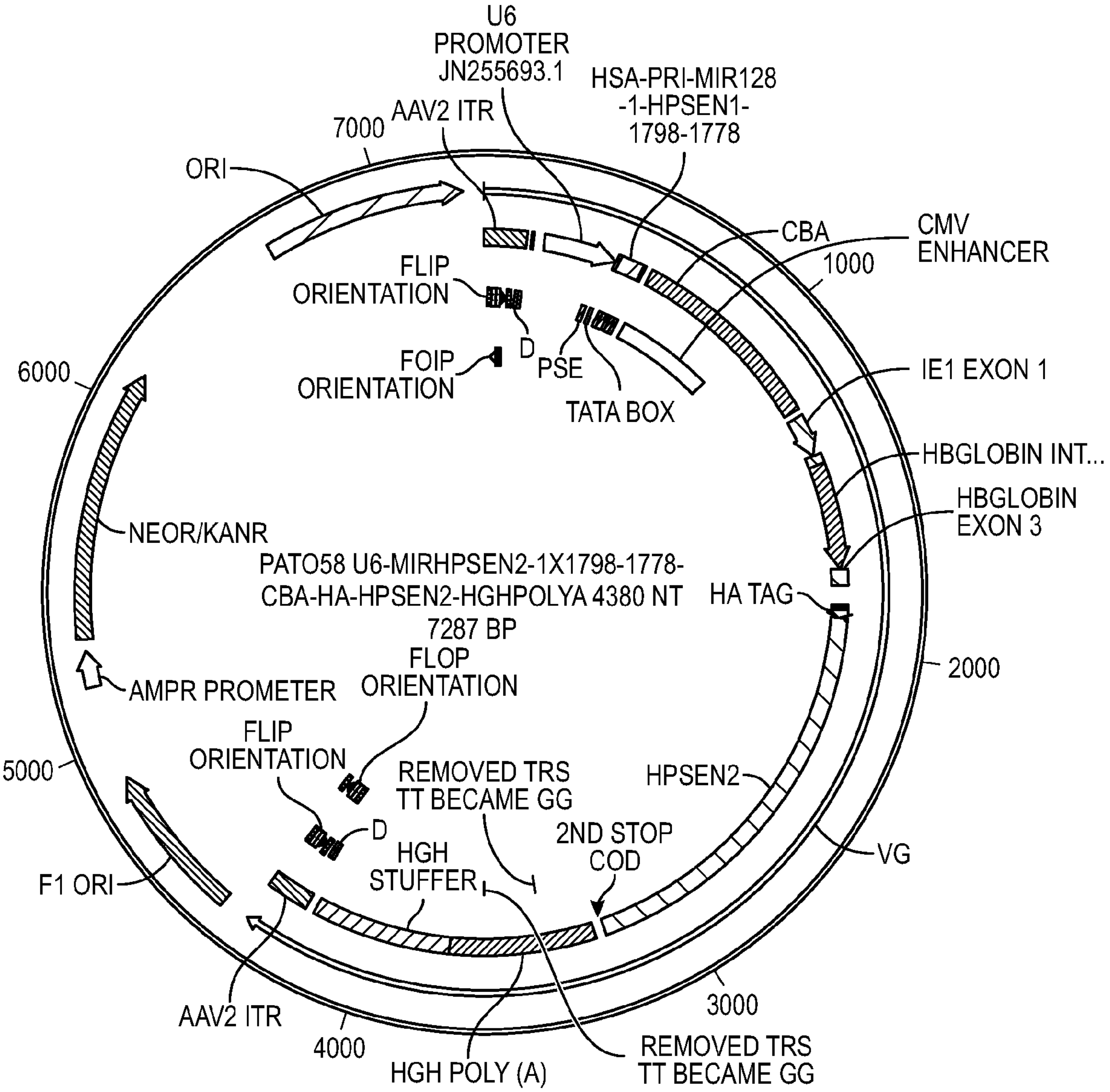
Figure 11:
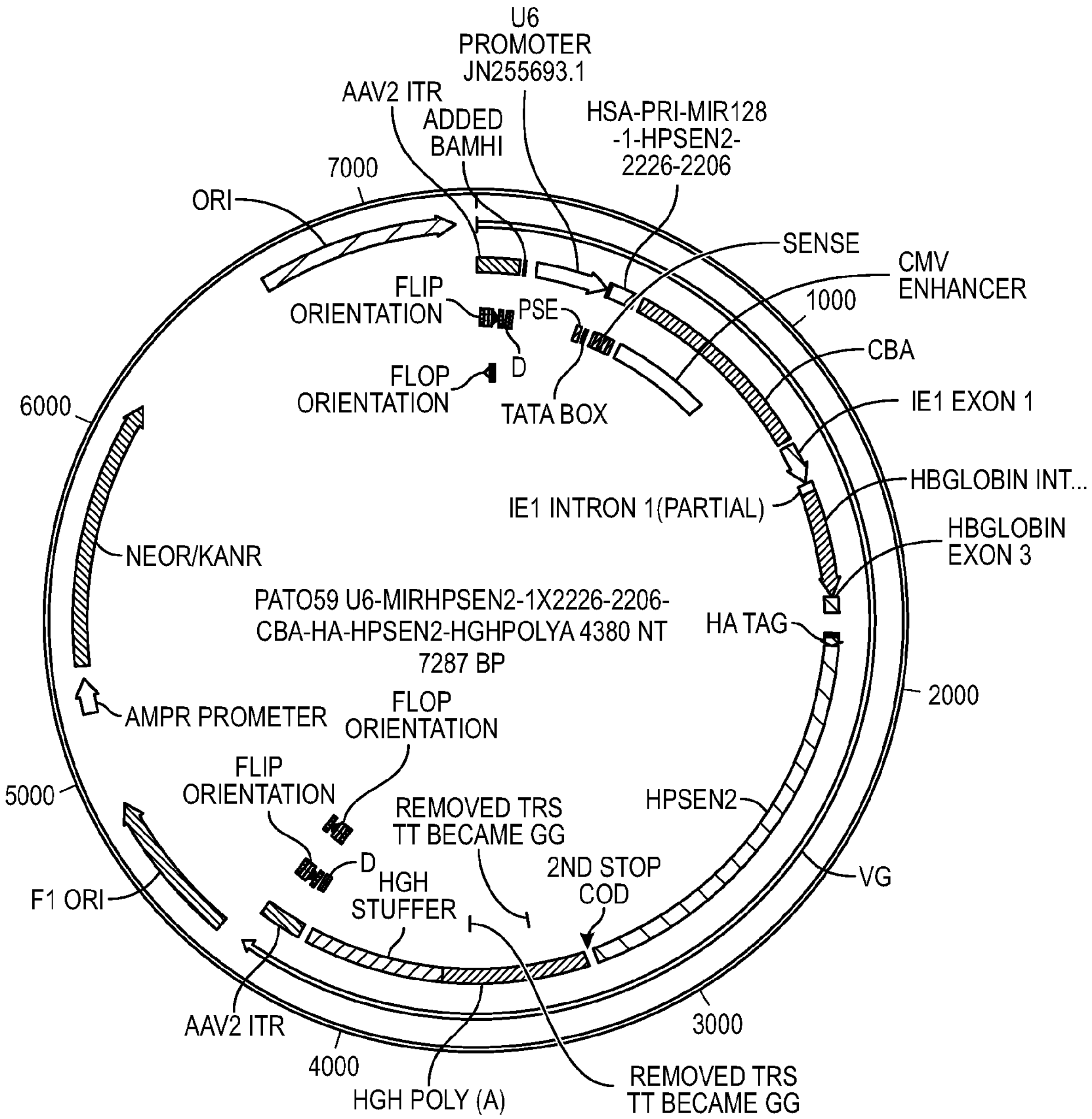
Figure 12:
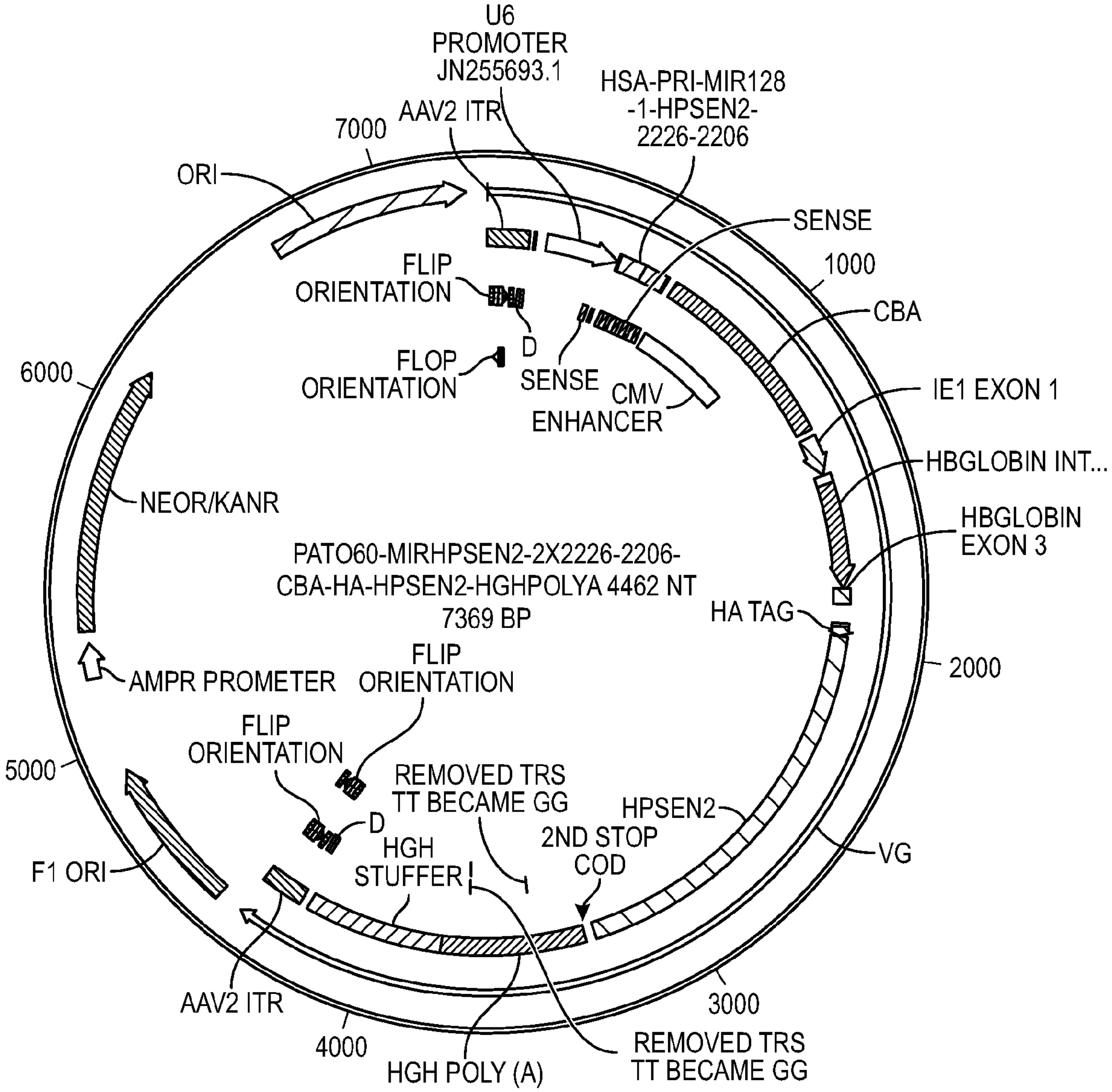
Figure 13:
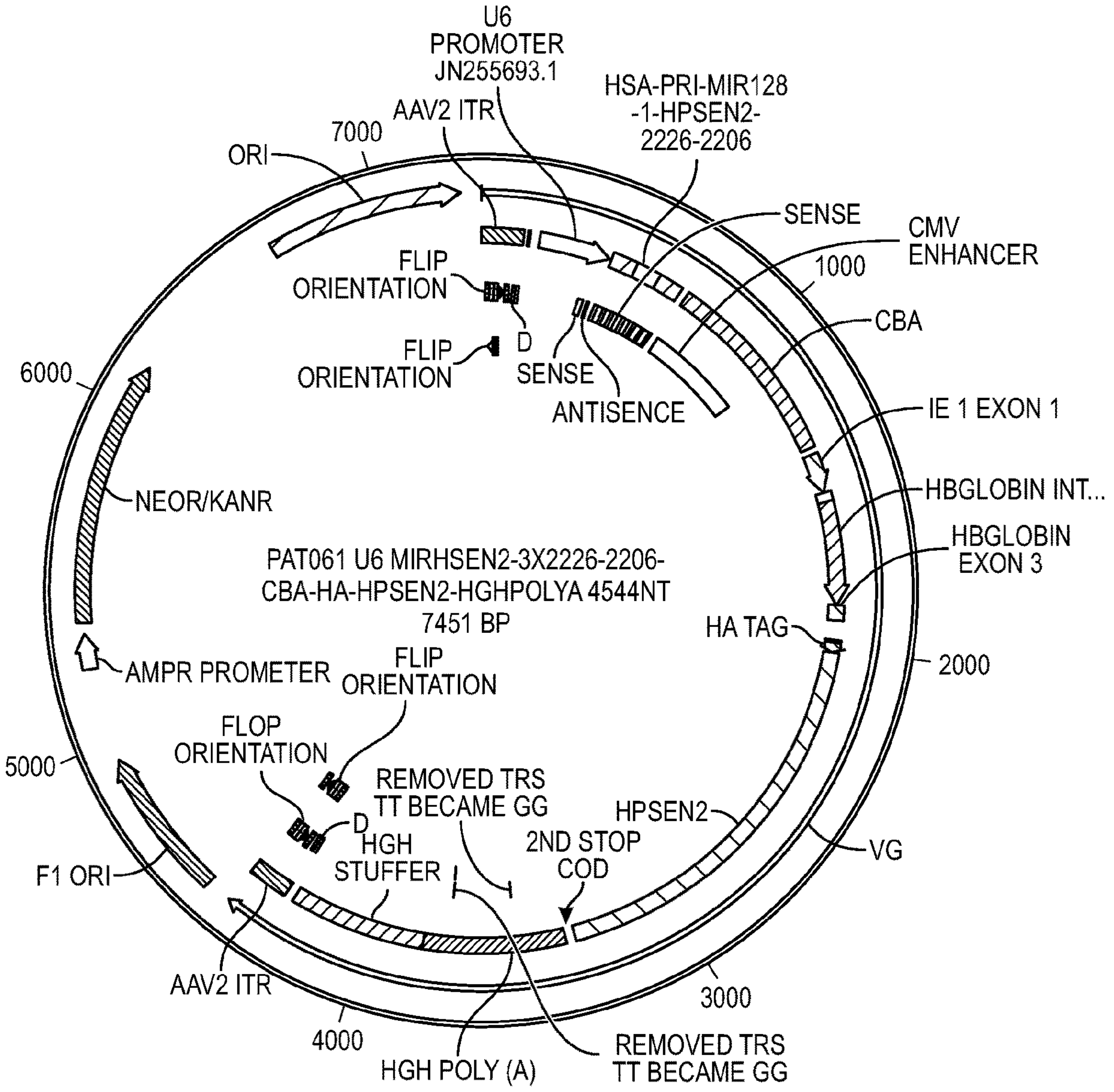
Figure 14:
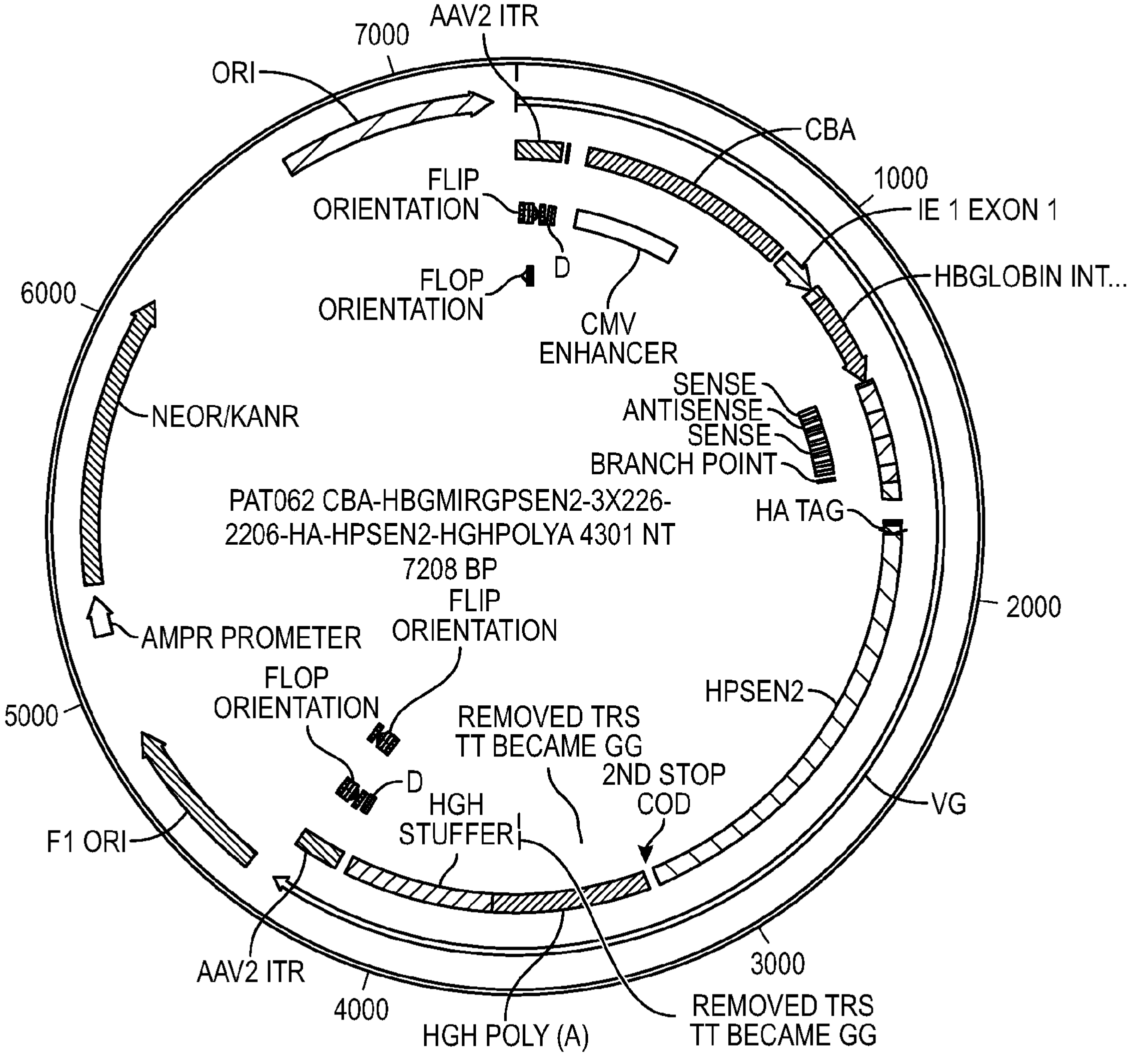

FIG. 1 is plasmid map of pAT049.
FIG. 2 is plasmid map of pAT050.
FIG. 3 is plasmid map of pAT051.
FIG. 4 is plasmid map of pAT052.
FIG. 5 is plasmid map of pAT053.
FIG. 6 is plasmid map of pAT054.
FIG. 7 is plasmid map of pAT055.
FIG. 8 is plasmid map of pAT056.
FIG. 9 is plasmid map of pAT057.
FIG. 10 is plasmid map of pAT058.
FIG. 11 is plasmid map of pAT059.
FIG. 12 is plasmid map of pAT060.
FIG. 13 is plasmid map of pAT061.
FIG. 14 is plasmid map of pAT062.

Figure 15:
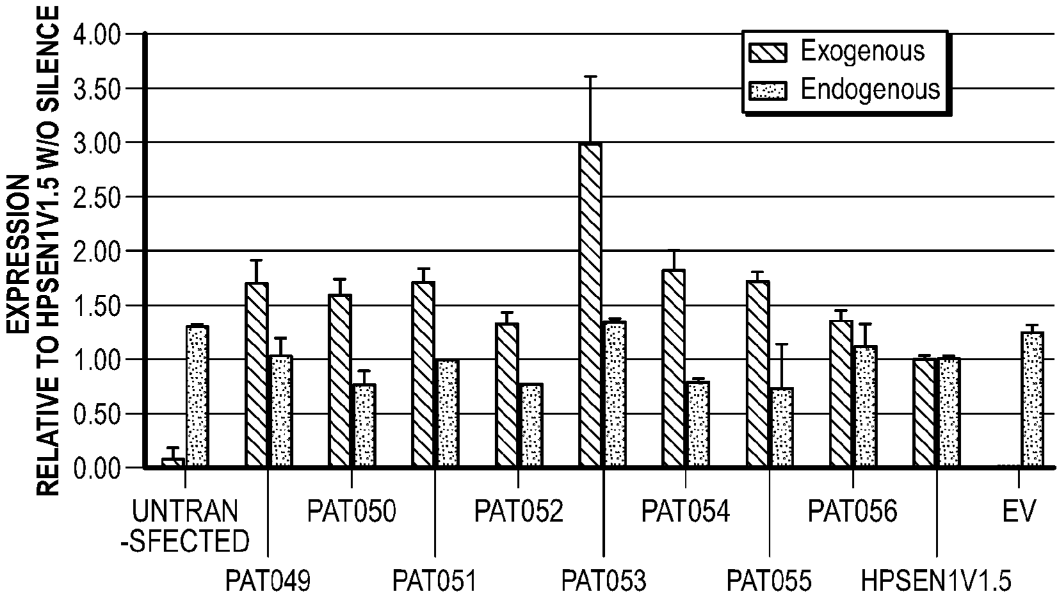

FIG. 15 is a bar graph representing the levels of endogenous PSEN1 (white bars) and plasmid-encoded (exogenous) PSEN1 transcripts (black bars) in HEK293 cells after transfection with different plasmids encoding exogenous PSEN1 and a miRNA targeting sequence that specifically hybridizes to endogenous PSEN1. Exogenous and endogenous transcript levels are compared to untrasnsfected cells, treatment with an empty vector (EV), and treatment with a vector encoding exogenous PSEN1 without any miRNA as controls.

Figure 16A:
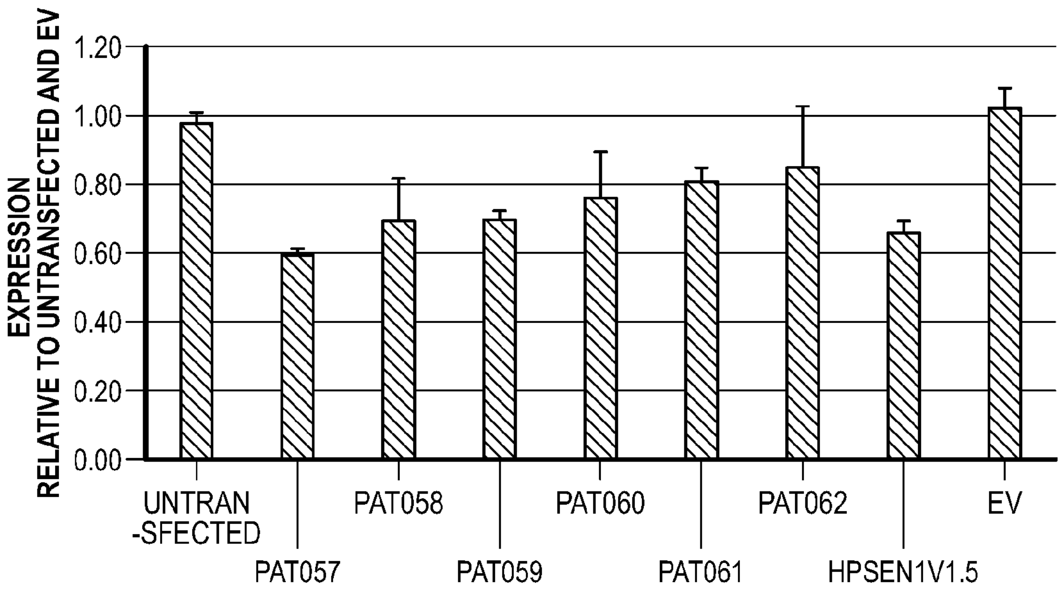
Figure 16B:
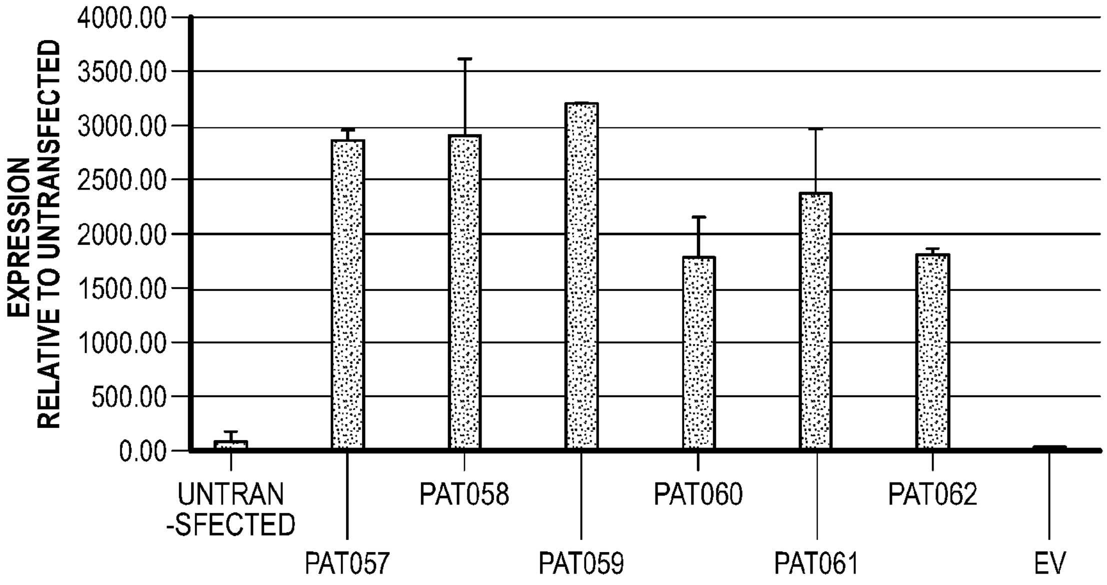

FIGS. 16A and 16B are bar graphs representing the levels of endogenous PSEN1 (FIG. 16A) and plasmid-encoded (exogenous) PSEN2 (FIG. 16B) transcripts in HEK293 cells after transfection with different plasmids encoding exogenous PSEN2 and a miRNA targeting sequence that specifically hybridizes to endogenous PSEN2. Exogenous and endogenous transcript levels are compared to untrasnsfected cells, and treatment with an empty vector (EV).

DEFINITIONS

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used. It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element. Thus, recitation of "a cell", for example, includes a plurality of the cells of the same type. Furthermore, to the extent that the terms "including", "includes", "having", "has", "with", or variants thereof are used in either the detailed description and/or the claims, such terms are intended to be inclusive in a manner similar to the term "comprising."

"About" as used herein when referring to a measurable value such as an amount, a temporal duration, and the like, is meant to encompass variations of +/−20%, +/−10%, +/−5%, +/−1%, or +/−0.1% from the specified value, as such variations are appropriate to perform the disclosed methods. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

As used herein, the term "antisense oligonucleotide" means an RNA or a single or double-stranded DNA molecule at least part of which binds to another RNA or DNA (target RNA, DNA) through hybridization. The portion of an antisense oligonucleotide that hybridizes to its target is term the "antisense portion". For example, if the antisense oligonucleotide is an RNA oligonucleotide, the antisense portion thereof binds to another RNA target by means of RNA-RNA interactions and alters the activity of the target RNA. The antisense oligonucleotides used herein downregulate expression of PSEN1 or PSEN2. The term "antisense oligonucleotide" is meant to include, for example, antisense RNA or DNA molecules, interference RNA (RNAi), micro interfering RNA (miRNA), siRNA, short hairpin RNA (shRNA), external guide sequence (EGS) oligonucleotides, alternate splicers, and any of the foregoing that comprise one or more modified nucleobases. As such, these compounds may be introduced in the form of single-stranded, double-stranded, partially single-stranded, or circular oligomeric compounds.

An antisense oligonucleotide is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

"Complementary," as used herein, refers to the capacity for precise pairing between two nucleotides on one or two oligomeric strands. For example, if a nucleobase at a certain position of an antisense oligonucleotide is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligomeric oligonucleotide and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which are used to indicate a sufficient degree of precise pairing or complementarity over a sufficient number of nucleotides such that stable and specific binding occurs between the oligomeric compound and a target nucleic acid.

It is understood in the art that the sequence of an antisense oligonucleotide need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The antisense oligonucleotides of the present invention typically contain no more than 4, no more than 3, no more than 2, no more than 1, or no mismatches with the portion of the PSEN1 or PSEN2 nucleic acid sequence to which they are targeted.

The term "mismatch" as used herein refers to: 1) the inability of a nucleotide in an antisense portion of an antisense oligonucleotide to base pair with its target mRNA or vice versa; or 2) the inability of a nucleotide in an antisense portion of an antisense oligonucleotide to base pair with its sense portion in that antisense oligonucleotide. The antisense portion of an antisense oligonucleotide may have a mismatch with its target mRNA or sense portion due to a substitution, deletion or addition of a nucleotide. Each nucleotide that is substituted, deleted, or added is considered a separate mismatch.

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

The term "expression" as used herein is defined as the transcription of a mRNA from a DNA sequence driven by a promoter and/or translation of a particular amino acid sequence from a mRNA sequence.

As used herein, the term "expression cassette" refers to a DNA sequence that encodes and is capable of producing one or more desired expression products (RNA or protein). Production of such a desired expression product requires the presence of various expression control sequences operatively linked to the DNA sequence encoding that product. Such control sequences include a promoter, as well as other non-coding nucleotide sequences. An expression cassette may include none, some or all of these expression control sequences. If some or all of these expression control sequences are absent from the expression cassette, they are supplied by a vector into which the expression cassette is inserted.

As used herein, a "subject" means a human. The terms, "patient", "individual" and "subject" are used interchangeably herein. A subject can be one who has been previously diagnosed with or identified as suffering from or having a condition in need of treatment (e.g., brain tumors) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. A "subject in need" of treatment for a particular condition, e.g. a neurodegenerative condition, can be a subject suspected of having that condition, diagnosed as having that condition, already treated or being treated for that condition, not treated for that condition, or at risk of developing that condition.

The term "polynucleotide" as used herein means a sequence of 20 or more nucleotides. A polynucleotide may RNA, DNA or a hybrid RNA or DNA molecule; and may be single stranded or double stranded. In certain embodiments, a polynucleotide is a single or double-stranded DNA molecule.

The term "target" and various forms thereof (e.g., "targeted", "targeting") with respect to a nucleic acid sequence e.g. a mRNA encoded by PSEN1 or PSEN2, means a portion of that nucleic acid sequence to which an antisense oligonucleotide is designed to specifically hybridize resulting in reduced or eliminated expression of that nucleic acid sequence.

The term "wild-type" with respect to PSEN1 means the amino acid sequence encoded by SEQ ID NO:39, whether present endogenously within the subject or encoded by a polynucleotide administered to the subject. The term "wild-type" with respect to PSEN2 means the amino acid sequence encoded by SEQ ID NO:40, whether present endogenously within the subject or encoded by a polynucleotide administered to the subject.

The term "endogenous" as used herein means a form of a gene, or mRNA that is naturally found in a human subject. An endogenous gene or mRNA encoding PSEN1 or PSEN2 includes sequences encoding wild-type PSEN1 or PSEN2, as well as those encoding mutant forms of PSEN1 or PSEN2 that are naturally found in a human subject.

The term "regulatory element" refers to a non-coding portion of a polynucleotide or vector that is necessary for and/or enhances expression of a coding portion of that polynucleotide. Examples of regulatory elements include, without limitation, promoters, enhancers, polyadenylation signals, chromatin insulators, translation initiation sequences such as strong and weak Kozak signal sequences and internal ribosomal entry sites, mRNA stability sequences, sequences that influence mRNA processing such as splicing and cleavage, sequences that influence mRNA export from the nucleus and/or mRNA retention, posttranslational response elements, non-coding sequences such as introns and untranslated regions (UTRs), poly A sequences, repressors, silencers, terminators, and others.

As used herein, "operably linked," "operable linkage," "operatively linked," or grammatical equivalents thereof refer to juxtaposition of genetic elements, e.g., typically a polynucleotide encoding an expression product, i.e., a protein or RNA, and a non-coding regulatory element, wherein the elements are in a relationship permitting them to operate in the expected manner. For example, a promoter is "operably linked" to a polynucleotide encoding a desired expression product when they are juxtaposed with respect to one another such that promoter can drive expression of the polynucleotide.

The term "codon modified" as used herein means a DNA or RNA sequence encoding the same amino acid sequence as a naturally occurring protein (i.e., wild-type PSEN1 or wild-type PSEN2), wherein, due to the redundancy of the genetic code, at least one codon has been altered as compared to the endogenous DNA or RNA encoding that protein.

The term "codon optimized" as used herein means a codon modified DNA or RNA sequence, wherein the modified codons are selected from the preferred codons or most preferred codons set forth in Table 1.

Where any amino acid sequence is specifically referred to by a Swiss Prot. or GENBANK Accession number, the sequence is incorporated herein by reference. Information associated with the accession number, such as identification of signal peptide, extracellular domain, transmembrane domain, promoter sequence and translation start, is also incorporated herein in its entirety by reference.

Genes: All genes, gene names, and gene products disclosed herein are intended to correspond to human homologs or mutated forms for which the compositions and methods disclosed herein are applicable.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DETAILED DESCRIPTION

The present disclosure provides compositions that comprise (1) antisense oligonucleotides (or polynucleotides that encode them) for silencing endogenous forms of PSEN1 and/or PSEN2 mRNA; and (2) polynucleotides that encode wild-type PSEN1 and/or PSEN 2 to replace the corresponding silenced forms of those proteins, as well as methods that utilize such compositions for treatment of neurodegenerative disorders such as Alzheimer's disease.

Polynucleotides

In certain embodiments, each of the antisense oligonucleotide and the wild-type PSEN1 and/or PSEN2 are encoded by polynucleotides. Polynucleotides encoding antisense oligonucleotides are typically shorter in length than polypeptides encoding wild-type PSEN1 and/or PSEN2 and can be synthesized in the laboratory, for example, using an automatic synthesizer, created from other, pre-existing polynucleotides using standard molecular biology and cloning techniques, or a combination of both synthesis and cloning. Polynucleotide encoding wild-type PSEN1 and/or PSEN2 and can also be synthesized in the laboratory, for example, using an automatic synthesizer, created from other, preexisting polynucleotides using standard molecular biology and cloning techniques, obtained from nucleic acid sequences present in, for example, a mammal such as a human (e.g., as a genomic fragment or as a cDNA reverse-transcribed from a naturally occurring or synthetic mRNA), or any combination of the foregoing. Moreover, any desired changes (i.e., codon modification) in a polynucleotide originally obtained or created from a natural source can be obtained by standard molecular biological techniques such as site-directed mutagenesis or removal and replacement of a portion of the original polynucleotide. One of ordinary skill in the molecular biology art can create the polynucleotides utilized in the present invention without undue experimentation using standard tools and protocols.

The polynucleotides of the present disclosure can be isolated prior to use or insertion into an expression cassette and/or vector. An isolated polynucleotide includes a naturally-occurring polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules.

Unless otherwise indicated, the term polynucleotide or gene includes reference to the specified sequence as well as the complementary sequence thereof.

Antisense Oligonucleotides

The antisense oligonucleotides utilized in the present expression cassettes, vectors, and methods disclosed herein are designed to hybridize to and prevent expression of endogenous PSEN1 or PSEN2 mRNA. As stated above, endogenous PSEN1 or PSEN2 mRNA includes both wild-type forms and naturally occurring mutant forms. It will be readily apparent to those of skill in the art that an antisense portion of an antisense oligonucleotide that is perfectly complementary to a target region of wild-type PSEN1 mRNA will necessarily have one or more mismatches to a mutant PSEN1 mRNA having mutation(s) that occur in the target region. While up to 4 mismatches can be tolerated and still cause reduced expression of a target mRNA, perfect complementarity increases the chance of full inhibition of mRNA expression. For this reason, in some embodiments, at least one antisense oligonucleotides has an antisense region that has perfect complementarity to a portion wild-type PSEN1 mRNA; and at least one antisense oligonucleotides has an antisense region that has perfect complementarity to a portion of the mutant PSEN1 mRNA present in a subject to whom the antisense oligonucleotide will be delivered. It should be understood that if an antisense oligonucleotide targets a region of PSEN1 mRNA which is not endogenously mutated, the antisense portion of that antisense oligonucleotide will have perfect complementarity to the corresponding region of both the wild-type and mutant form found in a subject. If the antisense portion of an antisense oligonucleotide targets a region of PSEN1 mRNA which comprises a mutation, then two or more antisense oligonucleotides, each targeting different regions of the PSEN1 mRNA, must be employed to obtain perfect complementarity with both the wild-type and mutant PSEN1 mRNAs. In some embodiments, two or more antisense oligonucleotides are employed even if one is capable of perfect complementarity with both wild-type and mutant PSEN1 mRNAs.

In some embodiments, the antisense oligonucleotides of the disclosure are encoded by a polynucleotide that is expressed in a subject (i.e., using gene therapy). In such embodiments, the antisense oligonucleotides are produced by expression of a DNA polynucleotide encoding the antisense oligonucleotide, which is present on a vector administered to a subject. Such encoded antisense oligonucleotides include shRNAs, and miRNAs.

In some embodiments, the antisense oligonucleotides of the disclosure are created ex vivo and administered directly to a subject. Method for direct delivery of such oligonucleotides are known in the art and include the use of lipid-based nanoparticles (i.e., liposomes, solid lipid nanoparticles, nanostructure lipid carriers), polymer-based delivery systems (i.e., cationic polymers such as natural DNA-binding proteins, synthetic polypeptides, poly-ethylenimine, and carbohydrate-based polymers such as chitosan), lipid-polymer hybrid nanoparticles, exosomes, and high-density lipoproteins. Such directly administered antisense oligonucleotides include dsRNAs, miRNAs, dsRNA, external guide sequence (EGS), alternate splicers, and any antisense oligonucleotide comprising one or more non-natural nucleobases. Examples of such directly delivered antisense oligonucleotides that target PSEN1 mRNA are those that comprise an RNA sequence encoded by any one of: a) SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:33, SEQ ID NO: 35, SEQ ID NO:42, SEQ ID NO:43, SEQ ID NO:44, SEQ ID NO:45, SEQ ID NO: 46, SEQ ID NO:47, nucleotides 448-529 of SEQ ID NO:68, nucleotides 448-529 of SEQ ID NO:69, nucleotides 448-529 of SEQ ID NO:70, or nucleotides 448-529 of SEQ ID NO:71; b) a modified version of any of the foregoing SEQ ID NOs, wherein the modification is 1, 2, 3, or 4 nucleotide changes; or c) a 19-21 base nucleotide sequence comprising Tor more consecutive bases taken from the 5' or 3' end of any of the foregoing SEQ ID NOs or the modified version thereof, wherein the 19-21 base nucleotide sequence comprises no more than 4 mismatches with a corresponding portion of an endogenous PSEN1 mRNA. Examples of such directly delivered antisense oligonucleotides that target PSEN2 mRNA are those that comprise an RNA sequence encoded by any one of: a) SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:34, SEQ ID NO: 36, nucleotides 448-529 of SEQ ID NO:76, nucleotides 448-529 of SEQ ID NO:77, or nucleotides 448-529 of SEQ ID NO:78; b) a modified version of any of the foregoing SEQ ID NOs, wherein the modification is 1, 2, 3, or 4 nucleotide changes; or c) a 19-21 base nucleotide sequence comprising 7 or more consecutive bases taken from the 5' or 3' end of any of the foregoing SEQ ID NOs or the modified version thereof, wherein the 19-21 base nucleotide sequence comprises no more than 4 mismatches with a corresponding portion of an endogenous PSEN1 mRNA.

RNA interference (RNAi) induces gene silencing by targeting complementary mRNA for degradation. The first step of RNAi involves processing and cleavage of longer double-stranded RNA into siRNAs, generally bearing a 2 nucleotide overhang on the 3' end of each strand. The enzyme responsible for this processing is an RNase III-like enzyme termed Dicer. When formed, siRNAs are bound by a multiprotein component complex referred to as RISC (RNA-induced silencing complex). Within the RISC complex, siRNA strands are separated and the strand with the more stable 5'-end, termed the guide strand, is typically integrated to the active RISC complex. The loading into RISC is asymmetric and the less thermodynamically stable strand or “passenger strand” is discarded. The guide strand is desirably the antisense strand and various strategies discussed both in the application and known in the art may be employed to favor the antisense strand being selected as the guide strand. The single-stranded siRNA guide strand then guides and aligns the RISC complex on the target mRNA and through the action of catalytic RISC protein, a member of the argonaute family (Ago2), mRNA is cleaved (Dana H, Chalbatani G M, Mahmoodzadeh H, et al. Molecular Mechanisms and Biological Functions of siRNA. *Int J Biomed Sci.* 2017; 13(2).48-57).

A modulator of expression, function and/or stability of the endogenous PSEN1, PSEN2 or mutants of PSEN1 or PSEN2, can be a double-stranded RNA molecule for use in RNA interference, for example a shRNA or a miRNA. RNA interference (RNAi) is a process of sequence-specific gene silencing by post-transcriptional RNA degradation or silencing (prevention of translation). RNAi is initiated by use of double-stranded RNA (dsRNA) that is homologous in sequence to the target gene to be silenced. A suitable double-stranded RNA (dsRNA) for RNAi contains sense and antisense strands of about 21 contiguous nucleotides corresponding to the gene to be targeted that form 19 RNA base pairs, leaving overhangs of two nucleotides at each 3' end (Elbashir et al., *Nature* 411:494-498 (2001); Bass, *Nature* 411:428-429 (2001); Zamore, *Nat. Struct. Biol.* 8:746-750 (2001)). dsRNAs of about 25-30 nucleotides have also been used successfully for RNAi (Karabinos et al., *Proc. Natl. Acad. Sci. USA* 98:7863-7868 (2001). dsRNA also can be synthesized in vitro and introduced into a cell by methods known in the art.

In some embodiments, an siRNA molecule of the present disclosure comprises a sense strand and a complementary, anti-sense strand in which both strands are hybridized together to form a duplex structure and where the start site of the hybridization to the PSEN1 mRNA is between nucleotide 1 to 5999 on the mRNA sequence (which corresponds to the GenBank NM_000021.4 cDNA sequence).

In certain embodiments, an siRNA molecule of the present disclosure comprises a sense strand and a complementary anti-sense strand in which both strands are hybridized together to form a duplex structure and where the start site of the hybridization is between nucleotide 1 to 2230 on the PSEN2 mRNA sequence (GenBank NM_000447).

In some embodiments, the antisense oligonucleotide comprises: ribonucleic acids (RNA), deoxyribonucleic acids (DNA), synthetic RNA or DNA sequences, modified RNA or DNA sequences, complementary DNA (cDNA), short guide RNA (sgRNA), a short interfering RNA (dsRNA), double-stranded DNA (dsDNA), a micro interfering RNA (miRNA), a small, temporal RNA (stRNA), a short hairpin RNA (shRNA), mRNA, nucleic acid sequences comprising one or more modified nucleobases or backbones, or combinations thereof. Another example of an antisense molecule is a double-stranded small interfering RNA (siRNA) or endoribonuclease-prepared siRNA (esiRNA). An esiRNA is a mixture of siRNA oligonucleotides resulting from cleavage of a long double-stranded RNA (dsRNA) with an endoribonuclease such as Escherichia coli RNase III or dicer. esiRNAs are an alternative concept to the usage of chemically synthesized siRNA for RNA Interference (RNAi). An esiRNAs is the enzymatic digestion of a long double stranded RNA in vitro.

Any method or combination of methods can be used to reduce expression of a gene or protein, including knockdown by techniques such as siRNA and antisense oligonucleotides, for example. Silencing polynucleotide molecules such as dsRNA, dsDNA or oligonucleotides of the present disclosure can be chemically synthesized using appropriately protected ribonucleoside phosphoramidites and a conventional RNA synthesizer. Suppliers of RNA synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK).

In some embodiments, the antisense oligonucleotide is a siRNA or a precursor to a siRNA (e.g., a shRNA or a miRNA). An siRNA is double-stranded RNA molecule having a polynucleotide sense strand and a polynucleotide antisense strand. Each strand of the siRNA molecule is from 15 to 30 nucleotides in length. At least 15 nucleotides of the antisense strand (not all of which need be consecutive) should base pair with a portion of endogenous PSEN1 or PSEN2 mRNA. At least a portion of the sense strand is complementary to at least a portion of the antisense strand, and the siRNA molecule has a duplex region of from 15 to 30 nucleotides in length (not all of which need to be consecutive). In some aspects of these embodiments, the duplex region of an siRNA is 19-27 base pairs in length (e.g, 19-21 base pairs, e.g., 19 base pairs) with an additional two nucleotide 3' overhang on each strand. In some aspects of these embodiments, the first nucleotide in the antisense strand is uracil (U). In some aspects of these embodiments, nucleotides 2-8 of the antisense strand have perfect complementarity to a portion of PSEN1 or PSEN2 mRNA. In some aspects of these embodiments, the antisense strand will have 1, 2, 3 or 4 mismatches with the PSEN1 or PSEN2 mRNA it targets. In some aspects of these embodiments, those mismatches are located at up to four of nucleotides 1, 10, 11, and 17-21 of the antisense strand. The antisense strand may also have up to 4 mismatches with the sense strand. This facilitates the in vivo unpairing of the duplex formed between the sense and antisense strand, releasing the antisense strand and enabling it to hybridize to the PSEN1 or PSEN2 mRNA. The design of siRNA molecules and the location of potential mismatches with target mRNA are disclosed in P Angart et al., Pharmaceuticals 2013, 6, pp. 440-68, the disclosure of which is herein incorporated by reference.

In some embodiments the antisense oligonucleotides may be isolated. In another embodiment, the antisense oligonucleotides may be recombinant, synthetic and/or modified, or in any other way non-natural or not a product of nature. As described above, the antisense oligonucleotides of the invention may be modified by use of non-natural nucleotides, or may be conjugated to another chemical moiety. For example, such chemical moieties may be a heterologous nucleic acid conferring increased stability or cell/nucleus penetration or targeting, or may be a non-nucleic acid chemical moiety conferring such properties, of may be a label.

Any nucleotide within an antisense oligonucleotide can be modified by including substituents coupled thereto, such as in a 2' modification. An antisense oligonucleotide can be modified with a diverse group of small molecules and/or conjugates. The antisense oligonucleotides of the disclosure, e.g. dsRNA and dsDNA, may comprise modified nucleotides such as locked nucleic acids (LNAs). The ribose moiety of an LNA nucleotide is modified with an extra bridge connecting the 2' oxygen and 4' carbon. The bridge “locks” the ribose in the 3'-endo (North) conformation, which is often found in the A-form duplexes. LNA nucleotides can be mixed with DNA or RNA residues in the oligonucleotide whenever desired. Such oligomers are synthesized chemically and are commercially available. The locked ribose conformation enhances base stacking and backbone pre-organization. This significantly increases the hybridization properties (melting temperature) of oligonucleotides.

In certain embodiments, the antisense oligonucleotide is a shRNA or miRNA. In certain embodiments, the antisense oligonucleotide is a shRNA or miRNA targeting either a coding region or a non-coding region of an mRNA translated from a human wild-type or mutant presenilin 1. In certain embodiments, the antisense oligonucleotide is a shRNA or miRNA targeting either a coding region or a non-coding region of an mRNA translated from a human wild-type or mutant presenilin 2.

As an example, knockdown by siRNAs derived from shRNAs or miRNAs can be combined with any other method to reduce gene or protein expression by a desired amount. In some embodiments, expression of endogenous PSEN1 is reduced by at least about 10%, 20%, 30%, 40%, 50%, 60%, 70%, 80%, 90%, 91%, 92%, 93%, 94%, 95%, 96%, 97%, 98%, 99%, 99.1%, 99.2%. 99.3%, 99.4%, 99.5%, 99.6%, 99.7%, 99.8%, 99.9% or 100% as compared to expression of the endogenous PSEN1 in untreated cells. In some aspects of these embodiments, expression of endogenous PSEN1 is reduced by at least 50%. In some aspects of these embodiments, expression of endogenous PSEN1 is reduced by at least 90%. In some aspects of these embodiments, endogenous PSEN1 expression (wild type and any mutant forms) is completely eliminated by the derived siRNAs.

In some embodiments, expression of endogenous PSEN2 is reduced by at least about 10%, 20%, 30%, 40%, 50%, 60%, 70%, 80%, 90%, 91%, 92%, 93%, 94%, 95%, 96%, 97%, 98%, 99%, 99.1%, 99.2%. 99.3%, 99.4%, 99.5%, 99.6%, 99.7%, 99.8%, 99.9% or 100% as compared to expression of the endogenous PSEN2 in untreated cells. In some aspects of these embodiments, endogenous PSEN1 expression (wild type and any mutant forms) is completely eliminated by the derived siRNAs.

Short Hairpin RNAs (shRNAs). In certain embodiments, the antisense oligonucleotide is a short hairpin RNA (shRNA). Short hairpin RNAs comprise an antisense portion, a substantially complementary sense portion and a short spacer in between that forms a loop between the duplex that forms between the substantially complementary antisense and sense strands. The loop (or hairpin) is recognized and cleaved in vivo by Dicer to generate a double stranded siRNA molecule.

Micro-RNA's. In some embodiments, therapeutic compositions and methods described herein take advantage of the miRNA pathway by altering the seed sequence of natural pri-miRNA or pre-miRNA clusters to target the endogenous PSEN1 or PSEN2 mRNA. The hairpin containing pri-miRNAs are successively cleaved by two RNase III enzymes, Drosha in the nucleus and Dicer in the cytoplasm, to yield ~70 nucleotides pre-miRNA and 21-23 nucleotides miRNAs respectively. The pre-miRNA is transported to the cytoplasm via Exportin-5 and further processed by Dicer to produce a short, partially double-stranded siRNA, in which one strand comprises the antisense portion and is preferably used as the miRNA guide strand.

In certain embodiments, the silencing polynucleotide is a micro-RNA (miRNA) or pre-micro-RNA (pre-miRNA) both referred as miRNA throughout this application. In some embodiments, the first polynucleotide encodes one, two or three miRNAs or pre-miRNAs to suppress expression of PSEN1, PSEN2 or the combination thereof. Pre-miRNAs and miRNAs contains a 19-25 nucleotide long RNA sequence that binds to complementary sequences in PSEN1 or PSEN2 mRNA and down-regulate gene expression either by reducing nucleic acid molecule stability or by inhibiting translation. A miRNA or pre-miRNA sequence comprises a "seed" region, i.e., a sequence in the region of positions 2-7 at the 5' end of the mature microRNA, which sequence has perfect Watson-Crick complementarity to the PSEN1 or PSEN2 mRNA target sequence. A miRNA or pre-miRNA will also have additional nucleotides that base pair with the PSEN1 or PSEN2 mRNA target sequence. miRNA mediated down-regulation of gene expression may be caused by cleavage of the target mRNAs, translational inhibition of the target mRNAs, or mRNA decay. miRNA targeting sequences are usually located in the 3'-UTR of the target mRNAs. An endogenous PSEN1 or PSEN2 mRNA may be targeted by more than one miRNAs. In some aspects of these embodiments, the polynucleotide encoding one or more miRNAs or pre-miRNAs is located within an intron of a polynucleotide sequence or an expression cassette.

In some embodiments, therapeutic compositions and methods described herein take advantage of the miRNA pathway by altering the seed sequence of natural miRNAs to target the endogenous PSEN1 or PSEN2 genes. In one embodiment, the shRNA or miRNA targeting the PSEN1 or PSNE2 mRNA comprise a miRNA seed match for the guide strand. In another embodiment, the siRNA duplexes or encoded dsRNA targeting the PSEN1 or PSNE2 mRNA comprise a miRNA seed match for the passenger strand.

In one embodiment, portion of the 3' stem arm of the shRNA or miRNA targeting the PSEN1 or PSEN2 mRNA may have partial complementarity to portion of the passenger strand in the 5' stem arm.

In one embodiment, the antisense strand of the shRNA or miRNA biding to Dicer and targeting the PSEN1 or PSEN2 mRNA will be more highly favored as the guide strand as compared to the sense strand (which will be favored to be the passenger strand). In one embodiment, the sense strand portion of a shRNA or miRNA is engineered with 1, 2, 3 or 4 mismatches to the antisense portion in order to favor antisense strand loading into RISC as the guide strand.

A shRNA or miRNA is an RNA molecule having a first region, a loop or hairpin region, and a second region. The first and second region can be substantially complementary to each other. In some embodiments, the first and second region are perfectly complementary to each other. Thus, shRNAs and miRNAs can have a stem-loop structure. As used herein the terms "complementary" and "complementarity" are meant to refer to the ability of polynucleotides to form base pairs with one another. Base pairs are typically formed by hydrogen bonds between nucleotides in antiparallel polynucleotide strands. Complementary polynucleotide strands can base pair in the Watson-Crick manner (e.g., A to T, A to U, C to G), or in any other manner that allows for the formation of duplexes. As persons skilled in the art appreciate, when using RNA as opposed to DNA, uracil rather than thymine is the base that is considered to be complementary to adenosine.

Perfect complementarity or 100% complementarity refers to a situation in which each nucleotide of one polynucleotide strand can hydrogen bond with a nucleotide of an antiparallel polynucleotide strand. Less than perfect complementarity refers to a situation in which some, but not all, nucleotides of two strands can hydrogen bond with each other. For example, for two 20-mers, if only two base pairs on each strand can hydrogen bond with each other, the polynucleotide strands exhibit 10% complementarity. As another example, if 18 nucleotides out of 20 nucleotides on each strand can hydrogen bond with each other, the polynucleotide strands exhibit 90% complementarity. "Substantial complementarity" refers to polynucleotide strands exhibiting 79% or greater complementarity, excluding regions of the polynucleotide strands, such as overhangs, that are selected to be non-complementary. Accordingly, complementarity does not consider overhangs that are selected to not be similar or complementary to the nucleotides on the anti-parallel strand, unless context clearly indicates otherwise.

The loop of an shRNA and miRNAs can be about 4 to 30 nucleotides in length. In some embodiments, the loop can be between about 4 and about 15 nucleotides in length. The first and the second region can be between about 19 and about 35 nucleotides in length. In some embodiments, the first and the second region are 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, or 30 nucleotides in length. The first and the second region can be of the same length or can be of different lengths. The lengths of the first and the second region can differ by 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, or more. Differences in length can appear as a bulge or as an overhang.

A shRNA and miRNA can be organized in a 5'-antisense-loop-sense-3' fashion or in a 5'-sense-loop-antisense-3' fashion. As used herein, the term “antisense strand” refers to a polynucleotide or region of a polynucleotide that is at least substantially (e.g., about 80% or more) complementary to a target nucleic acid of interest. The antisense strand can be about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and any number or range in between, complementary to a target nucleic acid of interest. Similarly, an antisense strand of a dsRNA can be at least substantially complementary to its sense strand.

The shRNA and miRNA antisense oligonucleotides can include nucleotides in addition to the antisense region, sense region and loop or linker region. For example, these antisense oligonucleotides can also contain overhang nucleotides and additional stem nucleotides that are complementary to other stem nucleotides, but not complementary to the target. The antisense and sense regions of a shRNA or miRNA can include mismatches (i.e., are not perfectly complementary). For example, a sense and an antisense region can have 1 mismatch, 2 mismatches, 3 mismatches, 4 mismatches, 5 mismatches, or more mismatches. Mismatches can be contiguous or can be located anywhere along the sense and antisense regions. Mismatches between a sense and antisense region can result in a bulge. In some embodiments, an antisense region can have perfect complementarity to the sense region. In some embodiments, and antisense and sense region of a shRNA or miRNA have at The degree of complementarity between the antisense portion of the shRNA or miRNA and the target region of the PSEN1 or PSEN2 mRNA is important in determining the degree to which that mRNA is silenced. In certain embodiments, the antisense portion of the shRNA or miRNA is perfectly complementary to a portion of the PSEN1 or PSEN2 mRNA. This typically results in degradation of the PSEN1 or PSEN2 mRNA with no endogenous protein production. In certain embodiments, the mRNA binding portion of the shRNA or miRNA comprises 1, 2, 3 or 4 mismatches with the target region of PSEN1 or PSEN2 mRNA. One or more mismatches between an antisense region and a target mRNA can result in translational repression rather than degradation of the target mRNA. The mRNA binding targets can be in any region of the PSEN1 or PSEN2 mRNA. In certain embodiments, the sequence targeted by shRNA comprises a GC content from about 30% to about 50% GC. In certain embodiments, the targeted sequence comprises 4 or less consecutive T residues. It should be understood that in a shRNA or miRNA the antisense region can have perfect complementarity to the sense region, but have 1, 2, 3, or 4 mismatches with respect to the target mRNA. Similarly, the antisense region can have mismatches with the sense region of a shRNA or miRNA, while the antisense region has prefect complementarity to the target mRNA.

In some embodiments, therapeutic compositions and methods described herein take advantage of combining 1, 2, 3, 4, 5 or 6 pri-miRNAs or pre-miRNAs under the same promoter to target the endogenous PSEN1 or PSEN2 mRNA at various sites. The target site sequence may comprise a total of 5-100, or more nucleotides, which need not be contiguous.

Expression of shRNAs can be driven by a RNA pol II or III promoter. Exemplary RNA pol III promoters include a U6 promoter, a U61 promoter, a U69 promoter, a H1 promoter, and others. Transcription from a RNA pol III promoter can terminate at a poly T stretch, such as 5 Ts or 6 Ts, for example. shRNAs can also be expressed using a RNA pol II promoter. Use of an RNA pol II promoter can allow for specific and inducible expression, for example.

In certain embodiments, the first polynucleotide encoding a shRNA or miRNA comprises a sequence set forth in any one of SEQ ID NOs:1-36 or 44-47. In some embodiments, the first polynucleotide encoding a shRNA or miRNA comprises a sequence that has 1, 2, 3 or 4 different nucleotides in the antisense region as compared to any one of SEQ ID NOs:1-36 or 44-47.

In certain embodiments, the first polynucleotide encoding a shRNA or miRNA comprises a nucleotides 497-517 of SEQ ID NO:68, nucleotides 497-517 of SEQ ID NO:69, nucleotides 497-517 of SEQ ID NO:70, nucleotides 497-517 of SEQ ID NO:71, nucleotides 497-517 of SEQ ID NO:76, nucleotides 497-517 of SEQ ID NO:77, or nucleotides 497-517 of SEQ ID NO:78. In some embodiments, the first polynucleotide encoding a shRNA or miRNA comprises a sequence that has 1, 2, 3 or 4 different nucleotides in the antisense region as compared to any one of nucleotides 497-517 of SEQ ID NO:68, nucleotides 497-517 of SEQ ID NO:69, nucleotides 497-517 of SEQ ID NO:70, nucleotides 497-517 of SEQ ID NO:71, nucleotides 497-517 of SEQ ID NO:76, nucleotides 497-517 of SEQ ID NO:77, or nucleotides 497-517 of SEQ ID NO:78.

In certain embodiments, the first polynucleotide encoding a shRNA or miRNA comprises a nucleotides 448-529 of SEQ ID NO:68, nucleotides 448-529 of SEQ ID NO:69, nucleotides 448-529 of SEQ ID NO:70, nucleotides 448-529 of SEQ ID NO:71, nucleotides 448-529 of SEQ ID NO:76, nucleotides 448-529 of SEQ ID NO:77, or nucleotides 448-529 of SEQ ID NO:78. In some embodiments, the first polynucleotide encoding a shRNA or miRNA comprises a sequence that has 1, 2, 3 or 4 different nucleotides in the antisense region as compared to any one of nucleotides 448-529 of SEQ ID NO:68, nucleotides 448-529 of SEQ ID NO:69, nucleotides 448-529 of SEQ ID NO:70, nucleotides 448-529 of SEQ ID NO:71, nucleotides 497-517 of SEQ ID NO:76, nucleotides 497-517 of SEQ ID NO:77, or nucleotides 497-517 of SEQ ID NO:78.

It should be understood by those of skill in the art, that in some embodiments, the shRNA or miRNA will be encoded on the same vector that encodes the replacement PSEN1 or PSEN2. The location of the shRNA or miRNA target encoding sequences in that vector can vary (e.g., they can be located 5' or 3' to the sequence encoding the replacement PSEN1 or PSEN2), as long as it does not disrupt the expression of the replacement PSEN1 or PSEN2. Multiple copies of the sequences encoding the shRNA or miRNA target sequences may be utilized (e.g., 2, 3, 4, 5, 6, 7, 8, 9, or 10 copies). When multiple copies are present, they may be located in tandem or placed at different locations with respect to the encoded PSEN1 or PSEN2 replacement sequence. When miRNA target encoding sequences are utilized, they may encode targeting sequences for a single miRNA or multiple miRNAs (e.g., 2, 3, 4 or 5 different miRNAs). Thus, in some embodiments, when miRNA target encoding sequences encoding targeting sequences for multiple miRNAs are utilized, 1, 2, 3, 4, or 5 copies of each specific miRNA target encoding sequences may be used.

Codon Modification

The polynucleotides encoding replacement PSEN1 or PSEN2 can be modified to prevent targeting of the mRNA transcribed therefrom by antisense oligonucleotides targeting endogenous PSEN1 or PSEN2. This can prevent mRNA degradation and RNA silencing or knockdown of the replacement PSEN1 or PSEN2 coding sequence that would otherwise occur. The redundancy of the genetic code can be used to change codons in a target sequence for antisense oligonucleotides, while preserving the amino acid sequence of the protein expressed from the replacement coding sequence.

An endogenous PSEN1 or PSEN2 mRNA being targeted can have mutations that result in the generation of a mutated protein. One or both alleles of an endogenous PSEN1 or PSEN2 gene can be mutated in a subject. In an embodiment, one allele of an endogenous PSEN1 or PSEN2 gene is wild-type and one allele is mutated. In another embodiment, both alleles are mutated. Any mutation can be present in an endogenous allele, including point mutations, substitutions, insertions, deletions, inversions, missense mutations, nonsense mutations, frameshift mutations, translocations, and others. Mutations can be single nucleotide changes (e.g., one or more point mutation) or can be 1, 2, 3, 4, 5, 6, 7, 8, 9, 10, or more nucleotide changes.

The mutation of an endogenous allele can be a dominant negative mutation. A dominant negative mutation can contribute to development of a disease, disorder, or condition or can contribute to susceptibility to a disease, disorder, or condition. In an embodiment, an endogenous PSEN1 gene is mutated in a subject. Dominant negative mutations of a PSEN1 gene can increase susceptibility to Alzheimer's disease by inhibiting the assembly and function of the gamma secretase, for example. A codon-modified or non-codon modified polynucleotide cDNA encoding PSEN1 can be used to restore wild-type PSEN1 expression. Simultaneously endogenous mutated PSEN1 expression can be reduced by targeting the coding regions or non-coding regions of the endogenous PSEN1 mRNA using one or more small RNAs, for example, one or more shRNAs. In an embodiment, the small RNA is an siRNA derived from a shRNA. In certain embodiments, the PSEN1 gene, the PSEN2 gene or the combination thereof, comprise one or more mutations. A codon-modified or non-codon modified polynucleotide cDNA encoding PSEN1, PSEN2 can be used to restore wild-type PSEN1, PSEN2 or the combination thereof, expression.

Alzheimer's disease (AD) patients with an inherited form of the disease carry mutations in the presenilin proteins (PSEN1-UniProtKB-P49768; PSEN2-UniProtKB -P49810) or in the amyloid precursor protein (APP). These disease-linked mutations result in increased production of the longer form of amyloid-beta (main component of amyloid deposits found in AD brains). AD typically begins with subtle memory failure that becomes more severe and is eventually incapacitating. Other common findings include confusion, poor judgment, language disturbance, agitation, withdrawal, hallucinations, seizures, Parkinsonian features, increased muscle tone, myoclonus, incontinence, and mutism. Familial AD (FAD) characterizes families that have more than one member with AD and usually implies multiple affected persons in more than one generation. Early-onset FAD (EOFAD) refers to families in which onset is consistently before age 60 to 65 years and often before age 55 years. The three clinically indistinguishable subtypes of EOFAD based on the underlying genetic mechanism are: Alzheimer disease type 1 (AD1), caused by mutation of APP (10%-15% of EOFAD); Alzheimer disease type 3 (AD3), caused by mutation of PSEN1, (30%-70% of EOFAD); and Alzheimer disease type 4 (AD4), caused by mutation of PSEN2 (<5% of EOFAD). Presenilins are postulated to regulate APP processing through their gamma-secretase function, an enzyme that cleaves APP. Also, it is thought that the presenilins are involved in the cleavage of the Notch receptor, such that they either directly regulate gamma-secretase activity or themselves are protease enzymes.

Mutated PSEN1s in subjects with early onset of Alzheimer's disease, have been found to include mutations such as substitutions, insertions (ins), deletions (del), inversions, missense, frameshift (fs), exon deletions (Δ) and the like. Examples of such amino acid changes throughout the PSEN1 protein include: Q15H, N32N, R35Q, N39Y, D40del (delGAC), D40del (delACG), R42L, E69D, A79V, V82L, I83_M84del (DelIM, ΔI83/M84, ΔI83/ΔM84), I83T, M84T, M84V, L85P, P88H, P88L, V89L (G>C), V89L (G>T), C92S, V94M, V96F, V97L, T99A, F105C, F105I, F105L, F105V, R108Q, G111V, G111W, L113_I114insT, L113P, L113Q, Y115C, Y115D, Y115H, T116I, T116S, P117T, T116N, T116R, P117A, P117L, P117Q, P117R, P117S, T119I, E120D (A>C), E120D (A>T), E120G, E120K, T122A, E123K, H131R, S132A, L134R, N135D, N135S, N135Y, A136G, A137T, M139I (G>C), M139I (G>A), M139K, M139L, M139T, M139V, V142F, V142I, I143F, I143M, I143N, I143T, I143V, M146I (G>T), M146I (G>C), M146I (G>A), M146L (A>C), M146L (A>T), M146V, T147I, T147P, L150P, L153V, Y154C, Y154N, Y156F, Y156 R157insIY, R157S, Y159F, H163P, H163R, H163Y, A164V, W165C (G>T), W165C (G>C), W165G, L166H, L166P, L166R, L166V, L166del, I167del (TTAdel), I167del (TATdel), I168T, S169del (ΔS169, Ser169del, ΔS170), S169L, S169P, S170F, S170P, L171P, L173F (G>T), L173F (G>C), L173S, L173W, L174del, L174M, L174R, F175del, F175S, F176L, F177L, F177S, S178P, I180N, G183V, E184D, E184G, V191A. I202F, W203C, F205_G206del;insC, G206A, G206D, G206S, G206V, G209A, G209E, G209R, G209V, M210R, S212Y, I213F, I213L, I213T, H214D, H214N, H214R, H214Y, G217D, G217R, L219F, L219P, L219R, R220P, Q222H, Q222P, Q222R, Q223R, L226F, L226R, I227V, I229F, S230I, S230N, S230R, A231P, A231T, A231V, L232P, M233I (G>A), M233I (G>C), M233L (A>C), M233L (A>T), M233T, M233V, L235P, L235R, L235V, F237C, F237I, F237L, I238M, K239N, L241R, T245P, A246E, A246P, L248P, L248R, I249L, L250F, L250S, L250V, Y256N, Y256S, A260V, V261F, V261I, V261L, L262F, L262S, L262V, C263F, C263R, P264L, G266S, P267A, P267L, R269G, R269H, L271V, V272A, V272D, E273A, E273G, T274R, A275V, R278I, R278K, R278S, R278T, E280A, E280G, E280K, L282F, L282R, L282V, F283L, P284L, P284S, A285V, L286P, L286V, T291A, T291P, P303L, K311R, E318G, D333G, R352C, R352 S353insR, T354I, R358Q, A360T, S365A, S365Y, R377M, R377W, G378E, G378V, G378fs, L381F, L381V, G384A, F386I, F386L, F386S, F388L, S390I, S390N, V391F, V391G, L392P, L392V, V393F, G394V, A396T, N405S, I408T, A409T, C410Y, V412I, I416T, G417A, G417S, L418F, L420R, L424F, L424H, L424P, L424R, L424V, A426P, A431E, A431V, P433S, A434C, A434T, L435F, P436Q, P436S, I437V, I439S, I439V, T440del, 869-2A>G, 869-22_869-23ins18 (4E9, 49, deltaE9), I238_K239insI, L171_L172insY, S290C; T291_S319del (ΔE9, Δ9), S290C; T291_S319del A>G (ΔE9, Δ9), S290C; T291_S319del G>A (ΔE9, Δ9), S290C; T291_S319del G>T (ΔE9, Δ9), S290W; S291_R377del (Δ9-10, Delta9-10, p.Ser290_Arg377delinsTrp, g.73671948_73682054del).

In a genetic screening study of familial and sporadic early-onset Alzheimer disease (EOAD), a censoring effect was observed in families of patients carrying the c.772T>C, p.(Leu241Arg), the c.539T>A, p.(Ile180Asn), and the c.710T>G, p.(Phe237Cys) substitutions, while the c.331G>T, p.(Gly111Trp), the c.350C>A, p.(Pro117Gln), and the c.614_616del, p.(Phe205_Gly206delinsCys) mutations occurred de novo. One patient carried the c.1078G>A p.(Ala360Thr) variant (Lanoiselée H M, Nicolas G, Wallon D, et al. APP, PSEN1, and PSEN2 mutations in early-onset Alzheimer disease: A genetic screening study of familial and sporadic cases. *PLoS Med.* 2017; 14(3):e1002270. Published 2017 Mar. 28. doi:10.1371/journal.pmed.1002270). There is a need for screening nonfamilial AD cases and compositions and methods for the treatment of neurodegenerative diseases such as AD, including effective gene and combination therapies.

PSEN2 mutations are associated with variable penetrance and a wide range in the age of disease onset, from 45 to 88 (Bird T D, Levy-Lahad E, Poorkaj P, et al. *Ann Neurol.* 1996; 40(6):932-936. Sherrington R, Froelich S, Sorbi S, et al. *Hum Mol Gen.* 1996; 5(7):985-988). PSEN2 mutations are associated with both EOAD and late-onset Alzheimer disease (LOAD). Only 17 of the 38 are predicted to be disease-causing mutations. Ten of the mutations are not pathogenic and the others are still unclear. Sixteen mutations are located within transmembrane domains. Cell-based studies suggest that four of these mutations, T122P, N141I, M239I, and M239V, cause an increase in the amount of Aβ peptide. The mutations T122R, S130L, and M239I were found to alter calcium signaling. Most of these mutations were discovered in European and African populations. Until now, only four missense mutations were described in Asian populations: Asn141Tyr was associated with EOAD in a Chinese Han family; Gly34Ser was found in a Japanese patient; and Arg62Cys and Va1214Leu were described in the Korean patients (Yan Cai et al., 2015, vol. 10, pages 1163-1172). Two PSEN2 mutations, Glu126fs and Lys306fs, are frameshift mutations, and the others are nonsynonymous substitutions (Lamer A J. *Epilepsy & Behavior.* 2011; 21(1): 20-22).

In certain embodiments the polynucleotide encoding replacement PSEN1 and/or PSEN2 is codon optimized. Codon optimization is a form of codon modification that can be utilized to enhance protein expression for heterologous gene expression. Codon optimization is a method of gene optimization, wherein the synthetic coding sequence is modified to match the "codon usage pattern" for a particular organism. For example, in order to optimize expression of a particular amino acid sequence in a specific organism, one would select the "most frequently used codons" (from a list of degenerate codons for an amino acid), by that organism. Upon codon optimization, the encoded amino acid sequence remains the same but with the DNA sequence encoding the amino acid sequence is different, optimized for that organism. Optimized codons for PSEN1 and PSEN2 coding sequences are shown in the Table below.

TABLE 1

Preferred Optimized Codons

| Amino acid | Most preferred codon | Preferred codon |
|---|---|---|
| A (Alanine) | GCC | GCT, GCA |
| C (Cysteine) | | TGT, TGC |
| D (Aspartate) | | GAT, GAC |
| E (Glutamate) | | GAA, GAG |
| F (Phenylalanine) | | TTT, TTC |
| G (Glycine) | GGC | GGA, GGG |
| H (Histidine) | | CAT, CAC |
| I (Isoleucine) | ATC | ATT |
| K (Lysine) | | AAA, AAG |
| L (Leucine) | CTG | TTG, CTT, CTC |
| M (Methionine) | | ATG |
| N (Asparagine) | | AAT, AAC |
| P (Proline) | | CCT, CCC, CCA |
| Q (Glutamine) | CAG | |
| R (Arginine) | AGA, AGG | CGC, CGG |
| S (Serine) | AGC | TCT, TCC, TCA, AGT |
| T (Threonine) | ACC | ACT, ACA |
| V (Valine) | GTG | GTT, GTC |
| W (Tryptophan) | | TGG |
| Y (Tyrosine) | | TAT, TAC |
| STOP | TGA | TAA |

In some embodiments, the polynucleotide encoding a replacement PSEN1 is nucleotides 1906-3303 of SEQ ID NO:68.

Expression Cassettes

In addition to polynucleotide sequences encoding replacement wild-type PSEN1 and/or PSEN2 that are resistant to silencing by an antisense oligonucleotide (and in certain embodiments, polynucleotide sequences encoding such antisense oligonucleotides), the expression cassettes provided herein may contain certain non-coding regions that are integral to the function of cells, particularly the control of gene activity. These are termed regulatory elements. It should be apparent to those of skill in the art, that some or even all of these non-coding regions may alternatively be provided in the vector into which the expression cassette is inserted. Regardless of the location of these non-coding sequences (expression cassette or vector), they must be operably linked to the polynucleotide sequence encoding the antisense oligonucleotide and the polynucleotide sequence encoding the replacement PSEN1 or PSEN2 coding sequence.

The role of these noncoding sequence varies. For example, noncoding DNA contains sequences that act as regulatory elements, including the transcriptional and translational regulation of protein-coding sequences, origins of DNA replication, centromeres, telomeres, scaffold attachment regions (SARs), genes for functional RNAs. Noncoding DNA contains many types of regulatory elements, such as, for example, promoters, enhancers or silencers which provide binding sites for proteins that repress transcription. Like enhancers, silencers can be found before or after the gene they control or are cis-acting. Insulators provide binding sites for proteins that control transcription in a number of ways. Some prevent enhancers from aiding in transcription (enhancer-blocker insulators). Others prevent structural changes in the DNA that repress gene activity (barrier insulators). Some insulators can function as both an enhancer blocker and a barrier. Non-coding regions can, for example, include a 5' untranslated region ("UTR"), a 3' UTR, or both.

An expression cassette can comprise a polynucleotide comprising a PSEN1 or PSEN2 coding sequence and optionally, regulatory elements preceding (5' non-coding sequences) and following (3' non-coding sequences) the coding sequence that are required for expression of the selected gene product. Thus, an expression cassette can comprise: 1) a promoter sequence; 2) an intron 3) a PSEN1 or PSEN2 coding sequence; and, 4) a 3' untranslated region (i.e., a terminator) that, in eukaryotes, usually contains a polyadenylation site.

Similarly, an expression cassette can comprise a polynucleotide encoding one or more antisense oligonucleotides, e.g., a shRNA, or a miRNA and can comprise regulatory elements preceding (i.e., 5' to) and following (i.e., 3' to) the sequence encoding the shRNA or miRNA that are required for expression. Thus, an expression cassette can comprise, for example: 1) a promoter sequence; 2) an intron 3) a sequence encoding one or more shRNAs or miRNAs; and, 4) a 3' region (i.e., a terminator) that specifies the end of transcription of the RNA. Each shRNA or miRNA can have its own promoter and intron. Alternatively, one promoter can be operably linked to a series of 2, 3, 4, 5, or more shRNAs or miRNAs.

One or more shRNAs or pre-miRNAs can occur in a series that is operably linked to a promoter. Pre-miRNAs or shRNAs occurring in a series means that the pre-miRNAs or shRNAs are arranged together or close together and are all operably linked to one or more 5' promoters. Accordingly, a first polynucleotide can comprise one or more 5' promoters driving miRNA or shRNA expression. In an embodiment, a first polynucleotide comprises one or more miRNAs or shRNAs linked to a single 5' promoter (see, e.g., SEQ ID NO: 37 and SEQ ID NO:38). In another embodiment, a first polynucleotide comprises one or more miRNAs or shRNAs, with each miRNA or shRNA linked to a different 5' promoter (see, e.g., SEQ ID NO: 49). Any number of promoters can drive expression of any number of miRNAs or shRNAs of a first polynucleotide. For example, a 5' promoter can drive one or more miRNAs or shRNAs, and another 5' promoter can drive one or more different miRNAs or shRNAs. Promoters driving expression of different miRNAs or shRNAs or different numbers of miRNAs or shRNAs can be the same or different promoters.

Methods for preparing polynucleotides operably linked to a regulatory element and expressing polypeptides in a host cell are well-known in the art. See, e.g., U.S. Pat. No. 4,366,246. A polynucleotide can be operably linked when it is positioned adjacent to or close to one or more regulatory elements, which direct transcription and/or translation of the polynucleotide.

An expression cassette can be a circular or linear nucleic acid molecule. In some cases, an expression cassette is delivered to cells (e.g., a plurality of different cells or cell types including target cells or cell types and/or non-target cell types) in a vector (e.g., an expression vector).

Regulatory Elements

As stated above, the expression cassettes disclosed herein can include one or more regulatory elements operably linked to a polynucleotide encoding PSEN1 (or PSEN2) or to a polynucleotide encoding an antisense oligonucleotide, such as a shRNA. A regulatory element is a genetic element or polynucleotide that either alone or together with one or more additional regulatory elements influences or modulates expression of a polynucleotide or gene. A regulatory element can facilitate polynucleotide or gene expression, increase polynucleotide or gene expression, decrease polynucleotide or gene expression and/or confer selective polynucleotide or gene expression in a particular cell type or tissue. A regulatory element can influence or modulate polynucleotide or gene expression temporally and/or spatially. As used herein, the term "regulate polynucleotide or gene expression," "influence polynucleotide or gene expression," or "modulate polynucleotide or gene expression" refers to increasing polynucleotide or gene expression, decreasing polynucleotide or gene expression, and/or conferring selective polynucleotide or gene expression. "Regulating polynucleotide or gene expression," "influencing polynucleotide or gene expression," or "modulating polynucleotide or gene expression" can refer to temporal and/or spatial regulation.

Any genetic element that modulates or influences polynucleotide or gene expression can be a regulatory element, including, for example, promoters, enhancers, chromatin insulators, translation initiation sequences such as strong and weak Kozak signal sequences, internal ribosomal entry sites, mRNA stability sequences, sequences that influence mRNA processing such as splicing and cleavage, sequences that influence mRNA export from the nucleus and/or mRNA retention, posttranslational response elements, non-coding sequences such as introns and untranslated regions (UTRs), poly A sequences, repressors, silencers, terminators, and others. Regulatory elements can function to modulate polynucleotide or gene expression at the transcriptional level, at the posttranscriptional level, at the translational level, or any combination thereof. Regulatory elements can increase the rate at which RNA transcripts are produced, increase the stability of RNA produced, increase the rate of protein synthesis from RNA transcripts, prevent RNA degradation and/or increase RNA stability to facilitate protein synthesis, for example. Regulatory elements can be located in an inverted terminal repeat (ITR) sequence or a long terminal repeat (LTR).

Nucleic acid expression cassettes described herein can comprise regulatory elements that regulate or modulate polynucleotide or gene expression at any step, including the transcriptional, posttranscriptional, and translational levels, for example. A regulatory element can regulate or modulate polynucleotide or gene expression at more than one level or function in more than one way to regulate or modulate polynucleotide or gene expression. Thus, a regulatory element can have any function or any combination of the functions described above. For example, a regulatory element can function as an mRNA stabilizing element and modulate, i.e., increase or decrease, translation. As yet another example, a regulatory element can modulate transcription initiation and modulate mRNA stability. A regulatory element can also have a predominant function by which it modulates polynucleotide or gene expression and have one or more additional functions that increase or decrease polynucleotide or gene expression. A regulatory element can comprise a sequence that is located within or overlaps with other regulatory elements that have the same or different functions in modulating polynucleotide or gene expression or that modulate polynucleotide or gene expression at the same or different steps.

Regulatory elements can be derived from coding or non-coding DNA sequences. Regulatory elements derived from non-coding DNA can be associated with genes, e.g., can be found in a gene, such as upstream sequences, introns, 3' and 5' untranslated regions (UTRs), and/or downstream regions. As used herein, the term "upstream" when referring to nucleic acid means 5' relative to another sequence and the term "downstream" means 3' relative to another sequence. The term "upstream" can be used interchangeably with the term "5'" when referring to location of sequences relative to each other, unless context clearly indicates otherwise. The term "downstream" can be used interchangeably with the term "3'" when referring to location of sequences relative to each other, unless context clearly indicates otherwise.

In some embodiments, regulatory elements derived from non-coding DNA sequences are not associated with a gene, e.g., may not be found in a gene. The genomic region from which a regulatory element is derived can be distinct from the genomic region from which an operably linked polynucleotide is derived. In some embodiments, a regulatory element is derived from a distal genomic region or location with respect to the genomic region or location from which the operably linked polynucleotide (such as a cDNA derived from an endogenous gene or an endogenous version of a heterologous gene, for example) is derived. In some embodiments, a regulatory element comprises intron sequences. Intron sequences can include sequences derived from any gene. In some embodiments, the intron sequences are derived from the genomic region from which an operatively linked polynucleotide is derived. For example, the nucleic acid expression cassettes described herein can include introns from an endogenous gene that corresponds to a polynucleotide or that gave rise to a polynucleotide in the form of a cDNA. As another example, nucleic acid expression cassettes described herein can include introns from an endogenous gene that does not correspond to or gave rise to a polynucleotide.

Promoters

A promoter is a nucleotide sequence that is capable of controlling the expression of a coding sequence or gene. Promoters are generally located 5' of the sequence that they regulate. Promoters may be derived in their entirety from a native gene, or be composed of different elements derived from promoters found in nature, and/or comprise synthetic nucleotide segments. Those skilled in the art will readily ascertain that different promoters may regulate expression of a coding sequence or gene in response to a particular stimulus, e.g., in a cell- or tissue-specific manner, in response to different environmental or physiological conditions, or in response to specific compounds. Promoters are typically classified into two classes: inducible and constitutive. A constitutive promoter refers to a promoter that allows for continual transcription of the coding sequence or gene under its control.

An inducible promoter refers to a promoter that initiates increased levels of transcription of the coding sequence or gene under its control in response to a stimulus or an exogenous environmental condition. If inducible, there are inducer polynucleotides present therein that mediate regulation of expression so that the associated polynucleotide is transcribed only when an inducer molecule is present. A directly inducible promoter refers to a regulatory region, wherein the regulatory region is operably linked to a gene encoding a protein or polypeptide, where, in the presence of an inducer of said regulatory region, the protein or polypeptide is expressed. An indirectly inducible promoter refers to a regulatory system comprising two or more regulatory regions, for example, a first regulatory region that is operably linked to a first gene encoding a first protein, polypeptide, or factor, e.g., a transcriptional regulator, which is capable of regulating a second regulatory region that is operably linked to a second gene, the second regulatory region may be activated or repressed, thereby activating or repressing expression of the second gene. Both a directly inducible promoter and an indirectly inducible promoter are encompassed by inducible promoter.

A promoter can be any polynucleotide that shows transcriptional activity in the chosen host organism (e.g., a mammal such as a human). A promoter can be naturally-occurring, can be composed of portions of various naturally-occurring promoters, or may be partially or totally synthetic. Guidance for the design of promoters is derived from studies of promoter structure, such as that of Harley and Reynolds, *Nucleic Acids Res.,* 15, 2343-61 (1987). In addition, the location of the promoter relative to the transcription start can be optimized. Many suitable promoters for use in mammals and mammalian cells are well known in the art, as are polynucleotides that enhance expression of an associated expressible polynucleotide.

Eukaryotic promoters include RNA pol I, RNA pol II, and RNA pol III promoters. RNA pol I can transcribe genes encoding ribosomal RNAs, for example. RNA pol II can transcribe genes encoding mRNAs, small nuclear RNAs, and micro interfering RNAs, for example. RNA pol III can transcribe genes encoding tRNAs, ribosomal RNAs, and other small RNAs, for example. RNA pol II promoters can provide inducible gene expression and selective or tissue-specific gene expression, for example.

A promoter can be a neuron-specific promoter. A neuron-specific promoter can provide selective expression of a polynucleotide or therapeutic gene in neuronal cells. Selective expression that is restricted or limited to a particular cell type can prevent or reduce off-target effects that are often undesirable and can result in side effects, for example. As used herein, "selective expression" refers to expression that is significantly greater (i.e, at least 2-fold, at least 5-fold, at least 10-fold, at least 50-fold, at least 100-fold or higher in neurons as compared to non-neuronal cells. In some embodiments, there is no expression in non-neuronal cells. Moreover, when a neuron specific promoter is utilized, the polynucleotides operatively linked thereto can be expressed in at least 1%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or in 100%, and any number or range in between, of neurons.

RNA pol II promoters that are selective for a particular cell type or target cell can provide strong expression in the target cell compared to a general promoter that can drive expression in any cell type or compared to a promoter that drives expression in one or more cell types other than the target cell. In some embodiments, a neuron-specific promoter of the nucleic acid expression cassettes described herein provides for expression that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, and any number or range in between, higher as compared to expression provided by a promoter that can drive expression in any cell type. In some embodiments, a neuron-specific promoter of the nucleic acid expression cassettes described herein provides for expression that is at least 5%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, and any number or range in between, higher as compared to expression provided by a promoter that can drive expression in one or more non-neuronal cell types.

Any neuron-specific promoter can be used in the nucleic acid expression cassettes provided herein. Exemplary promoters include the somatostatin (SST) gene promoter SEQ ID NO: 63, the neuropeptide Y (NPY) promoter SEQ ID NO: 62, the alpha-calcium/calmodulin kinase 2A promoter, a synapsin I promoter SEQ ID NO: 64 or SEQ ID NO: 65, neuron-specific enolase (NSE) SEQ ID NO: 56, dopaminergic receptor 1 (Drd1a) promoter, tubulin alpha I promoter, and others. Hybrid promoters can also be used. As used herein, the term "hybrid promoter" refers to a promoter that includes promoter sequences derived from more than one gene. Promoters can be from any species, including human, rhesus macaque, mouse, rat, and chicken, for example.

In alternate aspects of these embodiments, the promoter is selected from CAG (SEQ ID NO: 50), CBA (SEQ ID NO: 51 or nucleotides 941-1213 of SEQ ID NO:68), UBC (SEQ ID NO: 52), PGK (SEQ ID NO: 53), PKC, EF1a (SEQ ID NO: 54), GUSB (SEQ ID NO: 59), CMV (SEQ ID NO: 55), PDGF, desmin, MCK, MeCP2 (SEQ ID NO: 57), GFAP (SEQ ID NO: 58), MBP, RSV (SEQ ID NO: 60), SV40 (SEQ ID NO: 61), or beta-globin (SEQ ID NO:66).

Chromatin Insulator Sequence

A nucleic acid expression cassette can further comprise a chromatin insulator sequence. Packaging of genes into chromatin can render genes inaccessible to the transcription machinery of the cell, resulting in little or no gene expression. Chromatin insulators can protect a sequence from being packed into transcriptionally inactive chromatin. Including a chromatin insulator sequence in a nucleic acid expression cassette can keep a polynucleotide in an accessible state and allow transcription to occur. Any chromatin insulator can be used in the nucleic acid expression cassettes provided herein. Exemplary chromatin insulator sequences include the CTCF insulator, the gypsy insulator, and the β-globin locus. Chromatin insulator sequences from any species can be used, including mammals and non-mammals and vertebrates and non-vertebrates. As an example, a chromatin insulator sequence from the human beta globin locus HS4 can be used. Other examples of chromatin insulator sequences include sequences form chicken and *Drosophila*.

The nucleic acid expression cassettes described herein can include regulatory elements that function after transcription has occurred. Post-transcriptional regulatory elements can modulate RNA stability and degradation, processing such as splicing and cleavage, and export from the nucleus, for example. Posttranscriptional regulatory elements can also modulate translation by modulating the amount of mRNA available for translation and by modulation translation initiation, for example.

mRNA Stability Elements

A nucleic acid expression cassette can include at least one mRNA stability element. Any mRNA stability element can be included in the nucleic acid expression cassettes. An mRNA stability element can be an expression and nuclear retention element, a 5' UTR, a 3' UTR, elements within UTRs, and others. Exemplary mRNA stability elements include the MALAT1 mRNA stability element, NEAT1 stability element, viral expression and nuclear retention elements from the Kaposi's sarcoma-associated herpesvirus (KSHV), rhesus rhadinovirus (RRV); and equine herpesvirus 2 (EHV2), and woodchuck posttranscriptional regulatory element (WPRE), C-rich stability elements of the HBA1, HBA2, lipoxygenase, alpha(I)-collagen, and the tyrosine hydroxylase 3' UTRs, for example, AU-rich elements (AREs) of 3' UTRs, and others. An mRNA stability element can be, for example, an expression and nuclear retention element. An mRNA stability element can prevent or decrease degradation of mRNA. For example, degradation of mRNA can be decreased by about 5%, about 10%, about 20%, about 30%, about 40%, about 50%, about 60%, about 70%, about 80%, about 90%, about 95%, about 99%, and any number or range in between, when an mRNA stability element is included as compared to a nucleic acid expression cassette that does not include an mRNA stability element. In an embodiment, there is no degradation of mRNA. Any sequence that prevents or decreases degradation of the mRNA can be an mRNA stability element. In some embodiments, an untranslated region (UTR) is an mRNA stability element in the nucleic acid expression cassettes provided herein. A 3' UTR, a 5' UTR, or a 3' UTR and a 5' UTR can be included in the nucleic acid expression cassettes described herein. In some embodiments, the mRNA stability element is a sequence derived from a non-coding sequence or a UTR.

An mRNA stability element can be placed into any location in a nucleic acid expression cassette. For example, an mRNA stability element can be placed 3' to the open reading frame of a polynucleotide and before or 5' of a polyadenylation site. As another example, an mRNA stability element can be placed 5' to the open reading frame of a polynucleotide and 5' to a polyadenylation site.

A nucleic acid expression cassette can include untranslated regions (UTRs). Generally, a UTR is found on each side of a coding sequence on an mRNA, i.e., an mRNA generally has a 5' UTR upstream of the coding sequence and a 3' UTR or trailer sequence immediately following a stop codon.

A 5' UTR generally includes sequences that are recognized by the ribosome that allow the ribosome to bind and initiate translation. Exemplary sequences for translation initiation include Kozak initiation signal sequences and internal ribosomal entry sites. As used herein, the terms "Kozak initiation signal sequence," "Kozak consensus sequence," and "Kozak sequence" can be used interchangeably, unless context clearly indicates otherwise. A person of skill in the art will appreciate that a Kozak initiation signal sequence can be located in part in the 5' UTR and include the AUG translation initiation codon itself and the nucleotide immediately following or downstream of the AUG start codon, as described below.

Translation initiation of an mRNA typically occurs at an ATG codon that is recognized by a ribosome. The ATG codon at which translation begins may not be the first ATG start codon present in an mRNA sequence. A motif called a Kozak sequence can direct translation initiation to an ATG codon. The Kozak consensus sequence is defined as 5'-(gcc)gccRccAUGG-3, where the underlined AUG indicates the translation start codon; uppercase letters indicate conserved bases; "R" indicates the presence of a purine, with adenine more frequent; lowercase letters indicate the most common base at a position that can vary; and the sequence (gcc) is of uncertain significance. In addition to these features, other positions and features can contribute to translation initiation. Strong and weak Kozak consensus sequences have been described, with a strong Kozak consensus sequence including the features above that are considered optimal for translation initiation and a weak Kozak consensus sequence including features that deviate or differ from a strong Kozak consensus sequence. The amount of protein synthesized from an mRNA can depend on the strength of the Kozak sequence. For example, a CCACC sequence immediately upstream of an AUG translation initiation codon can increase the rate of translation initiation compared to a sequence that differs from CCACC.

In some embodiments, the nucleic acid expression cassettes provided herein comprise a Kozak translation initiation signal. The Kozak translation initiation signal can be located immediately upstream or 5' of a translation initiation AUG codon. Any Kozak consensus sequence that is a strong Kozak sequence can be used. In some embodiments, the Kozak translation initiation signal comprises a sequence CCACC. Additional Kozak translation initiation sequences that can be used include GCCACC, CCGCC, CCACG, CCGCG, CCACA, CCGCA, and others. As another example, any sequence of XYRYY can be used, where "X" is C or G, "R" is a purine, and "Y" is C, G, or A.

Transcription Termination Region

A transcription termination region of a recombinant construct or expression cassette is a downstream regulatory region including a stop codon and a transcription terminator sequence. Transcription termination regions that can be used can be homologous to the transcriptional initiation region, can be homologous to the polynucleotide encoding a polypeptide of interest, or can be heterologous (i.e., derived from another source). A transcription termination region can be naturally occurring, or wholly or partially synthetic. 3' non-coding sequences encoding transcription termination regions may be provided in a recombinant construct or expression construct and may be from the 3' region of the gene from which the initiation region was obtained or from a different gene. A large number of termination regions are known and function satisfactorily in a variety of hosts when utilized in both the same and different genera and species from which they were derived. Termination regions may also be derived from various genes native to the preferred hosts. The termination region is usually selected more for convenience rather than for any particular property.

A 3' UTR generally plays an important role in translation termination and in post-transcriptional gene expression. For example, regulatory regions in a 3' UTR can influence polyadenylation, translation efficiency, localization, and stability of the mRNA. A 3' UTR can contain binding sites for regulatory proteins and for micro interfering RNAs (miRNAs), for example. miRNA binding can decrease expression of an mRNA by inhibiting translation or causing degradation of the transcript. A 3' UTR can also have silencer regions which bind to repressor proteins, thereby inhibiting the expression or translation of the mRNA. 3' UTRs can contain AU-rich elements (AREs). Proteins binding to AREs can affect the stability or decay rate of transcripts in a localized manner or affect translation initiation. Generally, a 3' UTR contains the sequence AAUAAA that directs addition of several hundred adenine residues called the poly(A) tail to the end of the mRNA transcript. Poly(A) binding protein (PABP) can bind to this tail, contributing to regulation of mRNA translation, stability, and export. For example, poly (A) tail bound PABP interacts with proteins associated with the 5' end of the transcript, resulting in circularization of the mRNA that promotes translation. A 3' UTR can also contain sequences that attract proteins to associate the mRNA with the cytoskeleton, transport it to or from the cell nucleus, or perform other types of localization. Sequences within the 3' UTR and physical characteristics of a 3' UTR, including its length and secondary structure, can contribute to translation regulation. A 3' UTR can also include elements that modulate mRNA transcription, thus functioning as a transcriptional regulatory element.

In some embodiments, the nucleic acid expression cassettes described herein include a 5' UTR sequence, a 3' UTR sequence, or a 5' UTR sequence and a 3' UTR sequence. Any 5' UTR sequence and any 3' UTR sequence derived from any gene can be used. Preferably, 5' UTR and 3' UTR sequences included in the nucleic acid expression cassettes provided herein are derived from human genes, although 5' UTR and 3' UTR sequences can be from any gene and from any organism. In some embodiments, the nucleic acid expression cassettes described herein comprise a 5' UTR sequence, a 3' UTR sequence, or a 5' UTR sequence and a 3' UTR sequence of a presenilin 1 gene. In some embodiments, the nucleic acid expression cassettes described herein comprise a 5' UTR sequence, a 3' UTR sequence, or a 5' UTR sequence and a 3' UTR sequence of the human presenilin 1 gene. In some embodiments, the 5' UTR and 3' UTR sequences included in the nucleic acid expression cassettes function as mRNA stability elements, although any 5' UTR and/or 3' UTR sequence can contribute any other function, including any of the functions described above, to modulate expression of a polynucleotide encoding PSEN1 or other therapeutic gene of a nucleic acid expression cassette provided herein. In some embodiments, a 5' UTR sequence, a 3' UTR sequence, or a 5' UTR sequence and a 3' UTR sequence function to stabilize mRNA.

In some embodiments, the nucleic acid expression cassettes described herein comprise introns. Introns can promote splicing and enhance nuclear export, for example. Any intron sequences from any gene can be used. In some embodiments, the nucleic acid expression cassettes provided herein include intron sequences derived from a gene other than PSEN1. In some embodiments, the introns allow for alternative splicing to create protein isoforms with variant lengths and additional but overlapping functions. Protein isoforms can also have different cellular functions and properties. Alternative splicing can rearrange intron and exon sequences that are joined to alter the mRNA coding sequence. In some embodiments, the nucleic acid expression cassettes provided herein include intron sequences derived from the PSEN1 gene. For example, the cDNA of a polynucleotide encoding PSEN1 can include one or more intron sequences. The one or more intron sequences can be PSEN1 intron sequences or any other intron sequences. In some embodiments, entire intron sequences are included in the nucleic acid expression cassettes described herein. In some embodiments, partial intron sequences are included in the nucleic acid expression cassettes described herein. In some embodiments, a combination of entire and partial intron sequences are included in the nucleic acid expression cassettes described herein.

Regulatory elements and polynucleotides of the nucleic acid expression cassettes provided herein can be combined in any fashion.

Modified or Mutated Nucleic Acid Sequences

In some embodiments, an antisense oligonucleotide may be modified or derived from a native nucleic acid sequence, for example, by introduction of mutations, deletions, substitutions, modification of nucleobases, backbones and the like. The nucleic acid sequences include dsRNA, dsDNA and oligonucleotides, etc. Examples of some modified nucleic acid sequences envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. In some embodiments, modified oligonucleotides comprise those with phosphorothioate backbones and those with heteroatom backbones, $CH_2$—NH—O—$CH_2$, CH, —N($CH_3$)—O—$CH_2$ [known as a methylene(methylimino) or MMI backbone], $CH_2$—O—N ($CH_3$)—$CH_2$, $CH_2$—N($CH_3$)—N ($CH_3$)—$CH_2$ and O—N ($CH_3$)—$CH_2$ —$CH_2$ backbones, wherein the native phosphodiester backbone is represented as O—P—O—CH,). The amide backbones disclosed by De Mesmaeker et al. *Acc. Chem. Res.* 1995, 28:366-374) are also embodied herein. In some embodiments, the nucleic acid sequences having morpholino backbone structures (Summerton and Weller, U.S. Pat. No. 5,034,506), peptide nucleic acid (PNA) backbone wherein the phosphodiester backbone of the oligonucleotide is replaced with a polyamide backbone, the nucleobases being bound directly or indirectly to the aza nitrogen atoms of the polyamide backbone (Nielsen et al. *Science* 1991, 254, 1497). The nucleic acid sequences may also comprise one or more substituted sugar moieties. The nucleic acid sequences may also have sugar mimetics such as cyclobutyls in place of the pentofuranosyl group.

The antisense oligonucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, $N^6$ (6-aminohexyl)adenine and 2,6-diaminopurine. Kornberg, A., DNA Replication, W. H. Freeman & Co., San Francisco, 1980, pp 75-'7'7; Gebeyehu, G., et al. *Nucl. Acids Res.* 1987, 15:4513). A "universal" base known in the art, e.g., inosine may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278).

Examples of other modified nucleobases can be found, for example, in Genes VI, Chapter 9 ("Interpreting the Genetic Code"), Lewis, ed. (1997, Oxford University Press, New York), and Modification and Editing of RNA, Grosjean and Benne, eds. (1998, ASM Press, Washington DC). Modified RNA components include the following: 2'-O-methylcytidine; $N^4$-methylcytidine; $N^4$-2'-O-dimethylcytidine; $N^4$-acetylcytidine; 5-methylcytidine; 5,2'-O-dimethylcytidine; 5-hydroxymethylcytidine; 5-formylcytidine; 2'-O-methyl-5-formaylcytidine; 3-methylcytidine; 2-thiocytidine; lysidine; 2'-O-methyluridine; 2-thiouridine; 2-thio-2'-O-methyluridine; 3,2'-O-dimethyluridine; 3-(3-amino-3-carboxypropyl) uridine; 4-thiouridine; ribosylthymine; 5,2'-O-dimethyluridine; 5-methyl-2-thiouridine; 5-hydroxyuridine; 5-methoxyuridine; uridine 5-oxyacetic acid; uridine 5-oxyacetic acid methyl ester; 5-carboxymethyluridine; 5-methoxycarbonylmethyluridine; 5-methoxycarbonylmethyl-2'-O-methyluridine; 5-methoxycarbonylmethyl-2'-thiouridine; 5-carbamoylmethyluridine; 5-carbamoylmethyl-2'-O-methyluridine; 5-(carboxyhydroxymethyl) uridine; 5-(carboxyhydroxymethyl) uridinemethyl ester; 5-aminomethyl-2-thiouridine; 5-methylaminomethyluridine; 5-methylaminomethyl-2-thiouridine; 5-methylaminomethyl-2-selenouridine; 5-carboxymethylaminomethyluridine; 5-carboxymethylaminomethyl-2'-O-methyl-uridine; 5-carboxymethylaminomethyl-2-thiouridine; dihydrouridine; dihydroribosylthymine; 2'-methyladenosine; 2-methyladenosine; $N^6$Nmethyladenosine; $N^6$, $N^6$-dimethyladenosine; $N^6$,2'-O-trimethyladenosine; 2 methylthio-$N^6$Nisopentenyladenosine; $N^6$-(cis-hydroxyisopentenyl)-adenosine; 2-methylthio-$N^6$-(cis-hydroxyisopentenyl)-adenosine; $N^6$-glycinylcarbamoyl)adenosine; $N^6$ threonylcarbamoyl adenosine; $N^6$-methyl-$N^6$-threonylcarbamoyl adenosine; 2-methylthio-$N^6$-methyl-$N^6$-threonylcarbamoyl adenosine; $N^6$-hydroxynorvalylcarbamoyl adenosine; 2-methylthio-$N^6$-hydroxnorvalylcarbamoyl adenosine; 2'-O-ribosyladenosine (phosphate); inosine; 2'O-methyl inosine; 1-methyl inosine; 1,2'-O-dimethyl inosine; 2'-O-methyl guanosine; 1-methyl guanosine; $N^2$-methyl guanosine; $N^2$, $N^2$-dimethyl guanosine; $N^2$, 2'-O-dimethyl guanosine; $N^2$, $N^2$, 2'-O-trimethyl guanosine; 2'-O-ribosyl guanosine (phosphate); 7-methyl guanosine; $N^2$, 7-dimethyl guanosine; $N^2$, $N^2$;7-trimethyl guanosine; wyosine; methylwyosine; under-modified hydroxywybutosine; wybutosine; hydroxywybutosine; peroxywybutosine; queuosine; epoxyqueuosine; galactosyl-queuosine; mannosyl-queuosine; 7-cyano-7-deazaguanosine; arachaeosine [also called 7-formamido-7-deazaguanosine]; and 7-aminomethyl-7-deazaguanosine.

Another modification of the antisense oligonucleotides of the disclosure involves chemically linking to the nucleic acid sequences one or more moieties or conjugates which enhance the activity or cellular uptake of the oligonucleotide. Such moieties include but are not limited to lipid moieties such as a cholesterol moiety, a cholesteryl moiety (Letsinger et al., *Proc. Natl. Acad. Sci.* USA 1989, 86, 6553), cholic acid (Manoharan et al. *Bioorg. Med. Chem. Let.* 1994, 4, 1053), a thioether, e.g., hexyl-S-tritylthiol (Manoharan et al. *Ann. N.Y. Acad. Sci.* 1992, 660, 306; Manoharan et al. *Bioorg. Med. Chem. Let.* 1993, 3, 2765), a thiocholesterol (Oberhauser et al., *Nucl. Acids Res.* 1992, 20, 533), an aliphatic chain, e.g., dodecandiol or undecyl residues (Saison-Behmoaras et al. *EMBO J.* 1991, 10, 111; Kabanov et al. *FEBS Lett.* 1990, 259, 327; Svinarchuk et al. *Biochimie* 1993, 75, 49), a phospholipid, e.g., di-hexadecyl-rac-glycerol or triethylammonium 1,2-di-O-hexadecyl-rac-glycero-3-H-phosphonate (Manoharan et al. *Tetrahedron Lett.* 1995, 36, 3651; Shea et al. *Nucl. Acids Res.* 1990, 18, 3777), a polyamine or a polyethylene glycol chain (Manoharan et al. *Nucleosides & Nucleotides* 1995, 14, 969), or adamantane acetic acid (Manoharan et al. *Tetrahedron Lett.* 1995, 36, 3651). It is not necessary for all positions in a given nucleic acid sequence to be uniformly modified, and in fact more than one of the aforementioned modifications may be incorporated in a single nucleic acid sequence or even at within a single nucleoside within a nucleic acid sequence.

Vectors

A vector is a macromolecule or association of macromolecules that comprises or associates with one or more polynucleotides (or an expression vector comprising such polynucleotide(s)) and which can be used to mediate delivery of the polynucleotide(s) to a cell. Examples of vectors include plasmids, viral vectors, liposomes, and other gene delivery vehicles. A vector can be combined with a lipid, polymer carrier, or any other suitable carrier. The vector may comprise regulatory elements not provided by the expression vector, which become operatively linked to the polynucleotide(s) when they or the expression vector comprising them is inserted into the vector. A vector can be engineered to lack one or more elements for vector replication.

In some embodiments, a vector can comprise the nucleic acid expression cassettes described herein. In some embodiments, the vector can be a viral vector or a plasmid vector. In some embodiments, the vector is an adeno-associated virus (AAV) vector, a retroviral vector, a lentiviral vector, or an adenoviral vector or plasmid vector complexed with lipid or polymer carrier.

Viral gene therapy vectors or gene delivery vectors can have the ability to be reproducibly and/or stably propagated and purified to high titers; to mediate targeted delivery (e.g., to deliver the polynucleotide specifically to a tissue or organ of interest without widespread vector dissemination elsewhere or off-target delivery); and to mediate gene delivery and/or polynucleotide expression without inducing harmful side effects or off-target effects.

The term "AAV" is an abbreviation for adeno-associated virus, and may be used to refer to the virus itself or a derivative thereof. The term covers all serotypes, subtypes, and both naturally occurring and recombinant forms, except where required otherwise. The abbreviation "rAAV" refers to recombinant adeno-associated virus, also referred to as a recombinant AAV vector (or "rAAV vector"). The term "AAV" includes AAV1, AAV2, AAV3, AAV4, AAV5, AAV6, AAV7, AAV8, AAV9, AAV10, AAV11, AAV 12, rh10, and hybrids thereof, avian AAV, bovine AAV, canine AAV, equine AAV, primate AAV, non-primate AAV, and ovine AAV. The genomic sequences of various serotypes of AAV, as well as the sequences of the native inverted terminal repeats (ITRs), Rep proteins, and capsid subunits are known in the art. Such sequences may be found in the literature or in public databases such as GenBank. An "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two, AAV inverted terminal repeat sequences (ITRs). The term "rAAV vector" encompasses both rAAV vector particles and rAAV vector plasmids. An rAAV vector may either be single-stranded (ssAAV) or self-complementary (scAAV). An "AAV virus" or "AAV viral particle" or "rAAV vector particle" refers to a viral particle composed of at least one AAV capsid protein and an encapsidated polynucleotide rAAV vector. If the particle comprises a heterologous polynucleotide (i.e., a polynucleotide other than a wild-type AAV genome such as a polynucleotide or a nucleic acid expression cassette to be delivered to a mammalian cell), it is typically referred to as an "rAAV vector particle" or simply an "rAAV vector." Thus, production of rAAV particle necessarily includes production of an rAAV vector, as such a vector is contained within an rAAV particle.

The cloning capacity of vectors or viral expression vectors can be a particular challenge for expression of large polynucleotides. For example, AAV vectors typically have a packaging capacity of ~4.8 kb, lentiviruses typically have a capacity of ~8 kb, adenoviruses typically have a capacity of ~7.5 kb, and alphaviruses typically have a capacity of –7.5 kb. Some viruses can have larger packaging capacities, for example herpesvirus can have a capacity of >30 kb and vaccinia a capacity of ~25 kb. Advantages of using AAV for gene therapy include low pathogenicity, very low frequency of integration into the host genome, and the ability to infect dividing and non-dividing cells.

Several serotypes of AAV, non-pathogenic parvovirus, have been engineered for the purposes of gene delivery, some of which are known to have tropism for certain tissues or cell types. Viruses used for various gene-therapy applications can be engineered to be replication-deficient or to have low toxicity and low pathogenicity in a subject or a host. Such virus-based vectors can be obtained by deleting all, or some, of the coding regions from the viral genome, and leaving intact those sequences (e.g., inverted terminal repeat sequences) that are necessary for functions such as packaging the vector genome into the virus capsid or the integration of vector nucleic acid (e.g., DNA) into the host chromatin. A nucleic acid expression cassette comprising a polynucleotide, for example, can be cloned into a viral backbone such as a modified or engineered viral backbone lacking viral genes, and used in conjunction with additional vectors (e.g., packaging vectors), which can, for example, when co-transfected, produce recombinant viral vector particles.

In some cases, an AAV vector or an AAV viral particle, or virion, used to deliver a nucleic acid expression cassette into a cell, cell type, or tissue, in vivo or in vitro, is replication-deficient. In some cases, an AAV virus is engineered or genetically modified so that it can replicate and generate virions only in the presence of helper factors.

In some embodiments, a nucleic acid expression cassette is designed for delivery by an AAV or a recombinant AAV (rAAV). In some embodiments, a nucleic acid expression cassette is delivered using a lentivirus or a lentiviral vector. In some embodiments, larger polynucleotide, i.e., genes that exceed the cloning capacity of AAV, are preferably delivered using a lentivirus or a lentiviral vector.

In some embodiments, the AAV vector is AAV1, AAV2, AAV3, AAV4, AAV5, AAV6, AAV7, AAV8, AAV9, AAVDJ, AAVrh10, AAV11, AAV12, AAV2/1, AAV2/5, AAV2/6, AAV2/7, AAV2/8, AAV2/9, AAV2/rh10, AAV2/11, or AAV2/12, AAVPHP.A (PHP.A), AAVG2B-26, AAVG2B-13, AAVTH1.1-32, AAVTH1.1-35, AAVPHP.B2 (PHP.B2), AAVPHP.B3 (PHP.B3), AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP, AAVPHP.B-SNP(3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.S/G2A12, AAVG2A15/G2A3 (G2A3), AAVG2B4 (G2B4), AAVG2B5 (G2B5), PHP.S, AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu.15, AAV33.8/hu.16, AAV52/hu.19, AAV52.1/hu.20, AAV58.2/hu.25, AAVA3.3, AAVA3.4, AAVA3.5, AAVA3.7, AAVC1, AAVC2, AAVC5, AAV-DJ, AAV-DJ8, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.10, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R AS86R mutant, AAVrh8R R533A mutant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61 AAV, BNP62 AAV, BNP63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, Japanese AAV 10 serotypes, AAV CBr-7.1, AAV CBr-7.10, AAV CBr-7.2, AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-1, AAV CKd-10, AAV CKd-2, AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-1, AAV CLv1-1, AAV Clv1-10, AAV CLv1-2, AAV CLv-12, AAV CLv1-3, AAV CLv-13, AAV CLv1-4, AAV Clv1-7, AAV Clv1-8, AAV Clv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV.hu.48R3, AAV.VR-355, AAV3B, AAV4, AAV5, AAVF1/HSC1, AAVF11/HSC11, AAVF12/HSC12, AAVF13/HSC13, AAVF14/HSC14, AAVF15/HSC15, AAVF16/HSC16, AAVF17/HSC17, AAVF2/HSC2, AAVF3/HSC3, AAVF4/HSC4, AAVF5/HSC5, AAVF6/HSC6, AAVF7/HSC7, AAVF8/HSC8, and/or AAVF9/HSC9 and variants thereof. PHP.B, and PHP.B derivatives [PHP.eR, PHP.S], AAV8[K137R] AAV-TT, rAAV-retro, AAV9. HR, AAV1 CAM mutants, AAV9[586-590] swap mutants. In some embodiments, the AAV vector is a hybrid or chimeric AAV serotype. In some embodiments, the AAV is an engineered AAV designed to modify tropism or evade immune detection.

In some embodiments, the nucleic acid expression cassette can be designed for delivery by an optimized therapeutic retroviral vector, e.g., a lentiviral vector. The retroviral vector can be a lentiviral vector comprising a left (5') LTR; sequences which aid packaging and/or nuclear import of the virus, at least one regulatory element, optionally a lentiviral Rev response element (RRE); optionally a promoter or active portion thereof; a polynucleotide operably linked to one or more regulatory elements; optionally an insulator; and a right (3') retroviral LTR. A lentiviral vector can also include a posttranscriptional regulatory element, such as the Woodchuck Hepatitis Virus Posttranscriptional Regulatory Element (WPRE) and/or any of the transcriptional and posttranscriptional regulatory elements described herein. A lentiviral vector can be a self-inactivating (SIN) lentiviral vector. Any suitable packaging system can be used with a lentiviral vector, including second, third, and fourth generation packaging systems, for example. A lentiviral vector can be pseudotyped. Any envelope glycoprotein can be used for pseudotyping, including, for example, a glycoprotein from vesicular stomatitis virus (VSV), rabies virus, Lyssavirus, Mokola virus, lymphocytic choriomeningitis virus (LCMV), Lassa fever virus (LFV), retroviruses, Moloney murine leukemia virus (MuLV), filoviruses, paramyxoviruses, measles virus, Nipah virus, orthomyxoviruses, and others. A lentiviral vector can be pseudotyped to alter tropism. Any cell type can be targeted by pseudotyping, including neuronal cells, for example.

Also provided herein are vectors or sets of vectors comprising: (i) a vector comprising an expression cassette provided herein; or (ii) a set of vectors comprising (a) a first vector comprising a first polynucleotide provided herein (e.g., an antisense oligonucleotide coding sequence), and (b) a second vector comprising a second polynucleotide provided herein (e.g., a wild-type PSEN1 or PSEN2 coding sequence resistant to silencing by the encoded antisense oligonucleotide.

Techniques contemplated herein for gene therapy of somatic cells include delivery via a viral vector (e.g., retroviral, adenoviral, AAV, helper-dependent adenoviral systems, hybrid adenoviral systems, herpes simplex, pox virus, lentivirus, and Epstein-Barr virus), and non-viral systems, such as physical systems (naked DNA, DNA bombardment, electroporation, hydrodynamic, ultrasound, and magnetofection), and chemical systems (cationic lipids, different cationic polymers, and lipid polymers).

Delivery Routes

In certain embodiments, the expression cassettes and vectors disclosed herein can be formulated in any suitable formulation suitable for a particular route of administration. Various pharmaceutically acceptable formulations are commercially available and obtainable by a medical practitioner.

In certain embodiments, the expression cassettes and vectors disclosed herein are administered to the central nervous system (CNS) of a subject in need. In certain embodiments, the central nervous system includes brain, spinal cord and cerebral spinal fluid (CSF). In certain embodiments, the compositions are administered to the brain or spinal cord or CSF of a mammal. In certain embodiments, the compositions are administered to a portion of brain or spinal cord.

In certain embodiments, the expression cassettes and vectors disclosed herein are administered to brain parenchyma, subarachnoid space and/or intrathecal space. In certain embodiments, the compositions are administered to one or more of cisterna magna, intraventricular space, brain ventricle, subarachnoid space, and/or ependyma of said subject.

In further embodiments, the expression cassettes and vectors disclosed herein are administered to the ventricular system. In still further embodiments, the expression cassettes and vectors disclosed herein are administered to one or more of the rostral lateral ventricle; and/or caudal lateral ventricle; and/or right lateral ventricle; and/or left lateral ventricle; and/or right rostral lateral ventricle; and/or left rostral lateral ventricle; and/or right caudal lateral ventricle; and/or left caudal lateral ventricle.

In certain embodiments, the expression cassettes and vectors disclosed herein are administered to one or more cells that contact the CSF in a mammal, for example by contacting cells with the compositions. Non-limiting examples of cells that contact the CSF include ependymal cells, pial cells, endothelial cells and/or meningeal cells. In certain embodiments, the expression cassettes and vectors disclosed herein are administered to ependymal cells. In certain embodiments, the expression cassettes and vectors disclosed herein are delivered to ependymal cells, for example by contacting ependymal cells with the compositions.

In certain embodiments, the expression cassettes and vectors disclosed herein are administered/delivered locally. "Local delivery" refers to delivery directly to a target site within a mammal (e.g., directly to a tissue or fluid). For example, the expression cassettes and vectors disclosed herein can be locally delivered by direct injection into an organ, tissue or specified anatomical location. In certain embodiments, the expression cassettes and vectors disclosed herein are delivered or administered by direct injection to the brain, spinal cord, or a tissue or fluid thereof (e.g., CSF, such as ependymal cells, pial cells, endothelial cells and/or meningeal cells). For example, the expression cassettes and vectors disclosed herein can be directly delivered, by way of direct injection, to the CSF, cisterna magna, intraventricular space, a brain ventricle, subarachnoid space and/or intrathecal space; and/or ependymal; and/or rostral lateral ventricle; and/or caudal lateral ventricle; and/or right lateral ventricle; and/or left lateral ventricle; and/or right rostral lateral ventricle; and/or left rostral lateral ventricle; and/or right caudal lateral ventricle; and/or left caudal lateral ventricle.

In certain embodiments, the expression cassettes and vectors disclosed herein are delivered to a tissue, fluid or cell of the brain or spinal cord by direct injection into a tissue or fluid of the brain or spinal cord. In certain embodiments, the expression cassettes and vectors disclosed herein are not delivered systemically by, for example, intravenous, subcutaneous, or intramuscular injection, or by intravenous infusion. In certain embodiments, the expression cassettes and vectors disclosed herein are delivered to a tissue or fluid of the brain or spinal cord by stereotactic injection.

In certain embodiments, the expression cassettes and vectors disclosed herein are delivered or administered by direct injection to the brain, spinal cord, or portion thereof, or a tissue or fluid thereof (e.g., CSF such as ependyma).

In certain embodiments, a method or use includes administering the expression cassettes and vectors disclosed herein to the brain or spinal cord, or portion thereof, of a human. In certain embodiments, the wild-type PSEN1 or PSEN2 polypeptides (and the antisense oligonucleotides when encoded by an expression vector) are expressed and/or detected in a central nervous tissue (e.g., brain, e.g., striatum, thalamus, medulla, cerebellum, occipital cortex, prefrontal cortex) distal to the administration site. In certain embodiments, the polypeptide is present or detected broadly in a central nervous tissue (e.g., brain, e.g., striatum, thalamus, medulla, cerebellum, occipital cortex, and/or prefrontal cortex) that reflects distribution away from the administration site and optionally throughout a central nervous tissue (e.g., brain, e.g., striatum, thalamus, medulla, cerebellum, occipital cortex, and/or prefrontal cortex).

An effective amount of the expression cassettes and vectors disclosed herein, such as rAAV vector expressing the PSEN1 or PSEN2, an antisense oligonucleotide or both, can be empirically determined. Administration can be effected in one or more doses, continuously or intermittently throughout the course of treatment. Effective doses of administration can be determined by those of skill in the art and may vary according to the AAV serotype, viral titer and the weight, condition and species of mammal being treated. Single and multiple administrations (e.g., 1-5 or more) can be carried out with the dose level, target and timing being selected by the treating physician. Multiple doses may be administered as is required to maintain adequate enzyme activity, for example.

The expression cassettes and vectors disclosed herein, can be administered as a part of a combination therapy, for example, a subject with dementia or Alzheimer's Disease, with one or more additional therapeutic agents. For example, the U.S. Food and Drug Administration (FDA) has approved two types of medications—cholinesterase inhibitors (ARICEPT®, EXELON®, RAZADYNE®) and memantine (NAMENDA®)—to treat the cognitive symptoms (memory loss, confusion, and problems with thinking and reasoning) of Alzheimer's disease. For combination treatment with more than one active agent, where the active agents are in separate dosage formulations, the active agents may be administered separately or in conjunction. In addition, the administration of one element may be prior to, concurrent to, or subsequent to the administration of the other agent.

When "co-administered" with other agents, e.g., when co-administered with another medication, an "effective amount" of the second agent will depend on the type of drug used. Suitable dosages are known for approved agents and can be adjusted by the skilled artisan according to the condition of the subject, the type of condition(s) being treated and the amount of a compound described herein being used.

Kits

Provided herein are kits comprising one or more vectors or sets of vectors described herein. In some embodiments, the kit comprises: a) one or more antisense oligonucleotides, wherein each antisense oligonucleotide independently targets either a coding region or a non-coding region of an mRNA translated from each of a human wild-type and mutant presenilin 1 (PSEN1), each of a human wild-type or mutant presenilin 2 (PSEN2); and b) a vector comprising a polynucleotide encoding a wild-type presenilin 1 (PSEN1) amino acid sequence or a wild-type presenilin 2 (PSEN2) amino acid sequence, wherein the second polynucleotide is not targeted by any of the one or more antisense oligonucleotides; and wherein the polynucleotide is operably linked to a promoter in the vector. In some aspects of these embodiments, each of the one or more antisense oligonucleotides is independently selected from a short hairpin RNA (shRNA), a short interfering RNA (siRNA), a micro interfering RNA (miRNA), a small temporal RNA (stRNA) or an endoribonuclease-prepared siRNA (esiRNA). In some aspects of these embodiments, at least one of the one or more antisense oligonucleotides in the kit comprises one or more modified nucleobases. In some more specific aspects of these embodiments, each of the one or more modified nucleobases is independently selected from a non-naturally occurring nucleobase, a locked nucleic acids (LNA), or a peptide nucleic acids (PNA).

In addition to the active components (e.g., vectors and/or antisense oligonucleotides), the kits of the present disclosure may comprise one or more of any of the following: instructions for preparing the active components for administration to a subject, instructions for administering the active components to a subject, buffers, diluents, solvents, or other excipients to dissolve and/or dilute and/or prepare any of the active components for administration to a subject, extra vessels for diluting or dividing the active components, tools for administering the active components, and any other items that are useful in using the active components in therapy.

Methods of Treatment

The present polynucleotide sequences, antisense oligonucleotides, expression cassettes, vectors, sets of vectors, and kits are useful in methods of treating any disorder characterized by a mutant form of PSEN1 or PSEN2. Such methods comprise the step(s) of administering an antisense oligonucleotide (or a polynucleotide that encodes such antisense oligonucleotide) that targets PSEN1 or PSEN2; and a polynucleotide that encodes wild-type PSEN1 or PSEN2 and which is resistant to silencing by the antisense oligonucleotide. In some embodiments, these two components may be encoded in a single expression cassette or vector administered to a subject. In some embodiments, these two components may be encoded in separate expression cassettes or vectors administered sequentially in any order, or simultaneously to a subject. In some embodiments, the antisense oligonucleotide may be administered directly to the subject sequentially in any order, or simultaneously with a vector or expression cassette encoding the wild-type PSEN1 or PSEN2 protein.

Diseases and disorders useful in these methods include any neurodegenerative disease, disorder, or condition characterized by a mutant form of PSEN1 or PSEN2. In some embodiments, the neurodegenerative disease, disorder, or condition is Alzheimer's disease, familial Alzheimer's disease, sporadic Alzheimer's disease, late-onset Alzheimer's disease, frontotemporal dementia, frontotemporal lobar degeneration, Pick's disease, Lewy body dementia, memory loss, cognitive impairment, or mild cognitive impairment. Other exemplary neurodegenerative diseases, disorders, or conditions include tauopathy, primary age-related tauopathy (PART), chronic traumatic encephalopathy (CTE), progressive supranuclear palsy (PSP), corticobasal degeneration (CBD), frontotemporal dementia and parkinsonism linked to chromosome 17 (FTDP-17), amyotrophic lateral sclerosis-parkinsonism-dementia (ALS-PDC, Lytico-bodig disease), ganglioglioma, gangliocytoma, meningioangiomatosis, postencephalitic parkinsonism, subacute sclerosing panencephalitis (SSPE), lead encephalopathy, tuberous sclerosis, pantothenate kinase-associated neurodegeneration, synucleinopathy, Parkinson's disease, multiple system atrophy (MSA), neuraxonal dystrophies, Parkinson's-like disease, Parkinsonism, prion diseases, motor neuron diseases, dementia, transmissible spongiform encephalopathies, systemic atrophies primarily affecting the central nervous system, trinucleotide repeat disorders, proteopathies, amyloidosis, neuronal ceroid lipofuscinoses, amyotrophic lateral sclerosis (ALS), lysosomal storage diseases, seizure disorders, paraplegias, demyelinating diseases, Huntington's disease, traumatic brain injury, stroke, autism spectrum disorder (ASD), depression, anxiety, post-traumatic stress disorder (PTSD), schizophrenia, Attention-Deficit/Hyperactivity Disorder (ADHD), bipolar disorder, Obsessive-Compulsive Disorder (OCD), personality disorder, pain, and others.

As used herein, the terms "treat," "treatment," "therapy," "therapeutic," and the like refer to obtaining a desired pharmacologic and/or physiologic effect, including, but not limited to, alleviating, delaying or slowing the progression, reducing the effects or symptoms, preventing onset, inhibiting, ameliorating the onset of a diseases or disorder, obtaining a beneficial or desired result with respect to a disease, disorder, or medical condition, such as a therapeutic benefit and/or a prophylactic benefit. "Treatment," as used herein, covers any treatment of a disease in a mammal, particularly in a human, and includes (a) inhibiting the disease, i.e., arresting its development; and (b) relieving the disease, i.e., causing regression of the disease. In some embodiments, the methods disclosed herein are useful to preventing the disease from occurring in a subject which may be predisposed to the disease or at risk of acquiring the disease but has not yet been diagnosed as having it, or in a subject that possesses biomarkers associated with the disease but does not yet show any physical symptoms of the disease.

A therapeutic benefit includes eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In some cases, for prophylactic benefit, the compositions are administered to a subject at risk of developing a particular disease, or to a subject reporting one or more of the physiological symptoms of a disease, even though a diagnosis of this disease may not have been made. The methods of the present disclosure may be used with any mammal or other animal. In some cases, the treatment can result in a decrease or cessation of symptoms. A prophylactic effect includes delaying or eliminating the appearance of a disease or condition, delaying or eliminating the onset of symptoms of a disease or condition, slowing, halting, or reversing the progression of a disease or condition, or any combination thereof.

A subject is any individual or patient on which the methods disclosed herein are performed. The term "subject" can be used interchangeably with the term "individual" or "patient." The subject can be a human, although the subject may be an animal, as will be appreciated by those in the art. Thus, other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject. In some embodiments, the subject is a human.

Expression cassettes and vectors provided herein can be administered in an amount effective to treat the neurodegenerative disease, disorder, or condition, The term "effective amount" or "therapeutically effective amount" refers to that amount of a composition described herein that is sufficient to affect the intended application, including but not limited to disease treatment, as defined herein. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in a target cell. The specific dose will vary depending on the particular composition chosen, the dosing regimen to be followed, whether it is administered in combination with other compounds, timing of administration, the tissue to which it is administered, and the physical delivery system in which it is carried.

Expression cassettes and vectors can be delivered by any suitable method. Exemplary methods include intracranial injection, stereotaxic injection into the brain grey or white matter, injection into the cerebrospinal fluid (intrathecal, intracerebroventricular, intracisternal-magna), and intravenous injection.

The procedures described herein employ, unless otherwise indicated, conventional techniques of chemistry, molecular biology, microbiology, recombinant DNA, genetics, immunology, cell biology, cell culture and transgenic biology, which are within the skill of the art. (See, e.g., Maniatis, et al., *Molecular Cloning*, Cold Spring Harbor Laboratory Press, Cold Spring Harbor, N.Y. (1982); Sambrook, et al., (1989); Sambrook and Russell, *Molecular Cloning,* 3rd Ed., Cold Spring Harbor Laboratory Press, Cold Spring Harbor, N.Y. (2001); Ausubel, et al., *Current Protocols in Molecular Biology*, John Wiley & Sons (including periodic updates) (1992); Glover, *DNA Cloning*, IRL Press, Oxford (1985); Russell, *Molecular biology of plants: a laboratory course manual*, Cold Spring Harbor Laboratory Press, Cold Spring Harbor, N.Y. (1984); Anand, *Techniques for the Analysis of Complex Genomes*, Academic Press, NY (1992); Guthrie and Fink, *Guide to Yeast Genetics and Molecular Biology*, Academic Press, NY (1991); Harlow and Lane, *Antibodies*, Cold Spring Harbor Laboratory Press, Cold Spring Harbor, N.Y. (1988); *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, A. R. Liss, Inc. (1987); *Immobilized Cells And Enzymes*, IRL Press (1986); B. Perbal, *A Practical Guide To Molecular Cloning* (1984); the treatise, *Methods In Enzymology*, Academic Press, Inc., NY); *Methods In Enzymology*, Vols. 154 and 155, Wu, et al., eds.; *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds. (1986); Riott, *Essential Immunology,* 6th Edition, Blackwell Scientific Publications, Oxford (1988); Fire, et al., *RNA Interference Technology From Basic Science to Drug Development*, Cambridge University Press, Cambridge (2005); Schepers, *RNA Interference in Practice*, Wiley-VCH (2005); Engelke, *RNA Interference* (RNAi): *The Nuts & Bolts of siRNA Technology*, DNA Press (2003); Gott, *RNA Interference, Editing, and Modification: Methods and Protocols* (*Methods in Molecular Biology*), Human Press, Totowa, N.J. (2004); and Sohail, *Gene Silencing by RNA Interference: Technology and Application*, CRC (2004)).

The compositions and methods are more particularly described below and the Examples set forth herein are intended as illustrative only, as numerous modifications and variations therein will be apparent to those skilled in the art. As used in the description herein and throughout the claims that follow, the meaning of "a", "an", and "the" includes plural reference unless the context clearly dictates otherwise. The term "about" in association with a numerical value means that the value varies up or down by 5%. For example, for a value of about 100, means 95 to 105 (or any value between 95 and 105).

The terms used in the specification generally have their ordinary meanings in the art, within the context of the compositions and methods described herein, and in the specific context where each term is used. Some terms have been more specifically defined below to provide additional guidance to the practitioner regarding the description of the compositions and methods.

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods In addition, where features or aspects of the invention are described in terms of Markush groups or other grouping of alternatives, those skilled in the art will recognize that the invention is also thereby described in terms of any individual member or subgroup of members of the Markush group or other group.

The following are provided for exemplification purposes only and are not intended to limit the scope of the invention described in broad terms above.

Example 1. Design of siRNA Sequences for Silencing Endogenous PSEN1 Gene Expression in Humans We designed siRNA sequences that can target endogenous human PSEN1 mRNAs. These siRNA sequences may be used for direct administration to a subject or encoded by a polynucleotide as part of a shRNA or miRNA that is produced from a vector administered to the subject.

Once these siRNAs are used to inhibit endogenous PSEN1 genes, PSEN 1 expression can be restored by providing a PSEN1 cDNA for expression of an mRNA encoding a wild-type presenilin 1 protein and resistant to suppression by such siRNAs by codon modification or otherwise excluding the shRNA target sequences from the mRNA. siRNA sequences were designed using known art and principles in molecular biology including the use of online tools, including siRNA designer at Integrated DNA Technologies (IDT; biotools.idtdna.com/site/order/design-tool/index/DSIRNA_CUSTOM), siDirect (sidirect2.rnai.jp/), and Thermo Fisher (rnaidesigner.thermofisher.com/rnaiexpress/).

A set of potential targets for siRNA were identified in either the protein encoding region or the non-coding region of the human PSEN1 mRNA. The DNA sequences encoding the corresponding siRNA sequences that target PSEN1 mRNA are set forth in SEQ ID NOS: 1-32, 42 and 43. Table 2, below, shows the PSEN1 target location in the GenBank NM 000021.4 PSEN 1 cDNA sequence (and therefore the corresponding location in the transcribed PSEN1 mRNA) to which the encoded siRNA would hybridize. Sequences within a complementary location in NM_000021.4 between 213-1616 are within the PSEN1 protein-encoding region.

TABLE 2

DNA sequences encoding siRNA that target endogenous PSEN1 mRNA and complementary location of targeting within the GenBank NM_000021.4 cDNA sequence.

| SEQ ID NO: | Complementary Location in NM_000021.4 |
|---|---|
| 1 | 94-115 |
| 2 | 176-201 |
| 3 | 402-424 |
| 4 | 452-472 |
| 5 | 607-632 |
| 6 | 621-643 |
| 7 | 630-655 |
| 42 | 953-973 |
| 8 | 1026-1048 |
| 9 | 1091-1113 |
| 10 | 1285-1307 |
| 11 | 1410-1433 |
| 43 | 1581-1601 |
| 12 | 1630-1654 |
| 13 | 1638-1660 |
| 14 | 1697-1722 |
| 15 | 1930-1954 |
| 16 | 1916-1940 |
| 17 | 2950-2975 |
| 18 | 4522-4547 |
| 19 | 5931-5956 |

A similar list was generated for DNA sequences that encode PSEN2-specific siRNA (SEQ ID NOS: 20-32). Table 3, below, shows the PSEN2 target location in the GenBank NM_000447.3 PSEN2 cDNA sequence (and therefore the corresponding location in the transcribed PSEN2 mRNA) to which the encoded siRNA would hybridize. Sequences with a complementary location in NM_000447.3 between 384-1730 are within the PSEN2 mRNA coding region.

TABLE 3

DNA sequences encoding siRNA that target endogenous PSEN2 mRNA and complementary location of targeting within the (Genbank NM_000447.3) cDNA sequence.

| SEQ ID NO: | Complementary Location in NM_000447.3 |
|---|---|
| 20 | 110-135 |
| 21 | 143-168 |
| 22 | 735-760 |
| 23 | 736-761 |
| 24 | 737-762 |
| 25 | 819-844 |
| 26 | 849-874 |
| 27 | 1349-1374 |
| 28 | 1766-1791 |
| 29 | 1771-1796 |
| 30 | 1773-1798 |
| 31 | 1962-1987 |
| 32 | 2201-2226 |

These PSEN1- and PSEN2-specific siRNA encoding sequences, or other DNA sequences encoding a siRNA that hybridizes to endogenous PSEN2 mRNA and which comprise at least 7 or more consecutive nucleotides from either the 5' or 3' end of such sequences, can be used in a polynucleotide encoding an shRNA or an miRNA that targets endogenous PSEN1 or PSEN2 mRNA.

We next designed exogenous DNA molecules that, when introduced to target cells and transcribed into RNA, silence the translation of endogenous PSEN1 or PSEN2 mRNA, including both mRNA transcribed from wild-type alleles and mutant alleles, if present. These DNA molecules included shRNA-encoding molecules (SEQ ID NO:44-47) and miRNA-encoding molecules (SEQ ID NO: 33-36). See Table 4, below, which shows the type of antisense oligonucleotide encoded, the PSEN targeted and the target location in the corresponding GenBank cDNA sequence (and therefore the corresponding location in the transcribed PSEN mRNA) to which the siRNA would hybridize.

TABLE 4 miRNA sequences. The underlined siRNA coding sequences are used to generate artificial miRNAs or Pre-miRNAs

| SEQ ID NO: | Type | PSEN Targeted | Complementary Target Location in Corresponding GenBank cDNA Sequence |
|---|---|---|---|
| 33 | miRNA | PSEN1 | 1631-1652 |
| 34 | miRNA | PSEN2 | 1766-1788 |
| 35 | miRNA | PSEN1 | 1631-1651 |
| 36 | miRNA | PSEN2 | 1768-1790 |
| 44 | shRNA | PSEN1 | 401-421 |
| 45 | shRNA | PSEN1 | 953-973 |
| 46 | shRNA | PSEN1 | 1285-1305 |
| 47 | shRNA | PSEN1 | 1581-1601 |

In addition to these, other complementary locations targeted in GenBank NM_000021.4 and NM_000447.3 cDNA sequences are represented by the siRNA sequences embedded in miRNA targeting sequences and encoded by the plasmids set forth in SEQ ID NOs: 68-81. These are set forth below in Table 4A

TABLE 4A

Additional miRNA sequences and complementary targets

| Source SEQ ID NO: | Nucleotides encoding miRNA Targeting Sequence(s) (including siRNA sequence(s)) | Nucleotides encoding siRNA Sequence(s) | PSEN Targeted | Complementary Target Location in Corresponding GenBank cDNA Sequence |
|---|---|---|---|---|
| 68 | 448-529 | 497-517 | PSEN1 | 1639-1659 |
| 69 | 448-529 | 497-517 | PSEN1 | 1697-1717 |
| 70 | 448-529 | 497-517 | PSEN1 | 1796-1816 |
| 71 | 448-529 | 497-517 | PSEN1 | 1930-1950 |
| 72 | 448-611[1] | 497-517, 579-599 | PSEN1 | 1796-1816 |
| 73 | 448-693[2] | 497-517, 579-599, 661-681 | PSEN1 | 1639-1659 |
| 74 | 448-693[2] | 497-517, 579-599, 661-681 | PSEN1 | 1796-1816 |
| 75 | 1365-1610[2] | 1414-1434, 1496-1516, 1578-1598 | PSEN1 | 1796-1816 |
| 76 | 448-529 | 497-517 | PSEN2 | 1771-1791 |
| 77 | 448-529 | 497-517 | PSEN2 | 1778-1798 |
| 78 | 448-529 | 497-517 | PSEN2 | 2206-2226 |
| 79 | 448-611[1] | 497-517, 579-599 | PSEN2 | 2206-2226 |
| 80 | 448-693[2] | 497-517, 579-599, 661-681 | PSEN2 | 2206-2226 |
| 81 | 1365-1610[2] | 1414-1434, 1496-1516, 1578-1598 | PSEN2 | 2206-2226 |

[1]comprises two consecutive copies of the miRNA.
[2]comprises three consecutive copies of the miRNA.

Any of the polynucleotide sequences encoding shRNAs or miRNAs can be delivered simultaneously or consecutively with a polynucleotide that also expresses an mRNA encoding wild-type PSEN1 or PSEN2 that is resistant to silencing by the co-delivered shRNA or miRNA. The DNA encoding PSEN1 or PSEN2 mRNA and silencer polynucleotides may be delivered as polynucleotides in a single DNA vector or as a replication-deficient adeno-associated virus (AAV) vector. Alternatively, the polynucleotide encoding the shRNA or miRNA may be delivered in a separate DNA vector or AAV vector from the polynucleotide encoding PSEN1 or PSEN2 mRNA.

An encoded shRNA comprises between about 20-25 nucleotides that are identical to a portion of the target mRNA sequence followed by a linker and a sequence complementary to that same portion of the target mRNA. shRNAs are expressed from the DNA encoding them, which is typically operably linked to an RNA polymerase III driven promoter, such as U6, U61, U69, or H1. From one to four shRNAs, each targeting a different portion of the endogenous PSEN1 or PSEN2 mRNA are expressed from the same DNA or AAV vector to mediate degradation of the endogenous PSEN1 or PSEN2 mRNA and reduce PSEN1 or PSEN2 protein levels.

Some of the PSEN1 targets (the portions PSEN1 mRNA targeted by SEQ ID NOs:6, 11, and 42) are also present in the mouse PSEN1 mRNA (see the corresponding mouse PSEN1 cDNA sequence GenBank NM_001362271.1). Therefore, antisense oligonucleotides targeting those sequences will also suppress expression of endogenous mouse PSEN1 gene. These antisense oligonucleotides may be used as a tool for in vivo assessment in mouse models of Alzheimer's disease of the efficacy of antisense molecules and vectors suppressing endogenous PSEN1 gene with simultaneous replacement by a PSEN1 gene resistant to suppression.

In the dominant forms of PSEN1 deficiency, the expression of a mutant PSEN1 subunit inhibits the assembly and function of the gamma secretase. Without being limited by theory, we believe that a simple gene replacement method would provide more wildtype PSEN1 subunit of gamma secretase, but not suppress the inhibitory effect of the mutant subunit on assembly and/or function. However, by suppressing all endogenous PSEN1 expression and replacing it with an extra-chromosomally expressed wild-type PSEN1, the full gamma secretase activity can be restored. In addition to treating Alzheimer's disease or ameliorating the increased susceptibility to Alzheimer's disease that results from dominant mutations of the PSEN1 gene, the concept of silencing endogenous PSEN1 (or PSEN2) gene expression and replacement with a gene encoding a wild-type form of that protein and resistant to silencing can be applied to any disease which involves a defect in PSEN1 (or PSEN2).

Example 2. Codon Changes to Escape Silencing by shRNA Targeting Native PSEN1 mRNA We designed replacement PSEN1 genes that encode the native PSEN1 protein sequence, but whose encoded mRNA is not recognized by the shRNA targeting the endogenous PSEN1 by one of two methods:

1) If the shRNA(s) are designed to exclusively target PSEN1 mRNA outside the protein coding portion, then the replacement PSEN1 coding sequence can be identical to the portion of the endogenous mRNA that encodes the wild-type protein. The expression vector used to express the replacement PSEN 1 coding sequence encodes both upstream and downstream non-coding portions of mRNA from a totally unrelated source that will not hybridize to the shRNA(s).

2) If any of the shRNA(s) target endogenous PSEN1 mRNA within protein encoding regions, the replacement PSEN1 coding sequence is codon-modified and uses synonymous codons that provide the same amino acids sequence. By utilizing such modified codons, the ability of the shRNA(s) to target the mRNA expressed from replacement PSEN1 coding sequence is eliminated or greatly reduced. The ability to change synonymous codons depends on the amino acid sequence encoded by the target sequence within the mRNA. Ideally, a sufficient number of codons are changed in the shRNA targeted sequence to provide at least a 50%, at least 40%, at least 30% or at least 20% nucleotide differences, or at least 4 or at least 5 mismatches from the antisense portion of the shRNA.

The codon modifications only needs to occur in those portions of the coding sequence targeted by shRNA. Therefore, the replacement PSEN1 coding sequence can be identical to the endogenous nucleotide sequence throughout most of the coding region, with only a few regions of codon modification.

The same procedure is used to generate the codon modified PSEN2 nucleic acid sequence.

Example 3. In Vitro siRNA Suppression of PSEN1

Bioinformatic assessment is used to select in silico highly specific siRNA sequences and minimize cross-reactivity. Oligonucleotides complementary to PSEN1 are designed and synthesized for specifically binding to PSEN1 and degradation of PSEN1 mRNA by the RNA interference pathway.

PSEN1 suppression is evaluated in commercial cell lines like HEK293 or Hela cells by transfection or direct incubation of the oligonucleotides. When cells reached 65-75% confluency, the transfection reagent, for example LIPOFECTIN is used to introduce the oligonucleotide into cells. Other methods of transfection are well known to those skilled in the art. The method of screening is not a limitation of the instant invention. The oligonucleotide is mixed with LIPOFECTIN (Invitrogen Life Technologies) in culture media like, OPTI-MEM-1 (Invitrogen Life Technologies) to achieve the desired concentration of oligonucleotide and a LIPOFECTIN concentration. Cells are treated and data are obtained in duplicate or triplicate. After treatment, the medium containing the transfection mixture is replaced with fresh culture medium. Cells are harvested 16-24 hours after oligonucleotide treatment.

Quantitation of PSEN1 mRNA levels is accomplished by real-time quantitative PCR. After isolation from cells, RNA is subjected to sequential reverse transcriptase (RT) reaction and real-time PCR. RT and PCR reagents can be obtained from Invitrogen Life Technologies. RT, real-time PCR is carried out according to manufacturer's instructions using primers and probe set specific for PSEN1 and the real-time PCR data is normalized to a house keeping gene whose expression is constant. The percent of inhibition of PSEN1 mRNA levels relative to control scrambled or untreated cells is calculated. The target regions to which antisense oligonucleotides are inhibitory are used to design shRNA and miRNA.

Example 4. AAV Vector with a PSEN1 Silence and Replace System to Suppress Expression of Mutant PSEN1 and Express Wild-Type PSEN1

An adenovirus associated virus (AAV) vector is constructed to contain miRNA which target and cleave PSEN1 mRNA and the coding sequence for wild-type PSEN1. The AAV viral vector containing a genome construct which encodes both the miRNA and coding sequence is derived from a commercially available plasmid-based expression vector. The commercial plasmid is modified to include inverted terminal repeats (ITR) of an AAV2, U6 a polymerase III promoter, three miRNA sequences targeting the PSEN1 gene with binding sites in the 3'UTR, CBA a polymerase II promoter, the coding sequence for wild-type PSEN1 followed by a rabbit beta-globin polyadenylation sequence and another AAV2 ITR (SEQ ID NO:37,38).

Production of AAV viral particles with PSEN1 silence and replace genome is accomplished by co-transfection of human embryonic kidney (HEK293) or insect (Sf9) cells with the AAV viral vector genome plasmid and helper plasmids to supply protein essential to AAV and a plasmid to express viral capsid proteins. Methods and cell lines for producing AAV particles are well known to those skilled in the art. Following culture, the viral particles are harvested and concentrated to achieve viral genome copy numbers in range between $10^{11}$-$10^{13}$ VG/mL (see e.g., Chen et al, Human Gene Therapy Methods 24: 270-278, 2013).

Example 5. In Vitro and In Vivo Testing of AAV Vector with PSEN2 Silence and Replace An adenovirus associated virus (AAV) vector is constructed to contain elements of a contain miRNA which target and cleave PSEN2 mRNA and the coding sequence for wild-type PSEN2. The elements of a PSEN2 silence and replace system are delivered by an AAV vector which efficiently transduces mammalian tissues and resides long term in the cell nucleus as an epichromosome.

AAV particles containing PSEN2 silence and replace system may be tested in vitro using a mammalian cell line, e.g. HEK293 cells (available from American Type Culture Collection, Manassas, VA). Transduction of mammalian cells with AAV vectors in vitro is described (see e.g., Le Cong et al, Ibid., and Sen et al, Scientific Reports 3: 1832, 2013; DOI: 10.1038/srep01832 which is incorporated herein by reference). Following transduction, the endogenous and exogenous PSEN2 transcripts may be monitored by quantitative RT-PCR (qRT-PCR) using established methods (see e.g., Perez-Pinera et al, Nature Methods Advance Online Publication, Jul. 25, 2013; doi: 10.1038/nmeth.2600 which is incorporated herein by reference).

In order to evaluate the effects of containing PSEN2 silence and replace system in the central nervous system, it is beneficial to deliver the AAV vector directly to the central nervous system, for example by intracerebroventricular (ICV) or intracisternal magna (ICM) administrations. To evaluate the effect of PSEN2 silence and replace system in the central nervous system of animals, AAV can be administered to mice via ICV delivery.

Selected AAV vectors containing potent shRNAs or miRNAs and encoding PSEN2 can be used for in vivo testing. Formulation-treated mice can be used as control animals. Each treatment or control groups may include 4-12 animals. AAV is administered ICV at a dose of $10^{10}$-$10^{11}$ viral genomes. The treatment period may be four-weeks. During the treatment period, the mice are monitored for clinical changes such as body weight changes or abnormal behaviors. At the end of the treatment period, the mice are sacrificed, and the brain is dissected. RNA is prepared for quantitative real-time PCR analysis and brain homogenates are used for PSEN2 protein quantification by ELISA and characterization by western blot.

Example 6. In Vivo PSEN1 Silence and Replace in Models of Alzheimer's Disease To evaluate the effects of PSEN1 silence and replace in the central nervous system of an animal model of AD, AAV encoding PSEN1 silence and replace are administered to PSEN1 knockin (KI) mice carrying the FAD mutation L435F. KI mice heterogenous for either mutation in a background lacking PSEN2, Psen1$^{L435F/+}$; Psen2$^{-/-}$ (Xia et al., Neuron. 2015 doi: 10.1016/j.neuron.2015.02.010). The L435F mutation abolished the production of mature PSEN1 (N-terminal and C-terminal fragments) without any change in PSEN1 mRNA levels. The Psen1$^{L435F/+}$; Psen2$^{-/-}$ transgenic mouse model shows accelerated amyloid deposition, impaired hippocampal synaptic plasticity and memory, and cerebral cortical neurodegeneration reminiscent of AD.

To evaluate the effects of PSEN1 silence and replace in animal model of AD, AAV encoding PSEN1 silence and replace system is administered to Psen1$^{L435F/+}$; Psen2$^{-/-}$ transgenic mouse model via ICV delivery. Selected AAV vectors containing potent shRNAs or miRNAs and encoding PSEN1 can be used for in vivo testing. Formulation-treated mice can be used as control animals. Each treatment or control groups may include 4-12 animals. AAV is administered ICV at a dose of $10^{10}$-$10^{11}$ viral genomes. The treatment period may be six to eighteen months. During the treatment period, the mice are monitored for clinical changes such as body weight changes or abnormal behaviors. At the end of the treatment period, the mice are sacrificed, and the brain is dissected. RNA is prepared for quantitative real-time PCR analysis and brain homogenates are used for PSEN1 protein quantification by ELISA and characterization by western blot.

Example 7. PSEN1 and PSEN2 Silence and Replace Plasmids

A plasmid comprising AAV2 ITRs (nucleotides 1-141 and 4298-4438 of SEQ ID NO:68), a U6 promoter (nucleotides 198-241 of SEQ ID NO:68), a CMV enhancer (nucleotides 561-940 of SEQ ID NO:68), a CBA promoter (nucleotides 941-1213 of SEQ ID NO:68), an HA epitope tag (nucleotides 1873-1905 of SEQ ID NO:68), a codon optimized human PSEN1 coding sequence ("hPSEN1v1.5"; nucleotides 1906-3303 of SEQ ID NO:68) or a human PSEN2 coding sequence (nucleotides 1902-3245 of SEQ ID NO:76) functionally linked to that CBA promoter, and a human growth hormone (hGH) PolyA signal (nucleotides 3337-3813 of SEQ ID NO: 68) was used as the backbone to generate the human silence and replace constructs. Into those plasmids at various sites was inserted one, two or three copies of a nucleotide sequence consisting of a miR128 targeting sequence flanking an siRNA sequence that was complementary to a different region of either native PSEN1 or native PSEN2. The resulting plasmids (SEQ ID NOs: 68-81; FIGS. 1-14) were separately transfected into HEK293 (ATCC® CRL-1573™) cells using standard techniques. The HEK293 cells were harvested 48 hours post-transfection, lysed directly using 500 μL of QIAzol Lysis Reagent (Qiagen, #79306), and the supernatant was collected. Following lysis, the samples were homogenized using a Qiashredder (Qiagen, #79656) and RNA was isolated using RNeasy Plus Universal Mini kit (Qiagen, #74034) according to the manufacturers protocol. The total RNA concentration of each sample was measured using the DeNovix DS-11 FX+ spectrophotometer/fluorometer according to the manufacturer's instructions. After isolation from cells, RNA was subjected to sequential reverse transcriptase (RT) reaction and real-time PCR. RT and PCR reagents were obtained from ThermoFisher Scientific. RT and real-time PCR was carried out according to manufacturer's instructions using primers and probe set specific for (a) native PSEN1 that did not recognize the codon-optimized human PSEN1 present on the codon-optimized PSEN1-encoding plasmids (forward primer=SEQ ID NO:82; probe=SEQ ID NO: 83; reverse primer=SEQ ID NO:84); (b) plasmid-encoded transcripts (specific for the hGHpolyA stuffer present in the plasmids; forward primer=SEQ ID NO:85; probe=SEQ ID NO: 86; reverse primer=SEQ ID NO:87), or (c) a non-coding region of native PSEN2 not present in the PSEN2-encoding plasmids (forward primer=SEQ ID NO:88; probe=SEQ ID NO: 89; reverse primer=SEQ ID NO:90). The real-time PCR data was normalized to a house keeping gene whose expression was constant. Plasmids lacking either (a) the miRNA targeting sequences and siRNA sequences (e.g., hPSEN1v1.5, FIG. 15), or (b) the miRNA recognition sequences, siRNA sequences and any PSEN coding sequences (empty vector ("EV"), FIG. 15), were used as controls.

FIG. 15 shows the results of this experiment using plasmids that harbored the codon-optimized human PSEN1 coding sequence. Endogenous PSEN1 mRNA was detected and amplified with the forward primer SEQ ID NO:82; probe SEQ ID NO: 83; and reverse primer SEQ ID NO:84. Exogenous PSEN1 mRNA was detected and amplified with the forward primer SEQ ID NO:85; probe SEQ ID NO: 86; and reverse primer SEQ ID NO:87. In FIG. 15 the results have been normalized to the endogenous and exogenous levels detected when cells were transformed with a plasmid lacking any miRNA targeting sequences and siRNA sequences, but encoding a codon-optimized human PSEN1 (hPSEN1v1.5).

FIGS. 16A and 16B show the results of this experiment using plasmids that harbored the human PSEN2 coding sequence. Endogenous PSEN2 mRNA was detected and amplified with the forward primer SEQ ID NO:88; probe SEQ ID NO: 89; and reverse primer SEQ ID NO:90. Exogenous mRNA transcripts were detected and amplified with the forward primer SEQ ID NO:85; probe SEQ ID NO: 86; and reverse primer SEQ ID NO:87. In FIG. 16A the results have been normalized to the endogenous and exogenous levels detected Example 8. Sequences

SEQ ID NO: 1
GCAAAGGCTGTTGTCACTTGC

SEQ ID NO: 2
ATAGAAATACTGTTTCACAGAAAACAA

SEQ ID NO: 3
TCATCTTCTTCCTCATCTTGCTC

SEQ ID NO: 4
ACAAAGAGCATGATCACATGC

SEQ ID NO: 5
ATCATGATGGCAGCATTCAGAATTGAG

SEQ ID NO: 6
ACAATGACACTGATCATGATGGC

SEQ ID NO: 7
TAGTCATGACAACAATGACACTGATCA

SEQ ID NO: 8
TTTCTCTCCTGAGCTGTTTCAAC

SEQ ID NO: 9
CTTCTGCCATATTCACCAACCAC

SEQ ID NO: 10
GGAAAGTTCCTGGACAGCAGCTC

SEQ ID NO: 11
GGTTGTGTTCCAGTCTCCACTGGC

SEQ ID NO: 12
AAAGAAGAAACATCCATGGGATTCTAA

SEQ ID NO: 13
ATAGTCAAAGAAGAAACATCCAT

SEQ ID NO: 14
GTGTCCACATCTAACAAAGTCAAGATT

SEQ ID NO: 15
CAGTGAAATCGTCCTGTGACCACGCGT

SEQ ID NO: 16
TGTGACCACGCGTCAAGCTGCTGATGG

SEQ ID NO: 17
TTGACATCATTAGCTCACTGTATCCCC

SEQ ID NO: 18
TCCAAGTTGCTTAGAAAGCTTCTAC

SEQ ID NO: 19
ATATCTTACCAAGAATTTGAAAGGTAT

SEQ ID NO: 20
TTTCTTCATCAGTAAAATTCAGAGGGG

SEQ ID NO: 21
TTGGGAAAAGTCACTTTAGCTCTGTGG

SEQ ID NO: 22
CAGTGAATGGCGTGTAGATGAGCTGTC

SEQ ID NO: 23
TCAGTGAATGGCGTGTAGATGAGCTGT

-continued

SEQ ID NO: 24
CTCAGTGAATGGCGTGTAGATGAGCTG

SEQ ID NO: 25
TGGTCATAACCACGATGACGCTGATCA

SEQ ID NO: 26
AGCGGTACTTGTAGAGCACCACCAAGA

SEQ ID NO: 27
ACTGTCATAGGAGTCTTCTTCCATCTC

SEQ ID NO: 28
TATACAACTGCATCCAATGAAAATTCC

SEQ ID NO: 29
AAAACTATACAACTGCATCCAATGAAA

SEQ ID NO: 30
GTAAAACTATACAACTGCATCCAATGA

SEQ ID NO: 31
TTCTCAGTTCATCTGGATAAACCTGCT

SEQ ID NO: 32
TGATATTAGTATTAAGCCACTTCCGAG

SEQ ID NO: 33
GAATCCCATAGATACTTCTTCTTTAAATGTCCATACAAGAAGAAACATCCATGGGATTC

SEQ ID NO: 34
ACTTTTCATCAAATGCAGGTAAGGTTTACATTTTACAACTGCATCCAATGAAAATT

SEQ ID NO: 35
AGGCCTCTCTCTAGAATCCCATAGATACTTCTTCTTTAAATGTCCATACAAGAAGAAACATCCA
TGGGATTCGAATGGGGCTG

SEQ ID NO: 36
TGAGCTGTTGGATTAGTTTTCATCAAATGCAGGTAAGGTTTACATTTTACAACTGCATCCAATG
AAAATTTTCAGCTGCTTC

SEQ ID NO: 37

Example AAV-transgene containing AAV2 inverted terminal repeats, U6 promoter, 3 copies of hsa-pre-mir-124a-1-hPSEN1-1631-1652, CBA promoter, PSEN1 coding Sequence, rabbit polyadenylation Sequence, and AAV2 inverted terminal repeat.

CTGCGCGCTCGCTCGCTCACTGAGGCCGCCCGGGCAAAGCCCGGGCGTCGGGCGACCTTTGGTC

GCCCGGCCTCAGTGAGCGAGCGAGCGCGCAGAGAGGGAGTGGCCAACTCCATCACTAGGGGTTC

CTTGTAGTTAATGATTAACCCGCCATGCTACTTATCTACCAGGGTAATGAAGGTCGGGCAGGAA

GAGGGCCTATTTCCCATGATTCCTTCATATTTGCATATACGATACAAGGCTGTTAGAGAGATAA

TTAGAATTAATTTGACTGTAAACACAAAGATATTAGTACAAAATACGTGACGTAGAAAGTAATA

ATTTCTTGGGTAGTTTGCAGTTTTAAAATTATGTTTTAAAATGGACTATCATATGCTTACCGTA

ACTTGAAAGTATTTCGATTTCTTGGCTTTATATATCTTGTGGAAAGGACGAAACACCAGGCCTC

TCTCTAGAATCCCATAGATACTTCTTCTTTAAATGTCCATACAAGAAGAAACATCCATGGGATT

CGAATGGGGCTGAGGCCTCTCTCTAGAATCCCATAGATACTTCTTCTTTAAATGTCCATACAAG

AAGAAACATCCATGGGATTCGAATGGGGCTGAGGCCTCTCTCTAGAATCCCATAGATACTTCTT

CTTTAAATGTCCATACAAGAAGAAACATCCATGGGATTCGAATGGGGCTGTTTTTCGCGTCGAC

ATTGATTATTGACTAGTTATTAATAGTAATCAATTACGGGGTCATTAGTTCATAGCCCATATAT

GGAGTTCCGCGTTACATAACTTACGGTAAATGGCCCGCCTGGCTGACCGCCCAACGACCCCCGC

CCATTGACGTCAATAATGACGTATGTTCCCATAGTAACGCCAATAGGGACTTTCCATTGACGTC

AATGGGTGGAGTATTTACGGTAAACTGCCCACTTGGCAGTACATCAAGTGTATCATATGCCAAG

-continued

TACGCCCCCTATTGACGTCAATGACGGTAAATGGCCCGCCTGGCATTATGCCCAGTACATGACC

TTATGGGACTTTCCTACTTGGCAGTACATCTACGTATTAGTCATCGCTATTACCATGTCGAGGC

CACGTTCTGCTTCACTCTCCCCATCTCCCCCCCCTCCCCACCCCCAATTTTGTATTTATTTATT

TTTTAATTATTTTGTGCAGCGATGGGGGCGGGGGGGGGGGGGCGCGCGCCAGGCGGGGCGGGGCG

GGGCGAGGGGCGGGGCGGGGCGAGGCGGAGAGGTGCGGCGGCAGCCAATCAGAGCGGCGCGCTC

CGAAAGTTTCCTTTTATGGCGAGGCGGCGGCGGCGGCGGCCCTATAAAAAGCGAAGCGCGCGGC

GGGGCCACCATGACAGAGTTACCTGCACCGTTGTCCTACTTCCAGAATGCACAGATGTCTGAGG

ACAACCACCTGAGCAATACTGTACGTAGCCAGAATGACAATAGAGAACGGCAGGAGCACAACGA

CAGACGGAGCCTTGGCCACCCTGAGCCATTATCTAATGGACGACCCCAGGGTAACTCCCGGCAG

GTGGTGGAGCAAGATGAGGAAGAAGATGAGGAGCTGACATTGAAATATGGCGCCAAGCATGTGA

TCATGCTCTTTGTCCCTGTGACTCTCTGCATGGTGGTGGTCGTGGCTACCATTAAGTCAGTCAG

CTTTTATACCCGGAAGGATGGGCAGCTAATCTATACCCCATTCACAGAAGATACCGAGACTGTG

GGCCAGAGAGCCCTGCACTCAATTCTGAATGCTGCCATCATGATCAGTGTCATTGTTGTCATGA

CTATCCTCCTGGTGGTTCTGTATAAATACAGGTGCTATAAGGTCATCCATGCCTGGCTTATTAT

ATCATCTCTATTGTTGCTGTTCTTTTTTTCATTCATTTACTTGGGGGAAGTGTTTAAAACCTAT

AACGTTGCTGTGGACTACATTACTGTTGCACTCCTGATCTGGAATTTTGGTGTGGTGGGAATGA

TTTCCATTCACTGGAAAGGTCCACTTCGACTCCAGCAGGCATATCTCATTATGATTAGTGCCCT

CATGGCCCTGGTGTTTATCAAGTACCTCCCTGAATGGACTGCGTGGCTCATCTTGGCTGTGATT

TCAGTATATGATTTAGTGGCTGTTTTGTGTCCGAAAGGTCCACTTCGTATGCTGGTTGAAACAG

CTCAGGAGAGAAATGAAACGCTTTTTCCAGCTCTCATTTACTCCTCAACAATGGTGTGGTTGGT

GAATATGGCAGAAGGAGACCCGGAAGCTCAAAGGAGAGTATCCAAAAATTCCAAGTATAATGCA

GAAAGCACAGAAAGGGAGTCACAAGACACTGTTGCAGAGAATGATGATGGCGGGTTCAGTGAGG

AATGGGAAGCCCAGAGGGACAGTCATCTAGGGCCTCATCGCTCTACACCTGAGTCACGAGCTGC

TGTCCAGGAACTTTCCAGCAGTATCCTCGCTGGTGAAGACCCAGAGGAAAGGGGAGTAAAACTT

GGATTGGGAGATTTCATTTTCTACAGTGTTCTGGTTGGTAAAGCCTCAGCAACAGCCAGTGGAG

ACTGGAACACAACCATAGCCTGTTTCGTAGCCATATTAATTGGTTTGTGCCTTACATTATTACT

CCTTGCCATTTTCAAGAAAGCATTGCCAGCTCTTCCAATCTCCATCACCTTTGGGCTTGTTTTC

TACTTTGCCACAGATTATCTTGTAGAGCCTTTTATGGACCAATTAGCATTCCATCAATTTTATA

TCTAGCATAGTCGACCCCTATCCATCACACTGGCGGCCGCTCGAGGACGGGGTGAACTACGCCT

GAGGATCCGATCTTTTTCCCTCTGCCAAAAATTATGGGGACATCATGAAGCCCCTTGAGCATCT

GACTTCTGGCTAATAAAGGAAATTTATTTTCATTGCAATAGTGTGTTGGAATTTTTTGTGTCTC

TCACTCGGAAGCAATTCGTTGATCTGAATTTCGACCACCCATAATACCCATTACCCTGGTAGAT

AAGTAGCATGGCGGGTTAATCATTAACTACAAGGAACCCCTAGTGATGGAGTTGGCCACTCCCT

CTCTGCGCGCTCGCTCGCTCACTGAGGCCGGGCGACCAAAGGTCGCCCGACGCCCGGGCTTTGC

CCGGGCGGCCTCAGTGAGCGAGCGAGCGCGCAG

SEQ ID NO: 38—Example AAV-transgene containing AAV2 inverted terminal repeats, U6 promoter, 3 copies of hsa-pre-mir-128a-hPSEN2-1766-1788, CBA promoter, PSEN2 coding SEQuence, rabbit polyadenylation SEQuence, and AAV2 inverted terminal repeat.

CTGCGCGCTCGCTCGCTCACTGAGGCCGCCCGGGCAAAGCCCGGGCGTCGGGCGACCTTTGGTC

GCCCGGCCTCAGTGAGCGAGCGAGCGCGCAGAGAGGGAGTGGCCAACTCCATCACTAGGGGTTC

CTTGTAGTTAATGATTAACCCGCCATGCTACTTATCTACCAGGGTAATGAAGGTCGGGCAGGAA

GAGGGCCTATTTCCCATGATTCCTTCATATTTGCATATACGATACAAGGCTGTTAGAGAGATAA

TTAGAATTAATTTGAGTGTAAACACAAAGATATTAGTACAAAATACGTGACGTAGAAAGTAATA

ATTTCTTGGGTAGTTTGCAGTTTTAAAATTATGTTTTAAAATGGACTATCATATGCTTACCGTA

ACTTGAAAGTATTTCGATTTCTTGGCTTTATATATCTTGTGGAAAGGACGAAACACCATGAGCT

GTTGGATTAGTTTTCATCAAATGCAGGTAAGGTTTACATTTTACAACTGCATCCAATGAAAATT

TTCAGCTGCTTCTGAGCTGTTGGATTACTTTTCATCAAATGCAGGTAAGGTTTACATTTTACAA

CTGCATCCAATGAAAATTTTCAGCTGCTTCTGAGCTGTTGGATTACTTTTCATCAAATGCAGGT

AAGGTTTACATTTTACAACTGCATCCAATGAAAATTTTCAGCTGCTTCTTTTTCGCGTCGACAT

TGATTATTGACTAGTTATTAATAGTAATCAATTACGGGGTCATTAGTTCATAGCCCATATATGG

AGTTCCGCGTTACATAACTTACGGTAAATGGCCCGCCTGGCTGACCGCCCAACGACCCCCGCCC

ATTGAGGTCAATAATGAGGTATGTTCCCATAGTAACGCCAATAGGGAGTTTCCATTGAGGTCAA

TGGGTGGAGTATTTACGGTAAACTGCCCACTTGGCAGTACATCAAGTGTATCATATGCCAAGTA

CGCCCCCTATTGACGTCAATGACGGTAAATGGCCCGCCTGGCATTATGCCCAGTACATGACCTT

ATGGGACTTTCCTACTTGGCAGTACATCTACGTATTAGTCATCGCTATTACCATGTCGAGGCCA

CGTTCTGCTTCACTCTCCCCATCTCCCCCCCCTCCCCACCCCCAATTTTGTATTTATTTATTTT

TTAATTATTTTGTGCAGCGATGGGGGCGGGGGGGGGGGGCGCGCGCCAGGCGGGGCGGGGCGGG

GCGAGGGGCGGGGCGGGGCGAGGCGGAGAGGTGCGGCGGCAGCCAATCAGAGCGGCGCGCTCCG

AAAGTTTCCTTTTATGGCGAGGCGGCGGCGGCGGCGGCCCTATAAAAAGCGAAGCGCGCGGCGG

GGCCACCATGCTCACATTCATGGCCTCTGACAGCGAGGAAGAAGTGTGTGATGAGCGGACGTCC

CTAATGTCGGCTGAGAGCCCCACGCCGCGCTCCTGCCAGGAGGGCAGGCAGGGCCCAGAGGATG

GAGAGAACACTGCCCAGTGGAGAAGCCAGGAGAACGAGGAGGACGGTGAGGAGGACCCTGACCG

CTATGTCTGTAGTGGGGTTCCCGGGCGGCCGCCAGGCCTGGAGGAAGAGCTGACCCTCAAATAC

GGAGCGAAGCACGTGATCATGCTGTTTGTGCCTGTCACTCTGTGCATGATCGTGGTGGTAGCCA

CCATCAAGTCTGTGCGCTTCTACACAGAGAAGAATGGACAGCTCATCTACACGCCATTCACTGA

GGACACACCCTCGGTGGGCCAGCGCCTCCTCAACTCCGTGCTGAACACCCTCATCATGATCAGC

GTCATCGTGGTTATGACCATCTTCTTGGTGGTGCTCTACAAGTACCGCTGCTACAAGTTCATCC

ATGGCTGGTTGATCATGTCTTCACTGATGCTGCTGTTCCTCTTCACCTATATCTACCTTGGGGA

AGTGCTCAAGACCTACAATGTGGCCATGGACTACCCCACCCTCTTGCTGACTGTCTGGAACTTC

GGGGCAGTGGGCATGGTGTGCATCCACTGGAAGGGCCCTCTGGTGCTGCAGCAGGCCTACCTCA

TCATGATCAGTGCGCTCATGGCCCTAGTGTTCATCAAGTACCTCCCAGAGTGGTCCGCGTGGGT

CATCCTGGGCGCCATCTCTGTGTATGATCTCGTGGCTGTGCTGTGTCCCAAAGGGCCTCTGAGA

ATGCTGGTAGAAACTGCCCAGGAGAGAAATGAGCCCATATTCCCTGCCCTGATATACTCATCTG

CCATGGTGTGGACGGTTGGCATGGCGAAGCTGGACCCCTCCTCTCAGGGTGCCCTCCAGCTCCC

CTACGACCCGGAGATGGAAGAAGACTCCTATGACAGTTTTGGGGAGCCTTCATACCCCGAAGTC

-continued

TTTGAGCCTCCCTTGACTGGCTACCCAGGGGAGGAGCTGGAGGAAGAGGAGGAAAGGGGCGTGA

AGCTTGGCCTCGGGGACTTCATCTTCTACAGTGTGCTGGTGGGCAAGGCGGCTGCCACGGGCAG

CGGGGACTGGAATACCACGCTGGCCTGCTTCGTGGCCATCCTCATTGGCTTGTGTCTGACCCTC

CTGCTGCTTGCTGTGTTCAAGAAGGCGCTGCCCGCCCTCCCCATCTCCATCACGTTCGGGCTCA

TCTTTTACTTCTCCACGGACAACCTGGTGCGGCCGTTCATGGACACCCTGGCCTCCCATCAGCT

CTACATCTGACATAGTCGACCCCTATCCATCACACTGGCGGCCGCTCGAGGACGGGGTGAACTA

CGCCTGAGGATCCGATCTTTTTCCCTCTGCCAAAAATTATGGGGACATCATGAAGCCCCTTGAG

CATCTGACTTCTGGCTAATAAAGGAAATTTATTTTCATTGCAATAGTGTGTTGGAATTTTTTGT

GTCTCTCACTCGGAAGCAATTCGTTGATCTGAATTTCGACCACCCATAATACCCATTACCCTGG

TAGATAAGTAGCATGGCGGGTTAATCATTAACTACAAGGAACCCCTAGTGATGGAGTTGGCCAC

TCCCTCTCTGCGCGCTCGCTCGCTCACTGAGGCCGGGCGACCAAAGGTCGCCCGACGCCCGGGC

TTTGCCCGGGCGGCCTCAGTGAGCGAGCGAGCGCGCAG

-NM_000021.4 *Homo sapiens* presenilin 1 (PSEN1), coding sequence

SEQ ID NO: 39

ATGACAGAGTTACCTGCACCGTTGTCCTACTTCCAGAATGCACAGATGTCTGAGGACAACCACC

TGAGCAATACTGTACGTAGCCAGAATGACAATAGAGAACGGCAGGAGCACAACGACAGACGGAG

CCTTGGCCACCCTGAGCCATTATCTAATGGACGACCCCAGGGTAACTCCCGGCAGGTGGTGGAG

CAAGATGAGGAAGAAGATGAGGAGCTGACATTGAAATATGGCGCCAAGCATGTGATCATGCTCT

TTGTCCCTGTGACTCTCTGCATGGTGGTGGTCGTGGCTACCATTAAGTCAGTCAGCTTTTATAC

CCGGAAGGATGGGCAGCTAATCTATACCCCATTCACAGAAGATACCGAGACTGTGGGCCAGAGA

GCCCTGCACTCAATTCTGAATGCTGCCATCATGATCAGTGTCATTGTTGTCATGACTATCCTCC

TGGTGGTTCTGTATAAATACAGGTGCTATAAGGTCATCCATGCCTGGCTTATTATATCATCTCT

ATTGTTGCTGTTCTTTTTTTCATTCATTTACTTGGGGGAAGTGTTTAAAACCTATAACGTTGCT

GTGGACTACATTACTGTTGCACTCCTGATCTGGAATTTTGGTGTGGTGGGAATGATTTCCATTC

ACTGGAAAGGTCCACTTCGACTCCAGCAGGCATATCTCATTATGATTAGTGCCCTCATGGCCCT

GGTGTTTATCAAGTACCTCCCTGAATGGACTGCGTGGCTCATCTTGGCTGTGATTTCAGTATAT

GATTTAGTGGCTGTTTTGTGTCCGAAAGGTCCACTTCGTATGCTGGTTGAAACAGCTCAGGAGA

GAAATGAAACGCTTTTTCCAGCTCTCATTTACTCCTCAACAATGGTGTGGTTGGTGAATATGGC

AGAAGGAGACCCGGAAGCTCAAAGGAGAGTATCCAAAAATTCCAAGTATAATGCAGAAAGCACA

GAAAGGGAGTCACAAGACACTGTTGCAGAGAATGATGATGGCGGGTTCAGTGAGGAATGGGAAG

CCCAGAGGGACAGTCATCTAGGGCCTCATCGCTCTACACCTGAGTCACGAGCTGCTGTCCAGGA

ACTTTCCAGCAGTATCCTCGCTGGTGAAGACCCAGAGGAAAGGGGAGTAAAACTTGGATTGGGA

GATTTCATTTTCTACAGTGTTCTGGTTGGTAAAGCCTCAGCAACAGCCAGTGGAGACTGGAACA

CAACCATAGCCTGTTTCGTAGCCATATTAATTGGTTTGTGCCTTACATTATTACTCCTTGCCAT

TTTCAAGAAAGCATTGCCAGCTCTTCCAATCTCCATCACCTTTGGGCTTGTTTTCTACTTTGCC

ACAGATTATCTTGTAGAGCCTTTTATGGACCAATTAGCATTCCATCAATTTTATATCTAG

-NM_000447.3 *Homo sapiens* presenilin 2 (PSEN2), coding Sequence

SEQ ID NO: 40

ATGCTCACATTCATGGCCTCTGACAGCGAGGAAGAAGTGTGTGATGAGCGGACGTCCCTAATGT

CGGCTGAGAGCCCCACGCCGCGCTCCTGCCAGGAGGGCAGGCAGGGCCCAGAGGATGGAGAGAA

CACTGCCCAGTGGAGAAGCCAGGAGAACGAGGAGGACGGTGAGGAGGACCCTGACCGCTATGTC

TGTAGTGGGGTTCCCGGGCGGCCGCCAGGCCTGGAGGAAGAGCTGACCCTCAAATACGGAGCGA

AGCACGTGATCATGCTGTTTGTGCCTGTCACTCTGTGCATGATCGTGGTGGTAGCCACCATCAA

-continued

GTCTGTGCGCTTCTACACAGAGAAGAATGGACAGCTCATCTACACGCCATTCACTGAGGACACA

CCCTCGGTGGGCCAGCGCCTCCTCAACTCCGTGCTGAACACCCTCATCATGATCAGCGTCATCG

TGGTTATGACCATCTTCTTGGTGGTGCTCTACAAGTACCGCTGCTACAAGTTCATCCATGGCTG

GTTGATCATGTCTTCACTGATGCTGCTGTTCCTCTTCACCTATATCTACCTTGGGGAAGTGCTC

AAGACCTACAATGTGGCCATGGACTACCCCACCCTCTTGCTGACTGTCTGGAACTTCGGGGCAG

TGGGCATGGTGTGCATCCACTGGAAGGGCCCTCTGGTGCTGCAGCAGGCCTACCTCATCATGAT

CAGTGCGCTCATGGCCCTAGTGTTCATCAAGTACCTCCCAGAGTGGTCCGCGTGGGTCATCCTG

GGCGCCATCTCTGTGTATGATCTCGTGGCTGTGCTGTGTCCCAAAGGGCCTCTGAGAATGCTGG

TAGAAACTGCCCAGGAGAGAAATGAGCCCATATTCCCTGCCCTGATATACTCATCTGCCATGGT

GTGGACGGTTGGCATGGCGAAGCTGGACCCCTCCTCTCAGGGTGCCCTCCAGCTCCCCTACGAC

CCGGAGATGGAAGAAGACTCCTATGACAGTTTTGGGGAGCCTTCATACCCCGAAGTCTTTGAGC

CTCCCTTGACTGGCTACCCAGGGGAGGAGCTGGAGGAAGAGGAGGAAAGGGGCGTGAAGCTTGG

CCTCGGGGACTTCATCTTCTACAGTGTGCTGGTGGGCAAGGCGGCTGCCACGGGCAGCGGGGAC

TGGAATACCACGCTGGCCTGCTTCGTGGCCATCCTCATTGGCTTGTGTCTGACCCTCCTGCTGC

TTGCTGTGTTCAAGAAGGCGCTGCCCGCCCTCCCCATCTCCATCACGTTCGGGCTCATCTTTTA

CTTCTCCACGGACAACCTGGTGCGGCCGTTCATGGACACCCTGGCCTCCCATCAGCTCTACATC

TGA

>PSEN1 codon modified to avoid shRNAs

SEQ ID NO: 41

CCCAGATCTGCCACCATGACAGAGTTACCTGCACCGTTGTCCTACTTCCAGAATGCACAGATGT

CTGAGGACAACCACCTGAGCAATACTGTACGTAGCCAGAATGACAATAGAGAACGGCAGGAGCA

CAACGACAGACGGAGCCTTGGCCACCCTGAGCCATTATCTAATGGACGACCCCAGGGTAACTCC

CGGCAGGTGGTGGAACAGGACGAAGAGGAGGACGAAGAGCTGACATTGAAATATGGCGCCAAAC

ACGTCATAATGCTATTCGTGCCTGTGACTCTCTGCATGGTGGTGGTCGTGGCTACCATTAAGTC

AGTCAGCTTTTATACCCGGAAGGATGGGCAGCTAATCTATACCCCATTCACAGAAGATACCGAG

ACTGTGGGCCAGAGAGCCCTGCATAGCATACTCAAGGCAGCTATTATGATTTCCGTGATCGTTG

TCATGACTATCCTCCTGGTGGTTCTGTATAAATACAGGTGCTATAAGGTCATCCATGCCTGGCT

TATTATATCATCTCTATTGTTGCTGTTCTTTTTTTCATTCATTTACTTGGGGGAAGTGTTTAAA

ACCTATAACGTTGCTGTGGACTACATTACTGTTGCACTCCTGATCTGGAATTTTGGTGTGGTGG

GAATGATTTCCATTCACTGGAAAGGTCCACTTCGACTCCAGCAGGCATATCTCATTATGATTAG

TGCCCTCATGGCCCTGGTGTTTATCAAGTACCTCCCTGAATGGACTGCGTGGCTCATCTTGGCT

GTGATTTCAGTATATGATTTAGTGGCTGTTTTGTGTCCGAAAGGTCCACTTCGAATGCTAGTCG

AGACGGCACAAGAAAGAAATGAAACGCTTTTTCCAGCTCTCATTTACTCCTCAACTATGGTATG

GCTAGTCAACATGGCAGAAGGAGACCCGGAAGCTCAAAGGAGAGTATCCAAAAATTCCAAGTAT

AATGCAGAAAGCACAGAAAGGGAGTCACAAGACACTGTTGCAGAGAATGATGATGGCGGGTTCA

GTGAGGAATGGGAAGCCCAGAGGGACAGTCATCTAGGGCCTCATCGCTCTACACCTGAGTCACG

AGCAGCGGTGCAAGAGCTGTCTTCCAGTATCCTCGCTGGTGAAGACCCAGAGGAAAGGGGAGTA

AAACTTGGATTGGGAGATTTCATTTTCTACAGTGTTCTGGTTGGTAAAGCCTCAGCAACAGCGA

GTGGTGATTGGAATACTACGATAGCCTGTTTCGTAGCCATATTAATTGGTTTGTGCCTTACATT

-continued

ATTACTCCTTGCCATTTTCAAGAAAGCATTGCCAGCTCTTCCAATCTCCATCACCTTTGGGCTT

GTTTTCTACTTTGCCACAGATTATCTTGTAGAGCCTTTTATGGACCAATTAGCATTCCATCAAT

TTTATATCTAGCATAGTCGACCCC

SEQ ID NO: 42
GAAATCACAGCCAAGATGAGC

SEQ ID NO: 43
ATGGAATGCTAATTGGTCCAT

SEQ ID NO: 44
GGAGCAAGATGAGGAAGAAGACGAATCTTCTTCCTCATCTTGCTCCTT

SEQ ID NO: 45
GCTCATCTTGGCTGTGATTTCCGAAGAAATCACAGCCAAGATGAGCTT

SEQ ID NO: 46
AAAGTTCCTGGACAGCAGCTCCGAAGAGCTGCTGTCCAGGAACTTTTT

SEQ ID NO: 47
GATGGAATGCTAATTGGTCCATCGAAATGGACCAATTAGCATTCCATT

>Human PSEN1 with all tolerant, non-preferred codons changed to highly preferred synonymous codon. Changed codons in lower case:

SEQ ID NO: 48
ATGACAGAGTTACCTGCAcctTTGTCCTACTTCCAGAATGCACAGATGTCTGAGGACAACCACC

TGAGCAATACTGTACGTAGCCAGAATGACAATAGAGAACGGCAGGAGCACAACGACAGACGGAG

CctgGGCCACCCTGAGCCActgTCTAATGGAagaCCCCAGGGTAACTCCCGGCAGGTGGTGGAG cagGATGAGGAAGAAGATGAGGAGCTGACActgAAATATGGCGCCAAGcacGTGATCATGCTCT

TTGTCCCTGTGACTCTCTGCATGGTGGTGGTCGTGGCTACCATTAAGTCAGTCAGCTTTTATAC

CCGGAAGGATGGGCAGCTAATCTATACCCCATTCACAGAAGATACCGAGACTGTGGGCCAGAGA

GCCCTGCACTCAATTCTGAATGCTGCCATCATGATCAGTGTCATTGTTGTCATGACTATCCTCC

TGGTGGTTCTGTATAAATACAGGTGCTATAAGGTCATCCATGCCTGGctgATTATATCATCTct gTTGctgCTGTTCTTTTTTTCATTCATTTACctgGGGGAAGTGTTTAAAACCTATAACGTTGCT GTGGACTACATTACTGTTGCACTCCTGATCTGGAATTTTggcGTGGTGGGAATGATTTCCATTC ACTGGAAAggcCCActgagaCTCCAGCAGGCATATCTCATTATGATTAGTGCCCTCATGGCCCT GGTGTTTATCAAGTACCTCCCTGAATGGACTgccTGGCTCATCTTGGCTGTGATTTCAGTGTAT GATTTAGTGGCTGTTctgTGTcctAAAGGTCCActgCGTATGCTGgtgGAAACAGCTCAGGAGA GAAATGAAaccctgTTTCCAGCTCTCATTTACTCCTCAACAATGGTGTGGctgGTGAATATGGC AGAAGGAGACcctGAAGCTCAAAGGAGAgtgTCCAAAAATTCCAAGTATAATGCAGAAAGCACA GAAAGGGAGTCAcagGACACTGTTGCAGAGAATGATGATGGCGGGTTCAGTGAGGAATGGGAAG CCCAGAGGGACAGTcacctgGGGCCTcacCGCTCTACACCTGAGTCAagaGCTGCTGTCCAGGA ActgTCCAGCAGTATCCTCGCTggcGAAGACCCAGAGGAAAGGGGAGTAAAACTTGGATTGGGA GATTTCATTTTCTACAGTGTTCTGGTTggcAAAGCCTCAGCAACAGCCAGTGGAGACTGGAACA CAACCATAGCCTGTTTCGTAGCCatcTTAATTggcctgTGCCTTACActgctgCTCctgGCCAT TTTCAAGAAAGCActgCCAGCTctgCCAATCTCCATCACCTTTGGGCTTGTTTTCTACTTTGCC ACAGATTATctggtgCAGCCTTTTATGGACcagctgGCATTCcaccagTTTTATATCtaaATGA CAGAGTTACCTGCAcctTTGTCCTACTTCCAGAATGCACAGATGTCTGAGGACAACCACCTGAG CAATACTGTACGTAGCCAGAATGACAATAGAGAACGGCAGGAGCACAACGACAGACGGAGCctg GGCCACCCTGAGCCActgTCTAATGGAagaCCCCAGGGTAACTCCCGGCAGGTGGTGGAGcagG ATGAGGAAGAAGATGAGGAGCTGACActgAAATATGGCGCCAAGcacGTGATCATGCTCTTTGT

CCCTGTGACTCTCTGCATGGTGGTGGTCGTGGCTACCATTAAGTCAGTCAGCTTTTATACCCGG

-continued

AAGGATGGGCAGCTAATCTATACCCCATTCACAGAAGATACCGAGACTGTGGGCCAGAGAGCCC

TGCACTCAATTCTGAATGCTGCCATCATGATCAGTGTCATTGTTGTCATGACTATCCTCCTGGT

GGTTCTGTATAAATACAGGTGCTATAAGGTCATCCATGCCTGGctgATTATATCATCTctgTTG ctgCTGTTCTTTTTTTCATTCATTTACctgGGGGAAGTGTTTAAAACCTATAACGTTGCTGTGG ACTACATTACTGTTGCACTCCTGATCTGGAATTTTggcGTGGTGGGAATGATTTCCATTCACTG GAAAggcCCActgagaCTCCAGCAGGCATATCTCATTATGATTAGTGCCCTCATGGCCCTGGTG TTTATCAAGTACCTCCCTGAATGGACTgccTGGCTCATCTTGGCTGTGATTTCAGTGTATGATT TAGTGGCTGTTctgTGTcctAAAGGTCCActgCGTATGCTGgtgGAAACAGCTCAGGAGAGAAA TGAAaccctgTTTCCAGCTCTCATTTACTCCTCAACAATGGTGTGGctgGTGAATATGGCAGAA GGAGACcctGAAGCTCAAAGGAGAgtgTCCAAAAATTCCAAGTATAATGCAGAAAGCACAGAAA GGGAGTCAcagGACACTGTTGCAGAGAATGATGATGGCGGGTTCAGTGAGGAATGGGAAGCCCA GAGGGACAGTcacctgGGGCCTcacCGCTCTACACCTGAGTCAagaGCTGCTGTCCAGGAActg TCCAGCAGTATCCTCGCTggcGAAGACCCAGAGGAAAGGGGAGTAAAACTTGGATTGGGAGATT TCATTTTCTACAGTGTTCTGGTTggcAAAGCCTCAGCAACAGCCAGTGGAGACTGGAACACAAC CATAGCCTGTTTCGTAGCCatcTTAATTggcctgTGCCTTACActgctgCTCctgGCCATTTTC AAGAAAGCActgCCAGCTctgCCAATCTCCATCACCTTTGGGCTTGTTTTCTACTTTGCCACAG ATTATctggtgCAGCCTTTTATGGACcagctgGCATTCcaccagTTTTATATCtaa Example AAV-transgene containing AAV2 inverted terminal repeats, U6 promoter, 1 copy of Anti-hPSEN1-401-421 (underlined), H1 promoter, 1 copy of Anti-hPSEN1-953-973 (underlined), GAG promoter, codon modified PSEN1 coding SEQuence, rabbit polyadenylation SEQuence, and AAV2 inverted terminal repeat.

SEQ ID NO: 49

CTGCGCGCTCGCTCGCTCACTGAGGCCGCCCGGGCAAAGCCCGGGCGTCGGGCGACCTTTGGTC

GCCCGGCCTCAGTGAGCGAGCGAGCGCGCAGAGAGGGAGTGGCCAACTCCATCACTAGGGGTTC

CTTGTAGTTAATGATTAACCCGCCATGCTACTTATCTACCAGGGTAATGGGGATCCTCTAGAAC

TATGGTACCAAGGTCGGGCAGGAAGAGGGCCTATTTCCCATGATTCCTTCATATTTGCATATAC

GATACAAGGCTGTTAGAGAGATAATTAGAATTAATTTGACTGTAAACACAAAGATATTAGTACA

AAATACGTGACGTAGAAAGTAATAATTTCTTGGGTAGTTTGCAGTTTTAAAATTATGTTTTAAA

ATGGACTATCATATGCTTACCGTAACTTGAAAGTATTTCGATTTCTTGGCTTTATATATCTTGT

GGAAAGGACGAAACACCGGAGCAAGATGAGGAAGAAGACGAATCTTCTTCCTCATCTTGCTCCT

TTTTTCTAGAGAACGCTGACGTCATCAACCCGCTCCAAGGAATCGCGGGCCCAGTGTCACTAGG

CGGGAACACCCAGCGCGCGTGCGCCCTGGCAGGAAGATGGCTGTGAGGGACAGGGGAGTGGCGC

CCTGCAATATTTGCATGTCGCTATGTGTTCTGGGAAATCACCATAAACGTGAAATGTCTTTGGA

TTTGGGAATCTTATAAGTTCTGTATGAGACCACGCTCATCTTGGCTGTGATTTCCGAAGAAATC

ACAGCCAAGATGAGCTTTTTTCTAGTCGACATTGATTATTGACTAGTTATTAATAGTAATCAAT

TACGGGGTCATTAGTTCATAGCCCATATATGGAGTTCCGCGTTACATAACTTACGGTAAATGGC

CCGCCTGGCTGACCGCCCAACGACCCCCGCCCATTGACGTCAATAATGACGTATGTTCCCATAG

TAACGCCAATAGGGACTTTCCATTGACGTCAATGGGTGGAGTATTTACGGTAAACTGCCCACTT

GGCAGTACATCAAGTGTATCATATGCCAAGTACGCCCCCTATTGACGTCAATGACGGTAAATGG

CCCGCCTGGCATTATGCCCAGTACATGACCTTATGGGACTTTCCTACTTGGCAGTACATCTACG

TATTAGTCATCGCTATTACCATGGTCGAGGTGAGCCCCACGTTCTGCTTCACTCTCCCCATCTC

CCCCCCCTCCCCACCCCCAATTTTGTATTTATTTATTTTTTAATTATTTTGTGCAGCGATGGGG

-continued

GCGGGGGGGGGGGGGGGGCGCGCGCCAGGCGGGGCGGGGCGGGGCGAGGGGCGGGGCGGGGCGA

GGCGGAGAGGTGCGGCGGCAGCCAATCAGAGCGGCGCGCTCCGAAAGTTTCCTTTTATGGCGAG

GCGGCGGCGGCGGCGGCCCTATAAAAAGCGAAGCGCGCGGCGGGCGGGAGTCGCTGCGCGCTGC

CTTCGCCCCGTGCCCCGCTCCGCCGCCGCCTCGCGCCGCCCGCCCCGGCTCTGACTGACCGCGT

TACTCCCACAGGTGAGCGGGCGGGACGGCCCTTCTCCTCCGGGCTGTAATTAGCGCTTGGTTTA

ATGACGGCTTGTTTCTTTTCTGTGGCTGCGTGAAAGCCTTGAGGGGCTCCGGGAGGGCCCTTTG

TGCGGGGGGAGCGGCTCGGGGGGTGCGTGCGTGTGTGTGTGCGTGGGGAGCGCCGCGTGCGGCT

CCGCGCTGCCCGGCGGCTGTGAGCGCTGCGGGCGCGGCGCGGGGCTTTGTGCGCTCCGCAGTGT

GCGCGAGGGGAGCGCGGCCGGGGGCGGTGCCCCGCGGTGCGGGGGGGGCTGCGAGGGGAACAAA

GGCTGCGTGCGGGGTGTGTGCGTGGGGGGGTGAGCAGGGGGTGTGGGCGCGTCGGTCGGGCTGC

AACCCCCCCTGCACCCCCCTCCCCGAGTTGCTGAGCACGGCCCGGCTTCGGGTGCGGGGCTCCG

TACGGGGCGTGGCGCGGGGCTCGCCGTGCCGGGCGGGGGGTGGCGGCAGGTGGGGGTGCCGGGC

GGGGCGGGGCCGCCTCGGGCCGGGGAGGGCTCGGGGGAGGGGCGCGGCGGCCCCCGGAGCGCCG

GCGGCTGTCGAGGCGCGGCGAGCCGCAGCCATTGCCTTTTATGGTAATCGTGCGAGAGGGCGCA

GGGACTTCCTTTGTCCCAAATCTGTGCGGAGCCGAAATCTGGGAGGCGCCGCCGCACCCCCTCT

AGCGGGCGCGGGGCGAAGCGGTGCGGCGCCGGCAGGAAGGAAATGGGCGGGGAGGGCCTTCGTG

CGTCGCCGCGCCGCCGTCCCCTTCTCCCTCTCCAGCCTCGGGGCTGTCCGCGGGGGGACGGCTG

CCTTCGGGGGGGACGGGGCAGGGCGGGGTTCGGCTTCTGGCGTGTGACCGGCGGCTCTAGAGCC

TCTGCTAACCATGTTCATGCCTTCTTCTTTTTCCTACAGCTCCTGGGCAACGTGCTGGTTATTG

TGCTGTCTCATCATTTTGGCAAAGAATTCACGCCCCAGATCTGCCACCATGACAGAGTTACCTG

CACCGTTGTCCTACTTCCAGAATGCACAGATGTCTGAGGACAACCACCTGAGCAATACTGTACG

TAGCCAGAATGACAATAGAGAACGGCAGGAGCACAACGACAGACGGAGCCTTGGCCACCCTGAG

CCATTATCTAATGGACGACCCCAGGGTAACTCCCGGCAGGTGGTGGAACAGGACGAAGAGGAGG

ATGAGGAGCTGACATTGAAATATGGCGCCAAGCATGTGATCATGCTCTTTGTCCCTGTGACTCT

CTGCATGGTGGTGGTCGTGGCTACCATTAAGTCAGTCAGCTTTTATACCCGGAAGGATGGGCAG

CTAATCTATACCCCATTCACAGAAGATACCGAGACTGTGGGCCAGAGAGCCCTGCACTCAATTC

TGAATGCTGCCATCATGATCAGTGTCATTGTTGTCATGACTATCCTCCTGGTGGTTCTGTATAA

ATACAGGTGCTATAAGGTCATCCATGCCTGGCTTATTATATCATCTCTATTGTTGCTGTTCTTT

TTTTCATTCATTTACTTGGGGGAAGTGTTTAAAACCTATAACGTTGCTGTGGACTACATTACTG

TTGCACTCCTGATCTGGAATTTTGGTGTGGTGGGAATGATTTCCATTCACTGGAAAGGTCCACT

TCGACTCCAGCAGGCATATCTCATTATGATTAGTGCCCTCATGGCCCTGGTGTTTATCAAGTAC

CTCCCTGAATGGACTGCGTGGCTGATTCTAGCCGTAATCTCAGTATATGATTTAGTGGCTGTTT

TGTGTCCGAAAGGTCCACTTCGTATGCTGGTTGAAACAGCTCAGGAGAGAAATGAAACGCTTTT

TCCAGCTCTCATTTACTCCTCAACAATGGTGTGGTTGGTGAATATGGCAGAAGGAGACCCGGAA

GCTCAAAGGAGAGTATCCAAAAATTCCAAGTATAATGCAGAAAGCACAGAAAGGGAGTCACAAG

ACACTGTTGCAGAGAATGATGATGGCGGGTTCAGTGAGGAATGGGAAGCCCAGAGGGACAGTCA

TCTAGGGCCTCATCGCTCTACACCTGAGTCACGAGCTGCTGTCCAGGAACTTTCCAGCAGTATC

CTCGCTGGTGAAGACCCAGAGGAAAGGGGAGTAAAACTTGGATTGGGAGATTTCATTTTCTACA

GTGTTCTGGTTGGTAAAGCCTCAGCAACAGCCAGTGGAGACTGGAACACAACCATAGCCTGTTT

CGTAGCCATATTAATTGGTTTGTGCCTTACATTATTACTCCTTGCCATTTTCAAGAAAGCATTG

CCAGCTCTTCCAATCTCCATCACCTTTGGGCTTGTTTTCTACTTTGCCACAGATTATCTTGTAC

-continued

AGCCTTTTATGGACCAATTAGCATTCCATCAATTTTATATCTAGCATAGTCGACCCCTATCCAT

CACACTGGCGGCCGCTCGAGGACGGGGTGAACTACGCCTGAGGATCCGATCTTTTTCCCTCTGC

CAAAAATTATGGGGACATCATGAAGCCCCTTGAGCATCTGACTTCTGGCTAATAAAGGAAATTT

ATTTTCATTGCAATAGTGTGTTGGAATTTTTTGTGTCTCTCACTCGGAAGCAATTCGTTGATCT

GAATTTCGACCACCCATAATACCCATTACCCTGGTAGATAAGTAGCATGGCGGGTTAATCATTA

ACTACAAGGAACCCCTAGTGATGGAGTTGGCCACTCCCTCTCTGCGCGCTCGCTCGCTCACTGA

GGCCGGGCGACCAAAGGTCGCCCGACGCCCGGGCTTTGCCCGGGCGGCCTCAGTGAGCGAGCGA

GCGCGCAG

>CAG promoter

SEQ ID NO: 50

GACATTGATTATTGACTAGTTATTAATAGTAATCAATTACGGGGTCATTAGTTCATAGCCCATA

TATGGAGTTCCGCGTTACATAACTTACGGTAAATGGCCCGCCTGGCTGACCGCCCAACGACCCC

CGCCCATTGACGTCAATAATGACGTATGTTCCCATAGTAACGCCAATAGGGACTTTCCATTGAC

GTCAATGGGTGGAGTATTTACGGTAAACTGCCCACTTGGCAGTACATCAAGTGTATCATATGCC

AAGTACGCCCCCTATTGACGTCAATGACGGTAAATGGCCCGCCTGGCATTATGCCCAGTACATG

ACCTTATGGGACTTTCCTACTTGGCAGTACATCTACGTATTAGTCATCGCTATTACCATGGTCG

AGGTGAGCCCCACGTTCTGCTTCACTCTCCCCATCTCCCCCCCCTCCCCACCCCCAATTTTGTA

TTTATTTATTTTTTAATTATTTTGTGCAGCGATGGGGGCGGGGGGGGGGGGGGGGCCCCCCCCA

GGCGGGGCGGGGCGGGGCGAGGGGCGGGGCGGGGCGAGGCGGAAAGGTGCGGCGGCAGCCAATC

AGAGCGGCGCGCTCCGAAAGTTTCCTTTTATGGCGAGGCGGCGGCGGCGGCGGCCCTATAAAAA

GCGAAGCGCGCGGCGGGCGGGAGTCGTTGCGCGCTGCCTTCGCCCCGTGCCCCGCTCCGCCGCC

GCCTCGCGCCGCCCGCCCCGGCTCTGACTGACCGCGTTACTCCCACAGGTGAGCGGGCGGGACG

GCCCTTCTCCTCCGGGCTGTAATTAGCGCTTGGTTTAATGACGGCTTGTTTCTTTTCTGTGGCT

GCGTGAAAGCCTTGAGGGGCTCCGGGAGGGCCCTTTGTGCGGGGGGAGCGGCTCGGGGGGTGCG

TGCGTGTGTGTGTGCGTGGGGAGCGCCGCGTGCGGCTCCGCGCTGCCCGGCGGCTGTGAGCGCT

GCGGGCGCGGCGCGGGGCTTTGTGCGCTCCGCAGTGTGCGCGAGGGGAGCGCGGCCGGGGGCGG

TGCCCCGCGGTGCGGGGGGGGCTGCGAGGGGAACAAAGGCTGCGTGCGGGGTGTGTGCGTGGGG

GGGTGAGCAGGGGGTGTGGGCGCGTCGGTCGGGCTGCAACCCCCCCTGCACCCCCCTCCCCGAG

TTGCTGAGCACGGCCCGGCTTCGGGTGCGGGGCTCCGTACGGGGCGTGGCGCGGGGCTCGCCGT

GCCGGGCGGGGGGTGGCGGCAGGTGGGGGTGCCGGGCGGGGCGGGGCCGCCTCGGGCCGGGGAG

GGCTCGGGGGAAGGGGCGCGGCGGCCCCCGGAGCGCCGGCGGCTGTCGAGGCGCGGCGAGCCGC

AGCCATTGCCTTTTATGGTAATCGTGCGAGAGGGCGCAGGGACTTCCTTTGTCCCAAATCTGTG

CGGAGCCGAAATCTGGGAGGCGCCGCCGCACCCCCTCTAGCGGGCGCGGGGCGAAGCGGTGCGG

CGCCGGCAGGAAGGAAATGGGCGGGGAGGGCCTTCGTGCGTCGCCGCGCCGCCGTCCCCTTCTC

CCTCTCCAGCCTCGGGGCTGTCCGCGGGGGGACGGCTGCCTTCGGGGGGGACGGGGCAGGGCGG

GGTTCGGCTTCTGGCGTGTGACCGGCGGCTCTAGAGCCTCTGCTAACCATGTTCATGCCTTCTT

CTTTTTCCTACAG

>CBA promoter.

SEQ ID NO: 51

TCGAGGTGAGCCCCACGTTCTGCTTCACTCTCCCCATCTCCCCCCCCTCCCCACCCCCAATTTT

GTATTTATTTATTTTTTAATTATTTTGTGCAGCGATGGGGGCGGGGGGGGGGGGGGGGCGCGCG

-continued

CCAGGCGGGGCGGGGCGGGGCGAGGGGCGGGGCGGGGCGAGGCGGAGAGGTGCGGCGGCAGCCA

ATCAGAGCGGCGCGCTCCGAAAGTTTCCTTTTATGGCGAGGCGGCGGCGGCGGCGGCCCTATAA

AAAGCGAAGCGCGCGGCGGGCG

>UBC promoter

SEQ ID NO: 52

GGTGCAGCGGCCTCCGCGCCGGGTTTTGGCGCCTCCCGCGGGCGCCCCCCTCCTCACGGCGAGC

GCTGCCACGTCAGACGAAGGGCGCAGGAGCGTTCCTGATCCTTCCGCCCGGACGCTCAGGACAG

CGGCCCGCTGCTCATAAGACTCGGCCTTAGAACCCCAGTATCAGCAGAAGGACATTTTAGGACG

GGACTTGGGTGACTCTAGGGCACTGGTTTTCTTTCCAGAGAGCGGAACAGGCGAGGAAAAGTAG

TCCCTTCTCGGCGATTCTGCGGAGGGATCTCCGTGGGGCGGTGAACGCCGATGATTATATAAGG

ACGCGCCGGGTGTGGCACAGCTAGTTCCGTCGCAGCCGGGATTTGGGTCGCGGTTCTTGTTTGT

GGATCGCTGTGATCGTCACTTGGTGAGTTGCGGGCTGCTGGGCTGGCCGGGGCTTTCGTGGCCG

CCGGGCCGCTCGGTGGGACGGAAGCGTGTGGAGAGACCGCCAAGGGCTGTAGTCTGGGTCCGCG

AGCAAGGTTGCCCTGAACTGGGGGTTGGGGGGAGCGCACAAAATGGCGGCTGTTCCCGAGTCTT

GAATGGAAGACGCTTGTAAGGCGGGCTGTGAGGTCGTTGAAACAAGGTGGGGGGCATGGTGGGC

GGCAAGAACCCAAGGTCTTGAGGCCTTCGCTAATGCGGGAAAGCTCTTATTCGGGTGAGATGGG

CTGGGGCACCATCTGGGGACCCTGACGTGAAGTTTGTCACTGACTGGAGAACTCGGGTTTGTCG

TCTGGTTGCGGGGGCGGCAGTTATGCGGTGCCGTTGGGCAGTGCACCCGTACCTTTGGGAGCGC

GCGCCTCGTCGTGTCGTGACGTCACCCGTTCTGTTGGCTTATAATGCAGGGTGGGGCCACCTGC

CGGTAGGTGTGCGGTAGGCTTTTCTCCGTCGCAGGACGCAGGGTTCGGGCCTAGGGTAGGCTCT

CCTGAATCGACAGGCGCCGGACCTCTGGTGAGGGGAGGGATAAGTGAGGCGTCAGTTTCTTTGG

TCGGTTTTATGTACCTATCTTCTTAAGTAGCTGAAGCTCCGGTTTTGAACTATGCGCTCGGGGT

TGGCGAGTGTGTTTTGTGAAGTTTTTTAGGCACCTTTTGAAATGTAATCATTTGGGTCAATATG

TAATTTTGAGTGTTAGACTAGTAAA

>PGK promoter

SEQ ID NO: 53

TTCTACCGGGTAGGGGAGGCGCTTTTCCCAAGGCAGTCTGGAGCATGCGCTTTAGCAGCCCCGC

TGGGCACTTGGCGCTACACAAGTGGCCTCTGGCCTCGCACACATTCCACATCCACCGGTAGGCG

CCAACCGGCTCCGTTCTTTGGTGGCCCCTTCGCGCCACCTTCTACTCCTCCCCTAGTCAGGAAG

TTCCCCCCCGCCCCGCAGCTCGCGTCGTGCAGGACGTGACAAATGGAAGTAGCACGTCTCACTA

GTCTCGTGCAGATGGACAGCACCGCTGAGCAATGGAAGCGGGTAGGCCTTTGGGGCAGCGGCCA

ATAGCAGCTTTGCTCCTTCGCTTTCTGGGCTCAGAGGCTGGGAAGGGGTGGGTCCGGGGGCGGG

CTCAGGGGCGGGCTCAGGGGCGGGGCGGGCGCCCGAAGGTCCTCCGGAGGCCCGGCATTCTGCA

CGCTTCAAAAGCGCACGTCTGCCGCGCTGTTCTCCTCTTCCTCATCTCCGGGCCTTTCGACCT

>Ef1α promoter

SEQ ID NO: 54

GCTCCGGTGCCCGTCAGTGGGCAGAGCGCACATCGCCCACAGTCCCCGAGAAGTTGGGGGGAGG

GGTCGGCAATTGAACCGGTGCCTAGAGAAGGTGGCGCGGGGTAAACTGGGAAAGTGATGTCGTG

TACTGGCTCCGCCTTTTTCCCGAGGGTGGGGGAGAACCGTATATAAGTGCAGTAGTCGCCGTGA

ACGTTCTTTTTCGCAACGGGTTTGCCGCCAGAACACAGGTAAGTGCCGTGTGTGGTTCCCGCGG

GCCTGGCCTCTTTACGGGTTATGGCCCTTGCGTGCCTTGAATTACTTCCACGCCCCTGGCTGCA

GTACGTGATTCTTGATCCCGAGCTTCGGGTTGGAAGTGGGTGGGAGAGTTCGAGGCCTTGCGCT

TAAGGAGCCCCTTCGCCTCGTGCTTGAGTTGAGGCCTGGCCTGGGCGCTGGGGCCGCCGCGTGC

GAATCTGGTGGCACCTTCGCGCCTGTCTCGCTGCTTTCGATAAGTCTCTAGCCATTTAAAATTT

-continued

TTGATGACCTGCTGCGACGCTTTTTTTCTGGCAAGATAGTCTTGTAAATGCGGGCCAAGATCTG

CACACTGGTATTTCGGTTTTTGGGGCCGCGGGCGGCGACGGGGCCCGTGCGTCCCAGCGCACAT

GTTCGGCGAGGCGGGGCCTGCGAGCGCGGCCACCGAGAATCGGACGGGGGTAGTCTCAAGCTGG

CCGGCCTGCTCTGGTGCCTGGCCTCGCGCCGCCGTGTATCGCCCCGCCCTGGGCGGCAAGGCTG

GCCCGGTCGGCACCAGTTGCGTGAGCGGAAAGATGGCCGCTTCCCGGCCCTGCTGCAGGGAGCT

CAAAATGGAGGACGCGGCGCTCGGGAGAGCGGGCGGGTGAGTCACCCACACAAAGGAAAAGGGC

CTTTCCGTCCTCAGCCGTCGCTTCATGTGACTCCACGGAGTACCGGGCGCCGTCCAGGCACCTC

GATTAGTTCTCGAGCTTTTGGAGTACGTCGTCTTTAGGTTGGGGGGAGGGGTTTTATGCGATGG

AGTTTCCCCACACTGAGTGGGTGGAGACTGAAGTTAGGCCAGCTTGGCACTTGATGTAATTCTC

CTTGGAATTTGCCCTTTTTGAGTTTGGATCTTGGTTCATTCTCAAGCCTCAGACAGTGGTTCAA

AGTTTTTTTCTTCCATTTCAGGTGTCGTGA

>CMV promoter

SEQ ID NO: 55

GTCGACATTGATTATTGACTAGTTATTAATAGTAATCAATTACGGGGTCATTAGTTCATAGCCC

ATATATGGAGTTCCGCGTTACATAACTTACGGTAAATGGCCCGCCTGGCTGACCGCCCAACGAC

CCCCGCCCATTGACGTCAATAATGACGTATGTTCCCATAGTAACGCCAATAGGGACTTTCCATT

GACGTCAATGGGTGGAGTATTTACGGTAAACTGCCCACTTGGCAGTACATCAAGTGTATCATAT

GCCAAGTACGCCCCCTATTGACGTCAATGACGGTAAATGGCCCGCCTGGCATTATGCCCAGTAC

ATGACCTTATGGGACTTTCCTACTTGGCAGTACATCTACGTATTAGTCATCGCTATTACCATGG

TGATGCGGTTTTGGCAGTACATCAATGGGCGTGGATAGCGGTTTGACTCACGGGGATTTCCAAG

TCTCCACCCCATTGACGTCAATGGGAGTTTGTTTTGGCACCAAAATCAACGGGACTTTCCAAAA

TGTCGTAACAACTCCGCCCCATTGACGCAAATGGGCGGTAGGCGTGTACGGTGGGAGGTCTATA

TAAGCAGAGCTCTCTGGCTAACTAGAGAACCCACTGCTTACTGGCTTATCGAAATTAATACGAC

TCACTATAGGGAGACCCAAGCTGGCTAGCGTTTAAACTT

>NSE promoter

SEQ ID NO: 56

AGCTCTGAGCTCCTCCTCTGCTCGCCCAATCCTTCCAACCCCCTATGGTGGTATGGCTGACACA

GAAAATGTCTGCTCCTGTATGGGACATTTGCCCCTCTTCTCCAAATATAAGACAGGATGAGGCC

TAGCTTTTGCTGCTCCAAAGTTTTAAAAGAACACATTGCACGGCATTTAGGGACTCTAAAGGGT

GGAGGAGGAATGAGGGAATTGCATCATGCCAAGGCTGGTCCTCATCCATCACTGCTTCCAGGGC

CCAGAGTGGCTTCCAGGAAGTATTCTTACAAAGGAAGCCCGATCTGTAGCTAACACTCAGAGCC

CATTTTCCTGCGTTAACCCCTCCCGACCTCATATACAGGAGTAACATGATCAGTGACCTGGGGG

AGCTGGCCAAACTGCGGGACCTGCCCAAGCTGAGGGCCTTGGTGCTGCTGGACAACCCCTGTGC

CGATGAGACTGACTACCGCCAGGAGGCCCTGGTGCAGATGGCACACCTAGAGCGCCTAGACAAA

GAGTACTATGAGGACGAGGACCGGGCAGAAGCTGAGGAGATCCGACAGAGGCTGAAGGAGGAAC

AGGAGCAAGAACTCGACCCGGACCAAGACATGGAACCGTACCTCCCGCCAACTTAGTGGCTCCT

CTAGCCTGCAGGGACAGTAAAGGTGATGGCAGGAAGGCAGCCCCCGGAGGTCAAAGGCTGGGCA

CGCGGGAGGAGAGGCCAGAGTCAGAGGCTGCGGGTATCTCAGATATGAAGGAAAGATGAGAGAG

GCTCAGGAAGAGGTAAGAAAAAGACACAAGAGACCAGAGAAGGGAGAAGAATTAGAGAGGGAGGC

AGAGGACCGCTGTCTCTACAGACATAGCTGGTAGAGACTGGGAGGAAGGGATGAACCCTGAGCG

CATGAAGGGAAGGAGGTGGCTGGTGGTATATGGAGGATGTAGCTGGGCCAGGGAAAAGATCCTG

GAGTAAAAATCTGAAGCTAAAAATAACAGGACACGGGGTGGAGAGGCGAAAGGAGGGCAGAGTG

-continued

AGGCAGAGAGACTGAGAGGCCTGGGGATGTGGGCATTCCGGTAGGGCACACAGTTCACTTGTCT

TCTCTTTTTCCAGGAGGCCAAAGATGCTGACGTCAAGAACTCATAATACCCCAGTGGGGACCAC

CGCATTCATAGCCCTGTTACAAGAAGTGGGAGATGTTCCTTTTTGTCCCAGACTGGAAATCCGT

TACATCCCGAGGCTCAGGTTCTGTGGTGGTCATCTCTGTGTGGCTTGTTCTGTGGGCCTACCTA

AAGTCCTAAGCACAGCTCTCAAGCAGATCCGAGGCGACTAAGATGCTAGTAGGGGTTGTCTGGA

GAGAAGAGCCGAGGAGGTGGGCTGTGATGGATCAGTTCAGCTTTCAAATAAAAAGGCGTTTTTA

TATTCTGTGTCGAGTTCGTGAACCCCTGTGGTGGGCTTCTCCATCTGTCTGGGTTAGTACCTGC

CACTATACTGGAATAAGGGGACGCCTGCTTCCCTCGAGTTGGCTGGACAAGGTTATGAGCATCC

GTGTACTTATGGGGTTGCCAGCTTGGTCCTGGATCGCCCGGGCCCTTCCCCCACCCGTTCGGTT

CCCCACCACCACCCGCGCTCGTACGTGCGTCTCCGCCTGCAGCTCTTGACTCATCGGGGCCCCC

GGGTCACATGCGCTCGCTCGGCTCTATAGGCGCCGCCCCCTGCCCACCCCCCGCCCGCGCTGGG

AGCCGCAGCCGCCGCCACTCCTGCTCTCTCTGCGCCG

>MeCP2 promoter

SEQ ID NO: 57

TGCCCATTATAAACGTCTGCAAAGACCAAGGTTTGATATGTTGATTTTACTGTCAGCCTTAAGA

GTGCGAGATCTGCTAATTTAGTGTAATAATACAATGAGTAGACCCTTTAAAACAAGTCCCTTGG

CTTGGAACAACGCCAGGCTCCTCAACAGGCAACTTTGCTAGTTCTACAGAAAATGATAATAAAG

AAATGCTGGTGAAGTCAAATGCTTATCACAATGGTGAACTACTCAGCAGGGAGGCTCTAATAGG

CGCCAAGAGCCTAGACTTCCTTAAGCGCCAGAGTCCACAAGGGCCCAGTTAATCCTCAACATTC

AAATGCTGCCCACAAAACCAGCCCCTCTGTGCCCTAGCCGCCTCTTTTTTCCAAGTGACAGTAG

AACTCCACCAATCCGCAGCTGAATGGGGTCCGCCTCTTTTCCCTGCCTAAACAGACAGGAACTC

CTGCCAATTGAGGGCGTCACCGCTAAGGCTCCGCCCCAGCCTGGGCTCCACAACCAATGAAGGG

TAATCTCGACAAAGAGCAAGGGGTGGGGCGCGGGCGCGCAGGTGCAGCAGCACACAGGCTGGTC

GGGAGGGCGGGGCGCGACGTCTGCCGTGCGGGGTCCCGGCATCGGTTGCGCGCGCGCTCCCTCC

TCTCGGAGAGAGGGCTGTGGTAAAACCCGTCCGGAAAATGGCCGCCGCTGCCGCCACCGCCGCC

GCCGCCGCCGCGCCGAGCGGAGGAGGAGG

>GFAP promoter

SEQ ID NO: 58

GGCAACATGGCAAGACCCTATCTCTACAAAAAAAGTTAAAAAATCAGCCACGTGTGGTGACACA

CACCTGTAGTCCCAGCTATTCAGGAGGCTGAGGTGAGGGGATCACTTAAGGCTGGGAGGTTGAG

GCTGCAGTGAGTCGTGGTTGCGCCACTGCACTCCAGCCTGGGCAACAGTGAGACCCTGTCTCAA

AAGACAAAAAAAAAAAAAAAAAAAAAAAGAACATATCCTGGTGTGGAGTAGGGGACGCTGCTCT

GACAGAGGCTCGGGGGCCTGAGCTGGCTCTGTGAGCTGGGGAGGAGGCAGACAGCCAGGCCTTG

TCTGCAAGCAGACCTGGCAGCATTGGGCTGGCCGCCCCCCAGGGCCTCCTCTTCATGCCCAGTG

AATGACTCACCTTGGCACAGACACAATGTTCGGGGTGGGCACAGTGCCTGCTTCCCGCCGCACC

CCAGCCCCCCTCAAATGCCTTCCGAGAAGCCCATTGAGCAGGGGGCTTGCATTGCACCCCAGCC

TGACAGCCTGGCATCTTGGGATAAAAGCAGCACAGCCCCCTAGGGGCTGCCCTTGCTGTGTGGC

GCCACCGGCGGTGGAGAACAAGGCTCTATTCAGCCTGTGCCCAGGAAAGGGGATCAGGGGATGC

CCAGGCATGGACAGTGGGTGGCAGGGGGGGAGAGGAGGGCTGTCTGCTTCCCAGAAGTCCAAGG

ACACAAATGGGTGAGGGGACTGGGCAGGGTTCTGACCCTGTGGGACCAGAGTGGAGGGCGTAGA

TGGACCTGAAGTCTCCAGGGACAACAGGGCCCAGGTCTCAGGCTCCTAGTTGGGCCCAGTGGCT

CCAGCGTTTCCAAACCCATCCATCCCCAGAGGTTCTTCCCATCTCTCCAGGCTGATGTGTGGGA

ACTCGAGGAAATAAATCTCCAGTGGGAGACGGAGGGGTGGCCAGGGAAACGGGGCGCTGCAGGA

-continued

ATAAAGACGAGCCAGCACAGCCAGCTCATGTGTAACGGCTTTGTGGAGCTGTCAAGGCCTGGTC

TCTGGGAGAGAGGCACAGGGAGGCCAGACAAGGAAGGGGTGACCTGGAGGGACAGATCCAGGGG

CTAAAGTCCTGATAAGGCAAGAGAGTGCCGGCCCCCTCTTGCCCTATCAGGACCTCCACTGCCA

CATAGAGGCCATGATTGACCCTTAGACAAAGGGCTGGTGTCCAATCCCAGCCCCCAGCCCCAGA

ACTCCAGGGAATGAATGGGCAGAGAGCAGGAATGTGGGACATCTGTGTTCAAGGGAAGGACTCC

AGGAGTCTGCTGGGAATGAGGCCTAGTAGGAAATGAGGTGGCCCTTGAGGGTACAGAACAGGTT

CATTCTTCGCCAAATTCCCAGCACCTTGCAGGCACTTACAGCTGAGTGAGATAATGCCTGGGTT

ATGAAATCAAAAAGTTGGAAAGCAGGTCAGAGGTCATCTGGTACAGCCCTTCCTTCCCTTTTTT

TTTTTTTTTTTTGTGAGACAAGGTCTCTCTCTGTTGCCCAGGCTGGAGTGGCGCAAACACAGCT

CACTGCAGCCTCAACCTACTGGGCTCAAGCAATCCTCCAGCCTCAGCCTCCCAAAGTGCTGGGA

TTACAAGCATGAGCCACCCCACTCAGCCCTTTCCTTCCTTTTTAATTGATGCATAATAATTGTA

AGTATTCATCATGGTCCAACCAACCCTTTCTTGACCCACCTTCCTAGAGAGAGGGTCCTCTTGC

TTCAGCGGTCAGGGCCCCAGACCCATGGTCTGGCTCCAGGTACCACCTGCCTCATGCAGGAGTT

GGCGTGCCCAGGAAGCTCTGCCTCTGGGCACAGTGACCTCAGTGGGGTGAGGGGAGCTCTCCCC

ATAGCTGGGCTGCGGCCCAACCCCACCCCCTCAGGCTATGCCAGGGGGTGTTGCCAGGGGCACC

CGGGCATCGCCAGTCTAGCCCACTCCTTCATAAAGCCCTCGCATCCCAGGAGCGAGCAGAGCCA

GAGCAGG

>GUSB promoter

SEQ ID NO: 59

GAATTCCTGCTGGGAAAAGCAAGTGGAGGTGCTCCTTGAAGAAACAGGGGGATCCCACCGATCT

CAGGGGTTCTGTTCTGGCCTGCGGCCCTGGATCGTCCAGCCTGGGTCGGGGTGGGGAGCAGACC

TCGCCCTTATCGGCTGGGGCTGAGGGTGAGGGTCCCGTTTCCCCAAAGGCCTAGCCTGGGGTTC

CAGCCACGAAGCCCTACCGGGAGCGCCCGGCCCCGCCCCTCCAGGCCTGGCACTCGTCCTCAAC

CAAGATGGCGCGGATGGCTTCAGGCGCATCACGACACCGGCGCGTCACGCGACCCGCCCTACGG

GCACCTCCCGCGCTTTTCTTAGCGCCGCAGACGGTGGCCGAGCGGGGGACCGGGAAGC

>RSV promoter

SEQ ID NO: 60

AATGTAGTCTTATGCAATACTCTTGTAGTCTTGCAACATGGTAACGATGAGTTAGCAACATGCC

TTACAAGGAGAGAAAAAGCACCGTGCATGCCGATTGGTGGAAGTAAGGTGGTACGATCGTGCCT

TATTAGGAAGGCAACAGACGGGTCTGACATGGATTGGACGAACCACTGAATTGCCGCATTGCAG

AGATATTGTATTTAAGTGCCTAGCTCGATACATAAAC

SV40promoter

SEQ ID NO: 61

GGTGTGGAAAGTCCCCAGGCTCCCCAGCAGGCAGAAGTATGCAAAGCATGCATCTCAATTAGTC

AGCAACCAGGTGTGGAAAGTCCCCAGGCTCCCCAGCAGGCAGAAGTATGCAAAGCATGCATCTC

AATTAGTCAGCAACCATAGTCCCGCCCCTAACTCCGCCCATCCCGCCCCTAACTCCGCCCAGTT

CCGCCCATTCTCCGCCCCATGGCTGACTAATTTTTTTTATTTATGCAGAGGCCGAGGCCGCCTC

GGCCTCTGAGCTATTCCAGAAGTAGTGAGGAGGCTTTTTTGGAGGCCTAGGCTTTTGCAAAGAT

CGATCAAGAGACAGGATGAGGATCGTTTCGC

NPY promoter

SEQ ID NO: 62

TTTTGGCCAGGGGATGTGGCTTGGACTGGAGAGAAAGGAGATAAGGATGTAAACACATGTAGGG

CATATCACCCCCTATTTTTTATTCTCTGAATCCTTAACCCTCAGAATAAGTTCTTATTCTTGAG

AATCAATGACATTATCTTAAGCTAAATTAATCAAGCCTCCACAGTGTTCTTCTCTCAATAGTGG

-continued

TGTGGGCCTTCCTAGAAGTAATTTTTCCCAAATTCAGTGATACATTTTAAGTTCAGATTTTAAT

TGATATGAATCTGTGATACACTCTAAAATAAGATTATTTTATTGAAAAGTGGACTGTAACTTTC

CCTTTATCTAGGAAGAGCTCTAAGTTAGAAGATGTTTTGCACTTTTACCGAAGGCTGTGTCTTG

TAAGCACCCCCGAGCAACTCTGAGAGCCTTGATTTTTGTGTCCTCAGCATATGTTTGTGTAATA

CAGAAAGAGAAGCAGTTGCCAAGTGAAAGGGATGTTGGTCTCCAAAATTATAGTTTGATCCCAC

AAACACACAAACACATACATGCAAAGGATTGTTTGCTTCACGGTTTTTGATATTTAATTCAATG

CTGTTGGAACAGCACAAAAACTAAGTGTCAGTTTAACAGAATCACTTGTCCTTTTAGCATTAAA

ATAACATGGAACTTAATGCTTTAATTTCCCAACATGCCTTTTTATTTAGAAAGATTCAGACTTT

TATTTCATTTAGAAATAAAATGCCATTTTATTTAGAAAGATACAGGAGCATTCATTCACGGAAC

TTTCAGATCTCAGTCCACTGCATAAAATCTTGATCCTGTAATAATAGTTTCTGTATCTTGCATA

TTCATTCAACAGGTTTAACGCGATGAGCAAATTAATGTTCATCGTTTTTAACATGTTTCGTCTT

AATCAGAACCCACATTCTCAACGTTAATTGAACGTAGATAGGACTATACAAGGGTTAGTAAATA

AGACAGAAACTGTTGCTCATTTAACCACCGTCACTTTGGA

SST promoter

SEQ ID NO: 63

ACACTAAAATGTTAGAGTATGATGACAGATGGAGTTGTCTGGGTACATTTGTGTGCATTTAAGG

GTGATAGTGTATTTGCTCTTTAAGAGCTGAGTGTTTGAGCCTCTGTTTGTGTGTAATTGAGTGT

GCATGTGTGGGAGTGAAATTGTGGAATGTGTATGCTCATAGCACTGAGTGAAAATAAAAGATTG

TATAAATCGTGGGGCATGTGGAATTGTGTGTGCCTGTGCGTGTGCAGTATTTTTTTTTTTTTAA

GTAAGCCACTTTAGATCTTGTCACCTCCCCTGTCTTCTGTGATTGATTTTGCGAGGCTAATGGT

GCGTAAAAGGGCTGGTGAGATCTGGGGGCGCCTCCTAGCCTGACGTCAGAGAGAGAGTTTAAAA

CAGAGGGAGACGGTTGAGAGCACACAAGCCGCTTTAGGAGCGAGGTTCGGAGCCATCGCTGCTG

CCTGCTGATCCGCGCCTAGAGTTTGACCAGCC

Synapsin promoter 1

SEQ ID NO: 64

ACACCACCCAAGTGTCCACCTCCGCTTGTCTGATGCTGTCTATGACGCCCCCGCTCTCTGCCTA

GCTGAGCCTGTGTGGATGTGGGAGACTAATCTCCCCGCGGGCACTGCGTGTGACCTCACCCCCC

TCTGTGAGGGGGTTATTTCTCTACTTTCGTGTCTCTGAGTGTGCTTCCAGTGCCCCCCTCCCCC

CAAAAAATGCCTTCTGAGTTGAATATCAACACTACAAACCGAGTATCTGCAGAGGGCCCTGCGT

ATGAGTGCAAGTGGGTTTTAGGACCAGGATGAGGCGGGGTGGGGGTGCCTACCTGACGACCGAC

CCCGACCCACTGGACAAGCACCCAACCCCCATTCCCCAAATTGCGCATCCCCTATCAGAGAGGG

GGAGGGGAAACAGGATGCGGCGAGGCGCGTGCGCACTGCCAGCTTCAGCACCGCGGACAGTGCC

TTCGCCCCCGCCTGGCGGCGCGCGCCACCGCCGCCTCAGCACTGAAGGCGCGCTGACGTCACTC

GCCGGTCCCCCGCAAACTCCCCTTCCCGGCCACCTTGGTCGCGTCCGCGCCGCCGCCGGCCCAG

CCGGACCGCACCACGCGAGGCGCGAGATAGGGGGGCACGGGCGCGACCATCTGCGCTGCGGCGC

CGGCGACTCAGCGCTGCCTCAGTCTGCGGTGGGCAGCGGAGGAGTCGTGTCGTGCCTGAG

Synapsin promoter 2

SEQ ID NO: 65

ACACTACAAACCGAGTATCTGCAGAGGGCCCTGCGTATGAGTGCAAGTGGGTTTTAGGACCAGG

ATGAGGCGGGGTGGGGGTGCCTACCTGACGACCGACCCCGACCCACTGGACAAGCACCCAACCC

CCATTCCCCAAATTGCGCATCCCCTATCAGAGAGGGGGAGGGGAAACAGGATGCGGCGAGGCGC

GTGCGCACTGCCAGCTTCAGCACCGCGGACAGTGCCTTCGCCCCCGCCTGGCGGCGCGCGCCAC

CGCCGCCTCAGCACTGAAGGCGCGCTGACGTCACTCGCCGGTCCCCCGCAAACTCCCCTTCCCG

GCCACCTTGGTCGCGTCCGCGCCGCCGCCGGCCCAGCCGGACCGCACCACGCGAGGCGCGAGAT

-continued

AGGGGGGCACGGGCGCGACCATCTGCGCTGCGGCGCCGGCGACTCAGCGCTGCCTCAGTCTGCG

GTGGGCAGCGGAGGAGTCGTGTCGTGCCTGAG

>β-globin promoter

SEQ ID NO: 66

GCTTTGCTTCTCAATTTCTTATTTGCATAATGAGAAAAAAAGGAAAATTAATTTTAACACCAAT

TCAGTAGTTGATTGAGCAAATGCGTTGCCAAAAAGGATGCTTTAGAGACAGTGTTCTCTGCACA

GATAAGGACAAACATTATTCAGAGGGAGTACCCAGAGCTGAGACTCCTAAGCCAGTGAGTGGCA

CAGCATTCTAGGGAGAAATATGCTTGTCATCACCGAAGCCTGATTCCGTAGAGCCACACCTTGG

TAAGGGCCAATCTGCTCACACAGGATAGAGAGGGCAGGAGCCAGGGCAGAGCATATAAGGTGAG

GTAGGATCAGTTGCTCCTCACATTTGCTTCTGACATAGTTGTGTTG (consensus Kozak sequence)

SEQ ID NO: 67

GCCGCCRCCAUGG (pAT049)

SEQ ID NO: 68

CCTGCAGGCAGCTGCGCGCTCGCTCGCTCACTGAGGCCGCCCGGGCAAAGCCCGGGCGTCG

GGCGACCTTTGGTCGCCCGGCCTCAGTGAGCGAGCGAGCGCGCAGAGAGGGAGTGGCCAAC

TCCATCACTAGGGGTTCCTGCGGCCAATTCAGTGGATCCCGATAACTATAACGGTCCTAAG

GTAGCGATTTAAATGAGGGCCTATTTCCCATGATTCCTTCATATTTGCATATACGATACAA

GGCTGTTAGAGAGATAATTAGAATTAATTTGACTGTAAACACAAAGATATTAGTACAAAAT

ACGTGACGTAGAAAGTAATAATTTCTTGGGTAGTTTGCAGTTTTAAAATTATGTTTTAAAA

TGGACTATCATATGCTTACCGTAACTTGAAAGTATTTCGATTTCTTGGCTTTATATATCTT

GTGGAAAGGACGAGGTACCGTGAGCTGTTGGAATTATGTTTCGAATTTGACTTTAGAGGTT

TACATTTCTAGTCAAAGAAGAAACATCCATTCAGCTGCTCCTTTTTTCCGGGACGCGTCAA

TTGAGATCTCCGACATTGATTATTGACTAGTTATTAATAGTAATCAATTACGGGGTCATTA

GTTCATAGCCCATATATGGAGTTCCGCGTTACATAACTTACGGTAAATGGCCCGCCTGGCT

GACCGCCCAACGACCCCCGCCCATTGACGTCAATAATGACGTATGTTCCCATAGTAACGCC

AATAGGGACTTTCCATTGACGTCAATGGGTGGAGTATTTACGGTAAACTGCCCACTTGGCA

GTACATCAAGTGTATCATATGCCAAGTACGCCCCCTATTGACGTCAATGACGGTAAATGGC

CCGCCTGGCATTATGCCCAGTACATGACCTTATGGGACTTTCCTACTTGGCAGTACATCTA

CGTATTAGTCATCGCTATTACCATGTCGAGGCCACGTTCTGCTTCACTCTCCCCATCTCCC

CCCCCTCCCCACCCCCAATTTTGTATTTATTTATTTTTTAATTATTTTGTGCAGCGATGGG

GGCGGGGGGGGGGGGCGCGCGCCAGGCGGGGCGGGGCGGGGCGAGGGGCGGGGCGGGGCGA

GGCGGAGAGGTGCGGCGGCAGCCAATCAGAGCGGCGCGCTCCGAAAGTTTCCTTTTATGGC

GAGGCGGCGGCGGCGGCGGCCCTATAAAAAGCGAAGCGCGCGGCGGGCGGGAGCAAGCTTC

GTTTAGTGAACCGTCAGATCGCCTGGAGACGCCATCCACGCTGTTTTGACCTCCATAGAAG

ACACCGGGACCGATCCAGCCTCCGCGGATTCGAATCCCGGCCGGGAACGGTGCATTGGAAC

GCGGATTCCCCGTGCCAAGAGTGACGTAAGTACCGCCTATAGAGTCTATAGGCCCACAAAA

AATGCTTTCTTCTTTTAATATACTTTTTTGTTTATCTTATTTCTAATACTTTCCCTAATCT

CTTTCTTTGAGGGCAATAATGATACAATGTATCATGCCTCTTTGCACCATTCTAAAGAATA

ACAGTGATAATTTCTGGGTTAAGGCAATAGCAATATTTCTGCATATAAATATTTCTGCATA

TAAATTGTAACTGATGTAAGAGGTTTCATATTGCTAATAGCAGCTACAATCCAGCTACCAT

TCTGCTTTTATTTTGTGGTTGGGATAAGGCTGGATTATTCTGAGTCCAAGCTAGGCCCTTT

-continued

TGCTAATCGTGTTCATACCTCTTATCTTCCTCCCACAGCTCCTGGGCAACGTGCTGGTCTG

TGTGCTGGCCCATCACTTTGGCAAAGAATTACCGGTGGCAACGTGCTGGTTATTGTGCTGT

CTCATCATTTTGGCAAAGAATTCACGCCCCAGAGCCGCCACCATGGCCTACCCATACGATG

TTCCAGATTACGCTACAGAATTACCTGCCCCCTTGAGCTACTTCCAGAATGCACAGATGAG

CGAGGACAACCACCTGAGCAATACTGTACGTAGCCAGAATGACAACAGAGAACGGCAGGAA

CACAACGACAGGCGGAGCCTGGGCCACCCTGAGCCCCTGTCTAATGGAAGACCCCAGGGTA

ACAGCAGACAGGTGGTGGAACAAGATGAGGAAGAGGACGAGGAGCTGACCCTGAAGTACGG

CGCCAAGCACGTGATCATGCTCTTCGTGCCCGTGACTCTCTGCATGGTGGTGGTGGTGGCT

ACAATCAAGAGCGTCAGCTTTTATACCCGGAAGGATGGGCAGCTAATCTATACCCCATTCA

CAGAAGACACCGAGACTGTGGGCCAGAGAGCCCTGCACTCAATCCTGAATGCCGCCATCAT

GATCAGCGTCATTGTTGTCATGACTATCCTCCTGGTGGTTCTGTATAAATACAGGTGCTAT

AAGGTCATCCATGCCTGGCTGATCATATCATCTCTGTTGCTGCTGTTCTTTTTTAGCTTCA

TTTACCTGGGCGAAGTGTTTAAAACCTATAACGTTGCCGTGGACTACATTACTGTTGCCCT

CCTGATCTGGAACTTCGGCGTGGTGGGCATGATTTCCATTCACTGGAAAGGCCCCCTGAGA

CTGCAGCAGGCATACCTCATTATGATCTCCGCCCTCATGGCCCTGGTGTTCATCAAGTACC

TGCCCGAGTGGACTGCTTGGCTCATCTTGGCTGTGATCTCCGTGTATGATTTAGTGGCTGT

TCTGTGTCCTAAAGGTCCACTGCGTATGCTGGTGGAAACAGCTCAGGAAAGAAATGAAACA

CTGTTTCCTGCTCTGATTTACTCCTCAACAATGGTGTGGCTCGTGAATATGGCCGAAGGAG

ACCCTGAAGCCCAACGGAGAGTGTCCAAAAACTCCAAGTATAACGCCGAGAGCACAGAAAG

GGAGAGCCAGGATACAGTTGCCGAGAATGACGATGGCGGCTTCAGTGAGGAATGGGAAGCC

CAGAGGGACAGCCACCTGGGGCCTCACAGAAGCACCCCTGAGTCTAGAGCCGCTGTCCAGG

AACTGTCCAGCTCCATCCTGGCCGGCGAAGACCCCGAAGAAAGGGGAGTAAAACTTGGACT

GGGAGATTTCATCTTCTACAGTGTTCTCGTTGGCAAAGCCAGCGCAACAGCTAGCGGAGAC

TGGAACACAACAATAGCCTGTTTCGTAGCCATCTTAATTGGCCTGTGCCTTACACTTCTGC

TCCTGGCCATCTTCAAGAAGGCCCTGCCAGCCCTGCCTATCAGCATCACCTTCGGGCTTGT

TTTCTACTTTGCCACCGATTATCTGGTGCAGCCCTTCATGGACCAGCTGGCCTTCCACCAG

TTTTACATCTAGTAAGCGGCCGCCCTAGGGAGCTCCTCGAGGGGGTGGCATCCCTGTGACC

CCTCCCCAGTGCCTCTCCTGGCCCTGGAAGTTGCCACTCCAGTGCCCACCAGCCTTGTCCT

AATAAAATTAAGTTGCATCATTTTGTCTGACTAGGTGTCCTTCTATAATATTATGGGGTGG

AGGGGGGTGGTATGGAGCAAGGGGCAAGGGGGGAAGACAACCTGTAGGGCCTGCGGGGTCT

ATTGGGAACCAAGCTGGAGTGCAGTGGCACAATCTTGGCTCACTGCAATCTCCGCCTCCTG

GGTTCAAGCGATTCTCCTGCCTCAGCCTCCCGAGTTGTTGGGATTCCAGGCATGCATGACC

AGGCTCAGCTAATTTTTGTTTTTTTGGTAGAGACGGGGTTTCACCATATTGGCCAGGCTGG

TCTCCCCCTCCTAATCTCAGGTGATCTACCCACCTTGGCCTCCCAAATTGCTGGGATTACA

GGCGTGAACCACTGCTCCCTTCCCTGTCCTTCCTGGGCCTAGGGCTGTGCCAGCTGCCTCG

TCCCGTCACCTTCTGGCTTCTTCTCTCCCTCCATATCTTAGCTGTTTTCCTCATGAGAATG

TTCCAAATTCGAAATTTCTATTTAACCATTATATATTTACTTGTTTGCTATTATCTCTGCC

CCCAGTAGATTGTTAGCTCCAGAAGAGAAAGGATCATGTCTTTTGCTTATCTAGATATGCC

CATCTGCCTGGTACAATCTCTGGCACATGTTACAGGCAACAACTACTTGTGGAATTGGTGA

ATGCATGAATAGAAGAATGAGTGAATGAATGAATAGACAATAGGCAGAAATCGAGCCTCAA

AGAGCTTACAGTCTGGTAAGAGGAATAAAATGTCTGCAAATAGCCACAGGACAGGTCAAAG

-continued

GAAGGAGGGGCTATTTCCAGCTGAGGGCACCCCATCAGGAAAGCACCCCAGACTTCCTTAG

GGATAACAGGGTAATGGCGCGGGCCGCAGGAACCCCTAGTGATGGAGTTGGCCACTCCCTC

TCTGCGCGCTCGCTCGCTCACTGAGGCCGGGCGACCAAAGGTCGCCCGACGCCCGGGCTTT

GCCCGGGCGGCCTCAGTGAGCGAGCGAGCGCGCAGCTGCCTGCAGGGGCGCCTGATGCGGT

ATTTTCTCCTTACGCATCTGTGCGGTATTTCACACCGCATACGTCAAAGCAACCATAGTAC

GCGCCCTGTAGCGGCGCATTAAGCGCGGCGGGTGTGGTGGTTACGCGCAGCGTGACCGCTA

CACTTGCCAGCGCCTTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGCT

TTACGGCACCTCGACCCCAAAAAACTTGATTTGGGTGATGGTTCACGTAGTGGGCCATCGC

CCTGATAGACGGTTTTTCGCCCTTTGACGTTGGAGTCCACGTTCTTTAATAGTGGACTCTT

GTTCCAAACTGGAACAACACTCAACTCTATCTCGGGCTATTCTTTTGATTTATAAGGGATT

TTGCCGATTTCGGTCTATTGGTTAAAAAATGAGCTGATTTAACAAAAATTTAACGCGAATT

TTAACAAAATATTAACGTTTACAATTTTATGGTGCACTCTCAGTACAATCTGCTCTGATGC

CGCATAGTTAAGCCAGCCCCGACACCCGCCAACACCCGCTGACGCGCCCTGACGGGCTTGT

CTGCTCCCGGCATCCGCTTACAGACAAGCTGTGACCGTCTCCGGGAGCTGCATGTGTCAGA

GGTTTTCACCGTCATCACCGAAACGCGCGAGACGAAAGGGCCTCGTGATACGCCTATTTTT

ATAGGTTAATGTCATGATAATAATGGTTTCTTAGACGTCAGGTGGCACTTTTCGGGGAAAT

GTGCGCGGAACCCCTATTTGTTTATTTTTCTAAATACATTCAAATATGTATCCGCTCATGA

GACAATAACCCTGATAAATGCTTCAATAATATTGAAAAAGGAAGAGTCGATCGATCAAGAG

ACAGGATGAGGATCGTTTCGCATGATTGAACAAGATGGATTGCACGCAGGTTCTCCGGCCG

CTTGGGTGGAGAGGCTATTCGGCTATGACTGGGCACAACAGACAATCGGCTGCTCTGATGC

CGCCGTGTTCCGGCTGTCAGCGCAGGGGCGCCCGGTTCTTTTTGTCAAGACCGACCTGTCC

GGTGCCCTGAATGAACTGCAAGACGAGGCAGCGCGGCTATCGTGGCTGGCCACGACGGGCG

TTCCTTGCGCAGCTGTGCTCGACGTTGTCACTGAAGCGGGAAGGGACTGGCTGCTATTGGG

CGAAGTGCCGGGGCAGGATCTCCTGTCATCTCACCTTGCTCCTGCCGAGAAAGTATCCATC

ATGGCTGATGCAATGCGGCGGCTGCATACGCTTGATCCGGCTACCTGCCCATTCGACCACC

AAGCGAAACATCGCATCGAGCGAGCACGTACTCGGATGGAAGCCGGTCTTGTCGATCAGGA

TGATCTGGACGAAGAGCATCAGGGGCTCGCGCCAGCCGAACTGTTCGCCAGGCTCAAGGCG

AGCATGCCCGACGGCGAGGATCTCGTCGTGACCCATGGCGATGCCTGCTTGCCGAATATCA

TGGTGGAAAATGGCCGCTTTTCTGGATTCATCGACTGTGGCCGGCTGGGTGTGGCGGATCG

CTATCAGGACATAGCGTTGGCTACCCGTGATATTGCTGAAGAGCTTGGCGGCGAATGGGCT

GACCGCTTCCTCGTGCTTTACGGTATCGCCGCTCCCGATTCGCAGCGCATCGCCTTCTATC

GCCTTCTTGACGAGTTCTTCTGAACGAGCGTGACACCACGATGCCTGTAGCAATGGCAACA

ACGTTGCGCAAACTATTAACTGGCGAACTACTTACTCTAGCTTCCCGGCAACAATTAATAG

ACTGGATGGAGGCGGATAAAGTTGCAGGACCACTTCTGCGCTCGGCCCTTCCGGCTGGCTG

GTTTATTGCTGATAAATCTGGAGCCGGTGAGCGTGGGTCTCGCGGTATCATTGCAGCACTG

GGGCCAGATGGTAAGCCCTCCCGTATCGTAGTTATCTACACGACGGGGAGTCAGGCAACTA

TGGATGAACGAAATAGACAGATCGCTGAGATAGGTGCCTCACTGATTAAGCATTGGTAACT

GTCAGACCAAGTTTACTCATATATACTTTAGATTGATTTAAAACTTCATTTTTAATTTAAA

AGGATCTAGGTGAAGATCCTTTTTGATAATCTCATGACCAAAATCCCTTAACGTGAGTTTT

-continued

CGTTCCACTGAGCGTCAGACCCCGTAGAAAAGATCAAAGGATCTTCTTGAGATCCTTTTTT

TCTGCGCGTAATCTGCTGCTTGCAAACAAAAAAACCACCGCTACCAGCGGTGGTTTGTTTG

CCGGATCAAGAGCTACCAACTCTTTTTCCGAAGGTAACTGGCTTCAGCAGAGCGCAGATAC

CAAATACTGTTCTTCTAGTGTAGCCGTAGTTAGGCCACCACTTCAAGAACTCTGTAGCACC

GCCTACATACCTCGCTCTGCTAATCCTGTTACCAGTGGCTGCTGCCAGTGGCGATAAGTCG

TGTCTTACCGGGTTGGACTCAAGACGATAGTTACCGGATAAGGCGCAGCGGTCGGGCTGAA

CGGGGGGTTCGTGCACACAGCCCAGCTTGGAGCGAACGACCTACACCGAACTGAGATACCT

ACAGCGTGAGCTATGAGAAAGCGCCACGCTTCCCGAAGGGAGAAAGGCGGACAGGTATCCG

GTAAGCGGCAGGGTCGGAACAGGAGAGCGCACGAGGGAGCTTCCAGGGGGAAACGCCTGGT

ATCTTTATAGTCCTGTCGGGTTTCGCCACCTCTGACTTGAGCGTCGATTTTTGTGATGCTC

GTCAGGGGGGCGGAGCCTATGGAAAAACGCCAGCAACGCGGCCTTTTTACGGTTCCTGGCC

TTTTGCTGGCCTTTTGCTCACATGT (pAT050)

SEQ ID NO: 69

CCTGCAGGCAGCTGCGCGCTCGCTCGCTCACTGAGGCCGCCCGGGCAAAGCCCGGGCGTCG

GGCGACCTTTGGTCGCCCGGCCTCAGTGAGCGAGCGAGCGCGCAGAGAGGGAGTGGCCAAC

TCCATCACTAGGGGTTCCTGCGGCCAATTCAGTGGATCCCGATAACTATAACGGTCCTAAG

GTAGCGATTTAAATGAGGGCCTATTTCCCATGATTCCTTCATATTTGCATATACGATACAA

GGCTGTTAGAGAGATAATTAGAATTAATTTGACTGTAAACACAAAGATATTAGTACAAAAT

ACGTGAGGTAGAAAGTAATAATTTCTTGGGTAGTTTGGAGTTTTAAAATTATGTTTTAAAA

TGGACTATCATATGCTTACCGTAACTTGAAAGTATTTCGATTTCTTGGCTTTATATATCTT

GTGGAAAGGACGAGGTACCGTGAGCTGTTGGATAGCACATCTTTGAAAGTCATAAGAGGTT

TACATTTCTTGACTTTGTTAGATGTGGACTTCAGCTGCTTCTTTTTTCCGGGACGCGTCAA

TTGAGATCTCCGACATTGATTATTGACTAGTTATTAATAGTAATCAATTACGGGGTCATTA

GTTCATAGCCCATATATGGAGTTCCGCGTTACATAACTTACGGTAAATGGCCCGCCTGGCT

GACCGCCCAACGACCCCCGCCCATTGACGTCAATAATGACGTATGTTCCCATAGTAACGCC

AATAGGGACTTTCCATTGACGTCAATGGGTGGAGTATTTACGGTAAACTGCCCACTTGGCA

GTACATCAAGTGTATCATATGCCAAGTACGCCCCCTATTGACGTCAATGACGGTAAATGGC

CCGCCTGGCATTATGCCCAGTACATGACCTTATGGGACTTTCCTACTTGGCAGTACATCTA

CGTATTAGTCATCGCTATTACCATGTCGAGGCCACGTTCTGCTTCACTCTCCCCATCTCCC

CCCCCTCCCCACCCCCAATTTTGTATTTATTTATTTTTTAATTATTTTGTGCAGCGATGGG

GGCGGGGGGGGGGGGCGCGCGCCAGGCGGGGCGGGGCGGGGCGAGGGGCGGGGCGGGGCGA

GGCGGAGAGGTGCGGCGGCAGCCAATCAGAGCGGCGCGCTCCGAAAGTTTCCTTTTATGGC

GAGGCGGCGGCGGCGGCGGCCCTATAAAAAGCGAAGCGCGCGGCGGGCGGGAGCAAGCTTC

GTTTAGTGAACCGTCAGATCGCCTGGAGACGCCATCCACGCTGTTTTGACCTCCATAGAAG

ACACCGGGACCGATCCAGCCTCCGCGGATTCGAATCCCGGCCGGGAACGGTGCATTGGAAC

GCGGATTCCCCGTGCCAAGAGTGACGTAAGTACCGCCTATAGAGTCTATAGGCCCACAAAA

AATGCTTTCTTCTTTTAATATACTTTTTTGTTTATCTTATTTCTAATACTTTCCCTAATCT

CTTTCTTTCAGGGCAATAATGATACAATGTATCATGCCTCTTTGCACCATTCTAAAGAATA

ACAGTGATAATTTCTGGGTTAAGGCAATAGCAATATTTCTGCATATAAATATTTCTGCATA

TAAATTGTAACTGATGTAAGAGGTTTCATATTGCTAATAGCAGCTACAATCCAGCTACCAT

TCTGCTTTTATTTTGTGGTTGGGATAAGGCTGGATTATTCTGAGTCCAAGCTAGGCCCTTT

-continued

TGCTAATCGTGTTCATACCTCTTATCTTCCTCCCACAGCTCCTGGGCAACGTGCTGGTCTG

TGTGCTGGCCCATCACTTTGGCAAAGAATTACCGGTGGCAACGTGCTGGTTATTGTGCTGT

CTCATCATTTTGGCAAAGAATTCACGCCCCAGAGCCGCCACCATGGCCTACCCATACGATG

TTCCAGATTACGCTACAGAATTACCTGCCCCCTTGAGCTACTTCCAGAATGCACAGATGAG

CGAGGACAACCACCTGAGCAATACTGTACGTAGCCAGAATGACAACAGAGAACGGCAGGAA

CACAACGACAGGCGGAGCCTGGGCCACCCTGAGCCCCTGTCTAATGGAAGACCCCAGGGTA

ACAGCAGACAGGTGGTGGAACAAGATGAGGAAGAGGACGAGGAGCTGACCCTGAAGTACGG

CGCCAAGCACGTGATCATGCTCTTCGTGCCCGTGACTCTCTGCATGGTGGTGGTGGTGGCT

ACAATCAAGAGCGTCAGCTTTTATACCCGGAAGGATGGGCAGCTAATCTATACCCCATTCA

CAGAAGACACCGAGACTGTGGGCCAGAGAGCCCTGCACTCAATCCTGAATGCCGCCATCAT

GATCAGCGTCATTGTTGTCATGACTATCCTCCTGGTGGTTCTGTATAAATACAGGTGCTAT

AAGGTCATCCATGCCTGGCTGATCATATCATCTCTGTTGCTGCTGTTCTTTTTTAGCTTCA

TTTACCTGGGCGAAGTGTTTAAAACCTATAACGTTGCCGTGGACTACATTACTGTTGCCCT

CCTGATCTGGAACTTCGGCGTGGTGGGCATGATTTCCATTCACTGGAAAGGCCCCCTGAGA

CTGCAGCAGGCATACCTCATTATGATCTCCGCCCTCATGGCCCTGGTGTTCATCAAGTACC

TGCCCGAGTGGACTGCTTGGCTCATCTTGGCTGTGATCTCCGTGTATGATTTAGTGGCTGT

TCTGTGTCCTAAAGGTCCACTGCGTATGCTGGTGGAAACAGCTCAGGAAAGAAATGAAACA

CTGTTTCCTGCTCTGATTTACTCCTCAACAATGGTGTGGCTCGTGAATATGGCCGAAGGAG

ACCCTGAAGCCCAACGGAGAGTGTCCAAAAACTCCAAGTATAACGCCGAGAGCACAGAAAG

GGAGAGCCAGGATACAGTTGCCGAGAATGACGATGGCGGCTTCAGTGAGGAATGGGAAGCC

CAGAGGGACAGCCACCTGGGGCCTCACAGAAGCACCCCTGAGTCTAGAGCCGCTGTCCAGG

AACTGTCCAGCTCCATCCTGGCCGGCGAAGACCCCGAAGAAAGGGGAGTAAAACTTGGACT

GGGAGATTTCATCTTCTACAGTGTTCTCGTTGGCAAAGCCAGCGCAACAGCTAGCGGAGAC

TGGAACACAACAATAGCCTGTTTCGTAGCCATCTTAATTGGCCTGTGCCTTACACTTCTGC

TCCTGGCCATCTTCAAGAAGGCCCTGCCAGCCCTGCCTATCAGCATCACCTTCGGGCTTGT

TTTCTACTTTGCCACCGATTATCTGGTGCAGCCCTTCATGGACCAGCTGGCCTTCCACCAG

TTTTACATCTAGTAAGCGGCCGCCCTAGGGAGCTCCTCGAGGGGGTGGCATCCCTGTGACC

CCTCCCCAGTGCCTCTCCTGGCCCTGGAAGTTGCCACTCCAGTGCCCACCAGCCTTGTCCT

AATAAAATTAAGTTGCATCATTTTGTCTGACTAGGTGTCCTTCTATAATATTATGGGGTGG

AGGGGGGTGGTATGGAGCAAGGGGCAAGGGGGGAAGACAACCTGTAGGGCCTGCGGGGTCT

ATTGGGAACCAAGCTGGAGTGCAGTGGCACAATCTTGGCTCACTGCAATCTCCGCCTCCTG

GGTTCAAGCGATTCTCCTGCCTCAGCCTCCCGAGTTGTTGGGATTCCAGGCATGCATGACC

AGGCTCAGCTAATTTTTGTTTTTTTGGTAGAGACGGGGTTTCACCATATTGGCCAGGCTGG

TCTCCCCCTCCTAATCTCAGGTGATCTACCCACCTTGGCCTCCCAAATTGCTGGGATTACA

GGCGTGAACCACTGCTCCCTTCCCTGTCCTTCCTGGGCCTAGGGCTGTGCCAGCTGCCTCG

TCCCGTCACCTTCTGGCTTCTTCTCTCCCTCCATATCTTAGCTGTTTTCCTCATGAGAATG

TTCCAAATTCGAAATTTCTATTTAACCATTATATATTTACTTGTTTGCTATTATCTCTGCC

CCCAGTAGATTGTTAGCTCCAGAAGAGAAAGGATCATGTCTTTTGCTTATCTAGATATGCC

CATCTGCCTGGTACAATCTCTGGCACATGTTACAGGCAACAACTACTTGTGGAATTGGTGA

ATGCATGAATAGAAGAATGAGTGAATGAATGAATAGACAATAGGCAGAAATCCAGCCTCAA

-continued

AGAGCTTACAGTCTGGTAAGAGGAATAAAATGTCTGCAAATAGCCACAGGACAGGTCAAAG

GAAGGAGGGGCTATTTCCAGCTGAGGGCACCCCATCAGGAAAGCACCCCAGACTTCCTTAG

GGATAACAGGGTAATGGCGCGGGCCGCAGGAACCCCTAGTGATGGAGTTGGCCACTCCCTC

TCTGCGCGCTCGCTCGCTCACTGAGGCCGGGCGACCAAAGGTCGCCCGACGCCCGGGCTTT

GCCCGGGCGGCCTCAGTGAGCGAGCGAGCGCGCAGCTGCCTGCAGGGGCGCCTGATGCGGT

ATTTTCTCCTTACGCATCTGTGCGGTATTTCACACCGCATACGTCAAAGCAACCATAGTAC

GCGCCCTGTAGCGGCGCATTAAGCGCGGCGGGTGTGGTGGTTACGCGCAGCGTGACCGCTA

CACTTGCCAGCGCCTTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGCT

TTACGGCACCTCGACCCCAAAAAACTTGATTTGGGTGATGGTTCACGTAGTGGGCCATCGC

CCTGATAGACGGTTTTTCGCCCTTTGACGTTGGAGTCCACGTTCTTTAATAGTGGACTCTT

GTTCCAAACTGGAACAACACTCAACTCTATCTCGGGCTATTCTTTTGATTTATAAGGGATT

TTGCCGATTTCGGTCTATTGGTTAAAAAATGAGCTGATTTAACAAAAATTTAACGCGAATT

TTAACAAAATATTAACGTTTACAATTTTATGGTGCACTCTCAGTACAATCTGCTCTGATGC

CGCATAGTTAAGCCAGCCCCGACACCCGCCAACACCCGCTGACGCGCCCTGACGGGCTTGT

CTGCTCCCGGCATCCGCTTACAGACAAGCTGTGACCGTCTCCGGGAGCTGCATGTGTCAGA

GGTTTTCACCGTCATCACCGAAACGCGCGAGACGAAAGGGCCTCGTGATACGCCTATTTTT

ATAGGTTAATGTCATGATAATAATGGTTTCTTAGACGTCAGGTGGCACTTTTCGGGGAAAT

GTGCGCGGAACCCCTATTTGTTTATTTTTCTAAATACATTCAAATATGTATCCGCTCATGA

GACAATAACCCTGATAAATGCTTCAATAATATTGAAAAAGGAAGAGTCGATCGATCAAGAG

ACAGGATGAGGATCGTTTCGCATGATTGAACAAGATGGATTGCACGCAGGTTCTCCGGCCG

CTTGGGTGGAGAGGCTATTCGGCTATGACTGGGCACAACAGACAATCGGCTGCTCTGATGC

CGCCGTGTTCCGGCTGTCAGCGCAGGGGCGCCCGGTTCTTTTTGTCAAGACCGACCTGTCC

GGTGCCCTGAATGAACTGCAAGACGAGGCAGCGCGGCTATCGTGGCTGGCCACGACGGGCG

TTCCTTGCGCAGCTGTGCTCGACGTTGTCACTGAAGCGGGAAGGGACTGGCTGCTATTGGG

CGAAGTGCCGGGGCAGGATCTCCTGTCATCTCACCTTGCTCCTGCCGAGAAAGTATCCATC

ATGGCTGATGCAATGCGGCGGCTGCATACGCTTGATCCGGCTACCTGCCCATTCGACCACC

AAGCGAAACATCGCATCGAGCGAGCACGTACTCGGATGGAAGCCGGTCTTGTCGATCAGGA

TGATCTGGACGAAGAGCATCAGGGGCTCGCGCCAGCCGAACTGTTCGCCAGGCTCAAGGCG

AGCATGCCCGACGGCGAGGATCTCGTCGTGACCCATGGCGATGCCTGCTTGCCGAATATCA

TGGTGGAAAATGGCCGCTTTTCTGGATTCATCGACTGTGGCCGGCTGGGTGTGGCGGATCG

CTATCAGGACATAGCGTTGGCTACCCGTGATATTGCTGAAGAGCTTGGCGGCGAATGGGCT

GACCGCTTCCTCGTGCTTTACGGTATCGCCGCTCCCGATTCGCAGCGCATCGCCTTCTATC

GCCTTCTTGACGAGTTCTTCTGAACGAGCGTGACACCACGATGCCTGTAGCAATGGCAACA

ACGTTGCGCAAACTATTAACTGGCGAACTACTTACTCTAGCTTCCCGGCAACAATTAATAG

ACTGGATGGAGGCGGATAAAGTTGCAGGACCACTTCTGCGCTCGGCCCTTCCGGCTGGCTG

GTTTATTGCTGATAAATCTGGAGCCGGTGAGCGTGGGTCTCGCGGTATCATTGCAGCACTG

GGGCCAGATGGTAAGCCCTCCCGTATCGTAGTTATCTACACGACGGGGAGTCAGGCAACTA

TGGATGAACGAAATAGACAGATCGCTGAGATAGGTGCCTCACTGATTAAGCATTGGTAACT

GTCAGACCAAGTTTACTCATATATACTTTAGATTGATTTAAAACTTCATTTTTAATTTAAA

AGGATCTAGGTGAAGATCCTTTTTGATAATCTCATGACCAAAATCCCTTAACGTGAGTTTT

-continued

CGTTCCACTGAGCGTCAGACCCCGTAGAAAAGATCAAAGGATCTTCTTGAGATCCTTTTTT

TCTGCGCGTAATCTGCTGCTTGCAAACAAAAAAACCACCGCTACCAGCGGTGGTTTGTTTG

CCGGATCAAGAGCTACCAACTCTTTTTCCGAAGGTAACTGGCTTCAGCAGAGCGCAGATAC

CAAATACTGTTCTTCTAGTGTAGCCGTAGTTAGGCCACCACTTCAAGAACTCTGTAGCACC

GCCTACATACCTCGCTCTGCTAATCCTGTTACCAGTGGCTGCTGCCAGTGGCGATAAGTCG

TGTCTTACCGGGTTGGACTCAAGACGATAGTTACCGGATAAGGCGCAGCGGTCGGGCTGAA

CGGGGGGTTCGTGCACACAGCCCAGCTTGGAGCGAACGACCTACACCGAACTGAGATACCT

ACAGCGTGAGCTATGAGAAAGCGCCACGCTTCCCGAAGGGAGAAAGGCGGACAGGTATCCG

GTAAGCGGCAGGGTCGGAACAGGAGAGCGCACGAGGGAGCTTCCAGGGGGAAACGCCTGGT

ATCTTTATAGTCCTGTCGGGTTTCGCCACCTCTGACTTGAGCGTCGATTTTTGTGATGCTC

GTCAGGGGGGCGGAGCCTATGGAAAAACGCCAGCAACGCGGCCTTTTTACGGTTCCTGGCC

TTTTGCTGGCCTTTTGCTCACATGT (pAT051)

SEQ ID NO: 70

CCTGCAGGCAGCTGCGCGCTCGCTCGCTCACTGAGGCCGCCCGGGCAAAGCCCGGGCGTCG

GGCGACCTTTGGTCGCCCGGCCTCAGTGAGCGAGCGAGCGCGCAGAGAGGGAGTGGCCAAC

TCCATCACTAGGGGTTCCTGCGGCCAATTCAGTGGATCCCGATAACTATAACGGTCCTAAG

GTAGCGATTTAAATGAGGGCCTATTTCCCATGATTCCTTCATATTTGCATATACGATACAA

GGCTGTTAGAGAGATAATTAGAATTAATTTGACTGTAAACACAAAGATATTAGTACAAAAT

ACGTGACGTAGAAAGTAATAATTTCTTGGGTAGTTTGCAGTTTTAAAATTATGTTTTAAAA

TGGACTATCATATGCTTACCGTAACTTGAAAGTATTTCGATTTCTTGGCTTTATATATCTT

GTGGAAAGGACGAGGTACCGTGAGCTGTTGGAGACTAGAAAAGCCTTTTGACTACGAGGTT

TACATTTCGTTCAAAATCGTTTTCTATAGTTCAGCTGCTTCTTTTTTCCGGGACGCGTCAA

TTGAGATCTCCGACATTGATTATTGACTAGTTATTAATAGTAATCAATTACGGGGTCATTA

GTTCATAGCCCATATATGGAGTTCCGCGTTACATAACTTACGGTAAATGGCCCGCCTGGCT

GACCGCCCAACGACCCCCGCCCATTGACGTCAATAATGACGTATGTTCCCATAGTAACGCC

AATAGGGACTTTCCATTGACGTCAATGGGTGGAGTATTTACGGTAAACTGCCCACTTGGCA

GTACATCAAGTGTATCATATGCCAAGTACGCCCCCTATTGACGTCAATGACGGTAAATGGC

CCGCCTGGCATTATGCCCAGTACATGACCTTATGGGACTTTCCTACTTGGCAGTACATCTA

CGTATTAGTCATCGCTATTACCATGTCGAGGCCACGTTCTGCTTCACTCTCCCCATCTCCC

CCCCCTCCCCACCCCCAATTTTGTATTTATTTATTTTTTAATTATTTTGTGCAGCGATGGG

GGCGGGGGGGGGGGGCGCGCGCCAGGCGGGGCGGGGCGGGGCGAGGGGCGGGGCGGGGCGA

GGCGGAGAGGTGCGGCGGCAGCCAATCAGAGCGGCGCGCTCCGAAAGTTTCCTTTTATGGC

GAGGCGGCGGCGGCGGCGGCCCTATAAAAAGCGAAGCGCGCGGCGGGCGGGAGCAAGCTTC

GTTTAGTGAACCGTCAGATCGCCTGGAGACGCCATCCACGCTGTTTTGACCTCCATAGAAG

ACACCGGGACCGATCCAGCCTCCGCGGATTCGAATCCCGGCCGGGAACGGTGCATTGGAAC

GCGGATTCCCCGTGCCAAGAGTGACGTAAGTACCGCCTATAGAGTCTATAGGCCCACAAAA

AATGCTTTCTTCTTTTAATATACTTTTTTGTTTATCTTATTTCTAATACTTTCCCTAATCT

CTTTCTTTCAGGGCAATAATGATACAATGTATCATGCCTCTTTGCACCATTCTAAAGAATA

ACAGTGATAATTTCTGGGTTAAGGCAATAGCAATATTTCTGCATATAAATATTTCTGCATA

TAAATTGTAACTGATGTAAGAGGTTTCATATTGCTAATAGCAGCTACAATCCAGCTACCAT

-continued

TCTGCTTTTATTTTGTGGTTGGGATAAGGCTGGATTATTCTGAGTCCAAGCTAGGCCCTTT

TGCTAATCGTGTTCATACCTCTTATCTTCCTCCCACAGCTCCTGGGCAACGTGCTGGTCTG

TGTGCTGGCCCATCACTTTGGCAAAGAATTACCGGTGGCAACGTGCTGGTTATTGTGCTGT

CTCATCATTTTGGCAAAGAATTCACGCCCCAGAGCCGCCACCATGGCCTACCCATACGATG

TTCCAGATTACGCTACAGAATTACCTGCCCCCTTGAGCTACTTCCAGAATGCACAGATGAG

CGAGGACAACCACCTGAGCAATACTGTACGTAGCCAGAATGACAACAGAGAACGGCAGGAA

CACAACGACAGGCGGAGCCTGGGCCACCCTGAGCCCCTGTCTAATGGAAGACCCCAGGGTA

ACAGCAGACAGGTGGTGGAACAAGATGAGGAAGAGGACGAGGAGCTGACCCTGAAGTACGG

CGCCAAGCACGTGATCATGCTCTTCGTGCCCGTGACTCTCTGCATGGTGGTGGTGGTGGCT

ACAATCAAGAGCGTCAGCTTTTATACCCGGAAGGATGGGCAGCTAATCTATACCCCATTCA

CAGAAGACACCGAGACTGTGGGCCAGAGAGCCCTGCACTCAATCCTGAATGCCGCCATCAT

GATCAGCGTCATTGTTGTCATGACTATCCTCCTGGTGGTTCTGTATAAATACAGGTGCTAT

AAGGTCATCCATGCCTGGCTGATCATATCATCTCTGTTGCTGCTGTTCTTTTTTAGCTTCA

TTTACCTGGGCGAAGTGTTTAAAACCTATAACGTTGCCGTGGACTACATTACTGTTGCCCT

CCTGATCTGGAACTTCGGCGTGGTGGGCATGATTTCCATTCACTGGAAAGGCCCCCTGAGA

CTGCAGCAGGCATACCTCATTATGATCTCCGCCCTCATGGCCCTGGTGTTCATCAAGTACC

TGCCCGAGTGGACTGCTTGGCTCATCTTGGCTGTGATCTCCGTGTATGATTTAGTGGCTGT

TCTGTGTCCTAAAGGTCCACTGCGTATGCTGGTGGAAACAGCTCAGGAAAGAAATGAAACA

CTGTTTCCTGCTCTGATTTACTCCTCAACAATGGTGTGGCTCGTGAATATGGCCGAAGGAG

ACCCTGAAGCCCAACGGAGAGTGTCCAAAAACTCCAAGTATAACGCCGAGAGCACAGAAAG

GGAGAGCCAGGATACAGTTGCCGAGAATGACGATGGCGGCTTCAGTGAGGAATGGGAAGCC

CAGAGGGACAGCCACCTGGGGCCTCACAGAAGCACCCCTGAGTCTAGAGCCGCTGTCCAGG

AACTGTCCAGCTCCATCCTGGCCGGCGAAGACCCCGAAGAAAGGGGAGTAAAACTTGGACT

GGGAGATTTCATCTTCTACAGTGTTCTCGTTGGCAAAGCCAGCGCAACAGCTAGCGGAGAC

TGGAACACAACAATAGCCTGTTTCGTAGCCATCTTAATTGGCCTGTGCCTTACACTTCTGC

TCCTGGCCATCTTCAAGAAGGCCCTGCCAGCCCTGCCTATCAGCATCACCTTCGGGCTTGT

TTTCTACTTTGCCACCGATTATCTGGTGCAGCCCTTCATGGACCAGCTGGCCTTCCACCAG

TTTTACATCTAGTAAGCGGCCGCCCTAGGGAGCTCCTCGAGGGGGTGGCATCCCTGTGACC

CCTCCCCAGTGCCTCTCCTGGCCCTGGAAGTTGCCACTCCAGTGCCCACCAGCCTTGTCCT

AATAAAATTAAGTTGCATCATTTTGTCTGACTAGGTGTCCTTCTATAATATTATGGGGTGG

AGGGGGGTGGTATGGAGCAAGGGGCAAGGGGGGAAGACAACCTGTAGGGCCTGCGGGGTCT

ATTGGGAACCAAGCTGGAGTGCAGTGGCACAATCTTGGCTCACTGCAATCTCCGCCTCCTG

GGTTCAAGCGATTCTCCTGCCTCAGCCTCCCGAGTTGTTGGGATTCCAGGCATGCATGACC

AGGCTCAGCTAATTTTTGTTTTTTTGGTAGAGACGGGGTTTCACCATATTGGCCAGGCTGG

TCTCCCCCTCCTAATCTCAGGTGATCTACCCACCTTGGCCTCCCAAATTGCTGGGATTACA

GGCGTGAACCACTGCTCCCTTCCCTGTCCTTCCTGGGCCTAGGGCTGTGCCAGCTGCCTCG

TCCCGTCACCTTCTGGCTTCTTCTCTCCCTCCATATCTTAGCTGTTTTCCTCATGAGAATG

TTCCAAATTCGAAATTTCTATTTAACCATTATATATTTACTTGTTTGCTATTATCTCTGCC

CCCAGTAGATTGTTAGCTCCAGAAGAGAAAGGATCATGTCTTTTGCTTATCTAGATATGCC

CATCTGCCTGGTACAATCTCTGGCACATGTTACAGGCAACAACTACTTGTGGAATTGGTGA

ATGCATGAATAGAAGAATGAGTGAATGAATGAATAGACAATAGGCAGAAATCGAGCCTCAA

-continued

AGAGCTTACAGTCTGGTAAGAGGAATAAAATGTCTGCAAATAGCCACAGGACAGGTCAAAG

GAAGGAGGGGCTATTTCCAGCTGAGGGCACCCCATCAGGAAAGCACCCCAGACTTCCTTAG

GGATAACAGGGTAATGGCGCGGGCCGCAGGAACCCCTAGTGATGGAGTTGGCCACTCCCTC

TCTGCGCGCTCGCTCGCTCACTGAGGCCGGGCGACCAAAGGTCGCCCGACGCCCGGGCTTT

GCCCGGGCGGCCTCAGTGAGCGAGCGAGCGCGCAGCTGCCTGCAGGGGCGCCTGATGCGGT

ATTTTCTCCTTACGCATCTGTGCGGTATTTCACACCGCATACGTCAAAGCAACCATAGTAC

GCGCCCTGTAGCGGCGCATTAAGCGCGGCGGGTGTGGTGGTTACGCGCAGCGTGACCGCTA

CACTTGCCAGCGCCTTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGCT

TTACGGCACCTCGACCCCAAAAAACTTGATTTGGGTGATGGTTCACGTAGTGGGCCATCGC

CCTGATAGACGGTTTTTCGCCCTTTGACGTTGGAGTCCACGTTCTTTAATAGTGGACTCTT

GTTCCAAACTGGAACAACACTCAACTCTATCTCGGGCTATTCTTTTGATTTATAAGGGATT

TTGCCGATTTCGGTCTATTGGTTAAAAAATGAGCTGATTTAACAAAAATTTAACGCGAATT

TTAACAAAATATTAACGTTTACAATTTTATGGTGCACTCTCAGTACAATCTGCTCTGATGC

CGCATAGTTAAGCCAGCCCCGACACCCGCCAACACCCGCTGACGCGCCCTGACGGGCTTGT

CTGCTCCCGGCATCCGCTTACAGACAAGCTGTGACCGTCTCCGGGAGCTGCATGTGTCAGA

GGTTTTCACCGTCATCACCGAAACGCGCGAGACGAAAGGGCCTCGTGATACGCCTATTTTT

ATAGGTTAATGTCATGATAATAATGGTTTCTTAGACGTCAGGTGGCACTTTTCGGGGAAAT

GTGCGCGGAACCCCTATTTGTTTATTTTTCTAAATACATTCAAATATGTATCCGCTCATGA

GACAATAACCCTGATAAATGCTTCAATAATATTGAAAAAGGAAGAGTCGATCGATCAAGAG

ACAGGATGAGGATCGTTTCGCATGATTGAACAAGATGGATTGCACGCAGGTTCTCCGGCCG

CTTGGGTGGAGAGGCTATTCGGCTATGACTGGGCACAACAGACAATCGGCTGCTCTGATGC

CGCCGTGTTCCGGCTGTCAGCGCAGGGGCGCCCGGTTCTTTTTGTCAAGACCGACCTGTCC

GGTGCCCTGAATGAACTGCAAGACGAGGCAGCGCGGCTATCGTGGCTGGCCACGACGGGCG

TTCCTTGCGCAGCTGTGCTCGACGTTGTCACTGAAGCGGGAAGGGACTGGCTGCTATTGGG

CGAAGTGCCGGGGCAGGATCTCCTGTCATCTCACCTTGCTCCTGCCGAGAAAGTATCCATC

ATGGCTGATGCAATGCGGCGGCTGCATACGCTTGATCCGGCTACCTGCCCATTCGACCACC

AAGCGAAACATCGCATCGAGCGAGCACGTACTCGGATGGAAGCCGGTCTTGTCGATCAGGA

TGATCTGGACGAAGAGCATCAGGGGCTCGCGCCAGCCGAACTGTTCGCCAGGCTCAAGGCG

AGCATGCCCGACGGCGAGGATCTCGTCGTGACCCATGGCGATGCCTGCTTGCCGAATATCA

TGGTGGAAAATGGCCGCTTTTCTGGATTCATCGACTGTGGCCGGCTGGGTGTGGCGGATCG

CTATCAGGACATAGCGTTGGCTACCCGTGATATTGCTGAAGAGCTTGGCGGCGAATGGGCT

GACCGCTTCCTCGTGCTTTACGGTATCGCCGCTCCCGATTCGCAGCGCATCGCCTTCTATC

GCCTTCTTGACGAGTTCTTCTGAACGAGCGTGACACCACGATGCCTGTAGCAATGGCAACA

ACGTTGCGCAAACTATTAACTGGCGAACTACTTACTCTAGCTTCCCGGCAACAATTAATAG

ACTGGATGGAGGCGGATAAAGTTGCAGGACCACTTCTGCGCTCGGCCCTTCCGGCTGGCTG

GTTTATTGCTGATAAATCTGGAGCCGGTGAGCGTGGGTCTCGCGGTATCATTGCAGCACTG

GGGCCAGATGGTAAGCCCTCCCGTATCGTAGTTATCTACACGACGGGGAGTCAGGCAACTA

TGGATGAACGAAATAGACAGATCGCTGAGATAGGTGCCTCACTGATTAAGCATTGGTAACT

GTCAGACCAAGTTTACTCATATATACTTTAGATTGATTTAAAACTTCATTTTTAATTTAAA

-continued

AGGATCTAGGTGAAGATCCTTTTTGATAATCTCATGACCAAAATCCCTTAACGTGAGTTTT

CGTTCCACTGAGCGTCAGACCCCGTAGAAAAGATCAAAGGATCTTCTTGAGATCCTTTTTT

TCTGCGCGTAATCTGCTGCTTGCAAACAAAAAAACCACCGCTACCAGCGGTGGTTTGTTTG

CCGGATCAAGAGCTACCAACTCTTTTTCCGAAGGTAACTGGCTTCAGCAGAGCGCAGATAC

CAAATACTGTTCTTCTAGTGTAGCCGTAGTTAGGCCACCACTTCAAGAACTCTGTAGCACC

GCCTACATACCTCGCTCTGCTAATCCTGTTACCAGTGGCTGCTGCCAGTGGCGATAAGTCG

TGTCTTACCGGGTTGGACTCAAGACGATAGTTACCGGATAAGGCGCAGCGGTCGGGCTGAA

CGGGGGGTTCGTGCACACAGCCCAGCTTGGAGCGAACGACCTACACCGAACTGAGATACCT

ACAGCGTGAGCTATGAGAAAGCGCCACGCTTCCCGAAGGGAGAAAGGCGGACAGGTATCCG

GTAAGCGGCAGGGTCGGAACAGGAGAGCGCACGAGGGAGCTTCCAGGGGGAAACGCCTGGT

ATCTTTATAGTCCTGTCGGGTTTCGCCACCTCTGACTTGAGCGTCGATTTTTGTGATGCTC

GTCAGGGGGGCGGAGCCTATGGAAAAACGCCAGCAACGCGGCCTTTTTACGGTTCCTGGCC

TTTTGCTGGCCTTTTGCTCACATGT (pAT052)

SEQ ID NO: 71

CCTGCAGGCAGCTGCGCGCTCGCTCGCTCACTGAGGCCGCCCGGGCAAAGCCCGGGCGTCG

GGCGACCTTTGGTCGCCCGGCCTCAGTGAGCGAGCGAGCGCGCAGAGAGGGAGTGGCCAAC

TCCATCACTAGGGGTTCCTGCGGCCAATTCAGTGGATCCCGATAACTATAACGGTCCTAAG

GTAGCGATTTAAATGAGGGCCTATTTCCCATGATTCCTTCATATTTGCATATACGATACAA

GGCTGTTAGAGAGATAATTAGAATTAATTTGACTGTAAACACAAAGATATTAGTACAAAAT

ACGTGACGTAGAAAGTAATAATTTCTTGGGTAGTTTGCAGTTTTAAAATTATGTTTTAAAA

TGGACTATCATATGCTTACCGTAACTTGAAAGTATTTCGATTTCTTGGCTTTATATATCTT

GTGGAAAGGACGAGGTACCGTGAGCTGTTGGATTCTGGTCACTACACGATTCCTCGAGGTT

TACATTTCGAAATCGTCCTGTGACCACGCTTCAGCTGCTTCTTTTTTCCGGGACGCGTCAA

TTGAGATCTCCGACATTGATTATTGACTAGTTATTAATAGTAATCAATTACGGGGTCATTA

GTTCATAGCCCATATATGGAGTTCCGCGTTACATAACTTACGGTAAATGGCCCGCCTGGCT

GACCGCCCAACGACCCCCGCCCATTGACGTCAATAATGACGTATGTTCCCATAGTAACGCC

AATAGGGACTTTCCATTGACGTCAATGGGTGGAGTATTTACGGTAAACTGCCCACTTGGCA

GTACATCAAGTGTATCATATGCCAAGTACGCCCCCTATTGACGTCAATGACGGTAAATGGC

CCGCCTGGCATTATGCCCAGTACATGACCTTATGGGACTTTCCTACTTGGCAGTACATCTA

CGTATTAGTCATCGCTATTACCATGTCGAGGCCACGTTCTGCTTCACTCTCCCCATCTCCC

CCCCCTCCCCACCCCCAATTTTGTATTTATTTATTTTTTAATTATTTTGTGCAGCGATGGG

GGCGGGGGGGGGGGGCGCGCGCCAGGCGGGGCGGGGCGGGGCGAGGGGCGGGGCGGGGCGA

GGCGGAGAGGTGCGGCGGCAGCCAATCAGAGCGGCGCGCTCCGAAAGTTTCCTTTTATGGC

GAGGCGGCGGCGGCGGCGGCCCTATAAAAAGCGAAGCGCGCGGCGGGCGGGAGCAAGCTTC

GTTTAGTGAACCGTCAGATCGCCTGGAGACGCCATCCACGCTGTTTTGACCTCCATAGAAG

ACACCGGGACCGATCCAGCCTCCGCGGATTCGAATCCCGGCCGGGAACGGTGCATTGGAAC

GCGGATTCCCCGTGCCAAGAGTGACGTAAGTACCGCCTATAGAGTCTATAGGCCCACAAAA

AATGCTTTCTTCTTTTAATATACTTTTTTGTTTATCTTATTTCTAATACTTTCCCTAATCT

CTTTCTTTGAGGGCAATAATGATACAATGTATCATGCCTCTTTGCACCATTCTAAAGAATA

ACAGTGATAATTTCTGGGTTAAGGCAATAGCAATATTTCTGCATATAAATATTTCTGCATA

TAAATTGTAACTGATGTAAGAGGTTTCATATTGCTAATAGCAGCTACAATCCAGCTACCAT

-continued

TCTGCTTTTATTTTGTGGTTGGGATAAGGCTGGATTATTCTGAGTCCAAGCTAGGCCCTTT

TGCTAATCGTGTTCATACCTCTTATCTTCCTCCCACAGCTCCTGGGCAACGTGCTGGTCTG

TGTGCTGGCCCATCACTTTGGCAAAGAATTACCGGTGGCAACGTGCTGGTTATTGTGCTGT

CTCATCATTTTGGCAAAGAATTCACGCCCCAGAGCCGCCACCATGGCCTACCCATACGATG

TTCCAGATTACGCTACAGAATTACCTGCCCCCTTGAGCTACTTCCAGAATGCACAGATGAG

CGAGGACAACCACCTGAGCAATACTGTACGTAGCCAGAATGACAACAGAGAACGGCAGGAA

CACAACGACAGGCGGAGCCTGGGCCACCCTGAGCCCCTGTCTAATGGAAGACCCCAGGGTA

ACAGCAGACAGGTGGTGGAACAAGATGAGGAAGAGGACGAGGAGCTGACCCTGAAGTACGG

CGCCAAGCACGTGATCATGCTCTTCGTGCCCGTGACTCTCTGCATGGTGGTGGTGGTGGCT

ACAATCAAGAGCGTCAGCTTTTATACCCGGAAGGATGGGCAGCTAATCTATACCCCATTCA

CAGAAGACACCGAGACTGTGGGCCAGAGAGCCCTGCACTCAATCCTGAATGCCGCCATCAT

GATCAGCGTCATTGTTGTCATGACTATCCTCCTGGTGGTTCTGTATAAATACAGGTGCTAT

AAGGTCATCCATGCCTGGCTGATCATATCATCTCTGTTGCTGCTGTTCTTTTTTAGCTTCA

TTTACCTGGGCGAAGTGTTTAAAACCTATAACGTTGCCGTGGACTACATTACTGTTGCCCT

CCTGATCTGGAACTTCGGCGTGGTGGGCATGATTTCCATTCACTGGAAAGGCCCCCTGAGA

CTGCAGCAGGCATACCTCATTATGATCTCCGCCCTCATGGCCCTGGTGTTCATCAAGTACC

TGCCCGAGTGGACTGCTTGGCTCATCTTGGCTGTGATCTCCGTGTATGATTTAGTGGCTGT

TCTGTGTCCTAAAGGTCCACTGCGTATGCTGGTGGAAACAGCTCAGGAAAGAAATGAAACA

CTGTTTCCTGCTCTGATTTACTCCTCAACAATGGTGTGGCTCGTGAATATGGCCGAAGGAG

ACCCTGAAGCCCAACGGAGAGTGTCCAAAAACTCCAAGTATAACGCCGAGAGCACAGAAAG

GGAGAGCCAGGATACAGTTGCCGAGAATGACGATGGCGGCTTCAGTGAGGAATGGGAAGCC

CAGAGGGACAGCCACCTGGGGCCTCACAGAAGCACCCCTGAGTCTAGAGCCGCTGTCCAGG

AACTGTCCAGCTCCATCCTGGCCGGCGAAGACCCCGAAGAAAGGGGAGTAAAACTTGGACT

GGGAGATTTCATCTTCTACAGTGTTCTCGTTGGCAAAGCCAGCGCAACAGCTAGCGGAGAC

TGGAACACAACAATAGCCTGTTTCGTAGCCATCTTAATTGGCCTGTGCCTTACACTTCTGC

TCCTGGCCATCTTCAAGAAGGCCCTGCCAGCCCTGCCTATCAGCATCACCTTCGGGCTTGT

TTTCTACTTTGCCACCGATTATCTGGTGCAGCCCTTCATGGACCAGCTGGCCTTCCACCAG

TTTTACATCTAGTAAGCGGCCGCCCTAGGGAGCTCCTCGAGGGGGTGGCATCCCTGTGACC

CCTCCCCAGTGCCTCTCCTGGCCCTGGAAGTTGCCACTCCAGTGCCCACCAGCCTTGTCCT

AATAAAATTAAGTTGCATCATTTTGTCTGACTAGGTGTCCTTCTATAATATTATGGGGTGG

AGGGGGGTGGTATGGAGCAAGGGGCAAGGGGGGAAGACAACCTGTAGGGCCTGCGGGGTCT

ATTGGGAACCAAGCTGGAGTGCAGTGGCACAATCTTGGCTCACTGCAATCTCCGCCTCCTG

GGTTCAAGCGATTCTCCTGCCTCAGCCTCCCGAGTTGTTGGGATTCCAGGCATGCATGACC

AGGCTCAGCTAATTTTTGTTTTTTTGGTAGAGACGGGGTTTCACCATATTGGCCAGGCTGG

TCTCCCCCTCCTAATCTCAGGTGATCTACCCACCTTGGCCTCCCAAATTGCTGGGATTACA

GGCGTGAACCACTGCTCCCTTCCCTGTCCTTCCTGGGCCTAGGGCTGTGCCAGCTGCCTCG

TCCCGTCACCTTCTGGCTTCTTCTCTCCCTCCATATCTTAGCTGTTTTCCTCATGAGAATG

TTCCAAATTCGAAATTTCTATTTAACCATTATATATTTACTTGTTTGCTATTATCTCTGCC

CCCAGTAGATTGTTAGCTCCAGAAGAGAAAGGATCATGTCTTTTGCTTATCTAGATATGCC

CATCTGCCTGGTACAATCTCTGGCACATGTTACAGGCAACAACTACTTGTGGAATTGGTGA

-continued

ATGCATGAATAGAAGAATGAGTGAATGAATGAATAGACAATAGGCAGAAATCGAGCCTCAA

AGAGCTTACAGTCTGGTAAGAGGAATAAAATGTCTGCAAATAGCCACAGGACAGGTCAAAG

GAAGGAGGGGCTATTTCCAGCTGAGGGCACCCCATCAGGAAAGCACCCCAGACTTCCTTAG

GGATAACAGGGTAATGGCGCGGGCCGCAGGAACCCCTAGTGATGGAGTTGGCCACTCCCTC

TCTGCGCGCTCGCTCGCTCACTGAGGCCGGGCGACCAAAGGTCGCCCGACGCCCGGGCTTT

GCCCGGGCGGCCTCAGTGAGCGAGCGAGCGCGCAGCTGCCTGCAGGGGCGCCTGATGCGGT

ATTTTCTCCTTACGCATCTGTGCGGTATTTCACACCGCATACGTCAAAGCAACCATAGTAC

GCGCCCTGTAGCGGCGCATTAAGCGCGGCGGGTGTGGTGGTTACGCGCAGCGTGACCGCTA

CACTTGCCAGCGCCTTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGCT

TTACGGCACCTCGACCCCAAAAAACTTGATTTGGGTGATGGTTCACGTAGTGGGCCATCGC

CCTGATAGACGGTTTTTCGCCCTTTGACGTTGGAGTCCACGTTCTTTAATAGTGGACTCTT

GTTCCAAACTGGAACAACACTCAACTCTATCTCGGGCTATTCTTTTGATTTATAAGGGATT

TTGCCGATTTCGGTCTATTGGTTAAAAAATGAGCTGATTTAACAAAAATTTAACGCGAATT

TTAACAAAATATTAACGTTTACAATTTTATGGTGCACTCTCAGTACAATCTGCTCTGATGC

CGCATAGTTAAGCCAGCCCCGACACCCGCCAACACCCGCTGACGCGCCCTGACGGGCTTGT

CTGCTCCCGGCATCCGCTTACAGACAAGCTGTGACCGTCTCCGGGAGCTGCATGTGTCAGA

GGTTTTCACCGTCATCACCGAAACGCGCGAGACGAAAGGGCCTCGTGATACGCCTATTTTT

ATAGGTTAATGTCATGATAATAATGGTTTCTTAGACGTCAGGTGGCACTTTTCGGGGAAAT

GTGCGCGGAACCCCTATTTGTTTATTTTTCTAAATACATTCAAATATGTATCCGCTCATGA

GACAATAACCCTGATAAATGCTTCAATAATATTGAAAAAGGAAGAGTCGATCGATCAAGAG

ACAGGATGAGGATCGTTTCGCATGATTGAACAAGATGGATTGCACGCAGGTTCTCCGGCCG

CTTGGGTGGAGAGGCTATTCGGCTATGACTGGGCACAACAGACAATCGGCTGCTCTGATGC

CGCCGTGTTCCGGCTGTCAGCGCAGGGGCGCCCGGTTCTTTTTGTCAAGACCGACCTGTCC

GGTGCCCTGAATGAACTGCAAGACGAGGCAGCGCGGCTATCGTGGCTGGCCACGACGGGCG

TTCCTTGCGCAGCTGTGCTCGACGTTGTCACTGAAGCGGGAAGGGACTGGCTGCTATTGGG

CGAAGTGCCGGGGCAGGATCTCCTGTCATCTCACCTTGCTCCTGCCGAGAAAGTATCCATC

ATGGCTGATGCAATGCGGCGGCTGCATACGCTTGATCCGGCTACCTGCCCATTCGACCACC

AAGCGAAACATCGCATCGAGCGAGCACGTACTCGGATGGAAGCCGGTCTTGTCGATCAGGA

TGATCTGGACGAAGAGCATCAGGGGCTCGCGCCAGCCGAACTGTTCGCCAGGCTCAAGGCG

AGCATGCCCGACGGCGAGGATCTCGTCGTGACCCATGGCGATGCCTGCTTGCCGAATATCA

TGGTGGAAAATGGCCGCTTTTCTGGATTCATCGACTGTGGCCGGCTGGGTGTGGCGGATCG

CTATCAGGACATAGCGTTGGCTACCCGTGATATTGCTGAAGAGCTTGGCGGCGAATGGGCT

GACCGCTTCCTCGTGCTTTACGGTATCGCCGCTCCCGATTCGCAGCGCATCGCCTTCTATC

GCCTTCTTGACGAGTTCTTCTGAACGAGCGTGACACCACGATGCCTGTAGCAATGGCAACA

ACGTTGCGCAAACTATTAACTGGCGAACTACTTACTCTAGCTTCCCGGCAACAATTAATAG

ACTGGATGGAGGCGGATAAAGTTGCAGGACCACTTCTGCGCTCGGCCCTTCCGGCTGGCTG

GTTTATTGCTGATAAATCTGGAGCCGGTGAGCGTGGGTCTCGCGGTATCATTGCAGCACTG

GGGCCAGATGGTAAGCCCTCCCGTATCGTAGTTATCTACACGACGGGGAGTCAGGCAACTA

TGGATGAACGAAATAGACAGATCGCTGAGATAGGTGCCTCACTGATTAAGCATTGGTAACT

GTCAGACCAAGTTTACTCATATATACTTTAGATTGATTTAAAACTTCATTTTTAATTTAAA

-continued

AGGATCTAGGTGAAGATCCTTTTTGATAATCTCATGACCAAAATCCCTTAACGTGAGTTTT

CGTTCCACTGAGCGTCAGACCCCGTAGAAAAGATCAAAGGATCTTCTTGAGATCCTTTTTT

TCTGCGCGTAATCTGCTGCTTGCAAACAAAAAAACCACCGCTACCAGCGGTGGTTTGTTTG

CCGGATCAAGAGCTACCAACTCTTTTTCCGAAGGTAACTGGCTTCAGCAGAGCGCAGATAC

CAAATACTGTTCTTCTAGTGTAGCCGTAGTTAGGCCACCACTTCAAGAACTCTGTAGCACC

GCCTACATACCTCGCTCTGCTAATCCTGTTACCAGTGGCTGCTGCCAGTGGCGATAAGTCG

TGTCTTACCGGGTTGGACTCAAGACGATAGTTACCGGATAAGGCGCAGCGGTCGGGCTGAA

CGGGGGGTTCGTGCACACAGCCCAGCTTGGAGCGAACGACCTACACCGAACTGAGATACCT

ACAGCGTGAGCTATGAGAAAGCGCCACGCTTCCCGAAGGGAGAAAGGCGGACAGGTATCCG

GTAAGCGGCAGGGTCGGAACAGGAGAGCGCACGAGGGAGCTTCCAGGGGGAAACGCCTGGT

ATCTTTATAGTCCTGTCGGGTTTCGCCACCTCTGACTTGAGCGTCGATTTTTGTGATGCTC

GTCAGGGGGGCGGAGCCTATGGAAAAACGCCAGCAACGCGGCCTTTTTACGGTTCCTGGCC

TTTTGCTGGCCTTTTGCTCACATGT (pAT053)

SEQ ID NO: 72

CCTGCAGGCAGCTGCGCGCTCGCTCGCTCACTGAGGCCGCCCGGGCAAAGCCCGGGCGTCG

GGCGACCTTTGGTCGCCCGGCCTCAGTGAGCGAGCGAGCGCGCAGAGAGGGAGTGGCCAAC

TCCATCACTAGGGGTTCCTGCGGCCAATTCAGTGGATCCCGATAACTATAACGGTCCTAAG

GTAGCGATTTAAATGAGGGCCTATTTCCCATGATTCCTTCATATTTGCATATACGATACAA

GGCTGTTAGAGAGATAATTAGAATTAATTTGAGTGTAAACACAAAGATATTAGTACAAAAT

ACGTGAGGTAGAAAGTAATAATTTCTTGGGTAGTTTGGAGTTTTAAAATTATGTTTTAAAA

TGGACTATCATATGCTTACCGTAACTTGAAAGTATTTCGATTTCTTGGCTTTATATATCTT

GTGGAAAGGACGAGGTACCGTGAGCTGTTGGAGACTAGAAAAGCCTTTTGACTACGAGGTT

TACATTTCGTTCAAAATCGTTTTCTATAGTTCAGCTGCTTCTGAGCTGTTGGAGACTAGAA

AAGCCTTTTGACTACGAGGTTTACATTTCGTTCAAAATCGTTTTCTATAGTTCAGCTGCTT

CTTTTTTCCGGGACGCGTCAATTGAGATCTCCGACATTGATTATTGACTAGTTATTAATAG

TAATCAATTACGGGGTCATTAGTTCATAGCCCATATATGGAGTTCCGCGTTACATAACTTA

CGGTAAATGGCCCGCCTGGCTGACCGCCCAACGACCCCCGCCCATTGACGTCAATAATGAC

GTATGTTCCCATAGTAACGCCAATAGGGACTTTCCATTGACGTCAATGGGTGGAGTATTTA

CGGTAAACTGCCCACTTGGCAGTACATCAAGTGTATCATATGCCAAGTACGCCCCCTATTG

ACGTCAATGACGGTAAATGGCCCGCCTGGCATTATGCCCAGTACATGACCTTATGGGACTT

TCCTACTTGGCAGTACATCTACGTATTAGTCATCGCTATTACCATGTCGAGGCCACGTTCT

GCTTCACTCTCCCCATCTCCCCCCCCTCCCCACCCCCAATTTTGTATTTATTTATTTTTTA

ATTATTTTGTGCAGCGATGGGGGCGGGGGGGGGGGGCGCGCGCCAGGCGGGGCGGGGCGGG

GCGAGGGGCGGGGCGGGGCGAGGCGGAGAGGTGCGGCGGCAGCCAATCAGAGCGGCGCGCT

CCGAAAGTTTCCTTTTATGGCGAGGCGGCGGCGGCGGCGGCCCTATAAAAAGCGAAGCGCG

CGGCGGGCGGGAGCAAGCTTCGTTTAGTGAACCGTCAGATCGCCTGGAGACGCCATCCACG

CTGTTTTGACCTCCATAGAAGACACCGGGACCGATCCAGCCTCCGCGGATTCGAATCCCGG

CCGGGAACGGTGCATTGGAACGCGGATTCCCCGTGCCAAGAGTGACGTAAGTACCGCCTAT

AGAGTCTATAGGCCCACAAAAAATGCTTTCTTCTTTTAATATACTTTTTTGTTTATCTTAT

TTCTAATACTTTCCCTAATCTCTTTCTTTCAGGGCAATAATGATACAATGTATCATGCCTC

-continued

TTTGCACCATTCTAAAGAATAACAGTGATAATTTCTGGGTTAAGGCAATAGCAATATTTCT

GCATATAAATATTTCTGCATATAAATTGTAACTGATGTAAGAGGTTTCATATTGCTAATAG

CAGCTACAATCCAGCTACCATTCTGCTTTTATTTTGTGGTTGGGATAAGGCTGGATTATTC

TGAGTCCAAGCTAGGCCCTTTTGCTAATCGTGTTCATACCTCTTATCTTCCTCCCACAGCT

CCTGGGCAACGTGCTGGTCTGTGTGCTGGCCCATCACTTTGGCAAAGAATTACCGGTGGCA

ACGTGCTGGTTATTGTGCTGTCTCATCATTTTGGCAAAGAATTCACGCCCCAGAGCCGCCA

CCATGGCCTACCCATACGATGTTCCAGATTACGCTACAGAATTACCTGCCCCCTTGAGCTA

CTTCCAGAATGCACAGATGAGCGAGGACAACCACCTGAGCAATACTGTAGGTAGCCAGAAT

GACAACAGAGAACGGCAGGAACACAACGACAGGCGGAGCCTGGGCCACCCTGAGCCCCTGT

CTAATGGAAGACCCCAGGGTAACAGCAGACAGGTGGTGGAACAAGATGAGGAAGAGGACGA

GGAGCTGACCCTGAAGTACGGCGCCAAGCACGTGATCATGCTCTTCGTGCCCGTGACTCTC

TGCATGGTGGTGGTGGTGGCTACAATCAAGAGCGTCAGCTTTTATACCCGGAAGGATGGGC

AGCTAATCTATACCCCATTCACAGAAGACACCGAGACTGTGGGCCAGAGAGCCCTGCACTC

AATCCTGAATGCCGCCATCATGATCAGCGTCATTGTTGTCATGACTATCCTCCTGGTGGTT

CTGTATAAATACAGGTGCTATAAGGTCATCCATGCCTGGCTGATCATATCATCTCTGTTGC

TGCTGTTCTTTTTTAGCTTCATTTACCTGGGCGAAGTGTTTAAAACCTATAACGTTGCCGT

GGACTACATTACTGTTGCCCTCCTGATCTGGAACTTCGGCGTGGTGGGCATGATTTCCATT

CACTGGAAAGGCCCCCTGAGACTGCAGCAGGCATACCTCATTATGATCTCCGCCCTCATGG

CCCTGGTGTTCATCAAGTACCTGCCCGAGTGGACTGCTTGGCTCATCTTGGCTGTGATCTC

CGTGTATGATTTAGTGGCTGTTCTGTGTCCTAAAGGTCCACTGCGTATGCTGGTGGAAACA

GCTCAGGAAAGAAATGAAACACTGTTTCCTGCTCTGATTTACTCCTCAACAATGGTGTGGC

TCGTGAATATGGCCGAAGGAGACCCTGAAGCCCAACGGAGAGTGTCCAAAAACTCCAAGTA

TAACGCCGAGAGCACAGAAAGGGAGAGCCAGGATACAGTTGCCGAGAATGACGATGGCGGC

TTCAGTGAGGAATGGGAAGCCCAGAGGGACAGCCACCTGGGGCCTCACAGAAGCACCCCTG

AGTCTAGAGCCGCTGTCCAGGAACTGTCCAGCTCCATCCTGGCCGGCGAAGACCCCGAAGA

AAGGGGAGTAAAACTTGGACTGGGAGATTTCATCTTCTACAGTGTTCTCGTTGGCAAAGCC

AGCGCAACAGCTAGCGGAGACTGGAACACAACAATAGCCTGTTTCGTAGCCATCTTAATTG

GCCTGTGCCTTACACTTCTGCTCCTGGCCATCTTCAAGAAGGCCCTGCCAGCCCTGCCTAT

CAGCATCACCTTCGGGCTTGTTTTCTACTTTGCCACCGATTATCTGGTGCAGCCCTTCATG

GACCAGCTGGCCTTCCACCAGTTTTACATCTAGTAAGCGGCCGCCCTAGGGAGCTCCTCGA

GGGGGTGGCATCCCTGTGACCCCTCCCCAGTGCCTCTCCTGGCCCTGGAAGTTGCCACTCC

AGTGCCCACCAGCCTTGTCCTAATAAAATTAAGTTGCATCATTTTGTCTGACTAGGTGTCC

TTCTATAATATTATGGGGTGGAGGGGGGTGGTATGGAGCAAGGGGCAAGGGGGGAAGACAA

CCTGTAGGGCCTGCGGGGTCTATTGGGAACCAAGCTGGAGTGCAGTGGCACAATCTTGGCT

CACTGCAATCTCCGCCTCCTGGGTTCAAGCGATTCTCCTGCCTCAGCCTCCCGAGTTGTTG

GGATTCCAGGCATGCATGACCAGGCTCAGCTAATTTTTGTTTTTTTGGTAGAGACGGGGTT

TCACCATATTGGCCAGGCTGGTCTCCCCCTCCTAATCTCAGGTGATCTACCCACCTTGGCC

TCCCAAATTGCTGGGATTACAGGCGTGAACCACTGCTCCCTTCCCTGTCCTTCCTGGGCCT

AGGGCTGTGCCAGCTGCCTCGTCCCGTCACCTTCTGGCTTCTTCTCTCCCTCCATATCTTA

GCTGTTTTCCTCATGAGAATGTTCCAAATTCGAAATTTCTATTTAACCATTATATATTTAC

TTGTTTGCTATTATCTCTGCCCCCAGTAGATTGTTAGCTCCAGAAGAGAAAGGATCATGTC

-continued

TTTTGCTTATCTAGATATGCCCATCTGCCTGGTACAATCTCTGGCACATGTTACAGGCAAC

AACTACTTGTGGAATTGGTGAATGCATGAATAGAAGAATGAGTGAATGAATGAATAGACAA

TAGGCAGAAATCCAGCCTCAAAGAGCTTACAGTCTGGTAAGAGGAATAAAATGTCTGCAAA

TAGCCACAGGACAGGTCAAAGGAAGGAGGGGCTATTTCCAGCTGAGGGCACCCCATCAGGA

AAGCACCCCAGACTTCCTTAGGGATAACAGGGTAATGGCGCGGGCCGCAGGAACCCCTAGT

GATGGAGTTGGCCACTCCCTCTCTGCGCGCTCGCTCGCTCACTGAGGCCGGGCGACCAAAG

GTCGCCCGACGCCCGGGCTTTGCCCGGGCGGCCTCAGTGAGCGAGCGAGCGCGCAGCTGCC

TGCAGGGGCGCCTGATGCGGTATTTTCTCCTTACGCATCTGTGCGGTATTTCACACCGCAT

ACGTCAAAGCAACCATAGTACGCGCCCTGTAGCGGCGCATTAAGCGCGGCGGGTGTGGTGG

TTACGCGCAGCGTGACCGCTACACTTGCCAGCGCCTTAGCGCCCGCTCCTTTCGCTTTCTT

CCCTTCCTTTCTCGCCACGTTCGCCGGCTTTCCCCGTCAAGCTCTAAATCGGGGGCTCCCT

TTAGGGTTCCGATTTAGTGCTTTACGGCACCTCGACCCCAAAAAACTTGATTTGGGTGATG

GTTCACGTAGTGGGCCATCGCCCTGATAGACGGTTTTTCGCCCTTTGACGTTGGAGTCCAC

GTTCTTTAATAGTGGACTCTTGTTCCAAACTGGAACAACACTCAACTCTATCTCGGGCTAT

TCTTTTGATTTATAAGGGATTTTGCCGATTTCGGTCTATTGGTTAAAAAATGAGCTGATTT

AACAAAAATTTAACGCGAATTTTAACAAAATATTAACGTTTACAATTTTATGGTGCACTCT

CAGTACAATCTGCTCTGATGCCGCATAGTTAAGCCAGCCCCGACACCCGCCAACACCCGCT

GACGCGCCCTGACGGGCTTGTCTGCTCCCGGCATCCGCTTACAGACAAGCTGTGACCGTCT

CCGGGAGCTGCATGTGTCAGAGGTTTTCACCGTCATCACCGAAACGCGCGAGACGAAAGGG

CCTCGTGATACGCCTATTTTTATAGGTTAATGTCATGATAATAATGGTTTCTTAGACGTCA

GGTGGCACTTTTCGGGGAAATGTGCGCGGAACCCCTATTTGTTTATTTTTCTAAATACATT

CAAATATGTATCCGCTCATGAGACAATAACCCTGATAAATGCTTCAATAATATTGAAAAAG

GAAGAGTCGATCGATCAAGAGACAGGATGAGGATCGTTTCGCATGATTGAACAAGATGGAT

TGCACGCAGGTTCTCCGGCCGCTTGGGTGGAGAGGCTATTCGGCTATGACTGGGCACAACA

GACAATCGGCTGCTCTGATGCCGCCGTGTTCCGGCTGTCAGCGCAGGGGCGCCCGGTTCTT

TTTGTCAAGACCGACCTGTCCGGTGCCCTGAATGAACTGCAAGACGAGGCAGCGCGGCTAT

CGTGGCTGGCCACGACGGGCGTTCCTTGCGCAGCTGTGCTCGACGTTGTCACTGAAGCGGG

AAGGGACTGGCTGCTATTGGGCGAAGTGCCGGGGCAGGATCTCCTGTCATCTCACCTTGCT

CCTGCCGAGAAAGTATCCATCATGGCTGATGCAATGCGGCGGCTGCATACGCTTGATCCGG

CTACCTGCCCATTCGACCACCAAGCGAAACATCGCATCGAGCGAGCACGTACTCGGATGGA

AGCCGGTCTTGTCGATCAGGATGATCTGGACGAAGAGCATCAGGGGCTCGCGCCAGCCGAA

CTGTTCGCCAGGCTCAAGGCGAGCATGCCCGACGGCGAGGATCTCGTCGTGACCCATGGCG

ATGCCTGCTTGCCGAATATCATGGTGGAAAATGGCCGCTTTTCTGGATTCATCGACTGTGG

CCGGCTGGGTGTGGCGGATCGCTATCAGGACATAGCGTTGGCTACCCGTGATATTGCTGAA

GAGCTTGGCGGCGAATGGGCTGACCGCTTCCTCGTGCTTTACGGTATCGCCGCTCCCGATT

CGCAGCGCATCGCCTTCTATCGCCTTCTTGACGAGTTCTTCTGAACGAGCGTGACACCACG

ATGCCTGTAGCAATGGCAACAACGTTGCGCAAACTATTAACTGGCGAACTAGTTAGTCTAG

CTTCCCGGCAACAATTAATAGACTGGATGGAGGCGGATAAAGTTGCAGGACCACTTCTGCG

CTCGGCCCTTCCGGCTGGCTGGTTTATTGCTGATAAATCTGGAGCCGGTGAGCGTGGGTCT

CGCGGTATCATTGCAGCACTGGGGCCAGATGGTAAGCCCTCCCGTATCGTAGTTATCTACA

-continued

CGACGGGGAGTCAGGCAACTATGGATGAACGAAATAGACAGATCGCTGAGATAGGTGCCTC

ACTGATTAAGCATTGGTAACTGTCAGACCAAGTTTAGTCATATATACTTTAGATTGATTTA

AAACTTCATTTTTAATTTAAAAGGATCTAGGTGAAGATCCTTTTTGATAATCTCATGACCA

AAATCCCTTAACGTGAGTTTTCGTTCCACTGAGCGTCAGACCCCGTAGAAAAGATCAAAGG

ATCTTCTTGAGATCCTTTTTTTCTGCGCGTAATCTGCTGCTTGCAAACAAAAAAACCACCG

CTACCAGCGGTGGTTTGTTTGCCGGATCAAGAGCTACCAACTCTTTTTCCGAAGGTAACTG

GCTTCAGCAGAGCGCAGATACCAAATACTGTTCTTCTAGTGTAGCCGTAGTTAGGCCACCA

CTTCAAGAACTCTGTAGCACCGCCTACATACCTCGCTCTGCTAATCCTGTTACCAGTGGCT

GCTGCCAGTGGCGATAAGTCGTGTCTTACCGGGTTGGACTCAAGACGATAGTTACCGGATA

AGGCGCAGCGGTCGGGCTGAACGGGGGGTTCGTGCACACAGCCCAGCTTGGAGCGAACGAC

CTACACCGAACTGAGATACCTACAGCGTGAGCTATGAGAAAGCGCCACGCTTCCCGAAGGG

AGAAAGGCGGACAGGTATCCGGTAAGCGGCAGGGTCGGAACAGGAGAGCGCACGAGGGAGC

TTCCAGGGGGAAACGCCTGGTATCTTTATAGTCCTGTCGGGTTTCGCCACCTCTGACTTGA

GCGTCGATTTTTGTGATGCTCGTCAGGGGGGCGGAGCCTATGGAAAAACGCCAGCAACGCG

GCCTTTTTACGGTTCCTGGCCTTTTGCTGGCCTTTTGCTCACATGT (pAT054)

SEQ ID NO: 73

CCTGCAGGCAGCTGCGCGCTCGCTCGCTCACTGAGGCCGCCCGGGCAAAGCCCGGGCGTCG

GGCGACCTTTGGTCGCCCGGCCTCAGTGAGCGAGCGAGCGCGCAGAGAGGGAGTGGCCAAC

TCCATCACTAGGGGTTCCTGCGGCCAATTCAGTGGATCCCGATAACTATAACGGTCCTAAG

GTAGCGATTTAAATGAGGGCCTATTTCCCATGATTCCTTCATATTTGCATATACGATACAA

GGCTGTTAGAGAGATAATTAGAATTAATTTGACTGTAAACACAAAGATATTAGTACAAAAT

ACGTGAGGTAGAAAGTAATAATTTCTTGGGTAGTTTGGAGTTTTAAAATTATGTTTTAAAA

TGGACTATCATATGCTTACCGTAACTTGAAAGTATTTCGATTTCTTGGCTTTATATATCTT

GTGGAAAGGACGAGGTACCGTGAGCTGTTGGAATTATGTTTCGAATTTGACTTTAGAGGTT

TACATTTCTAGTCAAAGAAGAAACATCCATTCAGCTGCTCCTGAGCTGTTGGAATTATGTT

TCGAATTTGACTTTAGAGGTTTACATTTCTAGTCAAAGAAGAAACATCCATTCAGCTGCTC

CTGAGCTGTTGGAATTATGTTTCGAATTTGACTTTAGAGGTTTACATTTCTAGTCAAAGAA

GAAACATCCATTCAGCTGCTCCTTTTTTCCGGGACGCGTCAATTGAGATCTCCGACATTGA

TTATTGACTAGTTATTAATAGTAATCAATTACGGGGTCATTAGTTCATAGCCCATATATGG

AGTTCCGCGTTACATAACTTACGGTAAATGGCCCGCCTGGCTGACCGCCCAACGACCCCCG

CCCATTGACGTCAATAATGACGTATGTTCCCATAGTAACGCCAATAGGGACTTTCCATTGA

CGTCAATGGGTGGAGTATTTACGGTAAACTGCCCACTTGGCAGTACATCAAGTGTATCATA

TGCCAAGTACGCCCCCTATTGACGTCAATGACGGTAAATGGCCCGCCTGGCATTATGCCCA

GTAGATGACCTTATGGGACTTTCCTACTTGGCAGTAGATCTACGTATTAGTCATCGCTATT

ACCATGTCGAGGCCACGTTCTGCTTCACTCTCCCCATCTCCCCCCCCTCCCCACCCCCAAT

TTTGTATTTATTTATTTTTTAATTATTTTGTGCAGCGATGGGGGCGGGGGGGGGGGGCGCG

CGCCAGGCGGGGCGGGGCGGGGCGAGGGGCGGGGCGGGGCGAGGCGGAGAGGTGCGGCGGC

AGCCAATCAGAGCGGCGCGCTCCGAAAGTTTCCTTTTATGGCGAGGCGGCGGCGGCGGCGG

CCCTATAAAAAGCGAAGCGCGCGGCGGGCGGGAGCAAGCTTCGTTTAGTGAACCGTCAGAT

CGCCTGGAGACGCCATCCACGCTGTTTTGACCTCCATAGAAGACACCGGGACCGATCCAGC

CTCCGCGGATTCGAATCCCGGCCGGGAACGGTGCATTGGAACGCGGATTCCCCGTGCCAAG

-continued

AGTGACGTAAGTACCGCCTATAGAGTCTATAGGCCCACAAAAAATGCTTTCTTCTTTTAAT

ATACTTTTTTGTTTATCTTATTTCTAATACTTTCCCTAATCTCTTTCTTTCAGGGCAATAA

TGATACAATGTATCATGCCTCTTTGCACCATTCTAAAGAATAACAGTGATAATTTCTGGGT

TAAGGCAATAGCAATATTTCTGCATATAAATATTTCTGCATATAAATTGTAACTGATGTAA

GAGGTTTCATATTGCTAATAGCAGCTACAATCCAGCTACCATTCTGCTTTTATTTTGTGGT

TGGGATAAGGCTGGATTATTCTGAGTCCAAGCTAGGCCCTTTTGCTAATCGTGTTCATACC

TCTTATCTTCCTCCCACAGCTCCTGGGCAACGTGCTGGTCTGTGTGCTGGCCCATCACTTT

GGCAAAGAATTACCGGTGGCAACGTGCTGGTTATTGTGCTGTCTCATCATTTTGGCAAAGA

ATTCACGCCCCAGAGCCGCCACCATGGCCTACCCATACGATGTTCCAGATTACGCTACAGA

ATTACCTGCCCCCTTGAGCTACTTCCAGAATGCACAGATGAGCGAGGACAACCACCTGAGC

AATACTGTACGTAGCCAGAATGACAACAGAGAACGGCAGGAACACAACGACAGGCGGAGCC

TGGGCCACCCTGAGCCCCTGTCTAATGGAAGACCCCAGGGTAACAGCAGACAGGTGGTGGA

ACAAGATGAGGAAGAGGACGAGGAGCTGACCCTGAAGTACGGCGCCAAGCACGTGATCATG

CTCTTCGTGCCCGTGACTCTCTGCATGGTGGTGGTGGTGGCTACAATCAAGAGCGTCAGCT

TTTATACCCGGAAGGATGGGCAGCTAATCTATACCCCATTCACAGAAGACACCGAGACTGT

GGGCCAGAGAGCCCTGCACTCAATCCTGAATGCCGCCATCATGATCAGCGTCATTGTTGTC

ATGACTATCCTCCTGGTGGTTCTGTATAAATACAGGTGCTATAAGGTCATCCATGCCTGGC

TGATCATATCATCTCTGTTGCTGCTGTTCTTTTTTAGCTTCATTTACCTGGGCGAAGTGTT

TAAAACCTATAACGTTGCCGTGGACTACATTACTGTTGCCCTCCTGATCTGGAACTTCGGC

GTGGTGGGCATGATTTCCATTCACTGGAAAGGCCCCCTGAGACTGCAGCAGGCATACCTCA

TTATGATCTCCGCCCTCATGGCCCTGGTGTTCATCAAGTACCTGCCCGAGTGGACTGCTTG

GCTCATCTTGGCTGTGATCTCCGTGTATGATTTAGTGGCTGTTCTGTGTCCTAAAGGTCCA

CTGCGTATGCTGGTGGAAACAGCTCAGGAAAGAAATGAAACACTGTTTCCTGCTCTGATTT

ACTCCTCAACAATGGTGTGGCTCGTGAATATGGCCGAAGGAGACCCTGAAGCCCAACGGAG

AGTGTCCAAAAACTCCAAGTATAACGCCGAGAGCACAGAAAGGGAGAGCCAGGATACAGTT

GCCGAGAATGACGATGGCGGCTTCAGTGAGGAATGGGAAGCCCAGAGGGACAGCCACCTGG

GGCCTCACAGAAGCACCCCTGAGTCTAGAGCCGCTGTCCAGGAACTGTCCAGCTCCATCCT

GGCCGGCGAAGACCCCGAAGAAAGGGGAGTAAAACTTGGACTGGGAGATTTCATCTTCTAC

AGTGTTCTCGTTGGCAAAGCCAGCGCAACAGCTAGCGGAGACTGGAACACAACAATAGCCT

GTTTCGTAGCCATCTTAATTGGCCTGTGCCTTACACTTCTGCTCCTGGCCATCTTCAAGAA

GGCCCTGCCAGCCCTGCCTATCAGCATCACCTTCGGGCTTGTTTTCTACTTTGCCACCGAT

TATCTGGTGCAGCCCTTCATGGACCAGCTGGCCTTCCACCAGTTTTACATCTAGTAAGCGG

CCGCCCTAGGGAGCTCCTCGAGGGGGTGGCATCCCTGTGACCCCTCCCCAGTGCCTCTCCT

GGCCCTGGAAGTTGCCACTCCAGTGCCCACCAGCCTTGTCCTAATAAAATTAAGTTGCATC

ATTTTGTCTGACTAGGTGTCCTTCTATAATATTATGGGGTGGAGGGGGGTGGTATGGAGCA

AGGGGCAAGGGGGGAAGACAACCTGTAGGGCCTGCGGGGTCTATTGGGAACCAAGCTGGAG

TGCAGTGGCACAATCTTGGCTCACTGCAATCTCCGCCTCCTGGGTTCAAGCGATTCTCCTG

CCTCAGCCTCCCGAGTTGTTGGGATTCCAGGCATGCATGACCAGGCTCAGCTAATTTTTGT

TTTTTGGTAGAGACGGGGTTTCACCATATTGGCCAGGCTGGTCTCCCCCTCCTAATCTCA

GGTGATCTACCCACCTTGGCCTCCCAAATTGCTGGGATTACAGGCGTGAACCACTGCTCCC

-continued

TTCCCTGTCCTTCCTGGGCCTAGGGCTGTGCCAGCTGCCTCGTCCCGTCACCTTCTGGCTT

CTTCTCTCCCTCCATATCTTAGCTGTTTTCCTCATGAGAATGTTCCAAATTCGAAATTTCT

ATTTAACCATTATATATTTACTTGTTTGCTATTATCTCTGCCCCCAGTAGATTGTTAGCTC

CAGAAGAGAAAGGATCATGTCTTTTGCTTATCTAGATATGCCCATCTGCCTGGTACAATCT

CTGGCACATGTTACAGGCAACAACTACTTGTGGAATTGGTGAATGCATGAATAGAAGAATG

AGTGAATGAATGAATAGACAATAGGCAGAAATCCAGCCTCAAAGAGCTTACAGTCTGGTAA

GAGGAATAAAATGTCTGCAAATAGCCACAGGACAGGTCAAAGGAAGGAGGGGCTATTTCCA

GCTGAGGGCACCCCATCAGGAAAGCACCCCAGACTTCCTTAGGGATAACAGGGTAATGGCG

CGGGCCGCAGGAACCCCTAGTGATGGAGTTGGCCACTCCCTCTCTGCGCGCTCGCTCGCTC

ACTGAGGCCGGGCGACCAAAGGTCGCCCGACGCCCGGGCTTTGCCCGGGCGGCCTCAGTGA

GCGAGCGAGCGCGCAGCTGCCTGCAGGGGCGCCTGATGCGGTATTTTCTCCTTACGCATCT

GTGCGGTATTTCACACCGCATACGTCAAAGCAACCATAGTACGCGCCCTGTAGCGGCGCAT

TAAGCGCGGCGGGTGTGGTGGTTACGCGCAGCGTGACCGCTACACTTGCCAGCGCCTTAGC

GCCCGCTCCTTTCGCTTTCTTCCCTTCCTTTCTCGCCACGTTCGCCGGCTTTCCCCGTCAA

GCTCTAAATCGGGGGCTCCCTTTAGGGTTCCGATTTAGTGCTTTACGGCACCTCGACCCCA

AAAAACTTGATTTGGGTGATGGTTCACGTAGTGGGCCATCGCCCTGATAGACGGTTTTTCG

CCCTTTGACGTTGGAGTCCACGTTCTTTAATAGTGGACTCTTGTTCCAAACTGGAACAACA

CTCAACTCTATCTCGGGCTATTCTTTTGATTTATAAGGGATTTTGCCGATTTCGGTCTATT

GGTTAAAAAATGAGCTGATTTAACAAAAATTTAACGCGAATTTTAACAAAATATTAACGTT

TACAATTTTATGGTGCACTCTCAGTACAATCTGCTCTGATGCCGCATAGTTAAGCCAGCCC

CGACACCCGCCAACACCCGCTGACGCGCCCTGACGGGCTTGTCTGCTCCCGGCATCCGCTT

ACAGACAAGCTGTGACCGTCTCCGGGAGCTGCATGTGTCAGAGGTTTTCACCGTCATCACC

GAAACGCGCGAGACGAAAGGGCCTCGTGATACGCCTATTTTTATAGGTTAATGTCATGATA

ATAATGGTTTCTTAGACGTCAGGTGGCACTTTTCGGGGAAATGTGCGCGGAACCCCTATTT

GTTTATTTTTCTAAATACATTCAAATATGTATCCGCTCATGAGACAATAACCCTGATAAAT

GCTTCAATAATATTGAAAAAGGAAGAGTCGATCGATCAAGAGACAGGATGAGGATCGTTTC

GCATGATTGAACAAGATGGATTGCACGCAGGTTCTCCGGCCGCTTGGGTGGAGAGGCTATT

CGGCTATGACTGGGCACAACAGACAATCGGCTGCTCTGATGCCGCCGTGTTCCGGCTGTCA

GCGCAGGGGCGCCCGGTTCTTTTTGTCAAGACCGACCTGTCCGGTGCCCTGAATGAACTGC

AAGACGAGGCAGCGCGGCTATCGTGGCTGGCCACGACGGGCGTTCCTTGCGCAGCTGTGCT

CGACGTTGTCACTGAAGCGGGAAGGGACTGGCTGCTATTGGGCGAAGTGCCGGGGCAGGAT

CTCCTGTCATCTCACCTTGCTCCTGCCGAGAAAGTATCCATCATGGCTGATGCAATGCGGC

GGCTGCATACGCTTGATCCGGCTACCTGCCCATTCGACCACCAAGCGAAACATCGCATCGA

GCGAGCACGTACTCGGATGGAAGCCGGTCTTGTCGATCAGGATGATCTGGACGAAGAGCAT

CAGGGGCTCGCGCCAGCCGAACTGTTCGCCAGGCTCAAGGCGAGCATGCCCGACGGCGAGG

ATCTCGTCGTGACCCATGGCGATGCCTGCTTGCCGAATATCATGGTGGAAAATGGCCGCTT

TTCTGGATTCATCGACTGTGGCCGGCTGGGTGTGGCGGATCGCTATCAGGACATAGCGTTG

GCTACCCGTGATATTGCTGAAGAGCTTGGCGGCGAATGGGCTGACCGCTTCCTCGTGCTTT

ACGGTATCGCCGCTCCCGATTCGCAGCGCATCGCCTTCTATCGCCTTCTTGACGAGTTCTT

CTGAACGAGCGTGAGACCACGATGCCTGTAGCAATGGCAACAACGTTGCGCAAACTATTAA

CTGGCGAACTACTTACTCTAGCTTCCCGGCAACAATTAATAGACTGGATGGAGGCGGATAA

-continued

AGTTGCAGGACCACTTCTGCGCTCGGCCCTTCCGGCTGGCTGGTTTATTGCTGATAAATCT

GGAGCCGGTGAGCGTGGGTCTCGCGGTATCATTGCAGCACTGGGGCCAGATGGTAAGCCCT

CCCGTATCGTAGTTATCTACACGACGGGGAGTCAGGCAACTATGGATGAACGAAATAGACA

GATCGCTGAGATAGGTGCCTCACTGATTAAGCATTGGTAACTGTCAGACCAAGTTTACTCA

TATATACTTTAGATTGATTTAAAACTTCATTTTTAATTTAAAAGGATCTAGGTGAAGATCC

TTTTTGATAATCTCATGACCAAAATCCCTTAACGTGAGTTTTCGTTCCACTGAGCGTCAGA

CCCCGTAGAAAAGATCAAAGGATCTTCTTGAGATCCTTTTTTTCTGCGCGTAATCTGCTGC

TTGCAAACAAAAAAACCACCGCTACCAGCGGTGGTTTGTTTGCCGGATCAAGAGCTACCAA

CTCTTTTTCCGAAGGTAACTGGCTTCAGCAGAGCGCAGATACCAAATACTGTTCTTCTAGT

GTAGCCGTAGTTAGGCCACCACTTCAAGAACTCTGTAGCACCGCCTACATACCTCGCTCTG

CTAATCCTGTTACCAGTGGCTGCTGCCAGTGGCGATAAGTCGTGTCTTACCGGGTTGGACT

CAAGACGATAGTTACCGGATAAGGCGCAGCGGTCGGGCTGAACGGGGGGTTCGTGCACACA

GCCCAGCTTGGAGCGAACGACCTACACCGAACTGAGATACCTACAGCGTGAGCTATGAGAA

AGCGCCACGCTTCCCGAAGGGAGAAAGGCGGACAGGTATCCGGTAAGCGGCAGGGTCGGAA

CAGGAGAGCGCACGAGGGAGCTTCCAGGGGGAAACGCCTGGTATCTTTATAGTCCTGTCGG

GTTTCGCCACCTCTGACTTGAGCGTCGATTTTTGTGATGCTCGTCAGGGGGGCGGAGCCTA

TGGAAAAACGCCAGCAACGCGGCCTTTTTACGGTTCCTGGCCTTTTGCTGGCCTTTTGCTC

ACATGT (pAT055)

SEQ ID NO: 74

CCTGCAGGCAGCTGCGCGCTCGCTCGCTCACTGAGGCCGCCCGGGCAAAGCCCGGGCGTCG

GGCGACCTTTGGTCGCCCGGCCTCAGTGAGCGAGCGAGCGCGCAGAGAGGGAGTGGCCAAC

TCCATCACTAGGGGTTCCTGCGGCCAATTCAGTGGATCCCGATAACTATAACGGTCCTAAG

GTAGCGATTTAAATGAGGGCCTATTTCCCATGATTCCTTCATATTTGCATATACGATACAA

GGCTGTTAGAGAGATAATTAGAATTAATTTGACTGTAAACACAAAGATATTAGTACAAAAT

ACGTGACGTAGAAAGTAATAATTTCTTGGGTAGTTTGCAGTTTTAAAATTATGTTTTAAAA

TGGACTATCATATGCTTACCGTAACTTGAAAGTATTTCGATTTCTTGGCTTTATATATCTT

GTGGAAAGGACGAGGTACCGTGAGCTGTTGGAGACTAGAAAAGCCTTTTGACTACGAGGTT

TACATTTCGTTCAAAATCGTTTTCTATAGTTCAGCTGCTTCTGAGCTGTTGGAGACTAGAA

AAGCCTTTTGACTACGAGGTTTACATTTCGTTCAAAATCGTTTTCTATAGTTCAGCTGCTT

CTGAGCTGTTGGAGACTAGAAAAGCCTTTTGACTACGAGGTTTACATTTCGTTCAAAATCG

TTTTCTATAGTTCAGCTGCTTCTTTTTTCCGGGACGCGTCAATTGAGATCTCCGACATTGA

TTATTGACTAGTTATTAATAGTAATCAATTACGGGGTCATTAGTTCATAGCCCATATATGG

AGTTCCGCGTTACATAACTTACGGTAAATGGCCCGCCTGGCTGACCGCCCAACGACCCCCG

CCCATTGACGTCAATAATGACGTATGTTCCCATAGTAACGCCAATAGGGACTTTCCATTGA

CGTCAATGGGTGGAGTATTTACGGTAAACTGCCCACTTGGCAGTACATCAAGTGTATCATA

TGCCAAGTACGCCCCCTATTGACGTCAATGACGGTAAATGGCCCGCCTGGCATTATGCCCA

GTAGATGACCTTATGGGACTTTCCTACTTGGGAGTAGATCTAGGTATTAGTCATCGCTATT

ACCATGTCGAGGCCACGTTCTGCTTCACTCTCCCCATCTCCCCCCCCTCCCCACCCCCAAT

TTTGTATTTATTTATTTTTTAATTATTTTGTGCAGCGATGGGGGCGGGGGGGGGGGGGCGCG

CGCCAGGCGGGGCGGGGCGGGGCGAGGGGCGGGGCGGGGCGAGGCGGAGAGGTGCGGCGGC

-continued

AGCCAATCAGAGCGGCGCGCTCCGAAAGTTTCCTTTTATGGCGAGGCGGCGGCGGCGG

CCCTATAAAAAGCGAAGCGCGCGGCGGGCGGGAGCAAGCTTCGTTTAGTGAACCGTCAGAT

CGCCTGGAGACGCCATCCACGCTGTTTTGACCTCCATAGAAGACACCGGGACCGATCCAGC

CTCCGCGGATTCGAATCCCGGCCGGGAACGGTGCATTGGAACGCGGATTCCCCGTGCCAAG

AGTGACGTAAGTAGCGCCTATAGAGTCTATAGGCCCACAAAAAATGCTTTCTTCTTTTAAT

ATACTTTTTTGTTTATCTTATTTCTAATACTTTCCCTAATCTCTTTCTTTCAGGGCAATAA

TGATACAATGTATCATGCCTCTTTGCACCATTCTAAAGAATAACAGTGATAATTTCTGGGT

TAAGGCAATAGCAATATTTCTGCATATAAATATTTCTGCATATAAATTGTAACTGATGTAA

GAGGTTTCATATTGCTAATAGCAGCTACAATCCAGCTACCATTCTGCTTTTATTTTGTGGT

TGGGATAAGGCTGGATTATTCTGAGTCCAAGCTAGGCCCTTTTGCTAATCGTGTTCATACC

TCTTATCTTCCTCCCACAGCTCCTGGGCAACGTGCTGGTCTGTGTGCTGGCCCATCACTTT

GGCAAAGAATTACCGGTGGCAACGTGCTGGTTATTGTGCTGTCTCATCATTTTGGCAAAGA

ATTCACGCCCCAGAGCCGCCACCATGGCCTACCCATACGATGTTCCAGATTACGCTACAGA

ATTACCTGCCCCCTTGAGCTACTTCCAGAATGCACAGATGAGCGAGGACAACCACCTGAGC

AATACTGTACGTAGCCAGAATGACAACAGAGAACGGCAGGAACACAACGACAGGCGGAGCC

TGGGCCACCCTGAGCCCCTGTCTAATGGAAGACCCCAGGGTAACAGCAGACAGGTGGTGGA

ACAAGATGAGGAAGAGGACGAGGAGCTGACCCTGAAGTACGGCGCCAAGCACGTGATCATG

CTCTTCGTGCCCGTGACTCTCTGCATGGTGGTGGTGGTGGCTACAATCAAGAGCGTCAGCT

TTTATACCCGGAAGGATGGGCAGCTAATCTATACCCCATTCACAGAAGACACCGAGACTGT

GGGCCAGAGAGCCCTGCACTCAATCCTGAATGCCGCCATCATGATCAGCGTCATTGTTGTC

ATGACTATCCTCCTGGTGGTTCTGTATAAATACAGGTGCTATAAGGTCATCCATGCCTGGC

TGATCATATCATCTCTGTTGCTGCTGTTCTTTTTTAGCTTCATTTACCTGGGCGAAGTGTT

TAAAACCTATAACGTTGCCGTGGACTACATTACTGTTGCCCTCCTGATCTGGAACTTCGGC

GTGGTGGGCATGATTTCCATTCACTGGAAAGGCCCCCTGAGACTGCAGCAGGCATACCTCA

TTATGATCTCCGCCCTCATGGCCCTGGTGTTCATCAAGTACCTGCCCGAGTGGACTGCTTG

GCTCATCTTGGCTGTGATCTCCGTGTATGATTTAGTGGCTGTTCTGTGTCCTAAAGGTCCA

CTGCGTATGCTGGTGGAAACAGCTCAGGAAAGAAATGAAACACTGTTTCCTGCTCTGATTT

ACTCCTCAACAATGGTGTGGCTCGTGAATATGGCCGAAGGAGACCCTGAAGCCCAACGGAG

AGTGTCCAAAAACTCCAAGTATAACGCCGAGAGCACAGAAAGGGAGAGCCAGGATACAGTT

GCCGAGAATGACGATGGCGGCTTCAGTGAGGAATGGGAAGCCCAGAGGGACAGCCACCTGG

GGCCTCACAGAAGCACCCCTGAGTCTAGAGCCGCTGTCCAGGAACTGTCCAGCTCCATCCT

GGCCGGCGAAGACCCCGAAGAAAGGGGAGTAAAACTTGGACTGGGAGATTTCATCTTCTAC

AGTGTTCTCGTTGGCAAAGCCAGCGCAACAGCTAGCGGAGACTGGAACACAACAATAGCCT

GTTTCGTAGCCATCTTAATTGGCCTGTGCCTTACACTTCTGCTCCTGGCCATCTTCAAGAA

GGCCCTGCCAGCCCTGCCTATCAGCATCACCTTCGGGCTTGTTTTCTACTTTGCCACCGAT

TATCTGGTGCAGCCCTTCATGGACCAGCTGGCCTTCCACCAGTTTTACATCTAGTAAGCGG

CCGCCCTAGGGAGCTCCTCGAGGGGGTGGCATCCCTGTGACCCCTCCCCAGTGCCTCTCCT

GGCCCTGGAAGTTGCCACTCCAGTGCCCACCAGCCTTGTCCTAATAAAATTAAGTTGCATC

ATTTTGTCTGACTAGGTGTCCTTCTATAATATTATGGGGTGGAGGGGGGTGGTATGGAGCA

AGGGGCAAGGGGGGAAGACAACCTGTAGGGCCTGCGGGGTCTATTGGGAACCAAGCTGGAG

TGCAGTGGCACAATCTTGGCTCACTGCAATCTCCGCCTCCTGGGTTCAAGCGATTCTCCTG

-continued

CCTCAGCCTCCCGAGTTGTTGGGATTCCAGGCATGCATGACCAGGCTCAGCTAATTTTTGT

TTTTTTGGTAGAGACGGGGTTTCACCATATTGGCCAGGCTGGTCTCCCCCTCCTAATCTCA

GGTGATCTACCCACCTTGGCCTCCCAAATTGCTGGGATTACAGGCGTGAACCACTGCTCCC

TTCCCTGTCCTTCCTGGGCCTAGGGCTGTGCCAGCTGCCTCGTCCCGTCACCTTCTGGCTT

CTTCTCTCCCTCCATATCTTAGCTGTTTTCCTCATGAGAATGTTCCAAATTCGAAATTTCT

ATTTAACCATTATATATTTACTTGTTTGCTATTATCTCTGCCCCCAGTAGATTGTTAGCTC

CAGAAGAGAAAGGATCATGTCTTTTGCTTATCTAGATATGCCCATCTGCCTGGTACAATCT

CTGGCACATGTTACAGGCAACAACTAGTTGTGGAATTGGTGAATGCATGAATAGAAGAATG

AGTGAATGAATGAATAGACAATAGGCAGAAATCCAGCCTCAAAGAGCTTACAGTCTGGTAA

GAGGAATAAAATGTCTGCAAATAGCCACAGGACAGGTCAAAGGAAGGAGGGGCTATTTCCA

GCTGAGGGCACCCCATCAGGAAAGCACCCCAGACTTCCTTAGGGATAACAGGGTAATGGCG

CGGGCCGCAGGAACCCCTAGTGATGGAGTTGGCCACTCCCTCTCTGCGCGCTCGCTCGCTC

ACTGAGGCCGGGCGACCAAAGGTCGCCCGACGCCCGGGCTTTGCCCGGGCGGCCTCAGTGA

GCGAGCGAGCGCGCAGCTGCCTGCAGGGGCGCCTGATGCGGTATTTTCTCCTTACGCATCT

GTGCGGTATTTCACACCGCATACGTCAAAGCAACCATAGTACGCGCCCTGTAGCGGCGCAT

TAAGCGCGGCGGGTGTGGTGGTTACGCGCAGCGTGACCGCTACACTTGCCAGCGCCTTAGC

GCCCGCTCCTTTCGCTTTCTTCCCTTCCTTTCTCGCCACGTTCGCCGGCTTTCCCCGTCAA

GCTCTAAATCGGGGGCTCCCTTTAGGGTTCCGATTTAGTGCTTTACGGCACCTCGACCCCA

AAAAACTTGATTTGGGTGATGGTTCACGTAGTGGGCCATCGCCCTGATAGACGGTTTTTCG

CCCTTTGACGTTGGAGTCCACGTTCTTTAATAGTGGACTCTTGTTCCAAACTGGAACAACA

CTCAACTCTATCTCGGGCTATTCTTTTGATTTATAAGGGATTTTGCCGATTTCGGTCTATT

GGTTAAAAAATGAGCTGATTTAACAAAAATTTAACGCGAATTTTAACAAAATATTAACGTT

TACAATTTTATGGTGCACTCTCAGTACAATCTGCTCTGATGCCGCATAGTTAAGCCAGCCC

CGACACCCGCCAACACCCGCTGACGCGCCCTGACGGGCTTGTCTGCTCCCGGCATCCGCTT

ACAGACAAGCTGTGACCGTCTCCGGGAGCTGCATGTGTCAGAGGTTTTCACCGTCATCACC

GAAACGCGCGAGACGAAAGGGCCTCGTGATACGCCTATTTTTATAGGTTAATGTCATGATA

ATAATGGTTTCTTAGACGTCAGGTGGCACTTTTCGGGGAAATGTGCGCGGAACCCCTATTT

GTTTATTTTTCTAAATACATTCAAATATGTATCCGCTCATGAGACAATAACCCTGATAAAT

GCTTCAATAATATTGAAAAAGGAAGAGTCGATCGATCAAGAGACAGGATGAGGATCGTTTC

GCATGATTGAACAAGATGGATTGCACGCAGGTTCTCCGGCCGCTTGGGTGGAGAGGCTATT

CGGCTATGACTGGGCACAACAGACAATCGGCTGCTCTGATGCCGCCGTGTTCCGGCTGTCA

GCGCAGGGGCGCCCGGTTCTTTTTGTCAAGACCGACCTGTCCGGTGCCCTGAATGAACTGC

AAGACGAGGCAGCGCGGCTATCGTGGCTGGCCACGACGGGCGTTCCTTGCGCAGCTGTGCT

CGACGTTGTCACTGAAGCGGGAAGGGACTGGCTGCTATTGGGCGAAGTGCCGGGGCAGGAT

CTCCTGTCATCTCACCTTGCTCCTGCCGAGAAAGTATCCATCATGGCTGATGCAATGCGGC

GGCTGCATACGCTTGATCCGGCTACCTGCCCATTCGACCACCAAGCGAAACATCGCATCGA

GCGAGCACGTACTCGGATGGAAGCCGGTCTTGTCGATCAGGATGATCTGGACGAAGAGCAT

CAGGGGCTCGCGCCAGCCGAACTGTTCGCCAGGCTCAAGGCGAGCATGCCCGACGGCGAGG

ATCTCGTCGTGACCCATGGCGATGCCTGCTTGCCGAATATCATGGTGGAAAATGGCCGCTT

TTCTGGATTCATCGACTGTGGCCGGCTGGGTGTGGCGGATCGCTATCAGGACATAGCGTTG

-continued

GCTACCCGTGATATTGCTGAAGAGCTTGGCGGCGAATGGGCTGACCGCTTCCTCGTGCTTT

ACGGTATCGCCGCTCCCGATTCGCAGCGCATCGCCTTCTATCGCCTTCTTGACGAGTTCTT

CTGAACGAGCGTGACACCACGATGCCTGTAGCAATGGCAACAACGTTGCGCAAACTATTAA

CTGGCGAACTACTTACTCTAGCTTCCCGGCAACAATTAATAGACTGGATGGAGGCGGATAA

AGTTGCAGGACCACTTCTGCGCTCGGCCCTTCCGGCTGGCTGGTTTATTGCTGATAAATCT

GGAGCCGGTGAGCGTGGGTCTCGCGGTATCATTGCAGCACTGGGGCCAGATGGTAAGCCCT

CCCGTATCGTAGTTATCTACACGACGGGGAGTCAGGCAACTATGGATGAACGAAATAGACA

GATCGCTGAGATAGGTGCCTCACTGATTAAGCATTGGTAACTGTCAGACCAAGTTTACTCA

TATATACTTTAGATTGATTTAAAACTTCATTTTTAATTTAAAAGGATCTAGGTGAAGATCC

TTTTTGATAATCTCATGACCAAAATCCCTTAACGTGAGTTTTCGTTCCACTGAGCGTCAGA

CCCCGTAGAAAAGATCAAAGGATCTTCTTGAGATCCTTTTTTTCTGCGCGTAATCTGCTGC

TTGCAAACAAAAAAACCACCGCTACCAGCGGTGGTTTGTTTGCCGGATCAAGAGCTACCAA

CTCTTTTTCCGAAGGTAACTGGCTTCAGCAGAGCGCAGATACCAAATACTGTTCTTCTAGT

GTAGCCGTAGTTAGGCCACCACTTCAAGAACTCTGTAGCACCGCCTACATACCTCGCTCTG

CTAATCCTGTTACCAGTGGCTGCTGCCAGTGGCGATAAGTCGTGTCTTACCGGGTTGGACT

CAAGACGATAGTTACCGGATAAGGCGCAGCGGTCGGGCTGAACGGGGGGTTCGTGCACACA

GCCCAGCTTGGAGCGAACGACCTACACCGAACTGAGATACCTACAGCGTGAGCTATGAGAA

AGCGCCACGCTTCCCGAAGGGAGAAAGGCGGACAGGTATCCGGTAAGCGGCAGGGTCGGAA

CAGGAGAGCGCACGAGGGAGCTTCCAGGGGGAAACGCCTGGTATCTTTATAGTCCTGTCGG

GTTTCGCCACCTCTGACTTGAGCGTCGATTTTTGTGATGCTCGTCAGGGGGGCGGAGCCTA

TGGAAAAACGCCAGCAACGCGGCCTTTTTACGGTTCCTGGCCTTTTGCTGGCCTTTTGCTC

ACATGT (pAT056)

SEQ ID NO: 75

CCTGCAGGCAGCTGCGCGCTCGCTCGCTCACTGAGGCCGCCCGGGCAAAGCCCGGGCGTCG

GGCGACCTTTGGTCGCCCGGCCTCAGTGAGCGAGCGAGCGCGCAGAGAGGGAGTGGCCAAC

TCCATCACTAGGGGTTCCTGCGGCCAATTCAGTGGATCCCGATAACTATAACGGTCCTAAG

GTAGCGATTTAAATCCGGGACGCGTCAATTGAGATCTCCGACATTGATTATTGACTAGTTA

TTAATAGTAATCAATTACGGGGTCATTAGTTCATAGCCCATATATGGAGTTCCGCGTTACA

TAACTTACGGTAAATGGCCCGCCTGGCTGACCGCCCAACGACCCCCGCCCATTGACGTCAA

TAATGACGTATGTTCCCATAGTAACGCCAATAGGGACTTTCCATTGACGTCAATGGGTGGA

GTATTTACGGTAAACTGCCCACTTGGCAGTACATCAAGTGTATCATATGCCAAGTACGCCC

CCTATTGACGTCAATGACGGTAAATGGCCCGCCTGGCATTATGCCCAGTACATGACCTTAT

GGGACTTTCCTACTTGGCAGTACATCTACGTATTAGTCATCGCTATTACCATGTCGAGGCC

ACGTTCTGCTTCACTCTCCCCATCTCCCCCCCCTCCCCACCCCCAATTTTGTATTTATTTA

TTTTTTAATTATTTTGTGCAGCGATGGGGGCGGGGGGGGGGGGGCGCGCGCCAGGCGGGGCG

GGGCGGGGCGAGGGGCGGGGCGGGGCGAGGCGGAGAGGTGCGGCGGCAGCCAATCAGAGCG

GCGCGCTCCGAAAGTTTCCTTTTATGGCGAGGCGGCGGCGGCGGCGGCCCTATAAAAAGCG

AAGCGCGCGGCGGGCGGGAGCAAGCTTCGTTTAGTGAACCGTCAGATCGCCTGGAGACGCC

ATCCACGCTGTTTTGACCTCCATAGAAGACACCGGGACCGATCCAGCCTCCGCGGATTCGA

ATCCCGGCCGGGAACGGTGCATTGGAACGCGGATTCCCCGTGCCAAGAGTGACGTAAGTAC

CGCCTATAGAGTCTATAGGCCCACAAAAAATGCTTTCTTCTTTTAATATACTTTTTTGTTT

-continued

ATCTTATTTCTAATACTTTCCCTAATCTCTTTCTTTCAGGGCAATAATGATACAATGTATC

ATGCCTCTTTGCACCATTCTAAAGAATAACAGTGATAATTTCTGGGTTAAGGCAATAGCAA

TATTTCTGCATATAAATATTTCTGCATATAAATTGTAACTGATGTAAGAGGTTTCATATTG

CTAATAGCAGCTACAATCCAGCTACCATTCTGCTTTTATTTTGTGGTTGGGATAAGGCTGG

ATTATTCTGAGATATCGGTACCTGAGCTGTTGGAGACTAGAAAAGCCTTTTGACTACGAGG

TTTACATTTCGTTCAAAATCGTTTTCTATAGTTCAGCTGCTTCTGAGCTGTTGGAGACTAG

AAAAGCCTTTTGACTACGAGGTTTACATTTCGTTCAAAATCGTTTTCTATAGTTCAGCTGC

TTCTGAGCTGTTGGAGACTAGAAAAGCCTTTTGACTACGAGGTTTACATTTCGTTCAAAAT

CGTTTTCTATAGTTCAGCTGCTTCGTCGACGCTAGGCCCTTTTGCTAATCGTGTTCATACC

TCTTATCTTCCTCCCACAGCTCCTGGGCAACGTGCTGGTCTGTGTGCTGGCCCATCACTTT

GGCAAAGAATTACCGGTGGCAACGTGCTGGTTATTGTGCTGTCTCATCATTTTGGCAAAGA

ATTCACGCCCCAGAGCCGCCACCATGGCCTACCCATACGATGTTCCAGATTACGCTACAGA

ATTACCTGCCCCCTTGAGCTACTTCCAGAATGCACAGATGAGCGAGGACAACCACCTGAGC

AATACTGTACGTAGCCAGAATGACAACAGAGAACGGCAGGAACACAACGACAGGCGGAGCC

TGGGCCACCCTGAGCCCCTGTCTAATGGAAGACCCCAGGGTAACAGCAGACAGGTGGTGGA

ACAAGATGAGGAAGAGGACGAGGAGCTGACCCTGAAGTACGGCGCCAAGCACGTGATCATG

CTCTTCGTGCCCGTGACTCTCTGCATGGTGGTGGTGGTGGCTACAATCAAGAGCGTCAGCT

TTTATACCCGGAAGGATGGGCAGCTAATCTATACCCCATTCACAGAAGACACCGAGACTGT

GGGCCAGAGAGCCCTGCACTCAATCCTGAATGCCGCCATCATGATCAGCGTCATTGTTGTC

ATGACTATCCTCCTGGTGGTTCTGTATAAATACAGGTGCTATAAGGTCATCCATGCCTGGC

TGATCATATCATCTCTGTTGCTGCTGTTCTTTTTTAGCTTCATTTACCTGGGCGAAGTGTT

TAAAACCTATAACGTTGCCGTGGACTACATTACTGTTGCCCTCCTGATCTGGAACTTCGGC

GTGGTGGGCATGATTTCCATTCACTGGAAAGGCCCCCTGAGACTGCAGCAGGCATACCTCA

TTATGATCTCCGCCCTCATGGCCCTGGTGTTCATCAAGTACCTGCCCGAGTGGACTGCTTG

GCTCATCTTGGCTGTGATCTCCGTGTATGATTTAGTGGCTGTTCTGTGTCCTAAAGGTCCA

CTGCGTATGCTGGTGGAAACAGCTCAGGAAAGAAATGAAACACTGTTTCCTGCTCTGATTT

ACTCCTCAACAATGGTGTGGCTCGTGAATATGGCCGAAGGAGACCCTGAAGCCCAACGGAG

AGTGTCCAAAAACTCCAAGTATAACGCCGAGAGCACAGAAAGGGAGAGCCAGGATACAGTT

GCCGAGAATGACGATGGCGGCTTCAGTGAGGAATGGGAAGCCCAGAGGGACAGCCACCTGG

GGCCTCACAGAAGCACCCCTGAGTCTAGAGCCGCTGTCCAGGAACTGTCCAGCTCCATCCT

GGCCGGCGAAGACCCCGAAGAAAGGGGAGTAAAACTTGGACTGGGAGATTTCATCTTCTAC

AGTGTTCTCGTTGGCAAAGCCAGCGCAACAGCTAGCGGAGACTGGAACACAACAATAGCCT

GTTTCGTAGCCATCTTAATTGGCCTGTGCCTTACACTTCTGCTCCTGGCCATCTTCAAGAA

GGCCCTGCCAGCCCTGCCTATCAGCATCACCTTCGGGCTTGTTTTCTACTTTGCCACCGAT

TATCTGGTGCAGCCCTTCATGGACCAGCTGGCCTTCCACCAGTTTTACATCTAGTAAGCGG

CCGCCCTAGGGAGCTCCTCGAGGGGGTGGCATCCCTGTGACCCCTCCCCAGTGCCTCTCCT

GGCCCTGGAAGTTGCCACTCCAGTGCCCACCAGCCTTGTCCTAATAAAATTAAGTTGCATC

ATTTTGTCTGACTAGGTGTCCTTCTATAATATTATGGGGTGGAGGGGGGTGGTATGGAGCA

AGGGGCAAGGGGGGAAGACAACCTGTAGGGCCTGCGGGGTCTATTGGGAACCAAGCTGGAG

TGCAGTGGCACAATCTTGGCTCACTGCAATCTCCGCCTCCTGGGTTCAAGCGATTCTCCTG

-continued

CCTCAGCCTCCCGAGTTGTTGGGATTCCAGGCATGCATGACCAGGCTCAGCTAATTTTTGT

TTTTTTGGTAGAGACGGGGTTTCACCATATTGGCCAGGCTGGTCTCCCCCTCCTAATCTCA

GGTGATCTACCCACCTTGGCCTCCCAAATTGCTGGGATTACAGGCGTGAACCACTGCTCCC

TTCCCTGTCCTTCCTGGGCCTAGGGCTGTGCCAGCTGCCTCGTCCCGTCACCTTCTGGCTT

CTTCTCTCCCTCCATATCTTAGCTGTTTTCCTCATGAGAATGTTCCAAATTCGAAATTTCT

ATTTAACCATTATATATTTACTTGTTTGCTATTATCTCTGCCCCCAGTAGATTGTTAGCTC

CAGAAGAGAAAGGATCATGTCTTTTGCTTATCTAGATATGCCCATCTGCCTGGTACAATCT

CTGGCACATGTTACAGGCAACAACTAGTTGTGGAATTGGTGAATGCATGAATAGAAGAATG

AGTGAATGAATGAATAGACAATAGGCAGAAATCCAGCCTCAAAGAGCTTACAGTCTGGTAA

GAGGAATAAAATGTCTGCAAATAGCCACAGGACAGGTCAAAGGAAGGAGGGGCTATTTCCA

GCTGAGGGCACCCCATCAGGAAAGCACCCCAGACTTCCTTAGGGATAACAGGGTAATGGCG

CGGGCCGCAGGAACCCCTAGTGATGGAGTTGGCCACTCCCTCTCTGCGCGCTCGCTCGCTC

ACTGAGGCCGGGCGACCAAAGGTCGCCCGACGCCCGGGCTTTGCCCGGGCGGCCTCAGTGA

GCGAGCGAGCGCGCAGCTGCCTGCAGGGGCGCCTGATGCGGTATTTTCTCCTTACGCATCT

GTGCGGTATTTCACACCGCATACGTCAAAGCAACCATAGTACGCGCCCTGTAGCGGCGCAT

TAAGCGCGGCGGGTGTGGTGGTTACGCGCAGCGTGACCGCTACACTTGCCAGCGCCTTAGC

GCCCGCTCCTTTCGCTTTCTTCCCTTCCTTTCTCGCCACGTTCGCCGGCTTTCCCCGTCAA

GCTCTAAATCGGGGGCTCCCTTTAGGGTTCCGATTTAGTGCTTTACGGCACCTCGACCCCA

AAAAACTTGATTTGGGTGATGGTTCACGTAGTGGGCCATCGCCCTGATAGACGGTTTTTCG

CCCTTTGACGTTGGAGTCCACGTTCTTTAATAGTGGACTCTTGTTCCAAACTGGAACAACA

CTCAACTCTATCTCGGGCTATTCTTTTGATTTATAAGGGATTTTGCCGATTTCGGTCTATT

GGTTAAAAAATGAGCTGATTTAACAAAAATTTAACGCGAATTTTAACAAAATATTAACGTT

TACAATTTTATGGTGCACTCTCAGTACAATCTGCTCTGATGCCGCATAGTTAAGCCAGCCC

CGACACCCGCCAACACCCGCTGACGCGCCCTGACGGGCTTGTCTGCTCCCGGCATCCGCTT

ACAGACAAGCTGTGACCGTCTCCGGGAGCTGCATGTGTCAGAGGTTTTCACCGTCATCACC

GAAACGCGCGAGACGAAAGGGCCTCGTGATACGCCTATTTTTATAGGTTAATGTCATGATA

ATAATGGTTTCTTAGACGTCAGGTGGCACTTTTCGGGGAAATGTGCGCGGAACCCCTATTT

GTTTATTTTTCTAAATACATTCAAATATGTATCCGCTCATGAGACAATAACCCTGATAAAT

GCTTCAATAATATTGAAAAAGGAAGAGTCGATCGATCAAGAGACAGGATGAGGATCGTTTC

GCATGATTGAACAAGATGGATTGCACGCAGGTTCTCCGGCCGCTTGGGTGGAGAGGCTATT

CGGCTATGACTGGGCACAACAGACAATCGGCTGCTCTGATGCCGCCGTGTTCCGGCTGTCA

GCGCAGGGGCGCCCGGTTCTTTTTGTCAAGACCGACCTGTCCGGTGCCCTGAATGAACTGC

AAGACGAGGCAGCGCGGCTATCGTGGCTGGCCACGACGGGCGTTCCTTGCGCAGCTGTGCT

CGACGTTGTCACTGAAGCGGGAAGGGACTGGCTGCTATTGGGCGAAGTGCCGGGGCAGGAT

CTCCTGTCATCTCACCTTGCTCCTGCCGAGAAAGTATCCATCATGGCTGATGCAATGCGGC

GGCTGCATACGCTTGATCCGGCTACCTGCCCATTCGACCACCAAGCGAAACATCGCATCGA

GCGAGCACGTACTCGGATGGAAGCCGGTCTTGTCGATCAGGATGATCTGGACGAAGAGCAT

CAGGGGCTCGCGCCAGCCGAACTGTTCGCCAGGCTCAAGGCGAGCATGCCCGACGGCGAGG

ATCTCGTCGTGACCCATGGCGATGCCTGCTTGCCGAATATCATGGTGGAAAATGGCCGCTT

TTCTGGATTCATCGACTGTGGCCGGCTGGGTGTGGCGGATCGCTATCAGGACATAGCGTTG

GCTACCCGTGATATTGCTGAAGAGCTTGGCGGCGAATGGGCTGACCGCTTCCTCGTGCTTT

-continued

ACGGTATCGCCGCTCCCGATTCGCAGCGCATCGCCTTCTATCGCCTTCTTGACGAGTTCTT

CTGAACGAGCGTGACACCACGATGCCTGTAGCAATGGCAACAACGTTGCGCAAACTATTAA

CTGGCGAACTACTTACTCTAGCTTCCCGGCAACAATTAATAGACTGGATGGAGGCGGATAA

AGTTGCAGGACCACTTCTGCGCTCGGCCCTTCCGGCTGGCTGGTTTATTGCTGATAAATCT

GGAGCCGGTGAGCGTGGGTCTCGCGGTATCATTGCAGCACTGGGGCCAGATGGTAAGCCCT

CCCGTATCGTAGTTATCTACACGACGGGGAGTCAGGCAACTATGGATGAACGAAATAGACA

GATCGCTGAGATAGGTGCCTCACTGATTAAGCATTGGTAACTGTCAGACCAAGTTTACTCA

TATATACTTTAGATTGATTTAAAACTTCATTTTTAATTTAAAAGGATCTAGGTGAAGATCC

TTTTTGATAATCTCATGACCAAAATCCCTTAACGTGAGTTTTCGTTCCACTGAGCGTCAGA

CCCCGTAGAAAAGATCAAAGGATCTTCTTGAGATCCTTTTTTTCTGCGCGTAATCTGCTGC

TTGCAAACAAAAAAACCACCGCTACCAGCGGTGGTTTGTTTGCCGGATCAAGAGCTACCAA

CTCTTTTTCCGAAGGTAACTGGCTTCAGCAGAGCGCAGATACCAAATACTGTTCTTCTAGT

GTAGCCGTAGTTAGGCCACCACTTCAAGAACTCTGTAGCACCGCCTACATACCTCGCTCTG

CTAATCCTGTTACCAGTGGCTGCTGCCAGTGGCGATAAGTCGTGTCTTACCGGGTTGGACT

CAAGACGATAGTTACCGGATAAGGCGCAGCGGTCGGGCTGAACGGGGGGTTCGTGCACACA

GCCCAGCTTGGAGCGAACGACCTACACCGAACTGAGATACCTACAGCGTGAGCTATGAGAA

AGCGCCACGCTTCCCGAAGGGAGAAAGGCGGACAGGTATCCGGTAAGCGGCAGGGTCGGAA

CAGGAGAGCGCACGAGGGAGCTTCCAGGGGGAAACGCCTGGTATCTTTATAGTCCTGTCGG

GTTTCGCCACCTCTGACTTGAGCGTCGATTTTTGTGATGCTCGTCAGGGGGGCGGAGCCTA

TGGAAAAACGCCAGCAACGCGGCCTTTTTACGGTTCCTGGCCTTTTGCTGGCCTTTTGCTC

ACATGT (pAT057)

SEQ ID NO: 76

CCTGCAGGCAGCTGCGCGCTCGCTCGCTCACTGAGGCCGCCCGGGCAAAGCCCGGGCGTCG

GGCGACCTTTGGTCGCCCGGCCTCAGTGAGCGAGCGAGCGCGCAGAGAGGGAGTGGCCAAC

TCCATCACTAGGGGTTCCTGCGGCCAATTCAGTGGATCCCGATAACTATAACGGTCCTAAG

GTAGCGATTTAAATGAGGGCCTATTTCCCATGATTCCTTCATATTTGCATATACGATACAA

GGCTGTTAGAGAGATAATTAGAATTAATTTGACTGTAAACACAAAGATATTAGTACAAAAT

ACGTGAGGTAGAAAGTAATAATTTCTTGGGTAGTTTGGAGTTTTAAAATTATGTTTTAAAA

TGGACTATCATATGCTTACCGTAACTTGAAAGTATTTCGATTTCTTGGCTTTATATATCTT

GTGGAAAGGACGAGGTACCGTGAGCTGTTGGAAGCTTGGATGGTCTTGTATTCAGGAGGTT

TACATTTCCTATACAACTGCATCCAATGATTCAGCTGCTTCTTTTTCCGGGACGCGTCAAT

TGAGATCTCCGACATTGATTATTGACTAGTTATTAATAGTAATCAATTACGGGGTCATTAG

TTCATAGCCCATATATGGAGTTCCGCGTTACATAACTTACGGTAAATGGCCCGCCTGGCTG

ACCGCCCAACGACCCCCGCCCATTGACGTCAATAATGACGTATGTTCCCATAGTAACGCCA

ATAGGGACTTTCCATTGACGTCAATGGGTGGAGTATTTACGGTAAACTGCCCACTTGGCAG

TACATCAAGTGTATCATATGCCAAGTACGCCCCCTATTGACGTCAATGACGGTAAATGGCC

CGCCTGGCATTATGCCCAGTACATGACCTTATGGGACTTTCCTACTTGGCAGTACATCTAC

GTATTAGTCATCGCTATTACCATGTCGAGGCCACGTTCTGCTTCACTCTCCCCATCTCCCC

CCCCTCCCCACCCCCAATTTTGTATTTATTTATTTTTTAATTATTTTGTGCAGCGATGGGG

GCGGGGGGGGGGGGGCGCGCGCCAGGCGGGGCGGGGCGGGGCGAGGGGCGGGGCGGGGCGAG

-continued

GCGGAGAGGTGCGGCGGCAGCCAATCAGAGCGGCGCGCTCCGAAAGTTTCCTTTTATGGCG

AGGCGGCGGCGGCGGCGGCCCTATAAAAAGCGAAGCGCGCGGCGGGCGGGAGCAAGCTTCG

TTTAGTGAACCGTCAGATCGCCTGGAGACGCCATCCACGCTGTTTTGACCTCCATAGAAGA

CACCGGGACCGATCCAGCCTCCGCGGATTCGAATCCCGGCCGGGAACGGTGCATTGGAACG

CGGATTCCCCGTGCCAAGAGTGACGTAAGTACCGCCTATAGAGTCTATAGGCCCACAAAAA

ATGCTTTCTTCTTTTAATATACTTTTTTGTTTATCTTATTTCTAATACTTTCCCTAATCTC

TTTCTTTCAGGGCAATAATGATACAATGTATCATGCCTCTTTGCACCATTCTAAAGAATAA

CAGTGATAATTTCTGGGTTAAGGCAATAGCAATATTTCTGCATATAAATATTTCTGCATAT

AAATTGTAACTGATGTAAGAGGTTTCATATTGCTAATAGCAGCTACAATCCAGCTACCATT

CTGCTTTTATTTTGTGGTTGGGATAAGGCTGGATTATTCTGAGTCCAAGCTAGGCCCTTTT

GCTAATCGTGTTCATACCTCTTATCTTCCTCCCACAGCTCCTGGGCAACGTGCTGGTCTGT

GTGCTGGCCCATCACTTTGGCAAAGAATTACCGGTGGCAACGTGCTGGTTATTGTGCTGTC

TCATCATTTTGGCAAAGAATTCACGCCCCAGAGCCGCCACCATGGCCTACCCATACGATGT

TCCAGATTACGCTCTCACATTCATGGCCTCTGACAGCGAGGAAGAAGTGTGTGATGAGCGG

ACGTCCCTAATGTCGGCTGAGAGCCCCACGCCGCGCTCCTGCCAGGAGGGCAGGCAGGGCC

CAGAGGATGGAGAGAACACTGCCCAGTGGAGAAGCCAGGAGAACGAGGAGGACGGTGAGGA

GGACCCTGACCGCTATGTCTGTAGTGGGGTTCCCGGGCGGCCGCCAGGCCTGGAGGAAGAG

CTGACCCTCAAATACGGAGCGAAGCACGTGATCATGCTGTTTGTGCCTGTCACTCTGTGCA

TGATCGTGGTGGTAGCCACCATCAAGTCTGTGCGCTTCTACACAGAGAAGAATGGACAGCT

CATCTACACGCCATTCACTGAGGACACACCCTCGGTGGGCCAGCGCCTCCTCAACTCCGTG

CTGAACACCCTCATCATGATCAGCGTCATCGTGGTTATGACCATCTTCTTGGTGGTGCTCT

ACAAGTACCGCTGCTACAAGTTCATCCATGGCTGGTTGATCATGTCTTCACTGATGCTGCT

GTTCCTCTTCACCTATATCTACCTTGGGGAAGTGCTCAAGACCTACAATGTGGCCATGGAC

TACCCCACCCTCTTGCTGACTGTCTGGAACTTCGGGGCAGTGGGCATGGTGTGCATCCACT

GGAAGGGCCCTCTGGTGCTGCAGCAGGCCTACCTCATCATGATCAGTGCGCTCATGGCCCT

AGTGTTCATCAAGTACCTCCCAGAGTGGTCCGCGTGGGTCATCCTGGGCGCCATCTCTGTG

TATGATCTCGTGGCTGTGCTGTGTCCCAAAGGGCCTCTGAGAATGCTGGTAGAAACTGCCC

AGGAGAGAAATGAGCCCATATTCCCTGCCCTGATATACTCATCTGCCATGGTGTGGACGGT

TGGCATGGCGAAGCTGGACCCCTCCTCTCAGGGTGCCCTCCAGCTCCCCTACGACCCGGAG

ATGGAAGAAGACTCCTATGACAGTTTTGGGGAGCCTTCATACCCCGAAGTCTTTGAGCCTC

CCTTGACTGGCTACCCAGGGGAGGAGCTGGAGGAAGAGGAGGAAAGGGGCGTGAAGCTTGG

CCTCGGGGACTTCATCTTCTACAGTGTGCTGGTGGGCAAGGCGGCTGCCACGGGCAGCGGG

GACTGGAATACCACGCTGGCCTGCTTCGTGGCCATCCTCATTGGCTTGTGTCTGACCCTCC

TGCTGCTTGCTGTGTTCAAGAAGGCGCTGCCCGCCCTCCCCATCTCCATCACGTTCGGGCT

CATCTTTTACTTCTCCACGGACAACCTGGTGCGGCCGTTCATGGACACCCTGGCCTCCCAT

CAGCTCTACATCTAGTAAGCGGCCGCCCTAGGGAGCTCCTCGAGGGGGTGGCATCCCTGTG

ACCCCTCCCCAGTGCCTCTCCTGGCCCTGGAAGTTGCCACTCCAGTGCCCACCAGCCTTGT

CCTAATAAAATTAAGTTGCATCATTTTGTCTGACTAGGTGTCCTTCTATAATATTATGGGG

TGGAGGGGGGTGGTATGGAGCAAGGGGCAAGGGGGAAGACAACCTGTAGGGCCTGCGGGG

TCTATTGGGAACCAAGCTGGAGTGCAGTGGCACAATCTTGGCTCACTGCAATCTCCGCCTC

CTGGGTTCAAGCGATTCTCCTGCCTCAGCCTCCCGAGTTGTTGGGATTCCAGGCATGCATG

-continued

ACCAGGCTCAGCTAATTTTTGTTTTTTTGGTAGAGACGGGGTTTCACCATATTGGCCAGGC

TGGTCTCCCCCTCCTAATCTCAGGTGATCTACCCACCTTGGCCTCCCAAATTGCTGGGATT

ACAGGCGTGAACCACTGCTCCCTTCCCTGTCCTTCCTGGGCCTAGGGCTGTGCCAGCTGCC

TCGTCCCGTCACCTTCTGGCTTCTTCTCTCCCTCCATATCTTAGCTGTTTTCCTCATGAGA

ATGTTCCAAATTCGAAATTTCTATTTAACCATTATATATTTACTTGTTTGCTATTATCTCT

GCCCCCAGTAGATTGTTAGCTCCAGAAGAGAAAGGATCATGTCTTTTGCTTATCTAGATAT

GCCCATCTGCCTGGTACAATCTCTGGCACATGTTACAGGCAACAACTACTTGTGGAATTGG

TGAATGCATGAATAGAAGAATGAGTGAATGAATGAATAGACAATAGGCAGAAATCCAGCCT

CAAAGAGCTTAGAGTCTGGTAAGAGGAATAAAATGTCTGCAAATAGCCACAGGAGAGGTCA

AAGGAAGGAGGGGCTATTTCCAGCTGAGGGCACCCCATCAGGAAAGCACCCCAGACTTCCT

TAGGGATAACAGGGTAATGGCGCGGGCCGCAGGAACCCCTAGTGATGGAGTTGGCCACTCC

CTCTCTGCGCGCTCGCTCGCTCACTGAGGCCGGGCGACCAAAGGTCGCCCGACGCCCGGGC

TTTGCCCGGGCGGCCTCAGTGAGCGAGCGAGCGCGCAGCTGCCTGCAGGGGCGCCTGATGC

GGTATTTTCTCCTTACGCATCTGTGCGGTATTTCACACCGCATACGTCAAAGCAACCATAG

TACGCGCCCTGTAGCGGCGCATTAAGCGCGGCGGGTGTGGTGGTTACGCGCAGCGTGACCG

CTACACTTGCCAGCGCCTTAGCGCCCGCTCCTTTCGCTTTCTTCCCTTCCTTTCTCGCCAC

GTTCGCCGGCTTTCCCCGTCAAGCTCTAAATCGGGGGCTCCCTTTAGGGTTCCGATTTAGT

GCTTTACGGCACCTCGACCCCAAAAAACTTGATTTGGGTGATGGTTCACGTAGTGGGCCAT

CGCCCTGATAGACGGTTTTTCGCCCTTTGACGTTGGAGTCCACGTTCTTTAATAGTGGACT

CTTGTTCCAAACTGGAACAACACTCAACTCTATCTCGGGCTATTCTTTTGATTTATAAGGG

ATTTTGCCGATTTCGGTCTATTGGTTAAAAAATGAGCTGATTTAACAAAAATTTAAGGCGA

ATTTTAACAAAATATTAACGTTTACAATTTTATGGTGCACTCTCAGTACAATCTGCTCTGA

TGCCGCATAGTTAAGCCAGCCCCGACACCCGCCAACACCCGCTGACGCGCCCTGACGGGCT

TGTCTGCTCCCGGCATCCGCTTACAGACAAGCTGTGACCGTCTCCGGGAGCTGCATGTGTC

AGAGGTTTTCACCGTCATCACCGAAACGCGCGAGACGAAAGGGCCTCGTGATACGCCTATT

TTTATAGGTTAATGTCATGATAATAATGGTTTCTTAGACGTCAGGTGGCACTTTTCGGGGA

AATGTGCGCGGAACCCCTATTTGTTTATTTTTCTAAATACATTCAAATATGTATCCGCTCA

TGAGACAATAACCCTGATAAATGCTTCAATAATATTGAAAAAGGAAGAGTCGATCGATCAA

GAGACAGGATGAGGATCGTTTCGCATGATTGAACAAGATGGATTGCACGCAGGTTCTCCGG

CCGCTTGGGTGGAGAGGCTATTCGGCTATGACTGGGCACAACAGACAATCGGCTGCTCTGA

TGCCGCCGTGTTCCGGCTGTCAGCGCAGGGGCGCCCGGTTCTTTTTGTCAAGACCGACCTG

TCCGGTGCCCTGAATGAACTGCAAGACGAGGCAGCGCGGCTATCGTGGCTGGCCACGACGG

GCGTTCCTTGCGCAGCTGTGCTCGACGTTGTCACTGAAGCGGGAAGGGACTGGCTGCTATT

GGGCGAAGTGCCGGGGCAGGATCTCCTGTCATCTCACCTTGCTCCTGCCGAGAAAGTATCC

ATCATGGCTGATGCAATGCGGCGGCTGCATACGCTTGATCCGGCTACCTGCCCATTCGACC

ACCAAGCGAAACATCGCATCGAGCGAGCACGTACTCGGATGGAAGCCGGTCTTGTCGATCA

GGATGATCTGGACGAAGAGCATCAGGGGCTCGCGCCAGCCGAACTGTTCGCCAGGCTCAAG

GCGAGCATGCCCGACGGCGAGGATCTCGTCGTGACCCATGGCGATGCCTGCTTGCCGAATA

TCATGGTGGAAAATGGCCGCTTTTCTGGATTCATCGACTGTGGCCGGCTGGGTGTGGCGGA

TCGCTATCAGGACATAGCGTTGGCTACCCGTGATATTGCTGAAGAGCTTGGCGGCGAATGG

-continued

GCTGACCGCTTCCTCGTGCTTTACGGTATCGCCGCTCCCGATTCGCAGCGCATCGCCTTCT

ATCGCCTTCTTGACGAGTTCTTCTGAACGAGCGTGACACCACGATGCCTGTAGCAATGGCA

ACAACGTTGCGCAAACTATTAACTGGCGAACTACTTACTCTAGCTTCCCGGCAACAATTAA

TAGACTGGATGGAGGCGGATAAAGTTGCAGGACCACTTCTGCGCTCGGCCCTTCCGGCTGG

CTGGTTTATTGCTGATAAATCTGGAGCCGGTGAGCGTGGGTCTCGCGGTATCATTGCAGCA

CTGGGGCCAGATGGTAAGCCCTCCCGTATCGTAGTTATCTACACGACGGGGAGTCAGGCAA

CTATGGATGAACGAAATAGACAGATCGCTGAGATAGGTGCCTCACTGATTAAGCATTGGTA

ACTGTCAGACCAAGTTTACTCATATATACTTTAGATTGATTTAAAACTTCATTTTTAATTT

AAAAGGATCTAGGTGAAGATCCTTTTTGATAATCTCATGACCAAAATCCCTTAACGTGAGT

TTTCGTTCCACTGAGCGTCAGACCCCGTAGAAAAGATCAAAGGATCTTCTTGAGATCCTTT

TTTTCTGCGCGTAATCTGCTGCTTGCAAACAAAAAAACCACCGCTACCAGCGGTGGTTTGT

TTGCCGGATCAAGAGCTACCAACTCTTTTTCCGAAGGTAACTGGCTTCAGCAGAGCGCAGA

TACCAAATACTGTTCTTCTAGTGTAGCCGTAGTTAGGCCACCACTTCAAGAACTCTGTAGC

ACCGCCTACATACCTCGCTCTGCTAATCCTGTTACCAGTGGCTGCTGCCAGTGGCGATAAG

TCGTGTCTTACCGGGTTGGACTCAAGACGATAGTTACCGGATAAGGCGCAGCGGTCGGGCT

GAACGGGGGGTTCGTGCACACAGCCCAGCTTGGAGCGAACGACCTACACCGAACTGAGATA

CCTACAGCGTGAGCTATGAGAAAGCGCCACGCTTCCCGAAGGGAGAAAGGCGGACAGGTAT

CCGGTAAGCGGCAGGGTCGGAACAGGAGAGCGCACGAGGGAGCTTCCAGGGGGAAACGCCT

GGTATCTTTATAGTCCTGTCGGGTTTCGCCACCTCTGACTTGAGCGTCGATTTTTGTGATG

CTCGTCAGGGGGGCGGAGCCTATGGAAAAACGCCAGCAACGCGGCCTTTTTACGGTTCCTG

GCCTTTTGCTGGCCTTTTGCTCACATGT (pAT058)

SEQ ID NO: 77

CCTGCAGGCAGCTGCGCGCTCGCTCGCTCACTGAGGCCGCCCGGGCAAAGCCCGGGCGTCG

GGCGACCTTTGGTCGCCCGGCCTCAGTGAGCGAGCGAGCGCGCAGAGAGGGAGTGGCCAAC

TCCATCACTAGGGGTTCCTGCGGCCAATTCAGTGGATCCCGATAACTATAACGGTCCTAAG

GTAGCGATTTAAATGAGGGCCTATTTCCCATGATTCCTTCATATTTGCATATACGATACAA

GGCTGTTAGAGAGATAATTAGAATTAATTTGACTGTAAACACAAAGATATTAGTACAAAAT

ACGTGACGTAGAAAGTAATAATTTCTTGGGTAGTTTGCAGTTTTAAAATTATGTTTTAAAA

TGGACTATCATATGCTTACCGTAACTTGAAAGTATTTCGATTTCTTGGCTTTATATATCTT

GTGGAAAGGACGAGGTACCGTGAGCTGTTGGATTCCAGTTGTTATGTTTTATCCAGAGGTT

TACATTTCTGTAAAACTATACAACTGCATTTCAGCTGCTTCTTTTTCCGGGACGCGTCAAT

TGAGATCTCCGACATTGATTATTGACTAGTTATTAATAGTAATCAATTACGGGGTCATTAG

TTCATAGCCCATATATGGAGTTCCGCGTTACATAACTTACGGTAAATGGCCCGCCTGGCTG

ACCGCCCAACGACCCCCGCCCATTGACGTCAATAATGACGTATGTTCCCATAGTAACGCCA

ATAGGGACTTTCCATTGACGTCAATGGGTGGAGTATTTACGGTAAACTGCCCACTTGGCAG

TACATCAAGTGTATCATATGCCAAGTACGCCCCCTATTGACGTCAATGAGGGTAAATGGCC

CGCCTGGCATTATGCCCAGTACATGACCTTATGGGACTTTCCTACTTGGCAGTACATCTAC

GTATTAGTCATCGCTATTACCATGTCGAGGCCACGTTCTGCTTCACTCTCCCCATCTCCCC

CCCCTCCCCACCCCCAATTTTGTATTTATTTATTTTTTAATTATTTTGTGCAGCGATGGGG

GCGGGGGGGGGGGGCGCGCGCCAGGCGGGGCGGGGCGGGGCGAGGGGCGGGGCGGGGCGAG

GCGGAGAGGTGCGGCGGCAGCCAATCAGAGCGGCGCGCTCCGAAAGTTTCCTTTTATGGCG

-continued

AGGCGGCGGCGGCGGCGGCCCTATAAAAAGCGAAGCGCGCGGCGGGCGGGAGCAAGCTTCG

TTTAGTGAACCGTCAGATCGCCTGGAGACGCCATCCACGCTGTTTTGACCTCCATAGAAGA

CACCGGGACCGATCCAGCCTCCGCGGATTCGAATCCCGGCCGGGAACGGTGCATTGGAACG

CGGATTCCCCGTGCCAAGAGTGACGTAAGTACCGCCTATAGAGTCTATAGGCCCACAAAAA

ATGCTTTCTTCTTTTAATATACTTTTTTGTTTATCTTATTTCTAATACTTTCCCTAATCTC

TTTCTTTCAGGGCAATAATGATACAATGTATCATGCCTCTTTGCACCATTCTAAAGAATAA

CAGTGATAATTTCTGGGTTAAGGCAATAGCAATATTTCTGCATATAAATATTTCTGCATAT

AAATTGTAACTGATGTAAGAGGTTTCATATTGCTAATAGCAGCTACAATCCAGCTACCATT

CTGCTTTTATTTTGTGGTTGGGATAAGGCTGGATTATTCTGAGTCCAAGCTAGGCCCTTTT

GCTAATCGTGTTCATACCTCTTATCTTCCTCCCACAGCTCCTGGGCAACGTGCTGGTCTGT

GTGCTGGCCCATCACTTTGGCAAAGAATTACCGGTGGCAACGTGCTGGTTATTGTGCTGTC

TCATCATTTTGGCAAAGAATTCACGCCCCAGAGCCGCCACCATGGCCTACCCATACGATGT

TCCAGATTACGCTCTCACATTCATGGCCTCTGACAGCGAGGAAGAAGTGTGTGATGAGCGG

ACGTCCCTAATGTCGGCTGAGAGCCCCACGCCGCGCTCCTGCCAGGAGGGCAGGCAGGGCC

CAGAGGATGGAGAGAACACTGCCCAGTGGAGAAGCCAGGAGAACGAGGAGGACGGTGAGGA

GGACCCTGACCGCTATGTCTGTAGTGGGGTTCCCGGGCGGCCGCCAGGCCTGGAGGAAGAG

CTGACCCTCAAATACGGAGCGAAGCACGTGATCATGCTGTTTGTGCCTGTCACTCTGTGCA

TGATCGTGGTGGTAGCCACCATCAAGTCTGTGCGCTTCTACACAGAGAAGAATGGACAGCT

CATCTACACGCCATTCACTGAGGACACACCCTCGGTGGGCCAGCGCCTCCTCAACTCCGTG

CTGAACACCCTCATCATGATCAGCGTCATCGTGGTTATGACCATCTTCTTGGTGGTGCTCT

ACAAGTACCGCTGCTACAAGTTCATCCATGGCTGGTTGATCATGTCTTCACTGATGCTGCT

GTTCCTCTTCACCTATATCTACCTTGGGGAAGTGCTCAAGACCTACAATGTGGCCATGGAC

TACCCCACCCTCTTGCTGACTGTCTGGAACTTCGGGGCAGTGGGCATGGTGTGCATCCACT

GGAAGGGCCCTCTGGTGCTGCAGCAGGCCTACCTCATCATGATCAGTGCGCTCATGGCCCT

AGTGTTCATCAAGTACCTCCCAGAGTGGTCCGCGTGGGTCATCCTGGGCGCCATCTCTGTG

TATGATCTCGTGGCTGTGCTGTGTCCCAAAGGGCCTCTGAGAATGCTGGTAGAAACTGCCC

AGGAGAGAAATGAGCCCATATTCCCTGCCCTGATATACTCATCTGCCATGGTGTGGACGGT

TGGCATGGCGAAGCTGGACCCCTCCTCTCAGGGTGCCCTCCAGCTCCCCTACGACCCGGAG

ATGGAAGAAGACTCCTATGACAGTTTTGGGGAGCCTTCATACCCCGAAGTCTTTGAGCCTC

CCTTGACTGGCTACCCAGGGGAGGAGCTGGAGGAAGAGGAGGAAAGGGGCGTGAAGCTTGG

CCTCGGGGACTTCATCTTCTACAGTGTGCTGGTGGGCAAGGCGGCTGCCACGGGCAGCGGG

GACTGGAATACCACGCTGGCCTGCTTCGTGGCCATCCTCATTGGCTTGTGTCTGACCCTCC

TGCTGCTTGCTGTGTTCAAGAAGGCGCTGCCCGCCCTCCCCATCTCCATCACGTTCGGGCT

CATCTTTTACTTCTCCACGGACAACCTGGTGCGGCCGTTCATGGACACCCTGGCCTCCCAT

CAGCTCTACATCTAGTAAGCGGCCGCCCTAGGGAGCTCCTCGAGGGGGTGGCATCCCTGTG

ACCCCTCCCCAGTGCCTCTCCTGGCCCTGGAAGTTGCCACTCCAGTGCCCACCAGCCTTGT

CCTAATAAAATTAAGTTGCATCATTTTGTCTGACTAGGTGTCCTTCTATAATATTATGGGG

TGGAGGGGGGTGGTATGGAGCAAGGGGCAAGGGGGGAAGACAACCTGTAGGGCCTGCGGGG

TCTATTGGGAACCAAGCTGGAGTGCAGTGGCACAATCTTGGCTCACTGCAATCTCCGCCTC

CTGGGTTCAAGCGATTCTCCTGCCTCAGCCTCCCGAGTTGTTGGGATTCCAGGCATGCATG

-continued

ACCAGGCTCAGCTAATTTTTGTTTTTTTGGTAGAGACGGGGTTTCACCATATTGGCCAGGC

TGGTCTCCCCCTCCTAATCTCAGGTGATCTACCCACCTTGGCCTCCCAAATTGCTGGGATT

ACAGGCGTGAACCACTGCTCCCTTCCCTGTCCTTCCTGGGCCTAGGGCTGTGCCAGCTGCC

TCGTCCCGTCACCTTCTGGCTTCTTCTCTCCCTCCATATCTTAGCTGTTTTCCTCATGAGA

ATGTTCCAAATTCGAAATTTCTATTTAACCATTATATATTTACTTGTTTGCTATTATCTCT

GCCCCCAGTAGATTGTTAGCTCCAGAAGAGAAAGGATCATGTCTTTTGCTTATCTAGATAT

GCCCATCTGCCTGGTACAATCTCTGGCACATGTTACAGGCAACAACTACTTGTGGAATTGG

TGAATGCATGAATAGAAGAATGAGTGAATGAATGAATAGACAATAGGCAGAAATCCAGCCT

CAAAGAGCTTAGAGTCTGGTAAGAGGAATAAAATGTCTGCAAATAGCCACAGGAGAGGTCA

AAGGAAGGAGGGGCTATTTCCAGCTGAGGGCACCCCATCAGGAAAGCACCCCAGACTTCCT

TAGGGATAACAGGGTAATGGCGCGGGCCGCAGGAACCCCTAGTGATGGAGTTGGCCACTCC

CTCTCTGCGCGCTCGCTCGCTCACTGAGGCCGGGCGACCAAAGGTCGCCCGACGCCCGGGC

TTTGCCCGGGCGGCCTCAGTGAGCGAGCGAGCGCGCAGCTGCCTGCAGGGGCGCCTGATGC

GGTATTTTCTCCTTACGCATCTGTGCGGTATTTCACACCGCATACGTCAAAGCAACCATAG

TACGCGCCCTGTAGCGGCGCATTAAGCGCGGCGGGTGTGGTGGTTACGCGCAGCGTGACCG

CTACACTTGCCAGCGCCTTAGCGCCCGCTCCTTTCGCTTTCTTCCCTTCCTTTCTCGCCAC

GTTCGCCGGCTTTCCCCGTCAAGCTCTAAATCGGGGGCTCCCTTTAGGGTTCCGATTTAGT

GCTTTACGGCACCTCGACCCCAAAAAACTTGATTTGGGTGATGGTTCACGTAGTGGGCCAT

CGCCCTGATAGACGGTTTTTCGCCCTTTGACGTTGGAGTCCACGTTCTTTAATAGTGGACT

CTTGTTCCAAACTGGAACAACACTCAACTCTATCTCGGGCTATTCTTTTGATTTATAAGGG

ATTTTGCCGATTTCGGTCTATTGGTTAAAAAATGAGCTGATTTAACAAAAATTTAAGGCGA

ATTTTAACAAAATATTAACGTTTACAATTTTATGGTGCACTCTCAGTACAATCTGCTCTGA

TGCCGCATAGTTAAGCCAGCCCCGACACCCGCCAACACCCGCTGACGCGCCCTGACGGGCT

TGTCTGCTCCCGGCATCCGCTTACAGACAAGCTGTGACCGTCTCCGGGAGCTGCATGTGTC

AGAGGTTTTCACCGTCATCACCGAAACGCGCGAGACGAAAGGGCCTCGTGATACGCCTATT

TTTATAGGTTAATGTCATGATAATAATGGTTTCTTAGACGTCAGGTGGCACTTTTCGGGGA

AATGTGCGCGGAACCCCTATTTGTTTATTTTTCTAAATACATTCAAATATGTATCCGCTCA

TGAGACAATAACCCTGATAAATGCTTCAATAATATTGAAAAAGGAAGAGTCGATCGATCAA

GAGACAGGATGAGGATCGTTTCGCATGATTGAACAAGATGGATTGCACGCAGGTTCTCCGG

CCGCTTGGGTGGAGAGGCTATTCGGCTATGACTGGGCACAACAGACAATCGGCTGCTCTGA

TGCCGCCGTGTTCCGGCTGTCAGCGCAGGGGCGCCCGGTTCTTTTTGTCAAGACCGACCTG

TCCGGTGCCCTGAATGAACTGCAAGACGAGGCAGCGCGGCTATCGTGGCTGGCCACGACGG

GCGTTCCTTGCGCAGCTGTGCTCGACGTTGTCACTGAAGCGGGAAGGGACTGGCTGCTATT

GGGCGAAGTGCCGGGGCAGGATCTCCTGTCATCTCACCTTGCTCCTGCCGAGAAAGTATCC

ATCATGGCTGATGCAATGCGGCGGCTGCATACGCTTGATCCGGCTACCTGCCCATTCGACC

ACCAAGCGAAACATCGCATCGAGCGAGCACGTACTCGGATGGAAGCCGGTCTTGTCGATCA

GGATGATCTGGACGAAGAGCATCAGGGGCTCGCGCCAGCCGAACTGTTCGCCAGGCTCAAG

GCGAGCATGCCCGACGGCGAGGATCTCGTCGTGACCCATGGCGATGCCTGCTTGCCGAATA

TCATGGTGGAAAATGGCCGCTTTTCTGGATTCATCGACTGTGGCCGGCTGGGTGTGGCGGA

TCGCTATCAGGACATAGCGTTGGCTACCCGTGATATTGCTGAAGAGCTTGGCGGCGAATGG

GCTGACCGCTTCCTCGTGCTTTACGGTATCGCCGCTCCCGATTCGCAGCGCATCGCCTTCT

-continued

ATCGCCTTCTTGACGAGTTCTTCTGAACGAGCGTGACACCACGATGCCTGTAGCAATGGCA

ACAACGTTGCGCAAACTATTAACTGGCGAACTACTTACTCTAGCTTCCCGGCAACAATTAA

TAGACTGGATGGAGGCGGATAAAGTTGCAGGACCACTTCTGCGCTCGGCCCTTCCGGCTGG

CTGGTTTATTGCTGATAAATCTGGAGCCGGTGAGCGTGGGTCTCGCGGTATCATTGCAGCA

CTGGGGCCAGATGGTAAGCCCTCCCGTATCGTAGTTATCTACACGACGGGGAGTCAGGCAA

CTATGGATGAACGAAATAGACAGATCGCTGAGATAGGTGCCTCACTGATTAAGCATTGGTA

ACTGTCAGACCAAGTTTACTCATATATACTTTAGATTGATTTAAAACTTCATTTTTAATTT

AAAAGGATCTAGGTGAAGATCCTTTTTGATAATCTCATGACCAAAATCCCTTAACGTGAGT

TTTCGTTCCACTGAGCGTCAGACCCCGTAGAAAAGATCAAAGGATCTTCTTGAGATCCTTT

TTTTCTGCGCGTAATCTGCTGCTTGCAAACAAAAAAACCACCGCTACCAGCGGTGGTTTGT

TTGCCGGATCAAGAGCTACCAACTCTTTTTCCGAAGGTAACTGGCTTCAGCAGAGCGCAGA

TACCAAATACTGTTCTTCTAGTGTAGCCGTAGTTAGGCCACCACTTCAAGAACTCTGTAGC

ACCGCCTACATACCTCGCTCTGCTAATCCTGTTACCAGTGGCTGCTGCCAGTGGCGATAAG

TCGTGTCTTACCGGGTTGGACTCAAGACGATAGTTACCGGATAAGGCGCAGCGGTCGGGCT

GAACGGGGGGTTCGTGCACACAGCCCAGCTTGGAGCGAACGACCTACACCGAACTGAGATA

CCTACAGCGTGAGCTATGAGAAAGCGCCACGCTTCCCGAAGGGAGAAAGGCGGACAGGTAT

CCGGTAAGCGGCAGGGTCGGAACAGGAGAGCGCACGAGGGAGCTTCCAGGGGGAAACGCCT

GGTATCTTTATAGTCCTGTCGGGTTTCGCCACCTCTGACTTGAGCGTCGATTTTTGTGATG

CTCGTCAGGGGGGCGGAGCCTATGGAAAAACGCCAGCAACGCGGCCTTTTTACGGTTCCTG

GCCTTTTGCTGGCCTTTTGCTCACATGT (pAT059)

SEQ ID NO: 78

CCTGCAGGCAGCTGCGCGCTCGCTCGCTCACTGAGGCCGCCCGGGCAAAGCCCGGGCGTCG

GGCGACCTTTGGTCGCCCGGCCTCAGTGAGCGAGCGAGCGCGCAGAGAGGGAGTGGCCAAC

TCCATCACTAGGGGTTCCTGCGGCCAATTCAGTGGATCCCGATAACTATAACGGTCCTAAG

GTAGCGATTTAAATGAGGGCCTATTTCCCATGATTCCTTCATATTTGCATATACGATACAA

GGCTGTTAGAGAGATAATTAGAATTAATTTGACTGTAAACACAAAGATATTAGTACAAAAT

ACGTGACGTAGAAAGTAATAATTTCTTGGGTAGTTTGCAGTTTTAAAATTATGTTTTAAAA

TGGACTATCATATGCTTACCGTAACTTGAAAGTATTTCGATTTCTTGGCTTTATATATCTT

GTGGAAAGGACGAGGTACCGTGAGCTGTTGGATTCGCTTAATTCGAATATCCTAAGAGGTT

TACATTTCTTGATATTACTATTAAGCCACTTCAGCTGCTTCTTTTTCCGGGACGCGTCAAT

TGAGATCTCCGACATTGATTATTGACTAGTTATTAATAGTAATCAATTACGGGGTCATTAG

TTCATAGCCCATATATGGAGTTCCGCGTTACATAACTTACGGTAAATGGCCCGCCTGGCTG

ACCGCCCAACGACCCCCGCCCATTGACGTCAATAATGACGTATGTTCCCATAGTAACGCCA

ATAGGGACTTTCCATTGACGTCAATGGGTGGAGTATTTACGGTAAACTGCCCACTTGGCAG

TACATCAAGTGTATCATATGCCAAGTACGCCCCCTATTGACGTCAATGACGGTAAATGGCC

CGCCTGGCATTATGCCCAGTACATGACCTTATGGGACTTTCCTACTTGGCAGTACATCTAC

GTATTAGTCATCGCTATTACCATGTCGAGGCCACGTTCTGCTTCACTCTCCCCATCTCCCC

CCCCTCCCCACCCCCAATTTTGTATTTATTTATTTTTTAATTATTTTGTGCAGCGATGGGG

GCGGGGGGGGGGGGGCGCGCGCCAGGCGGGGCGGGGCGGGGCGAGGGGCGGGGCGGGGCGAG

GCGGAGAGGTGCGGCGGCAGCCAATCAGAGCGGCGCGCTCCGAAAGTTTCCTTTTATGGCG

-continued

AGGCGGCGGCGGCGGCGGCCCTATAAAAAGCGAAGCGCGCGGCGGGCGGGAGCAAGCTTCG

TTTAGTGAACCGTCAGATCGCCTGGAGACGCCATCCACGCTGTTTTGACCTCCATAGAAGA

CACCGGGACCGATCCAGCCTCCGCGGATTCGAATCCCGGCCGGGAACGGTGCATTGGAACG

CGGATTCCCCGTGCCAAGAGTGACGTAAGTACCGCCTATAGAGTCTATAGGCCCACAAAAA

ATGCTTTCTTCTTTTAATATACTTTTTTGTTTATCTTATTTCTAATACTTTCCCTAATCTC

TTTCTTTCAGGGCAATAATGATACAATGTATCATGCCTCTTTGCACCATTCTAAAGAATAA

CAGTGATAATTTCTGGGTTAAGGCAATAGCAATATTTCTGCATATAAATATTTCTGCATAT

AAATTGTAACTGATGTAAGAGGTTTCATATTGCTAATAGCAGCTACAATCCAGCTACCATT

CTGCTTTTATTTTGTGGTTGGGATAAGGCTGGATTATTCTGAGTCCAAGCTAGGCCCTTTT

GCTAATCGTGTTCATACCTCTTATCTTCCTCCCACAGCTCCTGGGCAACGTGCTGGTCTGT

GTGCTGGCCCATCACTTTGGCAAAGAATTACCGGTGGCAACGTGCTGGTTATTGTGCTGTC

TCATCATTTTGGCAAAGAATTCACGCCCCAGAGCCGCCACCATGGCCTACCCATACGATGT

TCCAGATTACGCTCTCACATTCATGGCCTCTGACAGCGAGGAAGAAGTGTGTGATGAGCGG

ACGTCCCTAATGTCGGCTGAGAGCCCCACGCCGCGCTCCTGCCAGGAGGGCAGGCAGGGCC

CAGAGGATGGAGAGAACACTGCCCAGTGGAGAAGCCAGGAGAACGAGGAGGAGGGTGAGGA

GGACCCTGACCGCTATGTCTGTAGTGGGGTTCCCGGGCGGCCGCCAGGCCTGGAGGAAGAG

CTGACCCTCAAATACGGAGCGAAGCACGTGATCATGCTGTTTGTGCCTGTCACTCTGTGCA

TGATCGTGGTGGTAGCCACCATCAAGTCTGTGCGCTTCTACACAGAGAAGAATGGACAGCT

CATCTACACGCCATTCACTGAGGACACACCCTCGGTGGGCCAGCGCCTCCTCAACTCCGTG

CTGAACACCCTCATCATGATCAGCGTCATCGTGGTTATGACCATCTTCTTGGTGGTGCTCT

ACAAGTACCGCTGCTACAAGTTCATCCATGGCTGGTTGATCATGTCTTCACTGATGCTGCT

GTTCCTCTTCACCTATATCTACCTTGGGGAAGTGCTCAAGACCTACAATGTGGCCATGGAC

TACCCCACCCTCTTGCTGACTGTCTGGAACTTCGGGGCAGTGGGCATGGTGTGCATCCACT

GGAAGGGCCCTCTGGTGCTGCAGCAGGCCTACCTCATCATGATCAGTGCGCTCATGGCCCT

AGTGTTCATCAAGTACCTCCCAGAGTGGTCCGCGTGGGTCATCCTGGGCGCCATCTCTGTG

TATGATCTCGTGGCTGTGCTGTGTCCCAAAGGGCCTCTGAGAATGCTGGTAGAAACTGCCC

AGGAGAGAAATGAGCCCATATTCCCTGCCCTGATATACTCATCTGCCATGGTGTGGACGGT

TGGCATGGCGAAGCTGGACCCCTCCTCTCAGGGTGCCCTCCAGCTCCCCTACGACCCGGAG

ATGGAAGAAGACTCCTATGACAGTTTTGGGGAGCCTTCATACCCCGAAGTCTTTGAGCCTC

CCTTGACTGGCTACCCAGGGGAGGAGCTGGAGGAAGAGGAGGAAAGGGGCGTGAAGCTTGG

CCTCGGGGACTTCATCTTCTACAGTGTGCTGGTGGGCAAGGCGGCTGCCACGGGCAGCGGG

GACTGGAATACCACGCTGGCCTGCTTCGTGGCCATCCTCATTGGCTTGTGTCTGACCCTCC

TGCTGCTTGCTGTGTTCAAGAAGGCGCTGCCCGCCCTCCCCATCTCCATCACGTTCGGGCT

CATCTTTTACTTCTCCACGGACAACCTGGTGCGGCCGTTCATGGACACCCTGGCCTCCCAT

CAGCTCTACATCTAGTAAGCGGCCGCCCTAGGGAGCTCCTCGAGGGGGTGGCATCCCTGTG

ACCCCTCCCCAGTGCCTCTCCTGGCCCTGGAAGTTGCCACTCCAGTGCCCACCAGCCTTGT

CCTAATAAAATTAAGTTGCATCATTTTGTCTGACTAGGTGTCCTTCTATAATATTATGGGG

TGGAGGGGGGTGGTATGGAGCAAGGGGCAAGGGGGGAAGACAACCTGTAGGGCCTGCGGGG

TCTATTGGGAACCAAGCTGGAGTGCAGTGGCACAATCTTGGCTCACTGCAATCTCCGCCTC

CTGGGTTCAAGCGATTCTCCTGCCTCAGCCTCCCGAGTTGTTGGGATTCCAGGCATGCATG

ACCAGGCTCAGCTAATTTTTGTTTTTTTGGTAGAGACGGGGTTTCACCATATTGGCCAGGC

-continued

TGGTCTCCCCCTCCTAATCTCAGGTGATCTACCCACCTTGGCCTCCCAAATTGCTGGGATT

ACAGGCGTGAACCACTGCTCCCTTCCCTGTCCTTCCTGGGCCTAGGGCTGTGCCAGCTGCC

TCGTCCCGTCACCTTCTGGCTTCTTCTCTCCCTCCATATCTTAGCTGTTTTCCTCATGAGA

ATGTTCCAAATTCGAAATTTCTATTTAACCATTATATATTTACTTGTTTGCTATTATCTCT

GCCCCCAGTAGATTGTTAGCTCCAGAAGAGAAAGGATCATGTCTTTTGCTTATCTAGATAT

GCCCATCTGCCTGGTACAATCTCTGGCACATGTTACAGGCAACAACTACTTGTGGAATTGG

TGAATGCATGAATAGAAGAATGAGTGAATGAATGAATAGACAATAGGCAGAAATCCAGCCT

CAAAGAGCTTACAGTCTGGTAAGAGGAATAAAATGTCTGCAAATAGCCACAGGACAGGTCA

AAGGAAGGAGGGGCTATTTCCAGCTGAGGGCACCCCATCAGGAAAGCACCCCAGACTTCCT

TAGGGATAACAGGGTAATGGCGCGGGCCGCAGGAACCCCTAGTGATGGAGTTGGCCACTCC

CTCTCTGCGCGCTCGCTCGCTCACTGAGGCCGGGCGACCAAAGGTCGCCCGACGCCCGGGC

TTTGCCCGGGCGGCCTCAGTGAGCGAGCGAGCGCGCAGCTGCCTGCAGGGGCGCCTGATGC

GGTATTTTCTCCTTACGCATCTGTGCGGTATTTCACACCGCATACGTCAAAGCAACCATAG

TACGCGCCCTGTAGCGGCGCATTAAGCGCGGCGGGTGTGGTGGTTACGCGCAGCGTGACCG

CTACACTTGCCAGCGCCTTAGCGCCCGCTCCTTTCGCTTTCTTCCCTTCCTTTCTCGCCAC

GTTCGCCGGCTTTCCCCGTCAAGCTCTAAATCGGGGGCTCCCTTTAGGGTTCCGATTTAGT

GCTTTACGGCACCTCGACCCCAAAAAACTTGATTTGGGTGATGGTTCACGTAGTGGGCCAT

CGCCCTGATAGACGGTTTTTCGCCCTTTGACGTTGGAGTCCACGTTCTTTAATAGTGGACT

CTTGTTCCAAACTGGAACAACACTCAACTCTATCTCGGGCTATTCTTTTGATTTATAAGGG

ATTTTGCCGATTTCGGTCTATTGGTTAAAAAATGAGCTGATTTAACAAAAATTTAACGCGA

ATTTTAACAAAATATTAACGTTTACAATTTTATGGTGCACTCTCAGTACAATCTGCTCTGA

TGCCGCATAGTTAAGCCAGCCCCGACACCCGCCAACACCCGCTGACGCGCCCTGACGGGCT

TGTCTGCTCCCGGCATCCGCTTACAGACAAGCTGTGACCGTCTCCGGGAGCTGCATGTGTC

AGAGGTTTTCACCGTCATCACCGAAACGCGCGAGACGAAAGGGCCTCGTGATACGCCTATT

TTTATAGGTTAATGTCATGATAATAATGGTTTCTTAGACGTCAGGTGGCACTTTTCGGGGA

AATGTGCGCGGAACCCCTATTTGTTTATTTTTCTAAATACATTCAAATATGTATCCGCTCA

TGAGACAATAACCCTGATAAATGCTTCAATAATATTGAAAAAGGAAGAGTCGATCGATCAA

GAGACAGGATGAGGATCGTTTCGCATGATTGAACAAGATGGATTGCACGCAGGTTCTCCGG

CCGCTTGGGTGGAGAGGCTATTCGGCTATGACTGGGCACAACAGACAATCGGCTGCTCTGA

TGCCGCCGTGTTCCGGCTGTCAGCGCAGGGGCGCCCGGTTCTTTTTGTCAAGACCGACCTG

TCCGGTGCCCTGAATGAACTGCAAGACGAGGCAGCGCGGCTATCGTGGCTGGCCACGACGG

GCGTTCCTTGCGCAGCTGTGCTCGACGTTGTCACTGAAGCGGGAAGGGACTGGCTGCTATT

GGGCGAAGTGCCGGGGCAGGATCTCCTGTCATCTCACCTTGCTCCTGCCGAGAAAGTATCC

ATCATGGCTGATGCAATGCGGCGGCTGCATACGCTTGATCCGGCTACCTGCCCATTCGACC

ACCAAGCGAAACATCGCATCGAGCGAGCACGTACTCGGATGGAAGCCGGTCTTGTCGATCA

GGATGATCTGGACGAAGAGCATCAGGGGCTCGCGCCAGCCGAACTGTTCGCCAGGCTCAAG

GCGAGCATGCCCGACGGCGAGGATCTCGTCGTGACCCATGGCGATGCCTGCTTGCCGAATA

TCATGGTGGAAAATGGCCGCTTTTCTGGATTCATCGACTGTGGCCGGCTGGGTGTGGCGGA

TCGCTATCAGGACATAGCGTTGGCTACCCGTGATATTGCTGAAGAGCTTGGCGGCGAATGG

GCTGACCGCTTCCTCGTGCTTTACGGTATCGCCGCTCCCGATTCGCAGCGCATCGCCTTCT

-continued

ATCGCCTTCTTGACGAGTTCTTCTGAACGAGCGTGACACCACGATGCCTGTAGCAATGGCA

ACAACGTTGCGCAAACTATTAACTGGCGAACTACTTACTCTAGCTTCCCGGCAACAATTAA

TAGACTGGATGGAGGCGGATAAAGTTGCAGGACCACTTCTGCGCTCGGCCCTTCCGGCTGG

CTGGTTTATTGCTGATAAATCTGGAGCCGGTGAGCGTGGGTCTCGCGGTATCATTGCAGCA

CTGGGGCCAGATGGTAAGCCCTCCCGTATCGTAGTTATCTACACGACGGGGAGTCAGGCAA

CTATGGATGAACGAAATAGACAGATCGCTGAGATAGGTGCCTCACTGATTAAGCATTGGTA

ACTGTCAGACCAAGTTTACTCATATATACTTTAGATTGATTTAAAACTTCATTTTTAATTT

AAAAGGATCTAGGTGAAGATCCTTTTTGATAATCTCATGACCAAAATCCCTTAACGTGAGT

TTTCGTTCCACTGAGCGTCAGACCCCGTAGAAAAGATCAAAGGATCTTCTTGAGATCCTTT

TTTTCTGCGCGTAATCTGCTGCTTGCAAACAAAAAAACCACCGCTACCAGCGGTGGTTTGT

TTGCCGGATCAAGAGCTACCAACTCTTTTTCCGAAGGTAACTGGCTTCAGCAGAGCGCAGA

TACCAAATACTGTTCTTCTAGTGTAGCCGTAGTTAGGCCACCACTTCAAGAACTCTGTAGC

ACCGCCTACATACCTCGCTCTGCTAATCCTGTTACCAGTGGCTGCTGCCAGTGGCGATAAG

TCGTGTCTTACCGGGTTGGACTCAAGACGATAGTTACCGGATAAGGCGCAGCGGTCGGGCT

GAACGGGGGGTTCGTGCACACAGCCCAGCTTGGAGCGAACGACCTACACCGAACTGAGATA

CCTACAGCGTGAGCTATGAGAAAGCGCCACGCTTCCCGAAGGGAGAAAGGCGGACAGGTAT

CCGGTAAGCGGCAGGGTCGGAACAGGAGAGCGCACGAGGGAGCTTCCAGGGGGAAACGCCT

GGTATCTTTATAGTCCTGTCGGGTTTCGCCACCTCTGACTTGAGCGTCGATTTTTGTGATG

CTCGTCAGGGGGGCGGAGCCTATGGAAAAACGCCAGCAACGCGGCCTTTTTACGGTTCCTG

GCCTTTTGCTGGCCTTTTGCTCACATGT (pAT060)

SEQ ID NO: 79

CCTGCAGGCAGCTGCGCGCTCGCTCGCTCACTGAGGCCGCCCGGGCAAAGCCCGGGCGTCG

GGCGACCTTTGGTCGCCCGGCCTCAGTGAGCGAGCGAGCGCGCAGAGAGGGAGTGGCCAAC

TCCATCACTAGGGGTTCCTGCGGCCAATTCAGTGGATCCCGATAACTATAACGGTCCTAAG

GTAGCGATTTAAATGAGGGCCTATTTCCCATGATTCCTTCATATTTGCATATACGATACAA

GGCTGTTAGAGAGATAATTAGAATTAATTTGAGTGTAAACACAAAGATATTAGTACAAAAT

ACGTGAGGTAGAAAGTAATAATTTCTTGGGTAGTTTGGAGTTTTAAAATTATGTTTTAAAA

TGGACTATCATATGCTTACCGTAACTTGAAAGTATTTCGATTTCTTGGCTTTATATATCTT

GTGGAAAGGACGAGGTACCGTGAGCTGTTGGATTCGCTTAATTCGAATATCCTAAGAGGTT

TACATTTCTTGATATTACTATTAAGCCACTTCAGCTGCTTCTGAGCTGTTGGATTCGCTTA

ATTCGAATATCCTAAGAGGTTTACATTTCTTGATATTAGTATTAAGCCACTTCAGCTGCTT

CTTTTTCCGGGACGCGTCAATTGAGATCTCCGACATTGATTATTGACTAGTTATTAATAGT

AATCAATTACGGGGTCATTAGTTCATAGCCCATATATGGAGTTCCGCGTTACATAACTTAC

GGTAAATGGCCCGCCTGGCTGACCGCCCAACGACCCCCGCCCATTGACGTCAATAATGACG

TATGTTCCCATAGTAACGCCAATAGGGACTTTCCATTGACGTCAATGGGTGGAGTATTTAC

GGTAAACTGCCCACTTGGCAGTACATCAAGTGTATCATATGCCAAGTACGCCCCCTATTGA

CGTCAATGACGGTAAATGGCCCGCCTGGCATTATGCCCAGTACATGACCTTATGGGACTTT

CCTACTTGGCAGTACATCTACGTATTAGTCATCGCTATTACCATGTCGAGGCCACGTTCTG

CTTCACTCTCCCCATCTCCCCCCCCTCCCCACCCCCAATTTTGTATTTATTTATTTTTTAA

TTATTTTGTGCAGCGATGGGGGCGGGGGGGGGGGGGCGCGCGCCAGGCGGGGCGGGGCGGGG

CGAGGGGCGGGGCGGGGCGAGGCGGAGAGGTGCGGCGGCAGCCAATCAGAGCGGCGCGCTC

-continued

CGAAAGTTTCCTTTTATGGCGAGGCGGCGGCGGCGGCGGCCCTATAAAAAGCGAAGCGCGC

GGCGGGCGGGAGCAAGCTTCGTTTAGTGAACCGTCAGATCGCCTGGAGACGCCATCCACGC

TGTTTTGACCTCCATAGAAGACACCGGGACCGATCCAGCCTCCGCGGATTCGAATCCCGGC

CGGGAACGGTGCATTGGAACGCGGATTCCCCGTGCCAAGAGTGACGTAAGTACCGCCTATA

GAGTCTATAGGCCCACAAAAAATGCTTTCTTCTTTTAATATACTTTTTTGTTTATCTTATT

TCTAATACTTTCCCTAATCTCTTTCTTTCAGGGCAATAATGATACAATGTATCATGCCTCT

TTGCACCATTCTAAAGAATAACAGTGATAATTTCTGGGTTAAGGCAATAGCAATATTTCTG

CATATAAATATTTCTGCATATAAATTGTAACTGATGTAAGAGGTTTCATATTGCTAATAGC

AGCTACAATCCAGCTACCATTCTGCTTTTATTTTGTGGTTGGGATAAGGCTGGATTATTCT

GAGTCCAAGCTAGGCCCTTTTGCTAATCGTGTTCATACCTCTTATCTTCCTCCCACAGCTC

CTGGGCAACGTGCTGGTCTGTGTGCTGGCCCATCACTTTGGCAAAGAATTACCGGTGGCAA

CGTGCTGGTTATTGTGCTGTCTCATCATTTTGGCAAAGAATTCACGCCCCAGAGCCGCCAC

CATGGCCTACCCATACGATGTTCCAGATTACGCTCTCACATTCATGGCCTCTGACAGCGAG

GAAGAAGTGTGTGATGAGCGGACGTCCCTAATGTCGGCTGAGAGCCCCACGCCGCGCTCCT

GCCAGGAGGGCAGGCAGGGCCCAGAGGATGGAGAGAACACTGCCCAGTGGAGAAGCCAGGA

GAACGAGGAGGACGGTGAGGAGGACCCTGACCGCTATGTCTGTAGTGGGGTTCCCGGGCGG

CCGCCAGGCCTGGAGGAAGAGCTGACCCTCAAATACGGAGCGAAGCACGTGATCATGCTGT

TTGTGCCTGTCACTCTGTGCATGATCGTGGTGGTAGCCACCATCAAGTCTGTGCGCTTCTA

CACAGAGAAGAATGGACAGCTCATCTACACGCCATTCACTGAGGACACACCCTCGGTGGGC

CAGCGCCTCCTCAACTCCGTGCTGAACACCCTCATCATGATCAGCGTCATCGTGGTTATGA

CCATCTTCTTGGTGGTGCTCTACAAGTACCGCTGCTACAAGTTCATCCATGGCTGGTTGAT

CATGTCTTCACTGATGCTGCTGTTCCTCTTCACCTATATCTACCTTGGGGAAGTGCTCAAG

ACCTACAATGTGGCCATGGACTACCCCACCCTCTTGCTGACTGTCTGGAACTTCGGGGCAG

TGGGCATGGTGTGCATCCACTGGAAGGGCCCTCTGGTGCTGCAGCAGGCCTACCTCATCAT

GATCAGTGCGCTCATGGCCCTAGTGTTCATCAAGTACCTCCCAGAGTGGTCCGCGTGGGTC

ATCCTGGGCGCCATCTCTGTGTATGATCTCGTGGCTGTGCTGTGTCCCAAAGGGCCTCTGA

GAATGCTGGTAGAAACTGCCCAGGAGAGAAATGAGCCCATATTCCCTGCCCTGATATACTC

ATCTGCCATGGTGTGGACGGTTGGCATGGCGAAGCTGGACCCCTCCTCTCAGGGTGCCCTC

CAGCTCCCCTACGACCCGGAGATGGAAGAAGACTCCTATGACAGTTTTGGGGAGCCTTCAT

ACCCCGAAGTCTTTGAGCCTCCCTTGACTGGCTACCCAGGGGAGGAGCTGGAGGAAGAGGA

GGAAAGGGGCGTGAAGCTTGGCCTCGGGGACTTCATCTTCTACAGTGTGCTGGTGGGCAAG

GCGGCTGCCACGGGCAGCGGGGACTGGAATACCACGCTGGCCTGCTTCGTGGCCATCCTCA

TTGGCTTGTGTCTGACCCTCCTGCTGCTTGCTGTGTTCAAGAAGGCGCTGCCCGCCCTCCC

CATCTCCATCACGTTCGGGCTCATCTTTTACTTCTCCACGGACAACCTGGTGCGGCCGTTC

ATGGACACCCTGGCCTCCCATCAGCTCTACATCTAGTAAGCGGCCGCCCTAGGGAGCTCCT

CGAGGGGGTGGCATCCCTGTGACCCCTCCCCAGTGCCTCTCCTGGCCCTGGAAGTTGCCAC

TCCAGTGCCCACCAGCCTTGTCCTAATAAAATTAAGTTGCATCATTTTGTCTGACTAGGTG

TCCTTCTATAATATTATGGGGTGGAGGGGGGTGGTATGGAGCAAGGGGCAAGGGGGGAAGA

CAACCTGTAGGGCCTGCGGGGTCTATTGGGAACCAAGCTGGAGTGCAGTGGCACAATCTTG

GCTCACTGCAATCTCCGCCTCCTGGGTTCAAGCGATTCTCCTGCCTCAGCCTCCCGAGTTG

-continued

TTGGGATTCCAGGCATGCATGACCAGGCTCAGCTAATTTTTGTTTTTTTGGTAGAGACGGG

GTTTCACCATATTGGCCAGGCTGGTCTCCCCCTCCTAATCTCAGGTGATCTACCCACCTTG

GCCTCCCAAATTGCTGGGATTACAGGCGTGAACCACTGCTCCCTTCCCTGTCCTTCCTGGG

CCTAGGGCTGTGCCAGCTGCCTCGTCCCGTCACCTTCTGGCTTCTTCTCTCCCTCCATATC

TTAGCTGTTTTCCTCATGAGAATGTTCCAAATTCGAAATTTCTATTTAACCATTATATATT

TACTTGTTTGCTATTATCTCTGCCCCCAGTAGATTGTTAGCTCCAGAAGAGAAAGGATCAT

GTCTTTTGCTTATCTAGATATGCCCATCTGCCTGGTACAATCTCTGGCACATGTTACAGGC

AACAACTAGTTGTGGAATTGGTGAATGCATGAATAGAAGAATGAGTGAATGAATGAATAGA

CAATAGGCAGAAATCCAGGCTCAAAGAGCTTACAGTCTGGTAAGAGGAATAAAATGTCTGC

AAATAGCCACAGGACAGGTCAAAGGAAGGAGGGGCTATTTCCAGCTGAGGGCACCCCATCA

GGAAAGCACCCCAGACTTCCTTAGGGATAACAGGGTAATGGCGCGGGCCGCAGGAACCCCT

AGTGATGGAGTTGGCCACTCCCTCTCTGCGCGCTCGCTCGCTCACTGAGGCCGGGCGACCA

AAGGTCGCCCGACGCCCGGGCTTTGCCCGGGCGGCCTCAGTGAGCGAGCGAGCGCGCAGCT

GCCTGCAGGGGCGCCTGATGCGGTATTTTCTCCTTACGCATCTGTGCGGTATTTCACACCG

CATACGTCAAAGCAACCATAGTACGCGCCCTGTAGCGGCGCATTAAGCGCGGCGGGTGTGG

TGGTTACGCGCAGCGTGACCGCTACACTTGCCAGCGCCTTAGCGCCCGCTCCTTTCGCTTT

CTTCCCTTCCTTTCTCGCCACGTTCGCCGGCTTTCCCCGTCAAGCTCTAAATCGGGGGCTC

CCTTTAGGGTTCCGATTTAGTGCTTTACGGCACCTCGACCCCAAAAAACTTGATTTGGGTG

ATGGTTCACGTAGTGGGCCATCGCCCTGATAGACGGTTTTTCGCCCTTTGACGTTGGAGTC

CACGTTCTTTAATAGTGGACTCTTGTTCCAAACTGGAACAACACTCAACTCTATCTCGGGC

TATTCTTTTGATTTATAAGGGATTTTGCCGATTTCGGTCTATTGGTTAAAAAATGAGCTGA

TTTAACAAAAATTTAACGCGAATTTTAACAAAATATTAACGTTTACAATTTTATGGTGCAC

TCTCAGTACAATCTGCTCTGATGCCGCATAGTTAAGCCAGCCCCGACACCCGCCAACACCC

GCTGACGCGCCCTGACGGGCTTGTCTGCTCCCGGCATCCGCTTACAGACAAGCTGTGACCG

TCTCCGGGAGCTGCATGTGTCAGAGGTTTTCACCGTCATCACCGAAACGCGCGAGACGAAA

GGGCCTCGTGATACGCCTATTTTTATAGGTTAATGTCATGATAATAATGGTTTCTTAGACG

TCAGGTGGCACTTTTCGGGGAAATGTGCGCGGAACCCCTATTTGTTTATTTTTCTAAATAC

ATTCAAATATGTATCCGCTCATGAGACAATAACCCTGATAAATGCTTCAATAATATTGAAA

AAGGAAGAGTCGATCGATCAAGAGACAGGATGAGGATCGTTTCGCATGATTGAACAAGATG

GATTGCACGCAGGTTCTCCGGCCGCTTGGGTGGAGAGGCTATTCGGCTATGACTGGGCACA

ACAGACAATCGGCTGCTCTGATGCCGCCGTGTTCCGGCTGTCAGCGCAGGGGCGCCCGGTT

CTTTTTGTCAAGACCGACCTGTCCGGTGCCCTGAATGAACTGCAAGACGAGGCAGCGCGGC

TATCGTGGCTGGCCACGACGGGCGTTCCTTGCGCAGCTGTGCTCGACGTTGTCACTGAAGC

GGGAAGGGACTGGCTGCTATTGGGCGAAGTGCCGGGGCAGGATCTCCTGTCATCTCACCTT

GCTCCTGCCGAGAAAGTATCCATCATGGCTGATGCAATGCGGCGGCTGCATACGCTTGATC

CGGCTACCTGCCCATTCGACCACCAAGCGAAACATCGCATCGAGCGAGCACGTACTCGGAT

GGAAGCCGGTCTTGTCGATCAGGATGATCTGGACGAAGAGCATCAGGGGCTCGCGCCAGCC

GAACTGTTCGCCAGGCTCAAGGCGAGCATGCCCGACGGCGAGGATCTCGTCGTGACCCATG

GCGATGCCTGCTTGCCGAATATCATGGTGGAAAATGGCCGCTTTTCTGGATTCATCGACTG

TGGCCGGCTGGGTGTGGCGGATCGCTATCAGGACATAGCGTTGGCTACCCGTGATATTGCT

GAAGAGCTTGGCGGCGAATGGGCTGACCGCTTCCTCGTGCTTTACGGTATCGCCGCTCCCG

-continued

ATTCGCAGCGCATCGCCTTCTATCGCCTTCTTGACGAGTTCTTCTGAACGAGCGTGACACC

ACGATGCCTGTAGCAATGGCAACAACGTTGCGCAAACTATTAACTGGCGAACTACTTACTC

TAGCTTCCCGGCAACAATTAATAGACTGGATGGAGGCGGATAAAGTTGCAGGACCACTTCT

GCGCTCGGCCCTTCCGGCTGGCTGGTTTATTGCTGATAAATCTGGAGCCGGTGAGCGTGGG

TCTCGCGGTATCATTGCAGCACTGGGGCCAGATGGTAAGCCCTCCCGTATCGTAGTTATCT

ACACGACGGGGAGTCAGGCAACTATGGATGAACGAAATAGACAGATCGCTGAGATAGGTGC

CTGAGTGATTAAGCATTGGTAACTGTCAGACCAAGTTTAGTCATATATACTTTAGATTGAT

TTAAAACTTCATTTTTAATTTAAAAGGATCTAGGTGAAGATCCTTTTTGATAATCTCATGA

CCAAAATCCCTTAACGTGAGTTTTCGTTCCACTGAGCGTCAGACCCCGTAGAAAAGATCAA

AGGATCTTCTTGAGATCCTTTTTTTCTGCGCGTAATCTGCTGCTTGCAAACAAAAAAACCA

CCGCTACCAGCGGTGGTTTGTTTGCCGGATCAAGAGCTACCAACTCTTTTTCCGAAGGTAA

CTGGCTTCAGCAGAGCGCAGATACCAAATACTGTTCTTCTAGTGTAGCCGTAGTTAGGCCA

CCACTTCAAGAACTCTGTAGCACCGCCTACATACCTCGCTCTGCTAATCCTGTTACCAGTG

GCTGCTGCCAGTGGCGATAAGTCGTGTCTTACCGGGTTGGACTCAAGACGATAGTTACCGG

ATAAGGCGCAGCGGTCGGGCTGAACGGGGGGTTCGTGCACACAGCCCAGCTTGGAGCGAAC

GACCTACACCGAACTGAGATACCTACAGCGTGAGCTATGAGAAAGCGCCACGCTTCCCGAA

GGGAGAAAGGCGGACAGGTATCCGGTAAGCGGCAGGGTCGGAACAGGAGAGCGCACGAGGG

AGCTTCCAGGGGGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAAACGCCAGCAAC

GCGGCCTTTTTACGGTTCCTGGCCTTTTGCTGGCCTTTTGCTCACATGT (pAT061)

SEQ ID NO: 80

CCTGCAGGCAGCTGCGCGCTCGCTCGCTCACTGAGGCCGCCCGGGCAAAGCCCGGGCGTCG

GGCGACCTTTGGTCGCCCGGCCTCAGTGAGCGAGCGAGCGCGCAGAGAGGGAGTGGCCAAC

TCCATCACTAGGGGTTCCTGCGGCCAATTCAGTGGATCCCGATAACTATAACGGTCCTAAG

GTAGCGATTTAAATGAGGGCCTATTTCCCATGATTCCTTCATATTTGCATATACGATACAA

GGCTGTTAGAGAGATAATTAGAATTAATTTGACTGTAAACACAAAGATATTAGTACAAAAT

ACGTGACGTAGAAAGTAATAATTTCTTGGGTAGTTTGCAGTTTTAAAATTATGTTTTAAAA

TGGACTATCATATGCTTACCGTAACTTGAAAGTATTTCGATTTCTTGGCTTTATATATCTT

GTGGAAAGGACGAGGTACCGTGAGCTGTTGGATTCGCTTAATTCGAATATCCTAAGAGGTT

TACATTTCTTGATATTACTATTAAGCCACTTCAGCTGCTTCTGAGCTGTTGGATTCGCTTA

ATTCGAATATCCTAAGAGGTTTACATTTCTTGATATTAGTATTAAGCCACTTCAGCTGCTT

CTGAGCTGTTGGATTCGCTTAATTCGAATATCCTAAGAGGTTTACATTTCTTGATATTACT

ATTAAGCCACTTCAGCTGCTTCTTTTTCCGGGACGCGTCAATTGAGATCTCCGACATTGAT

TATTGACTAGTTATTAATAGTAATCAATTACGGGGTCATTAGTTCATAGCCCATATATGGA

GTTCCGCGTTACATAACTTACGGTAAATGGCCCGCCTGGCTGACCGCCCAACGACCCCCGC

CCATTGACGTCAATAATGACGTATGTTCCCATAGTAACGCCAATAGGGACTTTCCATTGAC

GTCAATGGGTGGAGTATTTACGGTAAACTGCCCACTTGGCAGTACATCAAGTGTATCATAT

GCCAAGTACGCCCCCTATTGACGTCAATGACGGTAAATGGCCCGCCTGGCATTATGCCCAG

TACATGACCTTATGGGACTTTCCTACTTGGCAGTACATCTACGTATTAGTCATCGCTATTA

CCATGTCGAGGCCACGTTCTGCTTCACTCTCCCCATCTCCCCCCCCTCCCCACCCCCAATT

-continued

TTGTATTTATTTATTTTTTAATTATTTTGTGCAGCGATGGGGGCGGGGGGGGGGGGCGCGC

GCCAGGCGGGGCGGGGCGGGGCGAGGGGCGGGGCGGGGCGAGGCGGAGAGGTGCGGCGGCA

GCCAATCAGAGCGGCGCGCTCCGAAAGTTTCCTTTTATGGCGAGGCGGCGGCGGCGGCGGC

CCTATAAAAAGCGAAGCGCGCGGCGGGCGGGAGCAAGCTTCGTTTAGTGAACCGTCAGATC

GCCTGGAGACGCCATCCACGCTGTTTTGACCTCCATAGAAGACACCGGGACCGATCCAGCC

TCCGCGGATTCGAATCCCGGCCGGGAACGGTGCATTGGAACGCGGATTCCCCGTGCCAAGA

GTGACGTAAGTACCGCCTATAGAGTCTATAGGCCCACAAAAAATGCTTTCTTCTTTTAATA

TACTTTTTTGTTTATCTTATTTCTAATACTTTCCCTAATCTCTTTCTTTCAGGGCAATAAT

GATACAATGTATCATGCCTCTTTGCACCATTCTAAAGAATAACAGTGATAATTTCTGGGTT

AAGGCAATAGCAATATTTCTGCATATAAATATTTCTGCATATAAATTGTAACTGATGTAAG

AGGTTTCATATTGCTAATAGCAGCTACAATCCAGCTACCATTCTGCTTTTATTTTGTGGTT

GGGATAAGGCTGGATTATTCTGAGTCCAAGCTAGGCCCTTTTGCTAATCGTGTTCATACCT

CTTATCTTCCTCCCACAGCTCCTGGGCAACGTGCTGGTCTGTGTGCTGGCCCATCACTTTG

GCAAAGAATTACCGGTGGCAACGTGCTGGTTATTGTGCTGTCTCATCATTTTGGCAAAGAA

TTCACGCCCCAGAGCCGCCACCATGGCCTACCCATACGATGTTCCAGATTACGCTCTCACA

TTCATGGCCTCTGACAGCGAGGAAGAAGTGTGTGATGAGCGGACGTCCCTAATGTCGGCTG

AGAGCCCCACGCCGCGCTCCTGCCAGGAGGGCAGGCAGGGCCCAGAGGATGGAGAGAACAC

TGCCCAGTGGAGAAGCCAGGAGAACGAGGAGGACGGTGAGGAGGACCCTGACCGCTATGTC

TGTAGTGGGGTTCCCGGGCGGCCGCCAGGCCTGGAGGAAGAGCTGACCCTCAAATACGGAG

CGAAGCACGTGATCATGCTGTTTGTGCCTGTCACTCTGTGCATGATCGTGGTGGTAGCCAC

CATCAAGTCTGTGCGCTTCTACACAGAGAAGAATGGACAGCTCATCTACACGCCATTCACT

GAGGACACACCCTCGGTGGGCCAGCGCCTCCTCAACTCCGTGCTGAACACCCTCATCATGA

TCAGCGTCATCGTGGTTATGACCATCTTCTTGGTGGTGCTCTACAAGTACCGCTGCTACAA

GTTCATCCATGGCTGGTTGATCATGTCTTCACTGATGCTGCTGTTCCTCTTCACCTATATC

TACCTTGGGGAAGTGCTCAAGACCTACAATGTGGCCATGGACTACCCCACCCTCTTGCTGA

CTGTCTGGAACTTCGGGGCAGTGGGCATGGTGTGCATCCACTGGAAGGGCCCTCTGGTGCT

GCAGCAGGCCTACCTCATCATGATCAGTGCGCTCATGGCCCTAGTGTTCATCAAGTACCTC

CCAGAGTGGTCCGCGTGGGTCATCCTGGGCGCCATCTCTGTGTATGATCTCGTGGCTGTGC

TGTGTCCCAAAGGGCCTCTGAGAATGCTGGTAGAAACTGCCCAGGAGAGAAATGAGCCCAT

ATTCCCTGCCCTGATATACTCATCTGCCATGGTGTGGACGGTTGGCATGGCGAAGCTGGAC

CCCTCCTCTCAGGGTGCCCTCCAGCTCCCCTACGACCCGGAGATGGAAGAAGACTCCTATG

ACAGTTTTGGGGAGCCTTCATACCCCGAAGTCTTTGAGCCTCCCTTGACTGGCTACCCAGG

GGAGGAGCTGGAGGAAGAGGAGGAAAGGGGCGTGAAGCTTGGCCTCGGGGACTTCATCTTC

TACAGTGTGCTGGTGGGCAAGGCGGCTGCCACGGGCAGCGGGGACTGGAATACCACGCTGG

CCTGCTTCGTGGCCATCCTCATTGGCTTGTGTCTGACCCTCCTGCTGCTTGCTGTGTTCAA

GAAGGCGCTGCCCGCCCTCCCCATCTCCATCACGTTCGGGCTCATCTTTTACTTCTCCACG

GACAACCTGGTGCGGCCGTTCATGGACACCCTGGCCTCCCATCAGCTCTACATCTAGTAAG

CGGCCGCCCTAGGGAGCTCCTCGAGGGGGTGGCATCCCTGTGACCCCTCCCCAGTGCCTCT

CCTGGCCCTGGAAGTTGCCACTCCAGTGCCCACCAGCCTTGTCCTAATAAAATTAAGTTGC

ATCATTTTGTCTGACTAGGTGTCCTTCTATAATATTATGGGGTGGAGGGGGGTGGTATGGA

GCAAGGGGCAAGGGGGAAGACAACCTGTAGGGCCTGCGGGGTCTATTGGGAACCAAGCTG

-continued

GAGTGCAGTGGCACAATCTTGGCTCACTGCAATCTCCGCCTCCTGGGTTCAAGCGATTCTC
CTGCCTCAGCCTCCCGAGTTGTTGGGATTCCAGGCATGCATGACCAGGCTCAGCTAATTTT
TGTTTTTTTGGTAGAGACGGGGTTTCACCATATTGGCCAGGCTGGTCTCCCCCTCCTAATC
TCAGGTGATCTACCCACCTTGGCCTCCCAAATTGCTGGGATTACAGGCGTGAACCACTGCT
CCCTTCCCTGTCCTTCCTGGGCCTAGGGCTGTGCCAGCTGCCTCGTCCCGTCACCTTCTGG
CTTCTTCTCTCCCTCCATATCTTAGCTGTTTTCCTCATGAGAATGTTCCAAATTCGAAATT
TCTATTTAACCATTATATATTTACTTGTTTGCTATTATCTCTGCCCCCAGTAGATTGTTAG
CTCCAGAAGAGAAAGGATCATGTCTTTTGCTTATCTAGATATGCCCATCTGCCTGGTACAA
TCTCTGGCACATGTTACAGGCAACAACTAGTTGTGGAATTGGTGAATGCATGAATAGAAGA
ATGAGTGAATGAATGAATAGACAATAGGCAGAAATCGAGCCTCAAAGAGCTTACAGTCTGG
TAAGAGGAATAAAATGTCTGCAAATAGCCACAGGACAGGTCAAAGGAAGGAGGGGCTATTT
CCAGCTGAGGGCACCCCATCAGGAAAGCACCCCAGACTTCCTTAGGGATAACAGGGTAATG
GCGCGGGCCGCAGGAACCCCTAGTGATGGAGTTGGCCACTCCCTCTCTGCGCGCTCGCTCG
CTCACTGAGGCCGGGCGACCAAAGGTCGCCCGACGCCCGGGCTTTGCCCGGGCGGCCTCAG
TGAGCGAGCGAGCGCGCAGCTGCCTGCAGGGGCGCCTGATGCGGTATTTTCTCCTTACGCA
TCTGTGCGGTATTTCACACCGCATACGTCAAAGCAACCATAGTACGCGCCCTGTAGCGGCG
CATTAAGCGCGGCGGGTGTGGTGGTTACGCGCAGCGTGACCGCTACACTTGCCAGCGCCTT
AGCGCCCGCTCCTTTCGCTTTCTTCCCTTCCTTTCTCGCCACGTTCGCCGGCTTTCCCCGT
CAAGCTCTAAATCGGGGGCTCCCTTTAGGGTTCCGATTTAGTGCTTTACGGCACCTCGACC
CCAAAAAACTTGATTTGGGTGATGGTTCACGTAGTGGGCCATCGCCCTGATAGACGGTTTT
TCGCCCTTTGACGTTGGAGTCCACGTTCTTTAATAGTGGACTCTTGTTCCAAACTGGAACA
ACACTCAACTCTATCTCGGGCTATTCTTTTGATTTATAAGGGATTTTGCCGATTTCGGTCT
ATTGGTTAAAAAATGAGCTGATTTAACAAAAATTTAACGCGAATTTTAACAAAATATTAAC
GTTTACAATTTTATGGTGCACTCTCAGTACAATCTGCTCTGATGCCGCATAGTTAAGCCAG
CCCCGACACCCGCCAACACCCGCTGACGCGCCCTGACGGGCTTGTCTGCTCCCGGCATCCG
CTTACAGACAAGCTGTGACCGTCTCCGGGAGCTGCATGTGTCAGAGGTTTTCACCGTCATC
ACCGAAACGCGCGAGACGAAAGGGCCTCGTGATACGCCTATTTTTATAGGTTAATGTCATG
ATAATAATGGTTTCTTAGACGTCAGGTGGCACTTTTCGGGGAAATGTGCGCGGAACCCCTA
TTTGTTTATTTTTCTAAATACATTCAAATATGTATCCGCTCATGAGACAATAACCCTGATA
AATGCTTCAATAATATTGAAAAAGGAAGAGTCGATCGATCAAGAGACAGGATGAGGATCGT
TTCGCATGATTGAACAAGATGGATTGCACGCAGGTTCTCCGGCCGCTTGGGTGGAGAGGCT
ATTCGGCTATGACTGGGCACAACAGACAATCGGCTGCTCTGATGCCGCCGTGTTCCGGCTG
TCAGCGCAGGGGCGCCCGGTTCTTTTTGTCAAGACCGACCTGTCCGGTGCCCTGAATGAAC
TGCAAGACGAGGCAGCGCGGCTATCGTGGCTGGCCACGACGGGCGTTCCTTGCGCAGCTGT
GCTCGACGTTGTCACTGAAGCGGGAAGGGACTGGCTGCTATTGGGCGAAGTGCCGGGGCAG
GATCTCCTGTCATCTCACCTTGCTCCTGCCGAGAAAGTATCCATCATGGCTGATGCAATGC
GGCGGCTGCATACGCTTGATCCGGCTACCTGCCCATTCGACCACCAAGCGAAACATCGCAT
CGAGCGAGCACGTACTCGGATGGAAGCCGGTCTTGTCGATCAGGATGATCTGGACGAAGAG
CATCAGGGGCTCGCGCCAGCCGAACTGTTCGCCAGGCTCAAGGCGAGCATGCCCGACGGCG
AGGATCTCGTCGTGACCCATGGCGATGCCTGCTTGCCGAATATCATGGTGGAAAATGGCCG

-continued

CTTTTCTGGATTCATCGACTGTGGCCGGCTGGGTGTGGCGGATCGCTATCAGGACATAGCG

TTGGCTACCCGTGATATTGCTGAAGAGCTTGGCGGCGAATGGGCTGACCGCTTCCTCGTGC

TTTACGGTATCGCCGCTCCCGATTCGCAGCGCATCGCCTTCTATCGCCTTCTTGACGAGTT

CTTCTGAACGAGCGTGACACCACGATGCCTGTAGCAATGGCAACAACGTTGCGCAAACTAT

TAACTGGCGAACTACTTACTCTAGCTTCCCGGCAACAATTAATAGACTGGATGGAGGCGGA

TAAAGTTGCAGGACCACTTCTGCGCTCGGCCCTTCCGGCTGGCTGGTTTATTGCTGATAAA

TCTGGAGCCGGTGAGCGTGGGTCTCGCGGTATCATTGCAGCACTGGGGCCAGATGGTAAGC

CCTCCCGTATCGTAGTTATCTACACGACGGGGAGTCAGGCAACTATGGATGAACGAAATAG

ACAGATCGCTGAGATAGGTGCCTCACTGATTAAGCATTGGTAACTGTCAGACCAAGTTTAC

TCATATATACTTTAGATTGATTTAAAACTTCATTTTTAATTTAAAAGGATCTAGGTGAAGA

TCCTTTTTGATAATCTCATGACCAAAATCCCTTAACGTGAGTTTTCGTTCCACTGAGCGTC

AGACCCCGTAGAAAAGATCAAAGGATCTTCTTGAGATCCTTTTTTTCTGCGCGTAATCTGC

TGCTTGCAAACAAAAAAACCACCGCTACCAGCGGTGGTTTGTTTGCCGGATCAAGAGCTAC

CAACTCTTTTTCCGAAGGTAACTGGCTTCAGCAGAGCGCAGATACCAAATACTGTTCTTCT

AGTGTAGCCGTAGTTAGGCCACCACTTCAAGAACTCTGTAGCACCGCCTACATACCTCGCT

CTGCTAATCCTGTTACCAGTGGCTGCTGCCAGTGGCGATAAGTCGTGTCTTACCGGGTTGG

ACTCAAGACGATAGTTACCGGATAAGGCGCAGCGGTCGGGCTGAACGGGGGGTTCGTGCAC

ACAGCCCAGCTTGGAGCGAACGACCTACACCGAACTGAGATACCTAGAGCGTGAGCTATGA

GAAAGCGCCACGCTTCCCGAAGGGAGAAAGGCGGACAGGTATCCGGTAAGCGGCAGGGTCG

GAACAGGAGAGCGCACGAGGGAGCTTCCAGGGGGAAACGCCTGGTATCTTTATAGTCCTGT

CGGGTTTCGCCACCTCTGACTTGAGCGTCGATTTTTGTGATGCTCGTCAGGGGGGCGGAGC

CTATGGAAAAACGCCAGCAACGCGGCCTTTTTACGGTTCCTGGCCTTTTGCTGGCCTTTTG

CTCACATGT (pAT062)

SEQ ID NO: 81

CCTGCAGGCAGCTGCGCGCTCGCTCGCTCACTGAGGCCGCCCGGGCAAAGCCCGGGCGTCG

GGCGACCTTTGGTCGCCCGGCCTCAGTGAGCGAGCGAGCGCGCAGAGAGGGAGTGGCCAAC

TCCATCACTAGGGGTTCCTGCGGCCAATTCAGTGGATCCCGATAACTATAACGGTCCTAAG

GTAGCGATTTAAATCCGGGACGCGTCAATTGAGATCTCCGACATTGATTATTGACTAGTTA

TTAATAGTAATCAATTACGGGGTCATTAGTTCATAGCCCATATATGGAGTTCCGCGTTACA

TAACTTACGGTAAATGGCCCGCCTGGCTGACCGCCCAACGACCCCCGCCCATTGACGTCAA

TAATGACGTATGTTCCCATAGTAACGCCAATAGGGACTTTCCATTGACGTCAATGGGTGGA

GTATTTACGGTAAACTGCCCACTTGGCAGTACATCAAGTGTATCATATGCCAAGTACGCCC

CCTATTGACGTCAATGACGGTAAATGGCCCGCCTGGCATTATGCCCAGTACATGACCTTAT

GGGACTTTCCTACTTGGCAGTACATCTACGTATTAGTCATCGCTATTACCATGTCGAGGCC

ACGTTCTGCTTCACTCTCCCCATCTCCCCCCCCTCCCCACCCCCAATTTTGTATTTATTTA

TTTTTTAATTATTTTGTGCAGCGATGGGGGCGGGGGGGGGGGGGCGCGCGCCAGGCGGGGCG

GGGCGGGGCGAGGGGCGGGGCGGGGCGAGGCGGAGAGGTGCGGCGGCAGCCAATCAGAGCG

GCGCGCTCCGAAAGTTTCCTTTTATGGCGAGGCGGCGGCGGCGGCGGCCCTATAAAAAGCG

AAGCGCGCGGCGGGCGGGAGCAAGCTTCGTTTAGTGAACCGTCAGATCGCCTGGAGACGCC

ATCCACGCTGTTTTGACCTCCATAGAAGACACCGGGACCGATCCAGCCTCCGCGGATTCGA

ATCCCGGCCGGGAACGGTGCATTGGAACGCGGATTCCCCGTGCCAAGAGTGACGTAAGTAC

-continued

CGCCTATAGAGTCTATAGGCCCACAAAAAATGCTTTCTTCTTTTAATATACTTTTTTGTTT
ATCTTATTTCTAATACTTTCCCTAATCTCTTTCTTTCAGGGCAATAATGATACAATGTATC
ATGCCTCTTTGCACCATTCTAAAGAATAACAGTGATAATTTCTGGGTTAAGGCAATAGCAA
TATTTCTGCATATAAATATTTCTGCATATAAATTGTAACTGATGTAAGAGGTTTCATATTG
CTAATAGCAGCTACAATCCAGCTACCATTCTGCTTTTATTTTGTGGTTGGGATAAGGCTGG
ATTATTCTGAGATATCGGTACCTGAGCTGTTGGATTCGCTTAATTCGAATATCCTAAGAGG
TTTACATTTCTTGATATTACTATTAAGCCACTTCAGCTGCTTCTGAGCTGTTGGATTCGCT
TAATTCGAATATCCTAAGAGGTTTACATTTCTTGATATTACTATTAAGCCACTTCAGCTGC
TTCTGAGCTGTTGGATTCGCTTAATTCGAATATCCTAAGAGGTTTACATTTCTTGATATTA
CTATTAAGCCACTTCAGCTGCTTCGTCGACGCTAGGCCCTTTTGCTAATCGTGTTCATACC
TCTTATCTTCCTCCCACAGCTCCTGGGCAACGTGCTGGTCTGTGTGCTGGCCCATCACTTT
GGCAAAGAATTACCGGTGGCAACGTGCTGGTTATTGTGCTGTCTCATCATTTTGGCAAAGA
ATTCACGCCCCAGAGCCGCCACCATGGCCTACCCATACGATGTTCCAGATTACGCTCTCAC
ATTCATGGCCTCTGACAGCGAGGAAGAAGTGTGTGATGAGCGGACGTCCCTAATGTCGGCT
GAGAGCCCCACGCCGCGCTCCTGCCAGGAGGGCAGGCAGGGCCCAGAGGATGGAGAGAACA
CTGCCCAGTGGAGAAGCCAGGAGAACGAGGAGGACGGTGAGGAGGACCCTGACCGCTATGT
CTGTAGTGGGGTTCCCGGGCGGCCGCCAGGCCTGGAGGAAGAGCTGACCCTCAAATACGGA
GCGAAGCACGTGATCATGCTGTTTGTGCCTGTCACTCTGTGCATGATCGTGGTGGTAGCCA
CCATCAAGTCTGTGCGCTTCTACACAGAGAAGAATGGACAGCTCATCTACACGCCATTCAC
TGAGGACACACCCTCGGTGGGCCAGCGCCTCCTCAACTCCGTGCTGAACACCCTCATCATG
ATCAGCGTCATCGTGGTTATGACCATCTTCTTGGTGGTGCTCTACAAGTACCGCTGCTACA
AGTTCATCCATGGCTGGTTGATCATGTCTTCACTGATGCTGCTGTTCCTCTTCACCTATAT
CTACCTTGGGGAAGTGCTCAAGACCTACAATGTGGCCATGGACTACCCCACCCTCTTGCTG
ACTGTCTGGAACTTCGGGGCAGTGGGCATGGTGTGCATCCACTGGAAGGGCCCTCTGGTGC
TGCAGCAGGCCTACCTCATCATGATCAGTGCGCTCATGGCCCTAGTGTTCATCAAGTACCT
CCCAGAGTGGTCCGCGTGGGTCATCCTGGGCGCCATCTCTGTGTATGATCTCGTGGCTGTG
CTGTGTCCCAAAGGGCCTCTGAGAATGCTGGTAGAAACTGCCCAGGAGAGAAATGAGCCCA
TATTCCCTGCCCTGATATACTCATCTGCCATGGTGTGGACGGTTGGCATGGCGAAGCTGGA
CCCCTCCTCTCAGGGTGCCCTCCAGCTCCCCTACGACCCGGAGATGGAAGAAGACTCCTAT
GACAGTTTTGGGGAGCCTTCATACCCCGAAGTCTTTGAGCCTCCCTTGACTGGCTACCCAG
GGGAGGAGCTGGAGGAAGAGGAGGAAAGGGGCGTGAAGCTTGGCCTCGGGGACTTCATCTT
CTACAGTGTGCTGGTGGGCAAGGCGGCTGCCACGGGCAGCGGGGACTGGAATACCACGCTG
GCCTGCTTCGTGGCCATCCTCATTGGCTTGTGTCTGACCCTCCTGCTGCTTGCTGTGTTCA
AGAAGGCGCTGCCCGCCCTCCCCATCTCCATCACGTTCGGGCTCATCTTTTACTTCTCCAC
GGACAACCTGGTGCGGCCGTTCATGGACACCCTGGCCTCCCATCAGCTCTACATCTAGTAA
GCGGCCGCCCTAGGGAGCTCCTCGAGGGGGTGGCATCCCTGTGACCCCTCCCCAGTGCCTC
TCCTGGCCCTGGAAGTTGCCACTCCAGTGCCCACCAGCCTTGTCCTAATAAAATTAAGTTG
CATCATTTTGTCTGACTAGGTGTCCTTCTATAATATTATGGGGTGGAGGGGGGTGGTATGG
AGCAAGGGGCAAGGGGGAAGACAACCTGTAGGGCCTGCGGGGTCTATTGGGAACCAAGCT
GGAGTGCAGTGGCACAATCTTGGCTCACTGCAATCTCCGCCTCCTGGGTTCAAGCGATTCT

-continued

CCTGCCTCAGCCTCCCGAGTTGTTGGGATTCCAGGCATGCATGACCAGGCTCAGCTAATTT

TTGTTTTTTTGGTAGAGACGGGGTTTCACCATATTGGCCAGGCTGGTCTCCCCCTCCTAAT

CTCAGGTGATCTACCCACCTTGGCCTCCCAAATTGCTGGGATTACAGGCGTGAACCACTGC

TCCCTTCCCTGTCCTTCCTGGGCCTAGGGCTGTGCCAGCTGCCTCGTCCCGTCACCTTCTG

GCTTCTTCTCTCCCTCCATATCTTAGCTGTTTTCCTCATGAGAATGTTCCAAATTCGAAAT

TTCTATTTAACCATTATATATTTACTTGTTTGCTATTATCTCTGCCCCCAGTAGATTGTTA

GCTCCAGAAGAGAAAGGATCATGTCTTTTGCTTATCTAGATATGCCCATCTGCCTGGTACA

ATCTCTGGCACATGTTACAGGCAACAACTACTTGTGGAATTGGTGAATGCATGAATAGAAG

AATGAGTGAATGAATGAATAGACAATAGGCAGAAATCCAGCCTCAAAGAGCTTACAGTCTG

GTAAGAGGAATAAAATGTCTGCAAATAGCCACAGGACAGGTCAAAGGAAGGAGGGGCTATT

TCCAGCTGAGGGCACCCCATCAGGAAAGCACCCCAGACTTCCTTAGGGATAACAGGGTAAT

GGCGCGGGCCGCAGGAACCCCTAGTGATGGAGTTGGCCACTCCCTCTCTGCGCGCTCGCTC

GCTCACTGAGGCCGGGCGACCAAAGGTCGCCCGACGCCCGGGCTTTGCCCGGGCGGCCTCA

GTGAGCGAGCGAGCGCGCAGCTGCCTGCAGGGGCGCCTGATGCGGTATTTTCTCCTTACGC

ATCTGTGCGGTATTTCACACCGCATACGTCAAAGCAACCATAGTACGCGCCCTGTAGCGGC

GCATTAAGCGCGGCGGGTGTGGTGGTTACGCGCAGCGTGACCGCTACACTTGCCAGCGCCT

TAGCGCCCGCTCCTTTCGCTTTCTTCCCTTCCTTTCTCGCCACGTTCGCCGGCTTTCCCCG

TCAAGCTCTAAATCGGGGGCTCCCTTTAGGGTTCCGATTTAGTGCTTTACGGCACCTCGAC

CCCAAAAAACTTGATTTGGGTGATGGTTCACGTAGTGGGCCATCGCCCTGATAGACGGTTT

TTCGCCCTTTGACGTTGGAGTCCACGTTCTTTAATAGTGGACTCTTGTTCCAAACTGGAAC

AACACTCAACTCTATCTCGGGCTATTCTTTTGATTTATAAGGGATTTTGCCGATTTCGGTC

TATTGGTTAAAAAATGAGCTGATTTAACAAAAATTTAACGCGAATTTTAACAAAATATTAA

CGTTTACAATTTTATGGTGCACTCTCAGTACAATCTGCTCTGATGCCGCATAGTTAAGCCA

GCCCCGACACCCGCCAACACCCGCTGACGCGCCCTGACGGGCTTGTCTGCTCCCGGCATCC

GCTTACAGACAAGCTGTGACCGTCTCCGGGAGCTGCATGTGTCAGAGGTTTTCACCGTCAT

CACCGAAACGCGCGAGACGAAAGGGCCTCGTGATACGCCTATTTTTATAGGTTAATGTCAT

GATAATAATGGTTTCTTAGACGTCAGGTGGCACTTTTCGGGGAAATGTGCGCGGAACCCCT

ATTTGTTTATTTTTCTAAATACATTCAAATATGTATCCGCTCATGAGACAATAACCCTGAT

AAATGCTTCAATAATATTGAAAAAGGAAGAGTCGATCGATCAAGAGACAGGATGAGGATCG

TTTCGCATGATTGAACAAGATGGATTGCACGCAGGTTCTCCGGCCGCTTGGGTGGAGAGGC

TATTCGGCTATGACTGGGCACAACAGACAATCGGCTGCTCTGATGCCGCCGTGTTCCGGCT

GTCAGCGCAGGGGCGCCCGGTTCTTTTTGTCAAGACCGACCTGTCCGGTGCCCTGAATGAA

CTGCAAGACGAGGCAGCGCGGCTATCGTGGCTGGCCACGACGGGCGTTCCTTGCGCAGCTG

TGCTCGACGTTGTCACTGAAGCGGGAAGGGACTGGCTGCTATTGGGCGAAGTGCCGGGGCA

GGATCTCCTGTCATCTCACCTTGCTCCTGCCGAGAAAGTATCCATCATGGCTGATGCAATG

CGGCGGCTGCATACGCTTGATCCGGCTACCTGCCCATTCGACCACCAAGCGAAACATCGCA

TCGAGCGAGCACGTACTCGGATGGAAGCCGGTCTTGTCGATCAGGATGATCTGGACGAAGA

GCATCAGGGGCTCGCGCCAGCCGAACTGTTCGCCAGGCTCAAGGCGAGCATGCCCGACGGC

GAGGATCTCGTCGTGACCCATGGCGATGCCTGCTTGCCGAATATCATGGTGGAAAATGGCC

GCTTTTCTGGATTCATCGACTGTGGCCGGCTGGGTGTGGCGGATCGCTATCAGGACATAGC

GTTGGCTACCCGTGATATTGCTGAAGAGCTTGGCGGCGAATGGGCTGACCGCTTCCTCGTG

-continued

CTTTACGGTATCGCCGCTCCCGATTCGCAGCGCATCGCCTTCTATCGCCTTCTTGACGAGT

TCTTCTGAACGAGCGTGACACCACGATGCCTGTAGCAATGGCAACAACGTTGCGCAAACTA

TTAACTGGCGAACTACTTACTCTAGCTTCCCGGCAACAATTAATAGACTGGATGGAGGCGG

ATAAAGTTGCAGGACCACTTCTGCGCTCGGCCCTTCCGGCTGGCTGGTTTATTGCTGATAA

ATCTGGAGCCGGTGAGCGTGGGTCTCGCGGTATCATTGCAGCACTGGGGCCAGATGGTAAG

CCCTCCCGTATCGTAGTTATCTACACGACGGGGAGTCAGGCAACTATGGATGAACGAAATA

GACAGATCGCTGAGATAGGTGCCTCACTGATTAAGCATTGGTAACTGTCAGACCAAGTTTA

CTCATATATACTTTAGATTGATTTAAAACTTCATTTTTAATTTAAAAGGATCTAGGTGAAG

ATCCTTTTTGATAATCTCATGACCAAAATCCCTTAACGTGAGTTTTCGTTCCACTGAGCGT

CAGACCCCGTAGAAAAGATCAAAGGATCTTCTTGAGATCCTTTTTTTCTGCGCGTAATCTG

CTGCTTGCAAACAAAAAAACCACCGCTACCAGCGGTGGTTTGTTTGCCGGATCAAGAGCTA

CCAACTCTTTTTCCGAAGGTAACTGGCTTCAGCAGAGCGCAGATACCAAATACTGTTCTTC

TAGTGTAGCCGTAGTTAGGCCACCACTTCAAGAACTCTGTAGCACCGCCTACATACCTCGC

TCTGCTAATCCTGTTACCAGTGGCTGCTGCCAGTGGCGATAAGTCGTGTCTTACCGGGTTG

GACTCAAGACGATAGTTACCGGATAAGGCGCAGCGGTCGGGCTGAACGGGGGGTTCGTGCA

CACAGCCCAGCTTGGAGCGAACGACCTACACCGAACTGAGATACCTACAGCGTGAGCTATG

AGAAAGCGCCACGCTTCCCGAAGGGAGAAAGGCGGACAGGTATCCGGTAAGCGGCAGGGTC

GGAACAGGAGAGCGCACGAGGGAGCTTCCAGGGGGAAACGCCTGGTATCTTTATAGTCCTG

TCGGGTTTCGCCACCTCTGACTTGAGCGTCGATTTTTGTGATGCTCGTCAGGGGGGCGGAG

CCTATGGAAAAACGCCAGCAACGCGGCCTTTTTACGGTTCCTGGCCTTTTGCTGGCCTTTT

GCTCACATGT

SEQ ID NO: 82
(endogenous PSEN1 specific forward primer)

CCTGACCACCTTGCACTATT

SEQ ID NO: 83
(endogenous PSEN1 specific probe)

TGTGTCCCTCGGTGCAGAAACTAC

SEQ ID NO: 84
(endogenous PSEN1 specific reverse primer)

CAACTTCCGGGCCTATCATATC

SEQ ID NO: 85
(plasmid-encoded transcript specific forward primer)

TGGACCAATTAGCATTCCATCA

SEQ ID NO: 86
(plasmid-encoded transcript specific probe)

TGAACTACGCCTGAGGATCCGATCT

SEQ ID NO: 87
(plasmid-encoded transcript specific reverse primer)

GCCAGAAGTCAGATGCTCAA

SEQ ID NO: 88
(endogenous PSEN2 specific forward primer)

GAGAAGGTCAGATTAGGGCG

SEQ ID NO: 89
(endogenous PSEN2 specific probe)

AAAGAGTGTGCTCGGGAGTGC

SEQ ID NO: 90
(endogenous PSEN2 specific reverse primer)

TCGTAGGGAACTGGCTTTTC

Any and all references and citations to other documents, such as patents, patent applications, patent publications, journals, books, papers, web contents, that have been made throughout this disclosure are hereby incorporated herein by reference in their entirety for all purposes.

Although the present invention has been described with reference to specific details of certain embodiments thereof in the above examples, it will be understood that modifications and variations are encompassed within the spirit and scope of the invention. Accordingly, the invention is limited only by the following claims.

What is claimed is:

1. An expression cassette comprising:

a. a first polynucleotide comprising SEQ ID NO: 13, wherein the first polynucleotide is operably linked to one or more first promoters; and b. a second polynucleotide comprising SEQ ID NO: 41, SEQ ID NO: 48, or nucleotides 1906-3303 of SEQ ID NO: 68; and wherein the second polynucleotide is operably linked to a second promoter.

2. The expression cassette of claim 1, wherein at least one of the one or more first promoters is an RNA polymerase II or III promoter.

3. The expression cassette of claim 2, wherein each of the one or more first promoters is an RNA polymerase II or III promoter.

4. The expression cassette of claim 2, wherein the one or more first promoters comprise a U6 promoter, a U61 promoter, a U69 promoter, a H1 promoter, a ubiquitous or neuron-specific promoter, or any combination thereof.

5. The expression cassette of claim 1, wherein the second promoter is a RNA polymerase II promoter.

6. The expression cassette of claim 5, wherein the RNA polymerase II promoter is a ubiquitous or neuron-specific promoter.

7. A vector comprising the expression cassette of claim 1.

8. A set of vectors comprising:

a. a first vector comprising an expression cassette comprising a first polynucleotide encoding SEQ ID NO: 13, wherein the first polynucleotide is operably linked to one or more first promoters; and b. a second vector comprising a second polynucleotide encoding SEQ ID NO: 41, SEQ ID NO: 48, or nucleotides 1906-3303 of SEQ ID NO: 68 and wherein the second polynucleotide is operably linked to a second promoter.

9. The vector of claim 7, wherein the vector or vectors are viral vectors.

10. The vector of claim 9, wherein the viral vectors are an adeno-associated virus (AAV) vector, a retroviral vector, a lentiviral vector, or an adenoviral vector.

11. The vector of claim 10, wherein the AAV vectors are AAV1, AAV2, AAV3, AAV4, AAV5, AAV6, AAV7, AAV8, AAV9, AAVDJ, AAVrh10, AAV11, AAV12, AAV2/1, AAV2/5, AAV2/6, AAV2/7, AAV2/8, AAV2/9, AAV2/rh10, AAV2/11, AAV2/12, PHP.B, and PHP.B derivatives [PHP.eR, PHP.S], AAV8 [K137R], AAV-TT, rAAV-retro, AAV9.HR, AAV1 CAM mutants, or AAV9 [586-590] swap mutants.

12. A kit comprising the vector of claim 7.

13. A kit comprising:

a. one or more antisense oligonucleotides comprising SEQ ID NO: 13; and b. a vector comprising a polynucleotide encoding SEQ ID NO: 41, SEQ ID NO:

48, or nucleotides 1906-3303 of SEQ ID NO: 68; and wherein the polynucleotide is operably linked to a promoter in the vector.

14. The kit of claim 13, wherein each of the one or more antisense oligonucleotides is independently selected from a short hairpin RNA (shRNA), a short interfering RNA (siRNA), a micro interfering RNA (miRNA), a small temporal RNA (stRNA) or an endoribonuclease-prepared siRNA (esiRNA).

15. The kit of claim 14, wherein at least one of the one or more antisense oligonucleotides comprises one or more modified nucleobases.

16. The kit of claim 15, wherein each of the one or more modified nucleobases is independently selected from a non-naturally occurring nucleobase, a locked nucleic acids (LNA), or a peptide nucleic acids (PNA).

17. A method of treating a neurodegenerative disease, disorder, or condition comprising administering to a subject in need thereof the vector of claim 16.

18. The method of claim 17, wherein the neurodegenerative disease, disorder, or condition is Alzheimer's disease, sporadic Alzheimer's disease, familial Alzheimer's disease, frontotemporal dementia, frontotemporal lobar degeneration, Pick's disease, Lewy body dementia, memory loss, cognitive impairment, or mild cognitive impairment.

19. An isolated nucleic acid sequence comprising SEQ ID NO: 41, SEQ ID NO: 48, or nucleotides 1906-3303 of SEQ ID NO: 68.

20. A method of treating a neurodegenerative disease, disorder, or condition comprising administering to a subject in need thereof the set of vectors of claim 8.

* * * * *

SEQUENCE LISTING

<160> NUMBER OF SEQ ID NOS: 90

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
gcaaaggctg ttgtcacttg c 21

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2
atagaaatac tgtttcacag aaaacaa 27

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3
tcatcttctt cctcatcttg ctc 23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
acaaagagca tgatcacatg c 21

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
atcatgatgg cagcattcag aattgag 27

<210> SEQ ID NO 6

<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 6
acaatgacac tgatcatgat ggc 23

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 7
tagtcatgac aacaatgaca ctgatca 27

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 8
tttctctcct gagctgtttc aac 23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 9
cttctgccat attcaccaac cac 23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 10
ggaaagttcc tggacagcag ctc 23

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 11
ggttgtgttc cagtctccac tggc 24

<210> SEQ ID NO 12
<211> LENGTH: 27

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaagaagaaa catccatggg attctaa 27

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
atagtcaaag aagaaacatc cat 23

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtgtccacat ctaacaaagt caagatt 27

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cagtgaaatc gtcctgtgac cacgcgt 27

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tgtgaccacg cgtcaagctg ctgatgg 27

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ttgacatcat tagctcactg tatcccc 27

<210> SEQ ID NO 18
<211> LENGTH: 25
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 18
tccaagttgc ttagaaagct tctac 25

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 19
atatcttacc aagaatttga aaggtat 27

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 20
tttcttcatc agtaaaattc agagggg 27

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21
ttgggaaaag tcactttagc tctgtgg 27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 22
cagtgaatgg cgtgtagatg agctgtc 27

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 23
tcagtgaatg gcgtgtagat gagctgt 27

<210> SEQ ID NO 24
<211> LENGTH: 27
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 24

ctcagtgaat ggcgtgtaga tgagctg                                          27


<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25

tggtcataac cacgatgacg ctgatca                                          27


<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26

agcggtactt gtagagcacc accaaga                                          27


<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27

actgtcatag gagtcttctt ccatctc                                          27


<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28

tatacaactg catccaatga aaattcc                                          27


<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29

aaaactatac aactgcatcc aatgaaa                                          27


<210> SEQ ID NO 30
<211> LENGTH: 27
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 30
gtaaaactat acaactgcat ccaatga 27

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ttctcagttc atctggataa acctgct 27

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tgatattact attaagccac ttcccag 27

<210> SEQ ID NO 33
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gaatcccata gatacttctt ctttaaatgt ccatacaaga agaaacatcc atgggattc 59

<210> SEQ ID NO 34
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
acttttcatc aaatgcaggt aaggtttaca ttttacaact gcatccaatg aaaatt 56

<210> SEQ ID NO 35
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
aggcctctct ctagaatccc atagatactt cttctttaaa tgtccataca agaagaaaca 60
tccatgggat tcgaatgggg ctg 83

<210> SEQ ID NO 36
<211> LENGTH: 82
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 36
tgagctgttg gattactttt catcaaatgc aggtaaggtt tacattttac aactgcatcc 60
aatgaaaatt ttcagctgct tc 82

<210> SEQ ID NO 37
<211> LENGTH: 3169
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 37
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctaccag ggtaatgaag 180
gtcgggcagg aagagggcct atttcccatg attccttcat atttgcatat acgatacaag 240
gctgttagag agataattag aattaatttg actgtaaaca caaagatatt agtacaaaat 300
acgtgacgta gaaagtaata atttcttggg tagtttgcag ttttaaaatt atgttttaaa 360
atggactatc atatgcttac cgtaacttga aagtatttcg atttcttggc tttatatatc 420
ttgtggaaag gacgaaacac caggcctctc tctagaatcc catagatact tcttctttaa 480
atgtccatac aagaagaaac atccatggga ttcgaatggg gctgaggcct ctctctagaa 540
tcccatagat acttcttctt taaatgtcca tacaagaaga aacatccatg ggattcgaat 600
ggggctgagg cctctctcta gaatcccata gatacttctt ctttaaatgt ccatacaaga 660
agaaacatcc atgggattcg aatggggctg tttttcgcgt cgacattgat tattgactag 720
ttattaatag taatcaatta cggggtcatt agttcatagc ccatatatgg agttccgcgt 780
tacataactt acggtaaatg gcccgcctgg ctgaccgccc aacgaccccc gcccattgac 840
gtcaataatg acgtatgttc ccatagtaac gccaataggg actttccatt gacgtcaatg 900
ggtggagtat ttacggtaaa ctgcccactt ggcagtacat caagtgtatc atatgccaag 960
tacgccccct attgacgtca atgacggtaa atggcccgcc tggcattatg cccagtacat 1020
gaccttatgg gactttccta cttggcagta catctacgta ttagtcatcg ctattaccat 1080
gtcgaggcca cgttctgctt cactctcccc atctcccccc cctccccacc cccaattttg 1140
tatttattta tttttttaatt attttgtgca gcgatggggg cggggggggg gggcgcgcgc 1200
caggcggggc ggggcggggc gaggggcggg gcggggcgag gcggagaggt gcggcggcag 1260
ccaatcagag cggcgcgctc cgaaagtttc cttttatggc gaggcggcgg cggcggcggc 1320
cctataaaaa gcgaagcgcg cggcggggcc accatgacag agttacctgc accgttgtcc 1380
tacttccaga atgcacagat gtctgaggac aaccacctga gcaatactgt acgtagccag 1440
aatgacaata gagaacggca ggagcacaac gacagacgga gccttggcca ccctgagcca 1500
ttatctaatg gacgacccca gggtaactcc cggcaggtgg tggagcaaga tgaggaagaa 1560
gatgaggagc tgacattgaa atatggcgcc aagcatgtga tcatgctctt tgtccctgtg 1620
actctctgca tggtggtggt cgtggctacc attaagtcag tcagctttta tacccggaag 1680
gatgggcagc taatctatac cccattcaca gaagataccg agactgtggg ccagagagcc 1740

```
ctgcactcaa ttctgaatgc tgccatcatg atcagtgtca ttgttgtcat gactatcctc   1800
ctggtggttc tgtataaata caggtgctat aaggtcatcc atgcctggct tattatatca   1860
tctctattgt tgctgttctt tttttcattc atttacttgg gggaagtgtt taaaacctat   1920
aacgttgctg tggactacat tactgttgca ctcctgatct ggaattttgg tgtggtggga   1980
atgatttcca ttcactggaa aggtccactt cgactccagc aggcatatct cattatgatt   2040
agtgccctca tggccctggt gtttatcaag tacctccctg aatggactgc gtggctcatc   2100
ttggctgtga tttcagtata tgatttagtg gctgttttgt gtccgaaagg tccacttcgt   2160
atgctggttg aaacagctca ggagagaaat gaaacgcttt ttccagctct catttactcc   2220
tcaacaatgg tgtggttggt gaatatggca gaaggagacc cggaagctca aaggagagta   2280
tccaaaaatt ccaagtataa tgcagaaagc acagaaaggg agtcacaaga cactgttgca   2340
gagaatgatg atggcgggtt cagtgaggaa tgggaagccc agagggacag tcatctaggg   2400
cctcatcgct ctacacctga gtcacgagct gctgtccagg aactttccag cagtatcctc   2460
gctggtgaag acccagagga aaggggagta aaacttggat tgggagattt cattttctac   2520
agtgttctgg ttggtaaagc ctcagcaaca gccagtggag actggaacac aaccatagcc   2580
tgtttcgtag ccatattaat tggtttgtgc cttacattat tactccttgc cattttcaag   2640
aaagcattgc cagctcttcc aatctccatc acctttgggc ttgttttcta ctttgccaca   2700
gattatcttg tacagccttt tatggaccaa ttagcattcc atcaatttta tatctagcat   2760
agtcgacccc tatccatcac actggcggcc gctcgaggac ggggtgaact acgcctgagg   2820
atccgatctt tttccctctg ccaaaaatta tggggacatc atgaagcccc ttgagcatct   2880
gacttctggc taataaagga aatttatttt cattgcaata gtgtgttgga atttttgtg    2940
tctctcactc ggaagcaatt cgttgatctg aatttcgacc acccataata cccattaccc   3000
tggtagataa gtagcatggc gggttaatca ttaactacaa ggaaccccta gtgatggagt   3060
tggccactcc ctctctgcgc gctcgctcgc tcactgaggc cgggcgacca aaggtcgccc   3120
gacgcccggg ctttgcccgg gcggcctcag tgagcgagcg agcgcgcag              3169
```

```
<210> SEQ ID NO 38
<211> LENGTH: 3110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
```

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctaccag ggtaatgaag    180
gtcgggcagg aagagggcct atttcccatg attccttcat atttgcatat acgatacaag    240
gctgttagag agataattag aattaatttg actgtaaaca caaagatatt agtacaaaat    300
acgtgacgta gaaagtaata atttcttggg tagtttgcag ttttaaaatt atgttttaaa    360
atggactatc atatgcttac cgtaacttga aagtatttcg atttcttggc tttatatatc    420
ttgtggaaag gacgaaacac catgagctgt tggattactt ttcatcaaat gcaggtaagg    480
tttacatttt acaactgcat ccaatgaaaa ttttcagctg cttctgagct gttggattac    540
ttttcatcaa atgcaggtaa ggtttacatt ttacaactgc atccaatgaa aattttcagc    600
```

```
tgcttctgag ctgttggatt acttttcatc aaatgcaggt aaggtttaca ttttacaact    660
gcatccaatg aaaattttca gctgcttctt tttcgcgtcg acattgatta ttgactagtt    720
attaatagta atcaattacg gggtcattag ttcatagccc atatatggag ttccgcgtta    780
cataacttac ggtaaatggc ccgcctggct gaccgcccaa cgacccccgc ccattgacgt    840
caataatgac gtatgttccc atagtaacgc caatagggac tttccattga cgtcaatggg    900
tggagtattt acggtaaact gcccacttgg cagtacatca agtgtatcat atgccaagta    960
cgccccctat tgacgtcaat gacggtaaat ggcccgcctg gcattatgcc cagtacatga   1020
ccttatggga ctttcctact tggcagtaca tctacgtatt agtcatcgct attaccatgt   1080
cgaggccacg ttctgcttca ctctccccat ctcccccccc tccccacccc caattttgta   1140
tttatttatt ttttaattat tttgtgcagc gatgggggcg gggggggggg gcgcgcgcca   1200
ggcggggcgg ggcggggcga ggggcggggc ggggcgaggc ggagaggtgc ggcggcagcc   1260
aatcagagcg gcgcgctccg aaagtttcct tttatggcga ggcggcggcg gcggcggccc   1320
tataaaaagc gaagcgcgcg gcggggccac catgctcaca ttcatggcct ctgacagcga   1380
ggaagaagtg tgtgatgagc ggacgtccct aatgtcggct gagagcccca cgccgcgctc   1440
ctgccaggag ggcaggcagg gcccagagga tggagagaac actgcccagt ggagaagcca   1500
ggagaacgag gaggacggtg aggaggaccc tgaccgctat gtctgtagtg ggttcccgg    1560
gcggccgcca ggcctggagg aagagctgac cctcaaatac ggagcgaagc acgtgatcat   1620
gctgtttgtg cctgtcactc tgtgcatgat cgtggtggta gccaccatca agtctgtgcg   1680
cttctacaca gagaagaatg gacagctcat ctacacgcca ttcactgagg acacaccctc   1740
ggtgggccag cgcctcctca actccgtgct gaacaccctc atcatgatca gcgtcatcgt   1800
ggttatgacc atcttcttgg tggtgctcta caagtaccgc tgctacaagt tcatccatgg   1860
ctggttgatc atgtcttcac tgatgctgct gttcctcttc acctatatct accttgggga   1920
agtgctcaag acctacaatg tggccatgga ctacccccacc ctcttgctga ctgtctggaa  1980
cttcggggca gtgggcatgg tgtgcatcca ctggaagggc cctctggtgc tgcagcaggc   2040
ctacctcatc atgatcagtg cgctcatggc cctagtgttc atcaagtacc tcccagagtg   2100
gtccgcgtgg gtcatcctgg gcgccatctc tgtgtatgat ctcgtggctg tgctgtgtcc   2160
caaagggcct ctgagaatgc tggtagaaac tgcccaggag agaaatgagc ccatattccc   2220
tgccctgata tactcatctg ccatggtgtg gacggttggc atggcgaagc tggacccctc   2280
ctctcagggt gccctccagc tcccctacga cccggagatg gaagaagact cctatgacag   2340
ttttggggag ccttcatacc ccgaagtctt tgagcctccc ttgactggct acccagggga   2400
ggagctggag gaagaggagg aaaggggcgt gaagcttggc ctcggggact tcatcttcta   2460
cagtgtgctg gtgggcaagg cggctgccac gggcagcggg gactggaata ccacgctggc   2520
ctgcttcgtg gccatcctca ttggcttgtg tctgaccctc ctgctgcttg ctgtgttcaa   2580
gaaggcgctg cccgccctcc ccatctccat cacgttcggg ctcatctttt acttctccac   2640
ggacaacctg gtgcggccgt tcatggacac cctggcctcc catcagctct acatctgaca   2700
tagtcgaccc ctatccatca cactggcggc cgctcgagga cggggtgaac tacgcctgag   2760
gatccgatct ttttccctct gccaaaaatt atggggacat catgaagccc cttgagcatc   2820
tgacttctgg ctaataaagg aaatttattt tcattgcaat agtgtgttgg aatttttttgt  2880
gtctctcact cggaagcaat tcgttgatct gaatttcgac cacccataat acccattacc   2940
ctggtagata agtagcatgg cgggttaatc attaactaca aggaacccct agtgatggag   3000
```

ttggccactc cctctctgcg cgctcgctcg ctcactgagg ccgggcgacc aaaggtcgcc 3060
cgacgcccgg gctttgcccg ggcggcctca gtgagcgagc gagcgcgcag 3110

<210> SEQ ID NO 39
<211> LENGTH: 1404
<212> TYPE: DNA
<213> ORGANISM: Homo sapiens

<400> SEQUENCE: 39
atgacagagt tacctgcacc gttgtcctac ttccagaatg cacagatgtc tgaggacaac 60
cacctgagca atactgtacg tagccagaat gacaatagag aacggcagga gcacaacgac 120
agacggagcc ttggccaccc tgagccatta tctaatggac gaccccaggg taactcccgg 180
caggtggtgg agcaagatga ggaagaagat gaggagctga cattgaaata tggcgccaag 240
catgtgatca tgctctttgt ccctgtgact ctctgcatgg tggtggtcgt ggctaccatt 300
aagtcagtca gcttttatac ccggaaggat gggcagctaa tctatacccc attcacagaa 360
gataccgaga ctgtgggcca gagagccctg cactcaattc tgaatgctgc catcatgatc 420
agtgtcattg ttgtcatgac tatcctcctg gtggttctgt ataaatacag gtgctataag 480
gtcatccatg cctggcttat tatatcatct ctattgttgc tgttcttttt ttcattcatt 540
tacttggggg aagtgtttaa aacctataac gttgctgtgg actacattac tgttgcactc 600
ctgatctgga attttggtgt ggtgggaatg atttccattc actggaaagg tccacttcga 660
ctccagcagg catatctcat tatgattagt gccctcatgg ccctggtgtt tatcaagtac 720
ctccctgaat ggactgcgtg gctcatcttg gctgtgattt cagtatatga tttagtggct 780
gttttgtgtc cgaaaggtcc acttcgtatg ctggttgaaa cagctcagga gagaaatgaa 840
acgctttttc cagctctcat ttactcctca acaatggtgt ggttggtgaa tatggcagaa 900
ggagacccgg aagctcaaag gagagtatcc aaaaattcca agtataatgc agaaagcaca 960
gaaagggagt cacaagacac tgttgcagag aatgatgatg gcgggttcag tgaggaatgg 1020
gaagcccaga gggacagtca tctagggcct catcgctcta cacctgagtc acgagctgct 1080
gtccaggaac tttccagcag tatcctcgct ggtgaagacc cagaggaaag gggagtaaaa 1140
cttggattgg gagatttcat tttctacagt gttctggttg gtaaagcctc agcaacagcc 1200
agtggagact ggaacacaac catagcctgt ttcgtagcca tattaattgg tttgtgcctt 1260
acattattac tccttgccat tttcaagaaa gcattgccag ctcttccaat ctccatcacc 1320
tttgggcttg ttttctactt tgccacagat tatcttgtac agccttttat ggaccaatta 1380
gcattccatc aattttatat ctag 1404

<210> SEQ ID NO 40
<211> LENGTH: 1347
<212> TYPE: DNA
<213> ORGANISM: Homo sapiens

<400> SEQUENCE: 40
atgctcacat tcatggcctc tgacagcgag gaagaagtgt gtgatgagcg gacgtcccta 60
atgtcggctg agagccccac gccgcgctcc tgccaggagg gcaggcaggg cccagaggat 120
ggagagaaca ctgcccagtg gagaagccag gagaacgagg aggacggtga ggaggaccct 180
gaccgctatg tctgtagtgg ggttcccggg cggccgccag gcctggagga agagctgacc 240
ctcaaatacg gagcgaagca cgtgatcatg ctgtttgtgc ctgtcactct gtgcatgatc 300
gtggtggtag ccaccatcaa gtctgtgcgc ttctacacag agaagaatgg acagctcatc 360
tacacgccat tcactgagga cacaccctcg gtgggccagc gcctcctcaa ctccgtgctg 420
aacaccctca tcatgatcag cgtcatcgtg gttatgacca tcttcttggt ggtgctctac 480
aagtaccgct gctacaagtt catccatggc tggttgatca tgtcttcact gatgctgctg 540
ttcctcttca cctatatcta ccttggggaa gtgctcaaga cctacaatgt ggccatggac 600
taccccaccc tcttgctgac tgtctggaac ttcggggcag tgggcatggt gtgcatccac 660
tggaagggcc ctctggtgct gcagcaggcc tacctcatca tgatcagtgc gctcatggcc 720
ctagtgttca tcaagtacct cccagagtgg tccgcgtggg tcatcctggg cgccatctct 780
gtgtatgatc tcgtggctgt gctgtgtccc aaagggcctc tgagaatgct ggtagaaact 840
gcccaggaga gaaatgagcc catattccct gccctgatat actcatctgc catggtgtgg 900
acggttggca tggcgaagct ggacccctcc tctcagggtg ccctccagct cccctacgac 960
ccggagatgg aagaagactc ctatgacagt tttggggagc cttcataccc cgaagtcttt 1020
gagcctccct tgactggcta cccaggggag gagctggagg aagaggagga aaggggcgtg 1080
aagcttggcc tcggggactt catcttctac agtgtgctgg tgggcaaggc ggctgccacg 1140
ggcagcgggg actggaatac cacgctggcc tgcttcgtgg ccatcctcat tggcttgtgt 1200
ctgaccctcc tgctgcttgc tgtgttcaag aaggcgctgc ccgccctccc catctccatc 1260
acgttcgggc tcatctttta cttctccacg gacaacctgg tgcggccgtt catggacacc 1320
ctggcctccc atcagctcta catctga 1347

<210> SEQ ID NO 41
<211> LENGTH: 1432
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 41
cccagatctg ccaccatgac agagttacct gcaccgttgt cctacttcca gaatgcacag 60
atgtctgagg acaaccacct gagcaatact gtacgtagcc agaatgacaa tagagaacgg 120
caggagcaca acgacagacg gagccttggc caccctgagc cattatctaa tggacgaccc 180
cagggtaact cccggcaggt ggtggaacag gacgaagagg aggacgaaga gctgacattg 240
aaatatggcg ccaaacacgt cataatgcta ttcgtgcctg tgactctctg catggtggtg 300
gtcgtggcta ccattaagtc agtcagcttt tatacccgga aggatgggca gctaatctat 360
accccattca cagaagatac cgagactgtg ggccagagag ccctgcatag catactcaag 420
gcagctatta tgatttccgt gatcgttgtc atgactatcc tcctggtggt tctgtataaa 480
tacaggtgct ataaggtcat ccatgcctgg cttattatat catctctatt gttgctgttc 540 ttttttttcat tcatttactt gggggaagtg tttaaaacct ataacgttgc tgtggactac 600
attactgttg cactcctgat ctggaatttt ggtgtggtgg gaatgatttc cattcactgg 660
aaaggtccac ttcgactcca gcaggcatat ctcattatga ttagtgccct catggccctg 720
gtgtttatca agtacctccc tgaatggact gcgtggctca tcttggctgt gatttcagta 780
tatgatttag tggctgtttt gtgtccgaaa ggtccacttc gaatgctagt cgagacggca 840
caagaaagaa atgaaacgct tttccagct ctcatttact cctcaactat ggtatggcta 900
gtcaacatgg cagaaggaga cccggaagct caaaggagag tatccaaaaa ttccaagtat 960
aatgcagaaa gcacagaaag ggagtcacaa gacactgttg cagagaatga tgatggcggg 1020
ttcagtgagg aatgggaagc ccagagggac agtcatctag ggcctcatcg ctctacacct 1080
gagtcacgag cagcggtgca agagctgtct tccagtatcc tcgctggtga agacccagag 1140
gaaaggggag taaaacttgg attgggagat ttcattttct acagtgttct ggttggtaaa 1200
gcctcagcaa cagcgagtgg tgattggaat actacgatag cctgtttcgt agccatatta 1260
attggtttgt gccttacatt attactcctt gccattttca agaaagcatt gccagctctt 1320
ccaatctcca tcacctttgg gcttgttttc tactttgcca cagattatct tgtacagcct 1380
tttatggacc aattagcatt ccatcaattt tatatctagc atagtcgacc cc 1432

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
gaaatcacag ccaagatgag c 21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
atggaatgct aattggtcca t 21

<210> SEQ ID NO 44
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44
ggagcaagat gaggaagaag acgaatcttc ttcctcatct tgctcctt 48

<210> SEQ ID NO 45
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
gctcatcttg gctgtgattt ccgaagaaat cacagccaag atgagctt 48

<210> SEQ ID NO 46
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 46
aaagttcctg gacagcagct ccgaagagct gctgtccagg aacttttt 48

<210> SEQ ID NO 47
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 47
gatggaatgc taattggtcc atcgaaatgg accaattagc attccatt 48

<210> SEQ ID NO 48
<211> LENGTH: 2808
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 48
atgacagagt tacctgcacc tttgtcctac ttccagaatg cacagatgtc tgaggacaac 60
cacctgagca atactgtacg tagccagaat gacaatagag aacggcagga gcacaacgac 120
agacggagcc tgggccaccc tgagccactg tctaatggaa gaccccaggg taactcccgg 180
caggtggtgg agcaggatga ggaagaagat gaggagctga cactgaaata tggcgccaag 240
cacgtgatca tgctctttgt ccctgtgact ctctgcatgg tggtggtcgt ggctaccatt 300
aagtcagtca gcttttatac ccggaaggat gggcagctaa tctatacccc attcacagaa 360
gataccgaga ctgtgggcca gagagccctg cactcaattc tgaatgctgc catcatgatc 420
agtgtcattg ttgtcatgac tatcctcctg gtggttctgt ataaatacag gtgctataag 480
gtcatccatg cctggctgat tatatcatct ctgttgctgc tgttcttttt ttcattcatt 540
tacctggggg aagtgtttaa aacctataac gttgctgtgg actacattac tgttgcactc 600
ctgatctgga attttggcgt ggtgggaatg atttccattc actggaaagg cccactgaga 660
ctccagcagg catatctcat tatgattagt gccctcatgg ccctggtgtt tatcaagtac 720
ctccctgaat ggactgcctg gctcatcttg gctgtgattt cagtgtatga tttagtggct 780
gttctgtgtc ctaaaggtcc actgcgtatg ctggtggaaa cagctcagga gagaaatgaa 840
accctgtttc cagctctcat ttactcctca acaatggtgt ggctggtgaa tatggcagaa 900
ggagaccctg aagctcaaag gagagtgtcc aaaaattcca agtataatgc agaaagcaca 960
gaaagggagt cacaggacac tgttgcagag aatgatgatg gcgggttcag tgaggaatgg 1020
gaagcccaga gggacagtca cctggggcct caccgctcta cacctgagtc aagagctgct 1080
gtccaggaac tgtccagcag tatcctcgct ggcgaagacc cagaggaaag gggagtaaaa 1140
cttggattgg gagatttcat tttctacagt gttctggttg gcaaagcctc agcaacagcc 1200
agtggagact ggaacacaac catagcctgt ttcgtagcca tcttaattgg cctgtgcctt 1260
acactgctgc tcctggccat tttcaagaaa gcactgccag ctctgccaat ctccatcacc 1320
tttgggcttg ttttctactt tgccacagat tatctggtgc agccttttat ggaccagctg 1380
gcattccacc agttttatat ctaaatgaca gagttacctg cacctttgtc ctacttccag 1440
aatgcacaga tgtctgagga caaccacctg agcaatactg tacgtagcca gaatgacaat 1500
agagaacggc aggagcacaa cgacagacgg agcctgggcc accctgagcc actgtctaat 1560
ggaagacccc agggtaactc ccggcaggtg gtggagcagg atgaggaaga agatgaggag 1620
ctgacactga aatatggcgc caagcacgtg atcatgctct ttgtccctgt gactctctgc 1680
atggtggtgg tcgtggctac cattaagtca gtcagctttt atacccggaa ggatgggcag 1740
ctaatctata ccccattcac agaagatacc gagactgtgg gccagagagc cctgcactca 1800
attctgaatg ctgccatcat gatcagtgtc attgttgtca tgactatcct cctggtggtt 1860
ctgtataaat acaggtgcta taaggtcatc catgcctggc tgattatatc atctctgttg 1920
ctgctgttct ttttttcatt catttacctg gggggaagtgt ttaaaaccta taacgttgct 1980
gtggactaca ttactgttgc actcctgatc tggaattttg gcgtggtggg aatgatttcc 2040
attcactgga aaggcccact gagactccag caggcatatc tcattatgat tagtgccctc 2100
atggccctgg tgtttatcaa gtacctccct gaatggactg cctggctcat cttggctgtg 2160
atttcagtgt atgatttagt ggctgttctg tgtcctaaag gtccactgcg tatgctggtg 2220
gaaacagctc aggagagaaa tgaaaccctg tttccagctc tcatttactc ctcaacaatg 2280
gtgtggctgg tgaatatggc agaaggagac cctgaagctc aaaggagagt gtccaaaaat 2340
tccaagtata atgcagaaag cacagaaagg gagtcacagg acactgttgc agagaatgat 2400
gatggcgggt tcagtgagga atgggaagcc cagagggaca gtcacctggg gcctcaccgc 2460
tctacacctg agtcaagagc tgctgtccag gaactgtcca gcagtatcct cgctggcgaa 2520
gacccagagg aaaggggagt aaaacttgga ttgggagatt tcattttcta cagtgttctg 2580
gttggcaaag cctcagcaac agccagtgga gactggaaca caaccatagc ctgtttcgta 2640
gccatcttaa ttggcctgtg ccttacactg ctgctcctgg ccattttcaa gaaagcactg 2700
ccagctctgc caatctccat cacctttggg cttgttttct actttgccac agattatctg 2760
gtgcagcctt ttatggacca gctggcattc caccagtttt atatctaa 2808

<210> SEQ ID NO 49
<211> LENGTH: 4360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 49
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctaccag ggtaatgggg 180
atcctctaga actatggtac caaggtcggg caggaagagg gcctatttcc catgattcct 240
tcatatttgc atatacgata caaggctgtt agagagataa ttagaattaa tttgactgta 300
aacacaaaga tattagtaca aaatacgtga cgtagaaagt aataatttct tgggtagttt 360
gcagttttaa aattatgttt taaaatggac tatcatatgc ttaccgtaac ttgaaagtat 420
ttcgatttct tggctttata tatcttgtgg aaaggacgaa acaccggagc aagatgagga 480
agaagacgaa tcttcttcct catcttgctc cttttttcta gagaacgctg acgtcatcaa 540
cccgctccaa ggaatcgcgg gcccagtgtc actaggcggg aacacccagc gcgcgtgcgc 600
cctggcagga agatggctgt gagggacagg ggagtggcgc cctgcaatat ttgcatgtcg 660
ctatgtgttc tgggaaatca ccataaacgt gaaatgtctt tggatttggg aatcttataa 720
gttctgtatg agaccacgct catcttggct gtgatttccg aagaaatcac agccaagatg 780
agcttttttc tagtcgacat tgattattga ctagttatta atagtaatca attacggggt 840

```
cattagttca tagcccatat atggagttcc gcgttacata acttacggta aatggcccgc    900
ctggctgacc gcccaacgac ccccgcccat tgacgtcaat aatgacgtat gttcccatag    960
taacgccaat agggactttc cattgacgtc aatgggtgga gtatttacgg taaactgccc   1020
acttggcagt acatcaagtg tatcatatgc caagtacgcc ccctattgac gtcaatgacg   1080
gtaaatggcc cgcctggcat tatgcccagt acatgacctt atgggacttt cctacttggc   1140
agtacatcta cgtattagtc atcgctatta ccatggtcga ggtgagcccc acgttctgct   1200
tcactctccc catctccccc ccctccccac ccccaatttt gtatttattt atttttaat    1260
tattttgtgc agcgatgggg gcgggggggg gggggggcg cgcgccaggc ggggcggggc   1320
ggggcgaggg gcggggcggg gcgaggcgga gaggtgcggc ggcagccaat cagagcggcg   1380
cgctccgaaa gtttcctttt atggcgaggc ggcggcggcg gcggccctat aaaaagcgaa   1440
gcgcgcggcg ggcgggagtc gctgcgcgct gccttcgccc cgtgccccgc tccgccgccg   1500
cctcgcgccg cccgccccgg ctctgactga ccgcgttact cccacaggtg agcgggcggg   1560
acggcccttc tcctccgggc tgtaattagc gcttggttta atgacggctt gtttcttttc   1620
tgtggctgcg tgaaagcctt gaggggctcc gggagggccc tttgtgcggg gggagcggct   1680
cgggggtgc gtgcgtgtgt gtgtgcgtgg ggagcgccgc gtgcggctcc gcgctgcccg   1740
gcggctgtga gcgctgcggg cgcggcgcgg ggctttgtgc gctccgcagt gtgcgcgagg   1800
ggagcgcggc cgggggcggt gccccgcggt gcgggggggg ctgcgagggg aacaaaggct   1860
gcgtgcgggg tgtgtgcgtg ggggggtgag cagggggtgt gggcgcgtcg gtcgggctgc   1920
aacccccct gcacccccct ccccgagttg ctgagcacgg cccggcttcg ggtgcggggc   1980
tccgtacggg gcgtggcgcg gggctcgccg tgccgggcgg ggggtggcgg caggtggggg   2040
tgccgggcgg ggcggggccg cctcgggccg gggagggctc gggggagggg cgcggcggcc   2100
cccggagcgc cggcggctgt cgaggcgcgg cgagccgcag ccattgcctt ttatggtaat   2160
cgtgcgagag ggcgcaggga cttcctttgt cccaaatctg tgcggagccg aaatctggga   2220
ggcgccgccg cacccctct agcgggcgcg gggcgaagcg gtgcggcgcc ggcaggaagg   2280
aaatgggcgg ggagggcctt cgtgcgtcgc cgcgccgccg tccccttctc cctctccagc   2340
ctcggggctg tccgcggggg gacggctgcc ttcggggggg acggggcagg gcggggttcg   2400
gcttctggcg tgtgaccggc ggctctagag cctctgctaa ccatgttcat gccttcttct   2460
ttttcctaca gctcctgggc aacgtgctgg ttattgtgct gtctcatcat tttggcaaag   2520
aattcacgcc ccagatctgc caccatgaca gagttacctg caccgttgtc ctacttccag   2580
aatgcacaga tgtctgagga caaccacctg agcaatactg tacgtagcca gaatgacaat   2640
agagaacggc aggagcacaa cgacagacgg agccttggcc accctgagcc attatctaat   2700
ggacgacccc agggtaactc ccggcaggtg gtggaacagg acgaagagga ggatgaggag   2760
ctgacattga aatatggcgc caagcatgtg atcatgctct ttgtccctgt gactctctgc   2820
atggtggtgg tcgtggctac cattaagtca gtcagctttt atacccggaa ggatgggcag   2880
ctaatctata ccccattcac agaagatacc gagactgtgg gccagagagc cctgcactca   2940
attctgaatg ctgccatcat gatcagtgtc attgttgtca tgactatcct cctggtggtt   3000
ctgtataaat acaggtgcta taaggtcatc catgcctggc ttattatatc atctctattg   3060
ttgctgttct ttttttcatt catttacttg gggaagtgt ttaaaaccta taacgttgct   3120
gtggactaca ttactgttgc actcctgatc tggaattttg gtgtggtggg aatgatttcc   3180
```

attcactgga aaggtccact tcgactccag caggcatatc tcattatgat tagtgccctc 3240
atggccctgg tgtttatcaa gtacctccct gaatggactg cgtggctgat tctagccgta 3300
atctcagtat atgatttagt ggctgttttg tgtccgaaag gtccacttcg tatgctggtt 3360
gaaacagctc aggagagaaa tgaaacgctt tttccagctc tcatttactc ctcaacaatg 3420
gtgtggttgg tgaatatggc agaaggagac ccggaagctc aaaggagagt atccaaaaat 3480
tccaagtata atgcagaaag cacagaaagg gagtcacaag acactgttgc agagaatgat 3540
gatggcgggt tcagtgagga atgggaagcc cagagggaca gtcatctagg gcctcatcgc 3600
tctacacctg agtcacgagc tgctgtccag gaactttcca gcagtatcct cgctggtgaa 3660
gacccagagg aaaggggagt aaaacttgga ttgggagatt tcattttcta cagtgttctg 3720
gttggtaaag cctcagcaac agccagtgga gactggaaca caaccatagc ctgtttcgta 3780
gccatattaa ttggtttgtg ccttacatta ttactccttg ccattttcaa gaaagcattg 3840
ccagctcttc caatctccat cacctttggg cttgttttct actttgccac agattatctt 3900
gtacagcctt ttatggacca attagcattc catcaatttt atatctagca tagtcgaccc 3960
ctatccatca cactggcggc cgctcgagga cggggtgaac tacgcctgag gatccgatct 4020
ttttccctct gccaaaaatt atggggacat catgaagccc cttgagcatc tgacttctgg 4080
ctaataaagg aaatttattt tcattgcaat agtgtgttgg aatttttttgt gtctctcact 4140 cggaagcaat tcgttgatct gaatttcgac cacccataat acccattacc ctggtagata 4200
agtagcatgg cgggttaatc attaactaca aggaacccct agtgatggag ttggccactc 4260
cctctctgcg cgctcgctcg ctcactgagg ccgggcgacc aaaggtcgcc cgacgcccgg 4320
gctttgcccg ggcggcctca gtgagcgagc gagcgcgcag 4360

<210> SEQ ID NO 50
<211> LENGTH: 1677
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 50
gacattgatt attgactagt tattaatagt aatcaattac ggggtcatta gttcatagcc 60
catatatgga gttccgcgtt acataactta cggtaaatgg cccgcctggc tgaccgccca 120
acgacccccg cccattgacg tcaataatga cgtatgttcc catagtaacg ccaataggga 180
ctttccattg acgtcaatgg gtggagtatt tacggtaaac tgcccacttg gcagtacatc 240
aagtgtatca tatgccaagt acgcccccta ttgacgtcaa tgacggtaaa tggcccgcct 300
ggcattatgc ccagtacatg accttatggg actttcctac ttggcagtac atctacgtat 360
tagtcatcgc tattaccatg gtcgaggtga gccccacgtt ctgcttcact ctccccatct 420
cccccccctc cccaccccca attttgtatt tatttatttt ttaattattt tgtgcagcga 480
tgggggcggg gggggggggg gggcccccc caggcggggc ggggcggggc gaggggcggg 540
gcggggcgag gcggaaaggt gcggcggcag ccaatcagag cggcgcgctc cgaaagtttc 600
cttttatggc gaggcggcgg cggcggcggc cctataaaaa gcgaagcgcg cggcgggcgg 660
gagtcgttgc gcgctgcctt cgccccgtgc cccgctccgc cgccgcctcg cgccgcccgc 720
cccggctctg actgaccgcg ttactcccac aggtgagcgg gcgggacggc ccttctcctc 780
cgggctgtaa ttagcgcttg gtttaatgac ggcttgtttc ttttctgtgg ctgcgtgaaa 840
gccttgaggg gctccgggag ggccctttgt gcggggggag cggctcgggg ggtgcgtgcg 900
tgtgtgtgtg cgtggggagc gccgcgtgcg gctccgcgct gcccggcggc tgtgagcgct 960
gcgggcgcgg cgcggggctt tgtgcgctcc gcagtgtgcg cgaggggagc gcggccgggg 1020
gcggtgcccc gcggtgcggg gggggctgcg aggggaacaa aggctgcgtg cggggtgtgt 1080
gcgtgggggg gtgagcaggg ggtgtgggcg cgtcggtcgg gctgcaaccc cccctgcacc 1140
cccctccccg agttgctgag cacggcccgg cttcgggtgc ggggctccgt acggggcgtg 1200
gcgcggggct cgccgtgccg ggcggggggt ggcggcaggt gggggtgccg ggcggggcgg 1260
ggccgcctcg ggccggggag ggctcggggg aaggggcgcg gcggcccccg gagcgccggc 1320
ggctgtcgag gcgcggcgag ccgcagccat tgccttttat ggtaatcgtg cgagagggcg 1380
cagggacttc ctttgtccca aatctgtgcg gagccgaaat ctgggaggcg ccgccgcacc 1440
ccctctagcg ggcgcggggc gaagcggtgc ggcgccggca ggaaggaaat gggcggggag 1500
ggccttcgtg cgtcgccgcg ccgccgtccc cttctccctc tccagcctcg gggctgtccg 1560 cgggggggacg gctgccttcg ggggggacgg ggcagggcgg ggttcggctt ctggcgtgtg 1620
accggcggct ctagagcctc tgctaaccat gttcatgcct tcttcttttt cctacag 1677

<210> SEQ ID NO 51
<211> LENGTH: 278
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51
tcgaggtgag ccccacgttc tgcttcactc tccccatctc ccccccctcc ccaccccccaa 60 ttttgtattt atttattttt taattatttt gtgcagcgat gggggcgggg gggggggggg 120
ggcgcgcgcc aggcggggcg gggcggggcg aggggcgggg cggggcgagg cggagaggtg 180
cggcggcagc caatcagagc ggcgcgctcc gaaagtttcc ttttatggcg aggcggcggc 240
ggcggcggcc ctataaaaag cgaagcgcgc ggcgggcg 278

<210> SEQ ID NO 52
<211> LENGTH: 1177
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52
ggtgcagcgg cctccgcgcc gggttttggc gcctcccgcg ggcgcccccc tcctcacggc 60
gagcgctgcc acgtcagacg aagggcgcag gagcgttcct gatccttccg cccggacgct 120
caggacagcg gcccgctgct cataagactc ggccttagaa ccccagtatc agcagaagga 180
cattttagga cgggacttgg gtgactctag ggcactggtt ttctttccag agagcggaac 240
aggcgaggaa aagtagtccc ttctcggcga ttctgcggag ggatctccgt ggggcggtga 300
acgccgatga ttatataagg acgcgccggg tgtggcacag ctagttccgt cgcagccggg 360
atttgggtcg cggttcttgt ttgtggatcg ctgtgatcgt cacttggtga gttgcgggct 420
gctgggctgg ccggggcttt cgtggccgcc gggccgctcg gtgggacgga agcgtgtgga 480
gagaccgcca agggctgtag tctgggtccg cgagcaaggt tgccctgaac tgggggttgg 540
ggggagcgca caaaatggcg gctgttcccg agtcttgaat ggaagacgct tgtaaggcgg 600
gctgtgaggt cgttgaaaca aggtgggggg catggtgggc ggcaagaacc caaggtcttg 660
aggccttcgc taatgcggga aagctcttat tcgggtgaga tgggctgggg caccatctgg 720
ggaccctgac gtgaagtttg tcactgactg gagaactcgg gtttgtcgtc tggttgcggg 780
ggcggcagtt atgcggtgcc gttgggcagt gcacccgtac ctttgggagc gcgcgcctcg 840
tcgtgtcgtg acgtcacccg ttctgttggc ttataatgca gggtggggcc acctgccggt 900
aggtgtgcgg taggcttttc tccgtcgcag gacgcagggt tcgggcctag ggtaggctct 960
cctgaatcga caggcgccgg acctctggtg aggggaggga taagtgaggc gtcagtttct 1020
ttggtcggtt ttatgtacct atcttcttaa gtagctgaag ctccggtttt gaactatgcg 1080
ctcggggttg gcgagtgtgt tttgtgaagt tttttaggca ccttttgaaa tgtaatcatt 1140
tgggtcaata tgtaattttc agtgttagac tagtaaa 1177

<210> SEQ ID NO 53
<211> LENGTH: 511
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 53
ttctaccggg taggggaggc gcttttccca aggcagtctg gagcatgcgc tttagcagcc 60
ccgctgggca cttggcgcta cacaagtggc ctctggcctc gcacacattc cacatccacc 120
ggtaggcgcc aaccggctcc gttctttggt ggccccttcg cgccaccttc tactcctccc 180
ctagtcagga agttcccccc cgccccgcag ctcgcgtcgt gcaggacgtg acaaatggaa 240
gtagcacgtc tcactagtct cgtgcagatg gacagcaccg ctgagcaatg gaagcgggta 300
ggcctttggg gcagcggcca atagcagctt tgctccttcg ctttctgggc tcagaggctg 360
ggaaggggtg ggtccggggg cgggctcagg ggcgggctca ggggcggggc gggcgcccga 420
aggtcctccg gaggcccggc attctgcacg cttcaaaagc gcacgtctgc cgcgctgttc 480
tcctcttcct catctccggg cctttcgacc t 511

<210> SEQ ID NO 54
<211> LENGTH: 1182
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 54
gctccggtgc ccgtcagtgg gcagagcgca catcgcccac agtccccgag aagttggggg 60
gaggggtcgg caattgaacc ggtgcctaga gaaggtggcg cggggtaaac tgggaaagtg 120
atgtcgtgta ctggctccgc ctttttcccg agggtggggg agaaccgtat ataagtgcag 180
tagtcgccgt gaacgttctt tttcgcaacg ggtttgccgc cagaacacag gtaagtgccg 240
tgtgtggttc ccgcgggcct ggcctcttta cgggttatgg cccttgcgtg ccttgaatta 300
cttccacgcc cctggctgca gtacgtgatt cttgatcccg agcttcgggt tggaagtggg 360
tgggagagtt cgaggccttg cgcttaagga gccccttcgc ctcgtgcttg agttgaggcc 420
tggcctgggc gctggggccg ccgcgtgcga atctggtggc accttcgcgc ctgtctcgct 480
gctttcgata agtctctagc catttaaaat tttgatgac ctgctgcgac gcttttttc 540 tggcaagata gtcttgtaaa tgcgggccaa gatctgcaca ctggtatttc ggtttttggg 600
gccgcgggcg gcgacggggc ccgtgcgtcc cagcgcacat gttcggcgag gcggggcctg 660
cgagcgcggc caccgagaat cggacggggg tagtctcaag ctggccggcc tgctctggtg 720
cctggcctcg cgccgccgtg tatcgccccg ccctgggcgg caaggctggc ccggtcggca 780
ccagttgcgt gagcggaaag atggccgctt cccggccctg ctgcagggag ctcaaaatgg 840
aggacgcggc gctcgggaga gcgggcgggt gagtcaccca cacaaaggaa aagggccttt 900
ccgtcctcag ccgtcgcttc atgtgactcc acggagtacc gggcgccgtc caggcacctc 960
gattagttct cgagcttttg gagtacgtcg tctttaggtt ggggggaggg gttttatgcg 1020
atggagtttc cccacactga gtgggtggag actgaagtta ggccagcttg gcacttgatg 1080
taattctcct tggaatttgc cctttttgag tttggatctt ggttcattct caagcctcag 1140
acagtggttc aaagtttttt tcttccattt caggtgtcgt ga 1182

<210> SEQ ID NO 55
<211> LENGTH: 679
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55
gtcgacattg attattgact agttattaat agtaatcaat tacggggtca ttagttcata 60
gcccatatat ggagttccgc gttacataac ttacggtaaa tggcccgcct ggctgaccgc 120
ccaacgaccc ccgcccattg acgtcaataa tgacgtatgt tcccatagta acgccaatag 180
ggactttcca ttgacgtcaa tgggtggagt atttacggta aactgcccac ttggcagtac 240
atcaagtgta tcatatgcca agtacgcccc ctattgacgt caatgacggt aaatggcccg 300
cctggcatta tgcccagtac atgaccttat gggactttcc tacttggcag tacatctacg 360
tattagtcat cgctattacc atggtgatgc ggttttggca gtacatcaat gggcgtggat 420
agcggtttga ctcacgggga tttccaagtc tccaccccat tgacgtcaat gggagtttgt 480
tttggcacca aaatcaacgg gactttccaa aatgtcgtaa caactccgcc ccattgacgc 540
aaatgggcgg taggcgtgta cggtgggagg tctatataag cagagctctc tggctaacta 600
gagaacccac tgcttactgg cttatcgaaa ttaatacgac tcactatagg gagacccaag 660
ctggctagcg tttaaactt 679

<210> SEQ ID NO 56
<211> LENGTH: 1765
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56
agctctgagc tcctcctctg ctcgcccaat ccttccaacc ccctatggtg gtatggctga 60
cacagaaaat gtctgctcct gtatgggaca tttgcccctc ttctccaaat ataagacagg 120
atgaggccta gcttttgctg ctccaaagtt ttaaaagaac acattgcacg gcatttaggg 180
actctaaagg gtggaggagg aatgagggaa ttgcatcatg ccaaggctgg tcctcatcca 240
tcactgcttc cagggcccag agtggcttcc aggaagtatt cttacaaagg aagcccgatc 300
tgtagctaac actcagagcc cattttcctg cgttaacccc tcccgacctc atatacagga 360

```
gtaacatgat cagtgacctg ggggagctgg ccaaactgcg ggacctgccc aagctgaggg    420
ccttggtgct gctggacaac ccctgtgccg atgagactga ctaccgccag gaggccctgg    480
tgcagatggc acacctagag cgcctagaca aagagtacta tgaggacgag gaccgggcag    540
aagctgagga gatccgacag aggctgaagg aggaacagga gcaagaactc gacccggacc    600
aagacatgga accgtacctc ccgccaactt agtggctcct ctagcctgca gggacagtaa    660
aggtgatggc aggaaggcag cccccggagg tcaaaggctg ggcacgcggg aggagaggcc    720
agagtcagag gctgcgggta tctcagatat gaaggaaaga tgagagaggc tcaggaagag    780
gtaagaaaag acacaagaga ccagagaagg gagaagaatt agagagggag gcagaggacc    840
gctgtctcta cagacatagc tggtagagac tgggaggaag ggatgaaccc tgagcgcatg    900
aagggaagga ggtggctggt ggtatatgga ggatgtagct gggccaggga aaagatcctg    960
cactaaaaat ctgaagctaa aaataacagg acacggggtg gagaggcgaa aggagggcag   1020
agtgaggcag agagactgag aggcctgggg atgtgggcat tccggtaggg cacacagttc   1080
acttgtcttc tctttttcca ggaggccaaa gatgctgacg tcaagaactc ataataccc   1140
agtggggacc accgcattca tagccctgtt acaagaagtg ggagatgttc ctttttgtcc   1200
cagactggaa atccgttaca tcccgaggct caggttctgt ggtggtcatc tctgtgtggc   1260
ttgttctgtg ggcctaccta aagtcctaag cacagctctc aagcagatcc gaggcgacta   1320
agatgctagt aggggttgtc tggagagaag agccgaggag gtgggctgtg atggatcagt   1380
tcagctttca aataaaaagg cgtttttata ttctgtgtcg agttcgtgaa cccctgtggt   1440
gggcttctcc atctgtctgg gttagtacct gccactatac tggaataagg ggacgcctgc   1500
ttccctcgag ttggctggac aaggttatga gcatccgtgt acttatgggg ttgccagctt   1560
ggtcctggat cgcccgggcc cttcccccac ccgttcggtt ccccaccacc acccgcgctc   1620
gtacgtgcgt ctccgcctgc agctcttgac tcatcggggc ccccgggtca catgcgctcg   1680
ctcggctcta taggcgccgc cccctgccca ccccccgccc gcgctgggag ccgcagccgc   1740
cgccactcct gctctctctg cgccg                                         1765
```

```
<210> SEQ ID NO 57
<211> LENGTH: 733
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

tgcccattat aaacgtctgc aaagaccaag gtttgatatg ttgattttac tgtcagcctt     60
aagagtgcga catctgctaa tttagtgtaa taatacaatc agtagaccct ttaaaacaag    120
tcccttggct tggaacaacg ccaggctcct caacaggcaa ctttgctact tctacagaaa    180
atgataataa agaaatgctg gtgaagtcaa atgcttatca caatggtgaa ctactcagca    240
gggaggctct aataggcgcc aagagcctag acttccttaa gcgccagagt ccacaagggc    300
ccagttaatc ctcaacattc aaatgctgcc cacaaaacca gcccctctgt gccctagccg    360
cctctttttt ccaagtgaca gtagaactcc accaatccgc agctgaatgg ggtccgcctc    420
ttttccctgc ctaaacagac aggaactcct gccaattgag ggcgtcaccg ctaaggctcc    480
gccccagcct gggctccaca accaatgaag ggtaatctcg acaaagagca aggggtgggg    540
cgcgggcgcg caggtgcagc agcacacagg ctggtcggga gggcggggcg cgacgtctgc    600
```

cgtgcggggt cccggcatcg gttgcgcgcg cgctccctcc tctcggagag agggctgtgg 660
taaaacccgt ccggaaaatg gccgccgctg ccgccaccgc cgccgccgcc gccgcgccga 720
gcggaggagg agg 733

<210> SEQ ID NO 58
<211> LENGTH: 1968
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 58
ggcaacatgg caagacccta tctctacaaa aaaagttaaa aaatcagcca cgtgtggtga 60
cacacacctg tagtcccagc tattcaggag gctgaggtga ggggatcact taaggctggg 120
aggttgaggc tgcagtgagt cgtggttgcg ccactgcact ccagcctggg caacagtgag 180
accctgtctc aaaagacgaa catatcctgg tgtggagtag gggacgctgc tctgacagag 240
gctcgggggc ctgagctggc tctgtgagct ggggaggagg cagacagcca ggccttgtct 300
gcaagcagac ctggcagcat tggctggcc gccccccagg gcctcctctt catgcccagt 360
gaatgactca ccttggcaca gacacaatgt tcggggtggg cacagtgcct gcttcccgcc 420
gcaccccagc ccccctcaaa tgccttccga gaagcccatt gagcaggggg cttgcattgc 480
accccagcct gacagcctgg catcttggga taaaagcagc acagcccccct aggggctgcc 540 cttgctgtgt ggcgccaccg gcggtggaga acaaggctct attcagcctg tgcccaggaa 600
aggggatcag gggatgccca ggcatggaca gtgggtggca gggggggaga ggagggctgt 660
ctgcttccca gaagtccaag gacacaaatg ggtgagggga ctgggcaggg ttctgaccct 720
gtgggaccag agtggagggc gtagatggac ctgaagtctc cagggacaac agggcccagg 780
tctcaggctc ctagttgggc ccagtggctc cagcgtttcc aaacccatcc atccccagag 840
gttcttccca tctctccagg ctgatgtgtg ggaactcgag gaaataaatc tccagtggga 900
gacggagggg tggccaggga aacggggcgc tgcaggaata aagacgagcc agcacagcca 960
gctcatgtgt aacggctttg tggagctgtc aaggcctggt ctctgggaga gaggcacagg 1020
gaggccagac aaggaagggg tgacctggag ggacagatcc aggggctaaa gtcctgataa 1080
ggcaagagag tgccggcccc ctcttgccct atcaggacct ccactgccac atagaggcca 1140
tgattgaccc ttagacaaag ggctggtgtc caatcccagc cccagcccc agaactccag 1200 ggaatgaatg ggcagagagc aggaatgtgg gacatctgtg ttcaagggaa ggactccagg 1260
agtctgctgg gaatgaggcc tagtaggaaa tgaggtggcc cttgagggta cagaacaggt 1320
tcattcttcg ccaaattccc agcaccttgc aggcacttac agctgagtga gataatgcct 1380
gggttatgaa atcaaaaagt tggaaagcag gtcagaggtc atctggtaca gcccttcctt 1440
cccttttttt tttttttttt tgtgagacaa ggtctctctc tgttgcccag gctggagtgg 1500
cgcaaacaca gctcactgca gcctcaacct actgggctca agcaatcctc cagcctcagc 1560
ctcccaaagt gctgggatta caagcatgag ccaccccact cagccctttc cttccttttt 1620
aattgatgca taataattgt aagtattcat catggtccaa ccaacccttt cttgacccac 1680
cttcctagag agagggtcct cttgcttcag cggtcagggc cccagaccca tggtctggct 1740
ccaggtacca cctgcctcat gcaggagttg gcgtgcccag gaagctctgc ctctgggcac 1800
agtgacctca gtggggtgag ggagctctcc cccatagctg ggctgcggcc caaccccacc 1860
ccctcaggct atgccagggg gtgttgccag gggcacccgg gcatcgccag tctagcccac 1920
tccttcataa agccctcgca tcccaggagc gagcagagcc agagcagg 1968

<210> SEQ ID NO 59
<211> LENGTH: 378
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 59
gaattcctgc tgggaaaagc aagtggaggt gctccttgaa gaaacagggg gatcccaccg 60
atctcagggg ttctgttctg gcctgcggcc ctggatcgtc cagcctgggt cggggtgggg 120
agcagacctc gcccttatcg gctggggctg agggtgaggg tcccgtttcc ccaaaggcct 180
agcctggggt tccagccacg aagccctacc gggagcgccc ggccccgccc ctccaggcct 240
ggcactcgtc ctcaaccaag atggcgcgga tggcttcagg cgcatcacga caccggcgcg 300
tcacgcgacc cgccctacgg gcacctcccg cgcttttctt agcgccgcag acggtggccg 360
agcgggggac cgggaagc 378

<210> SEQ ID NO 60
<211> LENGTH: 229
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 60
aatgtagtct tatgcaatac tcttgtagtc ttgcaacatg gtaacgatga gttagcaaca 60
tgccttacaa ggagagaaaa agcaccgtgc atgccgattg gtggaagtaa ggtggtacga 120
tcgtgcctta ttaggaaggc aacagacggg tctgacatgg attggacgaa ccactgaatt 180
gccgcattgc agagatattg tatttaagtg cctagctcga tacataaac 229

<210> SEQ ID NO 61
<211> LENGTH: 351
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 61
ggtgtggaaa gtccccaggc tccccagcag gcagaagtat gcaaagcatg catctcaatt 60
agtcagcaac caggtgtgga aagtccccag gctccccagc aggcagaagt atgcaaagca 120
tgcatctcaa ttagtcagca accatagtcc cgcccctaac tccgcccatc ccgcccctaa 180
ctccgcccag ttccgcccat tctccgcccc atggctgact aattttttt atttatgcag 240 aggccgaggc cgcctcggcc tctgagctat tccagaagta gtgaggaggc ttttttggag 300
gcctaggctt ttgcaaagat cgatcaagag acaggatgag gatcgtttcg c 351

<210> SEQ ID NO 62
<211> LENGTH: 1000
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 62
ttttggccag gggatgtggc ttggactgga gagaaaggag ataaggatgt aaacacatgt 60
agggcatatc accccctatt ttttattctc tgaatcctta accctcagaa taagttctta 120
ttcttgagaa tcaatgacat tatcttaagc taaattaatc aagcctccac agtgttcttc 180
tctcaatagt ggtgtgggcc ttcctagaag taatttttcc caaattcagt gatacatttt 240
aagttcagat tttaattgat atgaatctgt gatacactct aaaataagat tattttattg 300
aaaagtggac tgtaactttc cctttatcta ggaagagctc taagttagaa gatgttttgc 360
acttttaccg aaggctgtgt cttgtaagca cccccgagca actctgagag ccttgatttt 420
tgtgtcctca gcatatgttt gtgtaataca gaaagagaag cagttgccaa gtgaaaggga 480
tgttggtctc caaaattata gtttgatccc acaaacacac aaacacatac atgcaaagga 540
ttgtttgctt cacggttttt gatatttaat tcaatgctgt tggaacagca caaaaactaa 600
gtgtcagttt aacagaatca cttgtccttt tagcattaaa ataacatgga acttaatgct 660
ttaatttccc aacatgcctt tttatttaga aagattcaga cttttatttc atttagaaat 720
aaaatgccat tttatttaga aagatacagg agcattcatt cacggaactt tcagatctca 780
gtccactgca taaaatcttg atcctgtaat aatagtttct gtatcttgca tattcattca 840
acaggtttaa cgcgatgagc aaattaatgt tcatcgtttt taacatgttt cgtcttaatc 900
agaacccaca ttctcaacgt taattgaacg tacataggac tatacaaggg ttagtaaata 960
agacagaaac tgttgctcat ttaaccaccg tcactttgga 1000

<210> SEQ ID NO 63
<211> LENGTH: 480
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 63
acactaaaat gttagagtat gatgacagat ggagttgtct gggtacattt gtgtgcattt 60
aagggtgata gtgtatttgc tctttaagag ctgagtgttt gagcctctgt ttgtgtgtaa 120
ttgagtgtgc atgtgtggga gtgaaattgt ggaatgtgta tgctcatagc actgagtgaa 180
aataaaagat tgtataaatc gtggggcatg tggaattgtg tgtgcctgtg cgtgtgcagt 240
attttttttt ttttaagtaa gccactttag atcttgtcac ctcccctgtc ttctgtgatt 300
gattttgcga ggctaatggt gcgtaaaagg gctggtgaga tctgggggcg cctcctagcc 360
tgacgtcaga gagagagttt aaaacagagg gagacggttg agagcacaca agccgcttta 420
ggagcgaggt tcggagccat cgctgctgcc tgctgatccg cgcctagagt ttgaccagcc 480

<210> SEQ ID NO 64
<211> LENGTH: 700
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 64
acaccaccca agtgtccacc tccgcttgtc tgatgctgtc tatgacgccc ccgctctctg 60
cctagctgag cctgtgtgga tgtgggagac taatctcccc gcgggcactg cgtgtgacct 120 caccccccctc tgtgaggggg ttatttctct actttcgtgt ctctgagtgt gcttccagtg 180 ccccccctccc cccaaaaaat gccttctgag ttgaatatca acactacaaa ccgagtatct 240
gcagagggcc ctgcgtatga gtgcaagtgg gttttaggac caggatgagg cggggtgggg 300
gtgcctacct gacgaccgac cccgacccac tggacaagca cccaaccccc attccccaaa 360
ttgcgcatcc cctatcagag agggggaggg gaaacaggat gcggcgaggc gcgtgcgcac 420
tgccagcttc agcaccgcgg acagtgcctt cgcccccgcc tggcggcgcg cgccaccgcc 480
gcctcagcac tgaaggcgcg ctgacgtcac tcgccggtcc cccgcaaact cccccttcccg 540 gccaccttgg tcgcgtccgc gccgccgccg gcccagccgg accgcaccac gcgaggcgcg 600
agataggggg gcacgggcgc gaccatctgc gctgcggcgc cggcgactca gcgctgcctc 660
agtctgcggt gggcagcgga ggagtcgtgt cgtgcctgag 700

<210> SEQ ID NO 65
<211> LENGTH: 480
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65
acactacaaa ccgagtatct gcagagggcc ctgcgtatga gtgcaagtgg gttttaggac 60
caggatgagg cggggtgggg gtgcctacct gacgaccgac cccgacccac tggacaagca 120
cccaaccccc attccccaaa ttgcgcatcc cctatcagag agggggaggg gaaacaggat 180
gcggcgaggc gcgtgcgcac tgccagcttc agcaccgcgg acagtgcctt cgcccccgcc 240
tggcggcgcg cgccaccgcc gcctcagcac tgaaggcgcg ctgacgtcac tcgccggtcc 300
cccgcaaact cccccttcccg gccaccttgg tcgcgtccgc gccgccgccg gcccagccgg 360
accgcaccac gcgaggcgcg agataggggg gcacgggcgc gaccatctgc gctgcggcgc 420
cggcgactca gcgctgcctc agtctgcggt gggcagcgga ggagtcgtgt cgtgcctgag 480

<210> SEQ ID NO 66
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66
gctttgcttc tcaatttctt atttgcataa tgagaaaaaa aggaaaatta attttaacac 60
caattcagta gttgattgag caaatgcgtt gccaaaaagg atgctttaga gacagtgttc 120
tctgcacaga taaggacaaa cattattcag agggagtacc cagagctgag actcctaagc 180
cagtgagtgg cacagcattc tagggagaaa tatgcttgtc atcaccgaag cctgattccg 240
tagagccaca ccttggtaag ggccaatctg ctcacacagg atagagaggg caggagccag 300
ggcagagcat ataaggtgag gtaggatcag ttgctcctca catttgcttc tgacatagtt 360
gtgttg 366

<210> SEQ ID NO 67
<211> LENGTH: 13
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 67
gccgccrcca ugg 13

<210> SEQ ID NO 68
<211> LENGTH: 7345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaat tcagtggatc ccgataacta taacggtcct 180
aaggtagcga tttaaatgag ggcctatttc ccatgattcc ttcatatttg catatacgat 240
acaaggctgt tagagagata attagaatta atttgactgt aaacacaaag atattagtac 300
aaaatacgtg acgtagaaag taataatttc ttgggtagtt tgcagtttta aaattatgtt 360
ttaaaatgga ctatcatatg cttaccgtaa cttgaaagta tttcgatttc ttggctttat 420
atatcttgtg gaaaggacga ggtaccgtga gctgttggaa ttatgtttcg aatttgactt 480
tagaggttta catttctagt caaagaagaa acatccattc agctgctcct tttttccggg 540
acgcgtcaat tgagatctcc gacattgatt attgactagt tattaatagt aatcaattac 600
ggggtcatta gttcatagcc catatatgga gttccgcgtt acataactta cggtaaatgg 660
cccgcctggc tgaccgccca acgacccccg cccattgacg tcaataatga cgtatgttcc 720
catagtaacg ccaataggga ctttccattg acgtcaatgg gtggagtatt tacggtaaac 780
tgcccacttg gcagtacatc aagtgtatca tatgccaagt acgcccccta ttgacgtcaa 840
tgacggtaaa tggcccgcct ggcattatgc ccagtacatg accttatggg actttcctac 900
ttggcagtac atctacgtat tagtcatcgc tattaccatg tcgaggccac gttctgcttc 960
actctcccca tctccccccc ctccccaccc ccaattttgt atttatttat tttttaatta 1020
ttttgtgcag cgatgggggc gggggggggg ggcgcgcgcc aggcggggcg gggcggggcg 1080
aggggcgggg cggggcgagg cggagaggtg cggcggcagc caatcagagc ggcgcgctcc 1140
gaaagtttcc ttttatggcg aggcggcggc ggcggcggcc ctataaaaag cgaagcgcgc 1200
ggcgggcggg agcaagcttc gtttagtgaa ccgtcagatc gcctggagac gccatccacg 1260
ctgttttgac ctccatagaa gacaccggga ccgatccagc ctccgcggat tcgaatcccg 1320
gccgggaacg gtgcattgga acgcggattc cccgtgccaa gagtgacgta agtaccgcct 1380
atagagtcta taggcccaca aaaaatgctt tcttctttta atatactttt ttgtttatct 1440
tatttctaat actttcccta atctctttct ttcagggcaa taatgataca atgtatcatg 1500
cctctttgca ccattctaaa gaataacagt gataatttct gggttaaggc aatagcaata 1560
tttctgcata taaatatttc tgcatataaa ttgtaactga tgtaagaggt ttcatattgc 1620
taatagcagc tacaatccag ctaccattct gcttttattt tgtggttggg ataaggctgg 1680
attattctga gtccaagcta ggcccttttg ctaatcgtgt tcatacctct tatcttcctc 1740
ccacagctcc tgggcaacgt gctggtctgt gtgctggccc atcactttgg caaagaatta 1800
ccggtggcaa cgtgctggtt attgtgctgt ctcatcattt tggcaaagaa ttcacgcccc 1860
agagccgcca ccatggccta cccatacgat gttccagatt acgctacaga attacctgcc 1920
cccttgagct acttccagaa tgcacagatg agcgaggaca accacctgag caatactgta 1980
cgtagccaga atgacaacag agaacggcag gaacacaacg acaggcggag cctgggccac 2040
cctgagcccc tgtctaatgg aagaccccag ggtaacagca gacaggtggt ggaacaagat 2100
gaggaagagg acgaggagct gaccctgaag tacggcgcca agcacgtgat catgctcttc 2160
gtgcccgtga ctctctgcat ggtggtggtg gtggctacaa tcaagagcgt cagcttttat 2220
acccggaagg atgggcagct aatctatacc ccattcacag aagacaccga gactgtgggc 2280
cagagagccc tgcactcaat cctgaatgcc gccatcatga tcagcgtcat tgttgtcatg 2340
actatcctcc tggtggttct gtataaatac aggtgctata aggtcatcca tgcctggctg 2400
atcatatcat ctctgttgct gctgttcttt tttagcttca tttacctggg cgaagtgttt 2460
aaaacctata acgttgccgt ggactacatt actgttgccc tcctgatctg gaacttcggc 2520
gtggtgggca tgatttccat tcactggaaa ggcccccctga gactgcagca ggcatacctc 2580
attatgatct ccgccctcat ggccctggtg ttcatcaagt acctgcccga gtggactgct 2640
tggctcatct tggctgtgat ctccgtgtat gatttagtgg ctgttctgtg tcctaaaggt 2700
ccactgcgta tgctggtgga aacagctcag gaaagaaatg aaacactgtt tcctgctctg 2760
atttactcct caacaatggt gtggctcgtg aatatggccg aaggagaccc tgaagcccaa 2820
cggagagtgt ccaaaaactc caagtataac gccgagagca cagaaaggga gagccaggat 2880
acagttgccg agaatgacga tggcggcttc agtgaggaat gggaagccca gagggacagc 2940
cacctggggc ctcacagaag caccccctgag tctagagccg ctgtccagga actgtccagc 3000
tccatcctgg ccggcgaaga ccccgaagaa aggggagtaa aacttggact gggagatttc 3060
atcttctaca gtgttctcgt tggcaaagcc agcgcaacag ctagcggaga ctggaacaca 3120
acaatagcct gtttcgtagc catcttaatt ggcctgtgcc ttacacttct gctcctggcc 3180
atcttcaaga aggccctgcc agccctgcct atcagcatca ccttcgggct tgtttttctac 3240
tttgccaccg attatctggt gcagcccttc atggaccagc tggccttcca ccagttttac 3300
atctagtaag cggccgccct agggagctcc tcgagggggt ggcatccctg tgacccctcc 3360
ccagtgcctc tcctggccct ggaagttgcc actccagtgc ccaccagcct tgtcctaata 3420
aaattaagtt gcatcatttt gtctgactag gtgtccttct ataatattat ggggtggagg 3480
ggggtggtat ggagcaaggg gcaagggggg aagacaacct gtagggcctg cggggtctat 3540
tgggaaccaa gctggagtgc agtggcacaa tcttggctca ctgcaatctc cgcctcctgg 3600
gttcaagcga ttctcctgcc tcagcctccc gagttgttgg gattccaggc atgcatgacc 3660
aggctcagct aatttttgtt tttttggtag agacggggtt tcaccatatt ggccaggctg 3720
gtctccccct cctaatctca ggtgatctac ccaccttggc ctcccaaatt gctgggatta 3780
caggcgtgaa ccactgctcc cttccctgtc cttcctgggc ctagggctgt gccagctgcc 3840
tcgtcccgtc accttctggc ttcttctctc cctccatatc ttagctgttt tcctcatgag 3900
aatgttccaa attcgaaatt tctatttaac cattatatat ttacttgttt gctattatct 3960
ctgcccccag tagattgtta gctccagaag agaaaggatc atgtcttttg cttatctaga 4020
tatgcccatc tgcctggtac aatctctggc acatgttaca ggcaacaact acttgtggaa 4080
ttggtgaatg catgaataga agaatgagtg aatgaatgaa tagacaatag gcagaaatcc 4140
agcctcaaag agcttacagt ctggtaagag gaataaaatg tctgcaaata gccacaggac 4200
aggtcaaagg aaggaggggc tatttccagc tgagggcacc ccatcaggaa agcaccccag 4260
acttccttag ggataacagg gtaatggcgc gggccgcagg aacccctagt gatggagttg 4320
gccactccct ctctgcgcgc tcgctcgctc actgaggccg ggcgaccaaa ggtcgcccga 4380
cgcccgggct ttgcccgggc ggcctcagtg agcgagcgag cgcgcagctg cctgcagggg 4440
cgcctgatgc ggtattttct ccttacgcat ctgtgcggta tttcacaccg catacgtcaa 4500
agcaaccata gtacgcgccc tgtagcggcg cattaagcgc ggcgggtgtg gtggttacgc 4560
gcagcgtgac cgctacactt gccagcgcct tagcgcccgc tcctttcgct ttcttccctt 4620
cctttctcgc cacgttcgcc ggctttcccc gtcaagctct aaatcggggg ctccctttag 4680
ggttccgatt tagtgcttta cggcacctcg accccaaaaa acttgatttg ggtgatggtt 4740
cacgtagtgg gccatcgccc tgatagacgg tttttcgccc tttgacgttg gagtccacgt 4800
tctttaatag tggactcttg ttccaaactg gaacaacact caactctatc tcgggctatt 4860
cttttgattt ataagggatt ttgccgattt cggtctattg gttaaaaaat gagctgattt 4920
aacaaaaatt taacgcgaat tttaacaaaa tattaacgtt tacaatttta tggtgcactc 4980
tcagtacaat ctgctctgat gccgcatagt taagccagcc ccgacacccg ccaacacccg 5040
ctgacgcgcc ctgacgggct tgtctgctcc cggcatccgc ttacagacaa gctgtgaccg 5100
tctccgggag ctgcatgtgt cagaggtttt caccgtcatc accgaaacgc gcgagacgaa 5160
agggcctcgt gatacgccta tttttatagg ttaatgtcat gataataatg gtttcttaga 5220
cgtcaggtgg cacttttcgg ggaaatgtgc gcggaacccc tatttgttta tttttctaaa 5280
tacattcaaa tatgtatccg ctcatgagac aataaccctg ataaatgctt caataatatt 5340
gaaaaaggaa gagtcgatcg atcaagagac aggatgagga tcgtttcgca tgattgaaca 5400
agatggattg cacgcaggtt ctccggccgc ttgggtggag aggctattcg gctatgactg 5460
ggcacaacag acaatcggct gctctgatgc cgccgtgttc cggctgtcag cgcaggggcg 5520
cccggttctt tttgtcaaga ccgacctgtc cggtgccctg aatgaactgc aagacgaggc 5580
agcgcggcta tcgtggctgg ccacgacggg cgttccttgc gcagctgtgc tcgacgttgt 5640
cactgaagcg ggaagggact ggctgctatt gggcgaagtg ccggggcagg atctcctgtc 5700
atctcacctt gctcctgccg agaaagtatc catcatggct gatgcaatgc ggcggctgca 5760
tacgcttgat ccggctacct gcccattcga ccaccaagcg aaacatcgca tcgagcgagc 5820
acgtactcgg atggaagccg gtcttgtcga tcaggatgat ctggacgaag agcatcaggg 5880
gctcgcgcca gccgaactgt tcgccaggct caaggcgagc atgcccgacg gcgaggatct 5940
cgtcgtgacc catggcgatg cctgcttgcc gaatatcatg gtggaaaatg gccgcttttc 6000
tggattcatc gactgtggcc ggctgggtgt ggcggatcgc tatcaggaca tagcgttggc 6060
tacccgtgat attgctgaag agcttggcgg cgaatgggct gaccgcttcc tcgtgcttta 6120
cggtatcgcc gctcccgatt cgcagcgcat cgccttctat cgccttcttg acgagttctt 6180
ctgaacgagc gtgacaccac gatgcctgta gcaatggcaa caacgttgcg caaactatta 6240
actggcgaac tacttactct agcttcccgg caacaattaa tagactggat ggaggcggat 6300
aaagttgcag gaccacttct gcgctcggcc cttccggctg gctggtttat tgctgataaa 6360
tctggagccg gtgagcgtgg gtctcgcggt atcattgcag cactggggcc agatggtaag 6420
ccctcccgta tcgtagttat ctacacgacg gggagtcagg caactatgga tgaacgaaat 6480
agacagatcg ctgagatagg tgcctcactg attaagcatt ggtaactgtc agaccaagtt 6540
tactcatata tactttagat tgatttaaaa cttcattttt aatttaaaag gatctaggtg 6600

```
aagatccttt ttgataatct catgaccaaa atcccttaac gtgagttttc gttccactga   6660
gcgtcagacc ccgtagaaaa gatcaaagga tcttcttgag atcctttttt tctgcgcgta   6720
atctgctgct tgcaaacaaa aaaaccaccg ctaccagcgg tggtttgttt gccggatcaa   6780
gagctaccaa ctctttttcc gaaggtaact ggcttcagca gagcgcagat accaaatact   6840
gttcttctag tgtagccgta gttaggccac cacttcaaga actctgtagc accgcctaca   6900
tacctcgctc tgctaatcct gttaccagtg gctgctgcca gtggcgataa gtcgtgtctt   6960
accgggttgg actcaagacg atagttaccg gataaggcgc agcggtcggg ctgaacgggg   7020
ggttcgtgca cacagcccag cttggagcga acgacctaca ccgaactgag atacctacag   7080
cgtgagctat gagaaagcgc cacgcttccc gaagggagaa aggcggacag gtatccggta   7140
agcggcaggg tcggaacagg agagcgcacg agggagcttc cagggggaaa cgcctggtat   7200
ctttatagtc ctgtcgggtt tcgccacctc tgacttgagc gtcgattttt gtgatgctcg   7260
tcaggggggc ggagcctatg gaaaaacgcc agcaacgcgg cctttttacg gttcctggcc   7320
ttttgctggc cttttgctca catgt                                         7345
```

<210> SEQ ID NO 69
<211> LENGTH: 7345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccaat tcagtggatc ccgataacta taacggtcct    180
aaggtagcga tttaaatgag ggcctatttc ccatgattcc ttcatatttg catatacgat    240
acaaggctgt tagagagata attagaatta atttgactgt aaacacaaag atattagtac    300
aaaatacgtg acgtagaaag taataatttc ttgggtagtt tgcagtttta aaattatgtt    360
ttaaaatgga ctatcatatg cttaccgtaa cttgaaagta tttcgatttc ttggctttat    420
atatcttgtg gaaaggacga ggtaccgtga gctgttggat agcacatctt tgaaagtcat    480
aagaggttta catttcttga ctttgttaga tgtggacttc agctgcttct tttttccggg    540
acgcgtcaat tgagatctcc gacattgatt attgactagt tattaatagt aatcaattac    600
ggggtcatta gttcatagcc catatatgga gttccgcgtt acataactta cggtaaatgg    660
cccgcctggc tgaccgccca acgacccccg cccattgacg tcaataatga cgtatgttcc    720
catagtaacg ccaataggga ctttccattg acgtcaatgg gtggagtatt tacggtaaac    780
tgcccacttg gcagtacatc aagtgtatca tatgccaagt acgcccccta ttgacgtcaa    840
tgacggtaaa tggcccgcct ggcattatgc ccagtacatg accttatggg actttcctac    900
ttggcagtac atctacgtat tagtcatcgc tattaccatg tcgaggccac gttctgcttc    960
actctcccca tctccccccc ctccccaccc ccaattttgt atttatttat tttttaatta   1020
ttttgtgcag cgatgggggc gggggggggg ggcgcgcgcc aggcggggcg gggcggggcg   1080
aggggcgggg cggggcgagg cggagaggtg cggcggcagc caatcagagc ggcgcgctcc   1140
gaaagtttcc ttttatggcg aggcggcggc ggcggcggcc ctataaaaag cgaagcgcgc   1200
ggcgggcggg agcaagcttc gtttagtgaa ccgtcagatc gcctggagac gccatccacg   1260
```

```
ctgttttgac ctccatagaa gacaccggga ccgatccagc ctccgcggat tcgaatcccg   1320
gccgggaacg gtgcattgga acgcggattc cccgtgccaa gagtgacgta agtaccgcct   1380
atagagtcta taggcccaca aaaaatgctt tcttctttta atatactttt ttgtttatct   1440
tatttctaat actttcccta atctctttct ttcagggcaa taatgataca atgtatcatg   1500
cctctttgca ccattctaaa gaataacagt gataatttct gggttaaggc aatagcaata   1560
tttctgcata taaatatttc tgcatataaa ttgtaactga tgtaagaggt ttcatattgc   1620
taatagcagc tacaatccag ctaccattct gcttttattt tgtggttggg ataaggctgg   1680
attattctga gtccaagcta ggcccttttg ctaatcgtgt tcatacctct tatcttcctc   1740
ccacagctcc tgggcaacgt gctggtctgt gtgctggccc atcactttgg caaagaatta   1800
ccggtggcaa cgtgctggtt attgtgctgt ctcatcattt tggcaaagaa ttcacgcccc   1860
agagccgcca ccatggccta cccatacgat gttccagatt acgctacaga attacctgcc   1920
cccttgagct acttccagaa tgcacagatg agcgaggaca accacctgag caatactgta   1980
cgtagccaga atgacaacag agaacggcag gaacacaacg acaggcggag cctgggccac   2040
cctgagcccc tgtctaatgg aagaccccag ggtaacagca gacaggtggt ggaacaagat   2100
gaggaagagg acgaggagct gaccctgaag tacggcgcca agcacgtgat catgctcttc   2160
gtgcccgtga ctctctgcat ggtggtggtg gtggctacaa tcaagagcgt cagcttttat   2220
acccggaagg atgggcagct aatctatacc ccattcacag aagacaccga gactgtgggc   2280
cagagagccc tgcactcaat cctgaatgcc gccatcatga tcagcgtcat tgttgtcatg   2340
actatcctcc tggtggttct gtataaatac aggtgctata aggtcatcca tgcctggctg   2400
atcatatcat ctctgttgct gctgttcttt tttagcttca tttacctggg cgaagtgttt   2460
aaaacctata acgttgccgt ggactacatt actgttgccc tcctgatctg gaacttcggc   2520
gtggtgggca tgatttccat tcactggaaa ggcccccctga gactgcagca ggcatacctc   2580
attatgatct ccgccctcat ggccctggtg ttcatcaagt acctgcccga gtggactgct   2640
tggctcatct tggctgtgat ctccgtgtat gatttagtgg ctgttctgtg tcctaaaggt   2700
ccactgcgta tgctggtgga aacagctcag gaaagaaatg aaacactgtt tcctgctctg   2760
atttactcct caacaatggt gtggctcgtg aatatggccg aaggagaccc tgaagcccaa   2820
cggagagtgt ccaaaaactc caagtataac gccgagagca cagaaaggga gagccaggat   2880
acagttgccg agaatgacga tggcggcttc agtgaggaat gggaagccca gagggacagc   2940
cacctggggc ctcacagaag cacccctgag tctagagccg ctgtccagga actgtccagc   3000
tccatcctgg ccggcgaaga ccccgaagaa aggggagtaa aacttggact gggagatttc   3060
atcttctaca gtgttctcgt tggcaaagcc agcgcaacag ctagcggaga ctggaacaca   3120
acaatagcct gtttcgtagc catcttaatt ggcctgtgcc ttacacttct gctcctggcc   3180
atcttcaaga aggccctgcc agccctgcct atcagcatca ccttcgggct tgttttctac   3240
tttgccaccg attatctggt gcagcccttc atggaccagc tggccttcca ccagttttac   3300
atctagtaag cggccgccct agggagctcc tcgagggggt ggcatccctg tgacccctcc   3360
ccagtgcctc tcctggccct ggaagttgcc actccagtgc ccaccagcct tgtcctaata   3420
aaattaagtt gcatcatttt gtctgactag gtgtccttct ataatattat ggggtggagg   3480
ggggtggtat ggagcaaggg gcaagggggg aagacaacct gtagggcctg cggggtctat   3540
tgggaaccaa gctggagtgc agtggcacaa tcttggctca ctgcaatctc cgcctcctgg   3600
```

gttcaagcga ttctcctgcc tcagcctccc gagttgttgg gattccaggc atgcatgacc 3660
aggctcagct aatttttgtt tttttggtag agacggggtt tcaccatatt ggccaggctg 3720
gtctccccct cctaatctca ggtgatctac ccaccttggc ctcccaaatt gctgggatta 3780
caggcgtgaa ccactgctcc cttccctgtc cttcctgggc ctagggctgt gccagctgcc 3840
tcgtcccgtc accttctggc ttcttctctc cctccatatc ttagctgttt tcctcatgag 3900
aatgttccaa attcgaaatt tctatttaac cattatatat ttacttgttt gctattatct 3960
ctgcccccag tagattgtta gctccagaag agaaaggatc atgtcttttg cttatctaga 4020
tatgcccatc tgcctggtac aatctctggc acatgttaca ggcaacaact acttgtggaa 4080
ttggtgaatg catgaataga agaatgagtg aatgaatgaa tagacaatag gcagaaatcc 4140
agcctcaaag agcttacagt ctggtaagag gaataaaatg tctgcaaata gccacaggac 4200
aggtcaaagg aaggaggggc tatttccagc tgagggcacc ccatcaggaa agcaccccag 4260
acttccttag ggataacagg gtaatggcgc gggccgcagg aacccctagt gatggagttg 4320
gccactccct ctctgcgcgc tcgctcgctc actgaggccg ggcgaccaaa ggtcgcccga 4380
cgcccgggct ttgcccgggc ggcctcagtg agcgagcgag cgcgcagctg cctgcagggg 4440
cgcctgatgc ggtattttct ccttacgcat ctgtgcggta tttcacaccg catacgtcaa 4500
agcaaccata gtacgcgccc tgtagcggcg cattaagcgc ggcgggtgtg gtggttacgc 4560
gcagcgtgac cgctacactt gccagcgcct tagcgcccgc tcctttcgct ttcttccctt 4620
cctttctcgc cacgttcgcc ggctttcccc gtcaagctct aaatcggggg ctccctttag 4680
ggttccgatt tagtgcttta cggcacctcg accccaaaaa acttgatttg ggtgatggtt 4740
cacgtagtgg gccatcgccc tgatagacgg tttttcgccc tttgacgttg gagtccacgt 4800
tctttaatag tggactcttg ttccaaactg gaacaacact caactctatc tcgggctatt 4860
cttttgattt ataagggatt ttgccgattt cggtctattg gttaaaaaat gagctgattt 4920
aacaaaaatt taacgcgaat tttaacaaaa tattaacgtt tacaatttta tggtgcactc 4980
tcagtacaat ctgctctgat gccgcatagt taagccagcc ccgacacccg ccaacacccg 5040
ctgacgcgcc ctgacgggct tgtctgctcc cggcatccgc ttacagacaa gctgtgaccg 5100
tctccgggag ctgcatgtgt cagaggtttt caccgtcatc accgaaacgc gcgagacgaa 5160
agggcctcgt gatacgccta tttttatagg ttaatgtcat gataataatg gtttcttaga 5220
cgtcaggtgg cacttttcgg ggaaatgtgc gcggaacccc tatttgttta tttttctaaa 5280
tacattcaaa tatgtatccg ctcatgagac aataaccctg ataaatgctt caataatatt 5340
gaaaaaggaa gagtcgatcg atcaagagac aggatgagga tcgtttcgca tgattgaaca 5400
agatggattg cacgcaggtt ctccggccgc ttgggtggag aggctattcg gctatgactg 5460
ggcacaacag acaatcggct gctctgatgc cgccgtgttc cggctgtcag cgcaggggcg 5520
cccggttctt tttgtcaaga ccgacctgtc cggtgccctg aatgaactgc aagacgaggc 5580
agcgcggcta tcgtggctgg ccacgacggg cgttccttgc gcagctgtgc tcgacgttgt 5640
cactgaagcg ggaagggact ggctgctatt gggcgaagtg ccggggcagg atctcctgtc 5700
atctcacctt gctcctgccg agaaagtatc catcatggct gatgcaatgc ggcggctgca 5760
tacgcttgat ccggctacct gcccattcga ccaccaagcg aaacatcgca tcgagcgagc 5820
acgtactcgg atggaagccg gtcttgtcga tcaggatgat ctggacgaag agcatcaggg 5880
gctcgcgcca gccgaactgt tcgccaggct caaggcgagc atgcccgacg gcgaggatct 5940
cgtcgtgacc catggcgatg cctgcttgcc gaatatcatg gtggaaaatg gccgcttttc 6000
tggattcatc gactgtggcc ggctgggtgt ggcggatcgc tatcaggaca tagcgttggc 6060
tacccgtgat attgctgaag agcttggcgg cgaatgggct gaccgcttcc tcgtgcttta 6120
cggtatcgcc gctcccgatt cgcagcgcat cgccttctat cgccttcttg acgagttctt 6180
ctgaacgagc gtgacaccac gatgcctgta gcaatggcaa caacgttgcg caaactatta 6240
actggcgaac tacttactct agcttcccgg caacaattaa tagactggat ggaggcggat 6300
aaagttgcag gaccacttct gcgctcggcc cttccggctg gctggtttat tgctgataaa 6360
tctggagccg gtgagcgtgg gtctcgcggt atcattgcag cactggggcc agatggtaag 6420
ccctcccgta tcgtagttat ctacacgacg gggagtcagg caactatgga tgaacgaaat 6480
agacagatcg ctgagatagg tgcctcactg attaagcatt ggtaactgtc agaccaagtt 6540
tactcatata tactttagat tgatttaaaa cttcattttt aatttaaaag gatctaggtg 6600
aagatccttt ttgataatct catgaccaaa atcccttaac gtgagttttc gttccactga 6660
gcgtcagacc ccgtagaaaa gatcaaagga tcttcttgag atcctttttt tctgcgcgta 6720
atctgctgct tgcaaacaaa aaaaccaccg ctaccagcgg tggtttgttt gccggatcaa 6780
gagctaccaa ctctttttcc gaaggtaact ggcttcagca gagcgcagat accaaatact 6840
gttcttctag tgtagccgta gttaggccac cacttcaaga actctgtagc accgcctaca 6900
tacctcgctc tgctaatcct gttaccagtg gctgctgcca gtggcgataa gtcgtgtctt 6960
accgggttgg actcaagacg atagttaccg gataaggcgc agcggtcggg ctgaacgggg 7020
ggttcgtgca cacagcccag cttggagcga acgacctaca ccgaactgag atacctacag 7080
cgtgagctat gagaaagcgc cacgcttccc gaagggagaa aggcggacag gtatccggta 7140
agcggcaggg tcggaacagg agagcgcacg agggagcttc cagggggaaa cgcctggtat 7200
ctttatagtc ctgtcgggtt tcgccacctc tgacttgagc gtcgattttt gtgatgctcg 7260
tcaggggggc ggagcctatg gaaaaacgcc agcaacgcgg cctttttacg gttcctggcc 7320
ttttgctggc cttttgctca catgt 7345

<210> SEQ ID NO 70
<211> LENGTH: 7345
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 70
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaat tcagtggatc ccgataacta taacggtcct 180
aaggtagcga tttaaatgag ggcctatttc ccatgattcc ttcatatttg catatacgat 240
acaaggctgt tagagagata attagaatta atttgactgt aaacacaaag atattagtac 300
aaaatacgtg acgtagaaag taataatttc ttgggtagtt tgcagtttta aaattatgtt 360
ttaaaatgga ctatcatatg cttaccgtaa cttgaaagta tttcgatttc ttggctttat 420
atatcttgtg gaaaggacga ggtaccgtga gctgttggag actagaaaag ccttttgact 480
acgaggttta catttcgttc aaaatcgttt tctatagttc agctgcttct tttttccggg 540
acgcgtcaat tgagatctcc gacattgatt attgactagt tattaatagt aatcaattac 600
ggggtcatta gttcatagcc catatatgga gttccgcgtt acataactta cggtaaatgg 660

```
cccgcctggc tgaccgccca acgacccccg cccattgacg tcaataatga cgtatgttcc    720
catagtaacg ccaataggga ctttccattg acgtcaatgg gtggagtatt tacggtaaac    780
tgcccacttg gcagtacatc aagtgtatca tatgccaagt acgcccccta ttgacgtcaa    840
tgacggtaaa tggcccgcct ggcattatgc ccagtacatg accttatggg actttcctac    900
ttggcagtac atctacgtat tagtcatcgc tattaccatg tcgaggccac gttctgcttc    960
actctcccca tctccccccc ctccccaccc ccaattttgt atttatttat tttttaatta   1020
ttttgtgcag cgatgggggc gggggggggg ggcgcgcgcc aggcggggcg gggcggggcg   1080
aggggcgggg cggggcgagg cggagaggtg cggcggcagc caatcagagc ggcgcgctcc   1140
gaaagtttcc ttttatggcg aggcggcggc ggcggcggcc ctataaaaag cgaagcgcgc   1200
ggcgggcggg agcaagcttc gtttagtgaa ccgtcagatc gcctggagac gccatccacg   1260
ctgttttgac ctccatagaa gacaccggga ccgatccagc ctccgcggat tcgaatcccg   1320
gccgggaacg gtgcattgga acgcggattc cccgtgccaa gagtgacgta agtaccgcct   1380
atagagtcta taggcccaca aaaaatgctt tcttctttta atatactttt ttgtttatct   1440
tatttctaat actttcccta atctctttct ttcagggcaa taatgataca atgtatcatg   1500
cctctttgca ccattctaaa gaataacagt gataatttct gggttaaggc aatagcaata   1560
tttctgcata taaatatttc tgcatataaa ttgtaactga tgtaagaggt ttcatattgc   1620
taatagcagc tacaatccag ctaccattct gcttttattt tgtggttggg ataaggctgg   1680
attattctga gtccaagcta ggcccttttg ctaatcgtgt tcatacctct tatcttcctc   1740
ccacagctcc tgggcaacgt gctggtctgt gtgctggccc atcactttgg caaagaatta   1800
ccggtggcaa cgtgctggtt attgtgctgt ctcatcattt tggcaaagaa ttcacgcccc   1860
agagccgcca ccatggccta cccatacgat gttccagatt acgctacaga attacctgcc   1920
cccttgagct acttccagaa tgcacagatg agcgaggaca accacctgag caatactgta   1980
cgtagccaga atgacaacag agaacggcag gaacacaacg acaggcggag cctgggccac   2040
cctgagcccc tgtctaatgg aagaccccag ggtaacagca gacaggtggt ggaacaagat   2100
gaggaagagg acgaggagct gaccctgaag tacggcgcca agcacgtgat catgctcttc   2160
gtgcccgtga ctctctgcat ggtggtggtg gtggctacaa tcaagagcgt cagcttttat   2220
acccggaagg atgggcagct aatctatacc ccattcacag aagacaccga gactgtgggc   2280
cagagagccc tgcactcaat cctgaatgcc gccatcatga tcagcgtcat tgttgtcatg   2340
actatcctcc tggtggttct gtataaatac aggtgctata aggtcatcca tgcctggctg   2400
atcatatcat ctctgttgct gctgttcttt tttagcttca tttacctggg cgaagtgttt   2460
aaaacctata acgttgccgt ggactacatt actgttgccc tcctgatctg gaacttcggc   2520
gtggtgggca tgatttccat tcactggaaa ggcccccctga gactgcagca ggcatacctc   2580
attatgatct ccgccctcat ggccctggtg ttcatcaagt acctgcccga gtggactgct   2640
tggctcatct tggctgtgat ctccgtgtat gatttagtgg ctgttctgtg tcctaaaggt   2700
ccactgcgta tgctggtgga aacagctcag gaaagaaatg aaacactgtt tcctgctctg   2760
atttactcct caacaatggt gtggctcgtg aatatggccg aaggagaccc tgaagcccaa   2820
cggagagtgt ccaaaaactc caagtataac gccgagagca cagaaaggga gagccaggat   2880
acagttgccg agaatgacga tggcggcttc agtgaggaat gggaagccca gagggacagc   2940
cacctggggc ctcacagaag cacccctgag tctagagccg ctgtccagga actgtccagc   3000
```

```
tccatcctgg ccggcgaaga ccccgaagaa aggggagtaa aacttggact gggagatttc   3060
atcttctaca gtgttctcgt tggcaaagcc agcgcaacag ctagcggaga ctggaacaca   3120
acaatagcct gtttcgtagc catcttaatt ggcctgtgcc ttacacttct gctcctggcc   3180
atcttcaaga aggccctgcc agccctgcct atcagcatca ccttcgggct tgttttctac   3240
tttgccaccg attatctggt gcagcccttc atggaccagc tggccttcca ccagttttac   3300
atctagtaag cggccgccct agggagctcc tcgagggggt ggcatccctg tgacccctcc   3360
ccagtgcctc tcctggccct ggaagttgcc actccagtgc ccaccagcct tgtcctaata   3420
aaattaagtt gcatcatttt gtctgactag gtgtccttct ataatattat ggggtggagg   3480
ggggtggtat ggagcaaggg gcaagggggg aagacaacct gtagggcctg cggggtctat   3540
tgggaaccaa gctggagtgc agtggcacaa tcttggctca ctgcaatctc cgcctcctgg   3600
gttcaagcga ttctcctgcc tcagcctccc gagttgttgg gattccaggc atgcatgacc   3660
aggctcagct aatttttgtt tttttggtag agacggggtt tcaccatatt ggccaggctg   3720
gtctccccct cctaatctca ggtgatctac ccaccttggc ctcccaaatt gctgggatta   3780
caggcgtgaa ccactgctcc cttccctgtc cttcctgggc ctagggctgt gccagctgcc   3840
tcgtcccgtc accttctggc ttcttctctc cctccatatc ttagctgttt tcctcatgag   3900
aatgttccaa attcgaaatt tctatttaac cattatatat ttacttgttt gctattatct   3960
ctgcccccag tagattgtta gctccagaag agaaaggatc atgtcttttg cttatctaga   4020
tatgcccatc tgcctggtac aatctctggc acatgttaca ggcaacaact acttgtggaa   4080
ttggtgaatg catgaataga agaatgagtg aatgaatgaa tagacaatag gcagaaatcc   4140
agcctcaaag agcttacagt ctggtaagag gaataaaatg tctgcaaata gccacaggac   4200
aggtcaaagg aaggaggggc tatttccagc tgagggcacc ccatcaggaa agcaccccag   4260
acttccttag ggataacagg gtaatggcgc gggccgcagg aacccctagt gatggagttg   4320
gccactccct ctctgcgcgc tcgctcgctc actgaggccg ggcgaccaaa ggtcgcccga   4380
cgcccgggct ttgcccgggc ggcctcagtg agcgagcgag cgcgcagctg cctgcagggg   4440
cgcctgatgc ggtattttct ccttacgcat ctgtgcggta tttcacaccg catacgtcaa   4500
agcaaccata gtacgcgccc tgtagcggcg cattaagcgc ggcgggtgtg gtggttacgc   4560
gcagcgtgac cgctacactt gccagcgcct tagcgcccgc tcctttcgct ttcttccctt   4620
cctttctcgc cacgttcgcc ggctttcccc gtcaagctct aaatcggggg ctccctttag   4680
ggttccgatt tagtgcttta cggcacctcg accccaaaaa acttgatttg ggtgatggtt   4740
cacgtagtgg gccatcgccc tgatagacgg tttttcgccc tttgacgttg gagtccacgt   4800
tctttaatag tggactcttg ttccaaactg gaacaacact caactctatc tcgggctatt   4860
cttttgattt ataagggatt ttgccgattt cggtctattg gttaaaaaat gagctgattt   4920
aacaaaaatt taacgcgaat tttaacaaaa tattaacgtt tacaatttta tggtgcactc   4980
tcagtacaat ctgctctgat gccgcatagt taagccagcc ccgacacccg ccaacacccg   5040
ctgacgcgcc ctgacgggct tgtctgctcc cggcatccgc ttacagacaa gctgtgaccg   5100
tctccgggag ctgcatgtgt cagaggtttt caccgtcatc accgaaacgc gcgagacgaa   5160
agggcctcgt gatacgccta tttttatagg ttaatgtcat gataataatg gtttcttaga   5220
cgtcaggtgg cacttttcgg ggaaatgtgc gcggaacccc tatttgttta tttttctaaa   5280
tacattcaaa tatgtatccg ctcatgagac aataaccctg ataaatgctt caataatatt   5340
gaaaaaggaa gagtcgatcg atcaagagac aggatgagga tcgtttcgca tgattgaaca   5400
```

agatggattg cacgcaggtt ctccggccgc ttgggtggag aggctattcg gctatgactg 5460
ggcacaacag acaatcggct gctctgatgc cgccgtgttc cggctgtcag cgcaggggcg 5520
cccggttctt tttgtcaaga ccgacctgtc cggtgccctg aatgaactgc aagacgaggc 5580
agcgcggcta tcgtggctgg ccacgacggg cgttccttgc gcagctgtgc tcgacgttgt 5640
cactgaagcg ggaagggact ggctgctatt gggcgaagtg ccggggcagg atctcctgtc 5700
atctcacctt gctcctgccg agaaagtatc catcatggct gatgcaatgc ggcggctgca 5760
tacgcttgat ccggctacct gcccattcga ccaccaagcg aaacatcgca tcgagcgagc 5820
acgtactcgg atggaagccg gtcttgtcga tcaggatgat ctggacgaag agcatcaggg 5880
gctcgcgcca gccgaactgt tcgccaggct caaggcgagc atgcccgacg gcgaggatct 5940
cgtcgtgacc catggcgatg cctgcttgcc gaatatcatg gtggaaaatg gccgcttttc 6000
tggattcatc gactgtggcc ggctgggtgt ggcggatcgc tatcaggaca tagcgttggc 6060
tacccgtgat attgctgaag agcttggcgg cgaatgggct gaccgcttcc tcgtgcttta 6120
cggtatcgcc gctcccgatt cgcagcgcat cgccttctat cgccttcttg acgagttctt 6180
ctgaacgagc gtgacaccac gatgcctgta gcaatggcaa caacgttgcg caaactatta 6240
actggcgaac tacttactct agcttcccgg caacaattaa tagactggat ggaggcggat 6300
aaagttgcag gaccacttct gcgctcggcc cttccggctg gctggtttat tgctgataaa 6360
tctggagccg gtgagcgtgg gtctcgcggt atcattgcag cactggggcc agatggtaag 6420
ccctcccgta tcgtagttat ctacacgacg gggagtcagg caactatgga tgaacgaaat 6480
agacagatcg ctgagatagg tgcctcactg attaagcatt ggtaactgtc agaccaagtt 6540
tactcatata tactttagat tgatttaaaa cttcattttt aatttaaaag gatctaggtg 6600
aagatccttt ttgataatct catgaccaaa atcccttaac gtgagttttc gttccactga 6660
gcgtcagacc ccgtagaaaa gatcaaagga tcttcttgag atcctttttt tctgcgcgta 6720
atctgctgct tgcaaacaaa aaaaccaccg ctaccagcgg tggtttgttt gccggatcaa 6780
gagctaccaa ctctttttcc gaaggtaact ggcttcagca gagcgcagat accaaatact 6840
gttcttctag tgtagccgta gttaggccac cacttcaaga actctgtagc accgcctaca 6900
tacctcgctc tgctaatcct gttaccagtg gctgctgcca gtggcgataa gtcgtgtctt 6960
accgggttgg actcaagacg atagttaccg gataaggcgc agcggtcggg ctgaacgggg 7020
ggttcgtgca cacagcccag cttggagcga acgacctaca ccgaactgag atacctacag 7080
cgtgagctat gagaaagcgc cacgcttccc gaagggagaa aggcggacag gtatccggta 7140
agcggcaggg tcggaacagg agagcgcacg agggagcttc cagggggaaa cgcctggtat 7200
ctttatagtc ctgtcgggtt tcgccacctc tgacttgagc gtcgattttt gtgatgctcg 7260
tcaggggggc ggagcctatg gaaaaacgcc agcaacgcgg cctttttacg gttcctggcc 7320
ttttgctggc cttttgctca catgt 7345

<210> SEQ ID NO 71
<211> LENGTH: 7345
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 71
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaat tcagtggatc ccgataacta taacggtcct 180
aaggtagcga tttaaatgag ggcctatttc ccatgattcc ttcatatttg catatacgat 240
acaaggctgt tagagagata attagaatta atttgactgt aaacacaaag atattagtac 300
aaaatacgtg acgtagaaag taataatttc ttgggtagtt tgcagtttta aaattatgtt 360
ttaaaatgga ctatcatatg cttaccgtaa cttgaaagta tttcgatttc ttggctttat 420
atatcttgtg gaaaggacga ggtaccgtga gctgttggat tctggtcact acacgattcc 480
tcgaggttta catttcgaaa tcgtcctgtg accacgcttc agctgcttct tttttccggg 540
acgcgtcaat tgagatctcc gacattgatt attgactagt tattaatagt aatcaattac 600
ggggtcatta gttcatagcc catatatgga gttccgcgtt acataactta cggtaaatgg 660
cccgcctggc tgaccgccca acgacccccg cccattgacg tcaataatga cgtatgttcc 720
catagtaacg ccaataggga ctttccattg acgtcaatgg gtggagtatt tacggtaaac 780
tgcccacttg gcagtacatc aagtgtatca tatgccaagt acgcccccta ttgacgtcaa 840
tgacggtaaa tggcccgcct ggcattatgc ccagtacatg accttatggg actttcctac 900
ttggcagtac atctacgtat tagtcatcgc tattaccatg tcgaggccac gttctgcttc 960
actctcccca tctccccccc ctccccaccc ccaattttgt atttatttat tttttaatta 1020
ttttgtgcag cgatgggggc gggggggggg ggcgcgcgcc aggcggggcg gggcggggcg 1080
aggggcgggg cggggcgagg cggagaggtg cggcggcagc caatcagagc ggcgcgctcc 1140
gaaagtttcc ttttatggcg aggcggcggc ggcggcggcc ctataaaaag cgaagcgcgc 1200
ggcgggcggg agcaagcttc gtttagtgaa ccgtcagatc gcctggagac gccatccacg 1260
ctgttttgac ctccatagaa gacaccggga ccgatccagc ctccgcggat tcgaatcccg 1320
gccgggaacg gtgcattgga acgcggattc cccgtgccaa gagtgacgta agtaccgcct 1380
atagagtcta taggcccaca aaaaatgctt tcttctttta atatactttt ttgtttatct 1440
tatttctaat actttcccta atctctttct ttcagggcaa taatgataca atgtatcatg 1500
cctctttgca ccattctaaa gaataacagt gataatttct gggttaaggc aatagcaata 1560
tttctgcata taaatatttc tgcatataaa ttgtaactga tgtaagaggt ttcatattgc 1620
taatagcagc tacaatccag ctaccattct gcttttattt tgtggttggg ataaggctgg 1680
attattctga gtccaagcta ggcccttttg ctaatcgtgt tcatacctct tatcttcctc 1740
ccacagctcc tgggcaacgt gctggtctgt gtgctggccc atcactttgg caaagaatta 1800
ccggtggcaa cgtgctggtt attgtgctgt ctcatcattt tggcaaagaa ttcacgcccc 1860
agagccgcca ccatggccta cccatacgat gttccagatt acgctacaga attacctgcc 1920
cccttgagct acttccagaa tgcacagatg agcgaggaca accacctgag caatactgta 1980
cgtagccaga atgacaacag agaacggcag gaacacaacg acaggcggag cctgggccac 2040
cctgagcccc tgtctaatgg aagaccccag ggtaacagca gacaggtggt ggaacaagat 2100
gaggaagagg acgaggagct gaccctgaag tacggcgcca agcacgtgat catgctcttc 2160
gtgcccgtga ctctctgcat ggtggtggtg gtggctacaa tcaagagcgt cagcttttat 2220
acccggaagg atgggcagct aatctatacc ccattcacag aagacaccga gactgtgggc 2280
cagagagccc tgcactcaat cctgaatgcc gccatcatga tcagcgtcat tgttgtcatg 2340
actatcctcc tggtggttct gtataaatac aggtgctata aggtcatcca tgcctggctg 2400
atcatatcat ctctgttgct gctgttcttt tttagcttca tttacctggg cgaagtgttt 2460
aaaacctata acgttgccgt ggactacatt actgttgccc tcctgatctg gaacttcggc 2520
gtggtgggca tgatttccat tcactggaaa ggcccccctga gactgcagca ggcatacctc 2580
attatgatct ccgccctcat ggccctggtg ttcatcaagt acctgcccga gtggactgct 2640
tggctcatct tggctgtgat ctccgtgtat gatttagtgg ctgttctgtg tcctaaaggt 2700
ccactgcgta tgctggtgga aacagctcag gaaagaaatg aaacactgtt tcctgctctg 2760
atttactcct caacaatggt gtggctcgtg aatatggccg aaggagaccc tgaagcccaa 2820
cggagagtgt ccaaaaactc caagtataac gccgagagca cagaaaggga gagccaggat 2880
acagttgccg agaatgacga tggcggcttc agtgaggaat gggaagccca gagggacagc 2940
cacctggggc ctcacagaag caccccctgag tctagagccg ctgtccagga actgtccagc 3000
tccatcctgg ccggcgaaga ccccgaagaa aggggagtaa aacttggact gggagatttc 3060
atcttctaca gtgttctcgt tggcaaagcc agcgcaacag ctagcggaga ctggaacaca 3120
acaatagcct gtttcgtagc catcttaatt ggcctgtgcc ttacacttct gctcctggcc 3180
atcttcaaga aggccctgcc agccctgcct atcagcatca ccttcgggct tgttttctac 3240
tttgccaccg attatctggt gcagcccttc atggaccagc tggccttcca ccagttttac 3300
atctagtaag cggccgccct agggagctcc tcgagggggt ggcatccctg tgacccctcc 3360
ccagtgcctc tcctggccct ggaagttgcc actccagtgc ccaccagcct tgtcctaata 3420
aaattaagtt gcatcatttt gtctgactag gtgtccttct ataatattat ggggtggagg 3480
ggggtggtat ggagcaaggg gcaagggggg aagacaacct gtagggcctg cggggtctat 3540
tgggaaccaa gctggagtgc agtggcacaa tcttggctca ctgcaatctc cgcctcctgg 3600
gttcaagcga ttctcctgcc tcagcctccc gagttgttgg gattccaggc atgcatgacc 3660
aggctcagct aatttttgtt tttttggtag agacggggtt tcaccatatt ggccaggctg 3720 gtctcccccct cctaatctca ggtgatctac ccaccttggc ctcccaaatt gctgggatta 3780
caggcgtgaa ccactgctcc cttccctgtc cttcctgggc ctagggctgt gccagctgcc 3840
tcgtcccgtc accttctggc ttcttctctc cctccatatc ttagctgttt tcctcatgag 3900
aatgttccaa attcgaaatt tctatttaac cattatatat ttacttgttt gctattatct 3960
ctgcccccag tagattgtta gctccagaag agaaaggatc atgtcttttg cttatctaga 4020
tatgcccatc tgcctggtac aatctctggc acatgttaca ggcaacaact acttgtggaa 4080
ttggtgaatg catgaataga agaatgagtg aatgaatgaa tagacaatag gcagaaatcc 4140
agcctcaaag agcttacagt ctggtaagag gaataaaatg tctgcaaata gccacaggac 4200
aggtcaaagg aaggaggggc tatttccagc tgagggcacc ccatcaggaa agcaccccag 4260
acttccttag ggataacagg gtaatggcgc gggccgcagg aacccctagt gatggagttg 4320
gccactccct ctctgcgcgc tcgctcgctc actgaggccg ggcgaccaaa ggtcgcccga 4380
cgcccgggct ttgcccgggc ggcctcagtg agcgagcgag cgcgcagctg cctgcagggg 4440
cgcctgatgc ggtattttct ccttacgcat ctgtgcggta tttcacaccg catacgtcaa 4500
agcaaccata gtacgcgccc tgtagcggcg cattaagcgc ggcgggtgtg gtggttacgc 4560
gcagcgtgac cgctacactt gccagcgcct tagcgcccgc tcctttcgct ttcttccctt 4620
cctttctcgc cacgttcgcc ggctttcccc gtcaagctct aaatcggggg ctccctttag 4680
ggttccgatt tagtgcttta cggcacctcg accccaaaaa acttgatttg ggtgatggtt 4740
cacgtagtgg gccatcgccc tgatagacgg tttttcgccc tttgacgttg gagtccacgt 4800

```
tctttaatag tggactcttg ttccaaactg gaacaacact caactctatc tcgggctatt   4860
cttttgattt ataagggatt ttgccgattt cggtctattg gttaaaaaat gagctgattt   4920
aacaaaaatt taacgcgaat tttaacaaaa tattaacgtt tacaatttta tggtgcactc   4980
tcagtacaat ctgctctgat gccgcatagt taagccagcc ccgacacccg ccaacacccg   5040
ctgacgcgcc ctgacgggct tgtctgctcc cggcatccgc ttacagacaa gctgtgaccg   5100
tctccgggag ctgcatgtgt cagaggtttt caccgtcatc accgaaacgc gcgagacgaa   5160
agggcctcgt gatacgccta tttttatagg ttaatgtcat gataataatg gtttcttaga   5220
cgtcaggtgg cacttttcgg ggaaatgtgc gcggaacccc tatttgttta tttttctaaa   5280
tacattcaaa tatgtatccg ctcatgagac aataaccctg ataaatgctt caataatatt   5340
gaaaaaggaa gagtcgatcg atcaagagac aggatgagga tcgtttcgca tgattgaaca   5400
agatggattg cacgcaggtt ctccggccgc ttgggtggag aggctattcg gctatgactg   5460
ggcacaacag acaatcggct gctctgatgc cgccgtgttc cggctgtcag cgcaggggcg   5520
cccggttctt tttgtcaaga ccgacctgtc cggtgccctg aatgaactgc aagacgaggc   5580
agcgcggcta tcgtggctgg ccacgacggg cgttccttgc gcagctgtgc tcgacgttgt   5640
cactgaagcg ggaagggact ggctgctatt gggcgaagtg ccggggcagg atctcctgtc   5700
atctcacctt gctcctgccg agaaagtatc catcatggct gatgcaatgc ggcggctgca   5760
tacgcttgat ccggctacct gcccattcga ccaccaagcg aaacatcgca tcgagcgagc   5820
acgtactcgg atggaagccg gtcttgtcga tcaggatgat ctggacgaag agcatcaggg   5880
gctcgcgcca gccgaactgt tcgccaggct caaggcgagc atgcccgacg gcgaggatct   5940
cgtcgtgacc catggcgatg cctgcttgcc gaatatcatg gtggaaaatg gccgcttttc   6000
tggattcatc gactgtggcc ggctgggtgt ggcggatcgc tatcaggaca tagcgttggc   6060
tacccgtgat attgctgaag agcttggcgg cgaatgggct gaccgcttcc tcgtgcttta   6120
cggtatcgcc gctcccgatt cgcagcgcat cgccttctat cgccttcttg acgagttctt   6180
ctgaacgagc gtgacaccac gatgcctgta gcaatggcaa caacgttgcg caaactatta   6240
actggcgaac tacttactct agcttcccgg caacaattaa tagactggat ggaggcggat   6300
aaagttgcag gaccacttct gcgctcggcc cttccggctg gctggtttat tgctgataaa   6360
tctggagccg gtgagcgtgg gtctcgcggt atcattgcag cactggggcc agatggtaag   6420
ccctcccgta tcgtagttat ctacacgacg gggagtcagg caactatgga tgaacgaaat   6480
agacagatcg ctgagatagg tgcctcactg attaagcatt ggtaactgtc agaccaagtt   6540
tactcatata tactttagat tgatttaaaa cttcattttt aatttaaaag gatctaggtg   6600
aagatccttt ttgataatct catgaccaaa atcccttaac gtgagttttc gttccactga   6660
gcgtcagacc ccgtagaaaa gatcaaagga tcttcttgag atcctttttt tctgcgcgta   6720
atctgctgct tgcaaacaaa aaaaccaccg ctaccagcgg tggtttgttt gccggatcaa   6780
gagctaccaa ctctttttcc gaaggtaact ggcttcagca gagcgcagat accaaatact   6840
gttcttctag tgtagccgta gttaggccac cacttcaaga actctgtagc accgcctaca   6900
tacctcgctc tgctaatcct gttaccagtg gctgctgcca gtggcgataa gtcgtgtctt   6960
accgggttgg actcaagacg atagttaccg gataaggcgc agcggtcggg ctgaacgggg   7020
ggttcgtgca cacagcccag cttggagcga acgacctaca ccgaactgag atacctacag   7080
cgtgagctat gagaaagcgc cacgcttccc gaagggagaa aggcggacag gtatccggta   7140
```

agcggcaggg tcggaacagg agagcgcacg agggagcttc cagggggaaa cgcctggtat 7200
ctttatagtc ctgtcgggtt tcgccacctc tgacttgagc gtcgattttt gtgatgctcg 7260
tcaggggggc ggagcctatg gaaaaacgcc agcaacgcgg cctttttacg gttcctggcc 7320
ttttgctggc cttttgctca catgt 7345

<210> SEQ ID NO 72
<211> LENGTH: 7427
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaat tcagtggatc ccgataacta taacggtcct 180
aaggtagcga tttaaatgag ggcctatttc ccatgattcc ttcatatttg catatacgat 240
acaaggctgt tagagagata attagaatta atttgactgt aaacacaaag atattagtac 300
aaaatacgtg acgtagaaag taataatttc ttgggtagtt tgcagtttta aaattatgtt 360
ttaaaatgga ctatcatatg cttaccgtaa cttgaaagta tttcgatttc ttggctttat 420
atatcttgtg gaaaggacga ggtaccgtga gctgttggag actagaaaag ccttttgact 480
acgaggttta catttcgttc aaaatcgttt tctatagttc agctgcttct gagctgttgg 540
agactagaaa agccttttga ctacgaggtt tacatttcgt tcaaaatcgt tttctatagt 600
tcagctgctt ctttttttccg ggacgcgtca attgagatct ccgacattga ttattgacta 660
gttattaata gtaatcaatt acggggtcat tagttcatag cccatatatg gagttccgcg 720
ttacataact tacggtaaat ggcccgcctg gctgaccgcc caacgacccc cgcccattga 780
cgtcaataat gacgtatgtt cccatagtaa cgccaatagg gactttccat tgacgtcaat 840
gggtggagta tttacggtaa actgcccact tggcagtaca tcaagtgtat catatgccaa 900
gtacgccccc tattgacgtc aatgacggta aatggcccgc ctggcattat gcccagtaca 960
tgaccttatg ggactttcct acttggcagt acatctacgt attagtcatc gctattacca 1020
tgtcgaggcc acgttctgct tcactctccc catctccccc ccctccccac ccccaatttt 1080
gtatttattt atttttaat tattttgtgc agcgatgggg gcgggggggg ggggcgcgcg 1140
ccaggcgggg cggggcgggg cgaggggcgg ggcggggcga ggcggagagg tgcggcggca 1200
gccaatcaga gcggcgcgct ccgaaagttt ccttttatgg cgaggcggcg gcggcggcgg 1260
ccctataaaa agcgaagcgc gcggcgggcg ggagcaagct tcgtttagtg aaccgtcaga 1320
tcgcctggag acgccatcca cgctgttttg acctccatag aagacaccgg gaccgatcca 1380
gcctccgcgg attcgaatcc cggccgggaa cggtgcattg gaacgcggat tccccgtgcc 1440
aagagtgacg taagtaccgc ctatagagtc tataggccca caaaaaatgc tttcttcttt 1500
taatatactt ttttgtttat cttatttcta atactttccc taatctcttt ctttcagggc 1560
aataatgata caatgtatca tgcctctttg caccattcta aagaataaca gtgataattt 1620
ctgggttaag gcaatagcaa tatttctgca tataaatatt tctgcatata aattgtaact 1680
gatgtaagag gtttcatatt gctaatagca gctacaatcc agctaccatt ctgcttttat 1740
tttgtggttg ggataaggct ggattattct gagtccaagc taggcccttt tgctaatcgt 1800

```
gttcatacct cttatcttcc tcccacagct cctgggcaac gtgctggtct gtgtgctggc   1860
ccatcacttt ggcaaagaat taccggtggc aacgtgctgg ttattgtgct gtctcatcat   1920
tttggcaaag aattcacgcc ccagagccgc caccatggcc tacccatacg atgttccaga   1980
ttacgctaca gaattacctg ccccccttgag ctacttccag aatgcacaga tgagcgagga   2040
caaccacctg agcaatactg tacgtagcca gaatgacaac agagaacggc aggaacacaa   2100
cgacaggcgg agcctgggcc accctgagcc cctgtctaat ggaagacccc agggtaacag   2160
cagacaggtg gtggaacaag atgaggaaga ggacgaggag ctgaccctga agtacggcgc   2220
caagcacgtg atcatgctct tcgtgcccgt gactctctgc atggtggtgg tggtggctac   2280
aatcaagagc gtcagctttt atacccggaa ggatgggcag ctaatctata ccccattcac   2340
agaagacacc gagactgtgg gccagagagc cctgcactca atcctgaatg ccgccatcat   2400
gatcagcgtc attgttgtca tgactatcct cctggtggtt ctgtataaat acaggtgcta   2460
taaggtcatc catgcctggc tgatcatatc atctctgttg ctgctgttct tttttagctt   2520
catttacctg ggcgaagtgt ttaaaaccta taacgttgcc gtggactaca ttactgttgc   2580
cctcctgatc tggaacttcg gcgtggtggg catgatttcc attcactgga aaggcccccct   2640
gagactgcag caggcatacc tcattatgat ctccgccctc atggccctgg tgttcatcaa   2700
gtacctgccc gagtggactg cttggctcat cttggctgtg atctccgtgt atgatttagt   2760
ggctgttctg tgtcctaaag gtccactgcg tatgctggtg gaaacagctc aggaaagaaa   2820
tgaaacactg tttcctgctc tgatttactc ctcaacaatg gtgtggctcg tgaatatggc   2880
cgaaggagac cctgaagccc aacggagagt gtccaaaaac tccaagtata acgccgagag   2940
cacagaaagg gagagccagg atacagttgc cgagaatgac gatggcggct tcagtgagga   3000
atgggaagcc cagagggaca gccacctggg gcctcacaga agcacccctg agtctagagc   3060
cgctgtccag gaactgtcca gctccatcct ggccggcgaa gaccccgaag aaaggggagt   3120
aaaacttgga ctgggagatt tcatcttcta cagtgttctc gttggcaaag ccagcgcaac   3180
agctagcgga gactggaaca caacaatagc ctgtttcgta gccatcttaa ttggcctgtg   3240
ccttacactt ctgctcctgg ccatcttcaa gaaggccctg ccagccctgc ctatcagcat   3300
caccttcggg cttgttttct actttgccac cgattatctg gtgcagccct tcatggacca   3360
gctggccttc caccagtttt acatctagta agcggccgcc ctagggagct cctcgagggg   3420
gtggcatccc tgtgacccct ccccagtgcc tctcctggcc ctggaagttg ccactccagt   3480
gcccaccagc cttgtcctaa taaaattaag ttgcatcatt ttgtctgact aggtgtcctt   3540
ctataatatt atggggtgga ggggggtggt atggagcaag gggcaagggg ggaagacaac   3600
ctgtagggcc tgcggggtct attgggaacc aagctggagt gcagtggcac aatcttggct   3660
cactgcaatc tccgcctcct gggttcaagc gattctcctg cctcagcctc ccgagttgtt   3720
gggattccag gcatgcatga ccaggctcag ctaatttttg tttttttggt agagacgggg   3780
tttcaccata ttggccaggc tggtctcccc ctcctaatct caggtgatct acccaccttg   3840
gcctcccaaa ttgctgggat tacaggcgtg aaccactgct cccttccctg tccttcctgg   3900
gcctagggct gtgccagctg cctcgtcccg tcaccttctg gcttcttctc tccctccata   3960
tcttagctgt tttcctcatg agaatgttcc aaattcgaaa tttctattta accattatat   4020
atttacttgt ttgctattat ctctgccccc agtagattgt tagctccaga agagaaagga   4080
tcatgtcttt tgcttatcta gatatgccca tctgcctggt acaatctctg gcacatgtta   4140
caggcaacaa ctacttgtgg aattggtgaa tgcatgaata gaagaatgag tgaatgaatg   4200
```

```
aatagacaat aggcagaaat ccagcctcaa agagcttaca gtctggtaag aggaataaaa   4260
tgtctgcaaa tagccacagg acaggtcaaa ggaaggaggg gctatttcca gctgagggca   4320
ccccatcagg aaagcacccc agacttcctt agggataaca gggtaatggc gcgggccgca   4380
ggaaccccta gtgatggagt tggccactcc ctctctgcgc gctcgctcgc tcactgaggc   4440
cgggcgacca aaggtcgccc gacgcccggg ctttgcccgg gcggcctcag tgagcgagcg   4500
agcgcgcagc tgcctgcagg ggcgcctgat gcggtatttt ctccttacgc atctgtgcgg   4560
tatttcacac cgcatacgtc aaagcaacca tagtacgcgc cctgtagcgg cgcattaagc   4620
gcggcgggtg tggtggttac gcgcagcgtg accgctacac ttgccagcgc cttagcgccc   4680
gctcctttcg ctttcttccc ttcctttctc gccacgttcg ccggctttcc ccgtcaagct   4740
ctaaatcggg ggctcccttt agggttccga tttagtgctt tacggcacct cgaccccaaa   4800
aaacttgatt tgggtgatgg ttcacgtagt gggccatcgc cctgatagac ggtttttcgc   4860
cctttgacgt tggagtccac gttctttaat agtggactct tgttccaaac tggaacaaca   4920
ctcaactcta tctcgggcta ttcttttgat ttataaggga ttttgccgat ttcggtctat   4980
tggttaaaaa atgagctgat ttaacaaaaa tttaacgcga attttaacaa aatattaacg   5040
tttacaattt tatggtgcac tctcagtaca atctgctctg atgccgcata gttaagccag   5100
ccccgacacc cgccaacacc cgctgacgcg ccctgacggg cttgtctgct cccggcatcc   5160
gcttacagac aagctgtgac cgtctccggg agctgcatgt gtcagaggtt ttcaccgtca   5220
tcaccgaaac gcgcgagacg aaagggcctc gtgatacgcc tatttttata ggttaatgtc   5280
atgataataa tggtttctta gacgtcaggt ggcacttttc ggggaaatgt gcgcggaacc   5340
cctatttgtt tatttttcta aatacattca aatatgtatc cgctcatgag acaataaccc   5400
tgataaatgc ttcaataata ttgaaaaagg aagagtcgat cgatcaagag acaggatgag   5460
gatcgtttcg catgattgaa caagatggat tgcacgcagg ttctccggcc gcttgggtgg   5520
agaggctatt cggctatgac tgggcacaac agacaatcgg ctgctctgat gccgccgtgt   5580
tccggctgtc agcgcagggg cgcccggttc tttttgtcaa gaccgacctg tccggtgccc   5640
tgaatgaact gcaagacgag gcagcgcggc tatcgtggct ggccacgacg ggcgttcctt   5700
gcgcagctgt gctcgacgtt gtcactgaag cgggaaggga ctggctgcta ttgggcgaag   5760
tgccggggca ggatctcctg tcatctcacc ttgctcctgc cgagaaagta tccatcatgg   5820
ctgatgcaat gcggcggctg catacgcttg atccggctac ctgcccattc gaccaccaag   5880
cgaaacatcg catcgagcga gcacgtactc ggatggaagc cggtcttgtc gatcaggatg   5940
atctggacga agagcatcag gggctcgcgc cagccgaact gttcgccagg ctcaaggcga   6000
gcatgcccga cggcgaggat ctcgtcgtga cccatggcga tgcctgcttg ccgaatatca   6060
tggtggaaaa tggccgcttt tctggattca tcgactgtgg ccggctgggt gtggcggatc   6120
gctatcagga catagcgttg gctacccgtg atattgctga agagcttggc ggcgaatggg   6180
ctgaccgctt cctcgtgctt tacggtatcg ccgctcccga ttcgcagcgc atcgccttct   6240
atcgccttct tgacgagttc ttctgaacga gcgtgacacc acgatgcctg tagcaatggc   6300
aacaacgttg cgcaaactat taactggcga actacttact ctagcttccc ggcaacaatt   6360
aatagactgg atggaggcgg ataaagttgc aggaccactt ctgcgctcgg cccttccggc   6420
tggctggttt attgctgata aatctggagc cggtgagcgt gggtctcgcg gtatcattgc   6480
agcactgggg ccagatggta agccctcccg tatcgtagtt atctacacga cggggagtca   6540
```

ggcaactatg gatgaacgaa atagacagat cgctgagata ggtgcctcac tgattaagca 6600
ttggtaactg tcagaccaag tttactcata tatactttag attgatttaa aacttcattt 6660
ttaatttaaa aggatctagg tgaagatcct ttttgataat ctcatgacca aaatccctta 6720
acgtgagttt tcgttccact gagcgtcaga ccccgtagaa aagatcaaag gatcttcttg 6780
agatcctttt tttctgcgcg taatctgctg cttgcaaaca aaaaaaccac cgctaccagc 6840
ggtggtttgt ttgccggatc aagagctacc aactcttttt ccgaaggtaa ctggcttcag 6900
cagagcgcag ataccaaata ctgttcttct agtgtagccg tagttaggcc accacttcaa 6960
gaactctgta gcaccgccta catacctcgc tctgctaatc ctgttaccag tggctgctgc 7020
cagtggcgat aagtcgtgtc ttaccgggtt ggactcaaga cgatagttac cggataaggc 7080
gcagcggtcg ggctgaacgg ggggttcgtg cacacagccc agcttggagc gaacgaccta 7140
caccgaactg agatacctac agcgtgagct atgagaaagc gccacgcttc ccgaagggag 7200
aaaggcggac aggtatccgg taagcggcag ggtcggaaca ggagagcgca cgagggagct 7260
tccaggggga aacgcctggt atctttatag tcctgtcggg tttcgccacc tctgacttga 7320
gcgtcgattt ttgtgatgct cgtcaggggg gcggagccta tggaaaaacg ccagcaacgc 7380
ggccttttta cggttcctgg ccttttgctg gccttttgct cacatgt 7427

<210> SEQ ID NO 73
<211> LENGTH: 7509
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 73
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaat tcagtggatc ccgataacta taacggtcct 180
aaggtagcga tttaaatgag ggcctatttc ccatgattcc ttcatatttg catatacgat 240
acaaggctgt tagagagata attagaatta atttgactgt aaacacaaag atattagtac 300
aaaatacgtg acgtagaaag taataatttc ttgggtagtt tgcagtttta aaattatgtt 360
ttaaaatgga ctatcatatg cttaccgtaa cttgaaagta tttcgatttc ttggctttat 420
atatcttgtg gaaaggacga ggtaccgtga gctgttggaa ttatgtttcg aatttgactt 480
tagaggttta catttctagt caaagaagaa acatccattc agctgctcct gagctgttgg 540
aattatgttt cgaatttgac tttagaggtt tacatttcta gtcaaagaag aaacatccat 600
tcagctgctc ctgagctgtt ggaattatgt ttcgaatttg actttagagg tttacatttc 660
tagtcaaaga agaaacatcc attcagctgc tcctttttc cgggacgcgt caattgagat 720
ctccgacatt gattattgac tagttattaa tagtaatcaa ttacggggtc attagttcat 780
agcccatata tggagttccg cgttacataa cttacggtaa atggcccgcc tggctgaccg 840
cccaacgacc cccgcccatt gacgtcaata atgacgtatg ttcccatagt aacgccaata 900
gggactttcc attgacgtca atgggtggag tatttacggt aaactgccca cttggcagta 960
catcaagtgt atcatatgcc aagtacgccc cctattgacg tcaatgacgg taaatggccc 1020
gcctggcatt atgcccagta catgacctta tgggactttc ctacttggca gtacatctac 1080
gtattagtca tcgctattac catgtcgagg ccacgttctg cttcactctc cccatctccc 1140

```
cccccctcccc acccccaatt ttgtatttat ttatttttta attattttgt gcagcgatgg   1200
gggcgggggg ggggggcgcg cgccaggcgg ggcggggcgg ggcgaggggc ggggcggggc   1260
gaggcggaga ggtgcggcgg cagccaatca gagcggcgcg ctccgaaagt ttccttttat   1320
ggcgaggcgg cggcggcggc ggccctataa aaagcgaagc gcgcggcggg cgggagcaag   1380
cttcgtttag tgaaccgtca gatcgcctgg agacgccatc cacgctgttt tgacctccat   1440
agaagacacc gggaccgatc cagcctccgc ggattcgaat cccggccggg aacggtgcat   1500
tggaacgcgg attccccgtg ccaagagtga cgtaagtacc gcctatagag tctataggcc   1560
cacaaaaaat gctttcttct tttaatatac tttttttgttt atcttatttc taatactttc   1620
cctaatctct ttctttcagg gcaataatga tacaatgtat catgcctctt tgcaccattc   1680
taaagaataa cagtgataat ttctgggtta aggcaatagc aatatttctg catataaata   1740
tttctgcata taaattgtaa ctgatgtaag aggtttcata ttgctaatag cagctacaat   1800
ccagctacca ttctgctttt attttgtggt tgggataagg ctggattatt ctgagtccaa   1860
gctaggccct tttgctaatc gtgttcatac ctcttatctt cctcccacag ctcctgggca   1920
acgtgctggt ctgtgtgctg gcccatcact ttggcaaaga attaccggtg gcaacgtgct   1980
ggttattgtg ctgtctcatc attttggcaa agaattcacg ccccagagcc gccaccatgg   2040
cctacccata cgatgttcca gattacgcta cagaattacc tgccccccttg agctacttcc   2100
agaatgcaca gatgagcgag gacaaccacc tgagcaatac tgtacgtagc cagaatgaca   2160
acagagaacg gcaggaacac aacgacaggc ggagcctggg ccaccctgag cccctgtcta   2220
atggaagacc ccagggtaac agcagacagg tggtggaaca agatgaggaa gaggacgagg   2280
agctgaccct gaagtacggc gccaagcacg tgatcatgct cttcgtgccc gtgactctct   2340
gcatggtggt ggtggtggct acaatcaaga gcgtcagctt ttatacccgg aaggatgggc   2400
agctaatcta taccccattc acagaagaca ccgagactgt gggccagaga gccctgcact   2460
caatcctgaa tgccgccatc atgatcagcg tcattgttgt catgactatc ctcctggtgg   2520
ttctgtataa atacaggtgc tataaggtca tccatgcctg gctgatcata tcatctctgt   2580
tgctgctgtt ctttttttagc ttcatttacc tgggcgaagt gtttaaaacc tataacgttg   2640
ccgtggacta cattactgtt gccctcctga tctggaactt cggcgtggtg ggcatgattt   2700
ccattcactg gaaaggcccc ctgagactgc agcaggcata cctcattatg atctccgccc   2760
tcatggccct ggtgttcatc aagtacctgc ccgagtggac tgcttggctc atcttggctg   2820
tgatctccgt gtatgattta gtggctgttc tgtgtcctaa aggtccactg cgtatgctgg   2880
tggaaacagc tcaggaaaga aatgaaacac tgtttcctgc tctgatttac tcctcaacaa   2940
tggtgtggct cgtgaatatg gccgaaggag accctgaagc ccaacggaga gtgtccaaaa   3000
actccaagta taacgccgag agcacagaaa gggagagcca ggatacagtt gccgagaatg   3060
acgatggcgg cttcagtgag gaatgggaag cccagaggga cagccacctg gggcctcaca   3120
gaagcacccc tgagtctaga gccgctgtcc aggaactgtc cagctccatc ctggccggcg   3180
aagaccccga agaaagggga gtaaaacttg gactgggaga tttcatcttc tacagtgttc   3240
tcgttggcaa agccagcgca acagctagcg gagactggaa cacaacaata gcctgtttcg   3300
tagccatctt aattggcctg tgccttacac ttctgctcct ggccatcttc aagaaggccc   3360
tgccagccct gcctatcagc atcaccttcg ggcttgtttt ctactttgcc accgattatc   3420
tggtgcagcc cttcatggac cagctggcct tccaccagtt ttacatctag taagcggccg   3480
ccctagggag ctcctcgagg gggtggcatc cctgtgaccc ctccccagtg cctctcctgg   3540
```

```
ccctggaagt tgccactcca gtgcccacca gccttgtcct aataaaatta agttgcatca   3600
ttttgtctga ctaggtgtcc ttctataata ttatggggtg gaggggggtg gtatggagca   3660
aggggcaagg ggggaagaca acctgtaggg cctgcggggt ctattgggaa ccaagctgga   3720
gtgcagtggc acaatcttgg ctcactgcaa tctccgcctc ctgggttcaa gcgattctcc   3780
tgcctcagcc tcccgagttg ttgggattcc aggcatgcat gaccaggctc agctaatttt   3840
tgtttttttg gtagagacgg ggtttcacca tattggccag gctggtctcc ccctcctaat   3900
ctcaggtgat ctacccacct tggcctccca aattgctggg attacaggcg tgaaccactg   3960
ctcccttccc tgtccttcct gggcctaggg ctgtgccagc tgcctcgtcc cgtcaccttc   4020
tggcttcttc tctccctcca tatcttagct gttttcctca tgagaatgtt ccaaattcga   4080
aatttctatt taaccattat atatttactt gtttgctatt atctctgccc ccagtagatt   4140
gttagctcca gaagagaaag gatcatgtct tttgcttatc tagatatgcc catctgcctg   4200
gtacaatctc tggcacatgt tacaggcaac aactacttgt ggaattggtg aatgcatgaa   4260
tagaagaatg agtgaatgaa tgaatagaca ataggcagaa atccagcctc aaagagctta   4320
cagtctggta agaggaataa aatgtctgca aatagccaca ggacaggtca aaggaaggag   4380
gggctatttc cagctgaggg caccccatca ggaaagcacc ccagacttcc ttagggataa   4440
cagggtaatg gcgcgggccg caggaacccc tagtgatgga gttggccact ccctctctgc   4500
gcgctcgctc gctcactgag gccgggcgac caaaggtcgc ccgacgcccg ggctttgccc   4560
gggcggcctc agtgagcgag cgagcgcgca gctgcctgca ggggcgcctg atgcggtatt   4620
ttctccttac gcatctgtgc ggtatttcac accgcatacg tcaaagcaac catagtacgc   4680
gccctgtagc ggcgcattaa gcgcggcggg tgtggtggtt acgcgcagcg tgaccgctac   4740
acttgccagc gccttagcgc ccgctccttt cgctttcttc ccttcctttc tcgccacgtt   4800
cgccggcttt ccccgtcaag ctctaaatcg ggggctccct ttagggttcc gatttagtgc   4860
tttacggcac ctcgacccca aaaaacttga tttgggtgat ggttcacgta gtgggccatc   4920
gccctgatag acggtttttc gccctttgac gttggagtcc acgttcttta atagtggact   4980
cttgttccaa actggaacaa cactcaactc tatctcgggc tattcttttg atttataagg   5040
gattttgccg atttcggtct attggttaaa aaatgagctg atttaacaaa aatttaacgc   5100
gaattttaac aaaatattaa cgtttacaat tttatggtgc actctcagta caatctgctc   5160
tgatgccgca tagttaagcc agccccgaca cccgccaaca cccgctgacg cgccctgacg   5220
ggcttgtctg ctcccggcat ccgcttacag acaagctgtg accgtctccg ggagctgcat   5280
gtgtcagagg ttttcaccgt catcaccgaa acgcgcgaga cgaaagggcc tcgtgatacg   5340
cctattttta taggttaatg tcatgataat aatggtttct tagacgtcag gtggcacttt   5400
tcggggaaat gtgcgcggaa cccctatttg tttatttttc taaatacatt caaatatgta   5460
tccgctcatg agacaataac cctgataaat gcttcaataa tattgaaaaa ggaagagtcg   5520
atcgatcaag agacaggatg aggatcgttt cgcatgattg aacaagatgg attgcacgca   5580
ggttctccgg ccgcttgggt ggagaggcta ttcggctatg actgggcaca acagacaatc   5640
ggctgctctg atgccgccgt gttccggctg tcagcgcagg ggcgcccggt tctttttgtc   5700
aagaccgacc tgtccggtgc cctgaatgaa ctgcaagacg aggcagcgcg gctatcgtgg   5760
ctggccacga cgggcgttcc ttgcgcagct gtgctcgacg ttgtcactga agcgggaagg   5820
gactggctgc tattgggcga agtgccgggg caggatctcc tgtcatctca ccttgctcct   5880
```

```
gccgagaaag tatccatcat ggctgatgca atgcggcggc tgcatacgct tgatccggct   5940

acctgcccat tcgaccacca agcgaaacat cgcatcgagc gagcacgtac tcggatggaa   6000

gccggtcttg tcgatcagga tgatctggac gaagagcatc aggggctcgc gccagccgaa   6060

ctgttcgcca ggctcaaggc gagcatgccc gacggcgagg atctcgtcgt gacccatggc   6120

gatgcctgct tgccgaatat catggtggaa aatggccgct tttctggatt catcgactgt   6180

ggccggctgg gtgtggcgga tcgctatcag gacatagcgt tggctacccg tgatattgct   6240

gaagagcttg gcggcgaatg ggctgaccgc ttcctcgtgc tttacggtat cgccgctccc   6300

gattcgcagc gcatcgcctt ctatcgcctt cttgacgagt tcttctgaac gagcgtgaca   6360

ccacgatgcc tgtagcaatg gcaacaacgt tgcgcaaact attaactggc gaactactta   6420

ctctagcttc ccggcaacaa ttaatagact ggatggaggc ggataaagtt gcaggaccac   6480

ttctgcgctc ggcccttccg gctggctggt ttattgctga taaatctgga gccggtgagc   6540

gtgggtctcg cggtatcatt gcagcactgg ggccagatgg taagccctcc cgtatcgtag   6600

ttatctacac gacggggagt caggcaacta tggatgaacg aaatagacag atcgctgaga   6660

taggtgcctc actgattaag cattggtaac tgtcagacca agtttactca tatatacttt   6720

agattgattt aaaacttcat ttttaattta aaaggatcta ggtgaagatc ctttttgata   6780

atctcatgac caaaatccct taacgtgagt tttcgttcca ctgagcgtca gaccccgtag   6840

aaaagatcaa aggatcttct tgagatcctt tttttctgcg cgtaatctgc tgcttgcaaa   6900

caaaaaaacc accgctacca gcggtggttt gtttgccgga tcaagagcta ccaactcttt   6960

ttccgaaggt aactggcttc agcagagcgc agataccaaa tactgttctt ctagtgtagc   7020

cgtagttagg ccaccacttc aagaactctg tagcaccgcc tacatacctc gctctgctaa   7080

tcctgttacc agtggctgct gccagtggcg ataagtcgtg tcttaccggg ttggactcaa   7140

gacgatagtt accggataag gcgcagcggt cgggctgaac ggggggttcg tgcacacagc   7200

ccagcttgga gcgaacgacc tacaccgaac tgagatacct acagcgtgag ctatgagaaa   7260

gcgccacgct tcccgaaggg agaaaggcgg acaggtatcc ggtaagcggc agggtcggaa   7320

caggagagcg cacgagggag cttccagggg gaaacgcctg gtatctttat agtcctgtcg   7380

ggtttcgcca cctctgactt gagcgtcgat ttttgtgatg ctcgtcaggg gggcggagcc   7440

tatggaaaaa cgccagcaac gcggcctttt tacggttcct ggccttttgc tggccttttg   7500

ctcacatgt                                                           7509
```

<210> SEQ ID NO 74
<211> LENGTH: 7509
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 74

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccaat tcagtggatc ccgataacta taacggtcct    180

aaggtagcga tttaaatgag ggcctatttc ccatgattcc ttcatatttg catatacgat    240

acaaggctgt tagagagata attagaatta atttgactgt aaacacaaag atattagtac    300

aaaatacgtg acgtagaaag taataatttc ttgggtagtt tgcagtttta aaattatgtt    360
```

```
ttaaaatgga ctatcatatg cttaccgtaa cttgaaagta tttcgatttc ttggctttat    420
atatcttgtg gaaaggacga ggtaccgtga gctgttggag actagaaaag ccttttgact    480
acgaggttta catttcgttc aaaatcgttt tctatagttc agctgcttct gagctgttgg    540
agactagaaa agccttttga ctacgaggtt tacatttcgt tcaaaatcgt tttctatagt    600
tcagctgctt ctgagctgtt ggagactaga aaagcctttt gactacgagg tttacatttc    660
gttcaaaatc gttttctata gttcagctgc ttcttttttc cgggacgcgt caattgagat    720
ctccgacatt gattattgac tagttattaa tagtaatcaa ttacggggtc attagttcat    780
agcccatata tggagttccg cgttacataa cttacggtaa atggcccgcc tggctgaccg    840
cccaacgacc cccgcccatt gacgtcaata atgacgtatg ttcccatagt aacgccaata    900
gggactttcc attgacgtca atgggtggag tatttacggt aaactgccca cttggcagta    960
catcaagtgt atcatatgcc aagtacgccc cctattgacg tcaatgacgg taaatggccc   1020
gcctggcatt atgcccagta catgacctta tgggactttc ctacttggca gtacatctac   1080
gtattagtca tcgctattac catgtcgagg ccacgttctg cttcactctc cccatctccc   1140
ccccctcccc acccccaatt ttgtatttat ttatttttta attattttgt gcagcgatgg   1200
gggcgggggg ggggggcgcg cgccaggcgg ggcggggcgg ggcgaggggc ggggcggggc   1260
gaggcggaga ggtgcggcgg cagccaatca gagcggcgcg ctccgaaagt ttccttttat   1320
ggcgaggcgg cggcggcggc ggccctataa aaagcgaagc gcgcggcggg cgggagcaag   1380
cttcgtttag tgaaccgtca gatcgcctgg agacgccatc cacgctgttt tgacctccat   1440
agaagacacc gggaccgatc cagcctccgc ggattcgaat cccggccggg aacggtgcat   1500
tggaacgcgg attccccgtg ccaagagtga cgtaagtacc gcctatagag tctataggcc   1560
cacaaaaaat gctttcttct tttaatatac ttttttgttt atcttatttc taatactttc   1620
cctaatctct ttctttcagg gcaataatga tacaatgtat catgcctctt tgcaccattc   1680
taaagaataa cagtgataat ttctgggtta aggcaatagc aatatttctg catataaata   1740
tttctgcata taaattgtaa ctgatgtaag aggtttcata ttgctaatag cagctacaat   1800
ccagctacca ttctgctttt attttgtggt tgggataagg ctggattatt ctgagtccaa   1860
gctaggccct tttgctaatc gtgttcatac ctcttatctt cctcccacag ctcctgggca   1920
acgtgctggt ctgtgtgctg gcccatcact ttggcaaaga attaccggtg gcaacgtgct   1980
ggttattgtg ctgtctcatc attttggcaa agaattcacg ccccagagcc gccaccatgg   2040
cctacccata cgatgttcca gattacgcta cagaattacc tgcccccttg agctacttcc   2100
agaatgcaca gatgagcgag gacaaccacc tgagcaatac tgtacgtagc cagaatgaca   2160
acagagaacg gcaggaacac aacgacaggc ggagcctggg ccaccctgag cccctgtcta   2220
atggaagacc ccagggtaac agcagacagg tggtggaaca agatgaggaa gaggacgagg   2280
agctgaccct gaagtacggc gccaagcacg tgatcatgct cttcgtgccc gtgactctct   2340
gcatggtggt ggtggtggct acaatcaaga gcgtcagctt ttatacccgg aaggatgggc   2400
agctaatcta taccccattc acagaagaca ccgagactgt gggccagaga gccctgcact   2460
caatcctgaa tgccgccatc atgatcagcg tcattgttgt catgactatc ctcctggtgg   2520
ttctgtataa atacaggtgc tataaggtca tccatgcctg gctgatcata tcatctctgt   2580
tgctgctgtt ctttttttagc ttcatttacc tgggcgaagt gtttaaaacc tataacgttg   2640
ccgtggacta cattactgtt gccctcctga tctggaactt cggcgtggtg ggcatgattt   2700
ccattcactg gaaaggcccc ctgagactgc agcaggcata cctcattatg atctccgccc   2760
```

tcatggccct ggtgttcatc aagtacctgc ccgagtggac tgcttggctc atcttggctg 2820
tgatctccgt gtatgattta gtggctgttc tgtgtcctaa aggtccactg cgtatgctgg 2880
tggaaacagc tcaggaaaga aatgaaacac tgtttcctgc tctgatttac tcctcaacaa 2940
tggtgtggct cgtgaatatg gccgaaggag accctgaagc ccaacggaga gtgtccaaaa 3000
actccaagta taacgccgag agcacagaaa gggagagcca ggatacagtt gccgagaatg 3060
acgatggcgg cttcagtgag gaatgggaag cccagaggga cagccacctg gggcctcaca 3120
gaagcacccc tgagtctaga gccgctgtcc aggaactgtc cagctccatc ctggccggcg 3180
aagaccccga agaaagggga gtaaaacttg gactgggaga tttcatcttc tacagtgttc 3240
tcgttggcaa agccagcgca acagctagcg gagactggaa cacaacaata gcctgtttcg 3300
tagccatctt aattggcctg tgccttacac ttctgctcct ggccatcttc aagaaggccc 3360
tgccagccct gcctatcagc atcaccttcg ggcttgtttt ctactttgcc accgattatc 3420
tggtgcagcc cttcatggac cagctggcct tccaccagtt ttacatctag taagcggccg 3480
ccctagggag ctcctcgagg gggtggcatc cctgtgaccc ctccccagtg cctctcctgg 3540
ccctggaagt tgccactcca gtgcccacca gccttgtcct aataaaatta agttgcatca 3600
ttttgtctga ctaggtgtcc ttctataata ttatggggtg gaggggggtg gtatggagca 3660
aggggcaagg ggggaagaca acctgtaggg cctgcggggt ctattgggaa ccaagctgga 3720
gtgcagtggc acaatcttgg ctcactgcaa tctccgcctc ctgggttcaa gcgattctcc 3780
tgcctcagcc tcccgagttg ttgggattcc aggcatgcat gaccaggctc agctaatttt 3840
tgtttttttg gtagagacgg ggtttcacca tattggccag gctggtctcc ccctcctaat 3900
ctcaggtgat ctacccacct tggcctccca aattgctggg attacaggcg tgaaccactg 3960
ctcccttccc tgtccttcct gggcctaggg ctgtgccagc tgcctcgtcc cgtcaccttc 4020
tggcttcttc tctccctcca tatcttagct gttttcctca tgagaatgtt ccaaattcga 4080
aatttctatt taaccattat atatttactt gtttgctatt atctctgccc ccagtagatt 4140
gttagctcca gaagagaaag gatcatgtct tttgcttatc tagatatgcc catctgcctg 4200
gtacaatctc tggcacatgt tacaggcaac aactacttgt ggaattggtg aatgcatgaa 4260
tagaagaatg agtgaatgaa tgaatagaca ataggcagaa atccagcctc aaagagctta 4320
cagtctggta agaggaataa aatgtctgca aatagccaca ggacaggtca aaggaaggag 4380
gggctatttc cagctgaggg caccccatca ggaaagcacc ccagacttcc ttagggataa 4440
cagggtaatg gcgcgggccg caggaacccc tagtgatgga gttggccact ccctctctgc 4500
gcgctcgctc gctcactgag gccgggcgac caaaggtcgc ccgacgcccg ggctttgccc 4560
gggcggcctc agtgagcgag cgagcgcgca gctgcctgca ggggcgcctg atgcggtatt 4620
ttctccttac gcatctgtgc ggtatttcac accgcatacg tcaaagcaac catagtacgc 4680
gccctgtagc ggcgcattaa gcgcggcggg tgtggtggtt acgcgcagcg tgaccgctac 4740
acttgccagc gccttagcgc ccgctccttt cgctttcttc ccttcctttc tcgccacgtt 4800
cgccggcttt ccccgtcaag ctctaaatcg ggggctccct ttagggttcc gatttagtgc 4860
tttacggcac ctcgacccca aaaaacttga tttgggtgat ggttcacgta gtgggccatc 4920
gccctgatag acggtttttc gccctttgac gttggagtcc acgttcttta atagtggact 4980
cttgttccaa actggaacaa cactcaactc tatctcgggc tattcttttg atttataagg 5040
gattttgccg atttcggtct attggttaaa aaatgagctg atttaacaaa aatttaacgc 5100

```
gaattttaac aaaatattaa cgtttacaat tttatggtgc actctcagta caatctgctc   5160
tgatgccgca tagttaagcc agccccgaca cccgccaaca cccgctgacg cgccctgacg   5220
ggcttgtctg ctcccggcat ccgcttacag acaagctgtg accgtctccg ggagctgcat   5280
gtgtcagagg ttttcaccgt catcaccgaa acgcgcgaga cgaaagggcc tcgtgatacg   5340
cctattttta taggttaatg tcatgataat aatggtttct tagacgtcag gtggcacttt   5400
tcggggaaat gtgcgcggaa cccctatttg tttatttttc taaatacatt caaatatgta   5460
tccgctcatg agacaataac cctgataaat gcttcaataa tattgaaaaa ggaagagtcg   5520
atcgatcaag agacaggatg aggatcgttt cgcatgattg aacaagatgg attgcacgca   5580
ggttctccgg ccgcttgggt ggagaggcta ttcggctatg actgggcaca acagacaatc   5640
ggctgctctg atgccgccgt gttccggctg tcagcgcagg ggcgcccggt tctttttgtc   5700
aagaccgacc tgtccggtgc cctgaatgaa ctgcaagacg aggcagcgcg gctatcgtgg   5760
ctggccacga cgggcgttcc ttgcgcagct gtgctcgacg ttgtcactga agcgggaagg   5820
gactggctgc tattgggcga agtgccgggg caggatctcc tgtcatctca ccttgctcct   5880
gccgagaaag tatccatcat ggctgatgca atgcggcggc tgcatacgct tgatccggct   5940
acctgcccat tcgaccacca agcgaaacat cgcatcgagc gagcacgtac tcggatggaa   6000
gccggtcttg tcgatcagga tgatctggac gaagagcatc aggggctcgc gccagccgaa   6060
ctgttcgcca ggctcaaggc gagcatgccc gacggcgagg atctcgtcgt gacccatggc   6120
gatgcctgct tgccgaatat catggtggaa aatggccgct tttctggatt catcgactgt   6180
ggccggctgg gtgtggcgga tcgctatcag gacatagcgt tggctacccg tgatattgct   6240
gaagagcttg gcggcgaatg ggctgaccgc ttcctcgtgc tttacggtat cgccgctccc   6300
gattcgcagc gcatcgcctt ctatcgcctt cttgacgagt tcttctgaac gagcgtgaca   6360
ccacgatgcc tgtagcaatg gcaacaacgt tgcgcaaact attaactggc gaactactta   6420
ctctagcttc ccggcaacaa ttaatagact ggatggaggc ggataaagtt gcaggaccac   6480
ttctgcgctc ggcccttccg gctggctggt ttattgctga taaatctgga gccggtgagc   6540
gtgggtctcg cggtatcatt gcagcactgg ggccagatgg taagccctcc cgtatcgtag   6600
ttatctacac gacggggagt caggcaacta tggatgaacg aaatagacag atcgctgaga   6660
taggtgcctc actgattaag cattggtaac tgtcagacca agtttactca tatatacttt   6720
agattgattt aaaacttcat ttttaattta aaaggatcta ggtgaagatc ctttttgata   6780
atctcatgac caaaatccct taacgtgagt tttcgttcca ctgagcgtca gaccccgtag   6840
aaaagatcaa aggatcttct tgagatcctt tttttctgcg cgtaatctgc tgcttgcaaa   6900
caaaaaaacc accgctacca gcggtggttt gtttgccgga tcaagagcta ccaactcttt   6960
ttccgaaggt aactggcttc agcagagcgc agataccaaa tactgttctt ctagtgtagc   7020
cgtagttagg ccaccacttc aagaactctg tagcaccgcc tacatacctc gctctgctaa   7080
tcctgttacc agtggctgct gccagtggcg ataagtcgtg tcttaccggg ttggactcaa   7140
gacgatagtt accggataag gcgcagcggt cgggctgaac ggggggttcg tgcacacagc   7200
ccagcttgga gcgaacgacc tacaccgaac tgagatacct acagcgtgag ctatgagaaa   7260
gcgccacgct tcccgaaggg agaaaggcgg acaggtatcc ggtaagcggc agggtcggaa   7320
caggagagcg cacgagggag cttccagggg gaaacgcctg gtatctttat agtcctgtcg   7380
ggtttcgcca cctctgactt gagcgtcgat ttttgtgatg ctcgtcaggg gggcggagcc   7440
tatggaaaaa cgccagcaac gcggcctttt tacggttcct ggccttttgc tggccttttg   7500
```

ctcacatgt 7509

<210> SEQ ID NO 75
<211> LENGTH: 7265
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 75
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaat tcagtggatc ccgataacta taacggtcct 180
aaggtagcga tttaaatccg ggacgcgtca attgagatct ccgacattga ttattgacta 240
gttattaata gtaatcaatt acggggtcat tagttcatag cccatatatg gagttccgcg 300
ttacataact tacggtaaat ggcccgcctg gctgaccgcc caacgacccc cgcccattga 360
cgtcaataat gacgtatgtt cccatagtaa cgccaatagg gactttccat tgacgtcaat 420
gggtggagta tttacggtaa actgcccact tggcagtaca tcaagtgtat catatgccaa 480
gtacgccccc tattgacgtc aatgacggta aatggcccgc ctggcattat gcccagtaca 540
tgaccttatg ggactttcct acttggcagt acatctacgt attagtcatc gctattacca 600
tgtcgaggcc acgttctgct tcactctccc catctccccc ccctccccac ccccaatttt 660
gtatttattt atttttaat tattttgtgc agcgatgggg gcgggggggg ggggcgcgcg 720
ccaggcgggg cggggcgggg cgaggggcgg ggcggggcga ggcggagagg tgcggcggca 780
gccaatcaga gcggcgcgct ccgaaagttt ccttttatgg cgaggcggcg gcggcggcgg 840
ccctataaaa agcgaagcgc gcggcgggcg ggagcaagct tcgtttagtg aaccgtcaga 900
tcgcctggag acgccatcca cgctgttttg acctccatag aagacaccgg gaccgatcca 960
gcctccgcgg attcgaatcc cggccgggaa cggtgcattg gaacgcggat tccccgtgcc 1020
aagagtgacg taagtaccgc ctatagagtc tataggccca caaaaaatgc tttcttcttt 1080
taatatactt ttttgtttat cttatttcta atactttccc taatctcttt ctttcagggc 1140
aataatgata caatgtatca tgcctctttg caccattcta aagaataaca gtgataattt 1200
ctgggttaag gcaatagcaa tatttctgca tataaatatt tctgcatata aattgtaact 1260
gatgtaagag gtttcatatt gctaatagca gctacaatcc agctaccatt ctgcttttat 1320
tttgtggttg ggataaggct ggattattct gagatatcgg tacctgagct gttggagact 1380
agaaaagcct tttgactacg aggtttacat ttcgttcaaa atcgttttct atagttcagc 1440
tgcttctgag ctgttggaga ctagaaaagc cttttgacta cgaggtttac atttcgttca 1500
aaatcgtttt ctatagttca gctgcttctg agctgttgga gactagaaaa gccttttgac 1560
tacgaggttt acatttcgtt caaaatcgtt ttctatagtt cagctgcttc gtcgacgcta 1620
ggcccttttg ctaatcgtgt tcatacctct tatcttcctc ccacagctcc tgggcaacgt 1680
gctggtctgt gtgctggccc atcactttgg caaagaatta ccggtggcaa cgtgctggtt 1740
attgtgctgt ctcatcattt tggcaaagaa ttcacgcccc agagccgcca ccatggccta 1800
cccatacgat gttccagatt acgctacaga attacctgcc cccttgagct acttccagaa 1860
tgcacagatg agcgaggaca accacctgag caatactgta cgtagccaga atgacaacag 1920
agaacggcag gaacacaacg acaggcggag cctgggccac cctgagcccc tgtctaatgg 1980
aagaccccag ggtaacagca gacaggtggt ggaacaagat gaggaagagg acgaggagct 2040
gaccctgaag tacggcgcca agcacgtgat catgctcttc gtgcccgtga ctctctgcat 2100
ggtggtggtg gtggctacaa tcaagagcgt cagcttttat acccggaagg atgggcagct 2160
aatctatacc ccattcacag aagacaccga gactgtgggc cagagagccc tgcactcaat 2220
cctgaatgcc gccatcatga tcagcgtcat tgttgtcatg actatcctcc tggtggttct 2280
gtataaatac aggtgctata aggtcatcca tgcctggctg atcatatcat ctctgttgct 2340
gctgttcttt tttagcttca tttacctggg cgaagtgttt aaaacctata acgttgccgt 2400
ggactacatt actgttgccc tcctgatctg gaacttcggc gtggtgggca tgatttccat 2460
tcactggaaa ggcccccctga gactgcagca ggcatacctc attatgatct ccgccctcat 2520
ggccctggtg ttcatcaagt acctgcccga gtggactgct tggctcatct tggctgtgat 2580
ctccgtgtat gatttagtgg ctgttctgtg tcctaaaggt ccactgcgta tgctggtgga 2640
aacagctcag gaaagaaatg aaacactgtt tcctgctctg atttactcct caacaatggt 2700
gtggctcgtg aatatggccg aaggagaccc tgaagcccaa cggagagtgt ccaaaaactc 2760
caagtataac gccgagagca cagaaaggga gagccaggat acagttgccg agaatgacga 2820
tggcggcttc agtgaggaat gggaagccca gagggacagc cacctggggc ctcacagaag 2880
cacccctgag tctagagccg ctgtccagga actgtccagc tccatcctgg ccggcgaaga 2940
ccccgaagaa aggggagtaa aacttggact gggagatttc atcttctaca gtgttctcgt 3000
tggcaaagcc agcgcaacag ctagcggaga ctggaacaca acaatagcct gtttcgtagc 3060
catcttaatt ggcctgtgcc ttacacttct gctcctggcc atcttcaaga aggccctgcc 3120
agccctgcct atcagcatca ccttcgggct tgttttctac tttgccaccg attatctggt 3180
gcagcccttc atggaccagc tggccttcca ccagttttac atctagtaag cggccgccct 3240
agggagctcc tcgagggggt ggcatccctg tgacccctcc ccagtgcctc tcctggccct 3300
ggaagttgcc actccagtgc ccaccagcct tgtcctaata aaattaagtt gcatcatttt 3360
gtctgactag gtgtccttct ataatattat ggggtggagg ggggtggtat ggagcaaggg 3420
gcaagggggg aagacaacct gtagggcctg cggggtctat tgggaaccaa gctggagtgc 3480
agtggcacaa tcttggctca ctgcaatctc cgcctcctgg gttcaagcga ttctcctgcc 3540
tcagcctccc gagttgttgg gattccaggc atgcatgacc aggctcagct aatttttgtt 3600
tttttggtag agacggggtt tcaccatatt ggccaggctg gtctccccct cctaatctca 3660
ggtgatctac ccaccttggc ctcccaaatt gctgggatta caggcgtgaa ccactgctcc 3720
cttccctgtc cttcctgggc ctagggctgt gccagctgcc tcgtcccgtc accttctggc 3780
ttcttctctc cctccatatc ttagctgttt tcctcatgag aatgttccaa attcgaaatt 3840
tctatttaac cattatatat ttacttgttt gctattatct ctgcccccag tagattgtta 3900
gctccagaag agaaaggatc atgtcttttg cttatctaga tatgcccatc tgcctggtac 3960
aatctctggc acatgttaca ggcaacaact acttgtggaa ttggtgaatg catgaataga 4020
agaatgagtg aatgaatgaa tagacaatag gcagaaatcc agcctcaaag agcttacagt 4080
ctggtaagag gaataaaatg tctgcaaata gccacaggac aggtcaaagg aaggaggggc 4140
tatttccagc tgagggcacc ccatcaggaa agcaccccag acttccttag ggataacagg 4200
gtaatggcgc gggccgcagg aacccctagt gatggagttg gccactccct ctctgcgcgc 4260
tcgctcgctc actgaggccg ggcgaccaaa ggtcgcccga cgcccgggct ttgcccgggc 4320
ggcctcagtg agcgagcgag cgcgcagctg cctgcagggg cgcctgatgc ggtattttct 4380
ccttacgcat ctgtgcggta tttcacaccg catacgtcaa agcaaccata gtacgcgccc 4440
tgtagcggcg cattaagcgc ggcgggtgtg gtggttacgc gcagcgtgac cgctacactt 4500
gccagcgcct tagcgcccgc tcctttcgct ttcttccctt cctttctcgc cacgttcgcc 4560
ggctttcccc gtcaagctct aaatcggggg ctccctttag ggttccgatt tagtgcttta 4620
cggcacctcg accccaaaaa acttgatttg ggtgatggtt cacgtagtgg gccatcgccc 4680
tgatagacgg tttttcgccc tttgacgttg gagtccacgt tctttaatag tggactcttg 4740
ttccaaactg gaacaacact caactctatc tcgggctatt cttttgattt ataagggatt 4800
ttgccgattt cggtctattg gttaaaaaat gagctgattt aacaaaaatt taacgcgaat 4860
tttaacaaaa tattaacgtt tacaatttta tggtgcactc tcagtacaat ctgctctgat 4920
gccgcatagt taagccagcc ccgacacccg ccaacacccg ctgacgcgcc ctgacgggct 4980
tgtctgctcc cggcatccgc ttacagacaa gctgtgaccg tctccgggag ctgcatgtgt 5040
cagaggtttt caccgtcatc accgaaacgc gcgagacgaa agggcctcgt gatacgccta 5100
tttttatagg ttaatgtcat gataataatg gtttcttaga cgtcaggtgg cacttttcgg 5160
ggaaatgtgc gcggaacccc tatttgttta tttttctaaa tacattcaaa tatgtatccg 5220
ctcatgagac aataaccctg ataaatgctt caataatatt gaaaaaggaa gagtcgatcg 5280
atcaagagac aggatgagga tcgtttcgca tgattgaaca agatggattg cacgcaggtt 5340
ctccggccgc ttgggtggag aggctattcg gctatgactg ggcacaacag acaatcggct 5400
gctctgatgc cgccgtgttc cggctgtcag cgcaggggcg cccggttctt tttgtcaaga 5460
ccgacctgtc cggtgccctg aatgaactgc aagacgaggc agcgcggcta tcgtggctgg 5520
ccacgacggg cgttccttgc gcagctgtgc tcgacgttgt cactgaagcg ggaagggact 5580
ggctgctatt gggcgaagtg ccggggcagg atctcctgtc atctcacctt gctcctgccg 5640
agaaagtatc catcatggct gatgcaatgc ggcggctgca tacgcttgat ccggctacct 5700
gcccattcga ccaccaagcg aaacatcgca tcgagcgagc acgtactcgg atggaagccg 5760
gtcttgtcga tcaggatgat ctggacgaag agcatcaggg gctcgcgcca gccgaactgt 5820
tcgccaggct caaggcgagc atgcccgacg gcgaggatct cgtcgtgacc catggcgatg 5880
cctgcttgcc gaatatcatg gtggaaaatg gccgcttttc tggattcatc gactgtggcc 5940
ggctgggtgt ggcggatcgc tatcaggaca tagcgttggc tacccgtgat attgctgaag 6000
agcttggcgg cgaatgggct gaccgcttcc tcgtgcttta cggtatcgcc gctcccgatt 6060
cgcagcgcat cgccttctat cgccttcttg acgagttctt ctgaacgagc gtgacaccac 6120
gatgcctgta gcaatggcaa caacgttgcg caaactatta actggcgaac tacttactct 6180
agcttcccgg caacaattaa tagactggat ggaggcggat aaagttgcag gaccacttct 6240
gcgctcggcc cttccggctg gctggtttat tgctgataaa tctggagccg gtgagcgtgg 6300
gtctcgcggt atcattgcag cactggggcc agatggtaag ccctcccgta tcgtagttat 6360
ctacacgacg gggagtcagg caactatgga tgaacgaaat agacagatcg ctgagatagg 6420
tgcctcactg attaagcatt ggtaactgtc agaccaagtt tactcatata tactttagat 6480
tgatttaaaa cttcattttt aatttaaaag gatctaggtg aagatccttt ttgataatct 6540
catgaccaaa atcccttaac gtgagttttc gttccactga gcgtcagacc ccgtagaaaa 6600
gatcaaagga tcttcttgag atcctttttt tctgcgcgta atctgctgct tgcaaacaaa 6660
aaaaccaccg ctaccagcgg tggtttgttt gccggatcaa gagctaccaa ctctttttcc 6720
gaaggtaact ggcttcagca gagcgcagat accaaatact gttcttctag tgtagccgta 6780
gttaggccac cacttcaaga actctgtagc accgcctaca tacctcgctc tgctaatcct 6840
gttaccagtg gctgctgcca gtggcgataa gtcgtgtctt accgggttgg actcaagacg 6900
atagttaccg gataaggcgc agcggtcggg ctgaacgggg ggttcgtgca cacagcccag 6960
cttggagcga acgacctaca ccgaactgag atacctacag cgtgagctat gagaaagcgc 7020
cacgcttccc gaagggagaa aggcggacag gtatccggta agcggcaggg tcggaacagg 7080
agagcgcacg agggagcttc cagggggaaa cgcctggtat ctttatagtc ctgtcgggtt 7140
tcgccacctc tgacttgagc gtcgattttt gtgatgctcg tcaggggggc ggagcctatg 7200
gaaaaacgcc agcaacgcgg cctttttacg gttcctggcc ttttgctggc cttttgctca 7260
catgt 7265

<210> SEQ ID NO 76
<211> LENGTH: 7287
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 76
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaat tcagtggatc ccgataacta taacggtcct 180
aaggtagcga tttaaatgag ggcctatttc ccatgattcc ttcatatttg catatacgat 240
acaaggctgt tagagagata attagaatta atttgactgt aaacacaaag atattagtac 300
aaaatacgtg acgtagaaag taataatttc ttgggtagtt tgcagtttta aaattatgtt 360
ttaaaatgga ctatcatatg cttaccgtaa cttgaaagta tttcgatttc ttggctttat 420
atatcttgtg gaaaggacga ggtaccgtga gctgttggaa gcttggatgg tcttgtattc 480
aggaggttta catttcctat acaactgcat ccaatgattc agctgcttct ttttccggga 540
cgcgtcaatt gagatctccg acattgatta ttgactagtt attaatagta atcaattacg 600
gggtcattag ttcatagccc atatatggag ttccgcgtta cataacttac ggtaaatggc 660
ccgcctggct gaccgcccaa cgacccccgc ccattgacgt caataatgac gtatgttccc 720
atagtaacgc caatagggac tttccattga cgtcaatggg tggagtattt acggtaaact 780
gcccacttgg cagtacatca agtgtatcat atgccaagta cgccccctat tgacgtcaat 840
gacggtaaat ggcccgcctg gcattatgcc cagtacatga ccttatggga ctttcctact 900
tggcagtaca tctacgtatt agtcatcgct attaccatgt cgaggccacg ttctgcttca 960
ctctccccat ctcccccccc tccccacccc caattttgta tttatttatt ttttaattat 1020
tttgtgcagc gatgggggcg gggggggggg gcgcgcgcca ggcggggcgg ggcggggcga 1080
ggggcggggc ggggcgaggc ggagaggtgc ggcggcagcc aatcagagcg gcgcgctccg 1140
aaagtttcct tttatggcga ggcggcggcg gcggcggccc tataaaaagc gaagcgcgcg 1200
gcgggcggga gcaagcttcg tttagtgaac cgtcagatcg cctggagacg ccatccacgc 1260
tgttttgacc tccatagaag acaccgggac cgatccagcc tccgcggatt cgaatcccgg 1320
ccgggaacgg tgcattggaa cgcggattcc ccgtgccaag agtgacgtaa gtaccgccta 1380
tagagtctat aggcccacaa aaaatgcttt cttcttttaa tatacttttt tgtttatctt 1440
atttctaata ctttccctaa tctctttctt tcagggcaat aatgatacaa tgtatcatgc 1500
ctctttgcac cattctaaag aataacagtg ataatttctg ggttaaggca atagcaatat 1560
ttctgcatat aaatatttct gcatataaat tgtaactgat gtaagaggtt tcatattgct 1620
aatagcagct acaatccagc taccattctg cttttatttt gtggttggga taaggctgga 1680
ttattctgag tccaagctag gcccttttgc taatcgtgtt catacctctt atcttcctcc 1740
cacagctcct gggcaacgtg ctggtctgtg tgctggccca tcactttggc aaagaattac 1800
cggtggcaac gtgctggtta ttgtgctgtc tcatcatttt ggcaaagaat tcacgcccca 1860
gagccgccac catggcctac ccatacgatg ttccagatta cgctctcaca ttcatggcct 1920
ctgacagcga ggaagaagtg tgtgatgagc ggacgtccct aatgtcggct gagagcccca 1980
cgccgcgctc ctgccaggag ggcaggcagg gcccagagga tggagagaac actgcccagt 2040
ggagaagcca ggagaacgag gaggacggtg aggaggaccc tgaccgctat gtctgtagtg 2100
gggttcccgg gcggccgcca ggcctggagg aagagctgac cctcaaatac ggagcgaagc 2160
acgtgatcat gctgtttgtg cctgtcactc tgtgcatgat cgtggtggta gccaccatca 2220
agtctgtgcg cttctacaca gagaagaatg gacagctcat ctacacgcca ttcactgagg 2280
acacaccctc ggtgggccag cgcctcctca actccgtgct gaacaccctc atcatgatca 2340
gcgtcatcgt ggttatgacc atcttcttgg tggtgctcta caagtaccgc tgctacaagt 2400
tcatccatgg ctggttgatc atgtcttcac tgatgctgct gttcctcttc acctatatct 2460
accttgggga agtgctcaag acctacaatg tggccatgga ctacccccacc ctcttgctga 2520
ctgtctggaa cttcggggca gtgggcatgg tgtgcatcca ctggaagggc cctctggtgc 2580
tgcagcaggc ctacctcatc atgatcagtg cgctcatggc cctagtgttc atcaagtacc 2640
tcccagagtg gtccgcgtgg gtcatcctgg gcgccatctc tgtgtatgat ctcgtggctg 2700
tgctgtgtcc caaagggcct ctgagaatgc tggtagaaac tgcccaggag agaaatgagc 2760
ccatattccc tgccctgata tactcatctg ccatggtgtg gacggttggc atggcgaagc 2820
tggacccctc ctctcagggt gccctccagc tcccctacga cccggagatg gaagaagact 2880
cctatgacag ttttggggag ccttcatacc ccgaagtctt tgagcctccc ttgactggct 2940
acccagggga ggagctggag gaagaggagg aaaggggcgt gaagcttggc ctcggggact 3000
tcatcttcta cagtgtgctg gtgggcaagg cggctgccac gggcagcggg gactggaata 3060
ccacgctggc ctgcttcgtg gccatcctca ttggcttgtg tctgaccctc ctgctgcttg 3120
ctgtgttcaa gaaggcgctg cccgccctcc ccatctccat cacgttcggg ctcatctttt 3180
acttctccac ggacaacctg gtgcggccgt tcatggacac cctggcctcc catcagctct 3240
acatctagta agcggccgcc ctagggagct cctcgagggg gtggcatccc tgtgacccct 3300
ccccagtgcc tctcctggcc ctggaagttg ccactccagt gcccaccagc cttgtcctaa 3360
taaaattaag ttgcatcatt ttgtctgact aggtgtcctt ctataatatt atggggtgga 3420
ggggggtggt atggagcaag gggcaagggg ggaagacaac ctgtagggcc tgcggggtct 3480
attgggaacc aagctggagt gcagtggcac aatcttggct cactgcaatc tccgcctcct 3540
gggttcaagc gattctcctg cctcagcctc ccgagttgtt gggattccag gcatgcatga 3600
ccaggctcag ctaatttttg tttttttggt agagacgggg tttcaccata ttggccaggc 3660
tggtctcccc ctcctaatct caggtgatct acccaccttg gcctcccaaa ttgctgggat 3720
tacaggcgtg aaccactgct cccttccctg tccttcctgg gcctagggct gtgccagctg 3780

```
cctcgtcccg tcaccttctg gcttcttctc tccctccata tcttagctgt tttcctcatg   3840
agaatgttcc aaattcgaaa tttctattta accattatat atttacttgt ttgctattat   3900
ctctgccccc agtagattgt tagctccaga agagaaagga tcatgtcttt tgcttatcta   3960
gatatgccca tctgcctggt acaatctctg gcacatgtta caggcaacaa ctacttgtgg   4020
aattggtgaa tgcatgaata gaagaatgag tgaatgaatg aatagacaat aggcagaaat   4080
ccagcctcaa agagcttaca gtctggtaag aggaataaaa tgtctgcaaa tagccacagg   4140
acaggtcaaa ggaaggaggg gctatttcca gctgagggca ccccatcagg aaagcacccc   4200
agacttcctt agggataaca gggtaatggc gcgggccgca ggaaccccta gtgatggagt   4260
tggccactcc ctctctgcgc gctcgctcgc tcactgaggc cgggcgacca aaggtcgccc   4320
gacgcccggg ctttgcccgg gcggcctcag tgagcgagcg agcgcgcagc tgcctgcagg   4380
ggcgcctgat gcggtatttt ctccttacgc atctgtgcgg tatttcacac cgcatacgtc   4440
aaagcaacca tagtacgcgc cctgtagcgg cgcattaagc gcggcgggtg tggtggttac   4500
gcgcagcgtg accgctacac ttgccagcgc cttagcgccc gctcctttcg ctttcttccc   4560
ttcctttctc gccacgttcg ccggctttcc ccgtcaagct ctaaatcggg ggctcccttt   4620
agggttccga tttagtgctt tacggcacct cgaccccaaa aaacttgatt tgggtgatgg   4680
ttcacgtagt gggccatcgc cctgatagac ggtttttcgc cctttgacgt tggagtccac   4740
gttctttaat agtggactct tgttccaaac tggaacaaca ctcaactcta tctcgggcta   4800
ttcttttgat ttataaggga ttttgccgat ttcggtctat tggttaaaaa atgagctgat   4860
ttaacaaaaa tttaacgcga attttaacaa aatattaacg tttacaattt tatggtgcac   4920
tctcagtaca atctgctctg atgccgcata gttaagccag ccccgacacc cgccaacacc   4980
cgctgacgcg ccctgacggg cttgtctgct cccggcatcc gcttacagac aagctgtgac   5040
cgtctccggg agctgcatgt gtcagaggtt ttcaccgtca tcaccgaaac gcgcgagacg   5100
aaagggcctc gtgatacgcc tatttttata ggttaatgtc atgataataa tggtttctta   5160
gacgtcaggt ggcacttttc ggggaaatgt gcgcggaacc cctatttgtt tatttttcta   5220
aatacattca aatatgtatc cgctcatgag acaataaccc tgataaatgc ttcaataata   5280
ttgaaaaagg aagagtcgat cgatcaagag acaggatgag gatcgtttcg catgattgaa   5340
caagatggat tgcacgcagg ttctccggcc gcttgggtgg agaggctatt cggctatgac   5400
tgggcacaac agacaatcgg ctgctctgat gccgccgtgt tccggctgtc agcgcagggg   5460
cgcccggttc tttttgtcaa gaccgacctg tccggtgccc tgaatgaact gcaagacgag   5520
gcagcgcggc tatcgtggct ggccacgacg ggcgttcctt gcgcagctgt gctcgacgtt   5580
gtcactgaag cgggaaggga ctggctgcta ttgggcgaag tgccggggca ggatctcctg   5640
tcatctcacc ttgctcctgc cgagaaagta tccatcatgg ctgatgcaat gcggcggctg   5700
catacgcttg atccggctac ctgcccattc gaccaccaag cgaaacatcg catcgagcga   5760
gcacgtactc ggatggaagc cggtcttgtc gatcaggatg atctggacga agagcatcag   5820
gggctcgcgc cagccgaact gttcgccagg ctcaaggcga gcatgcccga cggcgaggat   5880
ctcgtcgtga cccatggcga tgcctgcttg ccgaatatca tggtggaaaa tggccgcttt   5940
tctggattca tcgactgtgg ccggctgggt gtggcggatc gctatcagga catagcgttg   6000
gctacccgtg atattgctga agagcttggc ggcgaatggg ctgaccgctt cctcgtgctt   6060
tacggtatcg ccgctcccga ttcgcagcgc atcgccttct atcgccttct tgacgagttc   6120
ttctgaacga gcgtgacacc acgatgcctg tagcaatggc aacaacgttg cgcaaactat   6180
```

taactggcga actacttact ctagcttccc ggcaacaatt aatagactgg atggaggcgg 6240
ataaagttgc aggaccactt ctgcgctcgg cccttccggc tggctggttt attgctgata 6300
aatctggagc cggtgagcgt gggtctcgcg gtatcattgc agcactgggg ccagatggta 6360
agccctcccg tatcgtagtt atctacacga cggggagtca ggcaactatg gatgaacgaa 6420
atagacagat cgctgagata ggtgcctcac tgattaagca ttggtaactg tcagaccaag 6480
tttactcata tatactttag attgatttaa aacttcattt ttaatttaaa aggatctagg 6540
tgaagatcct ttttgataat ctcatgacca aaatccctta acgtgagttt tcgttccact 6600
gagcgtcaga ccccgtagaa aagatcaaag gatcttcttg agatcctttt tttctgcgcg 6660
taatctgctg cttgcaaaca aaaaaaccac cgctaccagc ggtggtttgt ttgccggatc 6720
aagagctacc aactcttttt ccgaaggtaa ctggcttcag cagagcgcag ataccaaata 6780
ctgttcttct agtgtagccg tagttaggcc accacttcaa gaactctgta gcaccgccta 6840
catacctcgc tctgctaatc ctgttaccag tggctgctgc cagtggcgat aagtcgtgtc 6900
ttaccgggtt ggactcaaga cgatagttac cggataaggc gcagcggtcg ggctgaacgg 6960
ggggttcgtg cacacagccc agcttggagc gaacgaccta caccgaactg agatacctac 7020
agcgtgagct atgagaaagc gccacgcttc ccgaagggag aaaggcggac aggtatccgg 7080
taagcggcag ggtcggaaca ggagagcgca cgagggagct tccaggggga aacgcctggt 7140
atctttatag tcctgtcggg tttcgccacc tctgacttga gcgtcgattt ttgtgatgct 7200
cgtcaggggg gcggagccta tggaaaaacg ccagcaacgc ggccttttta cggttcctgg 7260
ccttttgctg gccttttgct cacatgt 7287

<210> SEQ ID NO 77
<211> LENGTH: 7287
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 77
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaat tcagtggatc ccgataacta taacggtcct 180
aaggtagcga tttaaatgag ggcctatttc ccatgattcc ttcatatttg catatacgat 240
acaaggctgt tagagagata attagaatta atttgactgt aaacacaaag atattagtac 300
aaaatacgtg acgtagaaag taataatttc ttgggtagtt tgcagtttta aaattatgtt 360
ttaaaatgga ctatcatatg cttaccgtaa cttgaaagta tttcgatttc ttggctttat 420
atatcttgtg gaaaggacga ggtaccgtga gctgttggat tccagttgtt atgttttatc 480
cagaggttta catttctgta aaactataca actgcatttc agctgcttct tttccggga 540 cgcgtcaatt gagatctccg acattgatta ttgactagtt attaatagta atcaattacg 600
gggtcattag ttcatagccc atatatggag ttccgcgtta cataacttac ggtaaatggc 660
ccgcctggct gaccgcccaa cgacccccgc ccattgacgt caataatgac gtatgttccc 720
atagtaacgc caatagggac tttccattga cgtcaatggg tggagtattt acggtaaact 780
gcccacttgg cagtacatca agtgtatcat atgccaagta cgccccctat tgacgtcaat 840
gacggtaaat ggcccgcctg gcattatgcc cagtacatga ccttatggga ctttcctact 900
tggcagtaca tctacgtatt agtcatcgct attaccatgt cgaggccacg ttctgcttca 960
ctctccccat ctcccccccc tccccacccc caattttgta tttatttatt ttttaattat 1020
tttgtgcagc gatgggggcg gggggggggg gcgcgcgcca ggcggggcgg ggcggggcga 1080
ggggcggggc ggggcgaggc ggagaggtgc ggcggcagcc aatcagagcg gcgcgctccg 1140
aaagtttcct tttatggcga ggcggcggcg gcggcggccc tataaaaagc gaagcgcgcg 1200
gcgggcggga gcaagcttcg tttagtgaac cgtcagatcg cctggagacg ccatccacgc 1260
tgttttgacc tccatagaag acaccgggac cgatccagcc tccgcggatt cgaatcccgg 1320
ccgggaacgg tgcattggaa cgcggattcc ccgtgccaag agtgacgtaa gtaccgccta 1380
tagagtctat aggcccacaa aaaatgcttt cttcttttaa tatacttttt tgtttatctt 1440
atttctaata ctttccctaa tctctttctt tcagggcaat aatgatacaa tgtatcatgc 1500
ctctttgcac cattctaaag aataacagtg ataatttctg ggttaaggca atagcaatat 1560
ttctgcatat aaatatttct gcatataaat tgtaactgat gtaagaggtt tcatattgct 1620
aatagcagct acaatccagc taccattctg cttttatttt gtggttggga taaggctgga 1680
ttattctgag tccaagctag gcccttttgc taatcgtgtt catacctctt atcttcctcc 1740
cacagctcct gggcaacgtg ctggtctgtg tgctggccca tcactttggc aaagaattac 1800
cggtggcaac gtgctggtta ttgtgctgtc tcatcatttt ggcaaagaat tcacgcccca 1860
gagccgccac catggcctac ccatacgatg ttccagatta cgctctcaca ttcatggcct 1920
ctgacagcga ggaagaagtg tgtgatgagc ggacgtccct aatgtcggct gagagcccca 1980
cgccgcgctc ctgccaggag ggcaggcagg gcccagagga tggagagaac actgcccagt 2040
ggagaagcca ggagaacgag gaggacggtg aggaggaccc tgaccgctat gtctgtagtg 2100
gggttcccgg gcggccgcca ggcctggagg aagagctgac cctcaaatac ggagcgaagc 2160
acgtgatcat gctgtttgtg cctgtcactc tgtgcatgat cgtggtggta gccaccatca 2220
agtctgtgcg cttctacaca gagaagaatg gacagctcat ctacacgcca ttcactgagg 2280
acacaccctc ggtgggccag cgcctcctca actccgtgct gaacaccctc atcatgatca 2340
gcgtcatcgt ggttatgacc atcttcttgg tggtgctcta caagtaccgc tgctacaagt 2400
tcatccatgg ctggttgatc atgtcttcac tgatgctgct gttcctcttc acctatatct 2460
accttgggga agtgctcaag acctacaatg tggccatgga ctaccccacc ctcttgctga 2520
ctgtctggaa cttcggggca gtgggcatgg tgtgcatcca ctggaagggc cctctggtgc 2580
tgcagcaggc ctacctcatc atgatcagtg cgctcatggc cctagtgttc atcaagtacc 2640
tcccagagtg gtccgcgtgg gtcatcctgg gcgccatctc tgtgtatgat ctcgtggctg 2700
tgctgtgtcc caaagggcct ctgagaatgc tggtagaaac tgcccaggag agaaatgagc 2760
ccatattccc tgccctgata tactcatctg ccatggtgtg gacggttggc atggcgaagc 2820
tggacccctc ctctcagggt gccctccagc tcccctacga cccggagatg gaagaagact 2880
cctatgacag ttttggggag ccttcatacc ccgaagtctt tgagcctccc ttgactggct 2940
acccagggga ggagctggag gaagaggagg aaaggggcgt gaagcttggc ctcggggact 3000
tcatcttcta cagtgtgctg gtgggcaagg cggctgccac gggcagcggg gactggaata 3060
ccacgctggc ctgcttcgtg gccatcctca ttggcttgtg tctgaccctc ctgctgcttg 3120
ctgtgttcaa gaaggcgctg cccgccctcc ccatctccat cacgttcggg ctcatctttt 3180
acttctccac ggacaacctg gtgcggccgt tcatggacac cctggcctcc catcagctct 3240
acatctagta agcggccgcc ctagggagct cctcgagggg gtggcatccc tgtgacccct 3300
ccccagtgcc tctcctggcc ctggaagttg ccactccagt gcccaccagc cttgtcctaa 3360
taaaattaag ttgcatcatt ttgtctgact aggtgtcctt ctataatatt atggggtgga 3420
ggggggtggt atggagcaag gggcaagggg ggaagacaac ctgtagggcc tgcggggtct 3480
attgggaacc aagctggagt gcagtggcac aatcttggct cactgcaatc tccgcctcct 3540
gggttcaagc gattctcctg cctcagcctc ccgagttgtt gggattccag gcatgcatga 3600
ccaggctcag ctaatttttg tttttttggt agagacgggg tttcaccata ttggccaggc 3660
tggtctcccc ctcctaatct caggtgatct acccaccttg gcctcccaaa ttgctgggat 3720
tacaggcgtg aaccactgct cccttccctg tccttcctgg gcctagggct gtgccagctg 3780
cctcgtcccg tcaccttctg gcttcttctc tccctccata tcttagctgt tttcctcatg 3840
agaatgttcc aaattcgaaa tttctattta accattatat atttacttgt ttgctattat 3900
ctctgccccc agtagattgt tagctccaga agagaaagga tcatgtcttt tgcttatcta 3960
gatatgccca tctgcctggt acaatctctg gcacatgtta caggcaacaa ctacttgtgg 4020
aattggtgaa tgcatgaata gaagaatgag tgaatgaatg aatagacaat aggcagaaat 4080
ccagcctcaa agagcttaca gtctggtaag aggaataaaa tgtctgcaaa tagccacagg 4140
acaggtcaaa ggaaggaggg gctatttcca gctgagggca ccccatcagg aaagcacccc 4200
agacttcctt agggataaca gggtaatggc gcgggccgca ggaaccccta gtgatggagt 4260
tggccactcc ctctctgcgc gctcgctcgc tcactgaggc cgggcgacca aaggtcgccc 4320
gacgcccggg ctttgcccgg gcggcctcag tgagcgagcg agcgcgcagc tgcctgcagg 4380
ggcgcctgat gcggtatttt ctccttacgc atctgtgcgg tatttcacac cgcatacgtc 4440
aaagcaacca tagtacgcgc cctgtagcgg cgcattaagc gcggcgggtg tggtggttac 4500
gcgcagcgtg accgctacac ttgccagcgc cttagcgccc gctcctttcg ctttcttccc 4560
ttcctttctc gccacgttcg ccggctttcc ccgtcaagct ctaaatcggg ggctcccttt 4620
agggttccga tttagtgctt tacggcacct cgaccccaaa aaacttgatt tgggtgatgg 4680
ttcacgtagt gggccatcgc cctgatagac ggtttttcgc cctttgacgt tggagtccac 4740
gttctttaat agtggactct tgttccaaac tggaacaaca ctcaactcta tctcgggcta 4800
ttcttttgat ttataaggga ttttgccgat ttcggtctat tggttaaaaa atgagctgat 4860
ttaacaaaaa tttaacgcga attttaacaa aatattaacg tttacaattt tatggtgcac 4920
tctcagtaca atctgctctg atgccgcata gttaagccag ccccgacacc cgccaacacc 4980
cgctgacgcg ccctgacggg cttgtctgct cccggcatcc gcttacagac aagctgtgac 5040
cgtctccggg agctgcatgt gtcagaggtt ttcaccgtca tcaccgaaac gcgcgagacg 5100
aaagggcctc gtgatacgcc tatttttata ggttaatgtc atgataataa tggtttctta 5160
gacgtcaggt ggcacttttc ggggaaatgt gcgcggaacc cctatttgtt tatttttcta 5220
aatacattca aatatgtatc cgctcatgag acaataaccc tgataaatgc ttcaataata 5280
ttgaaaaagg aagagtcgat cgatcaagag acaggatgag gatcgtttcg catgattgaa 5340
caagatggat tgcacgcagg ttctccggcc gcttgggtgg agaggctatt cggctatgac 5400
tgggcacaac agacaatcgg ctgctctgat gccgccgtgt tccggctgtc agcgcagggg 5460
cgcccggttc tttttgtcaa gaccgacctg tccggtgccc tgaatgaact gcaagacgag 5520
gcagcgcggc tatcgtggct ggccacgacg ggcgttcctt gcgcagctgt gctcgacgtt 5580
gtcactgaag cgggaaggga ctggctgcta ttgggcgaag tgccggggca ggatctcctg 5640

```
tcatctcacc ttgctcctgc cgagaaagta tccatcatgg ctgatgcaat gcggcggctg   5700

catacgcttg atccggctac ctgcccattc gaccaccaag cgaaacatcg catcgagcga   5760

gcacgtactc ggatggaagc cggtcttgtc gatcaggatg atctggacga agagcatcag   5820

gggctcgcgc cagccgaact gttcgccagg ctcaaggcga gcatgcccga cggcgaggat   5880

ctcgtcgtga cccatggcga tgcctgcttg ccgaatatca tggtggaaaa tggccgcttt   5940

tctggattca tcgactgtgg ccggctgggt gtggcggatc gctatcagga catagcgttg   6000

gctacccgtg atattgctga agagcttggc ggcgaatggg ctgaccgctt cctcgtgctt   6060

tacggtatcg ccgctcccga ttcgcagcgc atcgccttct atcgccttct tgacgagttc   6120

ttctgaacga gcgtgacacc acgatgcctg tagcaatggc aacaacgttg cgcaaactat   6180

taactggcga actacttact ctagcttccc ggcaacaatt aatagactgg atggaggcgg   6240

ataaagttgc aggaccactt ctgcgctcgg cccttccggc tggctggttt attgctgata   6300

aatctggagc cggtgagcgt gggtctcgcg gtatcattgc agcactgggg ccagatggta   6360

agccctcccg tatcgtagtt atctacacga cggggagtca ggcaactatg gatgaacgaa   6420

atagacagat cgctgagata ggtgcctcac tgattaagca ttggtaactg tcagaccaag   6480

tttactcata tatactttag attgatttaa aacttcattt ttaatttaaa aggatctagg   6540

tgaagatcct ttttgataat ctcatgacca aaatccctta acgtgagttt tcgttccact   6600

gagcgtcaga ccccgtagaa aagatcaaag gatcttcttg agatcctttt tttctgcgcg   6660

taatctgctg cttgcaaaca aaaaaaccac cgctaccagc ggtggtttgt ttgccggatc   6720

aagagctacc aactcttttt ccgaaggtaa ctggcttcag cagagcgcag ataccaaata   6780

ctgttcttct agtgtagccg tagttaggcc accacttcaa gaactctgta gcaccgccta   6840

catacctcgc tctgctaatc ctgttaccag tggctgctgc cagtggcgat aagtcgtgtc   6900

ttaccgggtt ggactcaaga cgatagttac cggataaggc gcagcggtcg ggctgaacgg   6960

ggggttcgtg cacacagccc agcttggagc gaacgaccta caccgaactg agatacctac   7020

agcgtgagct atgagaaagc gccacgcttc ccgaagggag aaaggcggac aggtatccgg   7080

taagcggcag ggtcggaaca ggagagcgca cgagggagct tccaggggga aacgcctggt   7140

atctttatag tcctgtcggg tttcgccacc tctgacttga gcgtcgattt ttgtgatgct   7200

cgtcaggggg gcggagccta tggaaaaacg ccagcaacgc ggccttttta cggttcctgg   7260

ccttttgctg gccttttgct cacatgt                                        7287
```

<210> SEQ ID NO 78
<211> LENGTH: 7287
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 78

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccaat tcagtggatc ccgataacta taacggtcct    180

aaggtagcga tttaaatgag ggcctatttc ccatgattcc ttcatatttg catatacgat    240

acaaggctgt tagagagata attagaatta atttgactgt aaacacaaag atattagtac    300

aaaatacgtg acgtagaaag taataatttc ttgggtagtt tgcagtttta aaattatgtt    360
```

ttaaaatgga ctatcatatg cttaccgtaa cttgaaagta tttcgatttc ttggctttat 420
atatcttgtg gaaaggacga ggtaccgtga gctgttggat tcgcttaatt cgaatatcct 480
aagaggttta catttcttga tattactatt aagccacttc agctgcttct tttccggga 540
cgcgtcaatt gagatctccg acattgatta ttgactagtt attaatagta atcaattacg 600
gggtcattag ttcatagccc atatatggag ttccgcgtta cataacttac ggtaaatggc 660
ccgcctggct gaccgcccaa cgacccccgc ccattgacgt caataatgac gtatgttccc 720
atagtaacgc caatagggac tttccattga cgtcaatggg tggagtattt acggtaaact 780
gcccacttgg cagtacatca agtgtatcat atgccaagta cgccccctat tgacgtcaat 840
gacggtaaat ggcccgcctg gcattatgcc cagtacatga ccttatggga ctttcctact 900
tggcagtaca tctacgtatt agtcatcgct attaccatgt cgaggccacg ttctgcttca 960
ctctccccat ctcccccccc tccccacccc caattttgta tttatttatt ttttaattat 1020
tttgtgcagc gatgggggcg gggggggggg gcgcgcgcca ggcggggcgg ggcggggcga 1080
ggggcggggc ggggcgaggc ggagaggtgc ggcggcagcc aatcagagcg gcgcgctccg 1140
aaagtttcct tttatggcga ggcggcggcg gcggcggccc tataaaaagc gaagcgcgcg 1200
gcgggcggga gcaagcttcg tttagtgaac cgtcagatcg cctggagacg ccatccacgc 1260
tgttttgacc tccatagaag acaccgggac cgatccagcc tccgcggatt cgaatcccgg 1320
ccgggaacgg tgcattggaa cgcggattcc ccgtgccaag agtgacgtaa gtaccgccta 1380
tagagtctat aggcccacaa aaaatgcttt cttcttttaa tatacttttt tgtttatctt 1440
atttctaata ctttccctaa tctctttctt tcagggcaat aatgatacaa tgtatcatgc 1500
ctctttgcac cattctaaag aataacagtg ataatttctg ggttaaggca atagcaatat 1560
ttctgcatat aaatatttct gcatataaat tgtaactgat gtaagaggtt tcatattgct 1620
aatagcagct acaatccagc taccattctg cttttatttt gtggttggga taaggctgga 1680
ttattctgag tccaagctag gcccttttgc taatcgtgtt catacctctt atcttcctcc 1740
cacagctcct gggcaacgtg ctggtctgtg tgctggccca tcactttggc aaagaattac 1800
cggtggcaac gtgctggtta ttgtgctgtc tcatcatttt ggcaaagaat tcacgcccca 1860
gagccgccac catggcctac ccatacgatg ttccagatta cgctctcaca ttcatggcct 1920
ctgacagcga ggaagaagtg tgtgatgagc ggacgtccct aatgtcggct gagagcccca 1980
cgccgcgctc ctgccaggag ggcaggcagg gcccagagga tggagagaac actgcccagt 2040
ggagaagcca ggagaacgag gaggacggtg aggaggaccc tgaccgctat gtctgtagtg 2100
gggttcccgg gcggccgcca ggcctggagg aagagctgac cctcaaatac ggagcgaagc 2160
acgtgatcat gctgtttgtg cctgtcactc tgtgcatgat cgtggtggta gccaccatca 2220
agtctgtgcg cttctacaca gagaagaatg gacagctcat ctacacgcca ttcactgagg 2280
acacaccctc ggtgggccag cgcctcctca actccgtgct gaacaccctc atcatgatca 2340
gcgtcatcgt ggttatgacc atcttcttgg tggtgctcta caagtaccgc tgctacaagt 2400
tcatccatgg ctggttgatc atgtcttcac tgatgctgct gttcctcttc acctatatct 2460
accttgggga agtgctcaag acctacaatg tggccatgga ctaccccacc ctcttgctga 2520
ctgtctggaa cttcggggca gtgggcatgg tgtgcatcca ctggaagggc cctctggtgc 2580
tgcagcaggc ctacctcatc atgatcagtg cgctcatggc cctagtgttc atcaagtacc 2640
tcccagagtg gtccgcgtgg gtcatcctgg gcgccatctc tgtgtatgat ctcgtggctg 2700

-continued

```
tgctgtgtcc caaagggcct ctgagaatgc tggtagaaac tgcccaggag agaaatgagc   2760
ccatattccc tgccctgata tactcatctg ccatggtgtg gacggttggc atggcgaagc   2820
tggacccctc ctctcagggt gccctccagc tcccctacga cccggagatg gaagaagact   2880
cctatgacag ttttggggag ccttcatacc ccgaagtctt tgagcctccc ttgactggct   2940
acccagggga ggagctggag gaagaggagg aaaggggcgt gaagcttggc ctcggggact   3000
tcatcttcta cagtgtgctg gtgggcaagg cggctgccac gggcagcggg gactggaata   3060
ccacgctggc ctgcttcgtg gccatcctca ttggcttgtg tctgaccctc ctgctgcttg   3120
ctgtgttcaa gaaggcgctg cccgccctcc ccatctccat cacgttcggg ctcatctttt   3180
acttctccac ggacaacctg gtgcggccgt tcatggacac cctggcctcc catcagctct   3240
acatctagta agcggccgcc ctagggagct cctcgagggg gtggcatccc tgtgacccct   3300
ccccagtgcc tctcctggcc ctggaagttg ccactccagt gcccaccagc cttgtcctaa   3360
taaaattaag ttgcatcatt ttgtctgact aggtgtcctt ctataatatt atggggtgga   3420
ggggggtggt atggagcaag gggcaagggg ggaagacaac ctgtagggcc tgcggggtct   3480
attgggaacc aagctggagt gcagtggcac aatcttggct cactgcaatc tccgcctcct   3540
gggttcaagc gattctcctg cctcagcctc ccgagttgtt gggattccag gcatgcatga   3600
ccaggctcag ctaatttttg tttttttggt agagacgggg tttcaccata ttggccaggc   3660
tggtctcccc ctcctaatct caggtgatct acccaccttg gcctcccaaa ttgctgggat   3720
tacaggcgtg aaccactgct cccttccctg tccttcctgg gcctagggct gtgccagctg   3780
cctcgtcccg tcaccttctg gcttcttctc tccctccata tcttagctgt tttcctcatg   3840
agaatgttcc aaattcgaaa tttctattta accattatat atttacttgt ttgctattat   3900
ctctgccccc agtagattgt tagctccaga agagaaagga tcatgtcttt tgcttatcta   3960
gatatgccca tctgcctggt acaatctctg gcacatgtta caggcaacaa ctacttgtgg   4020
aattggtgaa tgcatgaata gaagaatgag tgaatgaatg aatagacaat aggcagaaat   4080
ccagcctcaa agagcttaca gtctggtaag aggaataaaa tgtctgcaaa tagccacagg   4140
acaggtcaaa ggaaggaggg gctatttcca gctgagggca ccccatcagg aaagcacccc   4200
agacttcctt agggataaca gggtaatggc gcgggccgca ggaaccccta gtgatggagt   4260
tggccactcc ctctctgcgc gctcgctcgc tcactgaggc cgggcgacca aaggtcgccc   4320
gacgcccggg ctttgcccgg gcggcctcag tgagcgagcg agcgcgcagc tgcctgcagg   4380
ggcgcctgat gcggtatttt ctccttacgc atctgtgcgg tatttcacac cgcatacgtc   4440
aaagcaacca tagtacgcgc cctgtagcgg cgcattaagc gcggcgggtg tggtggttac   4500
gcgcagcgtg accgctacac ttgccagcgc cttagcgccc gctcctttcg ctttcttccc   4560
ttcctttctc gccacgttcg ccggctttcc ccgtcaagct ctaaatcggg ggctcccttt   4620
agggttccga tttagtgctt tacggcacct cgaccccaaa aaacttgatt tgggtgatgg   4680
ttcacgtagt gggccatcgc cctgatagac ggtttttcgc cctttgacgt tggagtccac   4740
gttctttaat agtggactct tgttccaaac tggaacaaca ctcaactcta tctcgggcta   4800
ttcttttgat ttataaggga ttttgccgat ttcggtctat tggttaaaaa atgagctgat   4860
ttaacaaaaa tttaacgcga attttaacaa aatattaacg tttacaattt tatggtgcac   4920
tctcagtaca atctgctctg atgccgcata gttaagccag ccccgacacc cgccaacacc   4980
cgctgacgcg ccctgacggg cttgtctgct cccggcatcc gcttacagac aagctgtgac   5040
cgtctccggg agctgcatgt gtcagaggtt ttcaccgtca tcaccgaaac gcgcgagacg   5100
```

```
aaagggcctc gtgatacgcc tatttttata ggttaatgtc atgataataa tggtttctta   5160
gacgtcaggt ggcacttttc ggggaaatgt gcgcggaacc cctatttgtt tatttttcta   5220
aatacattca aatatgtatc cgctcatgag acaataaccc tgataaatgc ttcaataata   5280
ttgaaaaagg aagagtcgat cgatcaagag acaggatgag gatcgtttcg catgattgaa   5340
caagatggat tgcacgcagg ttctccggcc gcttgggtgg agaggctatt cggctatgac   5400
tgggcacaac agacaatcgg ctgctctgat gccgccgtgt tccggctgtc agcgcagggg   5460
cgcccggttc tttttgtcaa gaccgacctg tccggtgccc tgaatgaact gcaagacgag   5520
gcagcgcggc tatcgtggct ggccacgacg ggcgttcctt gcgcagctgt gctcgacgtt   5580
gtcactgaag cgggaaggga ctggctgcta ttgggcgaag tgccggggca ggatctcctg   5640
tcatctcacc ttgctcctgc cgagaaagta tccatcatgg ctgatgcaat gcggcggctg   5700
catacgcttg atccggctac ctgcccattc gaccaccaag cgaaacatcg catcgagcga   5760
gcacgtactc ggatggaagc cggtcttgtc gatcaggatg atctggacga agagcatcag   5820
gggctcgcgc cagccgaact gttcgccagg ctcaaggcga gcatgcccga cggcgaggat   5880
ctcgtcgtga cccatggcga tgcctgcttg ccgaatatca tggtggaaaa tggccgcttt   5940
tctggattca tcgactgtgg ccggctgggt gtggcggatc gctatcagga catagcgttg   6000
gctacccgtg atattgctga agagcttggc ggcgaatggg ctgaccgctt cctcgtgctt   6060
tacggtatcg ccgctcccga ttcgcagcgc atcgccttct atcgccttct tgacgagttc   6120
ttctgaacga gcgtgacacc acgatgcctg tagcaatggc aacaacgttg cgcaaactat   6180
taactggcga actacttact ctagcttccc ggcaacaatt aatagactgg atggaggcgg   6240
ataaagttgc aggaccactt ctgcgctcgg cccttccggc tggctggttt attgctgata   6300
aatctggagc cggtgagcgt gggtctcgcg gtatcattgc agcactgggg ccagatggta   6360
agccctcccg tatcgtagtt atctacacga cggggagtca ggcaactatg gatgaacgaa   6420
atagacagat cgctgagata ggtgcctcac tgattaagca ttggtaactg tcagaccaag   6480
tttactcata tatactttag attgatttaa aacttcattt ttaatttaaa aggatctagg   6540
tgaagatcct ttttgataat ctcatgacca aaatccctta acgtgagttt tcgttccact   6600
gagcgtcaga ccccgtagaa aagatcaaag gatcttcttg agatcctttt tttctgcgcg   6660
taatctgctg cttgcaaaca aaaaaaccac cgctaccagc ggtggtttgt ttgccggatc   6720
aagagctacc aactcttttt ccgaaggtaa ctggcttcag cagagcgcag ataccaaata   6780
ctgttcttct agtgtagccg tagttaggcc accacttcaa gaactctgta gcaccgccta   6840
catacctcgc tctgctaatc ctgttaccag tggctgctgc cagtggcgat aagtcgtgtc   6900
ttaccgggtt ggactcaaga cgatagttac cggataaggc gcagcggtcg ggctgaacgg   6960
ggggttcgtg cacacagccc agcttggagc gaacgaccta caccgaactg agatacctac   7020
agcgtgagct atgagaaagc gccacgcttc ccgaagggag aaaggcggac aggtatccgg   7080
taagcggcag ggtcggaaca ggagagcgca cgagggagct tccaggggga aacgcctggt   7140
atctttatag tcctgtcggg tttcgccacc tctgacttga gcgtcgattt ttgtgatgct   7200
cgtcaggggg gcggagccta tggaaaaacg ccagcaacgc ggccttttta cggttcctgg   7260
ccttttgctg gccttttgct cacatgt                                       7287
```

<210> SEQ ID NO 79
<211> LENGTH: 7369
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 79
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaat tcagtggatc ccgataacta taacggtcct 180
aaggtagcga tttaaatgag ggcctatttc ccatgattcc ttcatatttg catatacgat 240
acaaggctgt tagagagata attagaatta atttgactgt aaacacaaag atattagtac 300
aaaatacgtg acgtagaaag taataatttc ttgggtagtt tgcagtttta aaattatgtt 360
ttaaaatgga ctatcatatg cttaccgtaa cttgaaagta tttcgatttc ttggctttat 420
atatcttgtg gaaaggacga ggtaccgtga gctgttggat tcgcttaatt cgaatatcct 480
aagaggttta catttcttga tattactatt aagccacttc agctgcttct gagctgttgg 540
attcgcttaa ttcgaatatc ctaagaggtt tacatttctt gatattacta ttaagccact 600
tcagctgctt ctttttccgg gacgcgtcaa ttgagatctc cgacattgat tattgactag 660
ttattaatag taatcaatta cggggtcatt agttcatagc ccatatatgg agttccgcgt 720
tacataactt acggtaaatg gcccgcctgg ctgaccgccc aacgaccccc gcccattgac 780
gtcaataatg acgtatgttc ccatagtaac gccaataggg actttccatt gacgtcaatg 840
ggtggagtat ttacggtaaa ctgcccactt ggcagtacat caagtgtatc atatgccaag 900
tacgccccct attgacgtca atgacggtaa atggcccgcc tggcattatg cccagtacat 960
gaccttatgg gactttccta cttggcagta catctacgta ttagtcatcg ctattaccat 1020
gtcgaggcca cgttctgctt cactctcccc atctcccccc cctccccacc cccaattttg 1080
tatttattta tttttttaatt attttgtgca gcgatggggg cggggggggg gggcgcgcgc 1140
caggcggggc ggggcggggc gaggggcggg gcggggcgag gcggagaggt gcggcggcag 1200
ccaatcagag cggcgcgctc cgaaagtttc cttttatggc gaggcggcgg cggcggcggc 1260
cctataaaaa gcgaagcgcg cggcgggcgg gagcaagctt cgtttagtga accgtcagat 1320
cgcctggaga cgccatccac gctgttttga cctccataga agacaccggg accgatccag 1380
cctccgcgga ttcgaatccc ggccgggaac ggtgcattgg aacgcggatt ccccgtgcca 1440
agagtgacgt aagtaccgcc tatagagtct ataggcccac aaaaaatgct ttcttctttt 1500
aatatacttt tttgtttatc ttatttctaa tactttccct aatctctttc tttcagggca 1560
ataatgatac aatgtatcat gcctctttgc accattctaa agaataacag tgataatttc 1620
tgggttaagg caatagcaat atttctgcat ataaatattt ctgcatataa attgtaactg 1680
atgtaagagg tttcatattg ctaatagcag ctacaatcca gctaccattc tgcttttatt 1740
ttgtggttgg gataaggctg gattattctg agtccaagct aggccctttt gctaatcgtg 1800
ttcatacctc ttatcttcct cccacagctc ctgggcaacg tgctggtctg tgtgctggcc 1860
catcactttg gcaaagaatt accggtggca acgtgctggt tattgtgctg tctcatcatt 1920
ttggcaaaga attcacgccc cagagccgcc accatggcct acccatacga tgttccagat 1980
tacgctctca cattcatggc ctctgacagc gaggaagaag tgtgtgatga gcggacgtcc 2040
ctaatgtcgg ctgagagccc cacgccgcgc tcctgccagg agggcaggca gggcccagag 2100
gatggagaga acactgccca gtggagaagc caggagaacg aggaggacgg tgaggaggac 2160
cctgaccgct atgtctgtag tggggttccc gggcggccgc caggcctgga ggaagagctg 2220
accctcaaat acggagcgaa gcacgtgatc atgctgtttg tgcctgtcac tctgtgcatg 2280
atcgtggtgg tagccaccat caagtctgtg cgcttctaca cagagaagaa tggacagctc 2340
atctacacgc cattcactga ggacacaccc tcggtgggcc agcgcctcct caactccgtg 2400
ctgaacaccc tcatcatgat cagcgtcatc gtggttatga ccatcttctt ggtggtgctc 2460
tacaagtacc gctgctacaa gttcatccat ggctggttga tcatgtcttc actgatgctg 2520
ctgttcctct tcacctatat ctaccttggg gaagtgctca agacctacaa tgtggccatg 2580
gactacccca ccctcttgct gactgtctgg aacttcgggg cagtgggcat ggtgtgcatc 2640
cactggaagg gccctctggt gctgcagcag gcctacctca tcatgatcag tgcgctcatg 2700
gccctagtgt tcatcaagta cctcccagag tggtccgcgt gggtcatcct gggcgccatc 2760
tctgtgtatg atctcgtggc tgtgctgtgt cccaaagggc ctctgagaat gctggtagaa 2820
actgcccagg agagaaatga gcccatattc cctgccctga tatactcatc tgccatggtg 2880
tggacggttg gcatggcgaa gctggacccc tcctctcagg gtgccctcca gctcccctac 2940
gacccggaga tggaagaaga ctcctatgac agttttgggg agccttcata ccccgaagtc 3000
tttgagcctc ccttgactgg ctacccaggg gaggagctgg aggaagagga ggaaaggggc 3060
gtgaagcttg gcctcgggga cttcatcttc tacagtgtgc tggtgggcaa ggcggctgcc 3120
acgggcagcg gggactggaa taccacgctg gcctgcttcg tggccatcct cattggcttg 3180
tgtctgaccc tcctgctgct tgctgtgttc aagaaggcgc tgcccgccct ccccatctcc 3240
atcacgttcg ggctcatctt ttacttctcc acggacaacc tggtgcggcc gttcatggac 3300
accctggcct cccatcagct ctacatctag taagcggccg ccctagggag ctcctcgagg 3360
gggtggcatc cctgtgaccc ctccccagtg cctctcctgg ccctggaagt tgccactcca 3420
gtgcccacca gccttgtcct aataaaatta agttgcatca ttttgtctga ctaggtgtcc 3480
ttctataata ttatggggtg gaggggggtg gtatggagca aggggcaagg ggggaagaca 3540
acctgtaggg cctgcggggt ctattgggaa ccaagctgga gtgcagtggc acaatcttgg 3600
ctcactgcaa tctccgcctc ctgggttcaa gcgattctcc tgcctcagcc tcccgagttg 3660
ttgggattcc aggcatgcat gaccaggctc agctaatttt tgtttttttg gtagagacgg 3720
ggtttcacca tattggccag gctggtctcc ccctcctaat ctcaggtgat ctacccacct 3780
tggcctccca aattgctggg attacaggcg tgaaccactg ctcccttccc tgtccttcct 3840
gggcctaggg ctgtgccagc tgcctcgtcc cgtcaccttc tggcttcttc tctccctcca 3900
tatcttagct gttttcctca tgagaatgtt ccaaattcga aatttctatt taaccattat 3960
atatttactt gtttgctatt atctctgccc ccagtagatt gttagctcca gaagagaaag 4020
gatcatgtct tttgcttatc tagatatgcc catctgcctg gtacaatctc tggcacatgt 4080
tacaggcaac aactacttgt ggaattggtg aatgcatgaa tagaagaatg agtgaatgaa 4140
tgaatagaca ataggcagaa atccagcctc aaagagctta cagtctggta agaggaataa 4200
aatgtctgca aatagccaca ggacaggtca aaggaaggag gggctatttc cagctgaggg 4260
caccccatca ggaaagcacc ccagacttcc ttagggataa cagggtaatg gcgcgggccg 4320
caggaacccc tagtgatgga gttggccact ccctctctgc gcgctcgctc gctcactgag 4380
gccgggcgac caaaggtcgc ccgacgcccg ggctttgccc gggcggcctc agtgagcgag 4440
cgagcgcgca gctgcctgca ggggcgcctg atgcggtatt ttctccttac gcatctgtgc 4500
ggtatttcac accgcatacg tcaaagcaac catagtacgc gccctgtagc ggcgcattaa 4560
gcgcggcggg tgtggtggtt acgcgcagcg tgaccgctac acttgccagc gccttagcgc 4620
ccgctccttt cgctttcttc ccttcctttc tcgccacgtt cgccggcttt ccccgtcaag 4680
ctctaaatcg ggggctccct ttagggttcc gatttagtgc tttacggcac ctcgacccca 4740
aaaaacttga tttgggtgat ggttcacgta gtgggccatc gccctgatag acggtttttc 4800
gccctttgac gttggagtcc acgttcttta atagtggact cttgttccaa actggaacaa 4860
cactcaactc tatctcgggc tattcttttg atttataagg gattttgccg atttcggtct 4920
attggttaaa aaatgagctg atttaacaaa aatttaacgc gaattttaac aaaatattaa 4980
cgtttacaat tttatggtgc actctcagta caatctgctc tgatgccgca tagttaagcc 5040
agccccgaca cccgccaaca cccgctgacg cgccctgacg ggcttgtctg ctcccggcat 5100
ccgcttacag acaagctgtg accgtctccg ggagctgcat gtgtcagagg ttttcaccgt 5160
catcaccgaa acgcgcgaga cgaaagggcc tcgtgatacg cctattttta taggttaatg 5220
tcatgataat aatggtttct tagacgtcag gtggcacttt tcggggaaat gtgcgcggaa 5280
cccctatttg tttatttttc taaatacatt caaatatgta tccgctcatg agacaataac 5340
cctgataaat gcttcaataa tattgaaaaa ggaagagtcg atcgatcaag agacaggatg 5400
aggatcgttt cgcatgattg aacaagatgg attgcacgca ggttctccgg ccgcttgggt 5460
ggagaggcta ttcggctatg actgggcaca acagacaatc ggctgctctg atgccgccgt 5520
gttccggctg tcagcgcagg ggcgcccggt tctttttgtc aagaccgacc tgtccggtgc 5580
cctgaatgaa ctgcaagacg aggcagcgcg gctatcgtgg ctggccacga cgggcgttcc 5640
ttgcgcagct gtgctcgacg ttgtcactga agcgggaagg gactggctgc tattgggcga 5700
agtgccgggg caggatctcc tgtcatctca ccttgctcct gccgagaaag tatccatcat 5760
ggctgatgca atgcggcggc tgcatacgct tgatccggct acctgcccat tcgaccacca 5820
agcgaaacat cgcatcgagc gagcacgtac tcggatggaa gccggtcttg tcgatcagga 5880
tgatctggac gaagagcatc aggggctcgc gccagccgaa ctgttcgcca ggctcaaggc 5940
gagcatgccc gacggcgagg atctcgtcgt gacccatggc gatgcctgct tgccgaatat 6000
catggtggaa aatggccgct tttctggatt catcgactgt ggccggctgg gtgtggcgga 6060
tcgctatcag gacatagcgt tggctacccg tgatattgct gaagagcttg gcggcgaatg 6120
ggctgaccgc ttcctcgtgc tttacggtat cgccgctccc gattcgcagc gcatcgcctt 6180
ctatcgcctt cttgacgagt tcttctgaac gagcgtgaca ccacgatgcc tgtagcaatg 6240
gcaacaacgt tgcgcaaact attaactggc gaactactta ctctagcttc ccggcaacaa 6300
ttaatagact ggatggaggc ggataaagtt gcaggaccac ttctgcgctc ggcccttccg 6360
gctggctggt ttattgctga taaatctgga gccggtgagc gtgggtctcg cggtatcatt 6420
gcagcactgg ggccagatgg taagccctcc cgtatcgtag ttatctacac gacggggagt 6480
caggcaacta tggatgaacg aaatagacag atcgctgaga taggtgcctc actgattaag 6540
cattggtaac tgtcagacca agtttactca tatatacttt agattgattt aaaacttcat 6600
ttttaattta aaaggatcta ggtgaagatc ctttttgata atctcatgac caaaatccct 6660
taacgtgagt tttcgttcca ctgagcgtca gaccccgtag aaaagatcaa aggatcttct 6720
tgagatcctt tttttctgcg cgtaatctgc tgcttgcaaa caaaaaaacc accgctacca 6780
gcggtggttt gtttgccgga tcaagagcta ccaactcttt ttccgaaggt aactggcttc 6840
agcagagcgc agataccaaa tactgttctt ctagtgtagc cgtagttagg ccaccacttc 6900
aagaactctg tagcaccgcc tacatacctc gctctgctaa tcctgttacc agtggctgct 6960
gccagtggcg ataagtcgtg tcttaccggg ttggactcaa gacgatagtt accggataag 7020
gcgcagcggt cgggctgaac ggggggttcg tgcacacagc ccagcttgga gcgaacgacc 7080
tacaccgaac tgagatacct acagcgtgag ctatgagaaa gcgccacgct tcccgaaggg 7140
agaaaggcgg acaggtatcc ggtaagcggc agggtcggaa caggagagcg cacgagggag 7200
cttccagggg gaaacgcctg gtatctttat agtcctgtcg ggtttcgcca cctctgactt 7260
gagcgtcgat ttttgtgatg ctcgtcaggg gggcggagcc tatggaaaaa cgccagcaac 7320
gcggcctttt tacggttcct ggccttttgc tggccttttg ctcacatgt 7369

<210> SEQ ID NO 80
<211> LENGTH: 7451
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 80
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaat tcagtggatc ccgataacta taacggtcct 180
aaggtagcga tttaaatgag ggcctatttc ccatgattcc ttcatatttg catatacgat 240
acaaggctgt tagagagata attagaatta atttgactgt aaacacaaag atattagtac 300
aaaatacgtg acgtagaaag taataatttc ttgggtagtt tgcagtttta aaattatgtt 360
ttaaaatgga ctatcatatg cttaccgtaa cttgaaagta tttcgatttc ttggctttat 420
atatcttgtg gaaaggacga ggtaccgtga gctgttggat tcgcttaatt cgaatatcct 480
aagaggttta catttcttga tattactatt aagccacttc agctgcttct gagctgttgg 540
attcgcttaa ttcgaatatc ctaagaggtt tacatttctt gatattacta ttaagccact 600
tcagctgctt ctgagctgtt ggattcgctt aattcgaata tcctaagagg tttacatttc 660
ttgatattac tattaagcca cttcagctgc ttctttttcc gggacgcgtc aattgagatc 720
tccgacattg attattgact agttattaat agtaatcaat tacggggtca ttagttcata 780
gcccatatat ggagttccgc gttacataac ttacggtaaa tggcccgcct ggctgaccgc 840
ccaacgaccc ccgcccattg acgtcaataa tgacgtatgt tcccatagta acgccaatag 900
ggactttcca ttgacgtcaa tgggtggagt atttacggta aactgcccac ttggcagtac 960
atcaagtgta tcatatgcca agtacgcccc ctattgacgt caatgacggt aaatggcccg 1020
cctggcatta tgcccagtac atgaccttat gggactttcc tacttggcag tacatctacg 1080
tattagtcat cgctattacc atgtcgaggc cacgttctgc ttcactctcc ccatctcccc 1140
cccctcccca cccccaattt tgtatttatt tattttttaa ttattttgtg cagcgatggg 1200
ggcggggggg gggggcgcgc gccaggcggg gcggggcggg gcgaggggcg gggcggggcg 1260
aggcggagag gtgcggcggc agccaatcag agcggcgcgc tccgaaagtt tccttttatg 1320
gcgaggcggc ggcggcggcg gccctataaa aagcgaagcg cgcggcgggc gggagcaagc 1380
ttcgtttagt gaaccgtcag atcgcctgga gacgccatcc acgctgtttt gacctccata 1440
gaagacaccg ggaccgatcc agcctccgcg gattcgaatc ccggccggga acggtgcatt 1500
ggaacgcgga ttccccgtgc caagagtgac gtaagtaccg cctatagagt ctataggccc 1560

-continued

```
acaaaaaatg ctttcttctt ttaatatact tttttgttta tcttatttct aatactttcc   1620
ctaatctctt tctttcaggg caataatgat acaatgtatc atgcctcttt gcaccattct   1680
aaagaataac agtgataatt tctgggttaa ggcaatagca atatttctgc atataaatat   1740
ttctgcatat aaattgtaac tgatgtaaga ggtttcatat tgctaatagc agctacaatc   1800
cagctaccat tctgctttta ttttgtggtt gggataaggc tggattattc tgagtccaag   1860
ctaggccctt ttgctaatcg tgttcatacc tcttatcttc ctcccacagc tcctgggcaa   1920
cgtgctggtc tgtgtgctgg cccatcactt tggcaaagaa ttaccggtgg caacgtgctg   1980
gttattgtgc tgtctcatca ttttggcaaa gaattcacgc cccagagccg ccaccatggc   2040
ctacccatac gatgttccag attacgctct cacattcatg gcctctgaca gcgaggaaga   2100
agtgtgtgat gagcggacgt ccctaatgtc ggctgagagc ccacgccgc gctcctgcca   2160
ggagggcagg cagggcccag aggatggaga gaacactgcc cagtggagaa gccaggagaa   2220
cgaggaggac ggtgaggagg accctgaccg ctatgtctgt agtggggttc ccgggcggcc   2280
gccaggcctg gaggaagagc tgaccctcaa atacggagcg aagcacgtga tcatgctgtt   2340
tgtgcctgtc actctgtgca tgatcgtggt ggtagccacc atcaagtctg tgcgcttcta   2400
cacagagaag aatggacagc tcatctacac gccattcact gaggacacac cctcggtggg   2460
ccagcgcctc ctcaactccg tgctgaacac cctcatcatg atcagcgtca tcgtggttat   2520
gaccatcttc ttggtggtgc tctacaagta ccgctgctac aagttcatcc atggctggtt   2580
gatcatgtct tcactgatgc tgctgttcct cttcacctat atctaccttg ggaagtgct   2640
caagacctac aatgtggcca tggactaccc caccctcttg ctgactgtct ggaacttcgg   2700
ggcagtgggc atggtgtgca tccactggaa gggccctctg gtgctgcagc aggcctacct   2760
catcatgatc agtgcgctca tggccctagt gttcatcaag tacctcccag agtggtccgc   2820
gtgggtcatc ctgggcgcca tctctgtgta tgatctcgtg gctgtgctgt gtcccaaagg   2880
gcctctgaga atgctggtag aaactgccca ggagagaaat gagcccatat tccctgccct   2940
gatatactca tctgccatgg tgtggacggt tggcatggcg aagctggacc cctcctctca   3000
gggtgccctc cagctcccct acgacccgga gatggaagaa gactcctatg acagttttgg   3060
ggagccttca taccccgaag tctttgagcc tcccttgact ggctacccag gggaggagct   3120
ggaggaagag gaggaaaggg gcgtgaagct tggcctcggg gacttcatct tctacagtgt   3180
gctggtgggc aaggcggctg ccacgggcag cggggactgg aataccacgc tggcctgctt   3240
cgtggccatc ctcattggct tgtgtctgac cctcctgctg cttgctgtgt tcaagaaggc   3300
gctgcccgcc ctccccatct ccatcacgtt cgggctcatc ttttacttct ccacggacaa   3360
cctggtgcgg ccgttcatgg acaccctggc ctcccatcag ctctacatct agtaagcggc   3420
cgccctaggg agctcctcga gggggtggca tccctgtgac ccctccccag tgcctctcct   3480
ggccctggaa gttgccactc cagtgcccac cagccttgtc ctaataaaat taagttgcat   3540
cattttgtct gactaggtgt ccttctataa tattatgggg tggagggggg tggtatggag   3600
caaggggcaa ggggggaaga caacctgtag ggcctgcggg gtctattggg aaccaagctg   3660
gagtgcagtg gcacaatctt ggctcactgc aatctccgcc tcctgggttc aagcgattct   3720
cctgcctcag cctcccgagt tgttgggatt ccaggcatgc atgaccaggc tcagctaatt   3780
tttgtttttt tggtagagac ggggtttcac catattggcc aggctggtct ccccctccta   3840
atctcaggtg atctacccac cttggcctcc caaattgctg ggattacagg cgtgaaccac   3900
tgctcccttc cctgtccttc ctgggcctag ggctgtgcca gctgcctcgt cccgtcacct   3960
```

```
tctggcttct tctctccctc catatcttag ctgttttcct catgagaatg ttccaaattc   4020
gaaatttcta tttaaccatt atatatttac ttgtttgcta ttatctctgc ccccagtaga   4080
ttgttagctc cagaagagaa aggatcatgt cttttgctta tctagatatg cccatctgcc   4140
tggtacaatc tctggcacat gttacaggca acaactactt gtggaattgg tgaatgcatg   4200
aatagaagaa tgagtgaatg aatgaataga caataggcag aaatccagcc tcaaagagct   4260
tacagtctgg taagaggaat aaaatgtctg caaatagcca caggacaggt caaaggaagg   4320
aggggctatt tccagctgag ggcaccccat caggaaagca ccccagactt ccttagggat   4380
aacagggtaa tggcgcgggc cgcaggaacc cctagtgatg gagttggcca ctccctctct   4440
gcgcgctcgc tcgctcactg aggccgggcg accaaaggtc gcccgacgcc cgggctttgc   4500
ccgggcggcc tcagtgagcg agcgagcgcg cagctgcctg caggggcgcc tgatgcggta   4560
ttttctcctt acgcatctgt gcggtatttc acaccgcata cgtcaaagca accatagtac   4620
gcgccctgta gcggcgcatt aagcgcggcg ggtgtggtgg ttacgcgcag cgtgaccgct   4680
acacttgcca gcgccttagc gcccgctcct ttcgctttct tcccttcctt tctcgccacg   4740
ttcgccggct ttccccgtca agctctaaat cgggggctcc ctttagggtt ccgatttagt   4800
gctttacggc acctcgaccc caaaaaactt gatttgggtg atggttcacg tagtgggcca   4860
tcgccctgat agacggtttt tcgccctttg acgttggagt ccacgttctt taatagtgga   4920
ctcttgttcc aaactggaac aacactcaac tctatctcgg gctattcttt tgatttataa   4980
gggattttgc cgatttcggt ctattggtta aaaaatgagc tgatttaaca aaaatttaac   5040
gcgaatttta acaaaatatt aacgtttaca attttatggt gcactctcag tacaatctgc   5100
tctgatgccg catagttaag ccagccccga cacccgccaa cacccgctga cgcgccctga   5160
cgggcttgtc tgctcccggc atccgcttac agacaagctg tgaccgtctc cgggagctgc   5220
atgtgtcaga ggttttcacc gtcatcaccg aaacgcgcga gacgaaaggg cctcgtgata   5280
cgcctatttt tataggttaa tgtcatgata ataatggttt cttagacgtc aggtggcact   5340
tttcggggaa atgtgcgcgg aacccctatt tgtttatttt tctaaataca ttcaaatatg   5400
tatccgctca tgagacaata accctgataa atgcttcaat aatattgaaa aaggaagagt   5460
cgatcgatca agagacagga tgaggatcgt ttcgcatgat tgaacaagat ggattgcacg   5520
caggttctcc ggccgcttgg gtggagaggc tattcggcta tgactgggca caacagacaa   5580
tcggctgctc tgatgccgcc gtgttccggc tgtcagcgca ggggcgcccg gttctttttg   5640
tcaagaccga cctgtccggt gccctgaatg aactgcaaga cgaggcagcg cggctatcgt   5700
ggctggccac gacgggcgtt ccttgcgcag ctgtgctcga cgttgtcact gaagcgggaa   5760
gggactggct gctattgggc gaagtgccgg ggcaggatct cctgtcatct caccttgctc   5820
ctgccgagaa agtatccatc atggctgatg caatgcggcg gctgcatacg cttgatccgg   5880
ctacctgccc attcgaccac caagcgaaac atcgcatcga gcgagcacgt actcggatgg   5940
aagccggtct tgtcgatcag gatgatctgg acgaagagca tcaggggctc gcgccagccg   6000
aactgttcgc caggctcaag gcgagcatgc ccgacggcga ggatctcgtc gtgacccatg   6060
gcgatgcctg cttgccgaat atcatggtgg aaaatggccg cttttctgga ttcatcgact   6120
gtggccggct gggtgtggcg gatcgctatc aggacatagc gttggctacc cgtgatattg   6180
ctgaagagct tggcggcgaa tgggctgacc gcttcctcgt gctttacggt atcgccgctc   6240
ccgattcgca gcgcatcgcc ttctatcgcc ttcttgacga gttcttctga acgagcgtga   6300
```

caccacgatg cctgtagcaa tggcaacaac gttgcgcaaa ctattaactg gcgaactact 6360
tactctagct tcccggcaac aattaataga ctggatggag gcggataaag ttgcaggacc 6420
acttctgcgc tcggcccttc cggctggctg gtttattgct gataaatctg gagccggtga 6480
gcgtgggtct cgcggtatca ttgcagcact ggggccagat ggtaagccct cccgtatcgt 6540
agttatctac acgacgggga gtcaggcaac tatggatgaa cgaaatagac agatcgctga 6600
gataggtgcc tcactgatta agcattggta actgtcagac caagtttact catatatact 6660
ttagattgat ttaaaacttc atttttaatt taaaaggatc taggtgaaga tcctttttga 6720
taatctcatg accaaaatcc cttaacgtga gttttcgttc cactgagcgt cagaccccgt 6780
agaaaagatc aaaggatctt cttgagatcc tttttttctg cgcgtaatct gctgcttgca 6840
aacaaaaaaa ccaccgctac cagcggtggt ttgtttgccg gatcaagagc taccaactct 6900
ttttccgaag gtaactggct tcagcagagc gcagatacca aatactgttc ttctagtgta 6960
gccgtagtta ggccaccact tcaagaactc tgtagcaccg cctacatacc tcgctctgct 7020
aatcctgtta ccagtggctg ctgccagtgg cgataagtcg tgtcttaccg ggttggactc 7080
aagacgatag ttaccggata aggcgcagcg gtcgggctga acggggggtt cgtgcacaca 7140
gcccagcttg gagcgaacga cctacaccga actgagatac ctacagcgtg agctatgaga 7200
aagcgccacg cttcccgaag ggagaaaggc ggacaggtat ccggtaagcg gcagggtcgg 7260
aacaggagag cgcacgaggg agcttccagg gggaaacgcc tggtatcttt atagtcctgt 7320
cgggtttcgc cacctctgac ttgagcgtcg atttttgtga tgctcgtcag gggggcggag 7380
cctatggaaa aacgccagca acgcggcctt tttacggttc ctggcctttt gctggccttt 7440
tgctcacatg t 7451

<210> SEQ ID NO 81
<211> LENGTH: 7208
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 81
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaat tcagtggatc ccgataacta taacggtcct 180
aaggtagcga tttaaatccg ggacgcgtca attgagatct ccgacattga ttattgacta 240
gttattaata gtaatcaatt acggggtcat tagttcatag cccatatatg gagttccgcg 300
ttacataact tacggtaaat ggcccgcctg gctgaccgcc caacgacccc cgcccattga 360
cgtcaataat gacgtatgtt cccatagtaa cgccaatagg gactttccat tgacgtcaat 420
gggtggagta tttacggtaa actgcccact tggcagtaca tcaagtgtat catatgccaa 480
gtacgccccc tattgacgtc aatgacggta aatggcccgc ctggcattat gcccagtaca 540
tgaccttatg ggactttcct acttggcagt acatctacgt attagtcatc gctattacca 600
tgtcgaggcc acgttctgct tcactctccc catctccccc ccctccccac ccccaatttt 660
gtatttattt atttttaat tattttgtgc agcgatgggg gcgggggggg ggggcgcgcg 720
ccaggcgggg cggggcgggg cgaggggcgg ggcggggcga ggcggagagg tgcggcggca 780
gccaatcaga gcggcgcgct ccgaaagttt ccttttatgg cgaggcggcg gcggcggcgg 840

```
ccctataaaa agcgaagcgc gcggcgggcg ggagcaagct tcgtttagtg aaccgtcaga    900
tcgcctggag acgccatcca cgctgttttg acctccatag aagacaccgg gaccgatcca    960
gcctccgcgg attcgaatcc cggccgggaa cggtgcattg gaacgcggat tccccgtgcc   1020
aagagtgacg taagtaccgc ctatagagtc tataggccca caaaaaatgc tttcttcttt   1080
taatatactt ttttgtttat cttatttcta atactttccc taatctcttt ctttcagggc   1140
aataatgata caatgtatca tgcctctttg caccattcta aagaataaca gtgataattt   1200
ctgggttaag gcaatagcaa tatttctgca tataaatatt tctgcatata aattgtaact   1260
gatgtaagag gtttcatatt gctaatagca gctacaatcc agctaccatt ctgcttttat   1320
tttgtggttg ggataaggct ggattattct gagatatcgg tacctgagct gttggattcg   1380
cttaattcga atatcctaag aggtttacat ttcttgatat tactattaag ccacttcagc   1440
tgcttctgag ctgttggatt cgcttaattc gaatatccta agaggtttac atttcttgat   1500
attactatta agccacttca gctgcttctg agctgttgga ttcgcttaat tcgaatatcc   1560
taagaggttt acatttcttg atattactat taagccactt cagctgcttc gtcgacgcta   1620
ggcccttttg ctaatcgtgt tcatacctct tatcttcctc ccacagctcc tgggcaacgt   1680
gctggtctgt gtgctggccc atcactttgg caaagaatta ccggtggcaa cgtgctggtt   1740
attgtgctgt ctcatcattt tggcaaagaa ttcacgcccc agagccgcca ccatggccta   1800
cccatacgat gttccagatt acgctctcac attcatggcc tctgacagcg aggaagaagt   1860
gtgtgatgag cggacgtccc taatgtcggc tgagagcccc acgccgcgct cctgccagga   1920
gggcaggcag ggcccagagg atggagagaa cactgcccag tggagaagcc aggagaacga   1980
ggaggacggt gaggaggacc ctgaccgcta tgtctgtagt ggggttcccg ggcggccgcc   2040
aggcctggag gaagagctga ccctcaaata cggagcgaag cacgtgatca tgctgtttgt   2100
gcctgtcact ctgtgcatga tcgtggtggt agccaccatc aagtctgtgc gcttctacac   2160
agagaagaat ggacagctca tctacacgcc attcactgag gacacaccct cggtgggcca   2220
gcgcctcctc aactccgtgc tgaacaccct catcatgatc agcgtcatcg tggttatgac   2280
catcttcttg gtggtgctct acaagtaccg ctgctacaag ttcatccatg gctggttgat   2340
catgtcttca ctgatgctgc tgttcctctt cacctatatc taccttgggg aagtgctcaa   2400
gacctacaat gtggccatgg actaccccac cctcttgctg actgtctgga acttcggggc   2460
agtgggcatg gtgtgcatcc actggaaggg ccctctggtg ctgcagcagg cctacctcat   2520
catgatcagt gcgctcatgg ccctagtgtt catcaagtac ctcccagagt ggtccgcgtg   2580
ggtcatcctg ggcgccatct ctgtgtatga tctcgtggct gtgctgtgtc ccaaagggcc   2640
tctgagaatg ctggtagaaa ctgcccagga gagaaatgag cccatattcc ctgccctgat   2700
atactcatct gccatggtgt ggacggttgg catggcgaag ctggacccct cctctcaggg   2760
tgccctccag ctcccctacg acccggagat ggaagaagac tcctatgaca gttttgggga   2820
gccttcatac cccgaagtct ttgagcctcc cttgactggc tacccagggg aggagctgga   2880
ggaagaggag gaaaggggcg tgaagcttgg cctcggggac ttcatcttct acagtgtgct   2940
ggtgggcaag gcggctgcca cgggcagcgg ggactggaat accacgctgg cctgcttcgt   3000
ggccatcctc attggcttgt gtctgaccct cctgctgctt gctgtgttca agaaggcgct   3060
gcccgccctc cccatctcca tcacgttcgg gctcatcttt tacttctcca cggacaacct   3120
ggtgcggccg ttcatggaca ccctggcctc ccatcagctc tacatctagt aagcggccgc   3180
cctagggagc tcctcgaggg ggtggcatcc ctgtgacccc tccccagtgc ctctcctggc   3240
```

```
cctggaagtt gccactccag tgcccaccag ccttgtccta ataaaattaa gttgcatcat   3300
tttgtctgac taggtgtcct tctataatat tatggggtgg aggggggtgg tatggagcaa   3360
ggggcaaggg gggaagacaa cctgtagggc ctgcggggtc tattgggaac caagctggag   3420
tgcagtggca caatcttggc tcactgcaat ctccgcctcc tgggttcaag cgattctcct   3480
gcctcagcct cccgagttgt tgggattcca ggcatgcatg accaggctca gctaattttt   3540
gtttttttgg tagagacggg gtttcaccat attggccagg ctggtctccc cctcctaatc   3600
tcaggtgatc tacccacctt ggcctcccaa attgctggga ttacaggcgt gaaccactgc   3660
tcccttccct gtccttcctg ggcctagggc tgtgccagct gcctcgtccc gtcaccttct   3720
ggcttcttct ctccctccat atcttagctg ttttcctcat gagaatgttc caaattcgaa   3780
atttctattt aaccattata tatttacttg tttgctatta tctctgcccc cagtagattg   3840
ttagctccag aagagaaagg atcatgtctt ttgcttatct agatatgccc atctgcctgg   3900
tacaatctct ggcacatgtt acaggcaaca actacttgtg gaattggtga atgcatgaat   3960
agaagaatga gtgaatgaat gaatagacaa taggcagaaa tccagcctca aagagcttac   4020
agtctggtaa gaggaataaa atgtctgcaa atagccacag gacaggtcaa aggaaggagg   4080
ggctatttcc agctgagggc accccatcag gaaagcaccc cagacttcct tagggataac   4140
agggtaatgg cgcgggccgc aggaacccct agtgatggag ttggccactc cctctctgcg   4200
cgctcgctcg ctcactgagg ccgggcgacc aaaggtcgcc cgacgcccgg gctttgcccg   4260
ggcggcctca gtgagcgagc gagcgcgcag ctgcctgcag gggcgcctga tgcggtattt   4320
tctccttacg catctgtgcg gtatttcaca ccgcatacgt caaagcaacc atagtacgcg   4380
ccctgtagcg gcgcattaag cgcggcgggt gtggtggtta cgcgcagcgt gaccgctaca   4440
cttgccagcg ccttagcgcc cgctcctttc gctttcttcc cttcctttct cgccacgttc   4500
gccggctttc cccgtcaagc tctaaatcgg gggctccctt tagggttccg atttagtgct   4560
ttacggcacc tcgaccccaa aaaacttgat ttgggtgatg gttcacgtag tgggccatcg   4620
ccctgataga cggtttttcg ccctttgacg ttggagtcca cgttctttaa tagtggactc   4680
ttgttccaaa ctggaacaac actcaactct atctcgggct attcttttga tttataaggg   4740
attttgccga tttcggtcta ttggttaaaa aatgagctga tttaacaaaa atttaacgcg   4800
aattttaaca aaatattaac gtttacaatt ttatggtgca ctctcagtac aatctgctct   4860
gatgccgcat agttaagcca gccccgacac ccgccaacac ccgctgacgc gccctgacgg   4920
gcttgtctgc tcccggcatc cgcttacaga caagctgtga ccgtctccgg gagctgcatg   4980
tgtcagaggt tttcaccgtc atcaccgaaa cgcgcgagac gaaagggcct cgtgatacgc   5040
ctatttttat aggttaatgt catgataata atggtttctt agacgtcagg tggcactttt   5100
cggggaaatg tgcgcggaac ccctatttgt ttatttttct aaatacattc aaatatgtat   5160
ccgctcatga gacaataacc ctgataaatg cttcaataat attgaaaaag gaagagtcga   5220
tcgatcaaga gacaggatga ggatcgtttc gcatgattga acaagatgga ttgcacgcag   5280
gttctccggc cgcttgggtg gagaggctat tcggctatga ctgggcacaa cagacaatcg   5340
gctgctctga tgccgccgtg ttccggctgt cagcgcaggg gcgcccggtt ctttttgtca   5400
agaccgacct gtccggtgcc ctgaatgaac tgcaagacga ggcagcgcgg ctatcgtggc   5460
tggccacgac gggcgttcct tgcgcagctg tgctcgacgt tgtcactgaa gcgggaaggg   5520
actggctgct attgggcgaa gtgccggggc aggatctcct gtcatctcac cttgctcctg   5580
```

ccgagaaagt atccatcatg gctgatgcaa tgcggcggct gcatacgctt gatccggcta 5640
cctgcccatt cgaccaccaa gcgaaacatc gcatcgagcg agcacgtact cggatggaag 5700
ccggtcttgt cgatcaggat gatctggacg aagagcatca ggggctcgcg ccagccgaac 5760
tgttcgccag gctcaaggcg agcatgcccg acggcgagga tctcgtcgtg acccatggcg 5820
atgcctgctt gccgaatatc atggtggaaa atggccgctt ttctggattc atcgactgtg 5880
gccggctggg tgtggcggat cgctatcagg acatagcgtt ggctacccgt gatattgctg 5940
aagagcttgg cggcgaatgg gctgaccgct tcctcgtgct ttacggtatc gccgctcccg 6000
attcgcagcg catcgccttc tatcgccttc ttgacgagtt cttctgaacg agcgtgacac 6060
cacgatgcct gtagcaatgg caacaacgtt gcgcaaacta ttaactggcg aactacttac 6120
tctagcttcc cggcaacaat taatagactg gatggaggcg gataaagttg caggaccact 6180
tctgcgctcg gcccttccgg ctggctggtt tattgctgat aaatctggag ccggtgagcg 6240
tgggtctcgc ggtatcattg cagcactggg gccagatggt aagccctccc gtatcgtagt 6300
tatctacacg acggggagtc aggcaactat ggatgaacga aatagacaga tcgctgagat 6360
aggtgcctca ctgattaagc attggtaact gtcagaccaa gtttactcat atatacttta 6420
gattgattta aaacttcatt tttaatttaa aaggatctag gtgaagatcc tttttgataa 6480
tctcatgacc aaaatccctt aacgtgagtt ttcgttccac tgagcgtcag accccgtaga 6540
aaagatcaaa ggatcttctt gagatccttt ttttctgcgc gtaatctgct gcttgcaaac 6600
aaaaaaacca ccgctaccag cggtggtttg tttgccggat caagagctac caactctttt 6660
tccgaaggta actggcttca gcagagcgca gataccaaat actgttcttc tagtgtagcc 6720
gtagttaggc caccacttca agaactctgt agcaccgcct acatacctcg ctctgctaat 6780
cctgttacca gtggctgctg ccagtggcga taagtcgtgt cttaccgggt tggactcaag 6840
acgatagtta ccggataagg cgcagcggtc gggctgaacg gggggttcgt gcacacagcc 6900
cagcttggag cgaacgacct acaccgaact gagataccta cagcgtgagc tatgagaaag 6960
cgccacgctt cccgaaggga gaaaggcgga caggtatccg gtaagcggca gggtcggaac 7020
aggagagcgc acgagggagc ttccaggggg aaacgcctgg tatctttata gtcctgtcgg 7080
gtttcgccac ctctgacttg agcgtcgatt tttgtgatgc tcgtcagggg ggcggagcct 7140
atggaaaaac gccagcaacg cggccttttt acggttcctg gccttttgct ggccttttgc 7200
tcacatgt 7208

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
cctgaccacc ttgcactatt 20

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic probe

<400> SEQUENCE: 83
tgtgtccctc ggtgcagaaa ctac 24

<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
caacttccgg gcctatcata tc 22

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
tggaccaatt agcattccat ca 22

<210> SEQ ID NO 86
<211> LENGTH: 25
<212> TYPE: DNA
<213> ORGANISM: Artificial Sequence
<220> FEATURE:
<223> OTHER INFORMATION: Description of Artificial Sequence: Synthetic probe

<400> SEQUENCE: 86
tgaactacgc ctgaggatcc gatct 25

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
gccagaagtc agatgctcaa 20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
gagaaggtca gattagggcg 20

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic probe

<400> SEQUENCE: 89

-continued

```
aaagagtgtg ctcgggagtg c                                              21


<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90

tcgtagggaa ctggcttttc                                                20
```